United States Patent
Neya et al.

(12) 
(10) Patent No.: US 6,967,197 B2
(45) Date of Patent: Nov. 22, 2005

(54) THIAZEPINYL HYDROXAMIC ACID DERIVATIVES AS MATRIX METALLOPROTEINASE INHIBITORS

(75) Inventors: Masahiro Neya, Osaka (JP); Hitoshi Yamazaki, Osaka (JP); Kazuhiko Ohne, Osaka (JP); Yuki Sawada, Osaka (JP); Tsuyoshi Mizutani, Osaka (JP); Yoshimasa Imamura, Osaka (JP); Noriko Mukai, Osaka (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 129 days.

(21) Appl. No.: 10/203,627

(22) PCT Filed: Feb. 20, 2001

(86) PCT No.: PCT/JP01/01206
§ 371 (c)(1), (2), (4) Date: Aug. 19, 2002

(87) PCT Pub. No.: WO01/60808
PCT Pub. Date: Aug. 23, 2001

(65) Prior Publication Data
US 2003/0134849 A1 Jul. 17, 2003

(30) Foreign Application Priority Data

Feb. 21, 2000 (AU) .................................................. PQ5751
Jul. 6, 2000 (AU) .................................................. PQ8603

(51) Int. Cl.⁷ ...................... A61K 31/55; C07D 281/06; C07D 417/04; C07D 417/06; C07D 417/12

(52) U.S. Cl. .................................. 514/211.01; 540/544

(58) Field of Search ...................... 540/544; 514/211.01

(56) References Cited

U.S. PATENT DOCUMENTS

| | | | |
|---|---|---|---|
| 6,333,324 B1 | 12/2001 | Neya et al. | 514/235.5 |
| 6,489,324 B2 | 12/2002 | Neya et al. | 514/235.5 |

FOREIGN PATENT DOCUMENTS

| | | |
|---|---|---|
| WO | 97 24177 | 7/1997 |
| WO | 98 08823 | 3/1998 |
| WO | 98 08827 | 3/1998 |

*Primary Examiner*—Bruck Kifle
(74) *Attorney, Agent, or Firm*—Oblon, Spivak, McClelland, Maier & Neustadt, P.C.

(57) ABSTRACT

A compound of formula (I) in which $R^1$ is halo, lower alkoxy, optionally substituted aryl, optionally substituted aryloxy, optionally substituted heterecyclic group or optionally substituted lower alkynyl, $R^2$ is amidated carboxy, $R^3$ is hydrogen or acyl, Ar is aryl or heterocyclic group, X is thia, sulfinyl or sulfonyl, Y and Z are each lower alkylene, m and n are each an integer of 0 to 2, and a salt thereof, useful as inhibitors of matrix metalloproteinases (MMP) or the production of tumor necrosis factor α (TNF α)

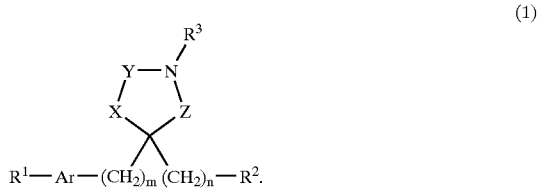

(1)

20 Claims, No Drawings

THIAZEPINYL HYDROXAMIC ACID DERIVATIVES AS MATRIX METALLOPROTEINASE INHIBITORS

FIELD OF THE INVENTION

The present invention relates to new compounds and pharmaceutically acceptable salts thereof.

More particularly, it relates to new compounds and pharmaceutically acceptable salts thereof which are useful as inhibitors of matrix metalloproteinases (hereinafter to be referred to as MMP) or the production of tumor necrosis factor α (hereinafter to be referred to as TNF α), to pharmaceutical compositions comprising the same, to use of the same as medicaments, and to methods for using the same therapeutically in the treatment and/or the prevention of MMP- or TNF α-mediated diseases.

BACKGROUND ART

Some compounds to be useful as metalloproteinase inhibitors, or the like are known (WO 97/20824, etc.).

DISCLOSURE OF THE INVENTION

One object of the present invention is to provide new and useful cyclic compounds and pharmaceutically acceptable salts thereof, and to provide a process for preparing said new cyclic compound and salts thereof, which have pharmacological activities such as MMP- or TNF α-inhibitory activity and the like.

Another object of the present invention is to provide a pharmaceutical composition comprising, as an active ingredient, said cyclic compound or a pharmaceutically acceptable salt thereof.

A further object of the present invention is to provide use of said cyclic compounds and pharmaceutically acceptable salts thereof as medicaments for prophylactic and therapeutic treatment of MMP- or TNF α-mediated diseases.

A still further object of the present invention is to provide a method for using the same for the treatment and/or the prevention of MMP- or TNF α-mediated diseases in mammals, especially humans.

The compounds of the present invention have inhibitory activity on MMP or the production of TNF α, and are useful for the treatment and/or prevention of diseases such as stroke, arthritis, cancer, tissue ulceration, decubitus ulcer, restenosis, periodontal disease, epidermolysis bullosa, scleritis, psoriasis and other diseases characterized by matrix metalloproteinase activity, as well as AIDS, sepsis, septic shock and other diseases caused by the production of TNF α.

There are a number of structurally related metalloproteases which effect the breakdown of structural proteins. Matrix-degrading metalloproteases, such as gelatinase (MMP-2, MMP-9), stromelysin (MMP-3) and collagenase (MMP-1, MMP-8, MMP-13), are involved in tissue matrix degradation and have been implicated in many pathological conditions involving abnormal connective tissue and basement membrane matrix metabolism, such as arthritis (e.g. osteoarthritis and rheumatoid arthritis, etc.), cerebral disease (e.g. stroke, etc.), tissue ulceration (e.g. corneal, epidermal and gastric ulcerations, etc.), abnormal wound healing, periodontal disease, bone disease (e.g. Paget's disease and osteoporosis, etc.), tumor metastasis or invasion and HIV-infection.

A tumor necrosis factor is recognized to be involved in many infections and autoimmune diseases. Furthermore, it has been shown that TNF is the prime mediator of the inflammatory response seen in sepsis and septic shock.

The object compounds of the present invention are novel and can be represented by the following formula (I):

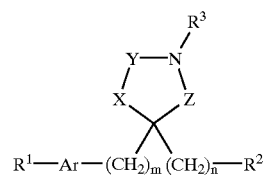

in which $R^1$ is halo, lower alkoxy, optionally substituted aryl, optionally substituted aryloxy, optionally substituted heterecyclic group or optionally substituted lower alkynyl, $R^2$ is amidated carboxy, $R^3$ is hydrogen or acyl, Ar is aryl or heterocyclic group, X is thia, sulfinyl or sulfonyl, Y and Z are each lower alkylene, m and n are each an integer of 0 to 2, and a salt thereof.

The object compounds of the present invention can be prepared by the following processes.

Process 1

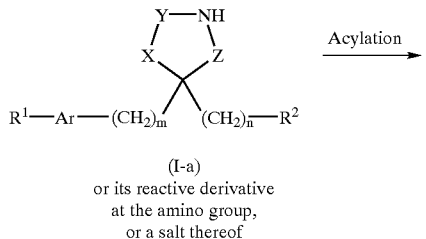

(I-a)
or its reactive derivative
at the amino group,
or a salt thereof

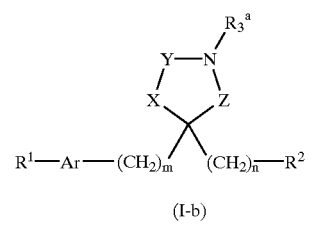

(I-b)
or a salt thereof

Process 2

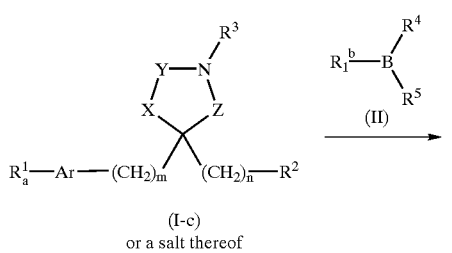

(I-c)
or a salt thereof

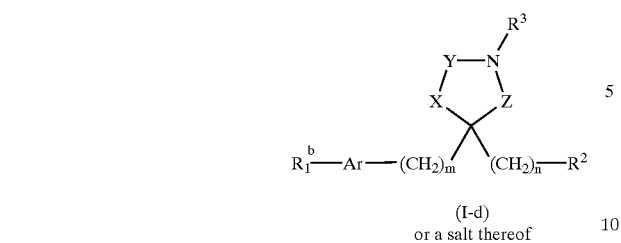

(I-d)
or a salt thereof

Process 3

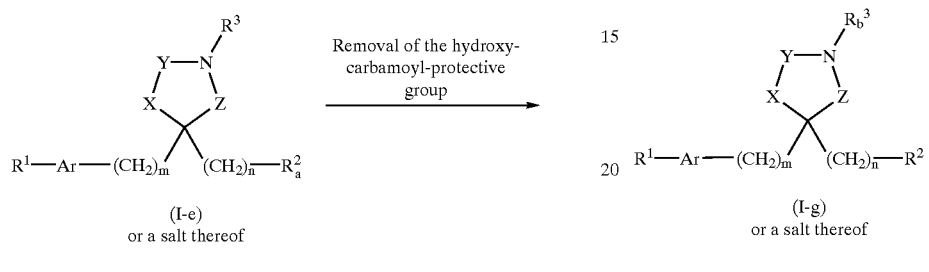

(I-e)
or a salt thereof

Removal of the hydroxy-
carbamoyl-protective
group

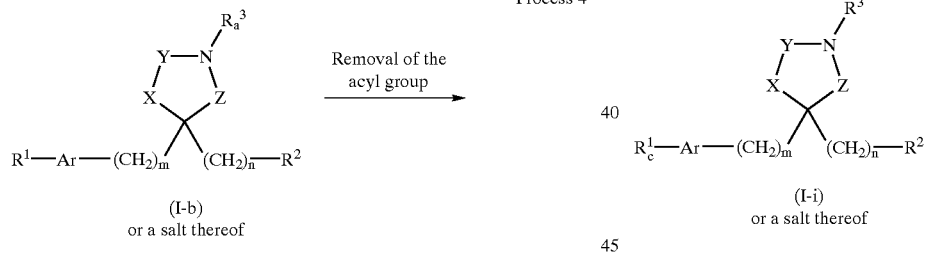

(I-f)
or a salt thereof

Process 4

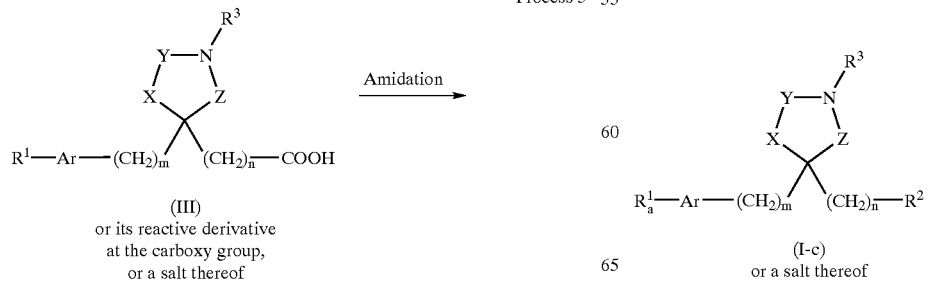

(I-b)
or a salt thereof

Removal of the
acyl group

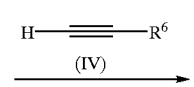

(I-a)
or a salt thereof

Process 5

(III)
or its reactive derivative
at the carboxy group,
or a salt thereof

Amidation

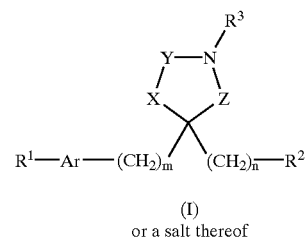

(I)
or a salt thereof

Process 6

Removal of the amino-
or imino-protective
group on $R_b^3$ (I-g)
or a salt thereof

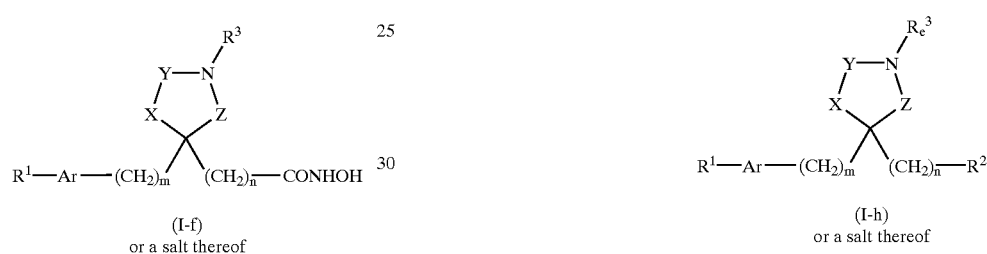

(I-h)
or a salt thereof

Process 7

Acylation (I-i)
or a salt thereof

(I-j)
or a salt thereof

Process 8

H≡≡≡R$^6$
(IV)

(I-c)
or a salt thereof

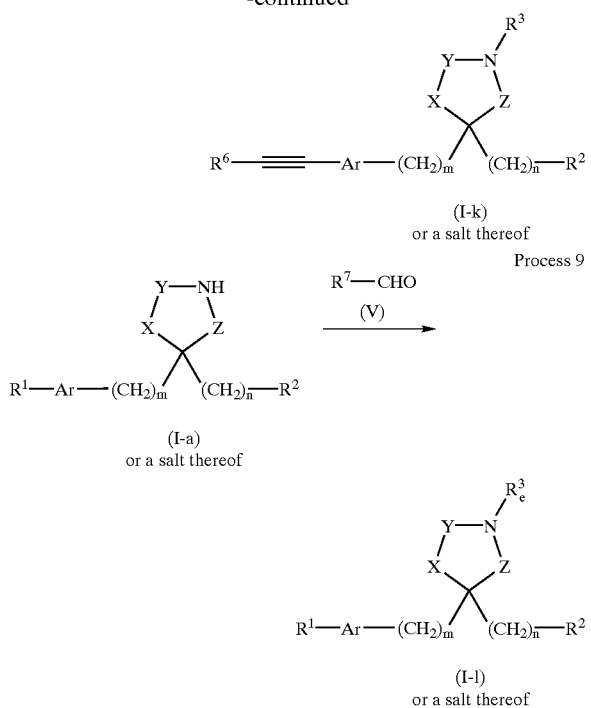

(I-k)
or a salt thereof

Process 9

(I-a)
or a salt thereof (I-l)
or a salt thereof wherein $R^1$, $R^2$, $R^3$, Ar, X, Y, Z, m and n are each as defined above, $R_a^1$ is halo, $R_b^1$ is optionally substituted aryl or optionally substituted-heterocyclic group, $R_c^1$ is aryl, aryloxy or heterocyclic group having at least amino- or imino-moiety, $R_d^1$ is aryl, aryloxy or heterocyclic group having at least acylamino- or acylimino-moiety, $R_a^2$ is protected hydroxycarbamoyl, $R_a^3$ is acyl, $R_b^3$ is acyl having at least protected amino- or protected imino-moiety, $R_c^3$ is acyl having at least amino- or imino-moiety, $R_d^3$ is optionally substituted lower alkyl, $R^4$ and $R^5$ are each hydroxy, lower alkyl, or combined together to form lower alkylene, a formula: H—≡—$R^6$ is optionally substituted lower alkynyl, and a formula: $R^7$—CHO is optionally substituted aldehyde.

The starting compounds used in the above processes can be prepared according to the following Preparations or by a conventional method.

Suitable salts of the object compounds (I) to (If) may be salts, and include a conventional non-toxic pharmaceutically acceptable acid addition salt such as an organic acid salt (e.g. acetate, trifluoroacetate, maleate, tartrate, fumarate, methanesulfonate, benzenesulfonate, formate, toluenesulfonate, etc.), an inorganic acid salt (e.g. hydrochloride, hydrobromide, hydroiodide, sulfate, nitrate, phosphate, etc.), or a conventional non-toxic pharmaceutically acceptable salt with a base such as an amino acid (e.g. arginine, aspartic acid, glutamic acid, etc.), an alkali metal salt (e.g. sodium salt, potassium salt, etc.), an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), or the like.

The object compounds and pharmaceutically acceptable salts thereof may include solvates such as enclosure compounds (e.g. hydrate, etc.).

Suitable examples and illustrations of the various definitions, which the present invention includes within its scope and which are shown in the above and subsequent descriptions of the present specification, are as follows.

The term "lower" is intended to mean up to 6 carbon atoms, preferably up to 4 carbon atoms, unless otherwise indicated.

Suitable "halo" includes fluoro, bromo, chloro and iodo.

Suitable "aryl" and aryl moiety in the term "optionally substituted aryl" may include an aryl having 6 to 10 carbon atoms, such as phenyl, tolyl, xylyl, cumenyl, mesityl, naphthyl, and the like, preferably phenyl and naphthyl, and the most preferably phenyl.

Suitable "aryloxy" in the term "optionally substituted aryloxy" may include an aryloxy having 6 to 10 carbon atoms, such as phenoxy, tolyloxy, xylyloxy, cumenyloxy, mesityloxy, naphthyloxy, and the like, preferably phenoxy.

Suitable "optionally substituted aryl" or "optionally substituted aryloxy" may include above-mentioned aryl or aryloxy respectively, where the aryl or aryloxy moiety is substituted by the group consisting of the following substituents:

(S1) lower alkoxy (e.g. methoxy, ethoxy, propoxy, etc.), (S2) lower alkoxycarbonylamino (e.g. methoxycarbonylamino, ethoxycarbonylamino, t-butoxycarbonylamino, etc.), (S3) lower alkylaminocarbonylamino (e.g. methylaminocarbonylamino, ethylaminocarbonylamino, etc.), (S4) lower alkoxy(lower)alkanoylamino (e.g. ethoxyacetylamino, etc.), (S5) $C_6$–$C_{10}$ aryloxy(lower)alkanoylamino (e.g. phenoxyacetylamino, etc.), (S6) halo (e.g. chloro, fluoro, etc.), (S7) lower alkyl (e.g. methyl, ethyl, propyl, isopropyl, t-butyl, etc.), (S8) lower alkylthio (e.g. methylthio, etc.), (S9) heterocyclic group such as unsaturated 3- to 8-membered, preferably 5- or 6-membered, heteromonocyclic group containing 1 or 2 oxygen atoms and 1 to 3 nitrogen atoms (e.g. oxazolyl, oxadiazolyl, etc.) which is optionally substituted by lower alkyl (e.g. methyloxadiazolyl, etc.), saturated 3- to 8-membered, preferably 5- or 6-membered, heteromonocyclic group containing 1 or 2 sulfur atoms and 1 to 3 nitrogen atoms (e.g. thiazolidinyl, isothiazolidinyl, etc.), which is optionally subis optionally substituted by oxo (e.g. 1,1-dioxothiazolidinyl, 1,1-dioxoisothiazolidinyl, etc.), or unsaturated 3- to 8-membered, preferably 5- or 6-membered, heteromonocyclic group containing 1 or 2 sulfur atoms (e.g. thienyl, etc.), (S10) lower alkenyl (e.g. vinyl, etc.), (S11) amino (e.g. amino), (S12) lower alkanoylamino (e.g. acetylamino, etc.), (S13) hydroxy (e.g. hydroxy), (S14) lower alkylsulfonyl, (S15) $C_6$–$C_{10}$ aryloxy, (S16) $C_6$–$C_{10}$ aryl (e.g. phenyl, etc.) optionally substituted by halogen (e.g. chlorophenyl, etc.), (S17) lower alkylcarbamoyl(lower)alkenyl, (S18) lower alkylcarbamoyl, (S19) trihalo(lower)alkyl (e.g. trifluoromethyl, etc.), (S20) cyano, (S21) cyano(lower)alkyl (e.g. cyanomethyl, etc.), (S22) lower alkoxy(lower)alkyl, (S23) hydroxy(lower)alkyl, (S24) oxo, (S25) aminosulfonyl, (S26) nitro, (S27) lower alkanoyl, (S28) trihalo(lower)alkyloxy, (S29) lower alkoxycarbonyl, (S30) lower cycloalkyl, (S31) lower alkoxy(lower)alkoxy, (S32) fluoernyl, and the like.

Preferable examples of the optionally substituted aryl thus defined may be;

(S0) $C_6$–$C_{10}$ aryl (e.g. phenyl, naphthyl, etc.), (S1) lower alkoxy($C_6$–$C_{10}$)aryl (e.g. methoxyphenyl, ethoxyphneyl, etc.), (S2) lower alkoxycarbonylamino($C_6$–$C_{10}$)aryl (e.g. methoxycarbonylaminophenyl, ethoxycarbonylaminophenyl, etc.), (S3) lower alkylaminocarbonylamino($C_6$–$C_{10}$)aryl (e.g. methylaminocarbonylaminophenyl, ethylaminocarbonylaminophenyl, etc.), (S4) lower alkoxy(lower)alkanoylamino($C_6$–$C_{10}$)aryl (e.g. ethoxyacetylaminophenyl, etc.), (S5) $C_6$–$C_{10}$ aryloxy(lower)alkanoylamino($C_6$–$C_{10}$)aryl (e.g. phenoxyacetylaminophenyl, etc.), (S6) halo($C_6$–$C_{10}$)aryl (e.g. chlorophenyl, fluorophenyl, etc.), (S7) lower alkyl($C_6$–$C_{10}$)aryl (e.g. methylphenyl, ethylphenyl, propylphenyl, isopropylphenyl, etc.), (S8) lower alkylthio($C_6$–$C_{10}$)aryl (e.g. methylthiophenyl, etc.), (S9) oxazolyl($C_6$–$C_{10}$)aryl (e.g. 2-(or 5-)oxazolylphenyl, etc.), oxadiazolyl($C_6$–$C_{10}$)aryl which is optionally substituted by lower alkyl (e.g. 1,2,4-oxadiazol-3-ylphenyl, 5-methyl-1,2,4-oxadiazol-3-ylphenyl, etc.), thiazolidinyl($C_6$–$C_{10}$)aryl which is optionally substituted by oxo (e.g. 1,1-dioxoisothiazolidin-2-ylphenyl, etc.), (S10) lower alkenyl($C_6$–$C_{10}$)aryl (e.g. vinylphenyl, etc.), (S11) amino($C_6$–$C_{10}$)aryl (e.g. aminophenyl, etc.), (S12) lower alkanoylamino($C_6$–$C_{10}$)aryl (e.g. acetylaminophenyl, etc.), (S16) $C_6$–$C_{10}$ aryl($C_6$–$C_{10}$)aryl (e.g. biphenylyl, etc.), (S19) trihalo(lower)alkyl($C_6$–$C_{10}$)aryl (e.g. trifluoromethylphenyl, etc.), (S20) cyano($C_6$–$C_{10}$)aryl (e.g. cyanophenyl, etc.), (S21) cyano(lower)alkyl($C_6$–$C_{10}$)aryl (e.g. cyanomethylphenyl, etc.), (S22) lower alkoxy(lower)alkyl($C_6$–$C_{10}$)aryl (e.g. methoxymethylphenyl, etc.), etc.

and the most preferable one may be;

phenyl, naphthyl (e.g. 2-naphthyl, etc.), methoxyphenyl (e.g. 4-methoxynaphthyl, etc.), ethoxyphenyl (e.g. 4-ethoxynaphthyl, etc.), methoxycarbonylaminophenyl (e.g. 3-methoxycarbonylaminophenyl, etc.), ethoxycarbonylaminophenyl (e.g. 4-ethoxycarbonylaminophenyl, etc.), methylaminocarbonylaminophenyl (e.g. 3-methylaminocarbonylaminophenyl, etc.), ethylaminocarbonylaminophenyl (e.g. 3-ethylaminocarbonylaminophenyl, etc.), ethoxyacetylaminophenyl (e.g. 3-ethoxyacetylaminophenyl, etc.), phenoxyacetylaminophenyl (e.g. 3-phenoxyacetylaminophenyl, etc.), chlorophenyl (e.g. 4-chlorophenyl, etc.), fluorophenyl (e.g. 4-fluorophenyl, etc.), methylphenyl (e.g. 4-methylphenyl, etc.), ethylphenyl (e.g. 4-ethylphenyl, etc.), propylphenyl (e.g. 4-propylphenyl, etc.), isopropylphenyl (e.g. 4-isopropylphenyl, etc.), methylthiophenyl (e.g. 4-methylthiophenyl, etc.), oxazolylphenyl (e.g. 2- (or 5-)oxazolylphenyl, etc.), methyoxadiazolylphenyl (e.g. 5-methyl-1,2,4-oxadiazol-3-ylphenyl, etc.), dioxoisothiazolidinylphenyl (e.g. 1,1-dioxoisothiazolidin-2-ylphenyl, etc.), vinylphenyl (e.g. 4-vinylphenyl, etc.), aminophenyl (e.g. 3-aminophenyl, etc.), acetylamoinophenyl (e.g. 3-acetylamoinophenyl, etc.), biphenylyl (e.g. 4-biphenylyl, etc.), trifluoromethylphenyl (e.g. 4-trifluoromethylphenyl, etc.), cyanophenyl (e.g. cyanophenyl, etc.), cyanomethylphenyl (e.g. 4-cyanomethylphenyl, etc.), methoxymethylphenyl (e.g. 4-methoxymethylphenyl, etc.), and the like.

Preferable examples of the optionally substituted aryloxy thus defined may be $C_6$–$C_{10}$ aryloxy (e.g. phenoxy, etc.), lower alkoxy($C_6$–$C_{10}$)aryloxy (e.g. methoxyphenoxy, etc.), lower alkyl($C_6$–$C_{10}$)aryloxy (e.g. methylphenoxy, etc.), halo ($C_6$–$C_{10}$)aryloxy (e.g. chlorophenoxy, fluorophenyl, etc.), and the most preferable one may be phenoxy, methoxyphenoxy (e.g. 4-methoxyphenoxy, etc.), methylphenoxy (e.g. methylphenoxy, etc.), chlorophenoxy (e.g. 4-chlorophenoxy, etc.), fluorophenyl (e.g. 4-fluorophenyl, etc.), and the like.

Suitable "lower alkoxy" may include a straight or branched alkyl having 1 to 6 carbon atoms, and exemplified by methoxy, ethoxy, propoxy, isopropoxy, butoxy, isobutoxy, tert-butoxy, pentyloxy, tert-pentyloxy, hexyloxy and the like, preferably methoxy.

Suitable "lower alkoxycarbonylamino" may include methoxycarbonylamino, ethoxycarbonylamino, propoxycarbonylamino, isopropoxycarbonylamino, butoxycarbonylamino, isobutoxycarbonylamino, tert-butoxycarbonylamino, pentyloxycarbonylamino, tert-pentyloxycarbonylamino, hexyloxycarbonoylamino, and the like, preferably methoxycarbonylamino and ethoxycarbonylamino.

Suitable "lower alkylaminocarbonylamino" may included methylaminocarbonylamino, ethylaminocarbonylamino, propylaminocarbonylamino, isopropylaminocarbonylamino, butylaminocarbonylamino, isobutylaminocarbonylamino, tert-butylaminocarbonylamino, pentylaminocarbonylamino, tert-pentylaminocarbonylamino, hexylaminocarbonoylamino, and the like, preferably methylaminocarbonylamino and ethylaminocarbonylamino.

Suitable "lower alkoxy(lower)alkanoylamino" methoxyacetylamino, ethoxyacetylamino, propoxyacetylamino, isopropoxyacetylamino, butoxypropanoylamino, isobutoxypropanoylamino, tert-butoxypropanoylamino, pentyloxypropanylamino, tert-pentyloxypropanylamino, hexyloxypropanylamino, and the like, preferably ethoxyacetylamino.

Suitable "aryloxy(lower)alkanoylamino" may include ($C_6$-$C_{10}$)aryloxy(lower)alkanoylamino such as phenoxyacetylamino, phenoxypropanoylamino, naphthylacetylamino, naphthyloxypropanoylamino, and the like, preferably phenoxyacetylamino.

Suitable "heterocyclic group" in the term "optionally substituted heterocyclic group" means saturated or unsaturated, monocyclic or polycyclic heterocyclic group containing at least one hetero atom such as oxygen atom, sulfur atom, nitrogen atom and the like.

Preferable heterocyclic groups are following (1) to (14):

(H1) unsaturated 3- to 8-membered, preferably 5- or 6-membered, heteromonocyclic group containing 1 to 4 nitrogen atoms
(e.g. pyrrolyl, pyrrolinyl, imidazolyl, pyrazolyl, pyridyl and its N-oxide, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), dihydrotriazinyl (e.g. 4,5-dihydro-1,2,4-triazinyl, 2,5-dihydro-1,2,4-triazinyl, etc.), and the like);

(H2) saturated 3- to 8-membered, preferably 5- or 6-membered, heteromonocyclic group containing 1 to 4 nitrogen atoms
(e.g. azetidinyl, pyrrolidinyl, imidazolidinyl, piperidinyl, piperidino, pyrazolidinyl, piperazinyl, and the like);

(H3) unsaturated 3- to 8-membered, preferably 5- or 6-membered, heteromonocyclic group containing 1 or 2 sulfur atoms
(e.g. thienyl, and the like);

(H4) unsaturated condensed (preferably bicyclic) 7- to 13-membered, preferably 9- or 10-membered, heterocyclic group containing 1 to 5 nitrogen atoms
(e.g. indolyl, isoindolyl, indolizinyl, benzimidazolyl, quinolyl, isoquinolyl, indazolyl, benzotriazolyl, tetrazolopyridyl, tetrazolopyridazinyl (e.g. tetrazolo[1,5-b]pyridazinyl, etc.), dihydrotriazolopyridazinyl, and the like);

(H5) unsaturated 3- to 8-membered, preferably 5- or 6-membered, heteromonocyclic group containing 1 or 2 oxygen atoms
(e.g. furyl, and the like);

(H6) saturated 3- to 8-membered, preferably 5- or 6-membered, heteromonocyclic group containing 1 or 2 oxygen atoms
(e.g. oxolanyl, and the like);

(H7) unsaturated 3- to 8-membered, preferably 5- or 6-membered, heteromonocyclic group containing 1 or 2 oxygen atoms and 1 to 3 nitrogen atoms
(e.g. oxazolyl, isoxazolyl, oxadiazolyl (e.g. 1,2,4-oxadiazolyl, 1,3,4-oxadiazolyl, 1,2,5-oxadiazolyl, etc.), and the like);

(H8) unsaturated condensed (preferably bicyclic) 7- to 13-membered, preferably 9- or 10-membered, heterocyclic group containing 1 or 2 oxygen atoms
(e.g. benzofuranyl, benzodihydrofuranyl, benzodioxolenyl, and the like);

(H9) unsaturated condensed (preferably bicyclic) 7- to 13-membered, preferably 9- or 10-membered, heterocyclic group containing 1 or 2 sulfur atoms
(e.g. benzothienyl, dihydrobenzothienyl, and the like);

(H10) saturated 3- to 8-membered, preferably 5- or 6-membered, heteromonocyclic group containing 1 or 2 oxygen atoms and 1 to 3 nitrogen atoms
(e.g. morpholinyl, morpholino, and the like);

(H11) unsaturated condensed (preferably bicyclic) 7- to 13-membered, preferably 9- or 10-membered, heterocyclic group containing 1 or 2 oxygen atoms and 1 to 3 nitrogen atoms
(e.g. benzoxazolyl, benzoxadiazolyl, and the like);

(H12) unsaturated 3- to 8-membered, preferably 5- or 6-membered, heteromonocyclic group containing 1 or 2 sulfur atoms and 1 to 3 nitrogen atoms
(e.g. thiazolyl, 1,2-thiazolyl, thiazolinyl, thiadiazolyl (e.g. 1,2,4-thiadiazolyl, 1,3,4-thiadiazolyl, 1,2,5-thiadiazolyl, 1,2,3-thiadiazolyl, etc.), and the like);

(H13) saturated 3- to 8-membered, preferably 5- or 6-membered, heteromonocyclic group containing 1 or 2 sulfur atoms and 1 to 3 nitrogen atoms
(e.g. thiazolidinyl, isothiazolidinyl, and the like);

(H14) unsaturated condensed (preferably bicyclic) 7- to 13-membered, preferably 9- or 10-membered, heterocyclic group containing 1 or 2 sulfur atoms and 1 to 3 nitrogen atoms
(e.g. benzothiazolyl, dihydrobenzothiazolyl, benzothiadiazolyl, and the like);
etc.

These heterocyclic groups may have one or more substituents. Examples of the substituents for substituted heterocyclic group may be the same as those for "optionally substituted aryl".

Preferable examples of heterocyclic group thus defined may be:

(H1) unsaturated 5- or 6-membered; heteromonocyclic group containing 1 to 4 nitrogen atoms (e.g. pyridyl, imidazolyl, pyrazolyl, pyrazinyl, etc.);

(H2) saturated 3- to 8-membered, preferably 5- or 6-membered, heteromonocyclic group containing 1 to 4 nitrogen atoms (e.g. pyrrolidinyl, piperidinyl, etc.);

(H3) unsaturated 5- or 6-membered, heteromonocyclic group containing 1 or 2 sulfur atoms (e.g. thienyl, and the like) which is optionally substituted by halogen (e.g. chlorothienyl, etc.);

(H4) unsaturated bicyclic 7- to 13-membered, preferably 9- or 10-membered, heterocyclic group containing 1 to 5 nitrogen atoms (e.g. quinolyl, isoquinolyl, etc.);

(H5) unsaturated 5- or 6-membered, heteromonocyclic group containing 1 or 2 oxygen atoms (e.g. furyl, and the like);

(H7) unsaturated 5- or 6-membered, heteromonocyclic group containing 1 or 2 oxygen atoms and 1 to 3 nitrogen atoms (e.g. oxazolyl, oxadiazolyl, etc.) which is optionally substituted by lower alkyl (e.g. methyloxadiazolyl, etc.);

(H8) unsaturated bicyclic 7- to 13-membered, preferably 9- or 10-membered, heterocyclic group containing 1 or 2 oxygen atoms (e.g. benzofuranyl, benzodihydrofuranyl, benzodioxolenyl, etc.) which is optionally substituted by hydroxy(lower)alkyl or lower alkylcarbamoyl (e.g. hydroxymethylbenzofuranyl, methylcarbamoylbenzofuranyl, etc.);

(H10) saturated 5- or 6-membered, heteromonocyclic group containing 1 or 2 oxygen atoms and 1 to 3 nitrogen atoms (e.g. morpholinyl, etc.);

(H13) saturated 5- or 6-membered, heteromonocyclic group containing 1 or 2 sulfur atoms and 1 to 3 nitrogen atoms (e.g. thiazolidinyl, isothiazolidinyl, etc.) which is optionally substituted by oxo (e.g. 1,1-dioxoisothiazolidinyl, etc.);

(H14) unsaturated bicyclic 7- to 13-membered, preferably 0.9- or 10-membered, heterocyclic group containing 1 or 2 sulfur atoms and 1 to 3 nitrogen atoms (e.g. benzothiazolyl, dihydrobenzothiazolyl, benzothiadiazolyl, etc.) which is optionally substituted by the group consisting of lower alkyl and oxo (e.g 3-methyl-2-oxo-2,3-dihydrobenzothiazolyl, etc.); and the like, and is optionally subthe most preferable examples may be:

(H3) thienyl (e.g. 2-thienyl, etc.), chlorothienyl (e.g. 5-chloro-2-thienyl, etc.), (H4) quinolyl (e.g. 6-quinolyl, etc.), (H5) furyl (e.g. 2-furyl, etc.), (H8) hydroxymethylbenzofuranyl (e.g. 2-hydroxymethyl-5-benzofuranyl, etc.), methylcarbamoylbenzofuranyl (e.g. 2-methylcarbamoyl-5-benzofuranyl, etc.), (H14) (methyl)(oxo)dihydrobenzothiazolyl (e.g. 3-methyl-2-oxo-2,3-dihydro-6-benzothiazolyl, etc.), and the like.

Suitable "lower alkynyl" may include a straight or branched alkynyl having 2 to 6 carbon atoms, and exemplified by ethynyl, propynyl, butynyl, penynyl, hexynyl, and the like, and the most preferably ethynyl, hexynyl, and the like, and these "lower alkynyl" is optionally substituted by aforementioned aryl (e.g. phenyl, aminosulfonylphenyl, etc.).

Preferable examples of "optionally substituted lower alkynyl" thus defined may be lower alkynyl, $C_6$–$C_{10}$ aryl (lower)alkynyl, aminosulfonyl($C_6$–$C_{10}$)aryl(lower)alkynyl, and the like, and the most preferable one may be hexynyl, phenylethynyl, aminosulfonylphenylethynyl (e.g. 4-(aminosulfonyl)phenylethynyl, etc.), and the like.

Suitable "lower alkyl" may include a straight or branched alkyl having 1 to 6 carbon atoms, and exemplified by methyl, ethyl, propyl, isopropyl, butyl, isobutyl, tert-butyl, pentyl, hexyl and the like, and the most preferably methyl, ethyl, and the like.

Suitable "lower alkylthio" may include a straight or branched alkylthio having 1 to 6 carbon atoms, and exemplified by methylthio, ethylthio, propylthio, isopropylthio, butylthio, isobutylthio, tert-butylthio, pentylthio, hexylthio and the like, and the most preferably methylthio, and the like.

Suitable "lower alkylsulfonyl" may include a straight or branched alkylsulfonyl having 1 to 6 carbon atoms, and exemplified by methylsulfonyl, ethylsulfonyl, propylsulfonyl, isopropylsulfonyl, butylsulfonyl, isobutylsulfonyl, tert-butylsulfonyl, pentylsulfonyl, hexylsulfonyl, and the like, and the most preferably methylsulfonyl, and the like.

Suitable "lower alkenyl" may include a straight or branched alkenyl having 2 to 6 carbon atoms, and exemplified by ethenyl, 1-propenyl, 2-propenyl, 1-butenyl, 2-butenyl, 1-pentenyl, 2-pentenyl and the like and the most preferably ethenyl, and the like.

Suitable "lower alkanoylamino" may include a straight or branched one having 1 to 6 carbon atoms, and exemplified by formylamino, acetylamino, propionylamino, butylylamino, isobutylylamino, valerylamino, isovalerylamino, pivaloylamino, hexanoylamino, and the like, and the most preferably acetylamino, and the like.

Suitable "lower alkylcarbamoyl(lower)alkenyl" may include a straight or branched alkenyl having 2 to 6 carbon atoms substituted by lower alkylcarbamoyl, and exemplified by methylcarbamoylvinyl, ethylcarbamoylvinyl, ethylcarbamoylpropenyl, methylcarbamoylbutenyl, methylcarbamoylpentenyl, and the like, and the most preferably methylcarbamoylvinyl, and the like.

Suitable "lower alkylcarbamoyl" may include a straight or branched alkyl having 1 to 6 carbon atoms, and exemplified by methylcarbamoyl, ethylcarbamoyl, propylcarbamoyl, isopropylcarbamoyl, butylcarbamoyl, isobutylcarbamoyl, tert-butylcarbamoyl, pentylcarbamoyl, hexylcarbamoyl, and the like, and the most preferably ethylcarbamoyl.

Suitable "mono- or di(lower)alkylaminosulfonyl" may include aminosulfonyl substituted by lower alkyl such as methylaminosulfonyl, ethylaminosulfonyl, propylaminosulfonyl, butylaminosulfonyl, pentylaminosulfonyl, hexylaminosulfonyl, dimethylaminosulfonyl, diethylaminosulfonyl, dipropylaminosulfonyl, dibutylaminosulfonyl, dipentylaminosulfonyl, dihexylaminosulfonyl, (methyl)(ethyl)aminosulfonyl, and the like, and the most preferably dimethylaminosulfonyl, and the like.

Suitable "aroyl" may include $C_6$–$C_{10}$ aroyl such as benzoyl, fluorenecarbonyl, and the like, and the most preferably benzoyl, naphthoyl, and the like.

Suitable "aryl(lower)alkanoyl" may include $C_6$–$C_{10}$ aryl (lower)alkanoyl such as benzoyl, fluorenecarbonyl, phenylacetyl, phenylpropionyl, phenylbutylyl, phenylisobutylyl, phenylvaleryl, phenylisovaleryl, phenylpivaloyl, phenylhexanoyl, and the like, preferably phenyl(lower)alkanoyl, and the most preferably benzoyl, phenylacetyl, phenylpropionyl, and the like. This "aryl (lower)alkanoyl" group is optionally substituted by a suitable substituent selected from the group as mentioned for "optionally substituted aryl".

Prferable examples of "optionally substituted aryl(lower) alkanoyl" thus defined may be benzoyl, phenylacetyl or phenylpropionyl, each of the being substituted by the group consisting of;

lower alkoxy (e.g. methoxy, ethoxy, propoxy, etc.), halogen (e.g. chloro, fluoro, etc.), lower alkyl (e.g. methyl, etc.), amino, lower alkoxycarbonylamino (e.g. t-butoxycarbonylamino, etc.), hydroxy, trihalo(lower)alkyl (e.g. trifluoromethyl, etc.), nitro, lower alkanoyl (e.g. acetyl, etc.), trihalo(lower)alkyloxy (e.g. trifluoromethoxy, etc.), and the like, and the most preferable one may be;

benzoyl, methoxybenzoyl (e.g. 2- or 3- or 4-methoxyvenzoyl, etc.), ethoxybenzoyl (e.g. 2-ethoxybenzoyl, etc.), propoxybenzoyl (e.g. 2-propoxybenzoyl, etc.), dimethoxybenzoyl (e.g. 2,3- or 2,4- or 2,5-dimethoxybenzoyl, etc.), trimethoxybenzoyl (e.g. 2,3,4-trimethoxybenzoyl, etc.), chlorobenzoyl (e.g. 2- or 3- or 4-chlorobenzoyl, etc.), dichlorobenzoyl (e.g. 2,3- or 2,4- or 2,5-dichlorobenzoyl, etc.), fluorobenzoyl (e.g. 2-fluorobenzoyl, etc.), methylbenzoyl (e.g. 2-methylbenzoyl, etc.), hydroxybenzoyl (e.g. 2-hydorxybenzoyl, etc.), trifluoromethybenzoyl (e.g. 2-trifluoromethylbenzoyl, etc.), bis(trifluoromethy)benzoyl (e.g. 2,4-bis(trifluoromethyl)benzoyl, etc.), nitrobenzoyl (e.g. 2-nitrobenzoyl, etc.), acetylbenzoyl (e.g. 2-adetylbenzoyl, etc.),
trifluoromethoxybenzoyl (e.g. 2-trifluoromethoxylbenzoyl, etc.),
(chloro)(methoxy)benzoyl (e.g. 4-chloro-2-methoxybenzoyl, etc.),
(hydroxy)(methoxy)benzoyl (e.g. 2-hydroxy-3-methoxybenzoyl, etc.),
(hydroxy)(phenyl)acetyl (e.g. 2-hydroxy-2-phenylacetyl, etc.),
(methoxy)(phenyl)acetyl (e.g. 2-methoxy-2-phenylacetyl, etc.),
(amino or t-butoxycarbonylamino)(phenyl)acetyl (e.g. 2-amino(or t-butoxycarbonylamino)-2-phneylacetyl, etc.),
phenylpropionyl (e.g. 3-phenylpropionyl, etc.),
(hydroxy)(phenyl)propionyl (e.g. 2-hydroxy-3-phenylpropionyl, etc.), and the like.

Suitable "lower cycloalkylcarbamoyl" may include $C_3$–$C_6$ cycloalkylcarbamonyl such as cyclopropylcarbamoyl, cyclobutyocarbamoyl, cyclopropylcarmamoyl, cyclobutylcarbamoyl, cyclopeantylcarbamoyl, cyclohexylcarbamoyl, and the like, and the most preferably cyclohexylcarbamoyl, and the like.

Suitable "arylcarbamoyl" may include $C_6$–$C_{10}$ arylcarbamonyl such as phenylcarbamoyl, tolylcarbamoyl, naphthylcarmamoyl, and the like, and the most preferably phenylcarbamoyl, and the like.

Suitable "lower alkanoyl" may include a straight or branched one having 1 to 6 carbon atoms, and exemplified by formyl, acetyl, propionyl, butylyl, isobutylyl, valeryl, isovaleryl, pivaloyl, hexanoyl, and the like, and the most preferably acetyl, and the like.

Suitable "trihalo(lower)alkoxy" may include trihalogenated lower alkoxy such as trifluoromethoxy, trifluoroethoxy, and the like, and the most preferably trifluoromethoxy.

Suitable "trihalo(lower)alkyl" may include trihalogenated lower alkyl such as trifluoromethyl, trifluoroethyl, and the like, and the most preferably trifluoromethyl.

Suitable "aryl(lower)alkenoyl" may include $C_6$–$C_{10}$ aryl ($C_2$–$C_6$)alkenyl such as phenylvinyl, phenylacryloyl, and the like, and the most prefabrably phenylacryloyl.

Suitable "amidated carboxy" can be referred to the ones as mentioned below.

Preferable examples of the amidated carboxy may include optionally substituted carbamoyl such as
carbamoyl,
N-hydroxycarbamoyl,
N-(protected hydroxy)carbamoyl, wherein said hydroxy-protective group may be the same as mentioned below (e.g. tetrahydropyranyl, etc.),
mono(or di)(lower)alkylcarbamoyl wherein the lower alkyl group may be the same as those mentioned above (e.g. methylcarbamoyl, ethylcarbamoyl, isopropylcarbamoyl, butylcarbamoyl, 3-methylbutylcarbamoyl, isobutylcarbamoyl, pentylcarbamoyl, dimethylcarbamoyl, diethylcarbamoyl, etc.),
N-(aryl(lower)alkyl)carbamoyl such as phenyl(lower)-alkylcarbamoyl (e.g. 1-phenylethylcarbamoyl, (R)-(+)-1-phenylethyl, etc.),
cyclo ($C_3$–$C_7$) alkylcarbamoyl (e.g. cyclohexylcarbamoyl, etc.),
carbamoyl substituted by amino or di(lower)alkylamino [e.g. N-aminocarbamoyl, N-(dimethylamino) carbamoyl, etc.],
lower alkyleneaminocarbonyl (e.g. pyrrolidin-1-ylcarbonyl, hexahydro-1H-azepin-1-ylcarbonyl, etc.), said alkylene being optionally substituted bycarboxy or protected carboxy as mentioned above such as lower alkoxycarbonyl [e.g. carboxypyrrolidin-1-ylcarbonyl, (methoxycarbonyl)pyrrolidin-1-ylcarbonyl, (ethoxycarbonyl)pyrrolidin-1-ylcarbonyl, etc.], or said lower alkylene being optionally interrupted by other hetero atom(s) such as nitrogen, oxygen or sulfur (e.g. morpholinocarbonyl, etc.),
lower alkylsulfonylcarbamoyl (e.g. methylsulfonylcarbamoyl, etc.),
arenesulfonylcarbamoyl (e.g. benzenesulfonylcarbamoyl, etc.), and the like.

More preferable example of the amidated carboxy thus defined may be:
N-hydroxycarbamoyl and N-tetrahydropyranyloxycarbamoyl.

Suitable "hydroxy-protective group" may include a conventional protective group, for example, substituted lower alkyl such as lower alkoxy(lower)alkyl (e.g. methoxymethyl), lower alkoxy(lower)alkoxy(lower)alkyl (e.g. methoxyethoxymethyl) and substituted or unsubstituted aryl(lower)alkyl (e.g. benzyl nitrobenzyl); acyl such as lower alkanoyl (e.g. acetyl, propionyl, pivaloyl), aroyl (e.g. benzoyl, fluorenecarbonyl), lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl), substituted or unsubstituted aryl(lower)alkoxycarbonyl (e.g. benzyloxycarbonyl, bromobenzyloxycarbonyl), arenesulfonyl (e.g. benzenesulfonyl, tosyl) and alkanesulfonyl (e.g. methanesulfonyl, ethanesulfonyl); tri(lower)alkylsilyl (e.g. trimethylsilyl); tetrahydropyranyl; and the like, preferably tetrahydropyranyl.

Suitable "amino-protective group" may include a conventional protective group, for example, acyl such as lower alkanoyl (e.g. acetyl, propionyl, pivaloyl), aroyl (e.g. benzoyl, fluorenecarbonyl), lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl), aryl(lower)alkoxycarbonyl such as phenyl(or fluorenyl)(lower)alkoxycarbonyl (e.g. benzyloxycarbonyl, phenethyloxycarbonyl, fluorenylmethoxyczrbonyl, etc.), substituted aryl(lower)alkoxycarbonyl (e.g. benzyloxycarbonyl, bromobenzyloxycarbonyl), arenesulfonyl (e.g. benzenesulfonyl, tosyl) and alkanesulfonyl (e.g. methanesulfonyl, ethanesulfonyl); tri(lower)alkylsilyl (e.g. trimethylsilyl); tetrahydropyranyl; and the like, preferably fluorenylmethoxycarbonyl.

Suitable "hydroxycarbamoyl-protective group" may include a conventional protective group, for example, substituted lower alkyl such as lower alkoxy(lower)alkyl (e.g. methoxymethyl), lower alkoxy(lower)alkoxy(lower)alkyl (e.g. methoxyethoxymethyl) and substituted or unsubstituted aryl(lower)alkyl (e.g. benzyl nitrobenzyl); acyl such as lower alkanoyl (e.g. acetyl, propionyl, pivaloyl), aroyl (e.g. benzoyl, fluorenecarbonyl), lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl), substituted or unsubstituted aryl(lower)alkoxycarbonyl (e.g. benzyloxycarbonyl, bromobenzyloxycarbonyl), arenesulfonyl (e.g. benzenesulfonyl, tosyl) and alkanesulfonyl (e.g. methanesulfonyl, ethanesulfonyl); tri(lower)alkylsilyl (e.g. trimethylsilyl); tetrahydropyranyl; and the like, preferably tetrahydropyranyl.

Suitable "arylcarbamoyl" may include $C_6$–$C_{10}$ arylcarbamoyl, such as phenylcarbamoyl, tolylcarbamoyl, xylylcarbamoyl, cumenylcarbamoyl, mesitylcarbamoyl, naphthylcarbamoyl, and the like, preferably phenylcarbamoyl, and the like.

Suitable "arylsulfonyl" may include $C_6$–$C_{10}$ arylsulfonyl, such as phenylsulfonyl, tolylsulfonyl, xylylsulfonyl, cumenylsulfonyl, mesitylsulfonyl, naphthylsulfonyl, and the like, preferably phenylsulfonyl, and the like.

Suitable "aryl(lower)alkylsulfonyl" may include $C_6$–$C_{10}$ aryl(lower)alkylsulfonyl, such as benzylsulfonyl, tolylethylsulfonyl, xylylmethylsulfonyl, cumenylpropylsulfonyl, mesitylbutylsulfonyl, naphthylmethylsulfonyl, and the like, preferably benzylsulfonyl, and the like.

Suitable "amino(lower)alkanoyl" may include a straight or branched one having 1 to 6 carbon atoms, and exemplified by aminoformyl, aminoacetyl, aminopropionyl, aminobutylyl, aminoisobutylyl, aminovaleryl, aminoisdvaleryl, aminopivaloyl, aminohexanoyl, and the like, and the most preferably aminoacetyl, and the like.

Suitable "arylaroyl" may include $C_6$–$C_{10}$ aroyl substituted by $C_6$–$C_{10}$ aryl lsuch as phenylbenzoyl, phenylfluorenecarbonyl, and the like, and the most preferably phenylbenzoyl, and the like.

Suitable "acyl" and acyl moiety includes acyl such as aliphatic acyl, aromatic acyl, heterocyclic acyl and aliphatic acyl substituted by aromatic or heterocyclic group(s) derived from carboxylic, carbonic, sulfonic and carbamic acids.

The aliphatic acyl may include saturated or unsaturated, acyclic or cyclic ones, for example, alkanoyl such as lower alkanoyl (e.g. formyl, acetyl, propionyl, butylyl, isobutylyl, valeryl, isovaleryl, pivaloyl, 3-methylbutyryl, hexanoyl, 3,3-dimethylbutylyl, 3-ethylbutyry, etc.), alkylsulfonyl such as lower alkylsulfonyl (e.g. mesyl, ethylsulfonyl, propylsulfonyl, isopropylsulfonyl, butylsulfonyl, isobutylsulfonyl, pentylsulfonyl, hexylsulfonyl, etc.), mono- or di(lower)alkylaminosulfonyl (e.g. dimethylaminosulfonyl, diethylaminosulfonyl, etc.), carbamoyl, mono- or di(lower)alkylcarbamoyl (e.g. methylcarbamoyl, dimethylcarbamoyl, ethylcarbamoyl, propylcarbamoyl, isopropylcarbamoyl, t-butylcarbamoyl, etc.), $C_6$–$C_{10}$ arylcarbamoyl (e.g. phenylcarbamoyl, etc.), $C_6$–$C_{10}$ ar(lower)alkylcarbamoyl (e.g. benzylcarbamoyl, etc.), alkoxycarbonyl such as lower alkoxycarbonyl (e.g. methoxycarbonyl, ethoxycarbonyl, propoxycarbonyl, butoxycarbonyl, isobutoxycarbonyl, tert-butoxycarbonyl, etc.), alkenyloxycarbonyl such as lower alkenyloxycarbonyl (e.g. vinyloxycarbonyl, allyloxycarbonyl, etc.), alkenoyl such as lower alkenoyl (e.g. acryloyl, methacryloyl, crotonoyl, 3-methylcrotonoyl, etc.), lower cycloalkanecarbonyl such as lower cycloalkanecarbonyl (e.g. cyclopropanecarbonyl, cyclobutanecarbonyl, cyclopentanecarbonyl, cyclohexanecarbonyl, etc.), lower cycloalkylcarbamoyl (e.g. cyclopropylcarbamoyl, cyclopentylcarbamoyl, cyclohexylcarbamoyl, etc.), lower cycloalkenecarbonyl such as lower cycloalkenecarbonyl (e.g. cyclobutenecarbonyl, cyclopentenecarbonyl, cyclohexenecarbonyl, etc.), aryloxycarbonyl (e.g. phenoxycarbonyl, and the like.

The aromatic acyl may include $C_6$–$C_{10}$ aroyl (e.g. benzoyl, toluoyl, xyloyl, naphthoyl, etc.) optionally substituted by the group consisting of halo (e.g. chloro, fluoro, etc.), lower alkyl (e.g. methyl, etc.), lower alkanoyl (e.g. acetyl, etc.) hydroxy, lower alkoxy (e.g. methoxy, ethoxy, propoxy, etc.) nitro, trihalo(lower)alkoxy (e.g. trifluoromethoxy, etc.), $C_6$–$C_{10}$ aryl (e.g. phenyl, etc.), $C_6$–$C_{10}$ aryloxy (e.g. phenoxy, etc.) and trihalo(lower)alkyl (e.g. trifluoromethyl, etc.), N-($C_6$–$C_{10}$)arylcarbamoyl (e.g. N-phenylcarbamoyl, N-tolylcarbamoyl, N-naphthylcarbamoyl, etc.), $C_6$–$C_{10}$ arenesulfonyl (e.g. benzenesulfonyl, tosyl, etc.) which is optionally substituted by lower alkoxy (e.g. methoxy, etc.), $C_6$–$C_{10}$ aryl($C_6$–$C_{10}$) aroyl (e.g. phenylbenzoyl, etc.), and the like.

The heterocyclic acyl may include heterocyclic-carbonyl, heterocyclic-carbamoyl, heterocyclic-sulfonyl, etc, wherein the heterocyclic group being selected from the above-mentioed groups (H1) to (H14), preferably (H1) unsaturated 3- to 8-membered, preferably 5- or 6-membered, heteromonocyclic group containing 1 to 4 nitrogen atoms (e.g. pyridyl, imidazolyl, pyrazolyl, pyrimidinyl, pyrazinyl, etc.) which is optionally substituted by lower alkyl (e.g. methyl, etc.), (H2) saturated 3- to 8-membered, preferably 5- or 6-membered, heteromonocyclic group containing 1 to 4 nitrogen atoms (e.g. pyrrolidinyl, piperidinyl, etc.) whicn is optionally substituted by lower alkanoyl (e.g. acetyl, etc.), lower alkoxy (e.g. methoxy, etc.);

(H3) unsaturated 3- to 8-membered, preferably 5- or 6-membered, heteromonocyclic group containing 1 or 2-sulfur atoms (e.g. thienyl, etc.), (H4) unsaturated condensed (preferably bicyclic) 7- to 13-membered, preferably 9- or 10-membered; heterocyclic group containing 1 to 5 nitrogen atoms (e.g. indolyl, quinolyl, etc.), (H5) unsaturated 3- to 8-membered, preferably 5- or 6-membered, heteromonocyclic group containing 1 or 2 oxygen atoms (e.g. furyl, etc.), (H7) unsaturated 3- to 8-membered, preferably 5- or 6-membered, heteromonocyclic group containing 1 or 2 oxygen atoms and 1 to 3 nitrogen atoms, (H9) unsaturated condensed (preferably bicyclic) 7- to 13-membered, preferably 9- or 10-membered, heterocyclic group containing 1 or 2 sulfur atoms (e.g. benzothienyl, etc.);

(H10) saturated 3- to 8-membered, preferably 5- or 6-membered, heteromonocyclic group containing 1 or 2 oxygen atoms and 1 to 3 nitrogen atoms (e.g. morpholinyl, etc.), (H12) unsaturated 3- to 8-membered, preferably 5- or 6-membered, heteromonocyclic group containing 1 or 2 sulfur atoms and 1 to 3 nitrogen atoms,
(e.g. pyridylcarbonyl (e.g 2- or 3-4-pyridylcarbonyl, etc.), lower alkylpyridylcarbonyl (e.g. 3-methyl-2-pyridylcarbonyl, etc.), pyridylsulfonyl (e.g. 3-pyridylsulfonyl, etc.), imidazolylcarbonyl optionally substituted by lower alkyl (e.g. 1-methyl-2-imidzolylcarbonyl, etc.), pyrazolylcarbonyl (e.g. 4-pyrazolylcarbonyl, etc.), pyrimidinylcarbonyl optionally substituted by lower alkyl (e.g. 4-methyl-5-pyrimidinyl, etc.), furylcarbonyl (e.g. 2-furylcarbonyl, etc.), thienylcarbonyl (e.g. 2- or 3-thenoyl, etc.), thienylsulfonyl (e.g. 2-thienylsulfonyl, etc.) indolylcarbonyl (e.g. 2-indolylcarbonyl, etc.), pyrazinylcarbonyl (e.g. 2-pyrazinylcarbonyl, etc.), quinolinecarbonyl (e.g. 3- or 8-quinolinecarbonyl, etc.), isoquinolylcarbonyl (e.g. 1-sioquinolinecarbonyl, etc.), pyrrolidinecarbonyl (e.g. 1-pyrrolidinecarbonyl, etc.), pyrrolidinesulfonyl (e.g.

1-pyrrolidinesulfonyl, etc.), piperidinecarbonyl (e.g. 1- or 4-piperidinecarbonyl) which is optionally substituted by lower alkanoyl (e.g. 1-acetyl-4-piperidinecarbonyl, etc.), piperidinesulfonyl (e.g. 1-piperidinesulfonyl, etc.) which is optionally substituted by lower alkoxy (e.g. 4-methoxy-1-piperidinesulfonyl, etc.), morpholinylcarbonyl (e.g. 4-morpholinylcarbonyl, etc.), morpholinylsulfonyl (e.g. 4-morpholinesulfonyl, etc.), benzofuranylcarbonyl (e.g. 2-benzofuranylcarbonyl, etc.), and the like.

The aliphatic acyl substituted by aromatic group(s) may include $C_6$–$C_{10}$ aralkanoyl such as phenyl(lower)alkanoyl (e.g. phenylacetyl, phenylpropionyl, phenylhexanoyl, etc.), $C_6$–$C_{10}$ aralkoxycarbonyl such as phenyl(or fluorenyl)(lower)alkoxycarbonyl (e.g. benzyloxycarbonyl, phenethyloxycarbonyl, fluorenylmethoxycarbonyl, etc.), $C_6$–$C_{10}$ aryloxyalkanoyl such as phenoxy(lower)alkanoyl (e.g. phenoxyacetyl, phenoxypropionyl, etc.), $C_6$–$C_{10}$ aryl(lower)alkylsulfonyl (e.g. benzylsulfonyl, etc.), $C_6$–$C_{10}$ aryl(lower)alkylcarabamoyl (e.g. phenylethylcarbamoyl, etc.), $C_6$–$C_{10}$ aryl(lower)cycloalkylcarbonyl (e.g. phenylcycloporopylcarbonyl, etc.), $C_6$–$C_{10}$ aryl(lower)alkenoyl (e.g. phenylacryloyl, etc.), and the like.

The aliphatic acyl substituted by heterocyclic group(s) may include heterocyclic(lower)alkanoyl (e.g. thienylacetyl, imidazolylacetyl, furylacetyl, tetrazolylacetyl, thiazolylacetyl, thiadiazolylacetyl, thienylpropionyl, thiadiazolylpropionyl, etc.), heterocyclic(lower)alkenoyl (e.g. pyridylacryloyl, etc.), heterocycliccarbamoyl optionally substituted by lower alkyl (e.g. methylisoxazolylcarbamoyl, etc.), heterocyclic(lower)alkylcarbamoyl (e.g. thienylethylcarbamoyl, etc.), and the like.

These acyl groups may be further substituted by one or more suitable substituents as those for "optionally substituted aryl".

Preferable examples of the acyl thus defined may be:

(A1) lower alkylsufonyl (e.g. methylsulfonyl, ethylsulfonyl, propylsulfonyl, etc.) optionally substituted by $C_6$–$C_{10}$ aryl (e.g. benzylsulfonyl, etc.), (A2) lower alkoxycarbonyl (e.g. methoxycarbonyl, ethoxycarbonyl, isobutoxycarbonyl, t-butoxycarbonyl, etc.) optionally substituted by lower alkoxy (e.g. methoxyethoxycarbonyl, etc.), (A3) $C_6$–$C_{10}$ ar(lower)alkoxycarbonyl (e.g. benzyloxycarbonyl, etc), (A4) 9-fluorenylmethoxycarbonyl, (A5) mono- or di(lower)alkylaminosulfonyl (e.g. ethylaminosulfonyl, dimethylaminosulfonyl, diethylaminosulfonyl, N-methyl-N-ethylaminosulfonyl, etc.) optionally substituted by lower alkoxy (e.g. N-(methoxyethyl)aminosulfonyl, N-methyl-N-(methoxyethyl)aminosulfonyl, etc.), (A6) mono- or di(lower)alkylcarbamoyl (e.g. methylcarbamoyl, ethylcarbamoyl, propylcarbamoyl, isopropylcarbamoyl, t-butylcarbamoyl, dimethylcarbamoyl, etc.) optionally substituted by $C_6$–$C_{10}$ aryl or thienyl (e.g. benzylcarbamoyl, 1-phenyletylcarbamoyl, 2-thienylethylcarbamoyl, etc.), (A7) $C_6$–$C_{10}$ aroyl (e.g. benzoyl, naphthoyl, etc.) optionally substituted by (S1) lower alkoxy (e.g. methoxy, ethoxy, propoxy, etc.), (S6) halo (e.g. chloro, fluoro, etc.), (S7) lower alkyl (e.g. methyl, ethyl, propyl, isopropyl t-butyl, etc.), (S13) hydroxy, (S15) $C_6$–$C_{10}$ aryloxy (e.g. phenoxy, etc.), (S16) $C_6$–$C_{10}$ aryl (e.g. phenyl, etc.) optionally substituted by halogen (e.g. chlorophenyl, etc.), (S19) trihalo(lower)alkyl (e.g. trifluoromethyl, etc.), (S26) nitro, (S27) lower alkanoyl (e.g. acetyl, etc.), (S28) trihalo(lower)alkyloxy (e.g. trifluoromethyloxy, etc.), and the like;

(preferable examples may be benzoyl, naphthoyl, benzoyl substituted by lower alkoxy (e.g. 2- or 3- or 4-methoxybenzoyl, 2-ethoxybenzoyl, 2-propoxybenzoyl, 2,3- or 2,4- or 2,5-methoxybenzoyl, 2,3,4-trimethoxybenzoyl, etc.), benzoyl substituted by halogen (e.g. 2- or 0.3- or 4-chlorobenzoyl, 2,3- or 2,4- or 2,5-dichlorobenzoyl, 2-fluorobenzoyl, etc.), benzoyl substituted by lower alkyl (e.g. 2-methylbenzoyl, etc.), benzoyl substituted by hydroxy (e.g. 2-hydroxybenzoyl, etc.), benzoyl substituted by phenoxy (e.g. 2-phenoxybenzoyl, etc.), benzoyl substituted by phenyl (e.g. 2-phenylbenzoyl, etc.), benzoyl substituted by trihalo(lower)alkyl (e.g. 2-trifluoromethylbenzoyl, 2,4-bis(trifluoromethyl) benzoyl, etc.), benzoyl substituted by nitro (e.g. 2-nitrobenzoyl, etc.), benzoyl substituted by lower alkanoyl (e.g. 2-acetylbenzoyl, etc.), benzoyl substituted by trihalo(lower)alkyloxy (e.g. 2-trifluoromethyloxybenzoyl, etc.), benzoyl substituted by the group consisting of lower alkoxy and halogen (e.g. 2-methoxy-4-chlorobenzoyl, etc.), benzoyl substituted by the group consisting of lower alkoxy and hydroxy (e.g. 3-methoxy-2-hydroxybenzoyl, etc.), (A8) heterocyclic acyl, wherein the heterocyclic group being substituted by lower alkyl, lower alkanoyl, or lowr alkoxy, and also being selected from;

(H1) unsaturated 3- to 8-membered, preferably 5- or 6-membered, heteromonocyclic group containing 1 to 4 nitrogen atoms (e.g. imidazolyl, pyrazolyl, pyridyl and its N-oxide, pyrimidyl, pyrazinyl, etc.);

(H2) saturated 3- to 8-membered, preferably 5- or 6-membered, heteromonocyclic group containing 1 to 4 nitrogen atoms (e.g. pyrrolidinyl, piperidinyl, piperidino, etc.); (H3) unsaturated 3- to 8-membered, preferably 5- or 6-membered, heteromonocyclic group containing 1 or 2 sulfur atoms (e.g. thienyl, etc.); (H4) unsaturated condensed (preferably bicyclic) 7- to 13-membered, preferably 9- or 10-membered, heterocyclic group containing 1 to 5 nitrogen atoms (e.g. indolyl, quinolyl, isoquinolyl, etc.);

(H5) unsaturated 3- to 8-membered, preferably 5- or 6-membered, heteromonocyclic group containing 1 or 2 oxygen atoms (e.g. furyl, etc.);

(H9) unsaturated condensed (preferably bicyclic) 7- to 13-membered, preferably 9- or 10-membered, heterocyclic group containing 1 or 2 sulfur atoms (e.g. benzothienyl, etc.); and (H10) saturated 3- to 8-membered, preferably 5- or 6-membered, heteromonocyclic group containing 1 or 2 oxygen atoms and 1 to 3 nitrogen atoms (e.g. morpholinyl, morpholino, etc.);

these heterocyclic group optionally being substituted by (S1) lower alkoxy (e.g. methoxy, etc.), (S7) lower alkyl (e.g. methyl, etc.), (S27) lower alkanoyl (e.g. acetyl, etc.), (preferable examples of heterocyclic acyl may be imidazolylcarbonyl (e.g. 2-imidazolylcarbonyl, etc.) optionally substituted by lower alkyl (e.g. 1-methyl-2-imidazolylcarbonyl, etc.), pyrazolylcarbonyl (e.g. 4-pyrazolylcarbonyl, etc.), pyridylcarbonyl (e.g. 2- or 3- or 4-pyridylcarbonyl, etc.) optionally substituted by lower alkyl (e.g. 3-methyl-2-pyridylcarbonyl, etc.), pyridylsulfonyl (e.g. 3-pyridylsulfonyl, etc.), pyrimidinylcarbonyl (e.g. 5-pyrimidinylcarbonyl, etc.) optionally substituted by lower alkyl (e.g. 4-methyl-5-pyrimidinylcarbonyl, etc.), pyrazinylcarbonyl (e.g. 2-pyrazinylcarbonyl, etc.), pyrrolidinylcarbonyl (e.g. 1-pyrrolidinylcarbonyl, etc.), pyrrolidinylsulfonyl (e.g. 1-pyrrolidinylsulfonyl, etc.), piperidinylcarbonyl (e.g. 1- or 4-piperidinylcarbonyl, etc.) optionally substituted by lower alkanoyl (e.g. 1-acetyl-4-piperidinylcarbonyl, etc.), piperidinylsulfonyl (e.g. 1-piperidinylsulfonyl, etc.) optionally substituted by lower alkoxy (e.g. 4-methoxy-1-piperidinylsulfonyl, etc.), thienylcarbonyl (e.g. 2- or 3-thienylcarbonyl, etc.), thienylsulfonyl (e.g. 2-thienylsulfonyl, etc.), indolylcarbonyl (e.g. 2-indolylcarbonyl, etc.), quinolylcarbonyl (e.g. 3- or 8-quinolylcarbonyl, etc.), isoquinolylcarbonyl (e.g. 1-isoquinolylcarbonyl, etc.), furylcarbonyl (e.g. 2-furylcarbonyl, etc.), benzothienylcarbonyl (e.g. 2-benzothienylcarbonyl, etc.), morpholinylcarbonyl (e.g. 4-morpholinylcarbonyl, etc.), morpholinylsulfonyl (e.g. 4-morpholinylsulfonyl, etc.), etc.), (A9) lower cycloalkylcarbamoyl (e.g. cyclopropylcarbamoyl, cyclohexylcarbamoyl, etc.), (A10) $C_6$–$C_{10}$ arylcarbamoyl (e.g. phenylcarbamoyl, etc.), wherein the aryl group is optionally substituted by the group consisting of halogen, lower alkyl and lower alkoxy (e.g. mono- or dicholophenylcarbamoyl, methylphenylcarbamoyl, methoxyphenylcarbamoyl, etc.), (A11) $C_6$–$C_{10}$ arylsulfonyl (e.g. phenylsulfonyl, etc.) optionally substituted by lower alkoxy (e.g. methoxyphenylsulfonyl, etc.), (A12) heterocycliccarbamoyl, wherein the heterocyclic group is (H7) unsaturated 3- to 8-membered, preferably 5- or 6-membered, heteromonocyclic group containing 1 or 2 oxygen atoms and 1 to 3 nitrogen atoms (e.g. isoxazolyl, etc.) optionally substituted by lower alkyl (e.g 5-methylisoxazolyl, etc.), (A13) lower cycloalkylcarbonyl (e.g. cyclopropylcarbonyl, cyclobutylcarbonyl, cyclopentylcarbonyl, cyclohexylcarbonyl, etc.) optionally substituted by phenyl (e.g. 1-phenyl-1-cyclopropylcarbonyl, etc.), (A14) lower alkenoyl (e.g. 3-methylcrotonoyl, etc.) optionally substituted by $C_6$–$C_{10}$ aryl (e.g. phenylacryloyl, etc.), (A15) heterocyclic(lower)alkenoyl wherein the heterocyclic group is unsaturated 3- to 8-membered, preferably 5- or 6-membered, heteromonocyclic group containing 1 to 4 nitrogen atoms (e.g. pyridylacryloyl, etc.)

(A16) lower alkanoyl (e.g. acetyl, propionyl, isobutyryl, isovaleryl, pivaloyl, hexanoyl, 3,3-dimethylbutyryl, 2-ethylbutyryl, etc.) optionally substituted by the group consisting of $C_6$–$C_{10}$ aryl, hydroxy, lower cycloalkyl, amino, lower alkoxycarbonylamino, lower alkoxy, lower alkoxy(lower)alkoxy, phenoxy, or heterocyclic group consisting of unsaturated 3- to 8-membered, preferably 5- or 6-membered, heteromonocyclic group containing 1 or 2 oxygen atoms and unsaturated 3- to 8-membered, preferably 5- or 6-membered, heteromonocyclic group containing 1 to 4 nitrogen atoms (e.g. phenylacetyl, phenylpropionyl, 2-amino-2-phenylacetyl, 2-t-butoxycarbonylamino-2-phenylacetyl, 2-hydroxy-2-phenylacetyl, 2-methoxy-2-pheylacetyl, 2-hydroxy-3-phenylpropionyl, cyclopropylacetyl, cyclopentylacetyl, aminoacetyl, t-butoxycarbonylaminoacetyl, 3-aminopropionyl, 3-t-butoxycarbonylaminopropionyl, 2-aminoisovaleryl, 2-t-butoxycarbonylaminoisovarelyl, 2-aminopivaloyl, 2-t-butoxycarbonylaminopivaloyl, methoxyacetyl, (2-methoxyethoxy)acetyl, phenoxyacetyl, 2-pyridylacetyl, 3-thienylacetyl, etc.), (A17) $C_6$–$C_{10}$ aryloxycarbonyl (e.g. phenoxycarbonyl, etc.), (A18) lower cycloalkenecarbonyl (e.g. cyclohexenecarbonyl, etc.), and the like, more preferable one may be (A1) lower alkylsufonyl (e.g. methylsulfonyl, ethylsulfonyl, propylsulfonyl, etc.) optionally substituted by $C_6$–$C_{10}$ aryl (e.g. benzylsulfonyl, etc.), (A2) lower alkoxycarbonyl (e.g. methoxycarbonyl, ethoxycarbonyl, isobutoxycarbonyl, t-butoxycarbonyl, etc.) optionally substituted by lower alkoxy (e.g. methoxyethoxycarbonyl, etc.), (A3) $C_6$–$C_{10}$ ar(lower)alkoxycarbonyl (e.g. benzyloxycarbonyl, etc), (A4) 9-fluorenylmethoxycarbonyl, (A5) mono- or di(lower)alkylaminosulfonyl (e.g. ethylaminosulfonyl, dimethylaminosulfonyl, diethylaminosulfonyl, N-methyl-N-ethylaminosulfonyl, etc.) optionally substituted by lower alkoxy (e.g. N-(methoxyethyl)aminosulfonyl, N-methyl-N-(methoxyethyl)aminosulfonyl, etc.), (A6) mono- or di(lower)alkylcarbamoyl (e.g. methylcarbamoyl, ethylcarbamoyl, propylcarbamoyl, isopropylcarbamoyl, t-butylcarbamoyl, dimethylcarbamoyl, etc.) optionally substituted by $C_6$–$C_{10}$ aryl or thienyl (e.g. benzylcarbamoyl, 1-phenyletylcarbamoyl, 2-thienylethylcarbamoyl, etc.), (A7) $C_6$–$C_{10}$ arylcarbonyl, $C_6$–$C_{10}$ arylcarbonyl substituted by lower alkoxy (e.g. 2- or 3- or 4-methoxybenzoyl, 2-ethoxybenzoyl, 2-propoxybenzoyl, 2,3- or 2,4- or 2,5-methoxybenzoyl, 2,3,4-trimethoxybenzoyl, etc.), $C_6$–$C_{10}$ arylcarbonyl substituted by halogen (e.g. 2- or 3- or 4-chlorobenzoyl, 2,3- or 2,4- or 2,5-dichlorobenzoyl, 2-fluorobenzoyl, etc.), $C_6$–$C_{10}$ arylcarbonyl substituted by lower alkyl (e.g. 2-methylbenzoyl, etc.), $C_6$–$C_{10}$ arylcarbonyl substituted by hydroxy (2-hydroxybenzoyl, etc.), $C_6$–$C_{10}$ arylcarbonyl substituted by $C_6$–$C_{10}$ aryloxy (e.g. 2-phenoxybenzoyl, etc.), $C_6$–$C_{10}$ arylcarbonyl substituted by $C_6$–$C_{10}$ aryl (e.g. 2-phenylbenzoyl, etc.), $C_6$–$C_{10}$ arylcarbonyl substituted by trihalo(lower)alkyl (e.g. 2-trifluoromethylbenzoyl, 2,4-bis(trifluoromethyl)benzoyl, etc.), $C_6$–$C_{10}$ arylcarbonyl substituted by nitro (e.g. 2-nitorobenzoyl, etc.), $C_6$–$C_{10}$ arylcarbonyl substituted by lower alkanoyl (e.g. 2-acetylbenzoyl, etc.), $C_6$–$C_{10}$ arylcarbonyl substituted by trihalo(lower)alkyloxy (e.g. 2-trifluoromethyloxybenzoyl, etc.), $C_6$–$C_{10}$ arylcarbonyl substituted by the group consisting of lower alkoxy and halogen (e.g. 2-methoxy-4-chlorobenzoyl, etc.), $C_6$–$C_{10}$ arylcarbonyl substituted by the group consisting of lower alkoxy and hydroxy (e.g. 3-methoxy-2-hydroxybenzoyl, etc.), (A8) imidazolylcarbonyl (e.g. 2-imidazolylcarbonyl, etc.) optionally substituted by lower alkyl (e.g. 1-methyl-2-imidazolylcarbonyl, etc.), pyrazolylcarbonyl (e.g. 4-pyrazolylcarbonyl, etc.), pyridylcarbonyl (e.g. 2- or 3- or 4-pyridylcarbonyl, etc.) optionally substituted by lower alkyl (e.g. 3-methyl-2-pyridylcarbonyl, etc.), pyridylsulfonyl (e.g. 3-pyridylsulfonyl, etc.), pyrimidinylcarbonyl (e.g. 5-pyrimidinylcarbonyl, etc.) optionally substituted by lower alkyl (e.g. 4-methyl-5-pyrimidinylcarbonyl, etc.), pyrazinylcarbonyl (e.g. 2-pyrazinylcarbonyl, etc.), pyrrolidinylcarbonyl (e.g. 1-pyrrolidinylcarbonyl, etc.), pyrrolidinylsulfonyl (e.g. 1-pyrrolidinylsulfonyl, etc.), piperidinylcarbonyl (e.g. 1- or 4-piperidinylcarbonyl, etc.) optionally substituted by lower alkanoyl (e.g. 1-acetyl-4-piperidinylcarbonyl, etc.), piperidinylsulfonyl (e.g. 1-piperidinylsulfonyl, etc.) optionally substituted by lower alkoxy (e.g. 4-methoxy-1-piperidinylsulfonyl, etc.), thienylcarbonoyl (e.g. 2- or 3-thienylcarbonyl, etc.), thienylsulfonyl (e.g. 2-thienylsulfonyl, etc.), indolylcarbonyl (e.g. 2-indolylcarbonyl, etc.), quinolylcarbonyl (e.g. 3- or 8-quinolylcarbonyl, etc.), isoquinolylcarbonyl (e.g. 1-isoquinolylcarbonyl, etc.), furylcarbonyl (e.g. 2-furylcarbonyl, etc.), benzothienylcarbonyl (e.g. 2-benzothienylcarbonyl, etc.), morpholinylcarbonyl (e.g. 4-morpholinylcarbonyl, etc.), morpholinylsulfonyl (e.g. 4-morpholinylsulfonyl, etc.), etc.), (A9) lower cycloalkylcarbamoyl (e.g. cyclopropylcarbamoyl, cyclohexylcarbamoyl, etc.), (A10) $C_6$–$C_{10}$ arylcarbamoyl, halo$C_6$–$C_{10}$ arylcarbamoyl, lower alkyl$C_6$–$C_{10}$ arylcarbamoyl, lower alkoxy$C_6$–$C_{10}$ arylcarbamoyl, (e.g. phenylcarbamoyl, etc.), wherein the aryl group is optionally substituted by the group consisting of halogen, lower alkyl and lower alkoxy (e.g. mono- or dicholophenylcarbamoyl, methylphenylcarbamoyl, methoxyphenylcarbamoyl, etc.), (A11) $C_6$–$C_{10}$ arylsulfonyl (e.g. phenylsulfonyl, etc.) optionally substituted by lower alkoxy (e.g. methoxyphenylsulfonyl, etc.), (A12) isoxazolylcarbamoyl, methylisoxazolylcarbamoyl, (A13) lower cycloalkylcarbonyl (e.g. cyclopropylcarbonyl, cyclobutylcarbonyl, cyclopentylcarbonyl, cyclohexylcarbonyl, etc.) optionally substituted by $C_6$–$C_{10}$ aryl (e.g. 1-phenyl-1-cyclopropylcarbonyl, etc.), (A14) lower alkenoyl (e.g. 3-methylcrotonoyl, etc.) optionally substituted by $C_6$–$C_{10}$ aryl (e.g. phenylacryloyl, etc.), (A15) pyridyl(lower)alkenoyl (e.g. pyridylacryloyl, etc.)

(A16) lower alkanoyl (e.g. acetyl, propionyl, isobutyryl, isovaleryl, pivaloyl, hexanoyl, 3,3-dimethylbutyryl, 2-ethylbutyryl, etc.), $C_6$–$C_{10}$ aryl(lower)alkanoyl, hydroxy(lower)alkanoyl, lower cycloalkyl(lower)alkanoyl, amino(lower)alkanoyl, lower alkoxycarbonylamino(lower)alkanoyl, lower alkoxy(lower)alkanoyl, lower alkoxy(lower)alkoxy(lower)alkanoyl, $C_6$–$C_{10}$ aryloxy(lower)alkanoyl, pyridyl(lower)alkanoyl, thienyl(lower)alkanoyl, (e.g. phenylacetyl, phenylpropionyl, 2-amino-2-phenylacetyl, 2-t-butoxycarbonylamino-2-phenylacetyl, 2-hydroxy-2-phenylacetyl, 2-methoxy-2-pheylacetyl, 2-hydroxy-3-phenylpropionyl, cyclopropylacetyl, cyclopentylacetyl, aminoacetyl, t-butoxycarbonylaminoacetyl, 3-aminopropionyl, 3-t-butoxycarbonylaminopropionyl, 2-aminoisovaleryl, 2-t-butoxycarbonylaminoisovarelyl, 2-aminopivaloyl, 2-t-butoxycarbonylaminopivaloyl, methoxyacetyl, (2-methoxyethoxy)acetyl, phenoxyacetyl, 2-pyridylacetyl, 3-thienylacetyl, etc.), (A17) $C_6$–$C_{10}$ aryloxycarbonyl (e.g. phenoxycarbonyl, etc.), (A18) lower cycloalkenecarbonyl (e.g. cyclohexenecarbonyl, etc.), and the like, and the most preferable one may be (A1) methylsulfonyl, ethylsulfonyl, propylsulfonyl, benzylsulfonyl, (A2) methoxycarbonyl, ethoxycarbonyl, isobutoxycarbonyl, t-butoxycarbonyl, 2-methoxyethoxycarbonyl, (A3) benzyloxycarbonyl, (A4) 9-fluorenylmethoxycarbonyl, (A5) dimethylaminosulfonyl, diethylaminosulfonyl, N-(2-methoxyethyl)aminosulfonyl, N-methyl-N-(2-methoxyethyl)aminosulfonyl, (A6) ethylcarbamoyl, propylcarbamoyl, isopropylcarbamoyl, t-butylcarbamoyl, dimethylcarbamoyl, benzylcarbamoyl, 1-phenyletylcarbamoyl, 2-(2-thienyl) ethylcarbamoyl, (A7) benzoyl, naphthoyl, 2- or 3- or 4-methoxybenzoyl, 2-ethoxybenzoyl, 2-propoxybenzoyl, 2,3- or 2,4- or 2,5-methoxybenzoyl, 2,3,4-trimethoxybenzoyl, 2- or 3- or 4-chlorobenzoyl, 2,3- or 2,4- or 2,5-dichlorobenzoyl, 2-fluorobenzoyl, 2-methylbenzoyl, 2-hydroxybenzoyl, 2-phenoxybenzoyl, 2-phenylbenzoyl, 2-trifluoromethylbenzoyl, 2,4-bis(trifluoromethyl)benzoyl, 2-nitrobenzoyl, 2-acetylbenzoyl, 2-trifluoromethyloxybenzoyl, 2-methoxy-4-chlorobenzoyl, 3-methoxy-2-hydroxybenzoyl, (A8) 1-methyl-2-imidazolylcarbonyl, 4-pyrazolylcarbonyl, 2- or 3- or 4-pyridylcarbonyl, 3-methyl-2-pyridylcarbonyl, 3-pyridylsulfonyl, 4-methyl-5-pyrimidinylcarbonyl, 2-pyrazinylcarbonyl, 1-pyrrolidinylcarbonyl, 1-pyrrolidinylsulfonyl, 1- or 4-piperidinylcarbonyl, 1-acetyl-4-piperidinylcarbonyl, 1-piperidinylsulfonyl, 4-methoxy-1-piperidinylsulfonyl, 2- or 3-thienylcarbonyl, 2-thienylsulfonyl, 2-indolylcarbonyl, 3- or 8-quinolylcarbonyl, 1-isoquinolylcarbonyl, 2-furylcarbonyl, 2-benzothienylcarbonyl, 4-morpholinylcarbonyl, 4-morpholinylsulfonyl, (A9) cyclopropylcarbamoyl, cyclohexylcarbamoyl, (A10) phenylcarbamoyl, 2- or 3- or 4-cholophenylcarbamoyl, 2,3- or 2,5-dichlorophenylcarbamoyl, 2-methylphenylcarbamoyl, 2-methoxypheriylcarbamoyl, (A11) phenylsulfonyl, 4-methoxyphenylsulfonyl, (A12) 5-methylisoxazolylcarbamoyl, (A13) cyclopropylcarbonyl, cyclobutylcarbonyl, cyclopentylcarbonyl, cyclohexylcarbonyl, 1-phenyl-1-cyclopropylcarbonyl, (A14) 3-methylcrotonoyl, 3-phenylacryloyl, (A15) 3-(4-pyridyl)acryloyl, (A16) acetyl, propionyl, isobutyryl, isovaleryl, pivaloyl, hexanoyl, 3,3-dimethylbutyryl, 2-ethylbutyryl, 3-phenylpropionyl, 2-amino-2-phenylacetyl, 2-t-butoxycarbonylamino-2-phenylacetyl, 2-hydroxy-2-phenylacetyl, 2-methoxy-2-pheylacetyl, 2-hydroxy-3-phenylpropionyl, cyclopropylacetyl, cyclopentylacetyl, aminoacetyl, t-butoxycarbonylaminoacetyl, 3-aminopropionyl, 3-t-butoxycarbonylaminopropionyl, 2-aminoisovaleryl, 2-t-butoxycarbonylaminoisovarelyl, 2-aminopivaloyl, 2-t-butoxycarbonylaminopivaloyl, methoxyacetyl, (2-methoxyethoxy)acetyl, phenoxyacetyl, 2-pyridylacetyl, 3-thienylacetyl, (A17) phenoxycarbonyl, (A18) cyclohexenecarbonyl, and the like.

Suitable "lower alkylene" may include straight or branched one such as methylene, ethylene, trimethylene, propylene, tetramethylene, ethylethylene, pentamethylene, hexamethylene, and the like, preferably ethylene, trimethylene, and the like.

Preferable examples of the formula:

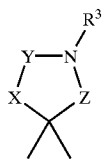

is one of the following formulae:

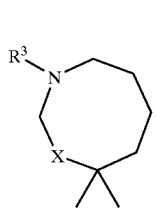 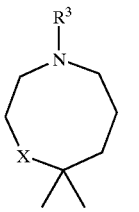 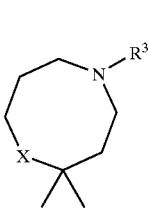

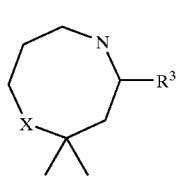 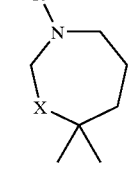 

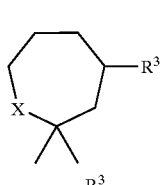 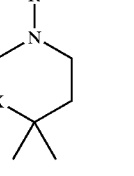 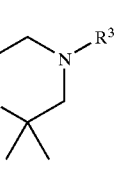

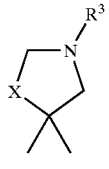

and the like, preferably

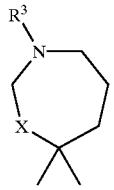 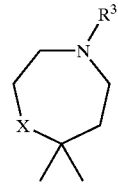 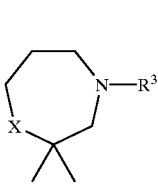

and the like, and the most preferably

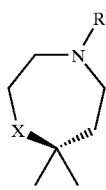

and the like, wherein X is thia, sulfinyl or sulfonyl, preferably sulfonyl, and
R$^3$ is hydrogen or acyl.

The preferred object compounds (I) are:

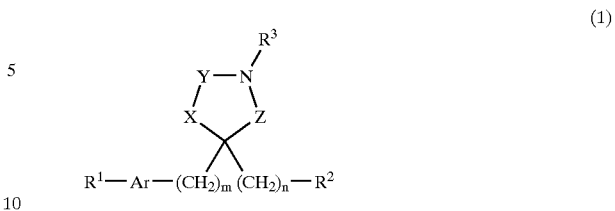

(1)

in which

R$^1$ is halo; C$_6$–C$_{10}$ aryl optionally substituted by the group consisting of lower alkoxy, lower alkoxycarbonylamino, lower alkylaminocarbonylamino, lower alkoxy(lower)alkanoylamino and C$_6$–C$_{10}$ aryloxy(lower)-alkanoylamino; or heterecyclic group optionally substituted by the group consisting of lower alkoxy, lower alkoxycarbonylamino, lower alkylaminocarbonylamino, lower alkoxy(lower)alkanoylamino and C$_6$–C$_{10}$ aryloxy (lower)-alkanoylamino, said heterocyclic group being unsaturated 3- to 8-membered, heteromonocyclic group containing 1 or 2 oxygen atoms;
R$^2$ is hydroxycarbamoyl or protected hydroxycarbamoyl,
R$^3$ is hydrogen, lower alkylsufonyl or lower alkoxycarbonyl,
Ar is phenyl or unsaturated 3- to 8-membered, heteromonocyclic group containing 1 or 2 sulfur atoms,
X is sulfonyl,
Y and Z are each C$_1$–C$_3$ alkylene,
m is an integer of 0, and
n is an integer of 1,
or pharmaceutically acceptable salts thereof,
and more preferred object compounds (I) are:

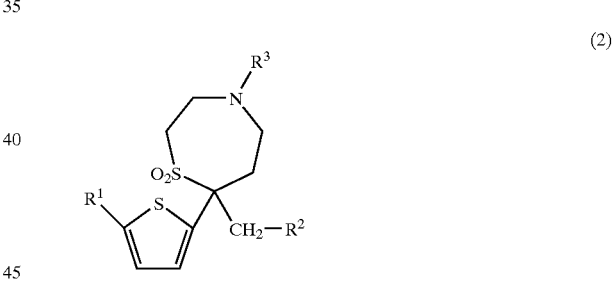

(2)

in which
R$^1$ is halo; phenyl optionally substituted by the group consisting of lower alkoxy, lower alkoxycarbonylamino, lower alkylaminocarbonylamino, lower alkoxy(lower) alkanoylamino and phenoxy(lower)-alkanoylamino; or furyl;
R$^2$ is hydroxycarbamoyl or protected hydroxycarbamoyl,
R$^3$ is hydrogen, lower alkylsufonyl or lower alkoxycarbonyl,
or pharmaceutically acceptable salts thereof.

Another preferred object compounds (I) are:

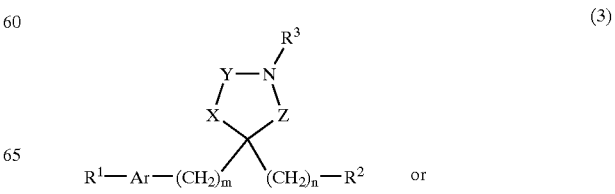

(3)

or

-continued

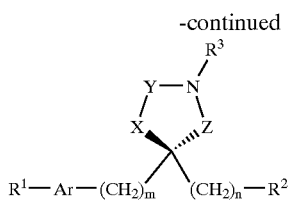

in which

R¹ is halo;
  lower alkoxy;
  aryl optionally substituted by the group consisting of lower alkoxy, lower alkoxycarbonylamino, lower alkylaminocarbonylamino, lower alkoxy(lower)alkanoylamino, $C_6$–$C_{10}$ aryloxy(lower)alkanoylamino, halo, lower alkyl, lower alkylthio, heterocyclic group, said heterocyclic group being unsaturated 3- to 8-membered heteromonocyclic group containing 1 or 2 oxygen atoms and 1 to 3 nitrogen atoms, or saturated 3- to 8-membered heteromonocyclic group containing 1 or 2 sulfur atoms and 1 to 3 nitrogen atoms which is optionally substituted by oxo, lower alkenyl, amino, lower alkanoylamino, hydroxy, lower alkylsulfonyl, $C_6$–$C_{10}$ aryloxy, $C_6$–$C_{10}$ aryl, lower alkylcarbamoyl (lower)alkenyl and lower alkylcarbamoyl; aryloxy optionally substituted by the group consisting of lower alkoxy, lower alkoxycarbonylamino, lower alkylaminocarbonylamino, lower alkoxy(lower) alkanoylamino, $C_6$–$C_{10}$ aryloxy(lower)alkanoylamino, halo, lower alkyl, lower alkylthio, heterocyclic group, said heterocyclic group being unsaturated 3- to 8-membered heteromonocyclic group containing 1 or 2 oxygen atoms and 1 to 3 nitrogen atoms, or saturated 3- to 8-membered heteromonocyclic group containing 1 or 2 sulfur atoms and 1 to 3 nitrogen atoms which is optionally substituted by oxo, lower alkenyl, amino, lower alkanoylamino, hydroxy, lower alkylsulfonyl, $C_6$–$C_{10}$ aryloxy, $C_6$–$C_{10}$ aryl, lower alkylcarbamoyl (lower)alkenyl and lower alkylcarbamoyl; or
  herecyclic group optionally substituted by the group consisting of lower alkoxy, lower alkoxycarbonylamino, lower alkylaminocarbonylamino, lower alkoxy(lower) alkanoylamino, $C_6$–$C_{10}$ aryloxy(lower)alkanoylamino, halo, lower alkyl, lower alkylthio, heterocyclic group, said heterocyclic group being unsaturated 3- to 8-membered heteromonocyclic group containing 1 or 2 oxygen atoms and 1 to 3 nitrogen atoms, or saturated 3- to 8-membered heteromonocyclic group containing 1 or 2 sulfur atoms and 1 to 3 nitrogen atoms which is optionally substituted by oxo, lower alkenyl, amino, lower alkanoylamino, hydroxy, lower alkylsulfonyl, $C_6$–$C_{10}$ aryloxy, $C_6$–$C_{10}$ aryl, lower alkylcarbamoyl (lower)alkenyl and lower alkylcarbamoyl;
R² is hydroxycarbamoyl or protected hydroxycarbamoyl,
R³ is hydrogen, lower alkylsufonyl, lower alkoxycarbonyl, $C_6$–$C_{10}$ ar(lower)alkoxycarbonyl, 9-fluorenylmethoxycarbonyl, mono- or di(lower) alkylaminosulfonyl, lower alkylcarbamoyl, $C_6$–$C_{10}$ aroyl, heterocyclic acyl, wherein the heterocyclic group being substituted by lower alkyl or oxo, and also being selected from unsaturated 3- to 8-membered heteromonocyclic group containing 1 to 4 nitrogen atoms, unsaturated 3- to 8-membered heteromonocyclic group containing 1 or 2 sulfur atoms, unsaturated bicyclic 7- to 13-membered heterocyclic group containing 1 to 5 nitrogen atoms, and saturated 3- to 8-membered heteromonocyclic group containing 1 or 2 oxygen atoms and 1 to 3 nitrogen atoms, lower cycloalkylcarbamoyl, $C_6$–$C_{10}$ ar(lower)alkylcarbamoyl, $C_6$–$C_{10}$ arylcarbamoyl, wherein the aryl group is optionally substituted by the group consisting of halogen, lower alkyl and lower alkoxy, $C_6$–$C_{10}$ arylsulfonyl optionally substituted by lower alkoxy, $C_6$–$C_{10}$ aryl(lower)alkylsulfonyl, amino(lower)alkanoyl, $C_6$–$C_{10}$ aroyl substituted by lower alkanoyl, $C_6$–$C_{10}$ aryl($C_6$–$C_{10}$) aroyl, $C_6$–$C_{10}$ aryl(lower)alkanoyl optionally substituted by amino, $C_6$–$C_{10}$ aryl(lower)alkanoyl substituted by lower alkoxy, heterocyclic(lower)alkylcarbamoyl, wherein the heterocyclic group is unsaturated 3- to 8-membered heteromonocyclic group containing 1 or 2 sulfur atoms, $C_6$–$C_{10}$ aroyl substituted by trihalo(lower)alkoxy, $C_6$–$C_{10}$ aroyl substituted by halogen, $C_6$–$C_{10}$ aroyl substituted by halogen and trihalo(lower)alkyl, $C_6$–$C_{10}$ aroyl substituted by lower alkyl, $C_6$–$C_{10}$ aroyl substituted by halogen and lower alkoxy, $C_6$–$C_{10}$ aryl(lower)cycloalkylcarbonyl, $C_6$–$C_{10}$ aryl(lower)alkenoyl, $C_6$–$C_{10}$ aroyl substituted by hydroxy and lower alkoxy,
Ar is phenyl or unsaturated 3- to 8-membered, heteromonocyclic group containing 1 or 2 sulfur atoms,
X is sulfonyl,
Y and Z are each $C_1$–$C_3$ alkylene,
m is an integer of 0, and
n is an integer of 1, or pharmacyeutically acceptable salts thereof; or (4) the compounds (I) of the above (3):

wherein
R¹ is halo; lower alkoxy; $C_6$–$C_1$ aryl optionally substituted by the group consisting of lower alkoxy, lower alkoxycarbonylamino, lower alkylaminocarbonylamino, lower alkoxy(lower)alkanoylamino, $C_6$–$C_{10}$ aryloxy (lower)alkanoylamino, halo, lower alkyl, lower alkylthio, heterecyclic group, lower alkenyl, amino, lower alkanoylamino; $C_6$–$C_{10}$ aryloxy optionally substituted by the group consisting of lower alkoxy, lower alkoxycarbonylamino, lower alkylaminocarbonylamino, lower alkoxy(lower)alkanoylamino, $C_6$–$C_{10}$ aryloxy (lower)-alkanoylamino, halo, lower alkyl, lower alkylthio, heterecyclic group, lower alkenyl, amino, lower alkanoylamino,; or heterecyclic group optionally substituted by the group consisting of lower alkoxy, lower alkoxycarbonylamino, lower alkylaminocarbonylamino, lower alkoxy(lower)alkanoylamino, $C_6$–$C_{10}$ aryloxy (lower)alkanoylamino, halo, lower alkyl, lower alkylthio, heterecyclic group, lower alkenyl, amino, lower alkanoylamino, said heterocyclic group being unsaturated 3- to 8-membered, heteromonocyclic group containing 1 or 2 oxygen atoms;
R³ is hydrogen, lower alkylsufonyl, lower alkoxycarbonyl, $C_6$–$C_{10}$ ar(lower)alkoxycarbonyl, 9-fluorenylmethoxycarbonyl, mono- or di(lower) alkylaminosulfonyl, N-(lower)alkylcarbamoyl, $C_6$–$C_{10}$ aroyl, heterocyclic acyl, and
Ar is phenyl or thienyl, or pharmaceutically acceptable salts thereof; or (5) the compounds (I) of the above (4) having the following formula:

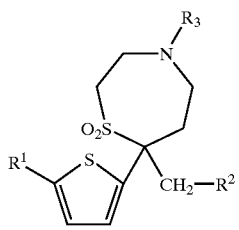 or 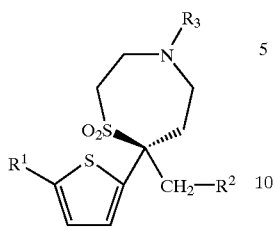

in which
R¹ is halo; lower alkoxy, $C_6$–$C_{10}$ aryl optionally substituted by the group consisting of lower alkoxy, lower alkoxycarbonylamino, lower alkylaminocarbonylamino, lower alkoxy(lower)alkanoylamino, $C_6$–$C_{10}$ aryloxy(lower)alkanoylamino, halo, lower alkyl, lower alkylthio, oxazolyl, lower alkenyl, amino and lower alkanoylamino; or furyl;

R² is hydroxycarbamoyl or protected hydroxycarbamoyl,

R³ is hydrogen, lower alkylsufonyl, lower alkoxycarbonyl, $C_6$–$C_{10}$ ar(lower)alkoxycarbonyl, 9-fluorenylmethoxycarbonyl, mono- or di(lower)alkylaminosulfonyl, N-(lower)alkylcarbamoyl, $C_6$–$C_{10}$ aroyl, pyridylcarbonyl, pyrazinylcarbonyl, or thienylcarbonyl, or pharmaceutically acceptable salts thereof; or (6) the compounds (I) of the above (4) having the following formula:

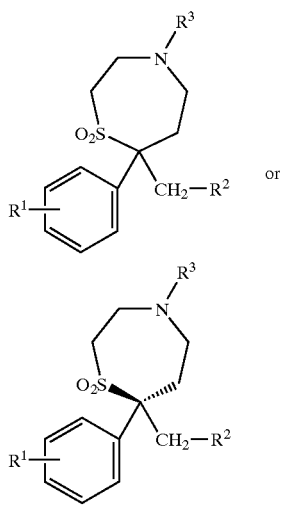 or

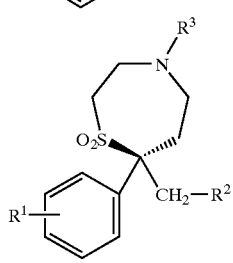

in which
R¹ is lower alkoxy; $C_6$–$C_{10}$ aryloxy optionally substituted by the group consisting of lower alkoxy, lower alkoxycarbonylamino, lower alkylaminocarbonylamino, lower alkoxy(lower)alkanoylamino, $C_6$–$C_{10}$ aryloxy(lower)alkanoylamino, halo, lower alkyl, lower alkylthio, oxazolyl, lower alkenyl, amino and lower alkanoylamino; (preferably lower alkoxy or $C_6$–$C_{10}$ aryloxy), R² is hydroxycarbamoyl or protected hydroxycarbamoyl, R³ is hydrogen, lower alkylsufonyl, lower alkoxycarbonyl, $C_6$–$C_{10}$ ar(lower)alkoxycarbonyl, 9-fluorenylmethoxycarbonyl, mono- or di(lower)alkylaminosulfonyl, N-(lower)alkylcarbamoyl, $C_6$–$C_{10}$ aroyl, pyridylcarbonyl, pyrazinylcarbonyl, or thienylcarbonyl; (preferably $C_6$–$C_{10}$ ar(lower)alkoxycarbonyl, 9-fluorenylmethoxycarbonyl, N-(lower)alkylcarbamoyl, $C_6$–$C_{10}$ aroyl or pyridylcarbonyl)

or pharmaceutically acceptable salts thereof;
and the like.

The more preferred object compounds (I) are selected from the following ones.

[1] A compound of the formula:

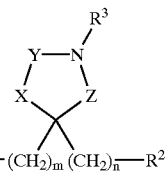

in which R¹ is halo, lower alkoxy, optionally substituted aryl, optionally substituted aryloxy, optionally substituted heterecyclic group or optionally substituted lower alkynyl, R² is amidated carboxy selected from N-hydroxycarbamoyl and N-(protected hydroxy)carbarnoyl, R³ is hydrogen or acyl, Ar is aryl or heterocyclic group, X is thia, sulfinyl or sulfonyl, Y and Z are each lower alkylene, m and n are each an integer of 0 to 2, and a salt thereof,
wherein the above-mentioned optional substituents for aryl, aryloxy, heterocyclic group and lower alkynyl in R¹ are each selected from the group consisting of:

(S1) lower alkoxy (e.g. methoxy, ethoxy, propoxy, etc.), (S2) lower alkoxycarbonylamino (e.g. methoxycarbonylamino, ethoxycarbonylamino, t-butoxycarbonylamino, etc.), (S3) lower alkylaminocarbonylamino (e.g. methylaminocarbonylamino, ethylaminocarbonylamino, etc.), (S4) lower alkoxy(lower)alkanoylamino (e.g. ethoxyacetylamino, etc.), (S5) aryloxy(lower)alkanoylamino (e.g. phenoxyacetylamino, etc.), (S6) halo (e.g. chloro, fluoro, etc.), (S7) lower alkyl (e.g. methyl, ethyl, propyl, isopropyl, t-butyl, etc.), (S8) lower alkylthio (e.g. methylthio, etc.), (S9) heterocyclic group selected from:
unsaturated 3- to 8-membered heteromonocyclic group containing 1 or 2 oxygen atoms and 1 to 3 nitrogen atoms, which is optionally substituted by lower alkyl (e.g. oxazolyl, oxadiazolyl, methyloxadiazolyl, etc.), and saturated 3- to 8-membered heteromonocyclic group containing 1 or 2 sulfur atoms and 1 to 3 nitrogen atoms, which is optionally substituted by oxo (e.g. thiazolidinyl, isothiazolidinyl, 1,1-dioxoisothiazolidinyl, etc.), (S10) lower alkenyl (e.g. vinyl, etc.), (S11) amino (e.g. amino, etc.), (S12) lower alkanoylamino (e.g. acetylamino, etc.), (S13) hydroxy (e.g. hydroxy, etc.), (S14) lower alkylsulfonyl (e.g. methylsulfonyl, etc.), (S15) aryloxy (e.g. phenoxy, etc.), (S16) aryl optionally substituted by halogen (e.g. phenyl, chlorophenyl, etc.), (S17) lower alkylcarbamoyl(lower)alkenyl (e.g. methylcarbamoylvinyl, etc.),
(S18) lower alkylcarbamoyl (e.g. methylcarbamoyl, ethylcarbamoyl, etc.),
(S19) trihalo(lower)alkyl (e.g. trifluoromethyl, etc.),
(S20) cyano (e.g. cyano, etc.),
(S21) cyano(lower)alkyl (e.g. cyanomethyl, etc.),
(S22) lower alkoxy(lower)alkyl (e.g. methoxymethyl, etc.),
(S23) hydroxy(lower)alkyl (e.g. hydroxymethyl, etc.),
(S24) oxo (e.g. oxo, etc.),
(S25) aminosulfonyl (e.g. aminosulfonyl, etc.),
(S26) nitro (e.g. nitro, etc.),
(S27) lower alkanoyl (e.g. acetyl, propionyl, isobutyryl, isovaleryl, pivaloyl, hexanoyl, 3,3,-dimethylbutyryl, 2-ethylbutyryl, etc.),
(S28) trihalo(lower)alkyloxy (e.g. trifluoromethyloxy, etc.),
(S29) lower alkoxycarbonyl (e.g. t-butoxycarbonyl, etc.),
(S30) lower cycloalkyl (e.g. cyclopropyl, cyclohexyl, etc.),
(S31) lower alkoxy(lower)alkoxy (e.g. methoxyethoxy, etc.), and
(S32) fluoernyl (e.g. 9-fluorenyl, etc.);
and above-mentioned heterocyclic groups for $R^1$ are each selected from:
(H1) unsaturated 3- to 8-membered, heteromonocyclic group containing 1 to 4 nitrogen atoms,
  (e.g. pyrrolyl, pyrrolinyl, imidazolyl, pyrazolyl, pyridyl and its N-oxide, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), dihydrotriazinyl (e.g. 4,5-dihydro-1,2,4-triazinyl, 2,5-dihydro-1,2,4-triazinyl, etc.);
(H2) saturated 3- to 8-membered, heteromonocyclic group containing 1 to 4 nitrogen atoms,
  (e.g. azetidinyl, pyrrolidinyl, imidazolidinyl, piperidinyl, piperidino, pyrazolidinyl, piperazinyl, etc.);
(H3) unsaturated 3- to 8-membered, heteromonocyclic group containing 1 or 2 sulfur atoms,
  (e.g. thienyl, etc.);
(H4) unsaturated condensed 7- to 13-membered, heterocyclic group containing 1 to 5 nitrogen atoms,
  (e.g. indolyl, isoindolyl, indolizinyl, benzimidazolyl, quinolyl, isoquinolyl, indazolyl, benzotriazolyl, tetrazolopyridyl, tetrazolopyridazinyl (e.g. tetrazolo-[1,5-b]pyridazinyl, etc.), dihydrotriazolopyridazinyl, etc.);
(H5) unsaturated 3- to 8-membered, heteromonocyclic group containing 1 or 2 oxygen atoms,
  (e.g. furyl, etc.);
(H6) saturated 3- to 8-membered, heteromonocyclic group containing 1 or 2 oxygen atoms,
  (e.g. oxolanyl, etc.);
(H7) unsaturated 3- to 8-membered, heteromonocyclic group containing 1 or 2 oxygen atoms and 1 to 3 nitrogen atoms,
  (e.g. oxazolyl, isoxazolyl, oxadiazolyl (e.g. 1,2,4-oxadiazolyl, 1,3,4-oxadiazolyl, 1,2,5-oxadiazolyl, etc.);
(H8) unsaturated condensed 7- to 13-membered, heterocyclic group containing 1 or 2 oxygen atoms,
  (e.g. benzofuranyl, benzodihydrofuranyl, benzodioxolenyl, etc.);
(H9) unsaturated condensed 7- to 13-membered, heterocyclic group containing 1 or 2 sulfur atoms,
  (e.g. benzothienyl, dihydrobenzothienyl, etc.);
(H10) saturated 3- to 8-membered, heteromonocyclic group containing 1 or 2 oxygen atoms and 1 to 3 nitrogen atoms,
  (e.g. morpholinyl, morpholino, etc.);
(H11) unsaturated condensed 7- to 13-membered, heterocyclic group containing 1 or 2 oxygen atoms and 1 to 3 nitrogen atoms,
  (e.g. benzoxazolyl, benzoxadiazolyl, etc.);
(H12) unsaturated 3- to 8-membered, heteromonocyclic group containing 1 or 2 sulfur atoms and 1 to 3 nitrogen atoms,
  (e.g. thiazolyl, 1,2-thiazolyl, thiazolinyl, thiadiazolyl (e.g. 1,2,4-thiadiazolyl, 1,3,4-thiadiazolyl, 1,2,5-thiadiazolyl, 1,2,3-thiadiazolyl, etc.);
(H13) saturated 3- to 8-membered, heteromonocyclic group containing 1 or 2 sulfur atoms and 1 to 3 nitrogen atoms, and
  (e.g. thiazolidinyl, isothiazolidinyl, etc.);
(H14) unsaturated condensed 7- to 13-membered, heterocyclic group containing 1 or 2 sulfur atoms and 1 to 3 nitrogen atoms,
  (e.g. benzothiazolyl, dihydrobenzothiazolyl, benzothiadiazolyl, etc.);
and above-mentioned acyl for $R^3$ is each selected from
(A1) lower alkylsufonyl optionally substituted by aryl (e.g. methylsulfonyl, ethylsulfonyl, propylsulfonyl, benzylsulfonyl, etc.),
(A2) lower alkoxycarbonyl optionally substituted by lower alkoxy (e.g. methoxycarbonyl, ethoxycarbonyl, isobutoxycarbonyl, t-butoxycarbonyl, methoxyethoxycarbonyl, etc.),
(A3) ar(lower)alkoxycarbonyl (e.g. benzyloxycarbonyl, etc),
(A4) fluorenylmethoxycarbonyl (e.g. 9-fluorenylmethoxycarbonyl, etc.),
(A5) mono- or di(lower)alkylaminosulfonyl optionally substituted by lower alkoxy (e.g. ethylaminosulfonyl, dimethylaminosulfonyl, diethylaminosulfonyl, N-methyl-N-ethylaminosulfonyl, N-(methoxyethyl)aminosulfonyl, N-methyl-N-(methoxyethyl)aminosulfonyl, etc.),
(A6) mono- or di(lower)alkylcarbamoyl optionally substituted by aryl or unsaturated 3- to 8-membered, heteromonocyclic group containing 1 or 2 sulfur atoms (e.g. methylcarbamoyl, ethylcarbamoyl, propylcarbamoyl, isopropylcarbamoyl, t-butylcarbamoyl, dimethylcarbamoyl, benzylcarbamoyl, 1-phenyletylcarbamoyl, 2-thienylethylcarbamoyl, etc.),
(A7) aroyl (e.g. benzoyl, naphthoyl, etc.) optionally substituted by the group consisting of:
  (S1) lower alkoxy (e.g. methoxy, ethoxy, propoxy, etc.),
  (S6) halo (e.g. chloro, fluoro, etc.),
  (S7) lower alkyl (e.g. methyl, ethyl, propyl, isopropyl, t-butyl, etc.),
  (S13) hydroxy (e.g. hydroxy, etc.),
  (S15) aryloxy (e.g. phenoxy, etc.),
  (S16) aryl optionally substituted by halogen (e.g. phenyl, chlorophenyl, etc.), (S19) trihalo(lower)alkyl (e.g. trifluoromethyl, etc.),
(S26) nitro (e.g nitro, etc.),
(S27) lower alkanoyl (e.g. acetyl, etc.), and
(S28) trihalo(lower)alkyloxy (e.g. trifluoromethyloxy, etc.);
(preferable examples of (A7) may be benzoyl, naphthoyl, benzoyl substituted by lower alkoxy (e.g. 2- or 3- or 4-methoxybenzoyl, 2-ethoxybenzoyl, 2-propoxybenzoyl, 2,3- or 2,4- or 2,5-methoxybenzoyl, 2,3,4-trimethoxybenzoyl, etc.), benzoyl substituted by halogen (e.g. 2- or 3- or 4-chlorobenzoyl, 2,3- or 2,4- or 2,5-dichlorobenzoyl, 2-fluorobenzoyl, etc.), benzoyl substituted by lower alkyl (e.g. 2-methylbenzoyl, etc.), benzoyl substituted by hydroxy (e.g. 2-hydroxybenzoyl, etc.), benzoyl substituted by phenoxy (e.g. 2-phenoxybenzoyl, etc.), benzoyl substituted by aryl (e.g. 2-phenylbenzoyl, etc.), benzoyl substituted by trihalo(lower)alkyl (e.g. 2-trifluoromethylbenzoyl, 2,4-bis(trifluoromethyl)benzoyl, etc.), benzoyl substituted by nitro (e.g. 2-nitrobenzoyl, etc.), benzoyl substituted by lower alkanoyl (e.g. 2-acetylbenzoyl, etc.), benzoyl substituted by trihalo(lower)alkyloxy (e.g. 2-trifluoromethyloxybenzoyl, etc.), benzoyl substituted by the group consisting of lower alkoxy and halogen (e.g. 2-methoxy-4-chlorobenzoyl, etc.), benzoyl substituted by the group consisting of lower alkoxy and hydroxy (e.g. 3-methoxy-2-hydroxybenzoyl, etc.), (A8) heterocyclic-carbonyl or heterocyclic-sulfonyl, wherein the heterocyclic group being selected from:
(H1) unsaturated 3- to 8-membered, heteromonocyclic group containing 1 to 4 nitrogen atoms (e.g. imidazolyl, pyrazolyl, pyridyl and its N-oxide, pyrimidyl, pyrazinyl, etc.);
(H2) saturated 3- to 8-membered, heteromonocyclic group containing 1 to 4 nitrogen atoms (e.g. pyrrolidinyl, piperidinyl, piperidino, etc.);
(H3) unsaturated 3- to 8-membered, heteromonocyclic group containing 1 or 2 sulfur atoms (e.g. thienyl, etc.);
(H4) unsaturated condensed 7- to 13-membered, heterocyclic group containing 1 to 5 nitrogen atoms (e.g. indolyl, quinolyl, isoquinolyl, etc.);
(H5) unsaturated 3- to 8-membered, heteromonocyclic group containing 1 or 2 oxygen atoms (e.g. furyl, etc.);
(H9) unsaturated condensed 7- to 13-membered, heterocyclic group containing 1 or 2 sulfur atoms (e.g. benzothienyl, etc.); and
(H10) saturated 3- to 8-membered, heteromonocyclic group containing 1 or 2 oxygen atoms and 1 to 3 nitrogen atoms (e.g. morpholinyl, morpholino, etc.);
these heterocyclic group being optionally substituted by the group consisting of:
(S1) lower alkoxy (e.g. methoxy, etc.),
(S7) lower alkyl (e.g. methyl, etc.), and
(S27) lower alkanoyl (e.g. acetyl, etc.),
(preferable examples of heterocyclic-carbonyl or heterocyclic-sulfonyl may be imidazolylcarbonyl (e.g. 2-imidazolylcarbonyl, etc.) optionally substituted by lower alkyl (e.g. 1-methyl-2-imidazolylcarbonyl, etc.), pyrazolylcarbonyl (e.g. 4-pyrazolylcarbonyl, etc.), pyridylcarbonyl (e.g. 2- or 3- or 4-pyridylcarbonyl, etc.) optionally substituted by lower alkyl (e.g. 3-methyl-2-pyridylcarbonyl, etc.), pyridylsulfonyl (e.g. 3-pyridylsulfonyl, etc.), pyrimidinylcarbonyl (e.g. 5-pyrimidinylcarbonyl, etc.) optionally substituted by lower alkyl (e.g. 4-methyl-5-pyrimidinylcarbonyl, etc.), pyrazinylcarbonyl (e.g. 2-pyrazinylcarbonyl, etc.), pyrrolidinylcarbonyl (e.g. 1-pyrrolidinylcarbonyl, etc.), pyrrolidinylsulfonyl (e.g. 1-pyrrolidinylsulfonyl, etc.), piperidinylcarbonyl (e.g. 1- or 4-piperidinylcarbonyl, etc.) optionally substituted by lower alkanoyl (e.g. 1-acetyl-4-piperidinylcarbonyl, etc.), piperidinylsulfonyl (e.g. 1-piperidinylsulfonyl, etc.) optionally substituted by lower alkoxy (e.g. 4-methoxy-1-piperidinylsulfonyl, etc.), thienylcarbonoyl (e.g. 2- or 3-thienylcarbonyl, etc.), thienylsulfonyl (e.g. 2-thienylsulfonyl, etc.), indolylcarbonyl (e.g. 2-indolylcarbonyl, etc.), quinolylcarbonyl (e.g. 3- or 8-quinolylcarbonyl, etc.), isoquinolylcarbonyl (e.g. 1-isoquinolylcarbonyl, etc.), furylcarbonyl (e.g. 2-furylcarbonyl, etc.), benzothienylcarbonyl (e.g. 2-benzothienylcarbonyl, etc.), morpholinylcarbonyl (e.g. 4-morpholinylcarbonyl, etc.), morpholinylsulfonyl (e.g. 4-morpholinylsulfonyl, etc.), etc.), (A9) lower cycloalkylcarbamoyl (e.g. cyclopropylcarbamoyl, cyclohexylcarbamoyl, etc.),
(A10) arylcarbamoyl, wherein the aryl group is optionally substituted by the group consisting of halogen, lower alkyl and lower alkoxy (e.g. phenylcarbamoyl, mono- or dicholophenylcarbamoyl, methylphenylcarbamoyl, methoxyphenylcarbamoyl, etc.),
(A11) $C_6$–$C_{10}$ arylsulfonyl optionally substituted by lower alkoxy (e.g. phenylsulfonyl, methoxyphenylsulfonyl, etc.),
(A12) heterocycliccarbamoyl, wherein the heterocyclic group is (H7) unsaturated 3- to 8-membered, heteromonocyclic group containing 1 or 2 oxygen atoms and 1 to 3 nitrogen atoms, optionally substituted by lower alkyl (e.g. isoxazolyl, 5-methylisoxazolyl, etc.),
(A13) lower cycloalkylcarbonyl optionally substituted by aryl (e.g. cyclopropylcarbonyl, cyclobutylcarbonyl, cyclopentylcarbonyl, cyclohexylcarbonyl, 1-phenyl-1-cyclopropylcarbonyl, etc.),
(A14) lower alkenoyl optionally substituted by aryl (e.g. 3-methylcrotonoyl, phenylacryloyl, etc.),
(A15) heterocyclic(lower)alkenoyl, wherein the heterocyclic group is unsaturated 3- to 8-membered, heteromonocyclic group containing 1 to 4 nitrogen atoms (e.g. pyridylacryloyl, etc.),
(A16) lower alkanoyl optionally substituted by the group consisting of aryl, hydroxy, lower cycloalkyl, amino, lower alkoxycarbonylamino, lower alkoxy, lower alkoxy(lower)alkoxy, aryloxy, and heterocyclic group consisting of unsaturated 3- to 8-membered, heteromonocyclic group containing 1 or 2 sulfur atoms and unsaturated 3- to 8-membered, heteromonocyclic group containing 1 to 4 nitrogen atoms (e.g. acetyl, propionyl, isobutyryl, isovaleryl, pivaloyl, hexanoyl, 3,3-dimethylbutyryl, 2-ethylbutyryl, phenylacetyl, phenylpropionyl, 2-amino-2-phenylacetyl, 2-t-butoxycarbonylamino-2-phenylacetyl, 2-hydroxy-2-phenylacetyl, 2-methoxy-2-pheylacetyl, 2-hydroxy-3-phenylpropionyl, cyclopropylacetyl, cyclopentylacetyl, aminoacetyl, t-butoxycarbonylaminoacetyl, 3-aminopropionyl, 3-t-butoxycarbonylaminopropionyl, 2-aminoisovaleryl, 2-t-butoxycarbonylaminoisovarelyl, 2-aminopivaloyl, 2-t-butoxycarbonylaminopivaloyl, methoxyacetyl, (2-methoxyethoxy)acetyl, phenoxyacetyl, 2-pyridylacetyl, 3-thienylacetyl, etc.),
(A17) aryloxycarbonyl (e.g. phenoxycarbonyl, etc.), and
(A18) lower cycloalkenecarbonyl (e.g. cyclohexenecarbonyl, etc.).

[2] The compound of above [1], wherein the formula:

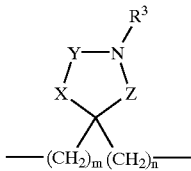

is one of the following formula:

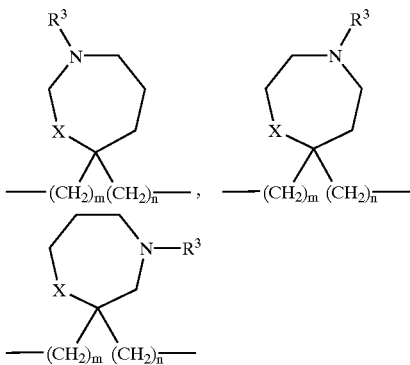

in which $R^3$ and X are each as defined in above [1],
m is an integer of 0 to 1, and
n is an integer of 1 or 2.

[3] The compound of above [2], wherein the compound has the following formula:

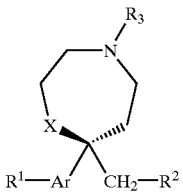

wherein $R^1$, $R^2$, $R^3$, and Ar are each as defined in above [2], and
X is sulfonyl.

[4] The compound of above [3], wherein
$R^1$ is halo;
lower alkoxy;
($C_6$–$C_{10}$)aryl optionally substituted by
(S1) lower alkoxy (e.g. methoxy, ethoxy, etc.),
(S2) lower alkoxycarbonylamino (e.g. methoxycarbonylamino, ethoxycarbonylamino, etc.),
(S3) lower alkylaminocarbonylamino (e.g. methylaminocarbonylamino, ethylaminocarbonylamino, etc.),
(S4) lower alkoxy(lower)alkanoylamino (e.g. ethoxyacetylamino, etc.),
(S5) $C_6$–$C_{10}$ aryloxy(lower)alkanoylamino (e.g. phenoxyacetylamino, etc.),
(S6) halo (e.g. chloro, fluoro, etc.),
(S7) lower alkyl (e.g. methyl, ethyl, propyl, isopropyl, etc.),
(S8) lower alkylthio (e.g. methylthio, etc.),
(S9) heterocyclic group selected from:
 unsaturated 5- or 6-membered, heteromonocyclic group containing 1 or 2 oxygen atoms and 1 to 3 nitrogen atoms, which is optionally substituted by lower alkyl (e.g. oxazolyl, methyloxadiazolyl, etc.), and
 saturated 5- or 6-membered, heteromonocyclic group containing 1 or 2 sulfur atoms and 1 to 3 nitrogen atoms, which is optionally substituted by oxo (e.g. 1,1-dioxoisothiazolidinyl, etc.),
(S10) lower alkenyl (e.g. vinyl, etc.),
(S11) amino (e.g. amino, etc.),
(S12) lower alkanoylamino (e.g. acetylamino, etc.),
(S15) $C_6$–$C_{10}$ aryloxy (e.g. phenoxy, etc.),
(S16) $C_6$–$C_{10}$ aryl (e.g. phenyl, etc.),
(S18) lower alkylcarbamoyl (e.g. methylcarbamoyl, ethylcarbamoyl, etc.),
(S19) trihalo(lower)alkyl (e.g. trifluoromethyl, etc.),
(S20) cyano (e.g. cyano, etc.),
(S21) cyano(lower)alkyl (e.g. cyanomethyl, etc.), and
(S22) lower alkoxy(lower)alkyl (e.g. methoxymethyl, etc.), and
(S28) trihalo(lower)alkyloxy (e.g. trifluoromethyloxy, etc.);
($C_6$–$C_{10}$)aryloxy optionally substituted by the group consisting of lower alkoxy, lower alkyl and halo (e.g. methoxyphenoxy, methylphenoxy, chlorophenoxy, fluorophenyl, etc.);
heterecyclic group selected from
 (H3) unsaturated 5- or 6-membered, heteromonocyclic group containing 1 or 2 sulfur atoms (e.g. thienyl, etc.);
 (H4) unsaturated bicyclic 9- or 10-membered, heterocyclic group containing 1 to 5 nitrogen atoms (e.g. quinolyl, isoquinolyl, etc.);
 (H5) unsaturated 5- or 6-membered, heteromonocyclic group containing 1 or 2 oxygen atoms (e.g. furyl, etc.);
 (H8) unsaturated bicyclic 9- or 10-membered, heterocyclic group containing 1 or 2 oxygen atoms (e.g. benzofuranyl, etc.); and
 ($H_{14}$) unsaturated bicyclic 9- or 10-membered, heterocyclic group containing 1 or 2 sulfur atoms and 1 to 3 nitrogen atoms (e.g. benzothiazolyl, dihydrobenzothiazolyl, benzothiadiazolyl, etc.);
 these heterocyclic group being optionally substituted by the group consisting of halogen, hydroxy (lower)alkyl, lower alkylcarbamoyl, lower alkyl and oxo; (e.g. chlorothienyl, hydroxymethylbenzofuranyl, methylcarbamoylbenzofuranyl, 3-methyl-2-oxo-2,3-dihydrobenzothiazolyl, etc.); or
lower alkynyl optionally substituted by ($C_6$–$C_{10}$)aryl or aminosulfonyl($C_6$–$C_{10}$)aryl (e.g. phenyl, aminosulfonylphenyl, etc.);
$R^2$ is N-hydroxycarbamoyl or N-(tetrahydropyranyl) carbamoyl;
$R^3$ is -hydrogen; or
acyl selected from the group consisting of:

(A1) lower alkylsufonyl optionally substituted by $C_6$–$C_{10}$ aryl (e.g. methylsulfonyl, ethylsulfonyl, propylsulfonyl, benzylsulfonyl, etc.), (A2) lower alkoxycarbonyl optionally substituted by lower alkoxy (e.g. methoxycarbonyl, ethoxycarbonyl, isobutoxycarbonyl, t-butoxycarbonyl, methoxyethoxycarbonyl, etc.), (A3) $C_6$–$C_{10}$ ar(lower)alkoxycarbonyl (e.g. benzyloxycarbonyl, etc), (A4) fluorenylmethoxycarbonyl (e.g. 9-fluorenylmethoxycarbonyl, etc.), (A5) mono- or di(lower)alkylaminosulfonyl optionally substituted by lower alkoxy (e.g. ethylaminosulfonyl, dimethylaminosulfonyl, diethylaminosulfonyl, N-methyl-N-ethylaminosulfonyl, N-(methoxyethyl)aminosulfonyl, N-methyl-N-(methoxyethyl)aminosulfonyl, etc.), (A6) mono- or di(lower)alkylcarbamoyl optionally substituted by $C_6$–$C_{10}$ aryl or (H3) unsaturated 5- or 6-membered, heteromonocyclic group containing 1 or 2 sulfur atoms (e.g. methylcarbamoyl, ethylcarbamoyl, propylcarbamoyl, isopropylcarbamoyl, t-butylcarbamoyl, dimethylcarbamoyl, benzylcarbamoyl, 1-phenyletylcarbamoyl, 2-thienylethylcarbamoyl, etc.), (A7) $C_6$–$C_{10}$ aroyl (e.g. benzoyl, naphthaoyl, etc.),
 $C_6$–$C_{10}$ aroyl substituted by lower alkoxy (e.g. 2- or 3- or 4-methoxybenzoyl, 2-ethoxybenzoyl, 2-propoxybenzoyl, 2,3- or 2,4- or 2,5-dimethoxybenzoyl, 2,3,4-trimethoxybenzoyl, etc.),
 $C_6$–$C_{10}$ aroyl substituted by halogen (e.g. 2- or 3- or 4-chlorobenzoyl, 2,3- or 2,4- or 2,5-dichlorobenzoyl, 2-fluorobenzoyl, etc.),
 $C_6$–$C_{10}$ aroyl substituted by lower alkyl (e.g. 2-methylbenzoyl, etc.),
 $C_6$–$C_{10}$ aroyl substituted by hydroxy (e.g. 2-hydroxybenzoyl, etc.),
 $C_6$–$C_{10}$ aroyl substituted by $C_6$–$C_{10}$ aryloxy. (e.g. 2-phenoxybenzoyl, etc.),
 $C_6$–$C_{10}$ aroyl substituted by $C_6$–$C_{10}$ aryl (e.g. 2-phenylbenzoyl, etc.),
 $C_6$–$C_{10}$ aroyl substituted by trihalo(lower)alkyl (e.g. 2-trifluoromethylbenzoyl, 2,4-bis(trifluoromethyl)benzoyl, etc.),
 $C_6$–$C_{10}$ aroyl substituted by nitro (e.g. 2-nitrobenzoyl, etc.),
 $C_6$–$C_{10}$ aroyl substituted by lower alkanoyl (e.g. 2-acetylbenzoyl, etc.),
 $C_6$–$C_{10}$ aroyl substituted by trihalo(lower)alkyloxy (e.g. 2-trifluoromethyloxybenzoyl, etc.),
 $C_6$–$C_{10}$ aroyl substituted by the group consisting of lower alkoxy and halogen (e.g. 2-methoxy-4-chlorobenzoyl, etc.),
 $C_6$–$C_{10}$ aroyl substituted by the group consisting of lower alkoxy and hydroxy (e.g. 3-methoxy-2-hydroxybenzoyl, etc.), (A8) heterocyclic-carbonyl or heterocyclic-sulfonyl, wherein the heterocyclic group being selected from;
 (H1) unsaturated 5- or 6-membered, heteromonocyclic group containing 1 to 4 nitrogen atoms, optionally substituted by lower alkyl or lower alkoxy (e.g. imidazolylcarbonyl, pyrazolylcarbonyl, pyridylcarbonyl, pyridylsulfonyl, pyrimidinylcarbonyl, pyrazinylcarbonyl, methylimidazolylcarbonyl, methylpyridylcarbonyl, methylpyrimidinylcarbonyl, 4-methoxy-1-piperidinylsulfonyl, etc.);
 (H2) saturated 5- or 6-membered, heteromonocyclic group containing 1 to 4 nitrogen atoms optionally substituted by lower alkanoyl or lower alkoxy (e.g. pyrrolidinylcarbonyl, pyrrolidinylsulfonyl, piperidinylcarbonyl, piperidinylsulfonyl, acetylpiperidinylcarbonyl, methoxypiperidinylsulfonyl, etc.);
 (H3) unsaturated 5- or 6-membered, heteromonocyclic group containing 1 or 2 sulfur atoms (e.g. thienylcarbonyl, thienylsulfonyl, etc.);
 (H4) unsaturated bicyclic 9- or 10-membered, heterocyclic group containing 1 to 5 nitrogen atoms (e.g. indolylcarbonyl, quinolylcarbonyl, isoquinolylcarbonyl, etc.);
 (H5) unsaturated 5- or 6-membered, heteromonocyclic group containing 1 or 2 oxygen atoms (e.g. furylcarbony, etc.);
 (H9) unsaturated bicyclic 9- or 10-membered, heterocyclic group containing 1 or 2 sulfur atoms (e.g. benzothienylcarbonyl, etc.); and
 (H10) saturated 5- or 6-membered, heteromonocyclic group containing 1 or 2 oxygen atoms and 1 to 3 nitrogen atoms (e.g. morpholinylcarbonyl, morpholinylsulfonyl, etc.);
 (preferable examples of heterocyclic acyl may be imidazolylcarbonyl (e.g. 2-imidazolylcarbonyl, etc.) optionally substituted by lower alkyl (e.g. 1-methyl-2-imidazolylcarbonyl, etc.), pyrazolylcarbonyl (e.g. 4-pyrazolylcarbonyl, etc.), pyridylcarbonyl (e.g. 2- or 3- or 4-pyridylcarbonyl, etc.) optionally substituted by lower alkyl (e.g. 3-methyl-2-pyridylcarbonyl, etc.), pyridylsulfonyl (e.g. 3-pyridylsulfonyl, etc.), pyrimidinylcarbonyl (e.g. 5-pyrimidinylcarbonyl, etc.) optionally substituted by lower alkyl (e.g. 4-methyl-5-pyrimidinylcarbonyl, etc.), pyrazinylcarbonyl (e.g. 2-pyrazinylcarbonyl, etc.), pyrrolidinylcarbonyl (e.g. 1-pyrrolidinylcarbonyl, etc.), pyrrolidinylsulfonyl (e.g. 1-pyrrolidinylsulfonyl, etc.), piperidinylcarbonyl (e.g. 1- or 4-piperidinylcarbonyl, etc.) optionally substituted by lower alkanoyl (e.g. 1-acetyl-4-piperidinylcarbonyl, etc.), piperidinylsulfonyl (e.g. 1-piperidinylsulfonyl, etc.) optionally substituted by lower alkoxy (e.g. 4-methoxy-1-piperidinylsulfonyl, etc.), thienylcarbonyl (e.g. 2- or 3-thienylcarbonyl, etc.), thienylsulfonyl (e.g. 2-thienylsulfonyl, etc.), indolylcarbonyl (e.g. 2-indolylcarbonyl, etc.), quinolylcarbonyl (e.g. 3- or 8-quinolylcarbonyl, etc.), isoquinolylcarbonyl (e.g. 1-isoquinolylcarbonyl, etc.), furylcarbonyl (e.g. 2-furylcarbonyl, etc.), benzothienylcarbonyl (e.g. 2-benzothienylcarbonyl, etc.), morpholinylcarbonyl (e.g. 4-morpholinylcarbonyl, etc.), morpholinylsulfonyl (e.g. 4-morpholinylsulfonyl, etc.), etc.), (A9) lower cycloalkylcarbamoyl (e.g. cyclopropylcarbamoyl, cyclohexylcarbamoyl, etc.), (A10) $C_6$–$C_{10}$ arylcarbamoyl, halo($C_6$–$C_{10}$)-arylcarbamoyl, lower alkyl($C_6$–$C_{10}$)-arylcarbamoyl, lower alkoxy($C_6$–$C_{10}$)-arylcarbamoyl (e.g. phenylcarbamoyl, mono- or dicholophenylcarbamoyl, methylphenylcarbamoyl, methoxyphenylcarbamoyl, etc.), (A11) $C_6$–$C_{10}$ arylsulfonyl (e.g. phenylsulfonyl, etc.) optionally substituted by lower alkoxy (e.g. methoxyphenylsulfonyl, etc.), (A12) heterocycliccarbamoyl, wherein the heterocyclic group is (H7) unsaturated 5- or 6-membered, heteromonocyclic group containing 1 or 2 oxygen atoms and 1 to 3 nitrogen atoms optionally substituted by lower alkyl (e.g. isoxazolyl, 5-methylisoxazolyl, etc.), (A13) lower cycloalkylcarbonyl (e.g. cyclopropylcarbonyl, cyclobutylcarbonyl, cyclopentylcarbonyl, cyclohexylcarbonyl, etc.) optionally substituted by $C_6$–$C_{10}$ aryl (e.g. 1-phenyl-1-cyclopropylcarbonyl, etc.), (A14) lower alkenoyl (e.g. 3-methylcrotonoyl, etc.) optionally substituted by $C_6$–$C_{10}$ aryl (e.g. phenylacryloyl, etc.), (A15) heterocyclic(lower)alkenoyl, wherein the heterocyclic group is unsaturated 5- or 6-membered, heteromonocyclic group containing 1 to 4 nitrogen atoms (e.g. pyridylacryloyl, etc.), (A16) lower alkanoyl optionally substituted by the group consisting of $C_6$–$C_{10}$ aryl, hydroxy, lower cycloalkyl, amino, lower alkoxycarbonylamino, lower alkoxy, lower alkoxy(lower)alkoxy, $C_6$–$C_{10}$ aryloxy, and heterocyclic group consisting of unsaturated 5- or 6-membered, heteromonocyclic group containing 1 or 2 sulfur atoms and unsaturated 5- or 6-membered, heteromonocyclic group containing 1 to 4 nitrogen atoms (e.g. acetyl, propionyl, isobutyryl, isovaleryl, pivaloyl, hexanoyl, 3,3-dimethylbutyryl, 2-ethylbutyryl, phenylacetyl, phenylpropionyl, 2-amino-2-phenylacetyl, 2-t-butoxycarbonylamino-2-phenylacetyl, 2-hydroxy-2-phenylacetyl, 2-methoxy-2-pheylacetyl, 2-hydroxy-3-phenylpropionyl, cyclopropylacetyl, cyclopentylacetyl, aminoacetyl, t-butoxycarbonylaminoacetyl, 3-aminopropionyl, 3-t-butoxycarbonylaminopropionyl, 2-aminoisovaleryl, 2-t-butoxycarbonylaminoisovarelyl, 2-aminopivaloyl, 2-t-butoxycarbonylaminopivaloyl, methoxyacetyl, (2-methoxyethoxy)acetyl, phenoxyacetyl, 2-pyridylacetyl, 3-thienylacetyl, etc.), (A17) $C_6$–$C_{10}$ aryloxycarbonyl (e.g. phenoxycarbonyl, etc.), and (A18) lower cycloalkenecarbonyl (e.g. cyclohexenecarbonyl, etc.), and Ar is $C_6$–$C_{10}$ aryl or (H3) unsaturated 5- or 6-membered, heteromonocyclic group containing 1 or 2 sulfur atoms.

[5] The compound of above [4], wherein
$R^1$ is -lower alkoxy;
optionally substituted phenyl or naphthyl selected from
(Sa0) phenyl or naphthyl (e.g. phenyl, naphthyl, etc.),
(Sa1) lower alkoxyphneyl (e.g. methoxyphenyl, ethoxyphneyl, etc.),
(Sa2) lower alkoxycarbonylaminophenyl (e.g. methoxycarbonylaminophenyl, ethoxycarbonylaminophenyl, etc.),
(Sa3) lower alkylaminocarbonylaminophenyl (e.g. methylaminocarbonylaminophenyl, ethylaminocarbonylaminophenyl, etc.),
(Sa4) lower alkoxy(lower)alkanoylaminophenyl (e.g. ethoxyacetylaminophenyl, etc.),
(Sa5) phenoxy(lower)alkanoylaminophenyl (e.g. phenoxyacetylaminophenyl, etc.),
(Sa6) halophenyl (e.g. chlorophenyl, fluorophenyl, etc.),
(Sa7) lower alkylphenyl (e.g. methylphenyl, ethylphenyl, propylphenyl, isopropylphenyl, etc.),
(Sa8) lower alkylthiophenyl (e.g. methylthiophenyl, etc.),
(Sa9) oxazolylphenyl (e.g. 2-(or 5-)oxazolylphenyl, etc.), oxadiazolylphenyl optionally substituted by lower alkyl (e.g. 1,2,4-oxadiazol-3-ylphenyl, 5-methyl-1,2,4-oxadiazol-3-ylphenyl, etc.), isothiazolidinylphenyl optionally substituted by oxo (e.g. 1,1-dioxoisothiazolidin-2-ylphenyl, etc.),
(Sa10) lower alkenylphenyl (e.g. vinylphenyl, etc.),
(Sa11) aminophenyl (e.g. aminophenyl, etc.),
(Sa12) lower alkanoylaminophenyl (e.g. acetylaminophenyl, etc.),
(Sa15) phenoxyphenyl (e.g. phenoxyphenyl, etc.),
(Sa16) phenyl optionally substituted by halogen (e.g. phenyl, chlorophenyl, etc.),
(Sa18) lower alkylcarbamoylphenyl (e.g. methylcarbamoylphenyl, ethylcarbamoylphenyl, etc.),
(Sa19) trihalo(lower)alkylphenyl (e.g. trifluoromethylphenyl, etc.),
(Sa20) cyanophenyl (e.g. cyanophenyl, etc.),
(Sa21) cyano(lower)alkylphenyl (e.g. cyanomethylphenyl, etc.),
(Sa22) lower alkoxy(lower)alkylphenyl (e.g. methoxymethylphenyl, etc.); and
(Sa23) hydroxy(lower)alkylphenyl (e.g. hydroxymethylphenyl, etc.), and
(Sa28) trihalo(lower)alkyloxyphenyl (e.g. trifluoromethyloxyphenyl, etc.);
phenoxy, lower alkoxyphenoxy, lower alkylphenoxy, halophenoxy (e.g. methoxyphenoxy, methylphenoxy, chlorophenoxy, fluorophenyl, etc.);

optionally substituted heterecyclic group selected from
(H3) thienyl optionally substituted by halogen (e.g. 2-thienyl, 5-chloro-2-thienyl, etc.),
(H4) quinolyl (e.g. 6-quinolyl, etc.),
(H5) furyl (e.g. 2-furyl, etc.),
(H8) benzofuranyl, hydroxy(lower)alkylbenzofuranyl, lower alkylcarbamoylbenzofuranyl (e.g. 2-(hydroxymethyl)-5-benzofuranyl, 2-(methylcarbamoyl)-5-benzofuranyl, etc.);
(H14) dihydrobenzothiazolyl substituted by lower alkyl and oxo (e.g 3-methyl-2-oxo-2,3-dihydrobenzothiazolyl, etc.); or lower alkynyl, phenyl(lower)alkynyl or aminosulfonyphenyl(lower)alkynyl;(e.g. 2-hexynyl, 2-phenylethynyl, 2-(4-aminosulfonylphenyl)ethynyl, etc.), $R^2$ is N-hydroxycarbamoyl,
$R^3$ is acyl selected from the group consisting of;
(A1) lower alkylsufonyl (e.g. methylsulfonyl, ethylsulfonyl, propylsulfonyl, etc.) optionally substituted by phenyl (e.g. benzylsulfonyl, etc.),
(A2) lower alkoxycarbonyl (e.g. methoxycarbonyl, ethoxycarbonyl, isobutoxycarbonyl, t-butoxycarbonyl, etc.) optionally substituted by lower alkoxy (e.g. methoxyethoxycarbonyl, etc.),
(A3) phenyl(lower)alkoxycarbonyl (e.g. benzyloxycarbonyl, etc),
(A4) fluorenylmethoxycarbonyl (e.g. 9-fluorenylmethoxycarbonyl, etc.),
(A5) mono- or di(lower)alkylaminosulfonyl (e.g. ethylaminosulfonyl, dimethylaminosulfonyl, diethylaminosulfonyl, N-methyl-N- ethylaminosulfonyl, etc.) optionally substituted by lower alkoxy (e.g. N-(methoxyethyl)aminosulfonyl, N-methyl-N-(methoxyethyl)aminosulfonyl, etc.), (A6) mono- or di(lower)alkylcarbamoyl (e.g. methylcarbamoyl, ethylcarbamoyl, propylcarbamoyl, isopropylcarbamoyl, t-butylcarbamoyl, dimethylcarbamoyl, etc.) optionally substituted by phenyl or thienyl (e.g. benzylcarbamoyl, 1-phenylethylcarbamoyl, 2-thienylethylcarbamoyl, etc.), (A7) benzoyl,
naphthoyl,
benzoyl substituted by lower alkoxy (e.g. 2- or 3- or 4-methoxybenzoyl, 2-ethoxybenzoyl, 2-propoxybenzoyl, 2,3- or 2,4- or 2,5-dimethoxybenzoyl, 2,3,4-trimethoxybenzoyl, etc.),
benzoyl substituted by halogen (e.g. 2- or 3- or 4-chlorobenzoyl, 2,3- or 2,4- or 2,5-dichlorobenzoyl, 2-fluorobenzoyl, etc.),
benzoyl substituted by lower alkyl (e.g. 2-methylbenzoyl, etc.),
benzoyl substituted by hydroxy (e.g. 2-hydroxybenzoyl, etc.),
benzoyl substituted by phenoxy (e.g. 2-phenoxybenzoyl, etc.),
benzoyl substituted by phenyl (e.g. 2-phenylbenzoyl, etc.),
benzoyl-substituted by trihalo(lower)alkyl (e.g. 2-trifluoromethylbenzoyl, 2,4-bis(trifluoromethyl)benzoyl, etc.),
benzoyl substituted by nitro (e.g. 2-nitrobenzoyl, etc.),
benzoyl substituted by lower alkanoyl (e.g. 2-acetylbenzoyl, etc.),
benzoyl substituted by trihalo(lower)alkyloxy (e.g. 2-trifluoromethyloxybenzoyl, etc.),
benzoyl substituted by lower alkoxy and halogen (e.g. 2-methoxy-4-chlorobenzoyl, etc.),
benzoyl substituted by lower alkoxy and hydroxy (e.g. 3-methoxy-2-hydroxybenzoyl, etc.), (A8) heterocyxlic-carbonyl or heterocyclic-sulfonyl selected from:
(Ha1) imidazolylcarbonyl (e.g. 2-imidazolylcarbonyl, etc.) optionally substituted by lower alkyl (e.g. 1-methyl-2-imidazolylcarbonyl, etc.), pyrazolylcarbonyl (e.g. 4-pyrazolylcarbonyl, etc.), pyridylcarbonyl (e.g. 2- or 3- or 4-pyridylcarbonyl, etc.) optionally substituted by lower alkyl (e.g. 3-methyl-2-pyridylcarbonyl, etc.), pyridylsulfonyl (e.g. 3-pyridylsulfonyl, etc.), pyrimidinylcarbonyl (e.g. 5-pyrimidinylcarbonyl, etc.) optionally substituted by lower alkyl (e.g. 4-methyl-5-pyrimidinylcarbonyl, etc.), pyrazinylcarbonyl (e.g. 2-pyrazinylcarbonyl, etc.),
(Ha2) pyrrolidinylcarbonyl (e.g. 1-pyrrolidinylcarbonyl, etc.), pyrrolidinylsulfonyl (e.g. 1-pyrrolidinylsulfonyl, etc.), piperidinylcarbonyl (e.g. 1- or 4-piperidinylcarbonyl, etc.) optionally substituted by lower alkanoyl (e.g. 1-acetyl-4-piperidinylcarbonyl, etc.), piperidinylsulfonyl (e.g. 1-piperidinylsulfonyl, etc.) optionally substituted by lower alkoxy (e.g. 4-methoxy-1-piperidinylsulfonyl, etc.),
(Ha3) thienylcarbonyl (e.g. 2- or 3-thienylcarbonyl, etc.), thienylsulfonyl (e.g. 2-thienylsulfonyl, etc.),
(Ha4) indolylcarbonyl (e.g. 2-indolylcarbonyl, etc.), quinolylcarbonyl (e.g. 3- or 8-quinolylcarbonyl, etc.), isoquinolylcarbonyl (e.g. 1-isoquinolylcarbonyl, etc.),
(Ha5) furylcarbonyl (e.g. 2-furylcarbonyl, etc.),
(Ha9) benzothienylcarbonyl (e.g. 2-benzothienylcarbonyl, etc.), and
(Ha10) morpholinylcarbonyl (e.g. 4-morpholinylcarbonyl, etc.), morpholinylsulfonyl (e.g. 4-morpholinylsulfonyl, etc.), (A9) lower cycloalkylcarbamoyl (e.g. cyclopropylcarbamoyl, cyclohexylcarbamoyl, etc.), (A10) phenylcarbamoyl, halophenylcarbamoyl, lower alkylphenylcarbamoyl, lower alkoxyphenylcarbamoyl (e.g. phenylcarbamoyl, mono- or dicholophenylcarbamoyl, methylphenylcarbamoyl, methoxyphenylcarbamoyl, etc.), (A11) phenylsulfonyl (e.g. phenylsulfonyl, etc.) optionally substituted by lower alkoxy (e.g. methoxyphenylsulfonyl, etc.), (A12) isoxazolylcarbamoyl, lower alkylisoxazolylcarbamoyl (e.g. methylisoxazolylcarbamoyl, etc.), (A13) lower cycloalkylcarbonyl (e.g. cyclopropylcarbonyl, cyclobutylcarbonyl, cyclopentylcarbonyl, cyclohexylcarbonyl, etc.) optionally substituted by phenyl (e.g. 1-phenyl-1-cyclopropylcarbonyl, etc.), (A14) lower alkenoyl (e.g. 3-methylcrotonoyl, etc.) optionally substituted by phenyl (e.g. phenylacryloyl, etc.), (A15) pyridyl(lower)alkenoyl (e.g. pyridylacryloyl, etc.)

(A16) lower alkanoyl (e.g. acetyl, propionyl, isobutyryl, isovaleryl, pivaloyl, hexanoyl, 3,3-dimethylbutyryl, 2-ethylbutyryl, etc.), phenyl(lower)alkanoyl, hydroxy(lower)alkanoyl, lower cycloalkyl(lower)alkanoyl, amino(lower)alkanoyl, lower alkoxycarbonylamino(lower)alkanoyl, lower alkoxy(lower)alkanoyl, lower alkoxy(lower)alkoxy(lower)alkanoyl, phenoxy(lower)alkanoyl, lower akanoyl substituted by amino and phenyl, lower alkanoyl substituted by lower alkoxycarbonylamino and phenyl, lower akanoyl substituted by hydroxy and phenyl, lower alkanoyl lower alkoxy and phenyl, pyridyl(lower)alkanoyl, thienyl(lower)alkanoyl, (e.g. phenylacetyl, phenylpropionyl, 2-amino-2-phenylacetyl, 2-t-butoxycarbonylamino-2-phenylacetyl, 2-hydroxy-2-phenylacetyl, 2-methoxy-2-pheylacetyl, 2-hydroxy-3-phenylpropionyl, cyclopropylacetyl, cyclopentylacetyl, aminoacetyl, t-butoxycarbonylaminoacetyl, 3-aminopropionyl, 3-t-butoxycarbonylaminopropionyl, 2-aminoisovaleryl, 2-t-butoxycarbonylaminoisovarelyl, 2-aminopivaloyl, 2-t-butoxycarbonylaminopivaloyl, methoxyacetyl, (2-methoxyethoxy)acetyl, phenoxyacetyl, 2-pyridylacetyl, 3-thienylacetyl, etc.), and (A17) phenoxycarbonyl (e.g. phenoxycarbonyl, etc.), (A18) lower cycloalkenecarbonyl (e.g. cyclohexenecarbonyl, etc.), and Ar is thienyl

[6] The compound of above [5], wherein the compound has the following formula:

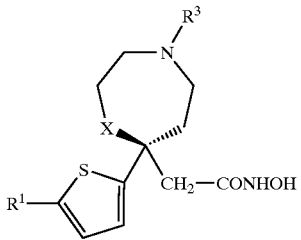

wherein $R^1$, $R^3$ and X are each as defined in above [5].

[7] The compound of above [6], wherein
$R^1$ is -optionally substituted phenyl or naphthyl selected from
(Sa0) phenyl, naphthyl (e.g. phenyl, 2-naphthyl, etc.),
(Sa1) lower alkoxyphenyl (e.g. 4-methoxyphenyl, 4-ethoxyphenyl, etc.),
(Sa2) lower alkoxycarbonylaminophenyl (e.g. 3-(methoxycarbonylamino)phenyl, 3-(ethoxycarbonylamino)phenyl, etc.),
(Sa3) lower alkylaminocarbonylaminophenyl (e.g. 3-(methylaminocarbonylamino)phenyl, 3-(ethylaminocarbonylamino)phenyl, etc.),
(Sa4) lower alkoxy(lower)alkanoylaminophenyl (e.g. 3-(ethoxyacetylamino)phenyl, etc.),
(Sa5) phenoxy(lower)alkanoylaminophenyl (e.g. 3-(phenoxyacetylamino)phenyl, etc.),
(Sa6) halophenyl (e.g. 4-chlorophenyl, 4-fluorophenyl, etc.),
(Sa7) lower alkylphenyl (e.g. 4-methylphenyl, 4-ethylphenyl, 4-propylphenyl, 4-isopropylphenyl, etc.),
(Sa8) lower alkylthiophenyl (e.g. 4-methylthiophenyl, etc.),
(Sa9) oxazolylphenyl (e.g. 2-(or 5-)oxazolylphenyl, etc.), lower alkyloxadiazolylphenyl (e.g. 5-methyl-1,2,4-oxadiazol-3-ylphenyl, etc.), 1,1-dioxoisothiazolidinylphenyl (e.g. 1,1-dioxoisothiazolidin-2-ylphenyl, etc.),
(Sa10) lower alkenylphenyl (e.g. 4-vinylphenyl, etc.),
(Sa11) aminophenyl (e.g. 3-aminophenyl, etc.),
(Sa12) lower alkanoylaminophenyl (e.g. 3-acetylaminophenyl, etc.),
(Sa16) biphenylyl (e.g. 4-biphenylyl, etc.),
(Sa19) trihalo(lower)alkylphenyl (e.g. 4-trifluoromethylphenyl, etc.),
(Sa20) cyanophenyl (e.g. 4-cyanophenyl, etc.),
(Sa21) cyano(lower)alkylphenyl (e.g. 4-cyanomethylphenyl, etc.),
(Sa22) lower alkoxy(lower)alkylphenyl (e.g. 4-methoxymethylphenyl, etc.), and
(Sa28) trihalo(lower)alkyloxyphenyl (e.g. 4-trifluoromethyloxyphenyl, etc.);
optionally substituted heterecyclic group selected from
(H3) thienyl (e.g. 2-thienyl, etc.), halothienyl (e.g. 5-chloro-2-thienyl, etc.),
(H4) quinolyl (e.g. 6-quinolyl, etc.),
(H5) furyl (e.g. 2-furyl, etc.),
(H8) benzofuranyl, hydroxy(lower)alkylbenzofuranyl (e.g. 2-(hydroxymethyl)-5-benzofuranyl, etc.), lower alkylcarbamoylbenzofuranyl (e.g. 2-(methylcarbamoyl)-5-benzofuranyl, etc.), and
(H14) dihydrobenzothiazolyl, dihydrobenzothiazolyl substituted by lower alkyl and oxo (e.g 3-methyl-2-oxo-2,3-dihydrobenzothiazolyl, etc.);

$R^3$ is acyl selected from the group consisting of;
(A1) lower alkylsufonyl, phenyl(lower)alkylsufonyl (e.g. methylsulfonyl, ethylsulfonyl, propylsulfonyl, benzylsulfonyl, etc.),
(A2) lower alkoxycarbonyl, lower alkoxy(lower) alkoxycarbonyl (e.g. methoxycarbonyl, ethoxycarbonyl, isobutoxycarbonyl, t-butoxycarbonyl, 2-methoxyethoxycarbonyl, etc.),
(A3) phenyl(lower)alkoxycarbonyl (e.g. benzyloxycarbonyl, etc),
(A4) fluorenylmethoxycarbonyl (e.g. 9-fluorenylmethoxycarbonyl, etc.),
(A5) mono- or di(lower)alkylaminosulfonyl, N-(lower) alkoxy(lower)alkylaminosulfonyl, N-(lower) alkyl-N-(lower)alkoxy(lower)alkylaminosulfonyl (e.g. dimethylaminosulfonyl, diethylaminosulfonyl, N-(2-methoxyethyl)aminosulfonyl, N-methyl-N-(2-methoxyethyl)aminosulfonyl, etc.),
(A6) mono- or di(lower)alkylcarbamoyl, phenyl(lower) alkylcarbamoyl, thienyl(lower)alkylcarbamoyl (e.g. ethylcarbamoyl, propylcarbamoyl, isopropylcarbamoyl, t-butylcarbamoyl, dimethylcarbamoyl, benzylcarbamoyl, 1-phenyletylcarbamoyl, 2-(2-thienyl)ethylcarbamoyl, etc.),
(A7) benzoyl, 2-naphthoyl, lower alkoxybenzoyl (e.g. 2- or 3- or 4-methoxybenzoyl, 2-ethoxybenzoyl, 2-propoxybenzoyl, 2,3- or 2,4- or 2,5-dimethoxybenzoyl, 2,3,4-trimethoxybenzoyl, etc.), mono- or di- or trihalobenzoyl (e.g. 2- or 3- or 4-chlorobenzoyl, 2,3- or 2,4- or 2,5-dichlorobenzoyl, 2-fluorobenzoyl, etc.), lower alkylbenzoyl (e.g. 2-methylbenzoyl, etc.), hydroxybenzoyl (e.g. 2-hydroxybenzoyl, etc.), phenoxybenzoyl (e.g. 2-phenoxybenzoyl, etc.), phenylbenzoyl (e.g. 2-phenylbenzoyl, etc.), mono- or bis(trihalo(lower) alkyl)benzoyl (e.g. 2-trifluoromethylbenzoyl, 2,4-bis (trifluoromethyl)benzoyl, etc.), nitrobenzoyl (e.g. 2-nitrobenzoyl, etc.), lower alkanoylbenzoyl (e.g. 2-acetylbenzoyl, etc.), trihalo(lower)alkyloxybenzoyl (e.g. 2-trifluoromethyloxybenzoyl, etc.), benzoyl substituted by lower alkoxy and halogen (e.g. 2-methoxy-4-chlorobenzoyl, etc.), and benzoyl substituted by lower alkoxy and hydroxy (e.g. 3-methoxy-2-hydroxybenzoyl, etc.),
(A8) heterocyclic-carbonyl or heterocyclic-sulfonyl selected from:
(Ha1) imidazolylcarbonyl, lower alkylimidazolylcarbonyl, pyrazolylcarbonyl, pyridylcarbonyl, lower alkylpyridylcarbonyl, pyridylsulfonyl, pyrimidinylcarbonyl, lower alkylpyrimidinylcarbonyl, pyrazinylcarbonyl,
(Ha2) pyrrolidinylcarbonyl, pyrrolidinylsulfonyl, piperidinylcarbonyl, lower alkanoylpiperidinylcarbonyl, piperidinylsulfonyl, lower alkoxypiperidinylsulfonyl,
(Ha3) thienylcarbonoyl, thienylsulfonyl,
(Ha4) indolylcarbonyl, quinolylcarbonyl, isoquinolylcarbonyl,
(Ha5) furylcarbonyl,
(Ha9) benzothienylcarbonyl,
(Ha10) morpholinylcarbonyl, morpholinylsulfonyl (e.g. 1-methyl-2-imidazolylcarbonyl, 4-pyrazolylcarbonyl, 2- or 3- or 4-pyridylcarbonyl, 3-methyl-2-pyridylcarbonyl, 3-pyridylsulfonyl, 4-methyl-5-pyrimidinylcarbonyl, 2-pyrazinylcarbonyl, 1-pyrrolidinylcarbonyl, 1-pyrrolidinylsulfonyl, 1- or 4-piperidinylcarbonyl, 1-acetyl-4-piperidinylcarbonyl, 1-piperidinylsulfonyl, 4-methoxy-1-piperidinylsulfonyl, 2- or 3-thienylcarbonyl, 2-thienylsulfonyl, 2-indolylcarbonyl, 3- or 8-quinolylcarbonyl, 1-isoquinolylcarbonyl, 2-furylcarbonyl, 2-benzothienylcarbonyl, 4-morpholinylcarbonyl, 4-morpholinylsulfonyl, etc.), (A9) lower cycloalkylcarbamoyl (e.g. cyclopropylcarbamoyl, cyclohexylcarbamoyl, etc.), (A10) phenylcarbamoyl, halophenylcarbamoyl, lower alkylphenylcarbamoyl, lower alkoxyphenylcarbamoyl, (e.g. phenylcarbamoyl, 2-, 3- or 4-chlorophenylcarbamoyl, 2,3- or 2,5-dicholophenylcarbamoyl, 2-methylphenylcarbamoyl, 2-methoxyphenylcarbamoyl, etc.), (A11) phenylsulfonyl, lower alkoxyphenylsulfonyl (e.g. phenylsulfonyl, 4-methoxyphenylsulfonyl, etc.), (A12) isoxazolylcarbamoyl, lower alkylisoxazolylcarbamoyl (e.g. 5-methyl-3-isoxazolylcarbamoyl, etc.), (A13) lower cycloalkylcarbonyl, phenyl(lower)cycloalkylcarbonyl (e.g. cyclopropylcarbonyl, cyclobutylcarbonyl, cyclopentylcarbonyl, cyclohexylcarbonyl, 1-phenyl-1-cyclopropylcarbonyl, etc.), (A14) lower alkenoyl, phenyl(lower)alkenoyl (e.g. 3-methylcrotonoyl, 3-phenylacryloyl, etc.), (A15) pyridyl(lower)alkenoyl (e.g. 3-pyridylacryloyl, etc.), (A16) lower alkanoyl (e.g. acetyl, propionyl, isobutyryl, isovaleryl, pivaloyl, hexanoyl, 3,3-dimethylbutyryl, 2-ethylbutyryl, etc.), phenyl(lower)alkanoyl, hydroxy(lower)alkanoyl, lower cycloalkyl(lower)alkanoyl, amino(lower)alkanoyl, lower alkoxy(lower)alkanoyl, lower alkoxy(lower)alkoxy(lower)alkanoyl, phenoxy(lower)alkanoyl, lower akanoyl substituted by amino and phenyl, lower akanoyl substituted by hydroxy and phenyl, lower alkanoyl substituted by lower alkoxy and phenyl, pyridyl(lower)alkanoyl, thienyl(lower)alkanoyl (e.g. 3-phenylpropionyl, 2-amino-2-phenylacetyl, 2-t-butoxycarbonylamino-2-phenylacetyl, 2-hydroxy-2-phenylacetyl, 2-hydroxy-3-phenylpropionyl, 2-methoxy-2-pheylacetyl, cyclopropylacetyl, cyclopentylacetyl, aminoacetyl, t-butoxycarbonylaminoacetyl, 3-aminopropionyl, 3-t-butoxycarbonylaminopropionyl, 2-aminoisovaleryl, 2-t-butoxycarbonylaminoisovarelyl, 2-aminopivaloyl, 2-t-butoxycarbonylaminopivaloyl, methoxyacetyl, (2-methoxyethoxy)acetyl, phenoxyacetyl, 2-pyridylacetyl, 3-thienylacetyl, etc.), (A17) phenoxycarbonyl (e.g. phenoxycarbonyl, etc.), and (A18) lower cycloalkenecarbonyl (e.g. 3-cyclohexenecarbonyl, etc.).

[8] The compound of above [7], wherein
$R^1$ is (Sa0) phenyl, 2-naphthyl,
(Sa1) 4-methoxyphenyl, 4-ethoxyphenyl,
(Sa2) 3-(methoxycarbonylamino)phenyl, 3-(ethoxycarbonylamino)phenyl,
(Sa3) 3-(methylaminocarbonylamino)phenyl, 3-(ethylaminocarbonylamino)phenyl,
(Sa4) 3-(ethoxyacetylamino)phenyl,
(Sa5) 3-(phenoxyacetylamino)phenyl,
(Sa6) 4-chlorophenyl, 4-fluorophenyl,
(Sa7) 4-methylphenyl, 4-ethylphenyl, 4-propylphenyl, 4-isopropylphenyl,
(Sa8) 4-methylthiophenyl,
(Sa9) 2-(or 5-)oxazolylphenyl, 5-methyl-1,2,4-oxadiazol-3-ylphenyl, 1,1-dioxoisothiazolidin-2-ylphenyl,
(Sa10) 4-vinylphenyl,
(Sa11) 3-aminophenyl,
(Sa12) 3-acetylaminophenyl,
(Sa16) 4-biphenylyl,
(Sa19) 4-trifluoromethylphenyl,
(Sa20) 4-cyanophenyl,
(Sa21) 4-cyanomethylphenyl,
(Sa22) 4-methoxymethylphenyl,
(Sa28) 4-trifluoromethyloxyphenyl,
optionally substituted heterecyclic group selected from
(H3) 2-thienyl, 5-chloro-2-thienyl,
(H4) 6-quinolyl,
(H5) 2-furyl,
(H8) 2-(hydroxymethyl)-5-benzofuranyl, 2-(methylcarbamoyl)-5-benzofuranyl, and
(H14) 3-methyl-2-oxo-2,3-dihydrobenzothiazolyl, etc.);

$R^3$ is acyl selected from the group consisting of;
(A1) methylsulfonyl, ethylsulfonyl, propylsulfonyl, benzylsulfonyl, (A2) methoxycarbonyl, ethoxycarbonyl, isobutoxycarbonyl, t-butoxycarbonyl, methoxyethoxycarbonyl, (A3) benzyloxycarbonyl, (A4) fluorenylmethoxycarbonyl, (A5) dimethylaminosulfonyl, diethylaminosulfonyl, N-(2-methoxyethyl)aminosulfonyl, N-methyl-N-(2-methoxyethyl)aminosulfonyl, (A6) ethylcarbamoyl, propylcarbamoyl, isopropylcarbamoyl, t-butylcarbamoyl, dimethylcarbamoyl, benzylcarbamoyl, 1-phenylethylcarbamoyl, 2-(2-thienyl)ethylcarbamoyl, (A7) benzoyl, 2-naphthoyl, 2- or 3- or 4-methoxybenzoyl, 2-ethoxybenzoyl, 2-propoxybenzoyl, 2,3- or 2,4- or 2,5-dimethoxybenzoyl, 2,3,4-trimethoxybenzoyl, 2- or 3- or 4-chlorobenzoyl, 2,3- or 2,4- or 2,5-dichlorobenzoyl, 2-fluorobenzoyl, 2-methylbenzoyl, 2-hydroxybenzoyl, 2-phenoxybenzoyl, 2-phenylbenzoyl, 2-trifluoromethylbenzoyl, 2,4-bis(trifluoromethyl)benzoyl, 2-nitrobenzoyl, 2-acetylbenzoyl, 2-trifluoromethyloxybenzoyl, 2-methoxy-4-chlorobenzoyl, 3-methoxy-2-hydroxybenzoyl, (A8) heterocyclic-caronyl or heterocyclic-sulfonyl selected from:
(Ha1) 1-methyl-2-imidazolylcarbonyl, 4-pyrazolylcarbonyl, 2- or 3- or 4-pyridylcarbonyl, 3-methyl-2-pyridylcarbonyl, 3-pyridylsulfonyl, 4-methyl-5-pyrimidinylcarbonyl, 2-pyrazinylcarbonyl,
(Ha2) 1-pyrrolidinylcarbonyl, 1-pyrrolidinylsulfonyl, 1- or 4-piperidinylcarbonyl, 1-acetyl-4-piperidinylcarbonyl, 1-piperidinylsulfonyl, 4-methoxy-1-piperidinylsulfonyl,
(Ha3) 2- or 3-thienylcarbonyl, 2-thienylsulfonyl,
(Ha4) 2-indolylcarbonyl, 3- or 8-quinolylcarbonyl, 1-isoquinolylcarbonyl,
(Ha5) 2-furylcarbonyl,
(Ha9) 2-benzothienylcarbonyl,
(Ha10) 4-morpholinylcarbonyl, 4-morpholinylsulfonyl, (A9) cyclopropylcarbamoyl, cyclohexylcarbamoyl, (A10) phenylcarbamoyl, 2-, 3- or 4-chlorophenylcarbamoyl, 2,3- or 2,5-dicholophenylcarbamoyl, 2-methylphenylcarbamoyl, 2-methoxyphenylcarbamoyl, (A11) phenylsulfonyl, 4-methoxyphenylsulfonyl, (A12) 5-methyl-3-isoxazolylcarbamoyl, (A13) cyclopropylcarbonyl, cyclobutylcarbonyl, cyclopentylcarbonyl, cyclohexylcarbonyl, 1-phenyl-1-cyclopropylcarbonyl, (A14) 3-methylcrotonoyl, 3-phenylacryloyl, (A15) 3-pyridylacryloyl, (A16) acetyl, propionyl, isobutyryl, isovaleryl, pivaloyl, hexanoyl, 3,3-dimethylbutyryl, 2-ethylbutyryl, 3-phenylpropionyl, 2-amino-2-phenylacetyl, 2-hydroxy-2-phenylacetyl, 2-hydroxy-3-phenylpropionyl, 2-methoxy-2-pheylacetyl, cyclopropylacetyl, cyclopentylacetyl, aminoacetyl, 3-aminopropionyl, 2-aminoisovaleryl, 2-aminopivaloyl, methoxyacetyl, (2-methoxyethoxy)acetyl, phenoxyacetyl, 2-pyridylacetyl, 3-thienylacetyl, (A17) phenoxycarbonyl, and (A18) 3-cyclohexenecarbonyl.

[9] The compound of above [7], wherein $R^1$ is -optionally substituted phenyl or naphthyl selected from:
(Sa1) lower alkoxyphenyl (e.g. 4-methoxyphenyl, 4-ethoxyphenyl, etc.),
(Sa6) halophenyl (e.g. 4-chlorophenyl, 4-fluorophenyl, etc.),
(Sa7) lower alkylphenyl (e.g. 4-methylphenyl, 4-ethylphenyl, 4-propylphenyl, 4-isopropylphenyl, etc.),
(Sa8) lower alkylthiophenyl (e.g. 4-methylthiophenyl, etc.),
(Sa9) oxazolylphenyl (e.g. 2-(or 5-)oxazolylphenyl, etc.), lower alkyloxadiazolylphenyl (e.g. 5-methyl-1,2,4-oxadiazol-3-ylphenyl, etc.), 1,1-dioxoisothiazolidinylphenyl (e.g. 1,1-dioxoisothiazolidin-2-ylphenyl, etc.), and
(Sa28) trihalo(lower)alkyloxyphenyl (e.g. 4-trifluoromethyloxyphenyl, etc.);

$R^3$ is acyl selected from the group consisting of;
(A1) lower alkylsufonyl, phenyl(lower)alkylsufonyl (e.g. methylsulfonyl, ethylsulfonyl, propylsulfonyl, benzylsulfonyl, etc.),
(A5) mono- or di(lower)alkylaminosulfonyl, N-(lower)alkoxy(lower)alkylaminosulfonyl, N-(lower)alkyl-N-(lower)alkoxy(lower)alkylaminosulfonyl (e.g. dimethylaminosulfonyl, diethylaminosulfonyl, N-(2-methoxyethyl)aminosulfonyl, N-methyl-N-(2-methoxyethyl)aminosulfonyl, etc.),
(A7) benzoyl, 2-naphthoyl, lower alkoxybenzoyl (e.g. 2- or 3- or 4-methoxybenzoyl, 2-ethoxybenzoyl, 2-propoxybenzoyl, 2,3- or 2,4- or 2,5-dimethoxybenzoyl, 2,3,4-trimethoxybenzoyl, etc.), mono- or di- or trihalobenzoyl (e.g. 2- or 3- or 4-chlorobenzoyl, 2,3- or 2,4- or 2,5-dichlorobenzoyl, 2-fluorobenzoyl, etc.), lower alkylbenzoyl (e.g. 2-methylbenzoyl, etc.), hydroxybenzoyl (e.g. 2-hydroxybenzoyl, etc.), phenoxybenzoyl (e.g. 2-phenoxybenzoyl, etc.), phenylbenzoyl (e.g. 2-phenylbenzoyl, etc.), mono- or bis(trihalo(lower)alkyl)benzoyl (e.g. 2-trifluoromethylbenzoyl, 2,4-bis(trifluoromethyl)benzoyl, etc.), nitrobenzoyl (e.g. 2-nitrobenzoyl, etc.), lower alkanoylbenzoyl (e.g. 2-acetylbenzoyl, etc.), trihalo(lower)alkyloxybenzoyl (e.g. 2-trifluoromethyloxybenzoyl, etc.), benzoyl substituted by lower alkoxy and halogen (e.g. 2-methoxy-4-chlorobenzoyl, etc.), benzoyl substituted by lower alkoxy and hydroxy (e.g. 3-methoxy-2-hydroxybenzoyl, etc.), (A8) heterocyclic-carbonyl or heterocyclic-sulfonyl selected from:
(Ha1) imidazolylcarbonyl, lower alkylimidazolylcarbonyl, pyrazolylcarbonyl, pyridylcarbonyl, lower alkylpyridylcarbonyl, pyridylsulfonyl, pyrimidinylcarbonyl, lower alkylpyrimidinylcarbonyl, pyrazinylcarbonyl,
(Ha2) pyrrolidinylcarbonyl, pyrrolidinylsulfonyl, piperidinylcarbonyl, lower alkanoylpiperidinylcarbonyl, piperidinylsulfonyl, lower alkoxypiperidinylsulfonyl,
(Ha3) thienylcarbonoyl, thienylsulfonyl,
(Ha4) indolylcarbonyl, quinolylcarbonyl, isoquinolylcarbonyl,
(Ha5) furylcarbonyl,
(Ha9) benzothienylcarbonyl,
(Ha10) morpholinylcarbonyl, morpholinylsulfonyl
(e.g. 1-methyl-2-imidazolylcarbonyl, 4-pyrazolylcarbonyl, 2- or 3- or 4-pyridylcarbonyl, 3-methyl-2-pyridylcarbonyl, 3-pyridylsulfonyl, 4-methyl-5-pyrimidinylcarbonyl, 2-pyrazinylcarbonyl, 1-pyrrolidinylcarbonyl, 1-pyrrolidinylsulfonyl, 1- or 4-piperidinylcarbonyl, 1-acetyl-4-piperidinylcarbonyl, 1-piperidinylsulfonyl, 4-methoxy-1-piperidinylsulfonyl, 2- or 3-thienylcarbonyl, 2-thienylsulfonyl, 2-indolylcarbonyl, 3- or 8-quinolylcarbonyl, 1-isoquinolylcarbonyl, 2-furylcarbonyl, 2-benzothienylcarbonyl, 4-morpholinylcarbonyl, 4-morpholinylsulfonyl, etc.), (A13) lower cycloalkylcarbonyl, phenyl(lower)cycloalkylcarbonyl (e.g. cyclopropylcarbonyl, cyclobutylcarbonyl, cyclopentylcarbonyl, cyclohexylcarbonyl, 1-phenyl-1-cyclopropylcarbonyl, etc.), (A14) lower alkenoyl, phenyl(lower)alkenoyl (e.g. 3-methylcrotonoyl, 3-phenylacryloyl, etc.), (A16) lower alkanoyl (e.g. acetyl, propionyl, isobutyryl, isovaleryl, pivaloyl, hexanoyl, 3,3-dimethylbutyryl, 2-ethylbutyryl, etc.), phenyl(lower)alkanoyl, hydroxy(lower)alkanoyl, lower cycloalkyl(lower)alkanoyl, amino (lower) alkanoyl, lower alkoxy(lower)alkanoyl, lower alkoxy(lower)alkoxy(lower)alkanoyl, phenoxy(lower)alkanoyl, lower akanoyl substituted by amino and phenyl, lower akanoyl substituted by hydroxy and phenyl, lower alkanoyl substituted by lower alkoxy and phenyl, pyridyl(lower)alkanoyl, thienyl(lower)alkanoyl, and (e.g. 3-phenylpropionyl, 2-amino-2-phenylacetyl, 2-t-butoxycarbonylamino-2-phenylacetyl, 2-hydroxy-2-phenylacetyl, 2-hydroxy-3-phenylpropionyl, 2-methoxy-2-pheylacetyl, cyclopropylacetyl, cyclopentylacetyl, aminoacetyl, t-butoxycarbonylaminoacetyl, 3-aminopropionyl, 3-t-butoxycarbonylaminopropionyl, 2-aminoisovaleryl, 2-t-butoxycarbonylaminoisovarelyl, 2-aminopivaloyl, 2-t-butoxycarbonylaminopivaloyl, methoxyacetyl, (2-methoxyethoxy)acetyl, phenoxyacetyl, 2-pyridylacetyl, 3-thienylacetyl, etc.),

[10] The compound of above [9], wherein
$R^1$ is -optionally substituted phenyl or naphthyl selected from:
(Sa1) 4-methoxyphenyl, 4-ethoxyphenyl,
(Sa6) 4-chlorophenyl, 4-fluorophenyl,
(Sa7) 4-methylphenyl, 4-ethylphenyl, 4-propylphenyl, 4-isopropylphenyl,
(Sa8) 4-methylthiophenyl,
(Sa9) 2-(or 5-)oxazolylphenyl, 5-methyl-1,2,4-oxadiazol-3-ylphenyl, 1,1-dioxoisothiazolidin-2-ylphenyl, and
(Sa28) 4-trifluoromethyloxyphenyl,
$R^3$ is acyl selected from the group consisting of;
(A1) methylsulfonyl, ethylsulfonyl, propylsulfonyl, benzylsulfonyl,
(A5) dimethylaminosulfonyl, diethylaminosulfonyl, N-(2-methoxyethyl)aminosulfonyl, N-methyl-N-(2-methoxyethyl)aminosulfonyl,
(A7) benzoyl, 2-naphthoyl, 2- or 3- or 4-methoxybenzoyl, 2-ethoxybenzoyl, 2-propoxybenzoyl, 2,3- or 2,4- or 2,5-dimethoxybenzoyl, 2,3,4-trimethoxybenzoyl, 2- or 3- or 4-chlorobenzoyl, 2,3- or 2,4- or 2,5-dichlorobenzoyl, 2-fluorobenzoyl, 2-methylbenzoyl, 2-hydroxybenzoyl, 2-phenoxybenzoyl, 2-phenylbenzoyl, 2-trifluoromethylbenzoyl, 2,4-bis(trifluoromethyl)benzoyl, 2-nitorobenzoyl, 2-acetylbenzoyl, 2-trifluoromethyloxybenzoyl, 2-methoxy-4-chlorobenzoyl, 3-methoxy-2-hydroxybenzoyl,
(A8) 1-methyl-2-imidazolylcarbonyl, 4-pyrazolylcarbonyl, 2- or 3- or 4-pyridylcarbonyl, 3-methyl-2-pyridylcarbonyl, 3-pyridylsulfonyl, 4-methyl-5-pyrimidinylcarbonyl, 2-pyrazinylcarbonyl, 1-pyrrolidinylcarbonyl, 1-pyrrolidinylsulfonyl, 1- or 4-piperidinylcarbonyl, 1-acetyl-4-piperidinylcarbonyl, 1-piperidinylsulfonyl, 4-methoxy-1-piperidinylsulfonyl, 2- or 3-thienylcarbonyl, 2-thienylsulfonyl, 2-indolylcarbonyl, 3- or 8-quinolylcarbonyl, 1-isoquinolylcarbonyl, 2-furylcarbonyl, 2-benzothienylcarbonyl, 4-morpholinylcarbonyl, 4-morpholinylsulfonyl,
(A13) cyclopropylcarbonyl, cyclobutylcarbonyl, cyclopentylcarbonyl, cyclohexylcarbonyl, 1-phenyl-1-cyclopropylcarbonyl,
(A14) 3-methylcrotonoyl, 3-phenylacryloyl,
(A16) acetyl, propionyl, isobutyryl, isovaleryl, pivaloyl, hexanoyl, 3,3-dimethylbutyryl, 2-ethylbutyryl, 3-phenylpropionyl, 2-amino-2-phenylacetyl, 2-t-butoxycarbonylamino-2-phenylacetyl, 2-hydroxy-2-phenylacetyl, 2-hydroxy-3-phenylpropionyl, 2-methoxy-2-pheylacetyl, cyclopropylacetyl, cyclopentylacetyl, aminoacetyl, t-butoxycarbonylaminoacetyl, 3-aminopropionyl, 3-t-butoxycarbonylaminopropionyl, 2-aminoisovaleryl, 2-t-butoxycarbonylaminoisovarelyl, 2-aminopivaloyl, 2-t-butoxycarbonylaminopivaloyl, methoxyacetyl, (2-methoxyethoxy)acetyl, phenoxyacetyl, 2-pyridylacetyl, 3-thienylacetyl,

[11] The compound of above [4], wherein
$R^1$ is -($C_6$–$C_{10}$)aryloxy optionally substituted by the group consisting of lower alkoxy, lower alkyl and halo (e.g. methoxyphenoxy, methylphenoxy, chlorophenoxy, fluorophenyl, etc.);

$R^2$ is N-hydroxycarbamoyl
$R^3$ is -acyl selected from the group consisting of:
(A1) lower alkylsufonyl (e.g. methylsulfonyl, ethylsulfonyl, propylsulfonyl, etc.),
(A3) $C_6$–$C_{10}$ ar(lower)alkoxycarbonyl (e.g. benzyloxycarbonyl, etc),
(A4) fluorenylmethoxycarbony (e.g. 9-fluorenylmethoxycarbonyl, etc.),
(A5) mono- or di(lower)alkylaminosulfonyl optionally substituted by lower alkoxy (e.g. dimethylaminosulfonyl, (A6) mono- or di(lower)alkylcarbamoyl (e.g. propylcarbamoyl, isopropylcarbamoyl, t-butylcarbamoyl, etc.),
(A7) $C_6$–$C_{10}$ aroyl (e.g. benzoyl, etc.), $C_6$–$C_{10}$ aroyl substituted by lower alkoxy (e.g. 2-methoxybenzoyl, etc.),
(A8) heterocyclic-carbonyl or heterocyclic-sulfonyl, wherein the heterocyclic group being selected from;
(H1) unsaturated 5- or 6-membered, heteromonocyclic group containing 1 to 4 nitrogen atoms (e.g. pyridylcarbonyl, pyrazinylcarbonyl, etc.),
(H2) saturated 5- or 6-membered, heteromonocyclic group containing 1 to 4 nitrogen atoms (e.g. piperidinylcarbonyl, etc.),
(H3) unsaturated 5- or 6-membered, heteromonocyclic group containing 1 or 2 sulfur atoms (e.g. 2- or 3-thienylcarbonyl, 2-thienylsulfonyl, etc.), and
(H10) saturated 5- or 6-membered, heteromonocyclic group containing 1 or 2 oxygen atoms and 1 to 3 nitrogen atoms (e.g. morpholinylsulfonyl, etc.);
(preferable examples of heterocyclic acyl may be pyridylcarbonyl (e.g. 2- or 3- or 4-pyridylcarbonyl, etc.), pyrazinylcarbonyl (e.g. 2-pyrazinylcarbonyl, etc.), piperidinylcarbonyl (e.g. 1-piperidinylcarbonyl, etc.), thienylcarbonyl (e.g. 2- or 3-thienylcarbonyl, etc.), thienylsulfonyl (e.g. 2-thienylsulfonyl, etc.), morpholinylsulfonyl (e.g. 1-morpholinylsulfonyl, etc.),
(A9) lower cycloalkylcarbamoyl (e.g. cyclohexylcarbamoyl, etc.),
(A13) lower cycloalkylcarbonyl (e.g. cyclopropylcarbonyl, etc.) (A16) lower alkanoyl optionally substituted by the group consisting of $C_6$–$C_{10}$ aryl and hydroxy (e.g. isovaleryl, etc.) 2-hydroxy-2-phenylacetyl, and
Ar is phenyl.

[12] The compound of above [11], wherein
the compound has the following formula:

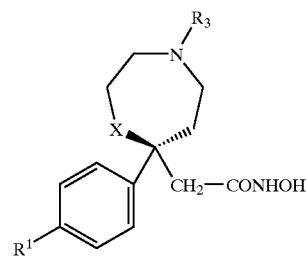

wherein $R^1$, $R^3$ and X are each as defined in above [11].

[13] The compound of above [12], wherein
$R^1$ is -($C_6$–$C_{10}$)aryloxy (e.g. phenoxy, etc.) optionally substituted by the group consisting of lower alkoxy, lower alkyl and halo (e.g. methoxyphenoxy, methylphenoxy, chlorophenoxy, fluorophenyl, etc.), $R^3$ is -acyl selected from the group consisting of:
(A1) lower alkylsufonyl (e.g. methylsulfonyl, ethylsulfonyl, propylsulfonyl, etc.),
(A3) $C_6$–$C_{10}$ ar(lower)alkoxycarbonyl (e.g. benzyloxycarbonyl, etc),
(A4) fluorenylmethoxycarbonyl (e.g. 9-fluorenylmethoxycarbonyl, etc.),
(A5) mono- or di(lower)alkylaminosulfonyl (e.g. dimethylaminosulfonyl, etc.),
(A6) mono- or di(lower)alkylcarbamoyl (e.g. propylcarbamoyl, isopropylcarbamoyl, t-butylcarbamoyl, etc.),
(A7) $C_6$–$C_{10}$ aroyl (e.g. benzoyl, etc.), $C_6$–$C_{10}$ aroyl substituted by lower alkoxy (e.g. 2-methoxybenzoyl, etc.),
(A8) heterocyclic-carbonyl or heterocyclic-sulfonyl, wherein the heterocyclic group being selected from;
(H1) unsaturated 5- or 6-membered, heteromonocyclic group containing 1 to 4 nitrogen atoms (e.g. pyridylcarbonyl, pyrazinylcarbonyl, etc.),
(H2) saturated 5- or 6-membered, heteromonocyclic group containing 1 to 4 nitrogen atoms (e.g. piperidinylcarbonyl, etc.),
(H3) unsaturated 5- or 6-membered, heteromonocyclic group containing 1 or 2 sulfur atoms (e.g. 2- or 3-thienylcarbonyl, 2-thienylsulfonyl, etc.), and
(H10) saturated 5- or 6-membered, heteromonocyclic group containing 1 or 2 oxygen atoms and 1 to 3 nitrogen atoms (e.g. morpholinylsulfonyl, etc.),
(preferable examples of heterocyclic acyl may be pyridylcarbonyl (e.g. 2- or 3- or 4-pyridylcarbonyl, etc.) pyrazinylcarbonyl (e.g. 2-pyrazinylcarbonyl, etc.), piperidinylcarbonyl (e.g. 1-piperidinylcarbonyl, etc.), thienylcarbonyl (e.g. 2- or 3-thienylcarbonyl, etc.), thienylsulfonyl (e.g. 2-thienylsulfonyl, etc.), morpholinylsulfonyl (e.g. 1-morpholinylsulfonyl, etc.),
(A9) lower cycloalkylcarbamoyl (e.g. cyclohexylcarbamoyl, etc.),
(A13) lower cycloalkylcarbonyl (e.g. cyclopropylcarbonyl, etc.), and
(A16) lower alkanoyl, lower alkanoyl substituted by the group consisting of $C_6$–$C_{10}$ and hydroxy (e.g. isovaleryl, 2-hydroxy-2-phenylacetyl, etc.).

[14] The compound of above [13], wherein
$R^1$ is -phenoxy, lower alkoxyphenoxy, lower alkylphenoxy or halophenoxy (e.g. 4-methoxyphenoxy, 4-ethoxyphenoxy, 4-methylphenoxy, 4-chlorophenoxy, 4-fluorophenyl, etc.);
$R^3$ is -acyl selected from the group consisting of:
(A1) lower alkylsufonyl (e.g. methylsulfonyl, ethylsulfonyl, propylsulfonyl, etc.),
(A3) phenyl(lower)alkoxycarbonyl (e.g. benzyloxycarbonyl, etc),
(A4) fluorenylmethoxycarbonyl (e.g. 9-fluorenylmethoxycarbonyl, etc.),
(A5) di(lower)alkylaminosulfonyl (e.g. dimethylaminosulfonyl, etc.),
(A6) (lower)alkylcarbamoyl (e.g. propylcarbamoyl, isopropylcarbamoyl, t-butylcarbamoyl, etc.),
(A7) benzoyl (e.g. benzoyl, etc.), benzoyl substituted by lower alkoxy (e.g. 2-methoxybenzoyl, etc.),
(A8) heterocyclic-carbonyl or heterocyclic-sulfonyl, selected from;
(H1) pyridylcarbonyl, pyrazinylcarbonyl (e.g. 2-pyridylcarbonyl, 2-pyrazinylcarbonyl, etc.),
(H2) piperidinylcarbonyl (e.g. 1-piperidinylcarbonyl, etc.),
(H3) thienylcarbonyl, thienylsulfonyl (e.g. 2- or 3-thienylcarbonyl, 2-thienylsulfonyl, etc.), and
(H10) morpholinylsulfonyl (e.g. 1-morpholinylsulfonyl, etc.),
(A9) lower cycloalkylcarbamoyl (e.g. cyclohexylcarbamoyl, etc.),
(A13) lower cycloalkylcarbonyl (e.g. cyclopropylcarbonyl, etc.), and
(A16) lower alkanoyl, lower alkanoyl substituted by phenyl and hydroxy (e.g. isovaleryl, 2-hydroxy-2-phenylacetyl, etc.).

[15] The compound of above [14], wherein
$R^1$ is -phenoxy, 4-methoxyphenoxy, 4-ethoxyphenoxy, 4-methylphenoxy, 4-chlorophenoxy, 4-fluorophenyl,
$R^3$ is -acyl selected from the group consisting of:
(A1) methylsulfonyl, ethylsulfonyl, propylsulfonyl,
(A3) benzyloxycarbonyl,
(A4) 9-fluorenylmethoxycarbonyl,
(A5) dimethylaminosulfonyl,
(A6) propylcarbamoyl, isopropylcarbamoyl, t-butylcarbamoyl,
(A7) benzoyl, 2-methoxybenzoyl,
(A8) heterocyclic-carbonyl or heterocyclic-sulfonyl, selected from;
(H1) 2-pyridylcarbonyl, 2-pyrazinylcarbonyl,
(H2) 1-piperidinylcarbonyl,
(H3) 2- or 3-thienylcarbonyl, 2-thienylsulfonyl, and
(H10) 1-morpholinylsulfonyl,
(A9) cyclohexylcarbamoyl,
(A13) cyclopropylcarbonyl, and
(A16) isovaleryl, 2-hydroxy-2-phenylacetyl.

The processes for preparing the object compounds are explained in detail in the following.

Process 1

The compound (I-b) or a salt thereof can be prepared by acylating the compound (I-a) or its reactive derivative at the amino group, or a salt thereof.

Suitable salts of the compounds (I-a) and (I-b) may be the same as those for the compound (I).

Suitable acylating agent used in this reaction may be a conventional acylating agent which is capable of introducing the acyl group as mentioned before, such as carboxylic acid, carbonic acid, sulfonic acid-and their reactive derivative, for example, an acid halide, an acid anhydride, an activated amide, an activated ester, and the like. Preferable example of such reactive derivative may include acid chloride, acid bromide, a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkyl carbonate (e.g. methyl carbonate, ethyl carbonate, propyl carbonate, etc.), aliphatic carboxylic acid (e.g. pivalic acid, pentanoic acid, isopentanoic acid, 2-ethylbutyric acid, trichloroacetic acid, etc.), aromatic carboxylic acid (e.g. benzoic acid, etc.), a symmetrical acid anhydride, an activated acid amide with a heterocyclic compound containing imino function such as imidazole, 4-substituted imidazole, dimethylpyrazole, triazole and tetrazole, an activated ester (e.g. p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyridyl ester, piperidinyl ester, 8-quinolyl thioester, or an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), isocyanic acid or a salt thereof (e.g. sodium isocyanate, etc.), lower alkylisocyanate (e.g. methylisocyanate, ethylisocyanate, etc.), and the like.

This reaction can be carried out in the presence of an organic or inorganic base such as alkali metal (e.g. lithium, sodium potassium, etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compound (e.g. pyridine, lutidine, picoline, 4-dimethylaminopyridine, etc.), quinoline, and the like.

In case that the acylating agent is used in a free form or its salt in this reaction, the reaction is preferably carried out in the presence of a condensing agent such as a carbodiimide compound [e.g. N,N'-dicyclohexylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), a ketenimine compound (e.g. N,N'-carbonylbis(2-methylimidazole), pentamethyleneketene-N-cyclohexylimine, diphenylketene-N-cyclohexylimine, etc.); an olefinic or acetylenic ether compounds (e.g. ethoxyacetylene, β-chlorovinylethyl ether), a sulfonic acid ester of N-hydroxybenzotriazole derivative [e.g. 1-(4-chlorobenzenesulfonyloxy)-6-chloro-1H-benzotriazole, etc.], a combination of trialkylphosphite or triphenylphosphine and carbon tetrachloride, disulfide or diazenedicarboxylate (e.g. diethyl diazenedicarboxylate, etc.), a phosphorus compound (e.g. ethyl polyphosphate, isopropyl polyphosphate, phosphoryl chloride, phosphorus trichloride, etc.), thionyl chloride, oxalyl chloride, N-ethylbenzisoxazolium salt, N-ethyl-5-phenylisoxazolium-3-sulfonate, a reagent (referred to a so-called "Vilsmeier reagent") formed by the reaction of an amide compound such as N,N-di(lower)alkylformamide (e.g. dimethylformamide, etc.), N-methylformamide or the like with a halogen compound such as thionyl chloride, phosphoryl chloride, phosgene or the like, and the like.

The reaction can be carried out in a conventional solvent which does not adversely influence the reaction such as water, acetone, dichloromethane, chloroform, alcohol (e.g. methanol, ethanol, etc.), tetrahydrofuran, pyridine, N,N-dimethylformamide, etc., or a mixture thereof.

The reaction temperature is not critical and the reaction can be carried out under from cooling to heating.

Process 2

The compound (I-d) or a salt thereof can be prepared by reacting the compound (I-c) or a salt thereof with the compound (II).

Suitable salts of the compound (I-c) and (I-d) may be the same as those exemplified for the compound (I).

The reaction can be carried out in a conventional solvent such as water, acetone, dioxane, acetonitrile, 1,2-dimethoxyethane, chloroform, methylene chloride, ethylene chloride, tetrahydrofuran, ethyl acetate, N,N-dimethylformamide, pyridine and dichloromethane, a mixture thereof, or any other organic solvents which do not adversely affect the reaction.

This reaction can be carried out in the presence of an organic or inorganic base such as alkali metal (e.g. lithium, sodium, potassium, etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compound (e.g. pyridine, lutidine, picoline, 4-dimethylaminopyridine, etc.), quinoline, lithium diisopropylamide, alkali metal halide (e.g. sodium iodide, potassium iodide, etc.), alkali metal thiocyanate (e.g. sodium thiocyanate, potassium thiocyanate, etc.), di(lower)alkyl azodicarboxylate (e.g. diethyl azodicarboxylate, diisopropyl azodicarboxylate, etc.), and the like.

The reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate (e.g. ethyl chloroformate, isopropyl chloroformate); triphenylphosphine; tetrakis(triphenylphosphine)palladium(0); 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; 1-hydroxybenzotriazole; or so-called Vilsmeier reagent prepared by the reaction of N,N-dimethylformamide with thionyl chloride, phosgene, trichloromethyl chloroformate, phosphorus oxychloride or oxalyl chloride.

The reaction temperature is not critical, and the reaction can be carried out under from warming to heating.

Process 3

The object compound (I-f) or a salt thereof can be prepared by subjecting a compound (I-e) or a salt thereof to a removal reaction of the hydroxycarbamoyl-protective group.

Suitable salts of the compounds (I-e) and (I-f) can be referred to the ones as exemplified for the compound (I).

This reaction is carried out in accordance with a conventional method such as solvolysis including hydrolysis, reduction or the like.

The solvolysis is preferably carried out in the presence of a base or an acid including Lewis acid.

Suitable base may include an inorganic base and an organic base such as an alkali metal [e.g. sodium, lithium, potassium, etc.], an alkaline earth metal [e.g. magnesium, calcium, etc.], the hydroxide or carbonate or bicarbonate thereof, hydrazine, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0] undec-7-ene, or the like.

Suitable acid may include and organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, hydrogen fluoride, boron trifluoride diethyl etherate, hydrogen iodide, etc.].

The removal reaction using Lewis acid such as trihaloacetic acid [e.g. trichloroacetic acid, trifluoroacetic acid, etc.] or the like, is preferably carried out in the presence of cation trapping agents [e.g. anisole, phenol, etc.].

The reaction can be carried out in a solvent such as water, an alcohol [e.g. methanol, ethanol, etc.], methylene chloride, chloroform, carbon tetrachloride, dioxane, tetrahydrofuran, N,N-dimethylformamide, a mixture thereof or any other solvent which does not adversely influence the reaction. A liquid base or acid can be also used as the solvent. The reaction temperature is not critical and the reaction can be carried out under cooling to heating.

The reduction method applicable for the removal reaction may include chemical reduction and catalytic reduction.

Suitable reducing agents to be used in chemical reduction may include a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like, and these catalysts may be used in a combination with ammonium formate (e.g. a combination of palladium on carbon and ammonium formate, etc.).

The reduction can be carried out in a conventional solvent which does not adversely influence the reaction such as water, methanol, ethanol, propanol, N,N-dimethylformamide, or a mixture thereof. Additionally, in case that the above-mentioned acid to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction can be carried out under cooling to heating.

Process 4

The compound (I-a) or a salt thereof can be prepared by subjecting the compound (I-b) or a salt thereof to a removal reaction of the acyl group.

The reaction of this process can be carried out in a manner similar to that of Process 3.

Process 5

The compound (I) or a salt thereof can be prepared by amidating the compound (III) or its reactive derivative at the carboxy group, or a salt thereof.

Suitable salts of the compound (III) may be the same as those for the compound (I).

Suitable reactive derivative at the carboxy group may include an acid halide, an acid anhydride, an activated amide, an activated ester, and the like. Suitable examples of the reactive derivatives may be an acid chloride; an acid azide; a mixed acid anhydride which acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl [$(CH_3)_2\overset{+}{N}=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (I-b) to be used.

The reaction can be carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may also be used in a mixture with water.

In this reaction, when the starting compound is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl) carbodiimide; N,N'-diethylcarbodiimide, N,N'-diisopropylcarbodiimide; 1-ethyl-3-(3-dimethylaminopropyl) carbodiimide (WSCD) its hydrochloricde; N,N'-carbonylbis (2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)-isoxazolium hydroxide intramolecular salt; N-hydroxybenzotriazole; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The amidation reaction applicable to this process may include a conventional amidation reaction which can convert a carboxy group to an amidated carboxy group as mentioned above, for example, reaction with an optionally protected hydroxylamine (e.g. hydroxylamine, tetrahydropyranyloxyamine, etc.), and the like.

The reaction may also be carried out in the presence of an inorganic or organic base as mentioned above such as an alkali metal bicarbonate, tri(lower)alkylamine, pyridine, N-(lower) alkylmorpholine, N,N-di (lower) alkylbenzylamine, alkali metal hydroxide, or the like.

The reaction temperature is not critical, and the reaction can be carried out under cooling to warming.

Process 6

The compound (I-h) or a salt thereof can be prepared by subjecting the compound (I-g) or a salt thereof to a removal reaction of the amino- or imino-protective group on $R_b^3$.

Suitable salts of the compounds (I-g) and (I-h) may be the same as those for the compound (I).

The reaction of this process can be carried out in a manner similar to that of Process 3.

Process 7

The compound (I-j) or a salt thereof can be prepared by acylating the compound (I-i) or a salt thereof.

Suitable salts of the compounds (I-i) and (I-j) may be the same as those for the compound (I).

The reaction of this process can be carried out in a manner similar to that of Process 1.

Process 8

The compound (I-k) or a salt thereof can be prepared by reacting the compound (I-c) or a salt thereof with the compound (IV).

Suitable salts of the compound (I-k) may be the same as those for the compound (I).

This reaction can preferably be carried out in the presence of palladium compound (e.g. palladium acetate, etc.), triphenylphosphine, copper compound (e.g. copper iodide, etc.), and aforementioned base (e.g. triethylamine, etc.).

The reaction can be carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction.

The reaction temperature is not critical, and the reaction is usually carried out under cooling to warming.

Process 9

The compound (I-l) or a salt thereof can be prepared by reacting the compound (I-a) or a salt thereof with the compound (V).

Suitable salts of the compound (I-l) may be the same as those for the compound (I).

This reaction can preferably be carried out in the presence of aforementioned chemical reducing agent (e.g. cyanoborohydride, triacetoxyborohydride, etc.), and aforementioned acid (e.g. acetic acid etc.).

The reaction can be carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction.

The reaction temperature is not critical, and the reaction is usually carried out under cooling to warming.

The compounds obtained above can be isolated and purified by a conventional method such as pulverization, recrystallization, column chromatography, reprecipitation and the like.

The object compounds can be transformed into their salts or solvates in a conventional manner.

It is to be noted that the object compounds may include one or more stereoisomers or optical isomers due to asymmetric carbon atoms, and all of such isomers and mixture thereof are included within the scope of this invention.

Collagenases initiate the degradation of collagen in vertebrates and, in addition to their normal function in the metabolism of connective tissue and wound healing, they have been implicated to be involved in a number of pathological conditions such as joint destruction in rheumatoid arthritis, periodontal disease, corneal ulceration, tumor metastasis, osteoarthritis, decubitus restenosis after percutaneous transluminal coronary angiopsty, osteoporosis, psoriasis, chronic active hepatitis, autoimmune keratitis, wrinkles, crow's-feet, crease, and the like, and therefore the compounds of the present invention are useful for treating and/or preventing such pathological conditions.

Inhibitory activity of MMP can be assayed by a conventional test method as mentioned below.

Test Methods:

Test Method 1:

Inhibitory Activity of Human MMP-1

Human collagenase was prepared from the culture medium of human skin fibroblast stimulated with interleukin-1β (1 ng/ml). Latent collagenase was activated by incubation with tryspin (200 μg/ml) at 37° C. for 60 minutes and the reaction was stopped by adding soybean trypsin inhibitor (800 μg/ml). Collagenase activity was determined using FITC-labeled calf skin type I collagen. FITC-collagen (2.5 mg/ml) was incubated at 37° C. for 120 minutes with the activated collagenase and test compound in 50 mM Tris buffer (containing 5 mM $CaCl_2$, 200 mM NaCl and 0.02% $NaN_3$, pH 7.5). After stopping the enzyme reaction by adding the equal volume of 70% ethanol-200 mM Tris buffer (pH 9.5), the reaction mixture was centrifuged, and collagenase activity was estimated by measuring the fluorescence intensity of supernatant at 495 nm (excitation) and 520 nm (emission).

Test Method 2:

Inhibitory Activity of Human MMP-8

The inhibitory potential of test compounds against human MMP-8 were assayed by using commercial kit (Chondrex, USA) contained recombinant human pro-MMP-8 and FITC-labeled telopeptide-free soluble bovine type I collagen as a substrate. Recombinant human pro-MMP-8 was activated by a sequential incubation with mercury compound and proteinase at 35° C. for 1 hour. Reaction mixture containing the activated MMP-8, substrate and test compounds were incubated at 35° C. for 2 hours. After stopping the enzyme reaction by adding the stop solution (o-phenathroline), the reaction mixture was centrifuged and MMP-8 activity was estimated by measuring the fluorescence intensity of supernatant at 490 nm (excitation) and 520 nm (emission).

Test Method 3:

Inhibitory Activity of Human MMP-9

The inhibitory activity of test compounds against human MMP-9 were measured by using commercial kits (Yagai, Japan). Gelatinolytic activity was determined by monitoring the degradation of FITC-labeled bovine type IV collagen after incubation for 4 hours at 42° C. The amount of degraded collagen was estimated by measuring the fluorescence intensity at 495 nm (excitation) and 520 nm (emission).

Test Method 4:

Inhibitory Activity of Human MMP-13

The inhibitory potential of test compounds against human MMP-13 were assayed by using commercial kit (Chondrex, USA) contained truncated form of human recombinant MMP-13 and fluorogenic peptide substrate. Activity of human MMP-13 was determined by monitoring the degradation of fluorogenic peptide substrate after incubation for 1 hour at 35° C. and estimated by measuring the fluorescence intensity of degraded peptide substrate at 495 nm (excitation) and 520 nm (emission).

For therapeutic purposes, the compounds and pharmaceutically acceptable salts thereof of the present invention can be used in the form of a pharmaceutical preparation containing, as an active ingredient, one of said compounds in admixture with a pharmaceutically acceptable carrier such as an organic or inorganic solid or liquid excipient suitable for oral, parenteral or external administration. The pharmaceutical preparations may be capsules, tablets, dragees, granules, solutions, suspensions, emulsions, sublingual tablets, suppositories, ointments, and the like. If desired, there may be included, in these preparations, auxiliary substances, stabilizing agents, wetting agents, emulsifying agents, buffers and other commonly used additives.

While the dose of the compound will vary depending upon the age and condition of patient and the like, in the case of intravenous administration, a daily dose of 0.01–100 mg of the active ingredient per kg weight of a human being, and in the case of intramuscular administration, a daily dose of 0.05–100 mg of the same per kg weight of a human being, or in the case of oral administration, a daily dose of 0.1–100 mg of the same per kg weight of a human being, is generally given for the treatment of MMP or TNFα-mediated diseases.

In order to illustrate the usefulness of the object compound, the pharmacological test data of a representative compound of the compounds are shown in the following.

Inhibitory Activity of MMP
1. Test Method
   Inhibitory activity of human MMP-9 as mentioned above.
2. Test Compound
   Compound of Example 17
3. Test Resut

| Test Compound | Inhibitory activity [IC$_{50}$ (nM)] |
|---|---|
| Example 17 | 2.85 |

The following Preparations and Examples are given for the purpose of illustrating the present invention in detail.

Preparation 1-1)

To a suspension of sodium hydride (60%, 16.6 g) in tetrahydrofuran (THF) (300 ml) was added a solution of triethyl phosphonoacetate (96.8 g) in tetrahydrofuran (300 ml) under ice-cooling. After the mixture was stirred at the same temperature for 30 minutes, a solution of 5-bromo-2-thiophenecarbaldehyde (75 g) in THF (500 ml) was added therein at −40° C. The reaction solution was allowed to warm to 0° C. for 2 hours. After addition of water (200 ml) under ice-cooling, the mixture was extracted with ethyl acetate.

The extract was washed successively with 5% hydrochloric acid, a saturated aqueous solution of sodium bicarbonate and brine, and dried over magnesium sulfate. After the solution was concentrated in vacuo, the resulting residue was purified by silica gel (SiO$_2$) column chromatography (eluent; hexane:ethyl acetate=10:1) to afford ethyl 3-(5-bromo-2-thienyl)acrylate as an oil (97.7 g).

NMR (CDCl$_3$, δ): 1.32 (3H, t, J=8 Hz), 4.24 (2H, q, J=8 Hz), 6.13 (1H, d, J=16 Hz), 6.99 (1H, d, J=3 Hz), 7.01 (1H, d, J=3 Hz), 7.65 (1H, d, J=16 Hz)

Preparation 1-2)

To a solution of 2-aminoethanethiol (37.5 g) and sodium hydroxide (15 g) in methanol (500 ml) was added a solution of ethyl 3-(5-bromo-2-thienylacrylate (97.7 g) in methanol (500 ml) under ice-cooling and a nitrogen atmosphere. After being stirred at room temperature for 3 days, the resulting precipitate was collected by filtration and washed with methanol (MeOH) to afford 7-(5-bromo-2-thienyl)perhydro-1,4-thiazepin-5-one (84.6 g) as a solid.

mp: 170–172° C. NMR (DMSO-d$_{36}$ δ): 2.67–2.87 (2H, m), 3.01 (1H, d, J=15 Hz), 3.20–3.32 (1H, m), 3.41–3.56 (2H, m), 4.50 (1H, d, J=9 Hz), 6.91 (1H, d, J=3 Hz), 7.07 (1H, d, J=3 Hz), 7.69–7.73 (1H, m)

Preparation 1-3)

Aluminum chloride (22.9 g) was added to a suspension of lithium aluminum hydride (19.5 g) in diethyl ether (400 ml) under ice-cooling and a nitrogen atmosphere, and the mixture was stirred for 20 minutes. After a suspension of 7-(5-bromo-2-thienyl)perhydro-1,4-thiazepin-5-one (75 g) in THF (500 ml) was added therein under the same condition, the reaction mixture was stirred at room temperature for 2 hours, poured into ice water and extracted with ethyl acetate (1500 ml). The extract was washed with brine, dried over magnesium sulfate and concentrated in vacuo to afford 7-(5-bromo-2-thienyl)perhydro-1,4-thiazepine (60.5 g) as a solid.

NMR (DMSO-d$_6$, δ): 1.86–2.02 (1H, m), 2.22–2.38 (1H, m), 2.66–2.98 (5H, m), 3.05–3.20 (1H, m), 4.44 (1H, dd, J=6, 10 Hz), 6.84 (1H, d, J=3 Hz), 7.04 (1H, d, J=3 Hz) MASS (ESI+) 279 (M+H)

Preparation 1-4)

To a solution of 7-(5-bromo-2-thienyl)perhydro-1,4-thiazepine (60.5 g) in chloroform (800 ml) was added a solution of di-tert-butyl dicarbonate (45.1 g) under ice-cooling. After being stirred for 30 minutes, the reaction mixture was concentrated in vacuo. The resulting solid was collected and washed with hexane to give 7-(5-bromo-2-thienyl)-4-tert-butoxycarbonylperhydro-1,4-thiazepine (73.8 g) as a solid.

mp: 78–79° C. NMR (CDCl$_3$, δ): 1.47 (9H, s), 2.03–2.25 (1H, m), 2.53–3.02 (3H, m), 3.15–3.38 (1H, m), 3.44–3.58 (1H, m), 3.65–3.75 (1H, m), 3.90–4.20 (2H, m), 6.71 (1H, d, J=3 Hz), 6.87 (1H, t, J=3 Hz)

Preparation 1-5)

To a solution of 7-(5-bromo-2-thienyl)-4-tert-butoxycarbonylperhydro-1,4-thiazepine (73.8 g) in methanol (500 ml) was added an aqueous solution (500 ml) of OXONE (2KHSO$_5$.KHSO$_4$.K$_2$SO$_4$) (156 g) under ice-cooling. After being stirred for 4 hours, the reaction mixture was concentrated in vacuo to remove methanol. The residue was extracted with ethyl acetate (1000 ml) and the extract was washed successively with a saturated aqueous solution of sodium bicarbonate and brine, dried over magnesium sulfate, and concentrated in vacuo. The residue was washed with hexane to afford 7-(5-bromo-2-thienyl)-4-tert-butoxycarbonylperhydro-1,4-thiazepine 1,1-dioxide (64.6 g) as a solid.

mp: 134–136° C. NMR (DMSO-d$_6$, δ): 1.42 (9H, s), 2.16–2.26 (2H, m), 3.32–3.78 (6H, m), 4.90–4.98 (1H, m), 6.97 (1H, d, J=3 Hz), 7.19 (1H, t, J=3 Hz) MASS (ESI−): 409 (MH)

Preparation 1-6)

To a solution of lithium diisopropylamide in tetrahydrofuran (10 ml) prepared from diisopropylamine (801 mg) and n-butyl lithium (5.18 ml, 1.53M in n-hexane) was added dropwise a solution of 7-(5-bromo-2-thienyl)-4-tert-butoxycarbonylperhydro-1,4-thiazepine 1,1-dioxide (2.5 g) in tetrahydrofuran (25 ml) at −50° C. under a nitrogen atmosphere. After the mixture was stirred for 15 minutes, a solution of tert-butyl bromoacetate (1.78 g) in tetrahydrofuran (5 ml) was added dropwise therein under the same condition and the reaction mixture was stirred for 30 minutes. After addition of a saturated aqueous solution of ammonium chloride, the mixture was extracted with ethyl acetate (50 ml). The extract was washed successively with 5% hydrochloric acid, a saturated aqueous solution of sodium bicarbonate and brine, dried over magnesium sulfate and concentrated in vacuo. The residue was purified by $SiO_2$ column chromatography (eluent; hexane:ethyl acetate=5:1) to afford tert-butyl-2-[7-(5-bromo-2-thienyl)-4-tert-butoxycarbonyl-1,1-dioxoperhydro-1,4-thiazepin-7-yl] acetate (1.62 g) as an amorphous powder.

NMR ($CDCl_3$, δ): 1.30, 1.32 (9H, s), 1.47, 1.50 (9H, s), 2.52–2.68 (1H, m), 2.80–2.90 (1H, m), 2.94–3.08 (1H, m), 3.13–3.42 (3H, m), 3.46–4.06 (4H, m), 6.96–7.02 (2H, m)

Preparation 1-7)

tert-Butyl 2-[7-(5-bromo-2-thienyl)-4-tert-butoxycarbonyl-1,1-dioxoperhydro-1,4-thiazepin-7-yl]acetate (6.0 g) was dissolved in trifluoroacetic acid (50 ml) and the reaction mixture was stirred at room temperature for 1 hour. After the mixture was concentrated in vacuo, the residue was dissolved in an aqueous solution (30 ml) of sodium carbonate (4.85 g). To the solution was added dropwise a solution of 9-fluorenylmethyl chloroformate (3.55 g) in dioxane (30 ml) at room temperature. After being stirred for 2 hours, the mixture was concentrated in vacuo to remove dioxane. The resulting aqueous layer was washed with diethyl ether, acidified with 6N hydrochloric acid to be pH 2 and extracted with ethyl acetate (150 ml). The extract was washed with brine, dried over magnesium sulfate, and concentrated in vacuo. The residue was washed with ethyl acetate and hexane to afford 2-[7-(5-bromo-2-thienyl)-4-(9-fluorenylmethoxycarbonyl)-1,1-dioxoperhydro-1,4-thiazepin-7-yl]acetic acid (5.38 g) as a solid.

mp: 190–191° C. (dec) NMR (DMSO-$d_6$ δ): 2.26–2.80 (2H, m), 3.01–3.26 (2H, m), 3.30–3.84 (6H, m), 4.26–4.49 (3H, m), 6.93, 7.02 (1H, d, J=3 Hz), 7.20, 7.21 (1H, d, J=3 Hz), 7.28–7.47 (4H, m), 7.62–7.73 (2H, m), 7.89 (2H, d, J=8 Hz) MASS (ESI-): 590 (MH)

Preparation 2

To a solution of 3-aminophenylboronic acid hemisulfate (5.0 g) in N,N-dimethylformamide was added triethylamine (7.49 ml) and ethyl chloroformate (3.5 g) at room temperature. After being stirred for 2 hours, the reaction mixture was concentrated in vacuo. The residue was partitioned between ethyl acetate and 1% aqueous citric acid solution. The separated organic layer was washed with brine, dried over sodium sulfate and evaporated in vacuo to give 3-(ethoxycarbonylamino)phenylboronic acid (3.5 g) as a solid.

NMR (DMSO-$d_6$, δ): 1.23 (3H, dd, J=7.5, 7.5 Hz), 4.10 (2H, ddd, J=7.5, 7.5, 7.5 Hz), 7.22 (1H, dd, J=7.5, 7.5 Hz), 7.40 (1H, d, J=7.5 Hz), 7.50 (1H, d, J=7.5 Hz), 7.76 (1H, s), 7.97 (2H, s), 9.48 (1H, s)

Preparation 3-1)

To a suspension of 2-[7-(5-bromo-2-thienyl)-4-(9-fluorenylmethoxycarbonyl)-1,1-dioxoperhydro-1,4-thiazepin-7-yl]acetic acid (68.5 g) in ethanol (500 ml) and acetonitrile (500 ml) was added a solution of (S)-(-)-α-methylbenzylamine (14.1 g) in ethanol (10 ml) at room temperature. After being stirred for 5 hours, the resulting solid was collected and washed with acetonitrile to give (S)-(-)-α-methylbenzylamine salt (42.5 g). A suspension of the resulting salt in ethanol (900 ml) and acetonitrile (600 ml) was refluxed with stirring to be dissolved. After the solution was cooled to room temperature, the resulting crystal was collected and washed with acetonitrile to afford 2-[(S)-7-(5-bromo-2-thienyl)-4-(9-fluorenylmethoxycarbonyl)-1,1-dioxoperhydro-1,4-thiazepin-7-yl]acetic acid (S)-(-)-α-methylbenzylamine salt (24.0 g).

optical purity: 95% ee analytical chiral HPLC (column: Chiralpack AS (4.6×250 mm, Daicel Chemical Industries, Ltd.), eluent: 20% EtOH in Hexane containing 0.1% TFA, detection: 220 nm, flow rate: 1 ml/minutes), retention time, (S)-form: 43.0 minutes, (R)-form: 19.8 minutes mp: 201–203° C. (dec.) NMR (DMSO-$d_6$, δ): 1.36 (3H, d, J=7 Hz), 2.39–3.03 (4H, m), 3.15–3.84 (6H, m), 4.18 (1H, q, J=7 Hz), 4.26–4.46 (3H, m), 6.88, 6.95 (1H, d, J=3 Hz), 7.09–7.17 (1H, m), 7.25–7.45 (9H, m), 7.59–7.71 (2H, m), 7.82–7.93 (2H, m) MLASS (ESI-): 590 (M-H)

Preparation 3-2)

To a suspension of 2-[(S)-7-(5-bromo-2-thienyl)-4-(9-fluorenylmethoxycarbonyl)-1,1-dioxoperhydro-1,4-thiazepin-7-yl]acetic acid (S)-(-)-α-methylbenzylamine salt (18.0 g) in ethyl acetate (500 ml) was added 1M hydrochloric acid (500 ml) at room temperature. After being stirred for 20 minutes, an organic layer was separated and washed successively with 5% hydrochloric acid and brine, dried over magnesium sulfate, and concentrated in vacuo to give 2-[(S)-7-(5-bromo-2-thienyl)-4-(9-fluorenylmethoxycarbonyl)-1,1-dioxoperhydro-1,4-thiazepin-7-yl]acetic acid (14.6 g) as an amorphous powder.

$[α]_D^{20}$: -72.0° (c1.0, MeOH) NMR (DMSO-$d_6$, δ): 2.31–2.80 (2H, m), 3.00–3.26 (2H, m), 3.40–3.82 (6H, m), 4.26–4.50 (3H, m), 6.93, 7.03 (1H, d, J=3 Hz), 7.20, 7.22 (1H, d, J=3 Hz), 7.28–7.47 (4H, m), 7.62–7.73 (2H, m), 7.90 (2H, d, J=7 Hz) MASS (ESI-): 590 (M-H)

Preparation 3-3)

N-(2-Tetrahydropyranyloxy)-2-[(S)-7-(5-bromo-2-thienyl)-4-(9-fluorenylmethoxycarbonyl)-1,1-dioxoperhydro-1,4-thiazepin-7-yl]acetamide (18.0) was obtained in a similar manner to that of Example 30.

NMR (DMSO-$d_6$, δ): 1.40–1.66 (6H, m), 2.62–3.04 (4H, m), 3.36–3.94 (8H, m), 4.26–4.48 (4H, m), 6.93–7.08 (1H, m), 7.17–7.24 (1H, m), 7.30–7.48 (4H, m), 7.63–7.73 (2H, m), 7.90 (2H, d, J=7 Hz) MASS (ESI-): 687 (M-H)

Preparation 4

3-(Methoxycarbonylamino)phenylboronic acid (5 g) was obtained in a similar manner to that of Preparation 2.

NMR (DMSO-$d_6$, δ): 3.65 (3H, s), 7.20–7.30 (2H, m) 7.50–7.55 (2H, m), 7.99 (2H, s)

Preparation 5

3-(Methylaminocarbonylamino)phenylboronic acid (3 g) was obtained by reacting with methyl isocyanate in a similar manner to that of Preparation 2.

NMR (DMSO-$d_6$, δ): 2.63 (3H, d, J=5.2 Hz), 5.97 (1H, d, J=5.2 Hz), 7.15 (1H, dd, J=7.5, 7.5 Hz), 7.31 (1H, d, J=7.5 Hz), 7.55–7.59 (2H, m), 7.97 (1H, s), 8.37 (1H, s)

Preparation 6

3-(Ethylaminocarbonylamino)phenylboronic acid (3 g) was obtained in a similar manner to that of Preparation 5.

NMR (DMSO-$d_6$, δ): 1.04 (3H, dd, J=7.2, 7.2 Hz), 3.09 (2H, m), 6.06 (1H, dd, J=6.5, 6.5 Hz), 7.17 (1H, dd, J=7.5, 7.5 Hz), 7.30 (2H, d, J=7.5 Hz), 7.56 (2H, d, J=7.5 Hz), 7.94 (2H, s), 8.29 (1H, s)

Preparation 7

To a solution of 3-aminophenylboronic acid hemisulfate (500 mg), ethoxyacetic acid (336 mg), 4-(dimethylamino) pyridine (50 mg) and 1-hydroxybenzotriazole (436 mg) in N,N-dimethylformamide (7 ml) was added water-soluble carbodiimide (WSCD) (501 mg). After being stirred for 5 hours at room temperature, the reaction mixture was concentrated in vacuo. The residue was partitioned between ethyl acetate and 1% aqueous citric acid solution. The separated organic layer was washed with brine, dried over sodium sulfate and evaporated in vacuo to give 3-(ethoxyacetylamino)phenylboronic acid (450 mg) as a solid.

NMR (DMSO-$d_6$, δ): 1.19 (3H, dd, J=7.2, 7.2 Hz), 3.56 (2H, ddd, J=7.2, 7.2, 7.2 Hz), 4.01 (2H, s), 7.27 (1H, dd, J=7.8, 7.8 Hz), 7.50 (1H, d, J=7.2 Hz), 7.71 (1H, d, J=7.2 Hz), 7.88 (1H, s), 8.02 (2H, s), 9.58 (1H, s)

Preparation 8

3-(Phenoxyacetylamino)phenylboronic acid (400 mg) was obtained in a similar manner to that of Preparation 7.

NMR (DMSO-$d_6$, δ): 4.68 (2H, s), 6.96–7.02 (3H, m), 7.27–7.35 (3R, m), 7.51 (1H, d, J=7.2 Hz), 7.71 (1H, d, J=7.2 Hz), 7.89 (1H, s), 8.03 (2H, s)

Preparation 9-1)

A mixture of 4-bromobenzaldehyde (5.00 g), p-toluenesulfonylmethyl isocyanide (5.43 g) and potassium carbonate (5.60 g) in methanol (50 ml) was heated under reflux for 2 hours. After evaporation of solvent, ethyl acetate and saturated ammonium chloride solution were added. The organic layer was separated, washed with water and brine, dried over magnesium sulfate, and evaporated in vacuo. The residue was purified by silica gel column chromatography eluting with a mixture of hexane and ethyl acetate (2:1) to give 5-(4-bromophenyl)oxazole as a pale yellow powder (5.77 g).

NMR (CDCl$_3$, δ): 7.37 (1H, s), 7.48–7.62 (5H, m), 7.92 (1H, s)

Preparation 9-2)

A mixture of 5-(4-bromophenyl)oxazole (1.34 g), bis(pinacolato)diboron (1.52 g), dichlorobis(triphenylphosphine)palladium(II) (126 mg) and potassium acetate (2.35 g) in 1,4-dioxane (20 ml) was stirred at 80° C. for 24 hours to give 4-(5-oxazolyl)phenylboronic acid pinacol cyclic ester. The mixture was used for the following reaction without purification.

Preparation 10

2-Naphthylboronic acid pinacol cyclic ester was obtained in a similar manner to that of Preparation 9-2).

Preparation 11-1)

tert-Butyl 2-[4-tert-butoxycarbonyl-7-(5-(4-(5-oxazolyl)phenyl)-2-thienyl)-1,1-dioxoperhydro-1,4-thiazepin-7-yl]acetate (5.3 g) was obtained in a similar manner to that of Example 8.

NMR (DMSO-$d_6$, δ): 1.25 (9H, d, J=4 Hz), 1.44 (9H, d, J=7 Hz), 2.54–3.36 (4H, m), 3.36–3.92 (6H, m), 7.19–7.24 (1H, m), 7.55–7.59 (1H, m), 7.25–7.31 (5H, m), 8.48 (1H, s) MASS (ES+) m/e: 589.07

Preparation 11-2)

To a solution of tert-butyl 2-[4-tert-butoxycarbonyl-7-(5-(4-(5-oxazolyl)phenyl)-2-thienyl)-1,1-dioxoperhydro-1,4-thiazepin-7-yl]acetate (4.7 g) in ethyl acetate (40 ml) was added dropwise a solution 4N-hydrogen chloride in ethyl acetate (40 ml) under ice-cooling. After being stirred at 0° C. for 30 minutes and at ambient temperature for 1 hour, reaction mixture was concentrated in vacuo and hydrogen chloride was azeotropically removed with toluene to give tert-butyl 2-[7-(5-(4-(5-oxazolyl)phenyl)-2-thienyl)-1,1-dioxoperhydro-1,4-thiazepin-7-yl]acetate hydrochloride (4.2 g) as an oil.

NMR (DMSO-$d_6$, δ): 1.23 (9H, s), 2.60–3.8.1 (8H, m), 4.12–4.26 (2H, m), 7.25 (1H, d, J=4 Hz), 7.51 (1H, d, J=4 Hz), 7.76–7.86 (5H, m), 8.49 (1H, s), 9.59 (2H, br peak) MASS (ES+) m/e: 489.25 (M(free)+H)

Preparation 11-3)

To a mixture of tert-butyl 2-(7-(5-(4-(5-oxazolyl)phenyl)-2-thienyl)-1,1-dioxoperhydro-1,4-thiazepin-7-yl]acetate hydrochloride (4.2 g) and triethylamine (2.43 g) in a mixture of chloroform (24 ml) and N,N-dimethylformamide (12 ml) was added dropwise a solution of 9-fluorenylmethyl chloroformate (2.28 g) in chloroform (5 ml) under ice-cooling. After being stirred for 30 minutes, the mixture was concentrated in vacuo. The residue was dissolved in ethyl acetate and the solution was washed with water, a saturated aqueous sodium bicarbonate solution and brine, dried over magnesium sulfate, and evaporated in vacuo to give tert-butyl 2-[4-(9-fluorenylmethoxycarbonyl)-7-(5-(4-(5-oxazolyl)phenyl)-2-thienyl)-1,1-dioxoperhydro-1,4-thiazepin-7-yl] acetate (5.8 g) as an amorphous powder.

NMR (DMSO-$d_6$, δ): 2.25–3.95 (10H, m), 4.23–4.54 (3H, m), 7.18, 7.20 (1H, d, J=4 Hz), 7.27–7.50 (4H, m), 7.57 (1H, d, J=4 Hz), 7.64–7.96 (9H, m), 8.48–8.49 (1H, m) MASS (ES+) m/e: 711.16

Preparation 11-4)

A mixture of tert-butyl 2-[4-(9-fluorenylmethoxycarbonyl)-7-(5-(4-(5-oxazolyl)phenyl)-2-thienyl)-1,1-dioxoperhydro-1,4-thiazepin-7-yl]acetate (5.8 g) in 4N-hydrogen chloride in ethyl acetate (60 ml) was stirred for 6 hours at ambient temperature. The reaction mixture was concentrated in vacuo and the residue was washed with a mixture of ethyl acetate and ether (5:1, v/v) to give 2-[4-(9-fluorenylmethoxycarbonyl-7-(5-(4-(5-oxazolyl)phenyl)-2-thienyl)-1,1-dioxoperhydro-1,4-thiazepin-7-yl)acetic acid (4.65 g) as a powder.

NMR (DMSO-$d_6$, δ): 2.36–3.93 (10H, m), 4.25–4.53 (3H, m), 7.12, 7.20 (1H, d, J=4 Hz), 7.28–7.50 (4H, m), 7.55–7.60 (1H, m), 7.64–7.99 (9H, m), 8.48–8.49 (1H, m) MASS (ES–) m/e: 653.07

Preparation 12

4–Chlorophenylboronic acid pinacol cyclic ester was obtained in a similar manner to that of Preparation 9-2).

Preparation 13-1)

To a suspension of 4-bromophenol (5.00 g) and potassium carbonate (5.99 g) in anhydrous dimethylformamide (25 ml) was added ethyl iodide (2.77 ml) under ice-water cooling and the mixture was stirred at 0° C. for 2 hours. The mixture was partitioned between ethyl acetate and water. The organic layer was separated, washed with 2N aqueous sodium hydroxide solution, water and brine, dried over magnesium sulfate, and evaporated in vacuo to give 4-ethoxybromobenzene as yellow oil (5.44 g).

NMR (CDCl$_3$, δ): 1.40 (3H, t, J=7 Hz), 3.99 (2H, q, J=7 Hz), 6.77 (2H, d, J=8 Hz), 7.35 (2H, d, J=8 Hz)

The following compounds were obtained in a similar manner to that of Preparation 9-2).

Preparation 13-2)

4-ethoxyphenylboronic acid pinacol cyclic ester

Preparation 14

4-Ethylphenylboronic acid pinacol cyclic ester

Preparation 15

4-Vinylphenylboronic acid pinacol cyclic ester

Preparation 16-1)

Ethyl 4-phenoxybenzeneacrylate (6.3 g) was obtained in a similar manner to that of Preparation 1-1).

NMR (CDCl$_3$, δ): 1.34 (3H, t, J=8 Hz), 4.26 (2H, q, J=8 Hz), 6.35 (1H, d, J=18 Hz), 6.98 (2H, d, J=8 Hz), 7.04 (2H, d, J=8 Hz), 7.16 (1H, t, J=8 Hz), 7.37 (2H, t, J=8 Hz), 7.49 (2H, d, J=8 Hz), 7.65 (1H, d, J=18 Hz) MASS (ESI+): 269 (MH)

Preparation 16-2)

7-(4-Phenoxyphenyl)perhydro-1,4-thiazepin-5-one (2.6 g) was obtained in a similar manner to that of Preparation 1-2).

mp: 217–219° C. NMR (DMSO-$d_6$, δ): 2.62–2.90 (3H, m), 3.41–3.65 (3H, m), 4.17 (1H, d, J=9.5 Hz), 6.92 (2H, d,

J=8 Hz), 7.02 (2H, d, J=8 Hz), 7.15 (1H, t, J=8 Hz), 7.39–7.44 (2H, m), 7.78 (1H, br s)

Preparation 16-3)

7-(4-Phenoxyphenyl)perhydro-1,4-thiazepine (470 mg) was obtained in a similar manner to that of Preparation 1-3).

NMR (CDCl$_3$ δ): 2.00–2.16 (1H, m), 2.28–2.42 (1H, m), 2.83–3.06 (4H, m), 3:16–3.35 (2H, m), 3.98 (1H, dd, J=5, 10 Hz), 6.95 (2H, d, J=8 Hz), 7.02 (2H, d, J=8 Hz), 7.11 (1H, t, J=8 Hz), 7.23–7.38 (4H, m)

Preparation 16-4)

4-tert-Butoxycarbonyl-7-(4-phenoxyphenyl)perhydro-1, 4-thiazepine (2.47 g) was obtained in a similar manner to that of Preparation 1-4).

NMR (DMSO-d$_6$, δ): 1.43 (9H, S), 2.00–2.30 (2H, m), 2.78–2.99 (2H, m), 3.29–3.75 (4H, m), 3.82–3.93 (1H, m), 6.93 (2H, d, J=8 Hz), 7.00 (2H, d, J=8 Hz), 7.14 (1H, t, J=8 Hz), 7.28 (2H, d, J=8 Hz), 7.39 (2H, t, J=8 Hz)

Preparation 16-5)

4-tert-Butoxycarbonyl-7-(4-phenoxyphenyl)perhydro-1, 4-thiazepine 1,1-dioxide (5.80 g) was obtained in a similar manner to that of Preparation 1-5).

mp: 152–153° C. NMR (DMSO-d$_6$, δ): 1.44 (9H, s), 2.01–2.16 (1H, m), 2.25–2.42 (1H, m), 3.36–3.77 (6H, m), 4.49–4.58 (1H, m), 6.96–7.02 (2H, m), 7.05 (2H, d, J=8 Hz), 7.18 (1H, t, J=8 Hz), 7.30–7.36 (2H, m), 7.42 (2H, t, J=8 Hz) MASS (ESI+): 418 (M+H)

Preparation 16-6)

tert-Butyl 2-[4-tert-butoxycarbonyl-7-(4-phenoxyphenyl) perhydro-1,1-dioxo-1,4-thiazepin-7-yl]acetate (2.02 g), was obtained in a similar manner to that of Preparation 1-6).

NMR (DMSO-d$_6$, δ): 1.20, 1.22 (9H, s), 1.44 (9H, s), 2.42–2.52 (1H, m), 2.57–2.74 (1H, m), 2.88–3.08 (2H, m), 3.32–3.94 (6H, m), 6.97–7.11 (4H, m), 7.18 (1H, t, J=8 Hz), 7.37–7.55 (4H, m)

Preparation 16-7)

2-[4-Benzoyl-7-(4-phenoxyphenyl)perhydro-1,1-dioxo-1,4-thiazepin-7-yl]acetic acid (170 mg) was obtained in a similar manner to that of Preparation 1-7).

NMR (DMSO-d$_6$, δ): 2.44–2.76 (1H, m), 2.92–3.30 (2H, m), 3.37–4.04 (7H, m), 6.92–7.09 (4H, m), 7.19 (1H, t, J=8 Hz), 7.37–7.56 (9H, m) MASS (ESI−): 478 (M−H)

Preparation 17

2-[4-(9-Fluorenylmethoxycarbonyl)-7-(4-phenoxyphenyl)perhydro-1,1-dioxo-1,4-thiazepin-7-yl] acetate (985 mg) was obtained in a similar manner to that of Preparation 1-7).

NMR (DMSO-d$_6$, δ): 2.25–2.58 (2H, m), 2.72–3.87 (8H, m), 4.28–4.51 (3H, m), 6.93–7.10 (4H, m), 7.16–7.24 (1H, m), 7.29–7.48 (8H, m), 7.62–7.71 (2H, m), 7.84–7.94 (2H, m)

Preparation 18-1)

4-Benzyloxycarbonyl-7-(4-phenoxyphenyl)perhydro-1, 4-thiazepine (670 mg) was obtained in a similar manner to that of Example 1.

NMR (CDCl$_3$, δ): 2.03–2.28 (1H, m), 2.36–2.59 (1H, m), 2.78–3.04 (2H, m), 3.33–3.84 (4H, m), 4.02–4.25 (1H, m), 5.13–5.27 (2H, m), 6.94 (2H, d, J=8 Hz), 7.00 (2H, d, J=8 Hz), 7.06–7.44 (10H, m)

Preparation 18-2)

4-Benzyloxycarbonyl-7-(4-phenoxyphenyl)perhydro-1, 1-dioxo-1,4-thiazepine (507 mg) was obtained in a similar manner to that of Preparation 1-5).

mp: 141–143° C. NMR (CDCl$_3$, δ): 2.26–2.46 (1H, m), 2.50–2.78 (1H, m), 3.22–3.63 (4H, m), 3.96–4.25 (3H, m), 5.13–5.30 (2H, m), 6.96 (2H, d, J=8 Hz), 7.04 (2H, d, J=8 Hz), 7.14 (1H, t, J=8 Hz), 7.19–7.43 (9H, m)

Preparation 18-3)

tert-Butyl 2-[4-benzyloxycarbonyl-7-(4-phenoxyphenyl) perhydro-1,1-dioxo-1,4-thiazepin-7-yl]acetate (75 mg) was obtained in a similar manner to that of Preparation 1-6).

NMR (CDCl$_3$, δ): 1.21, 1.26 (9H, s), 2.58–2.70 (1H, m), 2.86 (1H, d, J=16 Hz), 3.14–3.36 (3H, m), 3.47–3.76 (3H, m), 3.86–4.23 (2H, m), 5.11–5.25 (2H, m), 6.90–7.06 (4H, m), 7.15 (1H, t, J=8 Hz), 7.28–7.38 (7H, m), 7.44–7.55 (2H, m)

Preparation 18-4)

tert-Butyl 2-[4-benzyloxycarbonyl-7-(4-phenoxyphenyl) perhydro-1,1-dioxo-1,4-thiazepin-7-yl]acetate (56 mg) was dissolved in trifluoroacetic acid (6 ml) at room temperature. After being stirred at the same temperature for 2 hours, the reaction mixture was concentrated in vacuo to give 2-[4-benzyloxycarbonyl-7-(4-phenoxyphenyl)perhydro-1,1-dioxo-1,4-thiazepin-7-yl]acetic acid (46 mg) as a powder.

NMR (CDCl$_3$, δ): 2.52–2.70 (1H, m), 2.96 (1H, d, J=19 Hz), 3.10–3.36 (3H, m), 3.47–3.72 (3H, m), 3.38–4.22 (2H, m), 5.10–5.26 (2H, m), 6.93 (2H, t, J=8 Hz), 7.01 (2H, d, J=8 Hz), 7.15 (1H, t, J=8 Hz), 7.23–7.54 (9H, m) MASS (ESI−): 508 (M−H)

Preparation 19-1)

7-(4-Methoxyphenyl)perhydro-1,4-thiazepin-5-one (7.17 g) was obtained in a similar manner to that of Preparation 1-2).

mp: 192–193° C. NMR (DMSO-d$_6$, δ): 2.58–2.86 (3H, m), 3.38–3.63 (3H, m), 3.74 (3H, s), 4.10 (1H, d, J=14 Hz), 6.89 (2H, d, J=8 Hz), 7.27 (2H, d, J=8 Hz) MASS (ESI+): 238(M+H)

Preparation 19-2)

4-tert-Butoxycarbonyl-7-(4-methoxyphenyl)perhydro-1, 4-thiazepine (8.90 g) was obtained in a similar manner to those of Preparations 1-3) and 1-4).

NMR (CDCl$_3$, δ): 1.49, 5.00 (9H, s), 2.04–2.24 (1H, m), 2.37–2.56 (1H, m), 2.72–3.03 (2H, m), 3.20–3.46 (1H, m), 3.52–3.55 (2H, m), 3.70–3.78 (1H, m), 3.78, 3.80 (3H, s), 3.90–4.20 (1H, m), 6.79–6.88 (2H, m), 7.18–7.25 (2H, m) MASS (ESI−): 322 (M−H)

Preparation 19-3)

4-tert-Butoxycarbonyl-7-(4-methoxyphenyl)perhydro-1, 1-dioxo-1,4-thiazepine (7.30 g) was obtained in a similar manner to that of Preparation 1-5).

mp: 135–136° C. NMR (DMSO-d$_6$, δ): 1.44 (9H, s), 1.98–2.12 (1H, m), 2.25–2.44 (1H, m), 3.35–3.73 (6H, m), 3.76 (3H, s), 4.42–4.49 (1H, m), 6.92–6.97 (2H, m), 7.22–7.28 (2H, m) MASS (ESI−): 354(M−H)

Preparation 19-4)

tert-Butyl 2-[4-tert-butoxycarbonyl-7-(4-methoxyphenyl) perhydro-1,1-dioxo-1,4-thiazepin-7-yl]acetate (2.14 g) was obtained in a similar manner to that of Preparation 1-6).

NMR (DMSO-d$_6$, δ): 1.20, 1.21 (9H, s), 1.44 (9H, s), 2.38–2.52 (1H, m), 2.88–3.10 (2H, m), 3.35–4.93 (7H, m), 3.76 (3H, s), 6.95 (2H, d, J=8 Hz), 7.39 (2H, t, J=8 Hz)

Preparation 19-5)

2-[4-Benzoyl-7-(4-methoxyphenyl)perhydro-1,1-dioxo-1,4-thiazepin-7-yl]acetic acid (200 mg) was obtained in a similar manner to that of Preparation 1-7).

NMR (DMSO-d$_6$, δ): 2.40–2.74 (1H, m), 2.92–3.18 (2H, m), 3.35–4.32 (7H, m), 3.75, 3.77 (3H, m), 6.88–7.02 (2H, m), 7.32–7.55 (7H, m) MASS (ESI): 416 (M−H)

Preparation 20-1)

To a solution of tert-butyl 2-[7-(5-bromo-2-thienyl)-4-tert-butoxycarbonyl-1,1-dioxoperhydro-1,4-thiazepin-7-yl] acetate (5.00 g) in ethyl acetate (25 ml) was added 4N hydrochloric acid in ethyl acetate (13 ml) with ice-cooling. After stirring for 4 hours at room temperature, the mixture was poured into saturated aqueous sodium bicarbonate (50 ml). The separated organic layer was washed with brine, dried over sodium sulfate and filtered. The obtained filtrate was concentrated to give tert-butyl 2-[7-(5-bromo-2-thienyl)-1,1-dioxoperhydro-1,4-thiazepin-7-yl]acetate (3.03 g) as a solid.

NMR (CDCl$_3$, δ): 1.30 (9H, s), 2.48 (1H, td, J=5, 16 Hz), 2.88–3.00 (1H, m), 3.02–3.37 (7H, m), 3.46 (1H, d, J=15 Hz), 7.00 (2H, s)

Preparation 20-2)

To a solution of tert-butyl 2-[7-(5-bromo-2-thienyl)-1,1-dioxoperhydro-1,4-thiazepin-7-yl]acetate (3.03 g) in ethanol (90 ml) was added (1R)-10-camphorsulfonic acid (912 mg) at 80° C. The clear solution was allowed to cool to room temperature with stirring for 2 hours to form crystalline solids. After being cooled on an ice bath for 30 minutes, the solids were collected and washed with ethanol to give tert-butyl 2-[(S)-7-(5-bromo-2-thienyl)-1,1-dioxoperhydro-1,4-thiazepin-7-yl]acetate•(1R)-10-camphorsulfonate (1.79 g, 91.6% ee) as a white solid.

Optical purity of the amine was measured by HPLC according to the following condition.
 column: chiralcel OD-R (0.46 cm×25 cm, daicel),
 eluent: 40% CH$_3$CN in 0.5M aq. NaClO$_4$,
 flow rate: 0.5 ml/min, wave length: 254 nm,
 temperature: room temperature, retention time: 17 min ((R)-isomer), 20 min ((S)-isomer)

NMR (CDCl$_3$, δ): 0.85 (3H, s), 1.04 (3H, s), 1.29 (9H, s), 1.36–1.54 (1H, m), 1.55–1.88 (1H, m), 1.92 (1H, d, J=18 Hz), 1.96–2.13 (2H, m), 2.28–2.47 (2H, m), 2.86 (1H, d, J=11 Hz), 2.97–3.14 (2H, m), 3.25 (2H, t, J=14 Hz), 3.35 (1H, d, J=15 Hz), 3.46 (1H, dd, J=7, 15 Hz), 3.65–3.93 (4H, m), 3.99–4.11 (1H, m), 6.98 (1H, d, J=4 Hz), 7.23 (1H, d, J=4 Hz)

Preparation 20-3)

A suspension of tert-butyl 2-[7-(5-bromo-2-thienyl)-1,1-dioxoperhydro-1,4-thiazepin-7-yl]acetate•(1R)-10-camphorsulfonate (300 mg, 91.6% ee) in a mixture of ethanol (9 ml) and ethyl acetate (9 ml) was stirred for 30 minutes at 80° C. After cooling to room temperature, the suspension was stirred for 30 minutes on an ice bath. The obtained solid was collected and washed with ethanol-ethyl acetate (1:1) to give tert-butyl 2-[7-(5-bromo-2-thienyl)-1,1-dioxoperhydro-1,4-thiazepin-7-yl]acetate•(1R)-10-camphorsulfonate (256 mg, 99.6% ee.)

NMR (CDCl$_3$, δ): 0.85 (3H, s), 1.04 (3H, s), 1.29 (9H, s), 1.36–1.54 (1H, m), 1.55–1.88 (1H, m), 1.92 (1H, d, J=18 Hz), 1.96–2.13 (2H, m), 2.28–2.47 (2H, m), 2.86 (1H, d, J=11 Hz), 2.97–3.14 (2H, m), 3.25 (2H, t, J=14 Hz), 3.35 (1H, d, J=15 Hz), 3.46 (1H, dd, J=7, 15 Hz), 3.65–3.93 (4H, m), 3.99–4.11 (1H, m), 6.98 (1H, d, J=4 Hz), 7.23 (1H, d, J=4 Hz)

The following compounds were obtained in a similar manner to that of Preparation 9-2).

Preparation 21

2-(Methylcarbamoyl)benzofuran-5-boronic acid pinacol cyclic ester

Preparation 22

2-(Hydroxymethyl)benzofuran-5-boronic acid pinacol cyclic ester

Preparation 23-1)

To a solution of methyl 2-hydroxybenzoate (1.05 g) and potassium carbonate (1.43 g) in dimethylformamide (10 ml) was added propyl iodide (1.41 g) under ice-water cooling and the mixture was stirred at 0° C. for 2 hours. The mixture was partitioned between ethyl acetate and water. The organic layer was separated, washed with 1N sodium hydroxide solution, water and brine, dried over magnesium sulfate, and evaporated in vacuo. The residue was purified by silica gel column chromatography eluting with a mixture of hexane and ethyl acetate (20:1) to give methyl 2-(propyloxy)benzoate as colorless oil (853 mg).

NMR (CDCl$_6$, δ): 1.07 (3H, t, J=7 Hz), 1.83–1.96 (2H, m), 3.89 (3H, s), 4.00 (2H, t, J=7 Hz), 6.96 (2H, m), 7.40–7.50 (1H, m), 7.75–7.78 (1H, m)

Preparation 23-2)

To a solution of methyl 2-(propyloxy)benzoate (841 mg) in methanol (20 ml) was added 2N sodium hydroxide solution (5 ml) and the mixture was stirred at 60° C. for 2 hours. The reaction mixture was acidified with 6N hydrochloric acid to pH 4 and organic solvent was removed by evaporation. The aqueous layer was diluted with water and extracted with chloroform. The extract was washed with brine, dried over magnesium sulfate, and evaporated in vacuo to give 2-(propyloxy)benzoic acid as colorless oil (756 mg).

NMR (CDCl$_3$, δ): 1.11 (3H, t, J=7 Hz), 1.90–2.05 (2H, m), 4.23 (2H, t, J=7 Hz), 7.05 (1H, d, J=8 Hz), 7.13 (1H, t, J=8 Hz), 7.55 (1H, dt, J=2, 8 Hz), 8.19 (1H, dd, J=2, 8 Hz)

Preparation 24-1)

The following compound was obtained in a similar manner to that of Example 6.

t-Butyl 2-[(S)-4-t-butoxycarbonyl-7-(5-(4-chlorophenyl)-2-thienyl)-1,1-dioxoperhydro-1,4-thiazepin-7-yl]acetate (8.74 g)

NMR (CDCl$_3$, δ): 1.28, 1.31 (9H, s), 1.47, 1.52 (9H, s), 2.63–2.79 (1H, br), 2.88–2.98 (1H, br), 3.05–3.88 (7H, br), 3.92–4.10 (1H, br), 7.20 (2H, br), 7.33 (2H, d, J=8 Hz), 7.50 (2H, d, J=8 Hz)

Preparation 24-2)

t-Butyl 2-[(S)-7-(5-(4-chlorophenyl)-2-thienyl)-1,1-dioxoperhydro-1,4-thiazepin-7-yl]acetate•hydrochloride (7.74 g) was obtained in a similar manner to that of Preparation 11-2).

NMR (DMSO-d$_6$, δ): 1.27 (9H, s), 2.81–3.06 (2H, br), 3.17–3.79 (7H, br), 4.15–4.32 (1H, br), 7.23 (1H, m), 7.47 (2H, d, J=8 Hz), 7.54 (1H, m), 7.69 (2H, d, J=8 Hz) MASS (m/z): 456 (M+H)

Preparation 24-3)

t-Butyl 2-[(S)-7-(5-(4-chlorophenyl)-2-thienyl)-4-(9-fluorenylmethoxycarbonyl)-1,1-dioxoperhydro-1,4-thiazepin-7-yl]acetate (10.7 g) was obtained in a similar manner to that of Preparation 11-3).

NMR (CDCl$_3$, δ): 1.26, 1.29 (9H, s), 2.50–2.73 (2H, br), 2.82–3.15 (2H, br), 3.18–3.72 (4H, br), 3.88–4.15 (2H, br), 4.15–4.34, 4.45–4.72, 4.78–4.94 (3H, br), 7.07–7.17 (1H, m), 7.22–7.63 (10H, m), 7.69–7.82 (3H, m)

Preparation 24-4)

2-[(S)-7-(5-(4-chlorophenyl)-2-thienyl)-4-(9-fluorenylmethoxycarbonyl)-1,1-dioxoperhydro-1,4-thiazepin-7-yl]acetic acid (9.80 g) was obtained in a similar manner to that of Preparation 11-4).

NMR (DMSO-d$_6$, δ): 2.50–2.72, 2.78–3.95 (10H, br), 4.00–4.32, 4.36, 4.46–4.76, 4.86–4.96 (3H, m), 7.03–7.08–7.17 (1H, m), 7.22–7.63 (11H, m), 7.68–7.80 (2H, m)

Preparation 25

To a solution of N-(2-methoxyethyl)-N-methylamine (1.89 g) in ethyl acetate (20 ml) was added 4N hydrochloric acid-ethyl acetate solution (20 ml) and the mixture was stirred at ambient temperature for 0.5 hour. After evaporation of solvent, sulfuryl chloride (20 ml) was added into the residue and the mixture was stirred at 60° C. for 4 hours. After evaporation of solvent, ethyl acetate and brine were added. The organic layer was separated, dried over magnesium sulfate, and evaporated in vacuo to give N-(2-methoxyethyl)-N-methylaminosulfonyl chloride as pale yellow oil (2.15 g).

NMR (CDCl$_3$, δ): 3.10 (3H, s), 3.39 (3H, s), 3.40–3.55 (2H, br), 3.66 (2H, t, J=7 Hz)

Preparation 26-1)

To a solution of 1-t-butoxycarbonyl-4-piperidone (3.00 g) in ethanol was added sodium borohydride (854 mg) under ice-water cooling and the mixture was stirred at 0° C. for 2 hours. After evaporation of solvent, ethyl acetate and water were added. The organic layer was separated, washed with dilute hydrochloric acid, water, saturated sodium bicarbonate solution and brine, dried over magnesium sulfate, and evaporated in vacuo to give 1-t-butoxycarbonyl-4-hydroxypiperidine as colorless oil (3.15 g).

NMR (CDCl$_3$, δ): 1.38–1.55-(11H, br), 1.63 (1H, br), 1.80–1.94 (2H, br), 2.97–3.11 (2H, m), 3.76–3.98 (3H, br) MASS (m/z): 202 (M+H)

Preparation 26-2)

To a suspension of 60% sodium hydride (939 mg) in dimethylformamide (30 ml) was added 1-t-butoxycarbonyl-4-hydroxypiperidine (3.15 g) under ice-water cooling and the mixture was stirred at 0° C. for 0.5 hour. To the solution was added methyl iodide (1.17 ml) under ice-water cooling and the mixture was stirred at 0° C. for 1 hour. The mixture was partitioned between ethyl acetate and water. The organic layer was separated, washed with water and brine, dried over magnesium sulfate, and evaporated in vacuo. The residue was purified by silica gel column chromatography eluting with a mixture of hexane and ethyl acetate (3:1) to give 1-t-butoxycarbonyl-4-methoxypiperidine as colorless oil (2.84 g).

NMR (CDCl$_3$, δ): 1.46 (9H, s), 1.46–1.62 (2H, br), 1.78–1.93 (2H, br), 3.03–3.14 (2H, m), 3.35 (3H, s), 3.30–3.40 (1H, m), 3.70–3.85 (2H, br) MASS (m/z): 216 (M+H)

Preparation 26-3)

To a solution of 1-t-butoxycarbonyl-4-methoxypiperidine (2.84 g) in ethyl acetate (20 ml) was added 4N hydrochloric-acid-ethyl acetate solution (20 ml) and the mixture was stirred at ambient temperature for 1 hour. The solution was evaporated in vacuo to give 4-methoxypiperidine hydrochloride as a colorless amorphous powder (2.03 g).

NMR (DMSO-d$_6$, δ): 1.62–1.75 (2H, m), 1.90–2.05 (2H, m), 2.88–2.97 (2H, m), 3.05–3.17-(2H, m), 3.12 (3H, s), 3.40–3.53 (1H, m) MASS (m/z): 116 (M+H)

Preparation 26-4)

4-Methoxy-1-piperidinesulfonyl chloride (1.86 g) was obtained in a similar manner to that of Preparation 25.

NMR (CDCl$_3$, δ): 1.84–2.15 (4H, br), 3.26–3.58 (5H, br), 3.36 (3H, s)

Preparation 27-1)

To chlorosulfonylisocyanate (10.3 g) was added t-butyl alcohol (6.96 ml) in dichloromethane (30 ml) under ice-water cooling and the mixture was stirred at ambient temperature for 0.5 hour. The solution was added into a mixture of N-hydroxysuccinimide (8.38 g) and pyridine (6.47 ml) in dichloromethane (150 ml) under ice-water cooling and the mixture was stirred at 0° C. for 1 hour. The solution was washed with 0.1N hydrochloric acid, water and brine, dried over magnesium sulfate, and evaporated in vacuo. The residue was purified by silica gel column chromatography eluting with a mixture of chloroform and methanol (200:1, 100:1, 200:3, 50:1) to give N-(t-butoxycarbonylaminosulfonyloxy)succinimide as colorless oil (2.93 g).

NMR (CDCl$_3$, δ): 1.48 (9H, s), 2.83 (4H, s), 5.15 (1H, br)

Preparation 27-2)

To a solution of N-(t-butoxycarbonylaminosulfonyloxy)succinimide (272 mg), 2-methoxyethanol (84.4 mg) and triphenylphosphine (291 mg) in tetrahydrofuran (5 ml) was added diethyl azodicarboxylate (193 mg) under ice-water cooling and the mixture was stirred at 0° C. for 1 hour. After evaporation of solvent, the residue was purified by silica gel column chromatography eluting with a mixture of hexane and ethyl acetate (2:1, 1:1) to give N-(N-t-butoxycarbonyl-N-(2-methoxyethyl)aminosulfonyloxy)succinimide as colorless oil (205 mg).

NMR (CDCl$_3$, δ): 1.55 (9H, s), 2.80 (4H, s), 3.35 (3H, s), 3.57 (2H, t, J=7 Hz), 3.64 (2H, t, J=7 Hz)

Preparation 27-3)

To a solution of N-(N-t-butoxycarbonyl-N-(2-methoxyethyl)aminosulfonyloxy)succinimide (200 mg) in dichloromethane (2 ml) was added trifluoroacetic acid (2 ml) under ice-water cooling and the mixture was stirred at 0° C. for 2 hours. The solution was evaporated in vacuo to give N-(2-methoxyethylaminosulfonyloxy)succinimide as a colorless amorphous powder (149 mg).

NMR (CDCl$_3$, δ): 2.84 (4H, s), 3.40 (3H, s), 3.53–3.66 (4H, br), 5.58 (1H, br) MASS (m/z): 251 (M–H)

Preparation 28

4-(5-Methyl-1,2,4-oxadiazol-3-yl)benzeneboronic acid pinacol cyclic ester was obtained in a similar manner to that of Preparation 9-2).

Preparation 29

4-Biphenylylboronic acid pinacol cyclic ester was obtained in a similar manner to that of Preparation 9-2).

Preparation 30

A solution of diethylamine hydrochloride (1 g) in sulfuryl chloride (10 ml) was heated at 50° C. for 4 hours. The solution was allowed to cool to ambient temperature and sulfuryl cloride was evaporated in vacuo. To the residue were added ethyl acetate and water. The organic layer was washed with brine, dried over anhydrous magnesium sulfate and concentrated in vacuo to give diethylsulfamoyl chloride (720 mg) as a colorless oil.

NMR (CDCl$_3$, δ): 1.32 (6H, t, J=7.5 Hz), 3.43 (4H, q, J=7.5 Hz) MASS (ESI–): 170.2 (M–H)

Preparation 31

To a solution of cyclopropylamine (500 mg) in chloroform (5 ml) were added pyridine (1.04 mg) and a solution of phenyl chloroformate (1.65 g) in chloroform (2 ml) 0° C. and the reaction mixture was stirred at ambient temperature for 0.5 hour. To the mixture was added ethyl acetate and the solution was washed successively with water, a 5% aqueous citric acid solution, a saturated aqueous sodium hydrogen carbonate and brine, dried over anhydrous magnesium sulfate and concentrated in vacuo to give cyclopropylaminocarbonyloxybenzene (1.6 g) as a pale yellow powder.

NMR (CDCl$_3$, δ): 0.59–0.65 (2H, m), 0.75–0.83 (2H, m), 2.70 (1H, m), 7.10–7.41 (1H, m) MASS (ESI+): 178.0 (M+H)

Preparation 32-1)

4-Propylphenylboronic acid pinacol cyclic ester was obtained in a similar manner to that of Preparation 9-2).

Preparation 32-2)

t-Butyl 2-[4-t-butoxycarbonyl-7-(5-(4-propylphenyl)-2-thienyl)-1,1-dioxoperhydro-1,4-thiazepin-7-yl]acetate (3.25 g) was obtained in a similar manner to that of Example 39.

NMR (CDCl$_3$, δ): 0.95 (3H, t, J=7 Hz), 1.27, 1.30 (9H, s), 1.46, 1.51 (9H, s), 1.60–1.74 (2H, m), 2.59 (2H, t, J=7 Hz), 2.66–2.79 (1H, br), 2.88, 2.95 (1H, br), 3.05–3.26 (2H, br), 3.33–3.86 (5H, br), 3.90–4.18 (1H, br), 7.18 (4H, br), 7.48 (2H, br) MASS (m/z): 564 (M+H)

Preparation 32-3)
t-Butyl 2-[7-(5-(4-propylphenyl)-2-thienyl)-1,1-dioxoperhydro-1,4-thiazepin-7-yl]acetate•hydrochloride (2.87 g) was obtained in a similar manner to that of Preparation 11-2).

NMR (DMSO-$d_6$, δ): 0.90 (3H, t, J=7 Hz), 1.24 (9H, s), 1.56–1.68 (2H, m), 2.57 (2H, t, J=7 Hz), 2.75–3.78 (9H, br), 4.10–4.26 (1H, br), 7.20 (1H, m), 7.25 (2H, d, J=8 Hz), 7.44 (1H, m), 7.56 (2H, d, J=8 Hz) MASS (m/z): 464 (M+H)

Preparation 32-4)
t-Butyl 2-[4-(9-fluorenylmethoxycarbonyl)-7-(5-(4-propylphenyl)-2-thienyl)-1,1-dioxoperhydro-1,4-thiazepin-7-yl]acetate (4.01 g) was obtained in a similar manner to that of Preparation 11-3).

NMR (CDCl$_3$, δ): 0.95 (3H, t, J=7 Hz), 1.26, 1.27 (9H, s), 1.62–1.73 (2H, m), 2.45–2.69 (4H, m), 2.83–3.12 (2H, br), 3.18–3.73 (4H, br), 3.89–4.08 (2H, br), 4.28–4.34, 4.46–4.62, 4.78–4.85 (3H, m), 7.08–7.19 (3H, m), 7.25–7.48 (8H, m), 7.53–7.62 (1H, m), 7.65–7.80 (2H, m)

Preparation 32-5)
2-[4-(9-Fluorenylmethoxycarbonyl)-7-(5-(4-propylphenyl)-2-thienyl)-1,1-dioxoperhydro-1,4-thiazepin-7-yl]acetic acid (3.98 g) was obtained in a similar manner to that of Preparation 11-4).

NMR (CDCl$_3$, δ): 0.94 (3H, t, J=7 Hz), 1.56–1.78 (2H, m), 2.52–2.70 (4H, br), 2.83–4.11 (8H, br), 4.15–4.32, 4.38, 4.45–4.57, 4.62–4.70, 4.85–4.93 (3H, m), 7.03–7.62 (12H, m), 7.67–7.81 (2H, m)

Preparation 33
To a solution of phenylboronic acid (1.04 g) in 1,4-dioxane (10 ml) was added pinacol (1.11 g) and the mixture was stirred at 80° C. for 2 hours. After evaporation of solvent, the residue was purified by silica gel column chromatography eluting with a mixture of chloroform and hexane (5:1) to give phenylboronic acid pinacol cyclic ester as colorless oil (1.97 g).

NMR (CDCl$_3$, δ): 1.35 (12H, br), 7.36 (2H, t, J=8 Hz), 7.44 (2H, d, J=8 Hz), 7.80 (2H, d, J=8 Hz)

Preparation 34
4-Isopropylphenylboronic acid pinacol cyclic ester was obtained in a similar manner to that of Preparation 9-2).

Preparation 35-1)
t-Butyl 2-[4-t-butoxycarbonyl-7-(5-(4-fluorophenyl)-2-thienyl)-1,1-dioxoperhydro-1,4-thiazepin-7-yl]acetate (9.84 g) was obtained in a similar manner to that of Example 6.

NMR (CDCl$_3$, δ): 1.28, 1.31 (9H, s), 1.47, 1.51 (9H, s), 2.60–2.78 (1H, br), 2.86–2.98 (1H, br), 3.04–3.86 (7H, br), 3.90–4.15 (1H, br), 7.02–7.10 (2H, m), 7.12–7.34 (2H, m), 7.47–7.58 (2H, m)

Preparation 35-2)
t-Butyl 2-[7-(5-(4-fluorophenyl)-2-thienyl)-1,1-dioxoperhydro-1,4-thiazepin-7-yl]acetate (4.95 g) was obtained in a similar manner to that of Preparation 11-2).

NMR (CDCl$_3$, δ): 1.28 (9H, s), 2.50–2.65 (1H, m), 2.98–3.48 (9H, m), 7.03–7.12 (2H, m), 7.17 (1H, d, J=3 Hz), 7.19 (1H, d, J=3 Hz), 7.48–7.58 (2H, m) MASS (m/z): 440 (M+H)

Preparation 35-3)
t-Butyl 2-[4-(9-fluorenylmethoxycarbonyl)-7-(5-(4-fluorophenyl)-2-thienyl)-1,1-dioxoperhydro-1,4-thiazepin-7-yl]acetate (7.91 g) was obtained in a similar manner to that of Preparation 11-3).

NMR (CDCl$_3$, δ): 1.26, 1.28 (9H, s), 2.50–2.69 (2H, br), 2.85–3.10 (2H, br), 3.20–3.73 (4H, br), 3.89–4.10 (2H, br), 4.19–4.33, 4.46–4.53, 4.79–4.91 (3H, m), 6.98–7.16 (4H, m), 7.27–7.65 (8H, m), 7.73–7.82 (2H, m)

Preparation 35-4)
2-[4-(9-Fluorenylmethoxycarbonyl)-7-(5-(4-fluorophenyl)-2-thienyl)-1,1-dioxoperhydro-1,4-thiazepin-7-yl]acetic acid (7.74 g) was obtained in a similar manner to that of Preparation 11-4).

NMR (CDCl$_3$, δ): 2.48–2.73 (2H, br), 2.78–3.60 (6H, br), 3.72–4.10 (2H, br), 4.18–4.32, 4.46–4.58, 4.64–4.73, 4.88–4.95 (3H, m), 6.95–7.22 (4H, m), 7.26–7.58 (8H, m), 7.67–7.82 (2H, m)

Preparation 36-1)
4–Cyanophenylboronic acid pinacol cyclic ester was obtained in a similar manner to that of Preparation 9-2).

Preparation 36-2)
t-Butyl 2-[4-t-butoxycarbonyl-7-(5-(4-cyanophenyl)-2-thienyl)-1,1-dioxoperhydro-1,4-thiazepin-7-yl]acetate (2.20 g) was obtained in a similar manner to that of Example 39.

NMR (CDCl$_3$, δ): 1.29, 1.32 (9H, s), 1.47, 1.51 (9H, s), 2.64–2.82 (1H, br), 2.90, 2.98 (1H, br), 3.05–3.87 (7H, br), 3.93–4.08 (1H, br), 7.23 (1H, br), 7.33 (1H, br), 7.60–7.68 (4H, br)

Preparation 36-3)
t-Butyl 2-[7-(5-(4-cyanophenyl)-2-thienyl)-1,1-dioxoperhydro-1,4-thiazepin-7-yl]acetate•hydrochloride (2.38 g) was obtained in a similar manner to that of Preparation 11-2).

NMR (DMSO-$d_6$, δ): 1.26 (9H, s), 2.75–4.25 (10H, br), 710–7.32 (5H, m), 7.74 (1H, d, J=3 Hz) MASS (m/z): 447 (M+H)

Preparation 36-4)
t-Butyl 2-[7-(5-(4-cyanophenyl)-2-thienyl)-4-(9-fluorenylmethoxycarbonyl)-1,1-dioxoperhydro-1,4-thiazepin-7-yl]acetate (2.46 g) was obtained in a similar manner to that of Preparation 11-3).

NMR (CDCl$_3$, δ): 1.27, 1.30 (9H, s), 2.49–2.73 (2H, br), 2.83–3.12 (2H, br), 3.19–3.73 (4H, br), 3.89–4.10 (2H, br), 4.29–4.34, 4.45–4.64, 4.82–4.92 (3H, m), 7.15–7.20 (1H, d, J=3 Hz), 7.26–7.47 (6H, m), 7.53–7.66 (5H, m), 7.70–7.82 (2H, m)

Preparation 36-5)
2-[7-(5-(4–Cyanophenyl)-2-thienyl)-4-(9-fluorenylmethoxycarbonyl)-1,1-dioxoperhydro-1,4-thiazepin-7-yl]acetic acid (1.80 g) was obtained in a similar manner to that of Preparation 11-4).

NMR (DMSO-$d_6$, δ): 2.56–3.90 (10H; br), 4.29–4.55 (3H, m), 7.17, 7.24 (1H, d, J=3 Hz), 7.27–7.47 (4H, m), 7.60–7.75 (3H, m), 7.82–7.93 (6H, m) MASS (m/z): 611 (M−H)

Preparation 37-1)
t-Butyl 2-[4-t-butoxycarbonyl-7-(5-(5-chloro-2-thienyl)-2-thienyl)-1,1-dioxoperhydro-1,4-thiazepin-7-yl]acetate (975 mg) was obtained in a similar manner to that of Example 6.

NMR (CDCl$_3$, δ): 1.29, 1.32 (9H, s), 1.47, 1.58 (9H, s), 2.59–2.76 (1H, br), 2.87, 2.94 (1H, br), 2.98–3.14 (1H, br), 3.15–3.84 (6H, br), 3.88–4.08 (1H, br), 6.83 (1H, d, J=3 Hz), 6.93 (1H, br), 7.02 (1H, br), 7.13 (1H, br)

Preparation 37-2)
t-Butyl 2-[7-(5-(5-chloro-2-thienyl)-2-thienyl)-1,1-dioxoperhydro-1,4-thiazepin-7-yl]acetate•hydrochloride (860 mg) was obtained in a similar manner to that of Preparation 11-2).

NMR (CDCl$_3$, δ): 1.27 (9H, s), 2.98–3.42 (4H, br), 3.54–4.02 (6H, br), 6.82 (1H, d, J=3 Hz), 6.93 (1H, d, J=3 Hz), 7.02 (1H, d, J=3 Hz), 7.10 (1H, d, J=3 Hz) MASS (m/z): 462 (M+H)

Preparation 37-3)
t-Butyl 2-[7-(5-(5-chloro-2-thienyl)-2-thienyl)-4-(9-fluorenylmethoxycarbonyl)-1,1-dioxoperhydro-1,4-thiazepin-7-yl]acetate (1.26 g) was obtained in a similar manner to that of Preparation 11-3).

NMR (CDCl$_3$, δ): 1.30 (9H, s), 2.38–2.66 (2H, br), 2.80–3.05 (2H, br), 3.15–3.70 (4H, br), 3.85–4.10 (2H, br), 4.18–4.34, 4.46–4.63, 4.83–4.91 (3H, m), 6.83, 6.90, 6.96, 7.03, 7.08 (4H, m), 7.26–7.48, 7.53–7.64 (6H, m), 7.73–7.82 (2H, m)

Preparation 37-4)

2-[7-(5-(5-Chloro-2-thienyl)-2-thienyl)-4-(9-fluorenylmethoxycarbonyl)-1,1-dioxoperhydro-1,4-thiazepin-7-yl]acetic acid (1.15 g) was obtained in a similar manner to that of Preparation 11-4).

NMR (CDCl$_3$, δ): 2.20–3.58 (8H, br), 3.70–4.08 (2H, br), 4.18–4.32, 4.48–4.73, 4.87–4.97 (3H, m), 6.79, 6.85–7.00, 7.06 (4H, m), 7.27–7.62 (6H, m), 7.69–7.82 (2H, m)

Preparation 38-1)

To a suspension of 60% sodium hydride (1.6 g) in dimethylformamide (50 ml) was added 4-bromobenzyl alcohol (5.00 g) under ice-water cooling and the mixture was stirred at 0° C. for 0.5 hour. To the mixture was added methyl iodide (2 ml) under ice-water cooling and the mixture was stirred at 0° C. for 1 hour. The mixture was partitioned between ethyl acetate and water. The organic layer was separated, washed with water and brine, dried over magnesium sulfate, and evaporated in vacuo. The residue was purified by silica gel column chromatography eluting with hexane to give 4-(methoxymethyl)bromobenzene as colorless oil (3.63 g).

NMR (CDCl$_3$, δ): 3.38 (3H, s), 4.41 (2H, s), 7.21 (2H, d, J=8 Hz), 7.47 (2H, d, J=8 Hz)

Preparation 38-2)

4-Methoxymethyl)phenylboronic acid pinacol cyclic ester was obtained in a similar manner to that of Preparation 9-2).

Preparation 38-3)

t-Butyl 2-[4-t-butoxycarbonyl-7-(5-(4-methoxymethylphenyl)-2-thienyl)-1,1-dioxoperhydro-1,4-thiazepin-7-yl]acetate (2.19 g) was obtained in a similar manner to that of Example 39.

NMR (CDCl$_3$, δ): 1.28, 1.33 (9H, s), 1.47, 1.51 (9H, s), 2.62–2.78 (1H, br), 2.88, 2.93 (1H, br), 3.04–3.28 (2H, br), 3.32–3.83 (5H, br), 3.41 (3H, s), 3.92–4.12 (1H, br), 4.46 (2H, s), 7.23 (2H, m), 7.33 (2H, d, J=8 Hz), 7.58 (2H, br) MASS (m/z): 566 (M+H)

Preparation 38-4)

t-Butyl 2-[7-(5-(4-methoxymethylphenyl)-2-thienyl)-1,1-dioxoperhydro-1,4-thiazepin-7-yl]acetate•hydrochloride (1.95 g) was obtained in a similar manner to that of Preparation 11-2).

NMR (DMSO-d$_6$, δ): 1.26 (9H, s), 2.72–4.22 (10H, br), 3.31 (3H, s), 4.43 (2H, s), 7.21 (1H, d, J=3 Hz), 7.37 (2H, d, J=8 Hz), 7.51 (1H, d, J=3 Hz), 7.65 (2H, d, J=8 Hz) MASS (m/z): 466 (M+H)

Preparation 38-5)

t-Butyl 2-[4-(9-fluorenylmethoxycarbonyl)-7-(5-(4-methoxymethylphenyl)-2-thienyl)-1,1-dioxoperhydro-1,4-thiazepin-7-yl]acetate (2.65 g) was obtained in a similar manner to that of Preparation 11-3).

NMR (CDCl$_3$, δ): 1.26, 1.28 (9H, s), 2.42–2.69 (2H, br), 2.83–3.12 (2H, br), 3.18–3.75 (4H, br), 3.40 (3H, s), 3.89–4.15 (2H, br), 4.18–4.33, 4.46–4.63, 4.78–4.88 (3H, m), 4.45 (2H, s), 7.10–7.23 (2H, m), 7.26–7.47 (7H, m), 7.47–7.63 (3H, m), 7.68–7.80 (2H, m) MASS (m/z): 688 (M+H)

Preparation 38-6)

2-[4-(9-Fluorenylmethoxycarbonyl)-7-(5-(4-methoxymethylphenyl)-2-thienyl)-1,1-dioxoperhydro-114-thiazepin-7-yl]acetic acid (2.43 g) was obtained in a similar manner to that of Preparation 11-4).

NMR (CDCl$_6$, δ): 2.48–2.72 (2H, br), 2.80–2.97 (2H, br), 2.97–3.58 (4%, br), 3.39 (3H, s), 3.73–4.10 (2H, br), 4.46 (2H, s), 4.18–4.32, 4.45–4.73, 4.85–4.95 (3H, m), 7.05, 7.10–7.23 (2H, m), 7.23–7.63 (10H, m), 7.69–7.80 (2H, m)

Preparation 39-1)

tert-Butyl 2-[(S)-7-(5-bromo-2-thienyl)-4-(2-pyridinecarbonyl)-1,1-dioxoperhydro-1,4-thiazepin-7-yl]acetate (4.76 g) was obtained in a similar manner to that of Example 33.

NMR (CDCl$_3$, δ): 1.22, 1.30 (9H, s), 2.68–2.81 (1H, m), 2.88–3.26 (2H, m), 3.33–3.73 (3H, m), 3.80–4.00 (2H, m), 4.16–4.45 (2H, m), 6.90–7.04 (2H, m), 7.34–7.52 (1H, m), 7.17–7.88 (2H, m), 8.47–8.59 (1H, m) MASS (ESI+): 529, 531 (M+H)

Preparation 39-2)

tert-Butyl 2-[(S)-7-(5-(4-chlorophenyl)-2-thienyl-)-4-(2-pyridinecarbonyl)-1,1-dioxoperhydro-1,4-thiazepin-7-yl] acetate (2.46 g) was obtained in a similar manner to that of Example 6.

NMR (CDCl$_3$, δ): 1.20, 1.29 (9H, s), 2.25–2.87 (1H, m), 3.03–3.33 (2H, m), 3.42–3.75 (3H, m), 3.82–4.48 (4H, m), 7.14–7.50 (7H, m), 7.28–7.86 (2H, m), 8.45–8.62 (1H, m) MASS (ESI-): 560 (M-H)

Preparation 39-3)

2-[(S)-7-(5-(4-Chlorophenyl)-2-thienyl)-4-(2-pyridinecarbonyl)-1,1-dioxoperhydro-1,4-thiazepin-7-yl] acetic acid•hydrochloride (2.31 g) was obtained in a similar manner to that of Preparation 11-4).

NMR (DMSO-d$_6$, δ): 2.26–2.87 (1H, m), 2.94–3.11 (1H, m), 3.19–4.26 (8H, m), 7.17, 7.24 (1H, d, J=3 Hz), 7.17, 7.24 (1H, d, J=3 Hz), 7.43–7.56 (4H, m), 7.61–7.73 (3H, m), 7.93–8.03 (1H, m), 8.60, 8.62 (1H, s) MASS (ESI-): 503 (M-H)

Preparation 40-1)

tert-Butyl 2-(S)-7-(5-(4-ethylphenyl)-2-thienyl)-4-(2-pyradinecarbonyl)-1,1-dioxoperhydro-1,4-thiazepin-7-yl] acetate (3.15 g) was obtained in a similar manner to that of Example 33.

NMR (DMSO-d$_6$, δ): 1.23, 1.33 (9H, s), 1.29 (3H, t, J=8 Hz), 2.72 (2H, q, J=8 Hz), 2.75–2.90 (1H, m), 3.02–3.19 (1H, m), 3.24–3.38 (2H, m), 3.56–4.28 (6H, m), 7.24, 7.40 (1H, d, J=3 Hz), 7.36 (2H, d, J=8 Hz), 7.47–7.56 (1H, m), 7.62–7.70 (2H, m), 8.26–8.33 (1H, m), 8.35–8.92 (1H, m), 8.98, 9.03 (1H, s)

Preparation 40-2)

2-[(S)-7-(5-(4-Ethylphenyl)-2-thienyl)-4-(2-pyradinecarbonyl)-1,1-dioxoperhydro-1,4-thiazepin-7-yl) acetic acid (2.68 g) was obtained in a similar manner to that of Preparation 11-4).

NMR (DMSO-d$_6$, δ): 1.19 (3H, t, J=8 Hz), 2.63 (2H, q, J=8 Hz), 2.70–2.99 (1H, m), 2.94–3.10 (1H, m), 3.19–3.40 (2H, m), 3.48–4.20 (6H, m), 7.16, 7.21 (1H, d, J=3 Hz), 7.27 (2H, d, J=8 Hz), 7.40, 7.43 (1H, d, J=8 Hz), 7.55, 7.57 (2H, d, J=3 Hz), 8.65–8.72 (1H, m), 8.85–8.82 (1H, m), 8.90 (1H, d, J=8 Hz) MASS (ESI-): 498 (M-H)

Preparation 41-1)

tert-Butyl 2-[(S)-7-(5-(4-ethylphenyl)-2-thienyl)-4-(3-thiophenecarbonyl)-1,1-dioxoperhydro-1,4-thiazepin-7-yl] acetate (2.30 g) was obtained in a similar manner to that of Example 6.

NMR (DMSO-d$_6$, δ): 1.10, 1.23 (9H, s), 1.19 (3H, t, J=8 Hz), 2.62 (2H, q, J=8 Hz), 2.80–3.32 (4H, m), 3.50–4.22 (6H, m), 7.12–7.33 (4H, m), 7.38–7.46 (1H, m), 7.50–7.69 (3H, m), 7.80–7.95 (1H, m) MASS (ESI+): 560 (M+H)

Preparation 41-2)

2-[(S)-7-(5-(4-Ethylphenyl)-2-thienyl-4-(3-thiophenecarbonyl)-1,1-dioxoperhydro-1,4-thiazepin-7-yl)

acetic acid (2.03 g) was obtained in a similar manner to that of Preparation 11-4).

NMR (DMSO-$d_6$, δ): 1.91 (3H, t, J=8 Hz), 2.62 (2H, t, J=8 Hz), 2.68–4.15 (8H, m), 6.88–6.96 (1H, m), 7.15–7.33 (4H, m), 7.36–7.45 (1H, m), 7.52–7.69 (3H, m), 7.85 (1H, br) MASS (ESI–): 502 (M–H)

Preparation 42-1)

4-(2-Oxazolyl)phenylboronic acid pinacol cyclic ester was obtained in a similar manner to that of Preparation 9-2).

Preparation 42-2)

tert-Butyl 2-[7-(5-(4-(2-oxazolyl)phenyl)-2-thienyl)-4-(3-thiophenecarbonyl)-1,1-dioxoperhydro-1,4-thiazepin-7-yl]acetate (0.96 g) was obtained in a similar manner to that of Example 39.

NMR (DMSO-$d_6$, δ): 1.11, 1.25 (9H, s), 2.55–4.22 (10H, m), 7.20–7.33 (2H, m), 7.42 (1H, s), 7.53–7.68 (2H, m), 7.78–7.84 (3H, m), 8.03 (2H, d, J=8 Hz), 8.26 (1H, s) MASS (ESI): ND

Preparation 42-3)

2-[7-(5-(4-(2-Oxazolyl)phenyl)-2-thienyl)-4-(3-thiophenecarbonyl)-1,1-dioxoperhydro-1,4-thiazepin-7-yl] acetic acid (435 mg) was obtained in a similar manner to that of Preparation 11-4).

NMR (DMSO-$d_6$, δ): 2.64–4.17 (10H, m), 7.26 (2H, d, J=3 Hz), 7.55–7.68 (2H, m), 7.79–7.92 (3H, m), 8.02 (2H, d, J=8 Hz), 8.25 (1H, s) MASS (ESI): ND

Preparation 43-1)

tert-Butyl 2-[(S)-7-(5-(4-(5-oxazolyl)phenyl)-2-thienyl)-1,1-dioxoperhydro-4-(3,3-dimethylbutyryl)-1,4-thiazepin-7-yl]acetate (6.60 g) was obtained in a similar manner to that of Example 33.

NMR (DMSO-$d_6$, δ): 1.02–1.04 (9H, s), 1.24, 1.27 (9H, s), 2.24, 2.25 (1H, s), 2.52–2.96 (2H, m), 3.10–3.95 (8H, m), 7.19–7.25 (1H, m), 7.58 (1H, t, J=4 Hz), 7.76 (1H, s), 7.78 (4H, s), 8.48 (1H, s) MASS (ESI–): 585 (M–H)

Preparation 43-2)

2-[(S)-7-(5-(4-(5-Oxazolyl)phenyl)-2-thienyl)-1,1-dioxoperhydro-4-(3,3-dimethylbutyryl)-1,4-thiazepin-7-yl] acetic acid-hydrochloride (6.45 g) was obtained in a similar manner to that of Preparation 11-4).

NMR (DMSO-$d_6$, δ): 1.02, 1.03 (9H, s), 2.25 (1H, s), 2.30, 2.31 (1H, s), 2.58–2.94 (2H, m), 3.19–3.36 (2H, m), 3.48–4.94 (6H, m), 7.21, 7.24 (1H, d, J=4 Hz), 7.57 (1H, t, J=4 Hz), 7.78 (1H, s), 7.78 (4H, s), 8.48 (1H, s) MASS (ESI–): 529 (M–H)

Preparation 44-1)

tert-Butyl 2-[(S)-7-(5-bromo-2-thienyl)-1,1-dioxoperhydro-4-(3-thiophenecarbonyl)-1,4-thiazepin-7-yl] acetate (8.10 g) was obtained in a similar manner to that of Example 33.

NMR (DMSO-$d_6$, δ): 1.11, 1.25 (9H, s), 2.52–3.28 (4H, m), 3.41–4.18 (6H, m), 7.00–7.09 (1H, m), 7.18–7.31 (2H, m), 7.58–7.68 (1H, m), 7.80–7.92 (1H, m) MASS (ESI–): 532, 534 (M–H)

Preparation 44-2)

2-[(S)-7-(5-Bromo-2-thienyl)-1,1-dioxoperhydro-4-(3-thiophenecarbonyl)-1,4-thiazepin-7-yl]acetic acid (7.10 g) was obtained in a similar manner to that of Preparation 11–4).

NMR (DMSO-$d_6$, δ): 2.57–4.17 (10H, m), 7.05, 7.06 (1H, s), 7.16–7.29 (2H, m), 7.56–7.67 (1H, m), 7.84 (1H, s) MASS (ESI–): 477, 479 (M–H)

Preparation 45-1)

Ethyl 3-(4-(4-chlorophenoxy)benzene)acrylate (25.2 g) was obtained in a similar manner to that of Preparation 1-1).

NMR (CDCl$_3$, δ): 1.35 (3H, t, J=7 Hz), 4.27 (2H, q, J=7 Hz), 6.36 (1H, d, J=15 Hz), 6.97 (4H, dd, J=8, 2 Hz), 7.33 (2H, d, J=8 Hz), 7.50 (2H, d, J=8 Hz), 7.65 (1H, d, J=15 Hz)

Preparation 45-2)

7-[4-(4-Chlorophenoxy)phenyl]perhydro-1,4-thiazepin-5-one (19.9 g) was obtained in a similar manner to that of Preparation 1-2).

NMR (DMSO-$d_6$, δ): 2.65–2.87 (3H, m), 3.47–3.60 (3H, m), 4.17 (1H, d, J=7 Hz), 6.96–7.05 (4H, m), 7.35–7.45 (4H, m), 7.79 (1H, t, J=7 Hz)

Preparation 45-3)

To a mixture of lithium aluminum hydride (4.521 g) in tetrahydrofuran (130 ml) was added aluminum chloride (5.33 g) during 5 minutes in some portion at 6° C. (inner temperature: 6–16° C.) and the mixture was stirred at 12° C. for 30 minutes. 7-[4-(4(4- Chlorophenoxy)phenyl]perhydro-1,4-thiazepin-5-one (19.9 g) was added to this mixture during 7 minutes in some portion at 7° C. (inner temperature 7–30° C.) and the mixture was stirred at 13° C. for 1.5 hours. The reaction mixture was poured into ice-water (300 g) with vigorous stirring and stirred for 2 hours. To this was added a solution of di-tert-butyl dicarbonate (13 g) in tetrahydrofuran (40 ml) at 0° C. over 5 minutes. 1N Sodium hydroxide (63 ml) was added to the reaction mixture and stirred at 0° C. for 1 hour. The reaction mixture was diluted with ethyl acetate (200 ml), filtrated through celite pad and washed with ethyl acetate (900 ml). The filtrate was separated and the organic layer was washed with 0.5% hydrochloric acid (300 ml), saturated aqueous sodium hydrogen sulfate (300 ml) and brine (300 ml). The organic layer was dried over magnesium sulfate and concentrated in vacuo. The residue was purified by flash column chromatography on silica gel eluting with a mixture of ethyl acetate and n-hexane (1:4) to give 4-tert-butoxycarbonyl-7-[4-(4-chlorophenoxy)phenyl]perhydro-1,4-thiazepine (24.9 g) as a colorless oil.

NMR (CDCl$_3$, δ): 1.51 (9H, s), 2.04–2.25 (1H, m), 2.42–2.60 (1H, m), 2.75–3.17 (2H, m), 3.24–3.47 (1H, m), 3.59–3.67 (2H, m), 3.69–3.74 (1H, m), 3.94–4.24 (1H, m), 6.94 (4H, d, J=8 Hz), 7.24–7.30 (4H, m)

Preparation 45-4)

4-tert-Butoxycarbonyl-7-[4-(4-chlorophenoxy)phenyl]-1,1-dioxoperhydro-1,4-thiazepine (21.7 g) was obtained in a similar manner to that of Preparation 1-5).

NMR (CDCl$_3$, δ): 1.51 (9H, s), 2.30–2.45 (1H, m), 2.50–2.80 (1H, m), 3.23–3.32 (1H, m), 3.37–3.58 (3H, m), 3.87–4.21 (3H, m), 6.98 (4H, dd, J=8, 2 Hz), 7.32 (4H, t, J=8 Hz)

Preparation 45-5)

tert-Butyl 2-[4-tert-butoxycarbonyl-7-[4-(4-chlorophenoxy)phenyl]-1,1-dioxoperhydro-1,4-thiazepin-7-yl]acetate (4.3 g) was obtained in a similar manner to that of Preparation 1-6).

NMR (CDCl$_3$, δ): 1.26 and 1.92 (9H, s), 1.49 and 1.50 (9H, s), 2.59–2.67 (1H, m), 3.85–3.93 (1H, m), 3.13–3.24 (2H, m), 3.33–3.64 (4H, m), 4.02–4.15 (2H, m), 6.97 (4H, dd, J=8, 2 Hz), 7.30 (2H, d, J=8 Hz), 7.48–7.57 (2H, m)

Preparation 45-6)

2-[7-[4-(4-Chlorophenoxy)phenyl]-4-(9-fluorenylmethoxycarbonyl)-1,1-dioxoperhydro-1,4-thiazepin-7-yl]acetic acid (2.2 g) was obtained in a similar manner to that of Preparation 1-7).

NMR (CDCl$_3$, δ): 2.37–2.43 (2H, m), 2.50–2.65 (2H, m), 3.02–3.25 (2H, m), 3.33–3.45 (2H, m), 3.95–4.08 (1H, m), 4.18–4.25 (1H, m), 4.50–4.60 (2H, m), 4.99–5.05 (1H, m), 6.92 (2H, d, J=8 Hz), 6.95 (2H, d, J=8 Hz), 7.28–7.60 (10H, m), 7.73–7.82 (2H, m)

Preparation 46-1)

To a stirred solution of 4-fluorobenzaldehyde (24.1 g) and p-cresol (21 g) in N,N-dimethylformamide (400 ml) was added powdered potassium carbonate (26.8 g) and the reaction mixture was stirred at 150° C. for 7.5 hours. After cooling, the reaction mixture was poured into ice water (1.4 kg). The mixture was extracted with ethyl acetate (1 l), washed with water (1 l×3), brine (1 l), dried over anhydrous magnesium sulfate and concentrated in vacuo to give 4-(4-methylphenoxy)benzaldehyde (40.7 g) as a light yellow oil.

NMR (CDCl$_3$, δ): 2.38 (3H, s), 6.98 (2H, d, J=8 Hz), 7.04 (2H, d, J=8 Hz), 7.21 (2H, d, J=8 Hz), 7.83 (2H, d, J=8 Hz), 9.91 (1H, s)

Preparation 46-2)
Ethyl 3-(4-(4-methylphenoxy)benzene)acrylate (52.5 g) was obtained in a similar manner to that of Preparation 1-1).

NMR (CDCl$_3$, δ): 1.34 (3H, t, J=7 Hz), 2.36 (3H, s), 4.25 (2H, q, J=7 Hz), 6.34 (1H, d, J=15 Hz), 6.95 (4H, d, J=8 Hz), 7.18 (2H, d, J=8 Hz), 7.47 (2H, d, J=8 Hz), 7.65 (1H, d, J=15 Hz)

Preparation 46-3)
7-[4-(4-Methylphenoxy)phenyl]perhydro-1,4-thiazepin-5-one (38.8 g) was obtained in a similar manner to that of Preparation 1-2).

NMR (DMSO-d$_6$, δ): 2.29 (3H, s), 2.63–2.87 (3H, m), 3.47–3.63 (3H, m), 4.15 (1H, d, J=9 Hz), 6.93 (4H, d, J=7.5 Hz), 7.20 (2H, q, J=7.5 Hz), 7.34 (2H, d, J=7.5 Hz), 7.77 (1H, t, J=7 Hz)

Preparation 46-4)
4-tert-Butoxycarbonyl-7-[4-(4-methylphenoxy)phenyl]-perhydro-1,4-thiazepine (40.5 g) was obtained in a similar manner to that of Preparation 45-3).

NMR (CDCl$_3$, δ): 1.49 (9H, s), 2.07–2.20 (1H, m), 2.33 (3H, s), 2.40–2.55 (1H, m), 2.73–3.03 (2H, m), 3.21–3.45 (1H, m), 3.56–3.64 (2H, m), 3.72–3.80 (1H, m), 3.93–4.20 (1H, m), 6.87–6.93 (4H, m), 7.12 (2H, d, J=8 Hz), 7.20–7.25 (2H, m) MASS (m/z): 400 (M$^+$+H), 115 (bp)

Preparation 46-5)
4-tert-Butoxycarbonyl-7-[4-(4-methylphenoxy)phenyl]-1,1-dioxoperhydro-1,4-thiazepin (32.9 g) was obtained in a similar manner to that of Preparation 1-5).

NMR (CDCl$_3$, δ): 1.50 and 1.52 (9H, s), 2.30–2.44 (1H, m), 2.34 (3H, s), 2.49–2.75 (1H, m), 3.22–3.30 (1H, m), 3.35–3.57 (3H, m), 3.86–4.19 (3H, m), 6.93–6.99 (4H, m), 7.15 (2H, d, J=8 Hz), 7.29 (2H, t, J=8 Hz)

Preparation 46-6)
tert-Butyl 2-[4-tert-butoxycarbonyl-7-[4-(4-methylphenoxy)phenyl]-1,1-dioxoperhydro-1,4-thiazepin-7-yl]acetate (5.1 g) was obtained in a similar manner to that of Preparation 1-6).

NMR (CDCl$_3$, δ): 1.24 and 1.28 (9H, s), 1.46 and 1.49 (9H, s), 2.34 (3H, s), 2.57–2.67 (1H, m), 2.73–2.80 (1H, m), 3.10–3.25 (2H, m), 3.31–3.41 (1H, m), 3.49–3.65 (2H, m), 3.75–3.95 (1H, m), 4.00–4.13 (2H, m), 6.93 (4H, t, J=8 Hz), 7.14 (2H, d, J=8 Hz), 7.45–7.53 (2H, m)

Preparation 46-7)
2-[4-(9-Fluorenylmethoxycarbonyl)-7-[4-(4-methylphenoxy)phenyl]-1,1-dioxoperhydro-1,4-thiazepin-7-yl]acetic acid (5.0 g) was obtained in a similar manner to that of Preparation 1-7).

NMR (CDCl$_3$, δ): 2.33 (3H, s), 2.40–2.46 (2H, m), 2.50–2.65 (2H, m), 3.00–3.22 (2H, m), 3.34–3.44 (2H, m), 3.93–4.07 (1H, m), 4.18–4.25 (1H, m), 4.48–4.64 (2H, m), 4.99 (1H, d, J=9.5 Hz), 6.87–6.94 (4H, m), 7.09–7.15 (2H, m), 7.28–7.58 (8H, m), 7.72–7.82 (2H, m) MASS (m/z): 610 (M$^+$–H), 123 (bp)

Preparation 47-1)
Ethyl 3-(4-(4-fluorophenoxy)benzene)acrylate (61.7 g) was obtained in a similar manner to that of Preparation 1-1).

NMR (CDCl$_3$, δ): 1.34 (3H, t, J=7 Hz), 4.26 (2H, q, J=7 Hz), 6.34 (1H, d, J=15 Hz), 6.94 (2H, d, J=8 Hz), 6.99–7.10 (4H, m), 7.49 (2H, d, J=8 Hz), 7.64 (1H, d, J=15 Hz)

Preparation 47-2)
7-[4-(4-Fluorophenoxy)phenyl]perhydro-1,4-thiazepin-5-one (51 g) was obtained in a similar manner to that of Preparation 1-2).

NMR (DMSO-d$_6$, δ): 2.62–2.87 (3H, m), 3.45–3.60 (3H, m), 4.15 (1H, d, J=9 Hz), 6.93 (2H, d, J=8 Hz), 7.05–7.10 (2H, m), 7.24 (2H, t, J=8 Hz), 7.35 (2H, d, J=8 Hz), 7.77 (1H, t, J=7 Hz)

Preparation 47-3)
4-tert-Butoxycarbonyl-7-[4-(4-fluorophenoxy)phenyl]-perhydro-1,4-thiazepine (40.9 g) was obtained in a similar manner to that of Preparation 45-3).

NMR (CDCl$_3$, δ): 1.49 (9H, s), 2.03–2.24 (1H, m), 2.40–2.58 (1H, m), 2.74–3.13 (2H, m), 3.22–3.47 (1H, m), 3.57–3.65 (2H, m), 3.73–3.80 (1H, m), 3.93–4.23 (1H, m), 6.87–6.93 (2H, m), 6.96–7.05 (4H, m), 7.22–7.30 (2H, m)

Preparation 47-4)
4-tert-Butoxycarbonyl-7-[4-(4-fluorophenoxy)phenyl]-1,1-dioxoperhydro-1,4-thiazepine (32.9 g) was obtained in a similar manner to that of Preparation 1-5).

NMR (CDCl$_3$, δ): 1.51 (9H, s), 2.30–2.43 (1H, m), 2.52–2.79 (1H, m), 3.23–3.30 (1H, m), 3.35–3.57 (3H, m), 3.87–4.20 (3H, m), 6.92–7.08 (6H, m), 7.31 (2H, d, J=8 Hz)

Preparation 47-5) tert-Butyl 2-[4-tert-butoxycarbonyl-7-[4-(4-fluorophenoxy)phenyl]-1,1-dioxoperhydro-1,4-thiazepin-7-yl]acetate (4.3 g) was obtained in a similar manner to that of Preparation 1-6).

NMR (CDCl$_3$, δ): 1.25 and 1.29 (9H, s), 1.48 and 1.50 (9H, s), 2.58–2.67 (1H, m), 2.84–2.92 (1H, m), 3.12–3.27 (2H, m), 3.35–3.64 (4H, m), 4.00–4.17 (2H, m), 6.94 (2H, d, J=8 Hz), 6.97–7.08 (4H, m), 7.45–7.54 (2H, m) MASS (m/z): 550 (M$^+$+H), 74 (bp)

Preparation 47-6)
2-[4-(9-Fluorenylmethoxycarbonyl)-7-[4-(4-fluorophenoxy)phenyl]-1,1-dioxoperhydro-1,4-thiazepin-7-yl]acetic acid (2.4 g) was obtained in a similar manner to that of Preparation 1-7).

NMR (CDCl$_3$, δ): 1.51 and 1.53 (9H, s), 2.38–2.57 (1H, m), 2.73–3.02 (2H, m), 3.22–3.45 (1H, m), 3.55–3.77 (3H, m), 3.92–4.21 (2H, m), 7.16 (2H, d, J=8 Hz), 7.43 (2H, t, J=8 Hz) MASS (m/z): 610 (M$^+$–H), 123 (bp)

Preparation 48-1)
2-[(S)-7-[4-(4-Chlorophenoxy)phenyl]-4-(9-fluorenylmethoxycarbonyl)-1,1-dioxoperhydro-1,4-thiazepin-7-yl]acetic acid (R)-(+)-α-methylbenzylamine salt (912 mg) was obtained in a similar manner to that of Preparation 3-1).

NMR (DMSO-d$_6$, δ): 1.32 (3H, d, J=7 Hz), 2.64–3.10 (7H, m), 3.53–3.93 (3H, m), 4.08–4.15(1H, m), 4.28–4.51 (3H, m), 6.95–7.00 (3H, m), 7.04–7.09 (2H, m), 7.24–7.47 (16H, m), 7.63–7.69 (2H, m), 7.87–7.92 (3H, MASS (m/z): 632 (M$^+$–H), 134 (bp)

optical purity: 99.4% ee analytical chiral HPLC (column: Chiralpak AS (4.6×250 mm, Daicel Chemical Industries, Ltd.), eluent: 25% EtOH in hexane containing 0.1% TFA, detection: 254 nm, flow rate: 1 ml/min), retention time, (S)-form: 27.1 min, (R)-form: 15.4 min Preparation 48-2)
To a stirred solution of (2S)-2-[7-[4-(4-chlorophenoxy)phenyl]-4-(9-fluorenylmethoxycarbonyl)-1,1-dioxoperhydro-1,4-thiazepin-7-yl]acetic acid (R)-(+)-α-methylbenzylamine (1.345 g) in ethyl acetate (26 ml) was added 1N hydrochloric acid (25 ml) and the solution was stirred at room temperature for 1 hour. The mixture was diluted with ethyl acetate and separated. The organic layer was dried over anhydrous magnesium sulfate and concentrated in vacuo to give 2-[(S)-7-[4-(4-chlorophenoxy)

phenyl]-4-(9-fluorenylmethoxycarbonyl)-1,1-dioxoperhydro-1,4-thiazepin-7-yl]acetic acid (1.178 g) as an oil.

NMR (CDCl$_3$, δ): 2.37–2.47 (2H, m), 2.52–2.67 (2H, m), 3.02–3.25 (2H, m), 3.33–3.50 (2H, m), 3.90–4.10 (1H, m), 4.17–4.27 (1H, m), 4.51–4.59 (2H, m), 4.99–5.05 (1H, m), 6.93 (2H, d, J=8 Hz), 6.95 (2H, d, J=8 Hz), 7.28–7.60 (10H, m), 7.73–7.83 (2H, m)

Preparation 49-1)

tert-Butyl 2-((S)-7-(5-(4-ethylphenyl)-2-thienyl)-1,1-dioxoperhydro-4-(2-pyridinecarbonyl)-1,4-thiazepin-7-yl)acetate (1.61 g) was obtained in a similar manner to that of Example 39.

NMR (DMSO-d$_6$, δ): 1.08–1.26 (12H, m), 2.54–2.70 (2H, m), 2.78–3.38 (4H, m), 3.38–4.24 (6H, m), 7.13 (0.5H, d, J=3 Hz), 7.20 (0.5H, d, J=3 Hz), 7.25 (2H, d, J=8 Hz), 7.40 (0.5H, d, J=3 Hz), 7.44 (0.5H, d, J=3 Hz), 7.46–7.68 (4H, m), 7.92–8.03 (1H, m), 8.56–8.63 (1H, m) MASS (ES+)(m/z): 555.30

Preparation 49-2)

2-[(S)-7-(5-(4-Ethylphenyl)-2-thienyl)-1,1-dioxoperhydro-4-(2-pyridinecarbonyl)-1,4-thiazepin-7-yl]acetic acid hydrochloride (1.55 g) was obtained in a similar manner to that of Preparation 11-4).

NMR (DMSO-d$_6$, δ): 1.19 (3H, t, J=7.5 Hz), 2.62 (2H, q, J=7.5 Hz), 2.66–4.24 (10H, m), 7.14 (0.5H, d, J=3 Hz), 7.20 (0.5H, d, J=3 Hz), 7.25 (2H, d, J=8 Hz), 7.36–7.45 (1H, m), 7.47–7.59 (3H, m), 7.59–7.69 (1H, m), 7.93–8.03 (1H, m), 8.55–8.64 (1H, m)

Preparation 50-1)

tert-Butyl 2-[(S)-7-(5-(4-methoxyphenyl)-2-thienyl)-1,1-dioxoperhydro-4-(3-thienylcarbonyl)-1,4-thiazepin-7-yl]acetate (3.03 g) was obtained in-a similar manner to that of Example 39.

NMR (DMSO-d$_6$, δ): 1.01 (3H, s), 1.23 (6H, s), 2.55–3.40 (4H, m), 3.40–3.75 (3H, m), 3.79 (3H, s), 3.80–3.95 (2H, m), 3.95–4.20 (1H, m), 6.98 (2H, d, J=8 Hz), 7.06–7.20 (1H, m), 7.20–7.36 (2H, m), 7.51–7.69 (3H, m), 7.80–7.94 (1H, m) MASS (ES+) (m/z): 561.50

Preparation 50-2)

2-[(S)-7-(5-(4-Methoxyphenyl)-2-thienyl)-1,1-dioxoperhydro-4-(3-thienylcarbonyl)-1,4-thiazepin-7-yl]acetic acid (2.26 g) was obtained in a similar manner to that of Preparation 11-4).

NMR (DMSO-d$_6$, δ): 2.64–3.50 (4H, m), 3.50–4.15 (9H, m), 6.96 (2H, d, J=8 Hz), 7.15 (1H, br peak), 7.25 (1H, d, J=3 Hz), 7.32 (1H, br peak), 7.48–7.66 (3H, m), 7.84 (1H, br peak) MASS (ES-)(m/z): 504.11

Preparation 50-3)

tert-Butyl 2-[4-tert-butoxycarbonyl-7-(5-(4-methoxyphenyl)-2-thenyl)-1,1-dioxoperhydro-1,4-thiazepin-7-yl]acetate (5.06 g) was obtained in a similar manner to that of Example 39.

NMR (DMSO-d$_6$, δ): 1.24 (9H, d, J=4 Hz), 1.44 (9H, d, J=7 Hz), 2.54–3.29 (4H, m), 3.45–3.75 (6H, m), 3.79 (3H, s), 6.98 (2H, d, J=8 Hz), 7.10–7.15 (1H, m), 7.31–7.35 (1H, m), 7.56 (2H, d, J=8 Hz)

Preparation 50-4)

tert-Butyl 2-[7-(5-(4-methoxyphenyl)-2-thienyl)-1,1-dioxoperhydro-1,4-thiazepin-7-yl]acetate hydrochloride (4.5 g) was obtained in a similar manner to that of Preparation 11-2).

NMR (DMSO-d$_6$, δ): 1.25 (9H, s), 2.69–3.26 (5H, m), 3.40–3.26 (4H, m), 3.79 (3H, s), 4.08–4.23 (1H, m), 7.00 (2H, d, J=8 Hz), 7.16 (1H, d, J=3 Hz), 7.36 (1H, d, J=3 Hz), 7.60 (2H, d, J=8 Hz) MASS (ES+)(m/z): 452.30 (M(Free)+H)

Preparation 50-5)

tert-Butyl 2-[4-(9-fluorenylmethoxycarbonyl)-7-(5-(4-methoxyphenyl)-2-thienyl)-1,1-dioxoperhydro-1,4-thiazepin-7-yl]acetate (6.2 g) was obtained in a similar manner to that of Preparation 11-3).

NMR (DMSO-d$_6$, δ): 1.18–1.26 (9H, m), 2.36–3.25 (6H, m), 3.25–3.82 (8H, m), 4.26–4.51 (2H, m), 6.94–7.04 (2H, m), 7.04–7.47 (5H, m), 7.56 (2H, d, J=8 Hz), 7.63–7.75 (2H, m), 7.82–7.93 (3H, m)

Preparation 50-6)

2-[4-(9-Fluorenylmethoxycarbonyl)-7-(5-(4-methoxyphenyl)-2-thienyl)-1,1-dioxoperhydro-1,4-thiazepin-7-yl]acetic acid (2.0 g) was obtained in a similar manner to that of Preparation 11-4).

NMR (DMSO-d$_6$, δ): 2.61–3.45 (6H, m), 3.45–3.84 (7H, m), 4.26–4.53 (3H, m), 6.04–7.04 (2H, m), 7.04–7.15 (1H, m), 7.30–7.46 (5H, m), 7.56 (2H, d, J=8 Hz), 7.60–7.75 (2H, m), 7.90 (2H, d, J=8 Hz)

The following compounds were obtained in a similar manner to that of Preparation 9-2).

Preparation 51-1)

2-Naphthylboronic acid pinacol cyclic ester

Preparation 51-2)

4-(1,1-Dioxo-2-isothiazolidinyl)phenylboronic acid pinacol cyclic ester

Preparation 52

4-Cyanophenylboronic acid pinacol cyclic ester

Preparation 53

4-Trifluoromethylphenylboronic acid pinacol cyclic ester

Preparation 54

4-(Cyanomethyl)phenylboronic acid pinacol cyclic ester

Preparation 55-1)

A mixture of tert-butyl 2-[(S)-7-(5-bromo-2-thienyl)-1,1-dioxoperhydro-1,4-thiazepin-7-yl]acetate•(1R)-10-camphorsulfonate (2.00 g), dimethylaminosulfonyl chloride (569 mg) and 2M aqueous sodium carbonate (10.6 ml) in dioxane (40 ml) was stirred for 2.5 days at room temperature. After the reaction solution was concentrated in vacuo, the mixture was diluted with water. The obtained suspension was stirred for 30 minutes under ice-cooling. The resulting solid was collected, washed with water and dried in vacuo to give tert-butyl 2-[(S)-7-(5-bromo-2-thienyl)-4-dimethylaminosulfonyl-1,1-dioxoperhydro-1,4-thiazepin-7-yl]acetate (1.449 g) as a white solid.

NMR (CDCl$_3$, δ): 1.34 (9H, s), 2.74–2.82 (1H, m), 2.82 (6H, s), 3.02–3.15 (2H, m), 3.25–3.37 (4H, m), 3.40–3.62 (3H, m), 3.87–4.05 (2H, m), 7.00–7.03 (2H, m) MASS (ESI+): 531 (M+H)

Preparation 55-2)

tert-Butyl 2-[(S)-7-(5-(4-chlorophenyl)-2-thienyl)-4-dimethylaminosulfonyl-1,1-dioxoperhydro-1,4-thiazepin-7-yl]acetate was obtained in a similar manner to that of Example 39.

NMR (CDCl$_3$, δ): 1.33 (9H, s), 2.78–2.91 (7H, m), 3.10–3.24 (1H, m), 3.27–3.37 (2H, m), 3.41–3.65 (4H, m), 3.86–4.10 (2H, m), 7.22 (2H, s), 7.33 (2H, d, J=9 Hz), 7.51 (2H, d, J=9 Hz) MASS (ESI-): 561 (M-H)

Preparation 55-3)

2-[(S)-7-(5-(4-Chlorophenyl)-2-thienyl)-4-dimethylaminosulfonyl-1,1-dioxoperhydro-1,4-thiazepin-7-yl]acetic acid was obtained in a similar manner to that of Preparation 11-4).

NMR (CDCl$_3$, δ): 2.70–2.91 (7H, m), 3.12–3.26 (1H, m), 3.30–3.67 (6H, m), 3.85–4.07 (2H, m), 7.22 (2H, s), 7.29–7.40 (2H, m), 7.45–7.55 (2H, m) MASS (ESI+): 507 (M+H)

Preparation 56
Quinoline-6-boronic acid pinacol cyclic ester was obtained in a similar manner to that of Preparation 9-2).
Preparation 57-1)
tert-Butyl 2-[7-(5-(4-methylthiophenyl)-2-thienyl)-4-tert-butoxycarbonyl-1,1-dioxoperhydro-1,4-thiazepin-7-yl]acetate (6.0 g) was obtained in a similar manner to that of Example 39.
NMR (CDCl$_3$, δ): 1.28, 1.31 (9H, s), 1.47, 1.51 (9H, s), 2.51 (3H, s), 2.63–2.73 (1H, m), 2.87–2.93 (1H, m), 3.03–3.24 (2H, m), 3.31–3.81 (4H, m), 3.90–4.10 (2H, m), 7.19–7.25 (4H, m), 7.48–7.51 (2H, m) MASS (ESI+): 568 (M+H)
Preparation 57-2)
tert-Butyl 2-[7-(5-(4-methylthiophenyl)-2-thienyl)-1,1-dioxoperhydro-1,4-thiazepin-7-yl]acetate (4.8 g) was obtained in a similar manner to that of Preparation 11-2).
MASS (ESI+): 468 (M+H)
Preparation 57-3)
tert-Butyl 2-[4-(9-fluorenylmethoxycarbonyl)-7-(5-(4-methylthiophenyl)-2-thienyl)-1,1-dioxoperhydro-1,4-thiazepin-7-yl]acetate (6.2 g) was obtained in a similar manner to that of Preparation 11-3).
NMR (CDCl$_3$, δ): 1.26, 1.28 (9H, s), 2.49 (3H, s), 2.53–2.66 (2H, m), 2.82–3.08 (2H, m), 3.20–3.71 (4H, m), 3.86–4.05 (2H, m), 4.18–4.30 (1H, m), 4.47–4.58 (1H, m), 4.78–4.84 (1H, m), 7.11–7.24 (5H, m), 7.31–7.47 (6H, m), 7.54–7.61 (1H, m), 7.74–7.80 (2H, m)
Preparation 57-4)
2-[4-(9-Fluorenylmethoxycarbonyl)-7-(5-(4-methylthiophenyl)-2-thienyl)-1,1-dioxoperhydro-1,4-thiazepin-7-yl)acetic acid (5.0 g) was obtained in a similar manner to that of Preparation 11-4].
NMR (CDCl$_3$, δ): 2.48 (3H, s), 2.53–2.66 (2H, m), 2.82–3.08 (2H, m), 3.20–3.71 (4H, m), 3.86–4.05 (2H, m), 4.18–4.30 (1H, m), 4.47–4.58 (1H, m), 4.78–4.84 (1H, m), 7.11–7.24 (5H, m), 7.31–7.47 (6H, m), 7.54–7.61 (1H, m), 7.74–7.80 (2H, m)
Preparation 58-1)
tert-Butyl 2-[7-(5-(2-naphthyl)-2-thienyl)-4-tert-butoxycarbonyl-1,1-dioxoperhydro-1,4-thiazepin-7-yl]acetate (6.5 g) was obtained in a similar manner to that of Example 39.
MASS (ESI+): 572 (M+H)
Preparation 58-2)
tert-Butyl 2-[7-(5-(2-naphthyl)-2-thienyl)-1,1-dioxoperhydro-1,4-thiazepin-7-yl]acetate (4.0 g) was obtained in a similar manner to that of Preparation 11-2).
MASS (ESI+): 472 (M+H)
Preparation 58-3)
tert-Butyl 2-[4-(9-fluorenylmethoxycarbonyl)-7-(5-(2-naphthyl)-2-thienyl)-1,1-dioxoperhydro-1,4-thiazepin-7-yl]acetate (5.5 g) was obtained in a similar manner to that of Preparation 11-3).
MASS (ESI+): 694 (M+H)
Preparation 58-4)
2-4-(9-Fluorenylmethoxycarbonyl)-7-(5-(2-naphthyl)-2-thienyl)-1,1-dioxoperhydro-1,4-thiazepin-7-yl)acetic acid (3.5 g) was obtained in a similar manner to that of Preparation 11-4).
NMR (CDCl$_3$, δ): 2.60–3.15 (3H, m), 3.20–4.09 (6H, m), 4.11–4.90 (4H, m), 7.15–7.82 (17H, m), 8.00 (2H, d, J=7.2 Hz)
Preparation 59-1)
4-Biphenylylboronic acid pinacol cyclic ester was obtained in a similar manner to that of Preparation 9-2).

Preparation 59-2)
tert-Butyl 2-[7-(5-(4-biphenylyl)-2-thienyl)-4-tert-butoxycarbonyl-1,1-dioxoperhydro-1,4-thiazepin-7-yl]acetate (7.0 g) was obtained in a similar manner to that of Example 39.
NMR (CDCl$_3$, δ): 1.24, 1.27 (9H, s), 1.47, 1.52 (9H, s), 2.64–2.75 (1H, m), 2.89–2.95 (1H, m), 3.07–3.23 (2H, m), 3.35–3.75 (4H, m), 3.93–4.11 (2H, m), 7.21–7.25 (2H, m), 7.36–7.38 (1H, m), 7.43–7.48 (2H, m), 7.59–7.67 (6H, m)
MASS (ESI+): 598 (M+H)
Preparation 59-3)
tert-Butyl 2-[7-(5-(4-biphenylyl)-2-thienyl)-1,1-dioxoperhydro-1,4-thiazepin-7-yl]acetate was obtained in a similar manner to that of Preparation 11-2).
MASS (ESI+): 498 (M+H)
Preparation 59-4)
tert-Butyl 2-[4-(9-fluorenylmethoxycarbonyl)-7-(5-(4-biphenylyl)-2-thienyl)-1,1-dioxoperhydro-1,4-thiazepin-7-yl]acetate was obtained in a similar manner to that of Preparation 11-3).
NMR (CDCl$_3$, δ): 1.24, 1.27 (9H, s), 2.52–2.65 (2H, m), 2.80–4.06 (8H, m), 4.20–4.78 (3H, m), 7.20–7.80 (19H, m)
Preparation 59-5)
2-[4-(9-Fluorenylmethoxycarbonyl)-7-(5-(4-biphenylyl)-2-thienyl)-1,1-dioxoperhydro-1,4-thiazepin-7-yl]acetic acid was obtained in a similar manner to that of Preparation 11-4).
NMR (CDCl$_3$, δ): 2.50–2.68 (2H, m), 2.80–4.06 (8H, m), 4.10–4.75 (3H, m), 7.17–7.85 (19H, m)
Preparation 60-1)
tert-Butyl 2-[7-(5-(4-methylphenyl)-2-thienyl)-4-tert-butoxycarbonyl-1,1-dioxoperhydro-1,4-thiazepin-7-yl]acetate (230 mg) was obtained in a similar manner to that of Example 39.
NMR (CDCl$_3$, δ): 1.27, 1.30 (9H, s), 1.47, 1.51 (9H, s), 2.36 (3H, s), 2.60–2.72 (1H, m), 2.87–2.92 (1H, m), 3.05–3.24 (2H, m), 3.30–3.80 (4H, m), 3.88–4.13 (2H, m), 7.15–7.18 (4H, m), 7.45–7.48 (2H, m) MASS (ESI+): 536 (M+H)
Preparation 60-2)
tert-Butyl 2-[7-(5-(4-methylphenyl)-2-thienyl)-1,1-dioxoperhydro-1,4-thiazepin-7-yl]acetate (185 mg) was obtained in a similar manner to that of Preparation 11-2).
NMR (CDCl$_3$, δ): 1.24 (9H, s), 2.35 (3H, s), 3.00–3.38 (6H, m), 3.60–3.85 (4H, m), 7.14–7.16 (4H, m), 7.44 (2H, d, J=8.5 Hz) MASS (ESI+): 436 (M+H)
Preparation 60-3)
tert-Butyl 2-[4-(9-fluorenylmethoxycarbonyl)-7-(5-(4-methylphenyl)-2-thienyl)-1,1-dioxoperhydro-1,4-thiazepin-7-yl]acetate (210 mg) was obtained in a similar manner to that of Preparation 11-3).
NMR (CDCl$_3$, δ): 1.27, 1.30 (9H, s), 2.35 (3H, s), 2.53–4.05 (10H, m), 4.18–4.80 (3H, m), 7.10–7.24 (5H, m), 7.31–7.50 (6H, m), 7.54–7.61 (1H, m), 7.74–7.80 (2H, m)
Preparation 60-4)
2-[4-(9-Fluorenylmethoxycarbonyl)-7-(5-(4-methylphenyl)-2-thienyl)-1,1-dioxoperhydro-1,4-thiazepin-7-yl]acetic acid (190 mg) was obtained in a similar manner to that of Preparation 11-4).
NMR (CDCl$_3$, δ): 2.35 (3H, s), 2.53–4.05 (10H, m), 4.18–4.80 (3H, m), 7.10–7.24 (5H, m), 7.31–7.50 (6H, m), 7.54–7.61 (1H, m), 7.74–7.80 (2H, m)
Preparation 61
3-Methyl-2-oxo-2,3-dihydro-1,3-benzothiazol-6-ylboronic acid pinacol cyclic ester was obtained in a similar manner to that of Preparation 9-2).
Preparation 62-1)
tert-Butyl 2-[(S)-4-benzoyl-7-(5-(4-ethoxyphenyl-2-thienyl)-1,1-dioxoperhydro-1,4-thiazepin-7-yl)acetate (4.65 g) was obtained in a similar manner to that of Example 39.
NMR (CDCl$_3$, δ): 1.12 (5H, s), 1.28 (4H, s), 2.62–2.83 (2H, m), 2.91–3.08 (1H, m), 3.12–3.28 (1H, m), 3.28–3.88

(5H, m), 3.88–4.11 (3H, m), 4.17–4.32 (0.5H, m), 4.35–4.47 (0.5H, m), 6.83–6.94 (2H, m), 7.05–7.15 (2H, m), 7.20–7.55 (7H, m) MASS (ES+)(m/z): 570.18

Preparation 62-2)

2-[(S)-4-Benzoyl-7-(5-(4-ethoxyphenyl)-2-thienyl)-1,1-dioxoperhydro-1,4-thiazepin-7-yl]acetic acid was obtained in a similar manner to that of Preparation 11-4).

NMR (DMSO-d$_6$, δ): 1.34 (3H, t, J=7.5 Hz), 2.52–3.40 (4H, m), 3.40–3.99 (5+⅔H, m), 4.50 (2H, q, J=7.5 Hz), 4.10–4.24 (⅓H, m), 6.96 (2H, d, J=8 Hz), 7.11 (⅓H, d, J=3 Hz), 7.17 (⅔H, d, J=3 Hz), 7.38–7.50 (5H, m), 7.50–7.62 (2H, m) MASS (ES−)(m/z): 512.29

Preparation 63-1)

tert-Butyl 2-[4-tert-butoxycarbonyl-7-(5-(4-ethoxyphenyl)-2-thienyl)-1,1-dioxoperhydro-1,4-thiazepin-7-yl]acetate (5.06 g) was obtained in a similar manner to that of Example 39.

NMR (DMSO-d$_6$, δ): 1.24 (%2H, s), 1.25 (%2H, s), 1.33 (3H, t, J=7.5 Hz), 1.42 (%2H, s), 1.44 (%2H, s), 2.52–3.26 (4H, m), 3.38–3.90 (6H, m), 4.05 (2H, q, J=7.5 Hz), 6.06 (2H, d, J=8 Hz), 7.09–7.15 (1H, m), 7.30–7.35 (1H, m), 7.56 (2H, d, J=8 Hz) MASS (ES+)(m/z): 566.15

Preparation 63-2)

tert-Butyl 2-[7-(5-(4-ethoxyphenyl)-2-thienyl)-1,1-dioxoperhydro-1,4-thiazepin-7-yl]acetate hydrochloride (4.85 g) was obtained in a similar manner to that of Preparation 11-2).

NMR (DMSO-d$_6$, δ): 1.25 (9H, s), 1.32 (3H, t, J=7.5 Hz), 2.56–3.23 (4H, m), 3.40–3.76 (5H, m), 3.98–4.20 (3H, m), 6.96 (2H, d, J=8 Hz), 7.16 (1H, d, J=3 Hz), 7.37 (1H, d, J=3 Hz), 7.56 (2H, d, J=8 Hz) MASS (ES+)(m/z): 466.30 (M(Free)+H)

Preparation 63-3)

tert-Butyl 2-[4-(9-fluorenylmethoxycarbonyl)-7-(5-(4-ethoxyphenyl)-2-thienyl)-1,1-dioxoperhydro-1,4-thiazepin-7-yl]acetate (6.65 g) was obtained in a similar manner to that of Preparation 11-3).

NMR (DMSO-d$_6$, δ): 1.22 (%2H, s), 1.24 (%2H, s), 1.30–1.40 (3H, m), 2.55–3.25 (4H, m), 3.40–3.86 (6H, m), 3.96–4.11 (3H, m), 4.24–4.56 (2H, m), 6.94–7.02 (2H, m), 7.28–7.46 (6H, m), 7.55 (2H, d, J=8 Hz), 7.62–7.75 (2H, m), 7.90 (2H, d, J=8 Hz)

Preparation 63-4)

2-[4-(9-Fluorenylmethoxycarbonyl)-7-(5-(4-ethoxyphenyl)-2-thienyl)-1,1-dioxoperhydro-1,4-thiazepin-7-yl]acetic acid (4.0 g) was obtained in a similar manner to that of Preparation 11-4).

NMR (DMSO-d$_6$, δ): 1.30–1.40 (3H, m), 2.46–3.86 (10H, m), 3.99–4.11 (3H, m), 4.25–4.50 (2H, m), 6.91–7.04 (2H, m), 7.26–7.48 (6H, m), 7.56 (2H, d, J=8 Hz), 7.62–7.76 (2H, m), 7.90 (2H, d, J=8 Hz) MASS (ES+)(m/z): 632.03.

Preparation 64-1)

4-(4-Methoxyphenoxy)benzaldehyde (47.4 g) was obtained in a similar manner to that of Preparation 46-1).

NMR (CDCl$_3$, δ): 3.83 (3H, s), 6.91 (2H, d, J=8 Hz), 6.98–7.04 (4H, m), 7.82 (2H, d, J=8 Hz), 9.90 (1H, s)

Preparation 64-2)

Ethyl 3-(4-(4-methoxyphenoxy)benzene)acrylate (26.4 g) was obtained in a similar manner to that of Preparation 1-1).

NMR (CDCl$_3$, δ): 1.33 (3H, t, J=7 Hz), 3.82 (3H, s), 4.25 (2H, q, J=7 Hz), 6.33 (1H, d, J=15 Hz), 6.90 (4H, dd, J=8, 2 Hz), 7.46 (2H, d, J=8 Hz), 7.64 (1H, d, J=15 Hz)

Preparation 64-3)

7-[4-(4-Methoxyphenoxy)phenyl]perhydro-1,4-thiazepin-5-one (5.7 g) was obtained in a similar manner to that of Preparation 1-2).

NMR (DMSO-d$_6$, δ): 2.64–2.87 (3H, m), 3.45–3.63 (3H, m), 3.75 (3H, s), 4.14 (1H, d, J=9 Hz), 6.87 (2H, d, J=7.5 Hz), 6.99 (4H, q, J=7.5 Hz), 7.33 (2H, d, J=7.5 Hz), 7.77 (1H, t, J=7 Hz)

Preparation 64-4)

4-tert-Butoxycarbonyl-7-[4-(4-methoxyphenoxy)phenyl]-perhydro-1,4-thiazepine (6.6 g) was obtained in a similar manner to that of Preparation 45-3).

NMR (CDCl$_3$, δ): 1.50 (9H, s), 2.00–2.24 (1H, m), 2.38–2.55 (1H, m), 2.73–3.03 (2H, m), 3.22–3.45 (1H, m), 3.53–3.65 (2H, m), 3.71–3.79 (1H, m), 3.81 (3H, s), 3.92–4.22 (1H, m), 6.88 (4H, d, J=8 Hz), 6.97 (2H, d, J=8 Hz), 7.22 (2H, d, J=8 Hz)

Preparation 64-5)

4-tert-Butoxycarbonyl-7-[4-(4-methoxyphenoxy)phenyl]-1,1-dioxoperhydro-1,4-thiazepine (6.43 g) was obtained in a similar manner to that of Preparation 1-5).

NMR (CDCl$_3$, δ): 1.48 and 1.50 (9H, s), 2.28–2.43 (1H, m), 3.20–3.57 (5H, m), 3.81 (3H, s), 3.87–4.19 (4H, m), 6.85–7.03 (6H, m), 7.28–7.30 (2H, m)

Preparation 64-6)

tert-Butyl 2-[4-tert-butoxycarbonyl-7-[4-(4-methoxyphenoxy) phenyl]-1,1-dioxoperhydro-1,4-thiazepin-7-yl]acetate (2.3 g) was obtained in a similar manner to that of Preparation 1-6).

NMR (CDCl$_3$, δ): 1.24 and 1.28 (9H, s), 1.48 and 1.50 (9H, s), 2.56–2.66 (1H, m), 2.82–2.90 (1H, m), 3.10–3.24 (2H, m), 3.32–3.63 (4H, m), 3.81 (3H, s), 3.99–4.15 (2H, m), 6.87–7.00 (6H, m), 7.44–7.52 (2H, m)

Preparation 64-7)

2-[4-(9-Fluorenylmethoxycarbonyl)-7-[4-(4-methoxyphenoxy) phenyl]-1,1-dioxoperhydro-1,4-thiazepin-7-yl]acetic acid (2.3 g) was obtained in a similar manner to that of Preparation 1-7).

NMR (CDCl$_3$—CD$_3$OD, δ): 2.40–2.68 (4H, m), 3.04–3.25 (1H, m), 3.32–3.47 (3H, m), 3.30 and 3.32 (3H, s), 3.94–4.07 (1H, m), 4.20–4.28 (1H, m), 4.43–4.60 (1H, m), 4.90–4.96 (1H, m), 6.83–7.00 (7H, m), 7.35–7.60 (7H, m), 7.75–7.82 (2H, m) MASS (m/z): 626 (M$^+$−H), 123 (bp)

Preparation 65-1)

To a solution of tert-butyl 2-[(S)-7-[5-(4-ethylphenyl)-2-thienyl]-1,1-dioxoperhydro-1,4-thiazepin-7-yl]acetate (7.91 g) and pyridine (30 ml) in chloroform (15 ml) was added a solution of propanesulfonyl chloride (5.02 mg) in chloroform (15 ml) at 0° C. The resulting mixture was stirred for 3 hours at 0° C. Ethyl acetate (200 ml) was added and the solution was washed with 1N hydrochloric acid (150 ml) for two times, saturated sodium bicarbonate, and brine, dried over magnesium sulfate and evaporated to give a brown gum. The gum was dissolved in ethyl acetate (75 ml) and silica gel (12 ml) was added to the solution. The silica gel was removed by filtration, and the resulting filtrate was evaporated. Silica gel column chromatography (eluent: ethyl acetate/hexane from 13/27 to 9/11) afforded tert-butyl 2-[(S)-7-[5-(4-ethylphenyl)-2-thienyl]-1,1-dioxoperhydro-4-propanesulfonyl-1,4-thiazepin-7-yl]acetate (7.81 g) as an yellowish solid.

NMR (CDCl$_3$, δ): 1.08 (3H, t, J=8 Hz), 1.25 (3H, t, J=8 Hz), 1.32 (9H, s), 1.77–1.89 (2H, m), 2.76 (2H, q, J=7 Hz), 2.80–4.14 (12H, m), 7.17–7.22 (4H, m), 7.49 (2H, d, J=8 Hz) MASS (ESI+): 556.23 (MH)

Preparation 65-2)

A solution of tert-butyl 2-[(S)-7-[5-(4-ethylphenyl)-2-thienyl]-1,1-dioxoperhydro-4-propanesulfonyl-1,4-thiazepin-7-yl]acetate (4.70 g) in formic acid (50 ml) was stirred for 2 hours at room temperature. The volatile was removed in vacuo and three evaporation from chloroform (30 ml) afforded 2-[((S)-7-[5-(4-ethylphenyl)-2-thienyl]-1,1-dioxoperhydro-4-propanesulfonyl-1,4-thiazepin-7-yl] acetic acid (4.60 g) as a pale yellow solid.

NMR (CDCl₃, δ): 10.7 (3H, t, J=8 Hz), 1.24 (3H, t, J=8 Hz), 1.77–1.89 (2H, m), 2.86 (2H, q, J=7 Hz), 2.80–4.14 (12H, m), 7.17–7.22 (4H, m), 7.47–7.50 (2H, d, J=8 Hz) MASS (ESI+): 500.17 (MH) and ESI(−) 498.30 (M−H)

Preparation 66-1)

To a solution of t-butyl 2-[(S)-7-(5-bromo-2-thienyl)-1,1-dioxoperhydro-1,4-thiazepin-7-yl]acetate•(1R)-10-camphorsulfonate (140 g) and triethylamine (44.6 ml) in chloroform (1.4 l) were added di-t-butyl dicarbonate (46.5 g) under ice-water cooling and the mixture was stirred at ambient temperature for 15 hours. After evaporation of solvent, ethyl acetate was added. The solution was washed with 5% citric acid solution, water, saturated sodium bicarbonate solution and brine, dried over magnesium sulfate, and evaporated in vacuo to give t-butyl 2-[(S)-7-(5-bromo-2-thienyl)-4-t-butoxycarbonyl-1,1-dioxoperhydro-1,4-thiazepin-7-yl]acetate as colorless oil (117 g).

NMR (CDCl₃, δ): 1.28, 1.33 (9H, s), 1.52, 1.54 (9H, s), 2.54–2.70 (1H, br), 2.83, 2.92 (1H, br), 2.94–3.12 (1H, br), 3.14–3.79 (6H, br), 3.86–4.07 (1H, br), 6.94–7.03 (2H, br) MASS (m/z): 524, 526 (M+H)

Preparation 66-2)

t-Butyl 2-[(S)-4-t-butoxycarbonyl-7-(5-(4-propylphenyl)-2-thienyl)-1,1-dioxoperhydro-1,4-thiazepin-7-yl]acetate (12.6 g) was obtained in a similar manner to that of Example 39.

NMR (CDCl₃, δ): 0.95 (3H, t, J=7 Hz), 1.27, 1.30 (9H, s), 1.46, 1.51 (9H, s), 1.60–1.74 (2H, m), 2.59 (2H, t, J=7 Hz), 2.66–2.79 (1H, br), 2.88, 2.95 (1H, br), 3.05–3.26 (2H, br), 3.33–3.86 (5H, br), 3.90–4.18 (1H, br), 7.18 (3H, br), 7.48 (2H, br)

Preparation 66-3)

To a solution of t-butyl 2-[(S)-4-t-butoxycarbonyl-7-(5-(4-propylphenyl)-2-thienyl)-1,1-dioxoperhydro-1,4-thiazepin-7-yl]acetate (10.4 g) in tetrahydrofuran (120 ml) was added conc. hydrochloric acid (30 ml) in tetrahydrofuran (30 ml) under ice-water cooling and the mixture was stirred at ambient temperature for 15 hours. The mixture was basified with saturated sodium bicarbonate solution and extracted with ethyl acetate. The organic layer was separated, washed with brine, dried over magnesium sulfate, and evaporated in vacuo to give t-butyl 2-[(S)-7-(5-(4-propylphenyl)-2-thienyl)-1,1-dioxoperhydro-1,4-thiazepin-7-yl]acetate (8.94 g) as yellow oil.

NMR (CDCl₃, δ): 0.95 (3H, t, J=7 Hz), 1.27 (9H, s), 1.60–1.80 (2H, br), 2.48–2.60 (1H, br), 2.59 (2H, t, J=7 Hz), 2.97–3.80 (10H, m), 7.14–7.24 (4H, m), 7.46–7.53 (2H, d, J=8 Hz) MASS (m/z): 464 (M+H)

Preparation 66-4)

t-Butyl 2-[(S)-4-methanesulfonyl-7-(5-(4-propylphenyl)-2-thienyl)-1,1-dioxoperhydro-1,4-thiazepin-7-yl]acetate (6.38 g) was obtained in a similar manner to that of Preparation 11-3).

NMR (CDCl₃, δ): 0.95 (3H, s), 1.31 (9H, s), 1.62–1.73 (2H, m), 2.59 (2H, t, J=7 Hz), 2.78–2.92 (1H, br), 2.92 (3H, s), 3.13–3.61 (7H, br), 3.76–3.88 (1H, br), 4.12–4.23 (1H, br), 7.15–7.25 (4H, m), 7.48 (2H, d, J=8 Hz) MASS (m/z): 542 (M+H)

Preparation 66-5)

2-[(S)-4-Methanesulfonyl-7-(5-(4-propylphenyl)-2-thienyl)-1,1-dioxoperhydro-1,4-thiazepin-7-yl]acetic acid (6.95 g) was obtained in a similar manner to that of Preparation 11-4).

NMR (CDCl₃, δ): 0.94 (3H, t, J=7 Hz), 1.58–1.76 (2H, m), 2.58 (2H, t, J=7 Hz), 2.76–2.93 (1H, br), 2.91 (3H, s), 3.10–4.18 (9H, br), 7.12–7.28 (4H, m), 7.48 (2H, d, J=8 Hz) MASS (m/z): 484 (M−H)

Preparation 67-1)

4-Trifluoromethoxyphenylboronic acid pinacol cyclic ester was obtained in a similar manner to that of Preparation 9-2).

Preparation 67-2)

t-Butyl 2-[(S)-4-t-butoxycarbonyl-7-(5-(4-trifluoromethoxyphenyl)-2-thienyl)-1,1-dioxoperhydro-1,4-thiazepin-7-yl]acetate (18.4 g) was obtained in a similar manner to that of Example 39.

NMR (CDCl₃, δ): 1.28, 1.31 (9H, s), 1.47, 1.51 (9H, s), 2.63–2.78 (1H, br), 2.88, 2.95 (1H, br), 3.04–3.84 (7H, br), 3.92–4.06 (1H, br), 7.17–7.26 (4H, m), 7.59 (2H, d, J=8 Hz) MASS (m/z): 606 (M+H)

Preparation 67-3)

t-Butyl 2-[(S)-7-(5-(4-trifluoromethoxyphenyl)-2-thienyl)-1,1-dioxoperhydro-1,4-thiazepin-7-yl]acetate hydrochloride (5.56 g) was obtained in a similar manner to that of Preparation 11-2).

NMR (CDCl₃, δ): 1.29 (9H, s), 2.48–2.65 (1H, m), 2.97–3.96 (9H, m), 7.22 (4H, m), 7.60 (2H, d, J=8 Hz) MASS (m/z): 506 (M+H)

Preparation 67-4)

t-Butyl 2-[(S)-4-(2-pyridinecarbonyl)-7-(5-(4-trifluoromethoxyphenyl)-2-thienyl)-1,1-dioxoperhydro-1,4-thiazepin-7-yl]acetate (4.90 g) was obtained in a similar manner to that of Example 33.

NMR (CDCl₃, δ): 1.21, 1.32 (9H, s), 2.78–2.92 (1H, m), 3.06–4.52 (9H, m), 7.16–7.26 (4H, m), 7.33–7.42 (1H, m), 7.53–7.60 (2H, m), 7.78–7.88 (2H, m), 8.47, 8.58 (1H, m) MASS (m/z): 611 (M+H)

Preparation 67-5)

2-[(S)-4-(2-Pyridinecarbonyl)-7-(5-(4-trifluoromethoxyphenyl)-2-thienyl)-1,1-dioxoperhydro-1,4-thiazepin-7-yl]acetic acid hydrochloride (4.65 g) was obtained in a similar manner to that of Preparation 11-4).

NMR (DMSO-d₆, δ): 2.77–3.00 (2H, m), 3.05–3.23 (2H, m), 3.38–4.35 (6H, m), 7.27, 7.34 (1H, d, J=3 Hz), 7.50 (2H, d, J=8 Hz), 7.62 (2H, m), 7.74 (1H, m), 7.87 (2H, m), 8.06 (1H, m), 8.69 (1H, br) MASS (m/z): 555 (M+H)

Preparation 68-1)

t-Butyl 2-[(S)-4-(3-thiophenecarbonyl)-7-(5-(4-trifluoromethoxyphenyl)-2-thienyl)-1,1-dioxoperhydro-1,4-thiazepin-7-yl]acetate (5.84 g) was obtained in a similar manner to that of Preparation 68-1).

NMR (CDCl₃, δ): 1.07–1.42 (9H, br), 2.63–4.48 (10H, m), 7.08–7.47 (6H, br), 7.52–7.69 (3H, m) MASS (m/z): 616 (M+H)

Preparation 68-2)

2-[(S)-4-(3-Thiophenecarbonyl)-7-(5-(4-trifluoromethoxyphenyl)-2-thienyl)-1,1-dioxoperhydro-1,4-thiazepin-7-yl]acetic acid (5.00 g) was obtained in a similar manner to that of Preparation 11-4).

NMR (CDCl₃, δ): 2.60–2.88 (1H, br), 3.03–4.03 (8H, br), 4.03–4.46 (1H, br), 7.06–7.35 (6H, m), 7.33 (1H, m), 7.57 (2H, d, J=8 Hz) MASS (m/z): 558 (M−H), 560 (M+H)

Preparation 69-1)

t-Butyl 2-[(S)-7-(5-bromo-2-thienyl)-4-(2-pyridinecarbonyl)-1,1-dioxoperhydro-1,4-thiazepin-7-yl]acetate (9.40 g) was obtained in a similar manner to that of Example 33.

NMR (CDCl₃, δ): 1.22, 1.30 (9H, s), 2.68–2.85 (1H, br), 3.00–4.03 (8H, m), 4.18–4.48 (1H, m), 6.93–7.04 (2H, m), 7.38 (1H, m), 7.67–7.78 (2H, m), 8.48, 8.57 (1H, m) MASS (m/z): 529, 531 (M+H)

Preparation 69-2)

2-[(S)-7-(5-Bromo-2-thienyl)-4-(2-pyridinecarbonyl)-1,1-dioxoperhydro-1,4-thiazepin-7-yl]acetic acid hydrochloride (9.72 g) was obtained in a similar manner to that of Preparation 11-4).

NMR (DMSO-$d_6$, δ): 2.60–3.02 (2H, m), 3.14–4.23 (8H, m), 7.01, 7.07 (1H, d, J=3 Hz), 7.22 (1H, m), 7.53 (1H, m), 7.63 (1H, m), 7.93–8.03 (1H, m), 8.60 (1H, m)

Preparation 70-1)

4-(4-Ethylphenoxy)benzaldehyde (18.1 g) was obtained in a similar manner to that of Preparation 46-1).

NMR (CDCl$_3$, δ): 1.26 (3H, t, J=7 Hz), 2.67 (2H, q, J=7 Hz), 7.00 (2H, d, J=8 Hz), 7.04 (2H, d, J=8 Hz), 7.24 (2H, d, J=8 Hz), 7.83 (2H, d, J=8 Hz), 9.90 (1H, s)

Preparation 70-2)

Ethyl 3-(4-(4-ethylphenoxy)benzene)acrylate (22.8 g) was obtained in a similar manner to that of Preparation 1-1).

NMR (CDCl$_3$, δ): 1.25 (3H, t, J=7 Hz), 1.36 (3H, t, J=7 Hz), 2.65 (2H, q, J=7 Hz), 4.25 (2H, q, J=7 Hz), 6.33 (1H, d, J=15 Hz), 6.93–7.00 (4H, m), 7.19 (2H, d, J=8 Hz), 7.47 (2H, d, J=8 Hz), 7.64 (1H, d, J=15 Hz)

Preparation 70-3)

7-[4-(4-Ethylphenoxy)phenylperhydro-1,4-thiazepin-5-one (12 g) was obtained in a similar manner to that of Preparation 1-2).

NMR (DMSO-$d_6$, δ): 1.18 (3H, t, J=7 Hz), 2.60 (2H, q, J=7 Hz), 2.673–2.87 (3H, m), 3.45–3.65 (3H, m), 4.15 (1H, d, J=9 Hz), 6.93 (4H, d, J=8 Hz), 7.23 (2H, d, J=8 Hz), 7.35 (2H, d, J=8 Hz), 7.78 (1H, t, J=7 Hz)

Preparation 70-4)

4-tert-Butoxycarbonyl-7-[4-(4-ethylphenoxy)phenyl] perhydro-1,4-thiazepine (12.2 g) was obtained in a similar manner to that of Preparation 70-4).

NMR (CDCl$_3$, δ): 1.25 (3H, t, J=7 Hz), 1.50 (9H, s), 2.03–2.24 (1H, m), 2.39–2.56 (1H, m), 2.63 (2H, q, J=7 Hz), 2.73–3.03 (2H, m), 3.20–3.46 (1H, m), 3.56–3.65 (2H, m), 3.72–3.80 (1H, m), 3.92–4.22 (1H, m), 6.87–6.95 (4H, m), 7.15 (2H, d, J=8 Hz), 7.20–7.24 (2H, m)

Preparation 70-5)

4-tert-Butoxycarbonyl-7-[4-(4-ethylphenoxy)phenyl]-1,1-dioxoperhydro-1,4-thiazepine (10.3 g) was obtained in a similar manner to that of Preparation 1-5).

NMR (CDCl$_3$, δ): 1.25 (3H, t, J=7 Hz), 1.50 and 1.52 (9H, s), 2.29–2.43 (1H, m), 2.49–2.79 (1H, m), 2.64 (2H, q, J=7 Hz), 3.22–3.30 (1H, m), 3.33–3.57 (3H, m), 3.86–4.19 (3H, m), 6.97 (4H, d, J=8 Hz), 7.18 (2H, d, J=8 Hz), 7.30 (2H, d, J=8 Hz)

Preparation 70-6)

tert-Butyl 2-[4-tert-butoxycarbonyl-7-[4-(4-ethylphenoxy)phenyl]-1,1-dioxoperhydro-1,4-thiazepin-7-yl]acetate (3 g) was obtained in a similar manner to that of Preparation 1-6).

NMR (CDCl$_3$, δ): 1.23 (3H, t, J=7 Hz), 1.24 and 1.28 (9H, s), 1.47 and 1.49 (9H, s), 2.56–2.66 (1H, m), 2.64 (2H, q, J=7 Hz), 2.83–2.91 (1H, m), 3.10–3.24 (2H, m), 3.30–3.65 (4H, m), 3.98–4.13 (2H, m), 6.90–6.98 (4H, m), 7.17 (2H, d, J=8 Hz), 7.44–7.54 (2H, m)

Preparation 70-7)

2-[4-(9-Fluorenylmethoxycarbonyl)-7-[4-(4-ethylphenoxy)phenyl]-1,1-dioxoperhydro-1,4-thiazepin-7-yl]acetic acid (2.9 g) was obtained in a similar manner to that of Preparation 1-7).

NMR (CDCl$_3$, δ): 1.20 (3H, t, J=7 Hz), 2.34–2.48 (2H, m), 2.50–2.69 (4H, m), 3.00–3.24 (2H, m), 3.33–3.50 (2H, m), 3.94–4.07 (1H, m), 4.17–4.26 (1H, m), 4.50–4.60 (2H, m), 4.98 (1H, d, J=9, 5 Hz), 6.92 (2H, d, J=8 Hz), 6.95 (2H, d, J=8 Hz), 7.12–7.19 (2H, m), 7.30–7.59 (8H, m), 7.72–7.82 (2H, m)

EXAMPLE 1

To a solution of N-(2-tetrahydropyranyloxy)-2-[7-(5-bromo-2-thienyl)-1,1-dioxoperhydro-1,4-thiazepin-7-yl] acetamide (483 mg) in chloroform (8 ml) and pyridine (3 ml) was added dropwise a solution of methanesulfonyl chloride in chloroform (2 ml) at room temperature. After being stirred for 2 hours, the reaction mixture was concentrated in vacuo. The residue was dissolved in ethyl acetate (50 ml) and the solution was washed successively with 5% aqueous citric acid solution, a saturated aqueous sodium bicarbonate solution and brine, dried over magnesium sulfate, and concentrated in vacuo. The residue was purified by SiO$_2$ column chromatography (eluent; 2% MeOH in CHCl$_3$) to afford N-(2-tetrahydropyranyloxy)-2-[7-(5-bromo-2-thienyl)-4-methanesulfonyl-1,1-dioxoperhydrol-1,4-thiazepin-7-yl] acetamide (514 mg) as an amorphous powder.

NMR (CDCl$_3$, δ): 1.48–1.86 (6H, m), 2.79–2.95 (1H, m), 2.91 (3H, s), 3.02–3.22 (3H, m), 3.32–3.65 (5H, m), 3.24–3.95 (2H, m), 4.02–4.17 (1H, m), 4.68, 4.91 (1H, br), 6.98–7.07 (2H, m), 8.68 (1H, s) MASS (ESI–): 543 (M–H)

The following compounds were obtained in a similar manner to that of Example 1.

EXAMPLE 2

N-(2-Tetrahydropyranyloxy)-2-[7-(5-bromo-2-thienyl)-4-methoxycarbonyl-1,1-dioxoperhydro-1,4-thiazepin-7-yl] acetamide NMR (CDCl$_3$, δ): 1.55–1.76 (9H, m), 2.61–2.75 (2H, m), 3.00–3.07 (2H, m), 3.20–3.65 (4H, m), 3.75 (3H, s), 3.79–3.98 (2H, m), 6.95–7.03 (2H, m) MASS (ESI–): 523 (M–H)

EXAMPLE 3

N-(2-Tetrahydropyranyloxy)-2-[(S)-7-(5-bromo-2-thienyl)-4-methoxycarbonyl-1,1-dioxoperhydro-1,4-thiazepin-7-yl]acetamide (1.62 g)

NMR (CDCl$_3$, δ): 1.44–1.85 (6H, m), 2.60–2.88 (2H, m), 2.95–4.15 (10H, m), 3.72, 3.75 (3H, s), 4.52–4.95 (1H, m), 7.00 (2H, s), 8.63–8.78 (1H, m) MASS (ESI–): 525 (M–H)

EXAMPLE 4

N-(2-Tetrahydropyranyloxy)-2-[(S)-7-(5-bromo-2-thienyl)-4-tert-butoxycarbonyl-1,1-dioxoperhydro-1,4-thiazepin-7-yl]acetamide (514 mg)

NMR (CDCl$_3$, δ): 1.48, 1.49 (9H, s), 1.40–1.94 (6H, m), 2.58–3.12 (4H, m), 3.15–4.03 (8H, m), 4.52–4.94 (1H, m), 6.95–7.05 (2H, m), 8.50–8.71 (1H, m) MASS (ESI+): 589 (M+Na)

EXAMPLE 5

N-(2-Tetrahydropyranyloxy)-2-[(S)-7-(5-bromo-2-thienyl)-4-methanesulfonyl-1,1-dioxoperhydro-1,4-thiazepin-7-yl]acetamide (220 mg)

NMR (CDCl$_3$, δ): 1.47–1.88 (6H, m), 2.78–2.94 (1H, m), 2.91 (3H, s), 3.01–3.24 (3H, m), 3.32–3.65 (5H, m), 3.72–3.94 (2H, m), 4.04–4.22 (1H, m), 4.67, 4.90 (1H, br s), 6.98–7.07 (2H, m), 8.80 (1H, br s) MASS (ESI–): 543 (M–H)

EXAMPLE 6

A mixture of N-(2-tetrahydropyranyloxy)-2-[7-(5-bromo-2-thienyl)-4-methanesulfonyl-1,1-dioxoperhydro-1,4-thiazepin-7-yl]acetamide (200 mg), 4-methoxyphenylboronic acid (83.6 mg) and tetrakis (triphenylphosphine)palladium(0) (21.2 mg) in a mixture of 1,2-dimethoxyethane (2 ml) and aqueous 2M sodium carbonate (0.75 ml) was stirred for 2 hours at 80° C. After cooling to room temperature, the mixture was diluted with ethyl acetate, washed with aqueous saturated sodium bicarbonate and brine, dried over sodium sulfate and concentrated in vacuo. The obtained residue was purified with silica gel column chromatography (eluent; 0.5–3% methanol in chloroform) to give N-(2-tetrahydropyranyloxy)-2-[7-(5-(4-methoxyphenyl)-2-thienyl)-4-methanesulfonyl-1,1-dioxoperhydro-1,4-thiazepin-7-yl]acetamide (130 mg) as an amorphous powder.

NMR (CDCl$_3$, δ): 1.44–1.76 (9H, m), 2.92 (3H, s), 3.15–3.21 (2H, br), 3.35–3.65 (6H, m), 3.73–3.82 (2H, m), 3.83 (3H, s), 6.89 (2H, d, J=7.5 Hz), 7.14 (1H, d, J=4.5 Hz), 7.23 (1H, d, J=4.5 Hz), 7.50 (2H, d, J=7.5 Hz) MASS (ESI–): 571 (M–H)

The following compounds were obtained in a similar manner to that of Example 6.

EXAMPLE 7

N-(2-Tetrahydropyranyloxy)-2-[7-(5-(4-methoxyphenyl)-2-thienyl)-4-methoxycarbonyl-1,1-dioxoperhydro-1,4-thiazepin-7-yl]acetamide (111 mg)

NMR (CDCl$_3$, δ): 1.42–1.80 (9H, m), 2.64–2.95 (2H, m), 3.00–3.31 (2H, m), 3.35–3.61 (4H, m), 3.64–3.80 (4H, m), 3.81–3.88 (3H, s), 3.98–4.13 (1H, br), 6.90 (2H, d, J=7.5 Hz), 7.09–7.23 (2H, m), 7.45–7.53 (2H, m) MASS (ESI–): 551 (M–H)

EXAMPLE 8

N-(2-Tetrahydropyranyloxy)-2-[7-(5-(3-(ethoxycarbonylamino)phenyl)-2-thienyl)-4-methanesulfonyl-1,1-dioxoperhydro-1,4-thiazepin-7-yl]acetamide (130 mg)

NMR (CDCl$_3$, δ): 1.30–1.35 (3H, m), 1.55–1.75 (9H, m), 2.92 (3H, s), 3.13–3.22 (2H, m), 3.40–3.61 (6H, m), 3.71–3.87 (2H, m), 4.20–4.29 (2H, m), 6.53–6.77 (2H, m), 7.29–7.70 (4H, m) MASS (ESI–): 628 (M–H)

EXAMPLE 9

N-(2-Tetrahydropyranyloxy)-2-[(S)-7-(5-(2-furyl)-2-thienyl)-4-methoxycarbonyl-1,1-dioxoperhydro-1,4-thiazepin-7-yl]acetamide (147 mg)

NMR (CDCl$_3$, δ): 1.49–1.80 (6H, m), 2.63–2.78 (1H, m), 2.82–2.94 (1H, s), 3.00–4.23 (10H, m), 3.71, 3.76 (3H, s), 4.52–4.88 (1H, m), 6.44 (1H, s), 6.52 (1H, s), 7.12–7.22 (1H, m), 7.16 (1H, m), 7.40 (1H, m) MASS (ESI–): 511 (M–H)

EXAMPLE 10

N-(2-Tetrahydropyranyloxy)-2-[(S)-7-(5-(2-furyl)-2-thienyl)-4-tert-butoxycarbonyl-1,1-dioxoperhydro-1,4-thiazepin-7-yl]acetamide (147 mg)

NMR (CDCl$_3$, δ): 1.44, 1.48 (9H, s), 1.35–1.80 (6H, m), 2.62–2.94 (2H, m), 3.00–3.84 (9H, m), 3.88–4.03 (1H, m), 4.52–4.88 (1H, m), 6.42–6.46 (1H, m), 6.52 (1H, d, J=3 Hz), 7.15 (1H, d, J=3 Hz), 7.18–7.23 (1H, m), 7.40 (1H, s), 8.32–8.56 (1H, m) MASS (ESI–): 553 (M–H)

EXAMPLE 11

N-(2-Tetrahydropyranyloxy)-2-[(S)-7-(5-(3-(methoxycarbonylamino)phenyl)-2-thienyl)-4-methanesulfonyl-1,1-dioxoperhydro-1,4-thiazepin-7-yl]acetamide (64 mg)

NMR (CDCl$_3$, δ): 1.47–1.75 (9H, m), 2.92 (3H, s), 3.17–3.25 (2H, m), 3.40–3.63 (4H, m), 3.76–3.81 (5H, m), 4.08–4.20 (2H, m), 6.65–6.73 (2H, m), 7.28–7.53 (3H, m) MASS (ESI–): 614 (M–H)

EXAMPLE 12

N-(2-Tetrahydropyranyloxy)-2-[(S)-7-(5-(3-(methoxycarbonylamino)phenyl)-2-thienyl)-4-methoxycarbonyl-1,1-dioxoperhydro-1,4-thiazepin-7-yl]acetamide (118 mg)

NMR (CDCl$_3$, δ): 1.45–1.74 (9H, m), 2.65–2.83 (2H, m), 3.02–3.16 (2H, m), 3.26–3.61 (4H, m), 3.70–3.80 (8H, m), 7.10–7.70 (7H, m) MASS (ESI–): 594 (M–H)

EXAMPLE 13

N-(2-Tetrahydropyranyloxy)-2-[(S)-7-(5-(3-(methylaminocarbonylamino)phenyl)-2-thienyl)-4-methoxycarbonyl-1,1-dioxoperhydro-1,4-thiazepin-7-yl]acetamide (100 mg)

NMR (CDCl$_3$, δ): 1.45–1.70 (9H, m), 2.79 (3H, d, J=5.3 Hz), 2.80–2.90 (2H, m), 3.13–3.25 (2H, m), 3.39–3.56 (2H, m), 3.71–3.85 (5H, m), 4.05–4.16 (2H, m), 6.53–6.73 (2H, m), 7.01–7.35 (5H, m) MASS (ESI–): 593 (M–H)

EXAMPLE 14

N-(2-Tetrahydropyranyloxy)-2-[(S)-7-(5-(3-(ethylaminocarbonylamino)phenyl)-2-thienyl)-4-methanesulfonyl-1,1-dioxoperhydro-1,4-thiazepin-7-yl]acetamide (100 mg)

NMR (DMSO-d$_6$ δ): 1.06 (3H, dd, J=7.2, 7.2 Hz), 1.40–1.64 (9H, m), 2.85–2.92 (2H, m), 3.00 (3H, s), 3.06–3.16 (6H, m), 3.40–3.65 (4H, m), 6.10–6.13 (1H, m), 6.95–6.96 (1H, m), 7.16–7.38 (5H, m), 8.52–8.56 (1H, m) MASS (ESI–): 627 (M–H)

EXAMPLE 15

N-(2-Tetrahydropyranyloxy)-2-[(S)-7-(5-(3-(ethoxyacetylamino)phenyl)-2-thienyl)-4-methoxycarbonyl-1,1-dioxoperhydro-1,4-thiazepin-7-yl]acetamide (140 mg)

NMR (DMSO-d$_6$ δ): 1.20 (3H, dd, J=7.2, 7.2 Hz), 1.49–1.65 (9H, m), 2.68–2.80 (2H, m), 2.90–3.15 (4H, m), 3.40–3.88 (9H, m), 4.04 (2H, s), 7.00–7.03 (1H, m), 7.17–7.25 (1H, m), 7.34–7.41 (3H, m), 7.56–7.62 (1H, m), 8.01 (1H, s)

EXAMPLE 16

N-(2-Tetrahydropyranyloxy)-2-[(S)-7-(5-(3-(phenoxyacetylamino)phenyl)-2-thienyl)-4-methoxycarbonyl-1,1-dioxoperhydro-1,4-thiazepin-7-yl]acetamide (130 mg)

NMR (DMSO-d$_6$, δ): 1.45–1.64 (9H, m), 2.73–2.84 (2H, m), 2.95–3.15 (4H, m), 3.41–3.90 (7H, m), 4.70 (2H, s), 6.95–7.03 (3H, m), 7.19–7.24 (1H, m), 7.30–7.43 (5H, m), 7.52–7.61 (1H, m), 8.01 (1H, br)

EXAMPLE 17

To a solution of N-(2-tetrahydropyranyloxy)-2-[7-(5-(4-methoxyphenyl)-2-thienyl)-4-methanesulfonyl-1,1-dioxoperhydro-1,4-thiazepin-7-yl]acetamide (110 mg) in methanol (2 ml) was added 10% hydrogen chloride in methanol (0.5 ml) at room temperature. After being stirred for 30 minutes, the reaction mixture was concentrated in vacuo. The resulting residue was purified by silica gel column chromatography (eluent; 0.5–5% methanol in chloroform) to give N-hydroxy-2-[7-(5-(4-methoxyphenyl)-2-thienyl)-4-methanesulfonyl-1,1-dioxoperhydro-1,4-thiazepin-7-yl]acetamide (50 mg) as an amorphous powder.

NMR (DMSO-$d_6$, δ): 2.86–2.95 (2H, m), 3.00 (3H, s), 3.10–3.18 (2H, m), 3.39–3.65 (4H, m), 3.66–3.75 (1H, m), 3.79 (3H, s), 3.89–4.04 (1H, m), 6.99 (2H, d, J=9 Hz), 7.18 (1H, d, J=4.5 Hz), 7.34 (1H, d, J=4.5 Hz), 7.57 (2H, d, J=9 Hz), 8.93 (1H, s), 10.69 (1H, s) MASS (ESI-): 487 (M-H)

The following compounds were obtained in a similar manner to that of Example 17.

EXAMPLE 18

N-Hydroxy-2-[7-(5-bromo-2-thienyl)-4-methanesulfonyl-1,1-dioxoperhydro-1,4-thiazepin-7-yl]acetamide (514 mg)

NMR (DMSO-$d_6$, δ): 2.77–2.88 (2H, m), 2.98 (3H, s), 2.96–3.17 (2H, m), 3.38–3.75 (5H, m), 3.85–3.98 (1H, m), 7.05 (1H, d, J=3 Hz) 7.23 (1H, d, J=3 Hz), 8.94 (1H, s), 10.67 (1H, s) MASS (ESI-): 458, 460 (M-H)

EXAMPLE 19

N-Hydroxy-2-[7-(5-(4-methoxyphenyl)-2-thienyl)-4-methoxycarbonyl-1,1-dioxoperhydro-1,4-thiazepin-7-yl]acetamide (45 mg)

NMR (DMSO-$d_6$, δ): 2.71–3.10 (4H, m), 3.44–3.74 (8H, m), 3.79 (3H, s), 3.81–3.94 (1H, br), 6.99 (2H, d, J=8.7 Hz), 7.16 (2H, d, J=4.5 Hz), 7.34 (2H, d, J=4.5 Hz), 7.57 (2H, d, J=8.7 Hz), 8.9 (1H, s) MASS (ESI-): 467 (M-H)

EXAMPLE 20

N-Hydroxy-2-[7-(5-(3-(ethoxycarbonylamino)phenyl)-2-thienyl)-4-methanesulfonyl-1,1-dioxoperhydro-1,4-thiazepin-7-yl]acetamide (30 mg)

NMR (DMSO-$d_6$, δ): 1.26 (3H, dd, J=5.0, 5.0 Hz), 2.88–2.96 (2H, m), 3.00 (3H, s), 3.10–3.19 (2H, m), 3.39–3.75 (6H, m), 4.15 (2H, ddd, J=5.0, 5.0, 5.0 Hz), 7.19–7.40 (6H, m), 7.84 (1H, s), 8.92 (1H, s), 9.75 (1H, s) MASS (ESI-): 544 (M-H)

EXAMPLE 21

N-Hydroxy-2-[(S)-7-(5-(2-furyl)-2-thienyl)-4-methoxycarbonyl-1,1-dioxoperhydro-1,4-thiazepin-7-yl]acetamide (75 mg)

NMR (DMSO-$d_6$, δ): 2.66–3.08 (4H, m), 3.44–3.95 (6H, m), 3.64, 3.66 (3H, s), 6.57–6.64 (1H, m), 6.79 (1H, d, J=3 Hz), 7.18 (1H, d, J=3 Hz), 7.30 (1H, d, J=3 Hz), 7.22 (1H, s), 8.90 (1H, s), 10.65 (1H, s) MASS (ESI-): 427 (M-H)

EXAMPLE 22

N-Hydroxy-2-[(S)-7-(5-(3-(methoxycarbonylamino)phenyl)-2-thienyl)-4-methanesulfonyl-1,1-dioxoperhydro-1,4-thiazepin-7-yl]acetamide (40 mg)

NMR (DMSO-$d_6$, δ): 2.88–2.96 (2H, m), 3.00 (3H, s), 3.11–3.17 (2H, m), 3.41–3.65 (4H, m), 3.69 (3H, m), 3.90–4.00 (2H, m), 7.21 (1H, d, J=4.5 Hz), 7.30–7.40 (3H, m), 7.81 (1H, s), 8.92 (1H, s), 9.78 (1H, s), 10.70 (1H, s) MASS (ESI-): 530 (M-H)

EXAMPLE 23

N-Hydroxy-2-[(S)-7-(5-(3-(methoxycarbonylamino)phenyl)-2-thienyl)-4-methoxycarbonyl-1,1-dioxoperhydro-1,4-thiazepin-7-yl]acetamide (60 mg)

NMR (DMSO-$d_6$, δ): 2.73–2.85 (2H, m), 2.90–3.20 (4H, m), 3.51–3.80 (10H, m), 7.20 (1H, d, J=4.5 Hz), 7.30–7.40 (5H, m), 7.81 (1H, s), 8.90 (1H, s), 9.76 (1H, m) MASS (ESI-): 510 (M-H)

EXAMPLE 24

N-Hydroxy-2-[(S)-7-(5-(3-(methylaminocarbonylamino)-phenyl)-2-thienyl)-4-methoxycarbonyl-1,1-dioxoperhydro-1,4-thiazepin-7-yl]acetamide (100 mg)

NMR (DMSO-$d_6$ δ): 2.65 (3H, d, J=5.3 Hz), 2.70–2.83 (2H, m), 2.95–3.23 (4H, m), 3.49–3.60 (2H, m), 3.65–3.85 (5, m), 6.05–6.11 (1H, br), 6.95–6.99 (1H, m), 7.18–7.26 (5H, m), 7.32–7.37 (1H, m), 7.83 (1H, s), 8.70 (1H, s)

EXAMPLE 25

N-Hydroxy-2-[(S)-7-(5-(3-(ethylaminocarbonylamino)-phenyl)-2-thienyl)-4-methanesulfonyl-1,1-dioxoperhydro-1,4-thiazepin-7-yl]acetamide (50 mg)

NMR (DMSO-$d_6$ δ): 1.06 (3H, dd, J=7.2, 7.2 Hz), 2.89–2.96 (2H, m), 3.00 (3H, s), 3.10–3.19 (6H, m), 3.40–3.78 (4H, m), 6.15 (1H, dd, J=6.5, 6.5 Hz), 7.16–7.26 (4H, m), 7.37 (1H, d, J=4.5 Hz), 7.84 (1H, s), 8.57 (1H, s), 8.92 (1H, s), 10.7 (1H, s) MASS (ESI-): 543 (M-H)

EXAMPLE 26

N-Hydroxy-2-[(S)-7-(5-(3-(ethoxyacetylamino)phenyl)-2-thienyl)-4-methoxycarbonyl-1,1-dioxoperhydro-1,4-thiazepin-7-yl]acetamide (70 mg)

NMR (DMSO-$d_6$ δ): 1.20 (3H, dd, J=7.2, 7.2 Hz), 2.70–2.95 (6H, m), 3.45–3.68 (9H, m), 4.05 (2H, s), 7.03 (1H, d, J=4.5 Hz), 7.21 (2H, d, J=6.0, 6.0 Hz), 7.35–7.41 (3H, m), 7.59–7.61 (1H, m), 8.01 (1H, s), 9.80 (1H, s)

EXAMPLE 27

N-Hydroxy-2-[(S)-7-(5-(3-(phenoxyacetylamino)phenyl)-2-thienyl)-4-methoxycarbonyl-1,1-dioxoperhydro-1,4-thiazepin-7-yl]acetamide (50 mg)

NMR (DMSO-$d_6$ δ): 2.70–3.12 (6H, m), 3.45–3.95 (7H, m), 4.72 (2H, m), 6.95–7.02 (3H, m), 7.21 (1H, d, J=4.5 Hz), 7.29–7.44 (5H, m), 7.55–7.59 (1H, m), 8.00 (1H, s), 8.89 (1H, s), 10.20 (1H, m), 10.65 (1H, s)

EXAMPLE 28

N-(2-Tetrahydropyranyloxy)-2-[7-(5-bromo-2-thienyl)-4-(9-fluorenylmethoxycarbonyl)-1,1-dioxoperhydro-1,4-thiazepin-7-yl]acetamide (300 mg) was dissolved in a solution of 20% piperidine in N,N-dimethylformamide (5 ml). After being stirred at room temperature for 30 minutes, the reaction mixture was concentrated in vacuo. The resulting residue was purified by $SiO_2$ column chromatography (eluent; 1–5% MeOH in $CHCl_3$) to afford N-(2-tetrahydropyranyloxy)-2-(7-(5-bromo-2-thienyl)-1,1-dioxopherhydro-1,4-thiazepin-7-yl)acetamide (175 mg) as an amorphous powder.

NMR ($CDCl_3$ δ): 1.45–1.90 (6H, m), 2.46–2.65 (2H, m), 2.90–3.94 (10H, m), 4.58, 4.86 (1H, br), 7.01 (2H, s), 8.36, 8.47 (1H, br) MASS (ESI-): 465, 467 (M-H)

EXAMPLE 29

N-(2-Tetrahydropyranyloxy)-2-[(S)-7-(5-bromo-2-thienyl)-1,1-dioxoperhydro-1,4-thiazepin-7-yl]acetamide (8.40 g) was obtained in a similar manner to that of Example 28.

NMR (DMSO-$d_6$ δ): 1.35–1.76 (6H, m), 2.52–2.70 (2H, m), 2.85–3.96 (10H, m), 4.50, 4.76 (1H, s), 6.96–7.06 (1H, m), 7.14–7.23 (1H, m) MASS (ESI-): 467 (M-H)

EXAMPLE 30

To a solution of 2-[7-(5-bromo-2-thienyl)-4-(9-fluorenylmethoxycarbonyl)-1,1-dioxoperhydro-1,4-thiazepin-7-yl]acetic acid (400 mg), O-(2-tetrahydropyranyl)-hydroxylamine (95.2 mg) and 1-hydroxybenzotriazole (110 mg) in N,N-dimethylformamide (10 ml) was added WSCD-HCl (1-ethyl-3-(3-dimethylaminopropyl)carbodiimide hydrochloride) (156 mg) at room temperature. After being stirred at the same temperature overnight, the mixture was concentrated in vacuo. The residue was dissolved in ethyl acetate (30 ml) and the solution was washed successively with 5% aqueous citric acid solution, a saturated aqueous sodium bicarbonate solution and brine, dried over magnesium sulfate, and concentrated in vacuo. The residue was purified by $SiO_2$ column chromatography (eluent; 1% MeOH in chloroform ($CHCl_3$)) to afford N-(2-tetrahydropyranyloxy)-2-[7-(5-bromo-2-thienyl)-4-(9-fluorenylmethoxycarbonyl)-1,1-dioxoperhydro-1,4-thiazepin-7-yl]acetamide (313 mg) as an amorphous powder.

NMR ($CDCl_3$ $\delta$): 1.49–1.96 (6H, m), 2.50–2.63 (1H, m), 2.69–3.02 (3H, m), 3.32–3.66 (4H, m), 3.72–4.04 (3H, m), 4.16–4.30 (1H, m), 4.96, 4.88 (1H, br), 6.91–6.98 (2H, m), 7.29–7.62 (6H, m), 7.78 (2H, t, J=8 Hz), 8.43, 8.46 (1H, br)

EXAMPLE 31

A mixture of N-(2-tetrahydropyranyloxy)-2-[(S)-7-(5-bromo-2-thienyl)-4-methanesulfonyl-1,1-dioxoperhydro-1,4-thiazepin-7-yl]acetamide (230 mg), 3-(methylaminocarbonylamino)phenylboronic acid (123 mg) and tetrakis(triphenylphosphine)palladium(0) (24.4 mg) in a mixture of 1,2-dimethoxyethane (2 ml) and 2M aqueous sodium carbonate solution (0.85 ml) was stirred for 4 hours at 80° C. After cooling to room temperature, the mixture was diluted with ethyl acetate, washed with aqueous saturated sodium bicarbonate and brine, dried over sodium sulfate and concentrated in vacuo. The obtained residue was dissolved in methanol (2 ml) and 10% hydrogen chloride in methanol (0.5 ml) was added thereto. After being stirred for 30 minutes at room temperature, the solution was concentrated in vacuo. The residue was purified with silica gel column chromatography (eluent; 0.5–5% methanol in chloroform) to give N-hydroxy-2-[(S)-7-(5-(3-(methylaminocarbonylamino)-phenyl)-2-thienyl)-4-methanesulfonyl-1,1-dioxoperhydro-1,4-thiazepin-7-yl]acetamide (30 mg).

NMR ($CDCl_6$ $\delta$): 2.64 (3H, d, J=4.5 Hz), 2.90–2.95 (2H, m), 3.00 (3H, s), 3.11–3.18 (2H, m), 3.40–3.77 (5H, m), 3.91–4.01 (1H, m), 6.05–6.12 (1H, br), 7.19–7.27 (3H, m), 7.37 (1H, d, J=4.5 Hz), 7.83 (H1, s), 8.71 (1H, s), 8.92 (1H, s) MASS (ESI-): 529 (M-H)

EXAMPLE 32

To a solution of N-(2-tetrahydropyranyloxy)-2-[(S)-7-(5-(2-furyl)-2-thienyl)-4-tert-butoxycarbonyl-1,1-dioxoperhydro-1,4-thiazepin-7-yl]acetamide (160 mg) in methanol (5 ml) was added 4M hydrogen chloride in ethyl acetate (5 ml) at room temperature. After being stirred for 1 hour, the mixture was concentrated in vacuo. The resulting residue was triturated with diethyl ether to afford N-hydroxy-2-[(S)-7-(5-(2-furyl)-2-thienyl)-1,1-dioxoperhydro-1,4-thiazepin-7-yl]acetamide hydrochloride (75 mg) as a powder.

NMR (DMSO-$d_6$ $\delta$): 2.72–2.89 (1H, m), 2.98–3.75 (8H, m), 4.05–4.20 (1H, m), 6.56–6.63 (1H, m), 6.82 (1H, d, J=3 Hz), 7.21 (1H, d, J=3 Hz), 7.35 (1H, d, J=3 Hz), 7.74 (1H, s), 8.93 (1H, s) MASS (ESI+): 371 (M+H)

EXAMPLE 33

A mixture of N-(2-tetrahydropyranyloxy)-2-[(S)-7-(5-bromo-2-thienyl)-1,1-dioxoperhydro-1,4-thiazepin-7-yl] acetamide (2.40 g), 2-pyridinecarboxylic acid (695 mg), 1-ethyl-3-(3-dimethylaminopropyl)carbodiimide hydrochloride (1.48 g) and 1-hydroxybenzotriazole (1.04 g) in anhydrous dimethylformamide (24 ml) was stirred at 0° C. for 2 hours. The mixture was partitioned between ethyl acetate and water. The organic layer was separated, washed with saturated sodium bicarbonate solution, water and brine, dried over magnesium sulfate, and evaporated in vacuo. The residue was purified by silica gel column chromatography eluting with a mixture of chloroform and methanol (50:1) to give N-(2-tetrahydropyranyloxy)-2-[(S)-7-(5-bromo-2-thienyl)-4-(2-pyridinecarbonyl)-1,1-dioxoperhydro-1,4-thiazepin-7-yl]acetamide as a colorless amorphous powder (2.68 g).

NMR ($CDCl_3$, $\delta$): 1.48–1.90 (6H, br), 2.75–3.40 (5H, br), 3.45–4.10 (6H, br), 4.10–4.30, 4.60, 4.88 (2H, br), 6.88–7.08 (2H, br), 7.38 (1H, br), 7.60, 7.72–7.88 (2H, br), 8.27–8.65 (2H, br) MASS (ESI-): 570, 572 (M-H)

The following compounds were obtained in a similar manner to that of Example 33.

EXAMPLE 34

N-(2-Tetrahydropyranyloxy)-2-[(S)-7-(5-bromo-2-thienyl)-4-(3-thiophenecarbonyl)-1,1-dioxoperhydro-1,4-thiazepin-7-yl]acetamide (2.08 g)

NMR ($CDCl_3$, $\delta$): 1.45–1.87 (6H, m), 2.67–4.00 (10H, m), 4.00–4.90 (3H, m), 6.80–7.23 (3H, m), 7.30–7.38 (1H, m), 7.40–7.50 (1H, m), 8.36, 8.45 (1H, s) MASS (ES-) m/e: 576.99

EXAMPLE 35

N-(2-Tetrahydropyranyloxy)-2-[(S)-7-(5-bromo-2-thienyl)-4-(2-thiophenecarbonyl)-1,1-dioxoperhydro-1,4-thiazepin-7-yl]acetamide (2.15 g)

NMR ($CDCl_3$, $\delta$): 1.49–1.80 (6H, m), 2.75–4.40 (12H, m), 4.49–4.77 (1H, m), 6.96 (2H, br s), 7.06 (1H, dd, J=5.0, 5.0 Hz), 7.17–7.38 (1H, m), 7.50 (1H, d, J=5.0 Hz), 8.58–8.68 (1H, m), MASS (ESI-): 577.0 (M-H)

EXAMPLE 36

N-(2-Tetrahydropyranyloxy)-2-[(S)-7-(5-bromo-2-thienyl)-4-(2-pyradinecarbonyl)-1,1-dioxoperhydro-1,4-thiazepin-7-yl]acetamide (2.15 g).

NMR ($CDCl_3$, $\delta$): 1.55 (2H, br), 1.75 (4H, br), 2.75–2.95 (2H, m), 3.04 (1H, br s), 3.07 (1H, br s), 3.12–3.32 (1H, m), 3.50–3.59 (2H, m), 3.68–3.85 (3H, m), 4.04–4.35 (1H, m), 4.54–4.60 (½H, m), 4.80–4.86 (½H, m), 6.94–7.03 (2H, m), 8.30–8.36 (½H, m), 8.43 (1H, s), 8.52–8.58 (½H, m), 8.67 (1H, dd, J=7.0, 3.0 Hz), 8.94 (½H, s), 9.05 (½H, s) MASS (ESI-): 572.8 (M-H)

The following compounds were obtained in a similar manner to that of Example 1.

EXAMPLE 37

N-(2-Tetrahydropyranyloxy)-2-[4-benzoyl-7-(5-bromo-2-thienyl)-1,1-dioxoperhydro-1,4-thiazepin-7-yl]acetamide (1.12 g).

NMR ($CDCl_3$, $\delta$): 1.40–1.95 (6H, br), 2.67–3.29 (5H, br), 3.35–4.00 (6H, br), 4.17–4.90 (2H, br), 6.83–7.13 (2H, br), 7.23–7.52 (5H, br), 8.45–8.68 (1H, br) MASS (ES-): 569, 571 (M-H)

EXAMPLE 38

N-(2-Tetrahydropyranyloxy)-2-[7-(5-bromo-2-thienyl)-4-(dimethylaminosulfonyl)-1,1-dioxoperhydro-1,4-thiazepin-7-yl]acetamide (220 mg)

NMR (CDCl$_3$, δ): 1.50–1.95 (6H, br), 2.82 (6H, s), 3.05–3.28 (3H, br), 3.28–3.70 (6H, br), 3.83–4.15 (3H, br), 4.68, 4.92 (1H, br), 7.02 (2H, br), 8.57 (1H, br) MASS (ESI−): 572, 574 (M−H)

EXAMPLE 39

To a solution of 4-(5-oxazolyl)phenylboronic acid pinacol cyclic ester obtained in Preparation 9-2) were added N-(2-tetrahydropyranyloxy)-2-[(S)-4-benzoyl-7-(5-bromo-2-thienyl)-1,1-dioxoperhydro-1,4-thiazepin-7-yl]acetamide (1.70 g), tetrakis(triphenylphosphine)palladium(0) (103 mg) and 2M aqueous sodium carbonate solution (5 ml) and the mixture was stirred at 80° C. for 4 hours. After evaporation of solvent, ethyl acetate and water were added and the insolubles were filtered off. The organic layer was separated, washed with brine, dried over magnesium sulfate, and evaporated in vacuo. The residue was purified by silica gel column chromatography eluting with a mixture of chloroform and methanol (100:1 to 200:3) to give N-(2-tetrahydropyranyloxy)-2-[(S)-4-benzoyl-7-(5-(4-(5-oxazolyl)phenyl)-2-thienyl)-1,1-dioxoperhydro-1,4-thiazepin-7-yl]acetamide as a pale yellow amorphous powder (1.28 g).

NMR (CDCl$_3$, δ): 1.45–1.90 (6H, br), 2.78–4.08, 4.23–4.41 (12H, br), 4.46, 4.61, 4.72, 4.88 (1H, br), 7.13–7.47 (8H, br), 7.57–7.70 (4H, br), 7.94 (1H, s), 8.44, 8.53–8.64 (1H, br) MASS (ESI−) m/e: 634 (M−H)

The following compounds were obtained in a similar manner to that of Example 39.

EXAMPLE 40

N-(2-Tetrahydropyranyloxy)-2-[(S)-7-(5-(4-(5-oxazolyl)phenyl)-2-thienyl)-4-(2-pyridinecarbonyl)-1,1-dioxoperhydro-1,4-thiazepin-7-yl]acetamide (1.72 g)

NMR (CDCl$_3$, δ): 1.45–1.90 (6H, br), 2.85–4.45 (12H, br), 4.57–4.69, 4.77–4.93 (1H, br), 7.18–7.45 (3H, br), 7.56–7.68 (5H, br), 7.75–7.86 (2H, br), 7.95 (1H, s), 8.41–8.56, 8.58–8.73 (2H, br) MASS (ESI): 635 (M−H)

EXAMPLE 41

N-(2-Tetrahydropyranyloxy)-2-[(S)-7-(5-(4-(5-oxazolyl)phenyl)-2-thienyl)-4-(3-thiophenecarbonyl)-1,1-dioxoperhydro-1,4-thiazepin-7-yl]acetamide (1.56 g)

NMR (CDCl$_3$, δ): 1.39–1.88 (6H, m), 2.69–4.04 (10H, m), 4.04–4.90 (3H, m), 7.05–7.50 (5H, m), 7.50–7.70 (5H, m), 7.95 (1H, s), 8.36, 8.48 (1H, s) MASS (ES−) m/e: 640.08

EXAMPLE 42

N-(2-Tetrahydropyranyloxy)-2-[(S)-7-(5-(4-(5-oxazolyl)phenyl)-2-thienyl)-4-(2-thiophenecarbonyl)-1,1-dioxoperhydro-1,4-thiazepin-7-yl]acetamide (1.8 g).

NMR (CDCl$_3$, δ): 1.42–1.68 (6H, m), 2.82–4.13 (12H, m), 4.50–4.78 (1H, m), 7.04 (1H, br), 7.20–7.28 (2H, m), 7.37 (1H, s), 7.47 (1H, br), 7.58–7.65 (5H, m), 7.95 (1H, s), 8.55–8.76 (1H, m) MASS (ES−): 640.2 (M−H)

EXAMPLE 43

N-(2-Tetrahydropyranyloxy)-2-[(S)-7-(5-(4-(5-oxazolyl)phenyl)-2-thienyl)-4-(2-pyradinecarbonyl)-1,1-dioxoperhydro-1,4-thiazepin-7-yl]acetamide (1.96 g)

NMR (CDCl$_3$, δ): 1.49 (2H, br), 1.68–1.75 (4H, br), 2.80–3.05 (2H, m), 3.12–3.45 (2H, m), 3.48–3.64 (2H, m), 3.68–3.88 (4H, m), 4.11–4.39 (2H, m), 4.55–4.60 (½H, m), 4.81–4.87 (½H, m), 7.18–7.28 (2H, m), 7.40 (1H, s), 7.57–7.67 (4H, m), 7.94 (1H, s), 8.40 (1H, s), 8.55–8.69 (2H, m), 8.94 (½H, s), 9.07 (½H, s) MASS (ESI−): 636.0 (M−H)

The following compounds were obtained in a similar manner to that of Example 6.

EXAMPLE 44

N-(2-Tetrahydropyranyloxy)-2-[(S)-4-benzoyl-7-(5-(4-methylphenyl)-2-thienyl)-1,1-dioxoperhydro-1,4-thiazepin-7-yl]acetamide (1.5 g)

NMR (CDCl$_3$, δ): 1.40–1.75 (6H, m), 2.37 (3H, s), 2.73–3.24 (5H, m), 3.31–4.03 (6H, m), 4.18–4.20 (1H, m), 4.42, 4.71 (1H, s), 7.10–7.50 (1H, m) MASS (ESI−): 581 (M−H)

EXAMPLE 45

N-(2-Tetrahydropyranyloxy)-2-[4-benzoyl-7-(5-(4-methoxyphenyl)-2-thienyl)-1,1-dioxoperhydro-1,4-thiazepin-7-yl]acetamide (50 mg)

NMR (CDCl$_3$, δ): 1.40–1.75 (6H, m), 2.72–3.73 (10H, m), 3.84 (3H, s), 3.88–4.28 (2H, m), 4.40–4.85 (1H, m), 6.90 (2H, d, J=7.0 Hz), 7.08–7.13 (1H, m), 7.23–7.53 (8H, m), 8.31–8.42 (1H, m) MASS (ESI−): 597.1 (M−H)

The following compound was obtained in a similar manner to that of Example 39.

EXAMPLE 46

N-(2-Tetrahydropyranyloxy)-2-[4-(dimethylaminosulfonyl)-7-(5-(4-(5-oxazolyl)phenyl)-2-thienyl)-1,1-dioxoperhydro-1,4-thiazepin-7-yl]acetamide (214 mg)

NMR (CDCl$_3$, δ): 1.42–2.05 (6H, br), 2.83 (6H, s), 2.85–4.13 (12H, br), 4.70, 4.92 (1H, br), 7.20–7.40 (4H, br), 7.60–7.72 (3H, br), 7.93 (1H, s), 8.66–8.76 (1H, br) MASS (ESI−): 637 (M−H)

The following compounds were obtained in a similar manner to that of Example 6.

EXAMPLE 47

N-(2-Tetrahydropyranyloxy)-2-[4-benzoyl-7-(5-(3-acetamidophenyl)-2-thienyl)-1,1-dioxoperhydro-1,4-thiazepin-7-yl]acetamide (150 mg)

NMR (DMSO-$_6$, δ): 1.36–1.65 (6H, m), 2.07 (3H, s), 2.86–3.22 (7H, m), 3.51–3.56 (2H, m), 3.76–3.95 (3H, m), 4.47, 4.78 (1H, s), 7.23–7.25 (1H, m), 7.35–7.55 (9H, m), 7.93 (1H, s)

EXAMPLE 48

N-(2-Tetrahydropyranyloxy)-2-[4-benzoyl-7-(5-(3-aminophenyl)-2-thienyl)-1,1-dioxoperhydro-1,4-thiazepin-7-yl]acetamide (200 mg)

NMR (DMSO-d$_6$, δ): 1.36–1.66 (6H, m), 2.71–3.30 (7H, m), 3.50–3.59 (2H, m), 3.75–3.95 (3H, m), 4.46, 4.78 (1H, s), 5.23 (2H, s), 6.51 (1H, d, J=7.5 Hz), 6.75–6.85 (2H, m), 7.05 (1H, dd, J=7.5, 7.5 Hz), 7.14–7.30 (2H, m), 7.36–7.48 (5H, m) MASS (ESI−): 582 (M−H)

EXAMPLE 49

N-(2-Tetrahydropyranyloxy)-2-[4-benzoyl-7-(5-(4-methylthiophenyl)-2-thienyl)-1,1-dioxoperhydro-1,4-thiazepin-7-yl]acetamide (121 mg)

NMR (CDCl₃, δ): 1.50–1.80 (6H, m), 2.51 (3H, s), 2.73–3.25 (5H, m), 3.30–4.00 (6H, m), 4.19–4.23 (1H, m), 4.43, 4.71 (1H, s), 7.10–7.51 (11H, m) MASS (ESI–): 613 (M–H)

The following compounds were obtained in a similar manner to that of Example 39.

EXAMPLE 50

N-(2-Tetrahydropiranyloxy)-2-[7-(5-(2-naphthyl)-2-thienyl)-4-benzoyl-1,1-dioxoperhydro-1,4-thiazepin-7-yl]acetamide (204 mg)

NMR (CDCl₃, δ): 1.35–1.75 (6H, m), 2.75–3.20 (5H, m), 3.44–3.76 (6H, m), 4.19–4.93 (2H, m), 7.11–7.43 (7H, m), 7.45–7.55 (2H, m), 7.65–7.74 (2H, m), 7.76–7.88 (3H, m), 7.98–8.07 (1H, m), 8.17–8.38 (1H, m) MASS (ESI–): 617 (M–H)

The following compounds were obtained in a similar manner to that of Example 17.

EXAMPLE 51

N-Hydroxy-2-[(S)-4-benzoyl-7-(5-(4-(5-oxazolyl)phenyl)-2-thienyl)-1,1-dioxoperhydro-1,4-thiazepin-7-yl]acetamide (569 mg)

NMR (DMSO-d₆, δ): 2.75–3.30 (4H, br), 3.45–4.20 (6H, br), 7.24, 7.28 (1H, d, J=3 Hz), 7.45 (5H, br), 7.55, 7.62 (1H, d, J=3 Hz), 7.75 (5H, m), 8.48 (1H, s), 8.83, 8.90 (1H, br), 10.65, 10.72 (1H, br) MASS (ESI–): 550 (M–H)

EXAMPLE 52

N-Hydroxy-2-[(S)-7-(5-(4-(5-oxazolyl)phenyl)-2-thienyl)-4-(2-pyridinecarbonyl)-1,1-dioxoperhydro-1,4-thiazepin-7-yl]acetamide (1.17 g).

NMR (DMSO-d₆, δ): 2.95–3.18 (4H, br), 3–0.50–4.20 (6H, br), 7.23, 7.26 (1H, d, J=3 Hz), 7.48–7.66 (4H, m), 7.70–7.82 (5H, m), 7.91–8.02 (1H, m), 8.48 (1H, s), 8.58–8.64 (1H, br), 10.63, 10.68 (1H, s) MASS (ESI): 551 (M–H)

EXAMPLE 53

N-Hydroxy-2-[(S)-7-(5-(4-(5-oxazolyl)phenyl)-2-thienyl)-4-(3-thiophenecarbonyl)-1,1-dioxoperhydro-1,4-thiazepin-7-yl]acetamide (900 mg)

NMR (DMSO-d₆, δ): 2.79–3.24 (4H, m), 3.46–4.11 (6H, m), 7.22–7.30 (2H, m), 7.52–7.67 (2H, m), 7.70–7.81 (5H, m), 7.81–7.90 (1H, m), 8.48 (1H, s), 8.83–8.95 (1H, m), 10.67 (1H, br s) MASS (ES–) m/e: 556.08

EXAMPLE 54

N-Hydroxy-2-[(S)-7-(5-(4-(5-oxazolyl)phenyl)-2-thienyl)-4-(2-thiophenecarbonyl)-1,1-dioxoperhydro-1,4-thiazepin-7-yl]acetamide (1.12 g)

NMR (DMSO-d₆, δ): 2.72–3.13 (4H, m), 3.60–4.14 (6H, m), 7.16 (1H, br), 7.27 (1H, d, J=5.0 Hz), 7.52 (1H, br), 7.57 (1H, d, J=5.0 Hz), 7.72–7.81 (6H, m), 8.47 (1H, s), 8.90 (1H, br) MASS (ESI–): 556.2 (M–H)

EXAMPLE 55

N-Hydroxy-2-[(S)-7-(5-(4-(5-oxazolyl)phenyl)-2-thienyl)-4-(2-pyradinecarbonyl)-1,1-dioxoperhydro-1,4-thiazepin-7-yl]acetamide (975 mg)

NMR (DMSO-d₆, δ): 2.90–3.00 (2H, m), 3.05–3.10 (2H, m), 3.46–3.59 (1H, m), 3.68–3.74 (2H, m), 3.86–3.97 (2H, m), 4.03–4.15 (1H, m), 7.24–7.28 (1H, m), 7.55–7.60 (1H, m), 7.76–7.80 (5H, m), 8.48 (1H, s), 8.68–8.73 (1H, m), 8.78–8.82 (1H, m), 8.86–8.94 (2H, m), 10.68 (1H, br) MASS (ESI–): 552.0 (M–H)

EXAMPLE 56

N-Hydroxy-2-[(S)-4-benzoyl-7-(5-(4-methylphenyl)-2-thienyl)-1,1-dioxoperhydro-1,4-thiazepin-7-yl]acetamide (0.9 g)

NMR (DMSO-d₆, δ): 2.32 (3H, s), 2.70–3.18 (4H, m), 3.50–4.00 (6H, m), 7.19 (1H, d, J=4.5 Hz), 7.24 (2H, d, J=7.5 Hz), 7.39–7.52 (6H, m), 7.56 (2H, d, J=7.5 Hz), 8.92–9.00 (1H, m) MASS (ESI–): 497 (M–H)

EXAMPLE 57

N-Hydroxy-2-[4-benzoyl-7-(5-(4-methoxyphenyl)-2-thienyl)-1,1-dioxoperhydro-1,4-thiazepin-7-yl]acetamide (30 mg)

NMR (DMSO-d₆, δ): 2.70–3.11 (4H, m), 3.38–3.69 (2H, m), 3.78 (3H, s), 3.83–4.12 (4H, m), 6.98 (2H, d, J=8.0 Hz), 7.15–7.22 (1H, m), 7.32–7.36 (1H, m), 7.40–7.47 (5H, m), 7.54–7.62 (2H, m), 8.82–8.90 (1H, m) MASS (ESI–): 513.0 (M–H)

EXAMPLE 58

N-Hydroxy-2-[(S)-4-(dimethylaminosulfonyl)-7-(5-(4-(5-oxazolyl)phenyl)-2-thienyl)-1,1-dioxoperhydro-1,4-thiazepin-7-yl]acetamide (65.8 mg)

NMR (DMSO-d₆, δ): 2.76 (6H, s), 2.88–2.98 (2H, br), 3.13–3.20 (2H, br), 3.40–4.06 (6H, br), 7.25 (1H, d, J=3 Hz), 7.58 (1H, d, J=3 Hz), 7.77 (5H, m), 8.48 (1H, s), 8.94 (1H, br), 10.72 (1H, br) MASS (ESI–): 553 (M–H)

EXAMPLE 59

N-Hydroxy-2-(4-benzoyl-7-(5-(3-acetamidophenyl)-2-thienyl)-1,1-dioxoperhydro-1,4-thiazepin-7-yl]acetamide (50 mg)

NMR (DMSO-d₆, δ): 2.06 (3H, s), 2.85–3.20 (6H, m), 3.51–3.57 (2H, m), 3.82–3.95 (2H, m), 7.24 (1H, d, J=4.5 Hz), 7.31–7.51 (10H, m), 7.91 (1H, s), 8.90 (1H, s), 10.05 (1H, s), 10.66 (1H, s) MASS (ESI–): 540 (M–H)

EXAMPLE 60

N-Hydroxy-2-[4-benzoyl-7-(5-(3-aminophenyl)-2-thienyl)-1,1-dioxoperhydro-1,4-thiazepin-7-yl]acetamide hydrochloride (170 mg)

NMR (DMSO-d₆, δ): 2.73–3.15 (6H, m), 3.50–3.60 (2H, m), 3.81–3.96 (2H, m), 5.23 (2H, s), 6.51 (1H, d, J=7.5 Hz), 6.79–6.84 (2H, m), 7.05 (1H, dd, J=7.5, 7.5 Hz), 7.20 (1H, d, J=4.5 Hz), 7.32 (1H, s, J=4.5 Hz), 7.39–7.48 (5H, m), 8.90 (1H, s) MASS (ESI–): 534 (M–H)

EXAMPLE 61

N-Hydroxy-2-[4-benzoyl-7-(5-(4-methylthiophenyl)-2-thienyl)-1,1-dioxoperhydro-1,4-thiazepin-7-yl]acetamide (50 mg)

NMR (DMSO-d₆, δ): 2.50 (3H, s), 2.73–3.15 (6H, m), 3.50–3.68 (2H, m), 3.82–3.97 (2H, m), 7.23 (1H, d, J=4.5 Hz), 7.30 (2H, d, J=7.5 Hz), 7.40–7.46 (6H, m), 7.60 (2H, d, J=7.5 Hz), 8.90 (1H, s), 10.66 (1H, s) MASS (ESI–): 529 (M–H)

EXAMPLE 62

N-Hydroxy-2-[7-(5-(2-naphthyl)-2-thienyl)-4-benzoyl-1,1-dioxoperhydro-1,4-thiazepin-7-yl]acetamide (118 mg)

NMR (DMSO-d$_6$, δ): 2.76–3.24 (5H, m), 3.47–4.19 (5H, m), 7.25–7.32 (1H, m), 7.40–7.56 (7H, m), 7.59–7.67 (1H, m), 7.79–8.02 (4H, m), 8.15–8.23 (1H, m), 8.82–8.94 (1H, m) MASS (ESI–): 533 (M–H)

EXAMPLE 63

To a solution of N-hydroxy-2-[(S)-7-(5-(4-(5-oxazolyl) phenyl)-2-thienyl)-4-(2-pyridinecarbonyl)-1,1-dioxoperhydro-1,4-thiazepin-7-yl]acetamide (118 mg) in methanol (3 ml) was added 10% hydrochloric acid-methanol solution (5 ml) and the mixture was stirred at ambient temperature for 0.5 hour. After evaporation of solvent, the residue was triturated with isopropyl ether to give N-hydroxy-2-[7-(5-(4-(5-oxazolyl)phenyl)-2-thienyl)-4-(2-pyridinecarbonyl)-1,1-dioxoperhydro-1,4-thiazepin-7-yl] acetamide hydrochloride as a pale yellow amorphous powder (119 mg).

NMR (DMSO-d$_6$, δ): 2.80–3.28 (4H, br), 3.50–4.18 (6H, br), 7.24, 7.29 (1H, d, J=3 Hz), 7.49–7.60 (2H, m), 7.61–7.68 (1H, m), 7.77 (6H, m), 7.96–8.04 (1H, m), 8.48 (1H, s), 8.59–8.68 (1H, br), 10.70 (1, br) MASS (ESI–): 551 (M–H)

EXAMPLE 64

N-(2-Tetrahydropyranyloxy)-2-[7-(5-(4-(5-oxazolyl) phenyl)-2-thienyl)-4-(9-fluorenylmethoxycarbonyl)-1,1-dioxoperhydro-1,4-thiazepin-7-yl]acetamide (5.70 g) was obtained in a similar manner to that of Example 30.

NMR (DMSO-d$_6$, δ): 1.38–1.66 (6H, m), 2.61–3.90 (13H, m), 4.25–4.54 (3H, m), 7.13–7.99 (15H, m), 8.46–8.50 (1H, m) MASS (ES+) m/e: 753.86

EXAMPLE 65

N-(2-Tetrahydropyranyloxy)-2-[7-(5-(4-(5-oxazolyl) phenyl)-2-thienyl)-1,1-dioxoperhydro-1,4-thiazepin-7-yl] acetamide (2.99 g) was obtained in a similar manner to that of Example 28.

NMR (DMSO-d$_6$, δ): 1.37–1.66 (6H, m), 2.56–3.61 (12H, m), 3.74–3.96 (1H, m), 4.52, 4.77 (1H, br s), 7.16–7.24 (1H, m), 7.50–7.56 (1H, m), 7.71–7.82 (5H, m), 8.48 (1H, s) MASS (ES+) m/e: 532.29

EXAMPLE 66

To a mixture of N-(2-tetrahydropyranyloxy)-2-[7-(5-(4-(5-oxazolyl)phenyl)-2-thienyl)-1,1-dioxoperhydro-1,4-thiazepin-7-yl]acetamide (100 mg) in chloroform (1 ml) was added a solution of isopropyl isocyanate (18 mg) in chloroform (1 ml) at 0° C. under nitrogen atmosphere. After being stirred for 1 hour, the mixture was concentrated in vacuo. The residue was dissolved in ethyl acetate and the solution was washed with water, a saturated aqueous sodium bicarbonate solution and brine, dried over magnesium sulfate, and evaporated in vacuo. The residue was purified by preparative thin-layer chromatography (chloroform-methanol=10-1, v/v) to give N-(2-tetrahydropyranyloxy)-2-[4-isopropylcarbamoyl-7-(5-(4-(5-oxazolyl)phenyl)-2-thienyl)-1,1-dioxoperhydro-1,4-thiazepin-7-yl]acetamide (92 mg) as a pale yellow powder.

NMR (DMSO-d$_6$, δ): 1.04–1.13 (6H, m), 1.39–1.69 (6H, m), 2.75–3.93 (14H, m), 4.50, 4.75 (1H, br s), 6.18–6.26 (1H, m), 7.18–7.25 (1H, m), 7.52–7.58 (1H, m), 7.71–7.81 (5H, m), 8.48 (1H, s) MASS (ES–) m/e: 615.35

The following compounds were obtained in a similar manner to that of Example 17.

EXAMPLE 67

N-Hydroxy-2-[4-isopropylcarbamoyl-7-(5-(4-(5-oxazolyl)phenyl)-2-thienyl)-1,1-dioxoperhydro-1,4-thiazepin-7-yl]acetamide (62 mg)

NMR (DMSO-d$_6$, δ): 1.03–1.16 (6H, m), 2.69–3.00 (3H, m), 3.10 (1H, d, J=15 Hz), 3.40–4.40 (7H, m), 6.21 (1H, br peak), 7.21 (1H, d, J=4 Hz), 7.55 (1H, d, J=4 Hz), 7.72–7.83 (5H, m), 8.48 (1H, s) MASS (ES–) m/e: 531.28

EXAMPLE 68

N-Hydroxy-2-[4-benzoyl-7-(5-(4-chlorophenyl)-2-thienyl)-1,1-dioxoperhydro-1,4-thiazepin-7-yl]acetamide (71.8 mg)

NMR (DMSO-d$_6$, δ): 2.72–3.20 (4H, br), 3.35–4.30 (6H, br), 7.23, 7.28 (1H, d, J=3 Hz), 7.38–7.58 (9H, br), 7.68 (2H, t, J=8 Hz), 10.60–10.73 (1H, br) MASS (m/z): 517 (M–H)

EXAMPLE 69

N-Hydroxy-2-[4-benzoyl-7-(5-(4-ethoxyphenyl)-2-thienyl)-1,1-dioxoperhydro-1,4-thiazepin-7-yl]acetamide (31.0 mg)

NMR (DMSO-d$_6$, δ): 1.34 (3H, t, J=7 Hz), 2.72–3.21 (4H, br), 3.40–4.18 (6H, br), 4.07 (2H, q, J=7 Hz), 6.97 (2H, d, J=8 Hz), 7.17, 7.21 (1H, d, J=3 Hz), 7.32, 7.36 (1H, d, J=3 Hz), 7.40–7.52 (6H, br), 7.58 (2H, t, J=8 Hz), 10.62, 10.68 (1H, br) MASS (m/z): 527 (M–H)

EXAMPLE 70

N-Hydroxy-2-[4-benzoyl-7-(5-(4-ethylphenyl)-2-thienyl)-1,1-dioxoperhydro-1,4-thiazepin-7-yl]acetamide (55.0 mg)

NMR (DMSO-d$_6$, δ): 1.20 (3H, t, J=7 Hz), 2.63 (2H, q, J=7 Hz), 2.73–3.23 (4H, br), 3.45–4.20 (6H, br), 7.17, 7.21 (1H, d, J=3 Hz), 7.27 (2H, d, J=8 Hz), 7.46–7.50 (7H, br), 7.51–7.63 (2H, t, J=8 Hz), 10.61, 10.68 (1H, br) MASS (m/z): 511 (M–H)

EXAMPLE 71

N-Hydroxy-2-[4-benzoyl-7-(5-(4-vinylphenyl)-2-thienyl)-1,1-dioxoperhydro-1,4-thiazepin-7-yl]acetamide (30.0 mg)

NMR (DMSO-d$_6$, δ): 2.65–3.20 (4H, br), 3.35–4.20 (6H, br), 5.31 (1H, d, J=10 Hz), 5.89 (1H, d, J=15 Hz), 6.70–6.83 (1H, dd, J=10, 15 Hz), 7.22, 7.26 (1H, d, J=3 Hz), 7.40–7.57 (9H, m), 7.60–7.72 (2H, t, J=8 Hz), 10.62, 10.68 (1H, br) MASS (m/z): 509 (M–H)

The following compounds were obtained in a similar manner to that of Example 39.

EXAMPLE 72

N-(2-Tetrahydropyranyloxy)-2-[4-benzoyl-7-(5-(4-chlorophenyl)-2-thienyl)-1,1-dioxoperhydro-1,4-thiazepin-7-yl]acetamide (230 mg)

NMR (CDCl$_3$, δ): 1.43–1.90 (6H, br), 2.75–4.05 (11H, br), 4.20–4.90 (2H, br), 7.07–7.57 (11H, br), 8.29, 8.38 (1H, br) MASS (m/z): 601 (M–H)

EXAMPLE 73

N-(2-Tetrahydropyranyloxy)-2-[4-benzoyl-7-(5-(4-ethoxyphenyl)-2-thienyl)-1,1-dioxoperhydro-1,4-thiazepin-7-yl]acetamide (200 mg)

NMR (CDCl$_3$, δ): 1.44 (3H, t, J=7 Hz), 1.40–1.83 (6H, br), 2.70–3.25 (5H, br), 3.40–3.90 (6H, br), 3.90–4.35 (1H, br), 4.08 (2H, q, J=7 Hz), 4.58, 4.86 (1H, br), 6.85–6.95 (3H, br), 7.07–7.55 (8H, br), 8.18, 8.30–8.45 (1H, br) MASS (m/z): 611 (M–H)

EXAMPLE 74

N-(2-Tetrahydropyranyloxy)-2-[4-benzoyl-7-(5-(4-ethylphenyl)-2-thienyl)-1,1-dioxoperhydro-1,4-thiazepin-7-yl]acetamide (190 mg)

NMR (CDCl₃, δ): 1.24 (3H, br), 1.42–1.90 (6H, br), 2.66 (2H, q, J=7 Hz), 2.75–4.35 (12H, br), 4.44, 4.60, 4.72, 4.86 (1H, br), 6.85–7.55 (11H, br), 8.25, 8.35–8.50 (1H, br) MASS (m/z): 595 (M−H)

EXAMPLE 75

N-(2-Tetrahydropyranyloxy)-2-[4-benzoyl-7-(5-(4-vinylphenyl)-2-thienyl)-1,1-dioxoperhydro-1,4-thiazepin-7-yl]acetamide (140 mg)

NMR (CDCl₃, δ): 1.43–2.05 (6H, br), 2.73–4.35 (12H, br), 4.43, 4.60, 4.72, 4.86 (1H, br), 5.31 (1H, d, J=10 Hz), 5.79 (1H, d, J=15 Hz), 6.66–6.78 (1H, dd, J=10, 15 Hz), 6.86–7.63 (11H, br), 8.31, 8.42–8.55 (1H, br) MASS (m/z): 593 (M−H)

The following compound was obtained in a similar manner to that of Example 33.

EXAMPLE 76

N-(2-Tetrahydropyranyloxy)-2-[4-(2-pyridinecarbonyl)-7-(4-phenoxyphenyl)perhydro-1,1-dioxo-1,4-thiazepin-7-yl]acetamide (110 mg)

NMR (DMSO-d₆, δ): 1.36–1.75 (6H, m), 2.46–2.74 (2H, m), 2.90–4.25 (10H, m), 4.30–4.76 (1H, m), 6.86–7.10 (4H, m), 7.15–7.24 (1H, m), 7.37–7.72 (6H, m), 7.86–8.01 (1H, m), 8.54–8.62 (1H, m) MASS (ESI−): 578 (M−H)

EXAMPLE 77

N-(2-Tetrahydropyranyloxy)-2-[4-isopropylcarbamoyl-7-(4-phenoxyphenyl)perhydro-1,1-dioxo-1,4-thiazepin-7-yl]acetamide (82 mg) was obtained in a similar manner to that of Example 66.

NMR (DMSO-d₆, δ): 1.05 (6H, d, J=8 Hz), 1.34–1.65 (6H, m), 2.50–3.60 (10H, m), 3.18–3.40 (3H, m), 4.39, 4.72 (1H, s), 6.23, 6.37 (1H, d, J=8 Hz), 6.94 (2H, d, J=8 Hz), 7.07 (2H, t, J=8 Hz), 7.15–7.24 (1H, m), 7.36–7.52 (4 Hr, m) MASS (ESI−): 558 (M−H)

The following compounds were obtained in a similar manner to that of Example 17.

EXAMPLE 78

N-Hydroxy-2-[4-benzoyl-7-(4-phenoxyphenyl)perhydro-1,1-dioxo-1,4-thiazepin-7-yl]acetamide (75 mg)

NMR (DMSO-d₆, δ): 2.54–2.86 (2H, m), 2.96–4.28 (8H, m), 6.93 (1H, d, J=8 Hz), 6.98 (1H, d, J=8 Hz), 7.07 (2H, d, J=8 Hz), 7.20 (1H, t, J=8 Hz), 7.35–7.58 (9H, m), 8.76, 8.85 (1H, br) MASS (ESI−): 493 (M−H)

EXAMPLE 79

N-Hydroxy-2-[4-(2-pyridinecarbonyl)-7-(4-phenoxyphenyl)perhydro-1,1-dioxo-1,4-thiazepin-7-yl]acetamide (70 mg)

NMR (DMSO-d₆, δ): 2.55–4.30 (10H, m), 6.68–7.10 (4H, m), 7.15–7.24 (1H, m), 7.38–7.72 (6H, m), 7.88–8.04 (1H, m), 8.57–8.64 (1H, m) MASS (ESI−): 496 (M+H)

EXAMPLE 80

N-Hydroxy-2-[4-isopropylcarbamoyl-7-(4-phenoxyphenyl)perhydro-1,1-dioxo-1,4-thiazepin-7-yl]acetamide (54 mg)

NMR (DMSO-d₆, δ): 1.07 (6H, d, J=8 Hz), 2.56–2.79 (2H, m), 2.89–3.62 (6H, m), 3.69–3.95 (3H, m), 6.23 (1H, d, J=8 Hz), 6.93 (2H, d, J=8 Hz), 7.07 (2H, d, J=8 Hz), 7.20 (1H, t, J=8 Hz), 7.42 (2H, d, J=8 Hz), 7.47 (2H, d, J=8 Hz), 8.83 (1H, s), 10.62 (1H, s) MASS (ESI−): 474 (M−H)

EXAMPLE 81

N-Hydroxy-2-[4-benzyloxycarbonyl-7-(4-phenoxyphenyl)perhydro-1,1-dioxo-1,4-thiazepin-7-yl]acetamide (36 mg)

NMR (CDCl₃, δ): 2.56–2.90 (2H, m), 3.00–4.22 (8H, m), 5.02–5.24 (2H, m), 6.84–6.98 (2H, m), 7.02 (2H, d, J=8 Hz), 7.08–7.58 (10H, m) MASS (ESI−): 523 (M−H)

EXAMPLE 82

N-Hydroxy-2-[4-benzoyl-7-(4-methoxyphenyl)perhydro-1,1-dioxo-1,4-thiazepin-7-yl]acetamide (120 mg)

NMR (DMSO-d₆, δ): 2.45–2.84 (1H, m), 2.94–3.36 (2H, m), 3.43–4.26 (7H, m), 3.76, 3.77 (3H, s), 6.84–6.98 (2H, m), 7.36–7.54 (7H, m), 8.76, 8.82 (1H, s), 10.56, 10.62 (1H, s) MASS (ESI−): 431 (M−H)

EXAMPLE 83

N-(2-Tetrahydropyranyloxy)-2-[7-(4-phenoxyphenyl)perhydro-1,1-dioxo-1,4-thiazepin-7-yl]acetamide (560 mg) was obtained in a similar manner to that of Example 28.

NMR (DMSO-d₆, δ): 1.38–1.66 (6H, m), 2.36–2.56 (2H, m), 2.84–3.92 (10H, m), 4.40, 4.75 (1H, s), 6.93 (2H, d, J=8 Hz), 7.02–7.09 (2H, m), 7.14–7.23 (1H, m), 7.37–7.51 (4H, m) MASS (ESI−): 473 (M−H)

The following compounds were obtained in a similar manner to that of Example 30.

EXAMPLE 84

N-(Tetrahydropyranyloxy)-2-[4-benzoyl-7-(4-phenoxyphenyl)perhydro-1,1-dioxo-1,4-thiazepin-7-yl]acetamide (113 mg)

NMR (DMSO-d₆, δ): 1.35–1.65 (6H, m), 2.48–2.62 (1H, m), 2.68–2.82 (1H, m), 2.98–4.02 (9H, m), 4.15–4.76 (2H, m), 6.88–7.00 (2H, m), 7.03–7.12 (2H, m), 7.15–7.22 (1H, m), 7.35–7.59 (9H, m) MASS (ESI−): 577 (M−H)

EXAMPLE 85

N-(2-Tetrahydropyranyloxy)-2-[4-(9-fluorenylmethoxycarbonyl)-7-(4-phenoxyphenyl)perhydro-1,1-dioxo-1,4-thiazepin-7-yl]acetamide (960 mg)

NMR (DMSO-d₆, δ): 1.38–1.65 (6H, m), 2.55–3.02 (4H, m), 3.14–3.96 (8H, m), 4.26–4.53 (3H, m), 4.64–4.76 (1H, m), 6.90–6.97 (2H, m), 7.02–7.10 (2H, m), 7.16–7.24 (1H, m), 7.30–7.53 (9H, m), 7.62–7.71 (2H, m), 7.84–7.94 (2H, m)

EXAMPLE 86

N-(2-Tetrahydropyranyloxy)-2-[4-benzyloxycarbonyl-7-(4-phenoxyphenyl)perhydro-1,1-dioxo-1,4-thiazepin-7-yl]acetamide (45 mg)

NMR (CDCl₃, δ): 1.40–1.82 (6H, m), 2.62–2.85 (2H, m), 3.06–3.82 (4H, m), 3.34–4.10 (6H, m), 4.46–4.90 (1H, m), 5.04–5.22 (2H, m), 6.87–6.99 (2H, m), 7.03 (2H, d, J=8 Hz), 7.11–7.21 (1H, m), 7.25–7.64 (9H, m), 8.25–8.54 (1H, m) MASS (ESI−): 607 (M−H)

EXAMPLE 87

N-(Tetrahydropyranyloxy)-2-[4-benzoyl-7-(4-methoxyphenyl)perhydro-1,1-dioxo-1,4-thiazepin-7-yl]acetamide (206 mg)

NMR (CDCl₆, δ): 1.33–1.75 (6H, m), 2.46–2.80 (2H, m), 2.93–3.97 (9H, m), 3.76, 3.79 (3H, s), 4.12–5.01 (2H, m), 6.84–6.99 (2H, m), 7.34–7.78 (8H, m) MASS (ESI−): 515 (M−H)

EXAMPLE 88

N-(2-Tetrahydropyranyloxy)-2-((S)-4-benzoyl-7-(5-bromo-2-thienyl)-1,1-dioxoperhydro-1,4-thiazepin-7-yl]acetamide (1.78 g) was obtained in a similar manner to that of Example 1.

NMR (CDCl$_3$, δ): 1.45–1.93 (6H, br), 2.68–3.28 (5H, br), 3.35–4.05 (6H, br), 4.18–4.92 (2H, br), 6.84–7.13 (2H, br), 7.20–7.52 (5H, br), 8.40–8.58 (1H, br) MASS (ESI-): 569, 571 (M-H)

The following compounds were obtained in a similar manner to that of Example 1.

EXAMPLE 89

N-(2-Tetrahydropyranyloxy)-2-[7-(5-bromo-2-thienyl)-4-methanesulfonyl-1,1-dioxoperhydro-1,4-thiazepin-7-yl]acetamide (794 mg)

NMR (CDCl$_3$, δ): 1.48–1.93 (6H, br), 2.75–3.00 (1H, br), 2.91 (3H, s), 3.05–3.30 (3H, br), 3.33–3.68 (5H, br), 3.73–3.97 (2H, br), 4.03–4.23 (1H, br), 4.68, 4.90 (1H, br), 7.03 (2H, br), 8.66 (1H, s) MASS (m/z): 543, 545 (M-H)

EXAMPLE 90

N-(2-Tetrahydropyranyloxy)-2-[7-(5-bromo-2-thienyl)-4-methoxycarbonyl-1,1-dioxoperhydro-1,4-thiazepin-7-yl]acetamide (4.52 g)

NMR (CDCl$_3$, δ): 1.38–1.90 (6H, br), 2.60–4.15 (12H, br), 3.72, 3.75 (3H, s), 4.53–4.65, 4.87 (1H, br), 6.96–7.06 (2H, br), 8.32, 8.40–8.48 (1H, br) MASS (m/z): 524 (M-H)

EXAMPLE 91

N-(2-Tetrahydropyranyloxy)-2-[7-(5-bromo-2-thienyl)-4-(2-methoxybenzoyl)-1,1-dioxoperhydro-1,4-thiazepin-7-yl]acetamide (375 mg)

NMR (CDCl$_3$, δ): 1.48–1.93 (6H, br), 2.70–4.20 (12H, br), 3.83–3.84 (3H, s), 4.60, 4.66–4.97 (1H, br), 6.83–7.10 (4H, br), 7.32–7.42 (2H, br), 8.45 (1H, br) MASS (m/z): 599, 601 (M-H)

EXAMPLE 92

N-(2-Tetrahydropyranyloxy)-2-[7-(5-bromo-2-thienyl)-4-(3-methoxybenzoyl)-1,1-dioxoperhydro-1,4-thiazepin-7-yl]acetamide (373 mg)

NMR (CDCl$_3$, δ): 1.44–1.90 (6H, br), 2.68–4.30 (12H, br), 3.80, 3.83 (3H, s), 4.45, 4.59, 4.73, 4.88 (1H, br), 6.74–7.14 (5H, br), 7.25–7.40 (1H, br), 8.30–8.48 (1H, br) MASS (m/z): 599, 601 (M-H)

EXAMPLE 93

N-(2-Tetrahydropyranyloxy)-2-[7-(5-bromo-2-thienyl)-4-(4-methoxybenzoyl)-1,1-dioxoperhydro-1,4-thiazepin-7-yl]acetamide (415 mg)

NMR (CDCl$_3$, δ): 1.43–1.90 (6H, br), 2.60–4.30 (12H, br), 3.84 (3H, s), 4.45, 4.57–4.75, 4.85 (1H, br), 6.83–7.14 (4H, br), 7.23–7.46 (2H, br), 8.46, 8.59 (1H, br) MASS (m/z): 599, 601 (M-H)

EXAMPLE 94

N-(2-Tetrahydropyranyloxy)-2-[7-(5-bromo-2-thienyl)-4-phenylsulfonyl-1,1-dioxoperhydro-1,4-thiazepin-7-yl]acetamide (343 mg)

NMR (CDCl$_3$, δ): 1.50–1.95 (6H, br), 2.84–4.22 (12H, br), 4.73, 4.96 (1H, br), 6.96–7.07 (2H, br), 7.52–7.70 (3H, m), 7.79 (2H, d, J=8 Hz), 8.61 (1H, br) MASS (m/z): 605, 607 (M-H)

EXAMPLE 95

N-(2-Tetrahydropyranyloxy)-2-[7-(5-bromo-2-thienyl)-4-dimethylaminocarbonyl-1,1-dioxoperhydro-1,4-thiazepin-7-yl]acetamide (260 mg)

NMR (CDCl$_3$, δ): 1.47–1.88 (6H, br), 2.79 (6H, s), 2.68–3.25 (4H, br), 3.33–4.07 (8H, br), 4.56, 4.85 (1H, br), 6.95–7.05 (2H, br), 8.53, 8.69 (1H, br) MASS (m/z): 536, 538 (M-H)

EXAMPLE 96

N-(2-Tetrahydropyranyloxy)-2-[7-(5-bromo-2-thienyl)-4-dimethylaminosulfonyl-1,1-dioxoperhydro-1,4-thiazepin-7-yl]acetamide (220 mg)

NMR (CDCl$_3$, δ): 1.50–1.95 (6H, br), 2.82 (6H, s), 3.05–3.28 (3H, br), 3.28–3.70 (6H, br), 3.83–4.15 (3H, br), 4.68, 4.92 (1H, br), 7.02 (2H, br), 8.57 (1H, br)

EXAMPLE 97

N-(2-Tetrahydropyranyloxy)-2-[4-benzylsulfonyl-7-(5-bromo-2-thienyl)-1,1-dioxoperhydro-1,4-thiazepin-7-yl]acetamide (275 mg)

NMR (CDCl$_3$, δ): 1.48–1.92 (6H, br), 2.70–3.45 (9H, br), 3.51–3.68 (1H, br), 3.80–4.12 (2H, br), 4.24–4.39 (2H, br), 4.68, 4.90 (1H, br), 6.95–7.10 (2H, br), 7.30–7.50 (5H, br), 8.71 (1H, br) MASS (m/z): 619, 621 (M-H)

EXAMPLE 98

N-(2-Tetrahydropyranyloxy)-2-[4-acetyl-7-(5-(4-chlorophenyl)-2-thienyl)-1,1-dioxoperhydro-1,4-thiazepin-7-yl]acetamide (72.5 mg)

NMR (CDCl$_3$, δ): 1.43–1.87 (6H, br), 2.13, 2.23 (3H, s), 2.80–4.40 (12H, br), 4.57, 4.86 (1H, br), 7.18–7.26 (2H, br), 7.36 (2H, d, J=8 Hz), 7.49 (2H, m), 8.44, 8.56, 8.72, 8.83 (1H, br) MASS (m/z): 539 (M-H)

EXAMPLE 99

N-(2-Tetrahydropyranyloxy)-2-[7-(5-(4-chlorophenyl)-2-thienyl)-4-methanesulfonyl-1,1-dioxoperhydro-1,4-thiazepin-7-yl]acetamide (81.0 mg)

NMR (CDCl$_3$, δ): 1.46–1.95 (6H, br), 2.92 (3H, s), 2.86–3.03 (1H, br), 3.11–3.36 (3H, br), 3.36–3.72 (5H, br), 3.75–4.00 (2H, br), 4.07–4.26 (1H, br), 4.66, 4.90 (1H, br), 7.18–7.26 (2H, m), 7.33 (2H, d, J=8 Hz), 7.49 (2H, m), 8.67 (1H, br) MASS (m/z): 575 (M-H)

EXAMPLE 100

N-(2-Tetrahydropyranyloxy)-2-[7-(5-(4-chlorophenyl)-2-thienyl)-4-(2-thiophenesulfonyl)-1,1-dioxoperhydro-1,4-thiazepin-7-yl]acetamide (115 mg)

NMR (CDCl$_3$, δ): 1.47–1.93 (6H, br), 2.90–3.05 (1H, br), 3.07–3.75 (8H, br), 3.75–4.00 (2H, br), 4.02–4.26 (1H, br), 4.70, 4.93 (1H, br), 7.16 (1H, m), 7.20–7.26 (2H, br), 7.33 (2H, d, J=8 Hz), 7.45–7.54 (2H, br), 7.60 (1H, br), 7.66 (1H, d, J=3 Hz), 8.60 (1H, br) MASS (m/z): 643 (M-H)

EXAMPLE 101

N-(2-Tetrahydropyranyloxy)-2-[7-(5-(4-chlorophenyl)-2-thienyl)-4-isopropylcarbonyl-1,1-dioxoperhydro-1,4-thiazepin-7-yl]acetamide (109 mg)

NMR (CDCl$_3$, δ): 1.04–1.22 (6H, br), 1.43–1.90 (6H, br), 2.55–2.78 (1H, br), 2.78–3.03 (2H, br), 3.03–3.97 (8H, br), 4.00–4.46 (2H, br), 4.56, 4.84 (1H, br), 7.16–7.27 (2H, m), 7.33 (2H, d, J=8 Hz), 7.44–7.55 (2H, m), 8.65, 8.79, 9.06, 9.28 (1H, br) MASS (m/z): 567 (M–H)

EXAMPLE 102

N-(2-Tetrahydropyranyloxy)-2-[4-benzylsulfonyl-7-(5-(4-chlorophenyl)-2-thienyl)-1,1-dioxoperhydro-1,4-thiazepin-7-yl]acetamide (83.6 mg)

NMR (CDCl$_3$, δ): 1.46–1.98 (6H, br), 2.78–2.96 (1H, br), 2.98–3.65 (8H, br), 3.75–4.15 (3H, br), 4.26–4.42 (2H, br), 4.72, 4.91 (1H, br), 7.16–7.25 (2H, m), 7.26–7.55 (9H, m), 8.65 (1H, br) MASS (m/z) 651 (M–H)

EXAMPLE 103

N-(2-Tetrahydropyranyloxy)-2-[(S)-7-(5-(4-chlorophenyl)-2-thienyl)-4-ethanesulfonyl-1,1-dioxoperhydro-1,4-thiazepin-7-yl]acetamide (100 mg)

NMR (CDCl$_3$, δ): 1.37 (3H, t, J=7 Hz), 1.46–1.96 (6H, br)., 2.78–3.35 (6H, br), 3.35–3.76 (5H, br), 3.76–4.08 (2H, br), 4.08–4.32 (1H, br), 4.69, 4.92 (1H, br), 7.18–7.26 (2H, m), 7.33 (2H, d, J=8 Hz), 7.46–7.56 (2H, m), 8.86, 8.94 (1H, br) MASS (m/z): 589 (M–H)

EXAMPLE 104

N-(2-Tetrahydropyranyloxy)-2-[(S)-7-(5-(4-chlorophenyl)-2-thienyl)-4-propylsulfonyl-1,1-dioxoperhydro-1,4-thiazepin-7-yl]acetamide (78.5 mg)

NMR (CDCl$_3$, δ): 1.07 (3H, t, J=7 Hz), 1.42–1.96 (8H, br), 2.38–3.12 (3H, br), 3.12–3.36 (3H, br), 3.36–3.72 (5H, br), 3.75–4.00 (2H, br), 4.00–4.30 (1H, br), 4.68, 4.90 (1H, br), 7.15–7.27 (2H, m), 7.30 (2H, d, J=8 Hz), 7.42–7.54 (2H, m), 9.08, 9.22 (1H, br) MASS (m/z): 603 (M–H)

EXAMPLE 105

N-(2-Tetrahydropyranyloxy)-2-[(S)-7-(5-(4-chlorophenyl)-2-thienyl)-4-(4-morpholinesulfonyl)-1,1-dioxoperhydro-1,4-thiazepin-7-yl]acetamide (72.4 mg)

NMR (CDCl$_3$, δ): 1.45–1.93 (6H, br), 2.83–3.00 (1H, br), 3.08–3.30 (4H, br), 3.75 (4H, br), 3.08–4.22 (1H, br), 4.66, 4.89 (1H, br), 7.15–7.25 (2H, br), 7.34 (2H, d, J=8 Hz), 7.50 (2H, d, J=8 Hz), 8.44–8.57 (1H, br) MASS (m/z): 646 (M–H)

EXAMPLE 106

N-(2-Tetrahydropyranyloxy)-2-[(S)-7-(5-(4-chlorophenyl)-2-thienyl)-4-(1-pyrrolidinesulfonyl)-1,1-dioxoperhydro-1,4-thiazepin-7-yl]acetamide (86.0 mg)

NMR (CDCl$_3$, δ): 1.40–1.90 (6H, br), 1.90–1.98 (4H, m), 2.85–3.05 (1H, br), 3.15–3.68 (12H, br), 3.77–4.18 (3H, br), 4.68, 4.90 (1H, br), 7.22 (2H, s), 7.33 (2H, d, J=8 Hz), 7.49 (2H, d, J=8 Hz), 8.69 (1H, br) MASS (m/z): 630 (M–H)

EXAMPLE 107

N-(2-Tetrahydropyranyloxy)-2-[(S)-7-(5-(4-chlorophenyl)-2-thienyl)-4-(N-(2-methoxyethyl)-N-methylamino)sulfonyl-1,1-dioxoperhydro-1,4-thiazepin-7-yl]acetamide (72.5 mg)

NMR (CDCl$_3$, δ): 1.45–1.90 (6H, br), 2.88 (3H, s), 2.90–3.00 (1H, br), 3.12–3.68 (12H, br), 3.37 (3H, s), 3.77–4.16 (3H, br), 4.68, 4.90 (1H, br), 7.22 (2H, s), 7.33 (2H, d, J=8 Hz), 7.50 (2H, d, J=8 Hz), 8.66 (1H, br) MASS (m/z): 648 (M–H)

EXAMPLE 108

N-(2-Tetrahydropyranyloxy)-2-[(S)-7-(5-(4-chlorophenyl)-2-thienyl)-4-(4-methoxy-1-piperidinesulfonyl)-1,1-dioxoperhydro-1,4-thiazepin-7-yl]acetamide (86.7 mg)

NMR (CDCl$_3$, δ): 1.46–2.03 (10H, br), 2.85–2.97 (1H, br), 3.06–3.72 (12H, br), 3.35 (3H, s), 3.75–4.18 (4H, br), 4.68, 4.91 (1H, br), 7.22 (2H, s), 7.33 (2H, d, J=8 Hz), 7.48 (2H, m), 8.58 (1H, br) MASS (m/z): 674 (M–H)

EXAMPLE 109

N-(2-Tetrahydropyranyloxy)-2-[4-benzyloxycarbonyl-7-(5-bromo-2-thienyl)-1,1-dioxoperhydro-1,4-thiazepin-7-yl]acetamide (280 mg)

NMR (CDCl$_3$, δ): 1.56–1.69 (6H, m), 2.63–4.09 (12H, m), 4.53–4.86 (1H, m), 5.13 (2H, d, J=11.0 Hz), 6.86–6.91 (2H, m), 7.28–7.35 (5H, m), 8.19–8.38 (1H, m) MASS (ESI–): 601.2 (M–H)

EXAMPLE 110

N-(2-Tetrahydropyranyloxy)-2-[4-(dimethylamino)sulfonyl-7-[4-(4-methoxyphenoxy)phenyl]-1,1-dioxoperhydro-1,4-thiazepin-7-yl]acetamide (77 mg)

NMR (CDCl$_3$, δ): 1.50–1.60 (4H, m), 1.70–1.80 (2H, m), 2.82 (3H, s), 2.83 (3H, s), 3.17–3.67 (8H, m), 3.77–4.08 (4H, m), 3.82 (3H, s), 4.65–4.93 (1H, m), 6.94 (4H, t, J=8 Hz), 7.02 (2H, d, J=8 Hz), 7.46 (2H, d, J=8 Hz) MASS (m/z): 612 (M$^+$+H), 115 (bp)

EXAMPLE 111

N-(2-Tetrahydropyranyloxy)-2-[7-(5-bromo-2-thienyl)-4-(2-thiophenesulfonyl)-1,1-dioxoperhydro-1,4-thiazepin-7-yl]acetamide (360 mg)

NMR (CDCl$_3$, δ): 1.57–1.76 (6H, m), 2.74–4.24 (12H, m), 4.70–4.93 (1H, m), 7.14–7.18 (2H, m), 7.58 (1H, d, J=5.0 Hz), 7.65 (1H, d, J=5.0 Hz), 7.70–7.75 (1H, m), 8.61–8.64 (1H, m) MASS (ESI–): 612.9 (M–H)

EXAMPLE 112

N-(2-Tetrahydropyranyloxy)-2-[7-(5-bromo-2-thienyl)-4-(4-morpholinocarbonyl)-1,1-dioxoperhydro-1,4-thiazepin-7-yl]acetamide (305 mg)

NMR (CDCl$_3$, δ): 1.55–1.85 (6H, m), 2.65–3.91 (20H, m), 4.55 (½H, br), 4.84 (½H, br), 6.94–7.03 (2H, m), 8.57 (½H, s), 8.71 (½H, s) MASS (ESI–): 578.0 (M–H)

EXAMPLE 113

N-(2-Tetrahydropyranyloxy)-2-[4-diethylaminosulfonyl-7-(5-(4-(5-oxazolyl)phenyl)-2-thienyl)-1,1-dioxoperhydro-1,4-thiazepin-7-yl]acetamide (90 mg)

NMR (CDCl$_3$, δ): 1.30 (6H, t, J=7.0 Hz), 1.45–1.75 (6H, m), 2.92–4.08 (12H, m), 3.43 (4H, q, J=7.0 Hz), 9.65–4.89 (1H, m), 7.22–7.30 (2H, m), 7.37 (1H, br), 7.60–7.67 (4H, m), 7.95 (1H, s) MASS (ESI–): 665.3 (M–H)

EXAMPLE 114

N-(2-Tetrahydropyranyloxy)-2-[4-methanesulfonyl-7-(5-(4-propylphenyl)-2-thienyl)-1,1-dioxoperhydro-1,4-thiazepin-7-yl]acetamide (103 mg)

NMR (CDCl$_3$, δ): 0.94 (3H, t, J=7 Hz), 1.44–1.90 (8H, br), 2.59 (2H, t, J=7 Hz), 2.82–2.95 (1H, br), 2.92 (3H, s), 3.08–3.27 (3H, br), 3.36–3.67 (5H, br), 3.72–3.88 (2H, br), 4.07–4.25 (1H, br), 4.65, 4.89 (1H, br), 7.13–7.26 (4H, m), 7.48 (2H, d, J=8 Hz), 8.47, 8.56 (1H, br) MASS (m/z): 583 (M–H)

EXAMPLE 115

N-(2-Tetrahydropyranyloxy)-2-[4-dimethylaminosulfonyl-7-(5-(4-propylphenyl)-2-thienyl)-1,1-dioxoperhydro-1,4-thiazepin-7-yl]acetamide (131 mg)

NMR (CDCl₃, δ): 0.94 (3H, t, J=7 Hz), 1.45–1.90 (8H, br), 2.59 (2H, t, J=7 Hz), 2.78–2.98 (1H, br), 2.82 (6H, s), 3.10–3.28 (3H, br), 3.28–3.65 (5H, br), 3.73–4.17 (3H, br), 4.65, 4.88 (1H, br), 7.12–7.26 (4H, br), 7.48 (2H, d, J=8 Hz), 8.44, 8.53 (1H, br) MASS (m/z): 612 (M−H)

EXAMPLE 116

N-(2-Tetrahydropyranyloxy)-2-[7-(5-(4-propylphenyl)-2-thienyl)-4-(3-pyridinesuslfonyl)-1,1-dioxoperhydro-1,4-thiazepin-7-yl]acetamide (80.5 mg)

NMR (CDCl₃, δ): 0.94 (3H, t, J=7 Hz), 1.45–1.95 (8H, br), 2.61 (2H, t, J=7 Hz), 2.85–3.02 (1H, br), 3.07–3.33 (3H, br), 3.36–3.72 (5H, br), 3.75–4.05 (2H, br), 4.05–4.25 (1H, br), 4.66, 4.92 (1H, br), 7.10–7.30 (4H, m), 7.48 (2H, d, J=8 Hz), 7.52 (1H, m), 8.08 (1H, d, J=8 Hz), 8.46, 8.54 (1H, br), 8.87 (1H, d, J=3 Hz), 9.03 (1H, s) MASS (m/z): 646 (M−H)

EXAMPLE 117

N-(2-Tetrahydropyranyloxy)-2-[7-(5-(4-fluorophenyl)-2-thienyl)-4-(2-methoxybenzoyl)-1,1-dioxoperhydro-1,4-thiazepin-7-yl]acetamide (109 mg)

NMR (CDCl₃, δ): 1.40–1.95 (6H, br), 2.65–4.02 (11H, br), 3.84 (3H, s), 4.15–4.30, 4.40–4.65, 4.65–4.80, 4.80–4.96 (2H, br), 6.80–7.26 (8H, br), 7.45–7.60 (2H, br), 8.30, 840–8.50, 8.55, 8.63, 8.68 (1H, br) MASS (m/z): 615 (M−H)

EXAMPLE 118

N-(2-Tetrahydropyranyloxy)-2-[7-(5-(4-fluorophenyl)-2-thienyl)-4-methanesulfonyl-1,1-dioxoperhydro-1,4-thiazepin-7-yl]acetamide (110 mg)

NMR (CDCl₃, δ): 1.45–1.95 (6H, br), 2.84–3.02 (4H, br), 3.09–3.35 (3H, br), 3.39–3.68 (5H, br), 3.75–3.97 (2H, br), 4.06–4.27 (1H, br), 4.68, 4.90 (1H, br), 7.03–7.13 (2H, m), 7.19 (1H, d, J=3 Hz), 7.25 (1H, br), 7.50–7.58 (2H, m), 8.50–8.60 (1H, br) MASS (m/z): 559 (M−H)

EXAMPLE 119

N-(2-Tetrahydropyranyloxy)-2-[7-(5-(4-fluorophenyl)-2-thienyl)-4-(3-pyridinesulfonyl)-1,1-dioxoperhydro-1,4-thiazepin-7-yl]acetamide (73.6 mg)

NMR (CDCl₃, δ): 1.45–1.98 (6H, br), 2.40–3.07 (1H, br), 3.10–3.70 (8H, br), 3.75–4.00 (2H, br), 4.00–4.30 (1H, br), 4.68, 4.92, 5.10 (1H, br), 7.00–7.10 (2H, m), 7.15–7.20 (1H, m), 7.23 (1H, d, J=3 Hz), 7.46–7.58 (3H, m), 8.10 (1H, m), 8.87 (1H, d, J=4 Hz), 9.02–9.15 (2H, br) MASS (m/z): 622 (M−H)

EXAMPLE 120

N-(2-Tetrahydropyranyloxy)-2-[7-(5-(4-cyanophenyl)-2-thienyl)-4-(2-methoxybenzoyl)-1,1-dioxoperhydro-1,4-thiazepin-7-yl]acetamide (125 mg)

NMR (CDCl₃, δ): 1.40–1.90 (6H, br), 2.75–4.20 (12H, br), 3.85, 3.90 (3H, s), 4.30–5.00 (1H, br), 6.85–7.10 (2H, br), 7.15–7.26 (1H, br), 7.30–7.48 (3H, br), 7.62–7.74 (4H, m), 8.53, 8.62, 8.72, 8.78, 8.89 (1H, br) MASS (m/z): 622 (M−H)

EXAMPLE 121

N-(2-Tetrahydropyranyloxy)-2-[4-methanesulfonyl-7-(5-(4-methoxymethylphenyl)-2-thienyl)-1,1-dioxoperhydro-1,4-thiazepin-7-yl]acetamide (96.8 mg)

NMR (CDCl₃, δ): 1.45–1.90 (6H, br), 2.92 (3H, s), 2.85–3.00 (1H, br), 3.10–3.33 (2H, br), 3.40 (3H, s), 3.40–3.70 (6H, br), 3.75–3.95 (2H, br), 4.06–4.27 (1H, br), 4.46 (2H, S), 4.66, 4.90 (1H, br), 7.20–7.27 (2H, br), 7.33 (2H, d, J=8 Hz), 7.56 (2H, d, J=8 Hz), 8.47, 8.55 (1H, br) MASS (m/z): 585 (M−H)

EXAMPLE 122

N-(2-Tetrahydropyranyloxy)-2-[4-(dimethylamino)sulfonyl-1,1-dioxoperhydro-7-(4-phenoxyphenyl)-1,4-thiazepin-7-yl]acetamide (70 mg)

NMR (CDCl₃, δ): 1.55–1.63 (4H, m), 1.70–1.77 (2H, m), 2.77–2.86 (2H, m), 2.82 (6H, s), 3.19–3.70 (6H, m), 3.83–4.07 (4H, m), 4.67–4.74 (1H, m), 6.97–7.09 (4H, m), 7.13–7.20 (1H, m), 7.33–7.51 (4H, m), 8.67 (1H, d, J=2 Hz) MASS (m/z): 580 (M⁺−H), 159 (bp)

EXAMPLE 123

N-(2-Tetrahydropyranyloxy)-2-[4-(dimethylamino)sulfonyl-7-[4-(4-methylphenoxy)phenyl]-1,1-dioxoperhydro-1,4-thiazepin-7-yl]acetamide (75 mg)

NMR (CDCl₃, δ): 1.50–1.60 (4H, m), 1.70–1.80 (2H, m), 2.34 (3H, s), 2.81 (6H, s), 3.17–3.65 (8H, m), 3.80–4.05 (4H, m), 4.65–4.93 (1H, m), 6.90–6.97 (4H, m), 7.15 (2H, d, J=8 Hz), 7.45 (2H, d, J=8 Hz), 8.54 (1H, s) MASS (m/z): 594 (M⁺−H), 91 (bp)

EXAMPLE 124

N-2-(Tetrahydropyranyloxy)-2-[4-benzoyl-7-[4-(4-methylphenoxy) phenyl]-1,1-dioxoperhydro-1,4-thiazepin-7-yl]acetamide (79 mg)

NMR (CDCl₃, δ): 1.48–1.78 (6H, m), 2.35 (3H, s), 2.63–2.89 (2H, m), 3.04–3.18 (2H, m), 3.36–3.99 (6H, m), 4.08–4.20 (1H, m), 4.28–4.45 (1H, m), 4.53–4.70 (1H, m), 6.89–7.03 (4H, m), 7.17 (3H, d, J=8 Hz), 7.30–7.49 (5H, m), 7.63–7.70 (1H, m) MASS (m/z): 591 (M⁺−H), 145 (bp)

EXAMPLE 125

N-(2-Tetrahydropyranyloxy)-2-[7-[4-(4-chlorophenoxy)phenyl]-4-methanesulfonyl-1,1-dioxoperhydro-1,4-thiazepin-7-yl]acetamide (70 mg)

NMR (CDCl₃, δ): 1.49–1.63 (4H, m), 1.68–1.80 (2H, m), 2.80–2.98 (2H, m), 2.90 (3H, s), 3.20–3.39 (4H, m), 3.45–3.60 (3H, m), 3.77–3.92 (2H, m), 4.04–4.18 (1H, m), 4.65–4.94 (1H, m), 7.00 (4H, d, J=8 Hz), 7.32 (2H, d, J=8 Hz), 7.48–7.55 (2H, m), 8.63 (1H, s) MASS (m/z): 585 (M⁺−H), 122 (bp)

EXAMPLE 126

N-(2-Tetrahydropyranyloxy)-2-[7-[4-(4-chlorophenoxy)phenyl]-4-(dimethylamino) sulfonyl-1,1-dioxoperhydro-1,4-thiazepin-7-yl]acetamide (80 mg)

NMR (CDCl₃, δ): 1.55–1.62 (4H, m), 1.70–1.80 (2H, m), 2.81 (6H, s), 3.18–3.68 (8H, m), 3.82–4.10 (4H, m), 4.67–4.92 (1H, m), 6.95–7.00 (4H, m), 7.31 (2H, d, J=8 Hz), 7.49 (2H, d, J=8 Hz), 8.69 (1H, d, J=7 Hz) MASS (m/z): 614 (M⁺−H), 123 (bp)

EXAMPLE 127

N-(2-Tetrahydropyranyloxy)-2-[7-[4-(4-chlorophenoxy)phenyl]-4-(2-thiophene) sulfonyl-1,1-dioxoperhydro-1,4-thiazepin-7-yl]acetamide (55 mg)

NMR (CDCl₃, δ): 1.48–1.62 (4H, m), 1.70–1.80 (2H, m), 2.82–2.95 (1H, m), 3.13–3.68 (7H, m), 3.82–3.93 (3H, m), 4.00–4.15 (1H, m), 4.67–4.93 (1H, m), 6.94–7.00 (4H, m), 7.15–7.18 (1H, m), 7.31 (2H, d, J=8 Hz), 7.50 (2H, d, J=8 Hz), 7.59–7.67 (2H, m), 8.59–8.65 (1H, m) MASS (m/z): 653 (M$^+$–H), 123 (bp)

EXAMPLE 128

N-(2-Tetrahydropyranyloxy)-2-[7-[4-(4-chlorophenoxy)phenyl]-4-(2-methoxybenzoyl)-1,1-dioxoperhydro-1,4-thiazepin-7-yl]acetamide (90 mg)

NMR (CDCl$_3$, δ): 1.34–1.57 (6H, m), 2.47–2.70 (1H, m), 2.92–3.44 (4H, m), 3.50–3.92 (8H, m), 3.97–4.10 (1H, m), 4.35–4.68 (1H, m), 4.88–5.25 (2H, m), 6.64–6.77 (1H, m), 6.80–7.07 (6H, m), 7.18–7.28 (1H, m), 7.33–7.77 (4H, m) MASS (m/z): 641 (M$^+$–H), 45 (bp)

EXAMPLE 129

N-(2-Tetrahydropyranyloxy)-2-[7-[4-(4-fluorophenoxy)phenyl]-4-methanesulfonyl-1,1-dioxoperhydro-1,4-thiazepin-7-yl]acetamide (72 mg)

NMR (CDCl$_3$, δ): 1.48–1.62 (4H, m), 1.70–1.80 (2H, m), 2.78–2.87 (2H, m), 2.90 (3H, s), 3.18–3.37 (4H, m), 3.40–3.64 (3H, m), 3.78–3.92 (2H, m), 4.03–4.17 (1H, m), 4.65–4.93 (1H, m), 6.94 (2H, d, J=8 Hz), 7.02–7.07 (4H, m), 7.45–7.53 (2H, m), 8.60 (1H, s) MASS (m/z): 569 (M$^+$–H), 45 (bp)

EXAMPLE 130

N-(2-Tetrahydropyranyloxy)-2-[4-(dimethylamino)sulfonyl-7-[4-(4-fluorophenoxy)phenyl]-1,1-dioxoperhydro-1,4-thiazepin-7-yl]acetamide (75 mg)

NMR (CDCl$_3$, δ): 1.52–1.60 (4H, m), 1.70–1.80 (2H, m), 2.83 (6H, s), 3.18–3.69 (8H, m), 3.82–4.09 (4H, m), 4.67–4.93 (1H, m), 6.94 (2H, d, J=8 Hz), 7.00–7.07 (4H, m), 7.49 (2H, d, J=8 Hz), 8.63 (1H, d, J=7 Hz) MASS (m/z): 598 (M$^+$–H, bp)

EXAMPLE 131

N-(2-Tetrahydropyranyloxy)-2-[4-benzoyl-7-[4-(4-fluorophenoxy)phenyl]-1,1-dioxoperhydro-1,4-thiazepin-7-yl]acetamide (75 mg)

NMR (CDCl$_3$, δ): 1.50–1.75 (6H, m), 2.70–2.80 (2H, m), 3.07–3.20 (2H, m), 3.38–3.62 (3H, m), 3.65–3.84 (3H, m), 4.30–4.42 (1H, m), 6.89–6.93 (1H, m), 6.97–7.06 (4H, m), 7.14–7.22 (1H, m), 7.35–7.45 (5H, m), 7.66–7.72 (1H, m), 8.28–8.37 (1H, m) MASS (m/z): 595 (M$^+$–H), 123 (bp)

EXAMPLE 132

N-(2-Tetrahydropyranyloxy)-2-[(S)-7-4-(4-chlorophenoxy)phenyl]-4-(dimethylamino)sulfonyl-1,1-dioxoperhydro-1,4-thiazepin-7-yl]acetamide (1.031 g)

NMR (CDCl$_3$, δ): 1.55–1.62 (4H, m), 1.70–1.80 (2H, m), 2.82 (6H, s), 3.20–3.68 (8H, m), 3.82–4.10 (4H, m), 4.68–4.94 (1H, m), 6.95–7.00 (4H, m), 7.31 (2H, d, J=8 Hz), 7.49 (2H, d, J=8 Hz), 8.69 (1H, d, J=7 Hz) MASS (m/z): 614 (M$^+$+H), 123 (bp)

EXAMPLE 133

N-(2-Tetrahydropyranyloxy)-2-[(S)-4-benzoyl-7-(5-bromo-2-thienyl)-1,1-dioxoperhydro-1,4-thiazepin-7-yl]acetamide (1.83 g)

NMR (CDCl$_3$, δ): 1.45–1.93 (6H, br), 2.68–3.28 (5H, br), 3.35–4.05 (6H, br), 4.18–4.92 (2H, br), 6.84–7.13 (2H, br), 7.20–7.52 (5H, br), 8.40–8.58 (1H, br) MASS (m/z): 569, 571 (M–H)

EXAMPLE 134

N-(2-Tetrahydropyranyloxy)-2-[7-(5-(4-methylthiophenyl)-2-thienyl)-4-dimethylaminosulfonyl-1,1-dioxoperhydro-1,4-thiazepin-7-yl]acetamide (150 mg)

NMR (CDCl$_3$, δ): 1.46–1.75 (6H, m), 2.50 (3H, s), 2.82 (6H, s), 3.15–3.25 (3H, m), 3.35–3.63 (6H, m), 3.76–4.13 (3H, m), 4.65, 4.88 (1H, br), 7.20–7.24 (4H, m), 7.47–7.50 (2H, m), 8.68, 8.71 (1H, br) MASS (ESI–): 616 (M–H)

EXAMPLE 135

N-(2-Tetrahydropyranyloxy)-2-[7-(5-(4-methylthiophenyl)-2-thienyl)-4-(3-pyridinylsulfonyl)-1,1-dioxoperhydro-1,4-thiazepin-7-yl]acetamide (73 mg)

MASS (ESI–): 650 (M–H)

EXAMPLE 136

N-(2-Tetrahydropyranyloxy)-2-[7-(5-(4-methylthiophenyl)-2-thienyl)-4-methanesulfonyl-1,1-dioxoperhydro-1,4-thiazepin-7-yl]acetamide (90 mg)

MASS (ESI–): 587 (M–H)

EXAMPLE 137

N-(2-Tetrahydropyranyloxy)-2-[7-(5-(2-naphthyl)-2-thienyl)-4-dimethylaminosulfonyl-1,1-dioxoperhydro-1,4-thiazepin-7-yl]acetamide (150 mg)

NMR (CDCl$_3$, δ): 1.48–1.70 (6H, m), 2.83 (6H, s), 3.26 (2H, br), 3.40–3.64 (6H, m), 3.78–4.13 (4H, m), 4.66, 4.90 (1H, s), 7.37–7.38 (1H, m), 7.47–7.50 (2H, m), 7.68–7.71 (1H, m), 7.81–7.84 (3H, m), 8.03 (1H, br), 8.65–8.70 (1H, m) MASS (ESI–): 620 (M–H)

EXAMPLE 138

N-(2-Tetrahydropyranyloxy)-2-[7-(5-(4-methylphenyl)-2-thienyl)-4-dimethylaminosulfonyl-1,1-dioxoperhydro-1,4-thiazepin-7-yl]acetamide (150 mg)

NMR (CDCl$_3$, δ): 1.50–1.72 (6H, m), 2.36 (3H, s), 2.82 (6H, s), 2.85–2.95 (1H, m), 3.17–3.23 (2H, m), 3.37–3.64 (4H, m), 3.71–4.10 (3H, m), 4.65, 4.88 (1H, br), 7.15–7.21 (4H, m), 7.46 (2H, d, J=8.5 Hz), 8.51–8.58 (1H, br) MASS (ESI–): 584 (M–H)

EXAMPLE 139

N-(2-Tetrahydropyranyloxy)-2-[7-(5-(4-methylphenyl)-2-thienyl)-4-(3-pyridinylsulfonyl)-1,1-dioxoperhydro-1,4-thiazepin-7-yl]acetamide (150 mg)

MASS (ESI–): 618 (M–H)

EXAMPLE 140

N-(2-Tetrahydropyranyloxy)-2-[4-(4-methoxyphenylsulfonyl)-7-(5-(4-(5-oxazolyl)phenyl)-2-thienyl)-1,1-dioxoperhydro-1,4-thiazepin-7-yl]acetamide (115 mg)

NMR (CDCl$_3$, δ): 1.44–1.95 (6H, m), 2.84–3.94 (14H, m), 4.08 (1H, br), 4.75 (½H, s), 4.95 (½H, s), 7.03 (2H, d, J=8 Hz), 7.26 (2H, d, J=8 Hz), 7.39 (1H, s), 7.58–7.68 (4H, m), 7.73 (2H, d, J=8 Hz), 7.93 (1H, s), 8.64–7.73 (1H, m)

EXAMPLE 141

N-(2-Tetrahydropyranyloxy)-2-[7-(5-(4-(5-oxazolyl)phenyl)-2-thienyl)-1,1-dioxoperhydro-4-(1-piperidinylsulfonyl)-1,4-thiazepin-7-yl]acetamide (52 mg)

NMR (DMSO-d$_6$, δ): 1.38–1.65 (12H, m), 2.81–2.95 (2H, m), 3.09–3.44 (8H, m), 3.44–4.00 (8H, m), 4.49 (½H, s), 4.74 (½H, s), 7.23 (½H, d, J=3 Hz), 7.26 (½H, d, J=3 Hz), 7.73–7.84 (5H, m), 8.49 (1H, s) MASS (ES+)(m/z): 677.37

EXAMPLE 142

N-(2-Tetrahydropyranyloxy)-2-[4-[(N,N-dimethylamino)sulfonyl]-7-(5-(4-ethoxyphenyl)-2-thienyl)-1,1-dioxoperhydro-1,4-thiazepin-7-yl]acetamide (84 mg)

NMR (DMSO-$d_6$, δ): 1.34 (3H, t, J=7.5 Hz), 1.37–1.64 (6H, m), 2.75 (6H, s), 2.80–4.00 (12H, m), 4.06 (2H, q, J=7.5 Hz), 4.48 (½H, br s), 4.75 (½H, br s), 6.98 (2H, d, J=8 Hz), 7.15 (½H, d, J=3 Hz), 7.20 (½H, d, J=3 Hz), 7.31 (½H, d, J=3 Hz), 7.34 (½H, d, J=3 Hz), 7.56 (2H, d, J=8 Hz) MASS (ES−)(m/z): 614.20

EXAMPLE 143

N-(2-Tetrahydropyranyloxy)-2-[7-(5-(4-ethoxyphenyl)-2-thienyl)-4-(3-pyridylsulfonyl)-1,1-dioxoperhydro-1,4-thiazepin-7-yl]acetamide (70 mg)

NMR (DMSO-$d_6$, δ): 1.33 (3H, t, J=7.5 Hz), 1.36–1.66 (6H, m), 2.56–4.00 (12H, m), 4.05 (2H, q, J=7.5 Hz), 4.49 (½H, s), 4.75 (½H, s), 6.96 (2H, d, J=8 Hz), 7.12 (½H, d, J=3 Hz), 7.16 (½H, d, J=3 Hz), 7.30 (½H, d, J=3 Hz), 7.32 (½H, d, J=3 Hz), 7.55 (2H, d, J=8 Hz), 7.70 (1H, dd, J=8, 5 Hz), 8.26 (1H, dd, J=8, 2 Hz), 8.90 (1H, dd, J=5, 2 Hz), 9.01 (1H, d, J=2 Hz) MASS (ES−)(m/z): 648.38

EXAMPLE 144

N-(2-Tetrahydropyranyloxy)-2-[4-benzoyl-7-[4-(4-methoxyphenoxy)phenyl]-1,1-dioxoperhydro-1,4-thiazepin-7-yl]acetamide (75 mg)

NMR (CDCl$_3$, δ): 1.47–1.62 (4H, m), 1.64–1.77 (2H, m), 2.60–2.90 (2H, m), 2.95–3.18 (2H, m), 3.35–4.00 (6H, m), 3.82 (3H, s), 4.05–4.18 (1H, m), 4.28–4.42 (1H, m), 4.52–4.97 (1H, m), 6.85–7.02 (6H, m), 7.12–7.19 (1H, m), 7.33–7.48 (5H, m), 7.62–7.69 (1H, m), 8.13–8.26 (1H, m) MASS (m/z): 607 (M$^+$–H, bp)

The following compounds were obtained in a similar manner to that of Example 66.

EXAMPLE 145

N-(2-Tetrahydropyranyloxy)-2-[7-(5-bromo-2-thienyl)-4-ethylaminocarbonyl-1,1-dioxoperhydro-1,4-thiazepin-7-yl]acetamide (700 mg)

NMR (CDCl$_3$, δ): 1.14 (3H, t, J=7 Hz), 1.49–1.95 (6H, br), 2.75–2.95 (2H, br), 3.07–3.62 (7H, br), 3.70–3.97 (2H, br), 3.98–4.28 (2H, br), 4.58, 4.74–4.93 (2H, br), 7.02 (2H, br), 9.19 (1H, s) MASS (m/z): 536, 538 (M–H)

EXAMPLE 146

N-(2-Tetrahydropyranyloxy)-2-[7-(5-bromo-2-thienyl)-4-phenylaminocarbonyl-1,1-dioxoperhydro-1,4-thiazepin-7-yl]acetamide (264 mg)

NMR (CDCl$_3$, δ): 1.48–1.88 (6H, br), 2.75–4.10 (1H, br), 4.23–4.40 (1H, br), 4.57, 4.81 (1H, br), 6.97–7.12 (5H, br), 7.26–7.40 (2H, br), 8.79–8.88 (1H, br) MASS (m/z): 584, 586 (M–H)

EXAMPLE 147

N-(2-Tetrahydropyranyloxy)-2-[7-(5-(4-(5-oxazolyl)phenyl)-2-thienyl)-4-(((S)-1-phenylethylamino) carbonyl)-1,1-dioxoperhydro-1,4-thiazepin-7-yl]acetamide (120 mg)

NMR (CDCl$_3$, δ): 1.47–1.71 (9H, m), 2.72–4.24 (12H, m), 4.55–4.86 (1H, m), 4.96–5.10 (1H, m), 7.20–7.36 (9H, m), 7.57–7.66 (4H, m), 7.93 (1H, s), 8.72–8.83 (1H, m) MASS (ESI−): 677.3 (M–H)

EXAMPLE 148

N-(2-Tetrahydropyranyloxy)-2-[7-(5-(4-(5-oxazolyl)phenyl)-2-thienyl)-4-propylaminocarbonyl-1,1-dioxoperhydro-1,4-thiazepin-7-yl]acetamide (60 mg)

NMR (CDCl$_3$, δ): 0.92 (3H, t, J=6.0 Hz), 1.50–1.85 (8H, m), 2.82–4.84 (16H, m), 7.16–7.30 (1H, m), 7.38 (1H, br s), 7.55–7.66 (5H, m), 7.92 (1H, s), 8.90–8.96 (1H, m) MASS (ESI−): 615.3 (M–H)

EXAMPLE 149

N-(2-Tetrahydropyranyloxy)-2-[4-tert-butylaminocarbonyl-7-(5-(4-(5-oxazolyl)phenyl)-2-thienyl)-1,1-dioxoperhydro-1,4-thiazepin-7-yl]acetamide (86 mg)

NMR (CDCl$_3$, δ): 1.37 (9H, s), 1.50–1.83 (6H, br), 2.85–4.26 (12H, m), 4–0.60 (1H, br s), 4.65–4.86 (1H, m), 7.23–7.29 (2H, br), 7.46 (1H, s), 7.58–7.64 (4H, m), 7.94 (1H, s), 9.16–9.27 (1H, m) MASS (ESI−): 629.4 (M–H)

EXAMPLE 150

N-(2-Tetrahydropyranyloxy)-2-[7-(5-(4-(5-oxazolyl)-phenyl)-2-thienyl)-4-(2-(2-thienyl)ethylaminocarbonyl)-1,1-dioxoperhydro-1,4-thiazepin-7-yl]acetamide (100 mg)

NMR (CDCl$_3$, δ): 1.48–1.83 (6H, m), 2.80–2.90 (2H, m), 3.01–3.07 (2H, m), 3.15–3.92 (10H, m), 4.00–4.22 (2H, m), 4.59 (½H, br), 4.85 (½H, br), 5.00 (1H, dd, J=6.0, 6.0 Hz), 6.84 (1H, br), 6.93–6.96 (1H, m), 7.15 (1H, d, J=6.0 Hz), 7.21–7.28 (2H, m), 7.38 (1H, s), 7.57–7.65 (4H, m), 7.94 (1H, s), 8.94–8.97 (1H, m) MASS (ESI−): 683.5 (M–H)

EXAMPLE 151

N-(2-Tetrahydropyranyloxy)-2-[7-(5-bromo-2-thienyl)-4-(((R)-1-phenylethylamino)carbonyl)-1,1-dioxoperhydro-1,4-thiazepin-7-yl]acetamide (400 mg)

NMR (CDCl$_3$, δ): 1.41–1.87 (9H, m), 2.65–4.20 (12H, m), 4.55–4.86 (1H, m), 4.95–5.10 (1H, m), 6.93–7.03 (2H, m), 7.12 (1H, d, J=7.0 Hz), 7.22–7.35 (5H, m), 8.91–9.03 (1H, m) MASS (ESI−): 614.1 (M–H)

EXAMPLE 152

N-(2-Tetrahydropyranyloxy)-2-[4-cyclohexylaminocarbonyl-7-(5-(4-(5-oxazolyl)phenyl)-2-thienyl)-1,1-dioxoperhydro-1,4-thiazepin-7-yl]acetamide (110 mg)

NMR (CDCl$_3$, δ): 1.05–1.97 (16H, m), 2.83–3.82 (12H, m), 4.04–4.67 (1H, m), 4.60–4.84 (1H, m), 7.20–7.30 (1H, m), 7.37 (1H, s), 7.58–7.65 (4H, m), 7.90 (1H, s), 8.84–8.87 (1H, m) MASS (ESI−): 655.3 (M–H)

EXAMPLE 153

N-(2-Tetrahydropyranyloxy)-2-[4-benzylaminocarbonyl-7-(5-(4-(5-oxazolyl)phenyl)-2-thienyl)-1,1-dioxoperhydro-1,4-thiazepin-7-yl]acetamide (100 mg)

NMR (DMSO-$d_6$, δ): 1.44–1.62 (6H, m), 2.72–3.18 (4H, m), 3.22–3.93 (8H, m), 4.27–4.30 (2H, m), 4.51 (½H, br), 4.77 (½H, br), 7.15–7.34 (6H, m), 7.52–7.57 (1H, m), 7.74–7.80 (5H, m), 8.49 (1H, s) MASS (ESI−): 663.3 (M–H)

EXAMPLE 154

N-(2-Tetrahydropyranyloxy)-2-[(S)-7-(5-bromo-2-thienyl)-1,1-dioxoperhydro-4-isopropylcarbamoyl-1,4-thiazepin-7-yl]acetamide (1.5 g)

NMR (DMSO-d$_6$, δ): 1.04 (3H, d, J=6 Hz), 1.06 (3H, d, J=6 Hz), 1.38–1.76 (6H, m), 2.54–3.15 (4H, m), 3.38–3.93 (9H, m), 4.48, 4.74 (1H, br), 6.20 (1H, t, J=10 Hz), 7.00, 7.02 (1H, d, J=3 Hz), 7.18, 7.21 (1H, d, J=3 Hz) MASS (ESI-): 550, 552 (MH)

EXAMPLE 155

N-(2-Tetrahydropyranyloxy)-2-[4-cyclohexylcarbamoyl-1,1-dioxoperhydro-7-(4-phenoxyphenyl)-1,4-thiazepin-7-yl]acetamide (87 mg)

NMR (CDCl$_3$, δ): 1.02–1.18 (3H, m), 1.24–1.43 (2H, m), 1.48–1.77 (9H, m), 1.88–2.00 (2H, m), 2.73–2.90 (2H, m), 3.19–4.10 (10H, m), 4.16–4.29 (1H, m), 4.50–4.58 (1H, m), 6.93–7.00 (2H, m), 7.05 (2H, d, J=8 Hz), 7.15 (1H, t, J=8 Hz), 7.32–7.38 (2H, m), 7.45–7.53 (2H, m), 9.01 (1H, d, J=8 Hz) MASS (m/z): 600 (M$^+$+H), 115 (bp)

EXAMPLE 156

N-(2-Tetrahydropyranyloxy)-2-[4-tert-butylcarbamoyl-1,1-dioxoperhydro-7-(4-phenoxyphenyl)-1,4-thiazepin-7-yl]acetamide (83 mg)

NMR (CDCl$_3$, δ): 1.36 (9H, s), 1.52–1.62 (4H, m), 1.68–1.75 (2H, m), 2.75–2.92 (2H, m), 3.20–3.58 (6H, m), 3.72–4.23 (4H, m), 4.50–4.59 (1H, m), 6.96–7.07 (4H, m), 7.15 (1, t, J=8 Hz), 7.33–7.53 (4H, m), 8.55–8.70 (1H, m) MASS (ESI-): 572 (M$^+$-H), 169 (bp)

EXAMPLE 157

N-(2-Tetrahydropyranyloxy)-2-[1,1-dioxoperhydro-7-(4-phenoxyphenyl)-4-propylcarbamoyl-1,4-thiazepin-7-yl]acetamide (82 mg)

NMR (CDCl$_3$, δ): 0.91 (3H, t, J=7 Hz), 1.47–1.59 (6H, m), 1.68–1.75 (2H, m), 2.77–2.93 (2H, m), 3.10–3.60 (8H, m), 3.72–4.10 (2H, m), 4.22–4.35 (1H, m), 4.74–4.86 (2H, m), 6.95–7.01 (2H, m), 7.05 (2H, d, J=8 Hz), 7.15 (1H, t, J=8 Hz), 7.33–7.40 (2H, m), 7.45–7.53 (2H, m), 8.92 (1H, d, J=8 Hz) MASS (m/z): 558 (M$^+$-H), 123 (bp)

EXAMPLE 158

N-(2-Tetrahydropyranyloxy)-2-[4-tert-butylcarbamoyl-7-[4-(4-methylphenoxy)phenyl]-1,1-dioxoperhydro-1,4-thiazepin-7-yl]acetamide (69 mg)

NMR (CDCl$_3$, δ): 1.36 (9H, s), 1.50–1.60 (4H, m), 1.68–1.75 (2H, m), 2.35 (3H, s), 2.71–2.98 (2H, m), 3.19–3.58 (6H, m), 3.70–4.22 (4H, m), 4.49–4.57 (1H, m), 6.95 (4H, d, J=8 Hz), 7.16 (2H, d, J=8 Hz), 7.44–7.52 (2H, d, J=8 Hz), 8.49–8.65 (1H, m) MASS (m/z): 586 (M$^+$-H), 91 (bp)

EXAMPLE 159

N-(2-Tetrahydropyranyloxy)-2-[4-tert-butylcarbamoyl-7-[4-(4-chlorophenoxy)phenyl]-1,1-dioxoperhydro-1,4-thiazepin-7-yl]acetamide (83 mg)

NMR (CDCl$_3$, δ): 1.36 (9H, s), 1.53–1.60 (4H, m), 1.68–1.80 (2H, m), 2.72–2.88 (2H, m), 3.19–3.59 (6H, m), 3.75–4.22 (4H, m), 4.47–4.59 (1H, m), 6.99 (4H, d, J=8 Hz), 7.32 (2H, d, J=8 Hz), 7.52 (2H, d, J=8 Hz), 8.60–8.74 (1H, m) MASS (m/z): 572 (M$^+$-H), 169 (bp)

EXAMPLE 160

N-(2-Tetrahydropyranyloxy)-2-[7-[4-(4-chlorophenoxy)phenyl]-4-cyclohexylcarbamoyl-1,1-dioxoperhydro-1,4-thiazepin-7-yl]acetamide (87 mg)

NMR (CDCl$_3$, δ): 1.05–1.20 (3H, m), 1.28–1.40 (2H, m), 1.48–1.77 (9H, m), 1.88–2.00 (2H, m), 2.74–2.90 (2H, m), 3.19–4.05 (10H, m), 4.15–4.28 (1H, m), 4.49–4.59 (1H, m), 6.98 (4H, d, J=8 Hz), 7.33 (2H, d, J=8 Hz), 7.51 (2H, d, J=8H]z), 8.069 (1H, d, J=8 Hz) MASS (m/z) 632 (M$^+$-H), 91 (bp)

EXAMPLE 161

N-(2-Tetrahydropyranyloxy)-2-[(S)-7-(5-bromo-2-thienyl)-4-tert-butylcarbamoyl-1,1-dioxoperhydro-1,4-thiazepin-7-yl]acetamide (1.26 g)

NMR (CDCl$_3$, δ): 1.35, 1.37 (9H, s), 1.56–1.83 (6H, m), 2.75–2.86 (2H, m), 3.02–3.18 (2H, m), 3.30–3.62 (5H, m), 3.30–4.10 (4H, m), 4.56, 4.76 (1H, br), 7.00–7.05 (2H, m) MASS (ESI-): 564 (M-H)

The following compounds were obtained in a similar manner to that of Example 33.

EXAMPLE 162

N-(2-Tetrahydropyranyloxy)-2-[7-(5-bromo-2-thienyl)-4-(2-methylbenzoyl)-1,1-dioxoperhydro-1,4-thiazepin-7-yl]acetamide (342 mg)

NMR (CDCl$_3$, δ): 1.45–1.90 (6H, br), 2.18–2.35 (3H, br), 2.65–3.95 (12H, br), 4.45, 4.60, 4.76, 4.87 (1H, br), 6.88–7.70 (6H, br), 8.35–8.50 (1H, m) MASS (m/z): 583, 585 (M-H)

EXAMPLE 163

N-(2-Tetrahydropyranyloxy)-2-[7-(5-bromo-2-thienyl)-4-(4-pyridinecarbonyl)-1,1-dioxoperhydro-1,4-thiazepin-7-yl]acetamide (220 mg)

NMR (CDCl$_3$, δ): 1.50–1.90 (6H, br), 2.70–3.28 (4H, br), 3.38–3.96 (7H, br), 4.20–4.90 (2H, br), 6.88–7.12 (2H, br), 7.20–7.35 (2H, br), 8.22, 8.34 (1H, br), 8.65–8.78 (2H, br) MASS (m/z): 570, 572 (M-H)

EXAMPLE 164

N-(2-Tetrahydropyranyloxy)-2-[7-(5-bromo-2-thienyl)-4-(3-(4-pyridyl)acryloyl)-1,1-dioxoperhydro-1,4-thiazepin-7-yl]acetamide (246 mg)

NMR (CDCl$_3$, δ): 1.45–1.86 (6H, br), 2.60–3.95 (11H, br), 4.25–4.90 (2H, br), 6.86–7.14 (3H, br), 7.32–7.45 (2H, br), 7.53–7.69 (1H, br), 8.60–8.66 (2H, br), 8.76, 8.86 (1H, br) MASS (m/z): 596, 598 (M-H)

EXAMPLE 165

N-(2-Tetrahydropyranyloxy)-2-[7-(5-bromo-2-thienyl)-4-(2-pyridylacetyl)-1,1-dioxoperhydro-1,4-thiazepin-7-yl]acetamide (260 mg)

NMR (CDCl$_3$, δ): 1.40–1.92 (6H, br), 2.55–4.20 (12H, br), 4.40–4.55 (2H, br), 4.73, 5.03 (1H, br), 6.90–7.07 (3H, br), 7.15–7.43 (2H, br), 7.60–7.82 (1H, m), 8.40–8.60 (1H, br) MASS (m/z): 584, 586 (M-H)

EXAMPLE 166

N-(2-Tetrahydropyranyloxy)-2-[7-(5-bromo-2-thienyl)-4-(2-(propyloxy)benzoyl)-1,1-dioxoperhydro-1,4-thiazepin-7-yl]acetamide (275 mg)

NMR (CDCl$_3$, δ): 0.95–1.08 (3H, br), 1.50–1.93 (8H, br), 2.70–4.30 (14H, br), 4.50–5.00 (1H, br), 6.83–7.08 (4H, br), 7.20–7.44 (2H, br), 8.30–8.42 (1H, br) MASS (m/z): 627, 629 (M-H)

EXAMPLE 167

N-(2-Tetrahydropyranyloxy)-2-[7-(5-(4-chlorophenyl)-2-thienyl)-4-(2-pyridinecarbonyl)-1,1-dioxoperhydro-1,4-thiazepin-7-yl]acetamide (138 mg)

NMR (CDCl₃, δ): 1.43–1.86 (6H, br), 2.82–4.35 (12H, br), 4.62, 4.88 (1H, br), 7.12, 7.18 (2H, br), 7.26–7.43 (3H, br), 7.43–7.54 (2H, br), 7.62, 7.75–7.86 (2H, br), 8.29–8.45, 8.55–8.68 (2H, br) MASS (m/z): 602 (M–H)

EXAMPLE 168

N-(2-Tetrahydropyranyloxy)-2-[7-(5-(4-chlorophenyl)-2-thienyl)-4-(2-pyrazinecarbonyl)-1,1-dioxoperhydro-1,4-thiazepin-7-yl]acetamide (117 mg)

NMR (CDCl₃, δ): 1.40–1.90 (6H, br), 2.80–4.30 (12H, br), 4.50–4.65, 4.76–4.90 (1H, br), 7.07–7.23 (2H, br), 7.26–7.40 (2H, br), 7.40–7.55 (2H, br), 8.25–8.75 (3H, br), 894, 9.07 (1H, br) MASS (m/z): 603 (M–H)

EXAMPLE 169

N-(2-Tetrahydropyranyloxy)-2-[4-(2-chlorobenzoyl)-7-(5-(4-chlorophenyl)-2-thienyl)-1,1-dioxoperhydro-1,4-thiazepin-7-yl]acetamide (116 mg)

NMR (CDCl₃, δ): 1.40–1.90 (6H, br), 2.75–4.00 (12H, br), 4.55, 4.70–4.90 (1H, br), 7.10–7.58 (10H, br), 8.20, 8.38 (1H, br) MASS (m/z): 635 (M–H)

EXAMPLE 170

N-(2-Tetrahydropyranyloxy)-2-[7-(5-(4-chlorophenyl)-2-thienyl)-4-((S)-2-hydroxy-2-phenylacetyl)-1,1-dioxoperhydro-1,4-thiazepin-7-yl]acetamide (108 mg)

NMR (CDCl₃, δ): 1.42–1.90 (6H, br), 2.50–3.80 (12H, br), 4.40–4.97., 5.10, 5.26, 5.38–5.52 (2H, br), 7.10–7.56 (11H, br), 8.20, 8.30, 8.55, 8.87 (1H, br) MASS (m/z): 631 (M–H)

EXAMPLE 171

N-(2-Tetrahydropyranyloxy)-2-[4-((R)-2-t-butoxycarbonylamino-2-phenylacetyl)-7-(5-(4-chlorophenyl)-2-thienyl)-1,1-dioxoperhydro-1,4-thiazepin-7-yl]acetamide (68.5 mg)

NMR (CDCl₃, δ): 1.35–1.89 (6H, br), 1.38, 1.43 (9H, s), 2.73–4.20 (12H, br), 4.39–4.63, 4.72, 4.78, 4.91 (1H, br), 5.30–5.47, 5.53–5.66, 5.72–5.90 (1H, br), 7.10–7.54 (1H, m), 8.20, 8.63, 8.72 (1H, br) MASS (m/z): 730 (M–H)

EXAMPLE 172

N-(2-Tetrahydropyranyloxy)-2-[7-(5-(4-chlorophenyl)-2-thienyl)-4-(2-ethoxybenzoyl)-1,1-dioxoperhydro-1,4-thiazepin-7-yl]acetamide (106 mg)

NMR (CDCl₃, δ): 1.35–1.97 (9H, br), 2.70–4.22 (14H, br), 4.43–5.03 (1H, br), 6.83–7.15 (3H, br), 7.15–7.26 (1H, br), 7.26–7.40 (4H, br), 7.42–7.57 (2H, m), 8.36, 8.44–8.60, 8.72, 8.93 (1H, br) MASS (m/z) 645 (M–H)

EXAMPLE 173

N-(2-Tetrahydropyranyloxy)-2-[(S)-4-(1-t-butoxycarbonyl-4-piperidinecarbonyl)-7-(5-(4-chlorophenyl)-2-thienyl)-1,1-dioxoperhydro-1,4-thiazepin-7-yl]acetamide (125 mg)

NMR (CDCl₃, δ): 1.46 (9H, s), 1.40–2.00 (10H, br), 2.48–2.95 (5H, br), 3.00–3.22 (1H, br), 3.22–3.97 (7H, br), 4.02–4.36 (4H, br), 4.55, 4.85 (1H, br), 7.18–7.26 (2H, m), 7.35 (2H, d, J=8 Hz), 7.46–7.55 (2H, m), 8.22, 8.39, 8.46, 8.63 (1H, br) MASS (m/z): 708 (M–H)

EXAMPLE 174

N-(2-Tetrahydropyranyloxy)-2-[(S)-4-(1-acetyl-4-piperidinecarbonyl)-7-(5-(4-chlorophenyl)-2-thienyl)-1,1-dioxoperhydro-1,4-thiazepin-7-yl]acetamide (65.3 mg)

NMR (CDCl₃, δ): 1.43–2.10 (10H, br), 2.11 (3H, s), 2.52–3.98 (14H, br), 4.00–4.45 (2H, br), 4.49–4.72, 4.85 (2H, br), 7.16–7.28 (2H, br), 7.34 (2H, d, J=8 Hz), 7.48 (2H, br), 8.82, 8.97, 9.34 (1H, br) MASS (m/z): 650 (M–H)

EXAMPLE 175

N-(2-Tetrahydropyranyloxy)-2-[(S)-7-(5-(4-chlorophenyl)-2-thienyl)-4-isobutylcarbonyl-1,1-dioxoperhydro-1,4-thiazepin-7-yl]acetamide (87.0 mg)

NMR (CDCl₃, δ): 0.95–1.06 (6H, br), 1.45–1.90 (6H, br), 2.06–2.38 (3H, br), 2.55–3.95 (1H, br), 4.16–4.40 (1H, br), 4.55, 4.84 (1H, br), 7.15–7.25 (2H, br), 7.34 (2H, d, J=8 Hz), 7.45–7.54 (2H, m), 8.26, 8.38, 8.48, 8.60 (1H, br) MASS (m/z): 581 (M–H)

EXAMPLE 176

N-(2-Tetrahydropyranyloxy)-2-[(S)-7-(5-(4-chlorophenyl)-2-thienyl)-4-methoxyacetyl-1,1-dioxoperhydro-1,4-thiazepin-7-yl]acetamide (85.0 mg)

NMR (CDCl₃, δ): 1.43–1.94 (6H, br), 2.60–3.97 (1H, br), 3.45 (3H, s), 4.03–4.46 (3H, br), 4.59, 4.88 (1H, br), 7.22 (2H, s), 7.34 (2H, d, J=8 Hz), 7.46–7.54 (2H, m), 8.44, 8.55, 8.74, 8.83 (1H, br)

EXAMPLE 177

N-(2-Tetrahydropyranyloxy)-2-[(S)-7-(5-(4-chlorophenyl)-2-thienyl)-4-cyclopropylacetyl-1,1-dioxoperhydro-1,4-thiazepin-7-yl]acetamide (105 mg)

NMR (CDCl₃, δ): 0.04–0.26 (2H, br), 0.44–0.65 (2H, br), 1.00–1.16 (1H, br), 1.35–1.95 (6H, br), 2.10–2.45 (2H, br), 2.55–3.93 (1H, br), 4.14–4.40 (1H, br), 4.55, 4.84 (1H, br), 7.15–7.26 (2H, m), 7.33 (2H, m), 7.40–7.58 (2H, br), 8.68, 8.82, 9.18, 9.28 (1H, br) MASS (m/z): 579 (M–H)

EXAMPLE 178

N-(2-Tetrahydropyranyloxy)-2-[(S)-7-(5-(4-chlorophenyl)-2-thienyl)-4-(2-pyridylacetyl)-1,1-dioxoperhydro-1,4-thiazepin-7-yl]acetamide (110 mg)

NMR (CDCl₃, δ): 1.36–1.90 (6H, br), 2.60–2.78, 2.88–3.16 (3H, br), 3.16–3.57 (5H, br), 3.65–4.10 (3H, br), 4.10–4.33, 4.36–4.54 (3H, br), 4.71, 5.00 (1H, br), 7.07–7.26 (4H, m), 7.26–7.40 (2H, m), 7.43–7.53 (2H, m), 7.56–7.67, 7.68–7.79 (1H, m), 8.39, 8.53 (2H, br) MASS (m/z): 616 (M–H)

EXAMPLE 179

N-(2-Tetrahydropyranyloxy)-2-[(S)-7-(5-(4-chlorophenyl)-2-thienyl)-4-((R)-2-methoxy-2-phenylacetyl)-1,1-dioxoperhydro-1,4-thiazepin-7-yl] acetamide (110 mg)

NMR (CDCl₃, δ): 1.44–2.18 (6H, br), 2.65–3.97 (11H, br), 3.38, 3.44, 3.49 (3H, s), 4.33–4.47 (1H, br), 4.58, 4.89 (1H, br), 5.03, 5.14 (1H, s), 7.16–7.23 (2H, br), 7.23–7.55 (9H, br), 8.63, 8.77 (1H, br) MASS (m/z): 645 (M–H)

EXAMPLE 180

N-(2-Tetrahydropyranyloxy)-2-[7-(5-bromo-2-thienyl)-4-(3-chlorobenzoyl)-1,1-dioxoperhydro-1,4-thiazepin-7-yl] acetamide (345 mg)

NMR (CDCl₃, δ): 1.47–1.81 (6H, m), 2.70–4.33 (12H, m), 4.43–4.85 (1H, m), 6.83–7.07 (2H, m), 7.18–7.45 (4H, m), 8.26–8.40 (1H, m) MASS (ESI-): 604.9 (M–H)

EXAMPLE 181

N-(2-Tetrahydropyranyloxy)-2-[7-(5-bromo-2-thienyl)-4-((2S)-2-tert-butoxycarbonylamino-2-phenylacetyl)-1,1-dioxoperhydro-1,4-thiazepin-7-yl]acetamide (415 mg)

NMR (CDCl₃, δ): 1.41 (9H, s), 1.57–1.80 (6H, m), 2.64–4.50 (13H, m), 4.88–5.82 (1H, m), 6.90–7.02 (2H, m), 7.31–7.38 (6H, m) MASS (ESI-): 700.1 (M-H)

EXAMPLE 182

N-(2-Tetrahydropyranyloxy)-2-[4-(1-isoquinolinecarbonyl)-7-(5-(4-(5-oxazolyl)phenyl)-2-thienyl)-1,1-dioxoperhydro-1,4-thiazepin-7-yl]acetamide (95 mg)

NMR (CDCl₃, δ): 1.44–1.94 (6H, br), 2.75–4.90 (13H, m), 7.20–7.38 (3H, m), 7.55–7.75 (7H, m), 7.80–8.16 (3H, m), 8.36–8.52 (1H, m) MASS (ESI-): 685.3 (M-H)

EXAMPLE 183

N-(2-Tetrahydropyranyloxy)-2-[4-(2-tert-butoxycarbonyl-aminoacetyl)-7-(5-(4-(5-oxazolyl)phenyl)-2-thienyl)-1,1-dioxoperhydro-1,4-thiazepin-7-yl]acetamide (110 mg)

NMR (CDCl₃, δ): 1.44–1.47 (9H, br), 1.48–1.79 (6H, m), 2.84–5.47 (15H, m), 7.23–7.31 (2H, m), 7.36–7.40 (1H, m), 7.59–7.68 (4H, m), 7.94 (1H, s), 8.38–8.47 (1H, m), 9.21–9.41 (1H, m) MASS (ESI-): 687.4 (M-H)

EXAMPLE 184

N-(2-Tetrahydropyranyloxy)-2-[4-(2-acetylbenzoyl)-7-(5-bromo-2-thienyl)-1,1-dioxoperhydro-1,4-thiazepin-7-yl]acetamide (240 mg)

NMR (CDCl₃, δ): 1.45–1.74 (6H, br), 2.21 (3H, br), 2.68–5.35 (13H, m), 6.90–7.07 (2H, m), 7.29–8.00 (4H, m), 8.44–8.60 (1H, m) MASS (ESI-): 611.2 (M-H)

EXAMPLE 185

N-(2-Tetrahydropyranyloxy)-2-[4-((2R)-2-tert-butoxycarbonylamino-2-phenylacetyl)-7-(5-(4-(5-oxazolyl)phenyl)-2-thienyl)-1,1-dioxoperhydro-1,4-thiazepin-7-yl]acetamide (130 mg)

NMR (CDCl₃, δ): 1.37–1.50 (9H, m), 1.63–1.88 (6H, br), 2.74–5.85 (14H, m), 7.16–7.32 (2H, m), 7.35–7.42 (5H, m), 7.60–7.64 (5H, m), 7.94 (1H, br), 10.05–10.52 (1H, m) MASS (ESI-): 763.4 (M-H)

EXAMPLE 186

N-(2-Tetrahydropyranyloxy)-2-[4-(3-methylpyridin-2-ylcarbonyl)-7-(5-(4-(5-oxazolyl)phenyl)-2-thienyl)-1,1-dioxoperhydro-1,4-thiazepin-7-yl]acetamide (65 mg)

NMR (CDCl₃, δ): 1.44–1.74 (6H, br), 2.32–2.43 (3H, m), 2.82–4.50 (12H, m), 4.60–4.88 (1H, m), 7.20–7.29 (3H, m), 7.38 (1H, d, J=5.0 Hz), 7.54–7.63 (6H, m), 7.92 (1H, br s), 8.30–8.44 (1H, m) MASS (ESI-): 649.3 (M-H)

EXAMPLE 187

N-(2-Tetrahydropyranyloxy)-2-[7-(5-bromo-2-thienyl)-4-(2-trifluoromethylbenzoyl)-1,1-dioxoperhydro-1,4-thiazepin-7-yl]acetamide (340 mg)

NMR (CDCl₃, δ): 1.53 (2H, br), 1.73 (4H, br), 2.70–3.32 (6H, m), 3.43–3.62 (3H, m), 3.71–3.88 (2H, m), 4.42–4.62 (1H, m), 4.70–4.87 (1H, m), 6.95–7.06 (2H, m), 7.46–7.74 (4H, m), 7.81–7.90 (1H, m) MASS (ESI-): 639.0 (M-H)

EXAMPLE 188

N-(2-Tetrahydropyranyloxy)-7-(5-bromo-2-thienyl)-2-[4-(2,3-dimethoxybenzoyl)-1,1-dioxoperhydro-1,4-thiazepin-7-yl]acetamide (400 mg)

NMR (CDCl₃, δ): 1.50–1.80 (6H, m), 2.71–3.93 (11H, m), 3.87 (6H, s), 4.32–4.96 (2H, m), 6.48–6.70 (1H, m) 6.85–7.13 (3H, m), 7.42–7.67 (1H, m), 8.50–8.97 (1H, m) MASS (ESI-): 631.1 (M-H)

EXAMPLE 189

N-(2-Tetrahydropyranyloxy)-2-[7-(5-bromo-2-thienyl)-4-(2,4-dimethoxybenzoyl)-1,1-dioxoperhydro-1,4-thiazepin-7-yl]acetamide (340 mg)

NMR (CDCl₃, δ): 1.49 (1H, br), 1.74 (4H, br), 2.67–2.87 (2H, m), 2.94–3.18 (2H, m), 3.45–3.75 (6H, m), 3.79 (6H, s), 3.84–3.92 (1H, m), 4.45 (1H, br), 4.68 (½H, br), 4.87 (½H, br), 6.40–6.53 (2H, m), 6.88–7.02 (2H, m), 7.43–7.50 (1H, m) MASS (ESI-): 629.0 (M-H)

EXAMPLE 190

N-(2-Tetrahydropyranyloxy)-2-[7-(5-bromo-2-thienyl)-4-(3-phenylpropionyl)-1,1-dioxoperhydro-1,4-thiazepin-7-yl]acetamide (365 mg)

NMR (CDCl₃, δ): 1.48–1.82 (6H, m), 2.39–4.33 (16H, m), 4.50–4.94 (1H, m), 6.95–7.02 (2H, m), 7.17–7.32 (5H, m), 8.12–8.58 (1H, m) MASS (ESI-): 599.0 (M-H)

EXAMPLE 191

N-(2-Tetrahydropyranyloxy)-2-[7-(5-(4-(5-oxazolyl)phenyl)-2-thienyl)-4-propionyl-1,1-dioxoperhydro-1,4-thiazepin-7-yl]acetamide (60 mg)

NMR (CDCl₃, δ): 1.15 (3H, t, J=7.0 Hz), 1.45–1.72 (6H, br), 2.35–4.35 (1H, m), 4.56–4.85 (1H, m), 7.22–7.30 (2H, m), 7.39 (1H, br), 7.60–7.67 (4H, m), 7.94 (1H, s), 8.44–8.90 (1H, m) MASS (ESI-): 586.3 (M-H)

EXAMPLE 192

N-(2-Tetrahydropyranyloxy)-2-[4-cyclopropylcarbonyl-7-(5-(4-(5-oxazolyl)phenyl)-2-thienyl)-1,1-dioxoperhydro-1,4-thiazepin-7-yl]acetamide (105 mg)

NMR (CDCl₃, δ): 0.71–1.08 (4H, m), 1.50–1.90 (6H, m), 2.05–2.13 (1H, m), 2.81–4.26 (12H, m), 4.42–4.86 (1H, m), 7.22–7.31 (2H, m), 7.40 (1R, s), 7.60–7.67 (4H, m), 7.95 (1H, s), 8.53–8.69 (1H, m) MASS (ESI-): 598.3 (M-H)

EXAMPLE 193

N-(2-Tetrahydropyranyloxy)-2-[7-(5-bromo-2-thienyl)-4-(1-phenyl-1-cyclopropanecarbonyl)-1,1-dioxoperhydro-1,4-thiazepin-7-yl]acetamide (260 mg)

NMR (CDCl₃, δ): 1.45–1.75 (10H, m), 2.53–4.34 (12H, m), 4.48–4.85 (1H, m), 6.97–7.57 (7H, m), 7.85–8.58 (1H, m) MASS (ESI-): 611.1 (M-H)

EXAMPLE 194

N-(2-Tetrahydropyranyloxy)-2-[4-((2S)-2-hydroxy-3-phenylpropionyl)-7-(5-(4-(5-oxazolyl)phenyl)-2-thienyl)-1,1-dioxoperhydro-1,4-thiazepin-7-yl]acetamide (125 mg)

NMR (CDCl₃, δ): 1.47–1.75 (6H, m), 2.80–3.70 (14H, m), 4.33–4.63 (1H, m), 7.18–7.39 (8H, m), 7.59–7.65 (4H, m), 7.94 (1H, s) MASS (ESI-): 678.4 (M-H)

EXAMPLE 195

N-(2-Tetrahydropyranyloxy)-2-[4-(2-naphthylcarbonyl)-7-(5-(4-(5-oxazolyl)phenyl)-2-thienyl)-1,1-dioxoperhydro-1,4-thiazepin-7-yl]acetamide (125 mg)

NMR (CDCl₃, δ): 1.42–1.73 (6H, m), 2.82–4.32 (12H, m), 4.58–4.90 (1H, m), 7.10–7.85 (14H, m), 7.94 (1H, s), 8.42–8.54 (1H, m) MASS (ESI-): 684.3 (M-H)

EXAMPLE 196

N-(2-Tetrahydropyranyloxy)-2-[7-(5-(4-(5-oxazolyl)phenyl)-2-thienyl)-4-(2-phenylbenzoyl)-1,1-dioxoperhydro-1,4-thiazepin-7-yl]acetamide (165 mg)

NMR (CDCl$_3$, δ): 1.47–1.75 (6H, m), 2.70–3.80 (12H, m), 4.27–4.83 (1H, m), 7.13–7.52 (7H, m), 7.57–7.65 (5H, m), 7.92 (1H, s), 8.27–8.52 (1H, m) MASS (ESI-): 710.4 (M-H)

EXAMPLE 197

N-(2-Tetrahydropyranyloxy)-2-[4-cyclohexylcarbonyl-7-(5-(4-(5-oxazolyl)phenyl)-2-thienyl)-1,1-dioxoperhydro-1,4-thiazepin-7-yl]acetamide (90 mg)

NMR (CDCl$_3$, δ): 1.39–1.90 (16H, m), 2.14–4.25 (12H, m), 4.52–4.83 (1H, m), 7.17–7.30 (1H, m), 7.35–7.45 (1H, m), 7.50–7.67 (5H, m), 7.94 (1H, s), 8.42–8.59 (1H, m) MASS (ESI-): 639.4 (M-H)

EXAMPLE 198

N-(2-Tetrahydropyranyloxy)-2-[7-(5-bromo-2-thienyl)-4-(indol-2-ylcarbonyl)-1,1-dioxoperhydro-1,4-thiazepin-7-yl]acetamide (395 mg)

NMR (CDCl$_3$, δ): 1.43–1.69 (6H, m), 2.57–4.10 (12H, m), 4.33–5.00 (1H, m), 6.65–6.86 (3H, m), 7.12 (1H, dd, J=6.0, 6.0 Hz), 7.22–7.30 (1H, m), 7.36–7.42 (1H, m), 7.63–7.67 (1H, m), 9.20 (1H, br), 9.64 (1H, br) MASS (ESI-): 609.7 (M-H)

EXAMPLE 199

N-(2-Tetrahydropyranyloxy)-2-[4-(4-methylpyrimidin-5-ylcarbonyl)-7-(5-(4-(5-oxazolyl)phenyl)-2-thienyl)-1,1-dioxoperhydro-1,4-thiazepin-7-yl]acetamide (100 mg)

NMR (CDCl$_3$, δ): 1.47–1.73 (6H, m), 2.53–2.57 (13H, br), 2.77–3.82 (12H, m), 4.41–4.85 (1H, m), 7.21–7.30 (3H, m), 7.39 (1H, s), 7.60–7.68 (5H, m), 7.95 (1H, s), 9.10–9.14 (1H, m) MASS (ESI-): 650.2 (M-H)

EXAMPLE 200

N-(2-Tetrahydropyranyloxy)-2-[4-(benzo[b]thiophen-2-ylcarbonyl)-7-(5-(4-(5-oxazolyl)phenyl)-2-thienyl)-1,1-dioxoperhydro-1,4-thiazepin-7-yl]acetamide (95 mg)

NMR (CDCl$_3$, δ): 1.39–1.73 (6H, br), 2.81–5.10 (13H, m), 7.16–7.30 (1H, m), 7.37–7.44 (3H, m), 7.50–7.66 (6H, m), 7.77–7.85 (2H, m), 7.95 (1H, s), 8.50–8.63 (1H, m) MASS (ESI-): 690.3 (M-H)

EXAMPLE 201

N-(2-Tetrahydropyranyloxy)-2-[7-(5-bromo-2-thienyl)-4-(2,5-dimethoxybenzoyl)-1,1-dioxoperhydro-1,4-thiazepin-7-yl]acetamide (348 mg)

NMR (CDCl$_3$, δ): 1.45–1.97 (6H, br), 2.65–3.98 (12H, br), 3.77, 3.79 (6H, s), 4.37–4.63, 4.67–4.98 (1H, br), 6.80–7.35 (5H, br), 8.40, 8.53, 8.60–8.80, 8.86 (1H, br) MASS (m/z): 629, 631 (M-H)

EXAMPLE 202

N-(2-Tetrahydropyranyloxy)-2-[7-(5-bromo-2-thienyl)-4-(2,3,4-trimethoxybenzoyl)-1,1-dioxoperhydro-1,4-thiazepin-7-yl]acetamide (393 mg)

NMR (CDCl$_3$, δ): 1.45–1.97 (6H, br), 2.70–3.98 (21H, br), 4.20–5.00 (1H, br), 6.55–7.18 (4H, br), 8.44, 8.63, 8.76–8.94 (1H, br) MASS (m/z): 659, 661 (M-H)

EXAMPLE 203

N-(2-Tetrahydropyranyloxy)-2-[7-(5-bromo-2-thienyl)-4-((S)-2-hydroxy-2-phenylacetyl)-1,1-dioxoperhydro-1,4-thiazepin-7-yl]acetamide (270 mg)

NMR (CDCl$_3$, δ): 1.46–1.90 (6H, br), 2.63–4.00 (12H, br), 4.22–4.38, 4.40–4.96, 5.08, 5.19–5.30, 5.35–5.47 (2H, m), 6.85–7.05 (2H, br), 7.17–7.46 (5H, br), 8.03, 8.08, 8.23, 8.38, 8.69 (1H, br) MASS (m/z): 599, 601 (M-H)

EXAMPLE 204

N-(2-Tetrahydropyranyloxy)-2-[7-(5-bromo-2-thienyl)-4-(2-ethoxybenzoyl)-1,1-dioxoperhydro-1,4-thiazepin-7-yl]acetamide (240 mg)

NMR (CDCl$_3$, δ): 1.30–1.90 (9H, br), 2.70–4.20 (14H, br), 4.40–4.50 (1H, br), 6.75–7.08 (4H, br), 7.28–7.45 (2H, br), 8.30–8.70, 8.93 (1H, br) MASS (m/z): 613, 615 (M-H)

EXAMPLE 205

N-(2-Tetrahydropyranyloxy)-2-[7-(5-bromo-2-thienyl)-4-(2-trifluoromethoxybenzoyl)-1,1-dioxoperhydro-1,4-thiazepin-7-yl]acetamide (242 mg)

NMR (CDCl$_3$, δ): 1.45–1.90 (6H, br), 2.70–4.05 (12H, br), 4.40–4.90, 5.02, 5.13 (1H, br), 6.90–7.10 (2H, br), 7.23–7.66 (4H, br), 8.20, 8.30–8.43 (1H, br) MASS (m/z): 653, 655 (M-H)

EXAMPLE 206

N-(2-Tetrahydropyranyloxy)-2-[7-(5-bromo-2-thienyl)-4-(2,4-dichlorobenzoyl)-1,1-dioxoperhydro-1,4-thiazepin-7-yl]acetamide (374 mg)

NMR (CDCl$_3$, δ): 1.48–1.90 (6H, br), 2.70–4.02 (12H, br), 4.45–4.92 (1H, br), 6.86–7.17 (2H, br), 7.26–7.48 (3H, br), 8.28, 8.38–8.56 (1H, br) MASS (m/z): 637, 639 (M-H)

EXAMPLE 207

N-(2-Tetrahydropyranyloxy)-2-[7-(5-bromo-2-thienyl)-4-(4-chloro-2-methoxybenzoyl)-1,1-dioxoperhydro-1,4-thiazepin-7-yl]acetamide (170 mg)

NMR (CDCl$_3$, δ): 1.48–1.97 (6H, br), 2.60–4.00 (12H, br), 3.83, 3.84 (3H, s), 6.76–7.17 (5H, br), 7.25–7.40 (1H, br), 8.30, 8.40–8.54 (1H, br) MASS (m/z): 633, 635 (M-H)

EXAMPLE 208

N-(2-Tetrahydropyranyloxy)-2-[7-(5-bromo-2-thienyl)-4-((R)-2-methoxy-2-phenylacetyl]-1,1-dioxoperhydro-1,4-thiazepin-7-yl]acetamide (280 mg)

NMR (CDCl$_3$, δ): 1.50–1.90 (6H, br), 2.60–4.20 (13H, br), 3.39, 3.48 (3H, s), 4.30–4.60, 4.85, 4.97–5.05, 5.12 (1H, br), 6.85–7.05 (2H, br), 7.26–7.45 (5H, br), 8.20–8.30, 8.40 (1H, br) MASS (m/z): 613, 615 (M-H)

EXAMPLE 209

N-(2-Tetrahydropyranyloxy)-2-[7-(5-bromo-2-thienyl)-4-cinnamoyl-1,1-dioxoperhydro-1,4-thiazepin-7-yl]acetamide (296 mg)

NMR (CDCl$_3$, δ): 1.40–1.90 (6H, br), 2.65–4.45 (12H, br), 4.50–4.70, 4.88, 5.02, 5.10 (1H, br), 6.85–7.06 (3H, br), 7.35–7.45 (3H, br), 7.46–7.60 (2H, br), 7.65–7.80 (1H, m), 8.55–8.68 (1H, br) MASS (m/z): 595, 597 (M-H)

EXAMPLE 210

N-(2-Tetrahydropyranyloxy)-2-[7-(5-(4-fluorophenyl)-2-thienyl)-4-((S)-2-hydroxy-2-phenylacetyl)-1,1-dioxoperhydro-1,4-thiazepin-7-yl]acetamide (113 mg)

NMR (CDCl₃, δ): 1.45–1.90 (6H, br), 2.65–3.92 (12H, br), 4.43–4.97, 5.10, 5.25–5.33, 5.40–5.50 (2H, br), 7.03–7.45 (9H, m), 7.47–7.60 (2H, m), 8.22, 8.27, 8.39, 8.57, 8.90 (1H, br) MASS (m/z): 615 (M–H)

EXAMPLE 211

N-(2-Tetrahydropyranyloxy)-2-[7-(5-(4-fluorophenyl)-2-thienyl)-4-(3-thiophenecarbonyl)-1,1-dioxoperhydro-1,4-thiazepin-7-yl]acetamide (87.6 mg)

NMR (CDCl₃, δ): 1.40–1.90 (6H, br), 2.70–4.04 (11H, br), 4.06–4.42 (1H, br), 4.44–4.96 (1H, br), 7.02–7.25 (5H, br), 7.28 (1H, br), 7.29–7.65 (3H, br), 8.30–8.58 (1H, br) MASS (m/z): 591 (M–H)

EXAMPLE 212

N-(2-Tetrahydropyranyloxy)-2-[4-((R)-2-t-butoxycarbonylamino-2-phenylacetyl)-7-(5-(4-fluorophenyl)-2-thienyl)-1,1-dioxoperhydro-1,4-thiazepin-7-yl]acetamide (111 mg)

NMR (CDCl₃, δ): 1.38, 1.39, 1.43 (9H, s), 1.40–1.95 (6H, br), 2.70–4.33 (12H, br), 4.40–4.60, 4.68, 4.77, 4.89 (1H, br), 5.25–5.47, 5.55–5.66, 5.74–5.90 (1H, br), 6.97–7.22 (5H, m), 7.27–7.45 (4H, br), 7.46–7.57 (2H, br), 8.18, 8.60, 8.68 (1H, br) MASS (m/z): 714 (M–H)

EXAMPLE 213

N-(2-Tetrahydropyranyloxy)-2-[7-(5-(5-chloro-2-thienyl)-2-thienyl)-4-(2-pyridinecarbonyl)-1,1-dioxoperhydro-1,4-thiazepin-7-yl]acetamide (79.3 mg)

NMR (CDCl₃, δ): 1.45–1.90 (6H, br), 2.80–4.00 (11H, br), 4.00–4.42 (1H, br), 4.70, 4.80, 4.88 (1H, br), 6.82 (1H, m), 6.86–7.16 (2H, br), 7.17 (1H, br), 7.27–7.45 (1H, br), 7.63, 7.75–7.89 (2H, br), 8.32–8.52, 8.56–8.65 (2H, br) MASS (m/z): 608 (M–H)

EXAMPLE 214

N-(2-Tetrahydropyranyloxy)-2-[7-(5-(5-chloro-2-thienyl)-2-thienyl)-4-(3-thiophenecarbonyl)-1,1-dioxoperhydro-1,4-thiazepin-7-yl]acetamide (85.1 mg)

NMR (CDCl₃, δ): 1.44–1.90 (6H, br), 2.66–4.02 (1H, br), 4.06–4.35 (1H, br), 4.45–4.68, 4.69–4.80, 4.80–4.90 (1H, br), 6.83 (1H, d, J=3 Hz), 6.90–7.26 (4H, br), 7.26–7.64 (2H, br), 8.38, 8.52 (1H, br) MASS (m/z): 613 (M–H)

EXAMPLE 215

N-(2-Tetrahydropyranyloxy)-2-[7-(5-(5-chloro-2-thienyl)-2-thienyl)-4-(2-pyrazinecarbonyl)-1,1-dioxoperhydro-1,4-thiazepin-7-yl]acetamide (80.0 mg)

NMR (CDCl₃, δ): 1.46–1.88 (6H, br), 2.78–3.40 (11H, br), 4.06–4.42 (1H, br), 4.53–4.65, 4.78–4.91 (1H, br), 6.83 (1H, m), 6.86–7.02 (2H, m), 7.08–7.18 (1H, m), 8.24–8.48, 8.57, 8.62–8.69 (3H, br), 8.92, 9.06 (1H, br) MASS (m/z): 609 (M–H)

EXAMPLE 216

N-(2-Tetrahydropyranyloxy)-2-[(S)-4-((S)-2-(N-tert-butoxycarbonylamino)-3-methylbutyryl)-7-(5-(4-ethylphenyl)-2-thienyl)-1,1-dioxoperhydro-1,4-thiazepin-7-yl]acetamide (68 mg)

NMR (DMSO-d₆, δ): 0.82–1.00 (6H, m), 1.25 (3H, t, J=8 Hz), 1.42, 1.45 (9H, s), 1.46–1.78 (6H, m), 1.88–2.08 (1H, m), 2.66 (2H, q, J=8 Hz), 2.73–4.86 (13H, m), 5.13–5.32 (1H, m), 7.12–7.23 (4H, m), 7.49 (2H, d, J=8 Hz), 8.26–8.73 (1H, m) MASS (ESI–): 690 (M–H)

EXAMPLE 217

N-(2-Tetrahydropyranyloxy)-2-[(S)-4-(3-(N-tert-butoxycarbonylamino) propionyl)-7-(5-(4-ethylphenyl)-2-thienyl)-1,1-dioxoperhydro-1,4-thiazepin-7-yl]acetamide (130 mg)

NMR (DMSO-d₆, δ): 1.26 (3H, t, J=8 Hz), 1.45 (9H, s), 1.46–1.84 (6H, m), 2.30–3.88 (17H, m), 4.10–4.36 (1H, m), 4.57, 4.86 (1H, s), 5.20–5.52 (1H, m), 7.15–7.30 (4H, m), 7.44–7.55 (2H, m) MASS (ESI–): 662 (M–H)

EXAMPLE 218

N-(2-Tetrahydropyranyloxy)-2-[1,1-dioxoperhydro-7-(4-phenoxyphenyl)-4-(2-pyrazinecarbonyl)-1,4-thiazepin-7-yl]acetamide (50 mg)

NMR (CDCl₃, δ): 1.50–1.62 (4H, m), 1.68–1.77 (2H, m), 2.75–3.00 (2H, m), 3.15–3.66 (6H, m), 3.75–3.87 (4H, m), 4.51–4.60 (1H, m), 6.92–6.99 (3H, m), 7.03–7.20 (3H, m), 7.30–7.39 (3H, m), 7.49–7.65 (3H, m), 8.68 (1H, d, J=2 Hz) MASS (m/z): 579 (M⁺–H), 169 (bp)

EXAMPLE 219

N-(2-Tetrahydropyranyloxy)-2-[4-(cyclopropyranecarbonyl)-1,1-dioxoperhydro-7-(4-phenoxyphenyl)-1,4-thiazepin-7-yl]acetamide (78 mg)

NMR (CDCl₃, δ): 0.78–1.00 (2H, m), 1.02–1.13 (1H, m), 1.24–1.43 (1H, m), 1.50–1.60 (4H, m), 1.69–1.78 (2H, m), 1.80–1.87 (1H, m), 2.75–2.99 (2H, m), 3.20–3.65 (6H, m), 3.77–3.90 (2H, m), 4.15–4.35 (2H, m), 4.46–4.58 (1H, m), 6.99 (2H, d, J=8 Hz), 7.05 (2H, d, J=8 Hz), 7.17 (1H, t, J=8 Hz), 7.34–7.40 (2H, m), 7.43–7.62 (2H, m), 8.58 (1H, s) MASS (m/z): 543 (M⁺–H), 85 (bp)

EXAMPLE 220

N-(2-Tetrahydropyranyloxy)-2-[1, 1-dioxoperhydro-7-(4-phenoxyphenyl)-4-(2-thiophenecarbonyl-1,4-thiazepin-7-yl]acetamide (92 mg)

NMR (CDCl₃, δ): 1.47–1.64 (4H, m), 1.67–1.75 (2H, m), 2.77–3.00 (2H, m), 3.15–3.84 (6H, m), 3.93–4.14 (4H, m), 4.22–4.42 (1H, m), 6.99 (2H, d, J=8 Hz), 7.03–7.09 (3H, m), 7.17 (1H, t, J=8 Hz), 7.33–7.40 (2H, m), 7.45–7.59 (4H, m), 8.33–8.48 (1H, m) MASS (m/z): 585 (M⁺–H), 115 (bp)

EXAMPLE 221

N-(2-Tetrahydropyranyloxy)-2-[4-((2S)-2-hydroxy-2-phenylacetyl)-1,1-dioxoperhydro-7-(4-phenoxyphenyl)-1,4-thiazepin-7-yl]acetamide (85 mg)

NMR (CDCl₃, δ): 1.47–1.62 (4H, m), 1.67–1.78 (2H, m), 2.60–2.82 (2H, m), 3.00–3.40 (4H, m), 3.48–3.95 (3H, m), 4.07–4.28 (1H, m), 4.34–4.95 (3H, m), 5.05–5.45 (1H, m), 6.92–7.07 (4H, m), 7.12–7.24 (1H, m), 7.30–7.47 (9H, m) MASS (ESI–): 607 (M⁺–H), 169 (bp)

EXAMPLE 222

N-(2-Tetrahydropyranyloxy)-2-[7-(4-phenoxyphenyl)-4-(3-thiophenecarbonyl)-1,1-dioxoperhydro-1,4-thiazepin-7-yl]acetamide (85 mg)

NMR (DMSO-d₆, δ): 1.35–1.65 (6H, m), 2.57–4.32 (12H, m), 4.48–4.98 (1H, m), 6.95 (2H, t, J=8 Hz), 7.07 (2H, t, J=8 Hz), 7.15–7.30 (2H, m), 7.35–7.65 (5H, m), 7.77–7.92 (1H, m) MASS (ESI–): 583 (M–H)

EXAMPLE 223

N-(2-Tetrahydropyranyloxy-2-[7-[4-(4-methylphenoxy)phenyl]-1,1-dioxoperhydro-4-(2-pyrazinecarbonyl)-1,4-thiazepin-7-yl]acetamide (76 mg)

NMR (CDCl₃, δ): 1.48–1.62 (4H, m), 1.67–1.76 (2H, m), 2.35 (3H, s), 2.73–3.02 (2H, m), 3.13–3.63 (6H, m), 3.74–3.90 (H, m), 4.12–4.22 (1H, m), 6.82–6.97 (4H, m), 7.14 (2H, t, J=8 Hz), 7.49 (1H, d, J=8 Hz), 7.59 (1H, d, J=8 Hz), 8.41–8.57 (1H, m), 8.68 (1H, s), 8.89–9.05 (1H, m) MASS (m/z): 595 (M⁺–H), 74 (bp)

EXAMPLE 224

N-(2-Tetrahydropyranyloxy-2-[4-cyclopropanecarbonyl-7-[4-(4-methylphenoxy)phenyl]-1,1-dioxoperhydro-1,4-thiazepin-7-yl]acetamide (81 mg)

NMR (CDCl₃, δ): 0.78–1.11 (4H, m), 1.47–1.65 (4H, m), 1.69–1.74 (2H, m), 1.78–1.89 (1H, m), 2.35 (3H, s), 2.75–2.97 (3H, m), 3.22–3.45 (4H, m), 3.50–3.60 (1H, m), 3.72–3.88 (2H, m), 4.10–4.40 (2H, m), 4.43–4.87 (2H, m), 6.94 (4H, d, J=8 Hz), 7.15 (2H, d, J=8 Hz), 7.40–7.60 (2H, m) MASS (m/z): 557 (M⁺+H), 115 (bp)

EXAMPLE 225

N-(2-Tetrahydropyranyloxy)-2-[7-[4-(4-methylphenoxy)phenyl-4-(2-thiophenecarbonyl)-1,1-dioxoperhydro-1,4-thiazepin-7-yl]acetamide (86 mg)

NMR (CDCl₃, δ): 1.47–1.63 (4H, m), 1.65–1.75 (2H, m), 2.35 (3H, s), 2.85–2.97 (2H, m), 3.10–3.43 (4H, m), 3.45–3.85 (4H, m), 3.95–4.15 (1H, m), 4.20–4.52 (1H, m), 4.60–4.75 (1H, m), 6.93 (4H, d, J=8 Hz), 7.04–7.08 (1H, m), 7.24 (2H, d, J=8 Hz), 7.40–7.59 (4H, m) MASS (m/z): 597 (M⁺–H), 145 (bp)

EXAMPLE 226

N-(2-Tetrahydropyranyloxy)-2-[7-[4-(4-methylphenoxy)phenyl]-4-(3-thiophenecarbonyl)-1,1-dioxoperhydro-1,4-thiazepin-7-yl]acetamide (82 mg)

NMR (CDCl₃, δ): 1.47–1.52 (4H, m), 1.65–1.75 (2H, m), 2.35 (3H, s), 2.70–2.97 (2H, m), 3.05–3.30 (2H, m), 3.35–3.65 (4H, m), 3.70–3.87 (4H, m), 4.04–4.15 (1H, m), 6.93 (4H, d, J=8 Hz), 7.17 (2H, d, J=8 Hz), 7.20–7.27 (1H, m), 7.33–7.67 (4H, m) MASS (m/z): 599 (M⁺–H), 115 (bp)

EXAMPLE 227

N-(2-Tetrahydropyranyloxy)-2-[4-[(2S)-2-hydroxy-2-phenylacetyl]-7-[4-(4-methylphenoxy)phenyl]-1,1-dioxoperhydro-1,4-thiazepin-7-yl]acetamide (81 mg)

NMR (CDCl₃, δ): 1.47–1.62 (4H, m), 1.67–1.80 (2H, m), 2.35 (3H, s), 2.60–2.85 (2H, m), 2.99–3.38 (4H, m), 3.48–3.95 (3H, m), 4.30–4.93 (4H, m), 5.05–5.22 (1H, m), 6.90–7.00 (4H, m), 7.12–7.18 (1H, m), 7.30–7.45 (8H, m) MASS (m/z): 621 (M⁺–H), 137 (bp)

EXAMPLE 228

N-(2-Tetrahydropyranyloxy)-2-[7-[4-(4-methylphenoxy)phenyl]-1,1-dioxoperhydro-4-(2-pyridinecarbonyl)-1,4-thiazepin-7-yl]acetamide (70 mg)

NMR (CDCl₃, δ): 1.47–1.62 (4H, m), 1.66–1.77 (2H, m), 2.35 (3H, s), 2.70–2.90 (2H, m), 3.20–3.63 (6H, m), 3.73–3.86 (2H, m), 4.07–4.40 (2H, m), 4.52–4.87 (1H, m), 6.83–6.98 (4H, m), 7.10–7.19 (2H, m), 7.34–7.63 (4H, m), 7.72–7.86 (2H, m) MASS (m/z): 592 (M⁺–H), 91 (bp)

EXAMPLE 229

N-(2-Tetrahydropyranyloxy)-2-[7-[4-(4-chlorophenoxy)phenyl]-1,1-dioxoperhydro-4-(2-pyrazinecarbonyl)-1,4-thiazepin-7-yl]acetamide (80 mg)

NMR (CDCl₃, δ): 1.50–1.63 (4H, m), 1.70–1.76 (2H, m), 2.82–2.95 (2H, m), 3.19–3.27 (2H, m), 3.43–3.63 (4H, m), 3.78–3.90 (4H, m), 4.54–4.60 (1H, m) 6.90–7.03 (4H, m), 7.25–7.33 (5H, m), 7.50–7.66 (2H, m) MASS (m/z): 613 (M⁺–H), 45 (bp)

EXAMPLE 230

N-(2-Tetrahydropyranyloxy)-2-[7-[4-(4-chlorophenoxy)phenyl]-4-cyclopropanecarbonyl-1,1-dioxoperhydro-1,4-thiazepin-7-yl]acetamide (80 mg)

NMR (CDCl₃, δ): 0.80–1.14 (4H, m), 1.50–1.65 (4H, m), 1.73 (2H, br s), 1.78–1.97 (1H, m), 2.73–2.99 (3H, m), 3.23–3.47 (4H, m), 3.53–3.60 (1H, m), 3.78–3.90 (2H, m), 4.05–4.35 (2H, m), 4.49–4.55 (1H, m), 4.82–4.87 (1H, m), 6.97 (4H, d, J=8 Hz), 7.32 (2H, d, J=8 Hz), 7.53 (2H, d, J=8 Hz) MASS (m/z)): 575 (M⁺–H), 45 (bp)

EXAMPLE 231

N-(2-Tetrahydropyranyloxy)-2-[7-[4-(4-chlorophenoxy)phenyl-4-(3-thiophenecarbonyl-1,1-dioxoperhydro-1,4-thiazepin-7-yl]acetamide (84 mg)

NMR (CDCl₃, δ): 1.48–1.55 (4H, m), 1.64–1.75 (2H, m), 2.80–2.95 (2H, m), 3.18–3.30 (2H, m), 3.45–3.60 (4H, m), 3.77–3.90 (4H, m), 4.45–4.52 (1H, m), 6.90–7.00 (4H, m), 7.20–7.37 (5H, m), 7.42–7.55 (2H, m) MASS (m/z): 617 (M⁺–H), 45 (bp)

EXAMPLE 232

N-(2-Tetrahydropyranyloxy)-2-[7-[4-(4-chlorophenoxy)phenyl]-4-(2-thiophenecarbonyl)-1,1-dioxoperhydro-1,4-thiazepin-7-yl]acetamide (85 mg)

NMR (CDCl₃, δ): 1.47–1.60 (4H, m), 1.68 (2H, br s), 2.85–2.99 (2H, m), 3.05–3.45 (4H, m), 3.50–3.84-(4H, m), 3.97–4.17 (1H, m), 4.24–4.40 (1H, m), 4.45–4.69 (1H, m), 6.92–7.00 (4H, m), 7.05–7.08 (1H, m), 7.32 (2H, d, J=8 Hz), 7.47–7.57 (4H, m) MASS (m/z) 617 (M⁺–H), 45 (bp)

EXAMPLE 233

N-(2-Tetrahydropyranyloxy)-2-[7-[4-(4-chlorophenoxy)phenyl]-4-[(2S)-2-hydroxy-2-phenylacetyl]-1,1-dioxoperhydro-1,4-thiazepin-7-yl]acetamide (77 mg)

NMR (CDCl₃, δ): 0.48–1.62 (4H, m), 1.67–1.80 (2H, m), 2.60–2.85 (2H, m), 3.02–3.40 (2H, m), 3.48–3.95 (3H, m), 4.15–4.30 (1H, m), 4.35–4.95 (3H, m), 5.05–5.45 (1H, m), 6.97 (4H, d, J=8 Hz), 7.17–7.23 (1H, m), 7.30–7.47 (8H, m) MASS (m/z): 641 (M⁺–H). 45 (bp)

EXAMPLE 234

N-(2-Tetrahydropyranyloxy)-2-[7-[4-(4-chlorophenoxy)phenyl]-1,1-dioxoperhydro-4-(2-pyridinecarbonyl)-1,4-thiazepin-7-yl]acetamide (80 mg)

NMR (CDCl₃, δ): 1.50–1.64 (4H, m), 1.73 (2H, s), 2.76–3.05 (2H, m), 3.25–3.44 (3H, m), 3.52–3.63 (3H, m), 3.78–3.87 (3H, m), 4.10–4.30 (1H, m), 6.90–7.01 (5H, m), 7.27–7.41 (2H, m), 7.50–7.65 (3H, m), 7.78–7.87 (2H, m) MASS (m/z): 579 (M⁺–H), 169 (bp)

EXAMPLE 235

N-(2-Tetrahydropyranyloxy)-2-[4-benzoyl-7-[4-(4-chlorophenoxy)phenyl]-1,1-dioxoperhydro-1,4-thiazepin-7-yl]acetamide (70 mg)

NMR (CDCl₃, δ): 1.50–1.62 (4H, m), 1.65–1.77 (2H, m), 2.68–2.90 (2H, m), 3.09–3.30 (2H, m), 3.40–4.00 (6H, m), 4.09–4.23 (1H, m), 4.35–4.45 (1H, m), 4.57–4.90 (1H, m), 6.93–7.05 (4H, m), 7.15–7.24 (1H, m), 7.32 (2H, d, J=8 Hz), 7.38–7.75 (6H, m) MASS (m/z): 611 (M$^+$–H), 45 (bp)

EXAMPLE 236

N-(2-Tetrahydropyranyloxy)-2-[7-[4-(4-fluorophenoxy)phenyl]-1,1-dioxoperhydro-4-(2-pyrazinecarbonyl)-1,4-thiazepin-7-yl]acetamide (72 mg)

NMR (CDCl$_3$, δ): 1.50–1.60 (4H, m), 1.68–1.76 (2H, m), 2.70–3.03 (2H, m), 3.16–3.63 (6H, m), 3.73–3.90 (4H, m), 4.51–4.60 (1H, m), 6.87–6.94 (4H, m), 7.00–7.06 (5H, m), 7.46–7.62 (2H, m), 8.68 (1H, d, J=2 Hz) MASS (m/z): 599 (M$^+$–H), 79 (bp)

EXAMPLE 237

N-(2-Tetrahydropyranyloxy)-2-[7-[4-(4-flurophenoxy)phenyl]-4-cyclopropanecarbonyl-1,1-dioxoperhydro-1,4-thiazepin-7-yl]acetamide (79 mg)

NMR (CDCl$_3$, δ): 0.76–0.97 (3H, m), 1.03–1.13 (1H, m), 1.50–1.62 (4H, m), 1.67–1.86 (4H, m), 2.73–2.99 (2H, m), 3.15–3.64 (6H, m), 3.75–3.89 (2H, m), 4.15–4.35 (2H, m), 4.48–4.54 (1H, m), 6.99–7.09 (6H, m), 7.44–7.58 (2H, m), 8.46–8.59 (1H, m) MASS (m/z): 561 (M$^+$+H), 85 (bp)

EXAMPLE 238

N-(2-Tetrahydropyranyloxy)-2-[7-[4-(4-flurophenoxy)phenyl-4-(2-thiophenecarbonyl)-1,1-dioxoperhydro-1,4-thiazepin-7-yl]acetamide (58 mg)

NMR (CDCl$_3$, δ): 1.47–1.73 (8H, m), 2.63–2.95 (3H, m), 3.18–3.31 (1H, m), 3.40–3.65 (3H, m), 3.47–3.63 (2H, m), 3.72–3.83 (1H, m), 4.63–4.70 (1H, m), 6.88–6.95 (1H, m), 6.97–7.05 (4H, m), 7.17–7.22 (1H, m), 7.32–7.38 (1H, m), 7.42–7.50 (1H, m), 7.56–7.68 (2H, m), 8.37–8.44 (1H, m) MASS (m/z): 601 (M$^+$–H). 123 (bp)

EXAMPLE 239

N-(2-Tetrahydropyranyloxy)-2-[7-[4-(4-fluorophenoxy)phenyl]-4-(3-thiophenecarbonyl)-1,1-dioxoperhydro-1,4-thiazepin-7-yl]acetamide (66 mg)

NMR (CDCl$_3$, δ): 1.47–1.72 (8H, m), 2.74–2.94 (3H, m), 3.04–3.13 (1H, m), 3.27–3.41 (2H, m), 3.47–3.63 (2H, m), 3.72–3.83 (1H, m), 3.95–4.09 (1H, m), 4.60–4.70 (1H, m), 6.89–6.93 (3H, m), 6.95–7.02 (4H, m), 7.45–7.53 (3H, m), 8.29–8.40 (1H, m) MASS (m/z): 601 (M$^+$–H), 123 (bp)

EXAMPLE 240

N-(2-Tetrahydropyranyloxy)-2-[7-[4-(4-fluorophenoxy)phenyl]-4-[(2S)-2-hydroxy-2-phenylacetyl]-1,1-dioxoperhydro-1,4-thiazepin-7-yl]acetamide (65 mg)

NMR (CDCl$_3$, δ): 1.48–1.63 (4H, m), 1.68–1.80 (2H, m), 2.60–2.90 (2H, m), 3.03–3.40 (4H, m), 3.48–3.95 (3H, m), 4.30–4.93 (4H, m), 5.04–5.45 (1H, m), 6.88–6.97 (2H, m), 7.00–7.07 (4H, m), 7.29–7.45 (7H, m) MASS (m/z): 625 (M$^+$–H, bp)

EXAMPLE 241

N-(2-Tetrahydropyranyloxy)-2-[7-[4-(4-fluorophenoxy)phenyl]-1,1-dioxoperhydro-4-(2-pyridinecarbonyl)-1,4-thiazepin-7-yl]acetamide (72 mg)

NMR (CDCl$_3$, δ): 1.46–1.63 (4H, m), 1.68–1.80 (2H, m), 2.75–3.03 (2H, m), 3.23–3.43 (3H, m), 3.47–3.63 (3H, m), 3.73–3.87 (2H, m), 4.02–4.38 (2H, m), 4.55–4.88 (1H, m), 6.88–6.94 (3H, m), 6.98–7.05 (3H, m), 7.34–7.63 (4H, m), 7.75–7.86 (2H, m), 8.60 (1H, s) MASS (m/z): 596 (M$^+$–H), 45 (bp)

EXAMPLE 242

N-(2-Tetrahydropyranyloxy)-2-[(S)-7-[4-(4-chlorophenoxy)phenyl-4-(3-thiophenecarbonyl)-1,1-dioxoperhydro-1,4-thiazepin-7-yl]acetamide (864 mg)

NMR (CDCl$_3$, δ): 1.48–1.55 (4H, m), 1.64–1.75 (2H, m), 2.58–2.98 (2H, m), 3.09–3.30 (2H, m), 3.38–3.63 (4H, m), 3.73–3.90 (2H, m), 4.07–4.23 (2H, m), 4.30–4.70 (1H, m), 6.90–7.00 (4H, m), 7.20–7.35 (5H, m), 7.42–7.70 (2H, m) MASS (m/z): 617 (M$^+$–H), 123 (bp)

EXAMPLE 243

N-(2-Tetrahydropyranyloxy)-2-[(S)-7-[4-(4-chlorophenoxy)phenyl]-4-cyclopropanecarbonyl-1,1-dioxoperhydro-1,4-thiazepin-7-yl]acetamide (1.01 g)

NMR (CDCl$_3$, δ): 0.77–1.13 (4H, m), 1.50–1.63 (4H, m), 1.67–1.78 (2H, m), 1.79–1.90 (1H, m), 2.73–3.00 (3H, m), 3.20–3.49 (4H, m), 3.53–3.62 (1H, m), 3.77–3.90 (2H, m), 4.00–4.35 (2H, m), 4.47–4.55 (1H, m), 4.82–4.88 (1H, m), 7.01 (4H, d, J=8 Hz), 7.33 (2H, d, J=8 Hz), 7.54 (2H, d, J=8 Hz), 8.42–8.53 (1H, m) MASS (m/z): 575 (M$^+$–H), 137 (bp)

EXAMPLE 244

N-(2-Tetrahydropyranyloxy)-2-[7-(5-bromo-2-thienyl)-4-cyclopropylcarbonyl-1,1-dioxoperhydro-1,4-thiazepin-7-yl]acetamide (1.3 g)

NMR (CDCl$_3$, δ): 0.85–1.03 (4H, m), 1.56–1.73 (6H, m), 2.75–2.96 (3H, m), 3.10–3.55 (6H, m), 3.80–3.88 (2H, m), 4.10–4.52 (2H, m), 4.55, 4.86 (1H, br), 6.99–7.02 (2H, m) MASS (ESI+): 535 (M+H)

EXAMPLE 245

N-(2-Tetrahydropyranyloxy)-2-[7-(5-(2-naphthyl)-2-thienyl)-4-cyclopropylcarbonyl-1,1-dioxoperhydro-1,4-thiazepin-7-yl]acetamide (150 mg)

NMR (CDCl$_3$, δ): 0.85 (2H, br), 1.04 (2H, br), 1.46–1.86 (7H, m), 2.65–2.99 (5H, m), 3.20–3.58 (4H, m), 3.70–3.97 (2H, m), 4.09–4.21 (1H, m), 4.57, 4.85 (1H, s), 7.36 (1H, m), 7.45–7.48 (2H, m), 7.67–7.72 (1H, m), 7.82 (4H, br), 8.02 (1H, br) MASS (ESI–): 581 (M–H)

EXAMPLE 246

N-(2-Tetrahydropyranyloxy)-2-[7-(5-(4-biphenylyl)-2-thienyl)-4-tert-butoxycarbonylaminoacetyl)-1,1-dioxoperhydro-1,4-thiazepin-7-yl]acetamide (100 mg)

MASS (ESI–): 670 (M–H)

EXAMPLE 247

N-(2-Tetrahydropyranyloxy)-2-[7-(5–4-methylphenyl)-2-thienyl)-4-(2-pyridinylcarbonyl)-1,1-dioxoperhydro-1,4-thiazepin-7-yl]acetamide (118 mg)

NMR (CDCl$_3$, δ): 1.43–1.75 (6H, m), 2.36 (3H, s), 2.80–3.95 (11H, m), 4.16–4.38 (1H, m), 4.57, 4.85 (1H, s), 7.09–7.20 (3H, m), 7.29–7.45 (3H, m), 7.73–7.81 (2H, m), 8.40–8.60 (1H, m) MASS (ESI–): 582 (M–H)

EXAMPLE 248

N-(2-Tetrahydropyranyloxy)-2-[7-(5-(4-methylphenyl)-2-thienyl)-4-((S)-2-hydroxy-2-phenylacetyl)-1,1-dioxoperhydro-1,4-thiazepin-7-yl]acetamide (140 mg) MASS (ESI–): 611 (M–H)

EXAMPLE 249

N-(2-Tetrahydropyranyloxy)-2-[7-(5-(4-(5-oxazolyl)phenyl)-2-thienyl)-1,1-dioxoperhydro-4-(1H-pyrazol-4-ylcarbonyl)-1,4-thiazepin-7-yl]acetamide (84 mg)

NMR (DMSO-d$_6$, δ): 1.36–1.65 (6H, m), 2.57–4.00 (12H, m), 4.46 (½H, s), 4.76 (½H, s), 7.23–7.31 (1H, m), 7.52–7.60 (1H, m), 7.73–7.83 (6H, m), 8.10–8.20 (1H, m), 8.48 (1H, s) MASS (ES-)(m/z): 624.15

EXAMPLE 250

N-(2-Tetrahydropyranyloxy)-2-[4-cyclopropanecarbonyl-7-[4-(4-methoxyphenoxy)phenyl]-1,1-dioxoperhydro-1,4-thiazepin-7-yl]acetamide (73 mg)

NMR (CDCl$_3$, δ): 0.78–1.10 (4H, m), 1.50–1.63 (4H, m), 1.68–1.75 (2H, m), 1.77–1.87 (1H, m), 2.80–2.95 (3H, m), 3.20–3.45 (4H, m), 3.50–3.62 (1H, m), 3.72–3.90 (2H, m), 3.82 (3H, s), 4.10–4.30 (2H, m), 4.45–4.87 (2H, m), 6.92 (4H, t, J=8 Hz), 7.00 (2H, d, J=8 Hz), 7.40–7.58 (2H, m) MASS (m/z): 571 (M$^+$–H, bp)

EXAMPLE 251

N-(2-Tetrahydropyranyloxy)-2-[7-[4-(4-methoxyphenoxy)phenyl-4-(2-thiophenecarbonyl)-1,1-dioxoperhydro-1,4-thiazepin-7-yl]acetamide (66 mg)

NMR (CDCl$_3$, δ): 1.48–1.60 (4H, m), 1.65–1.75 (2H, m), 2.85–3.00 (2H, m), 3.12–3.43 (4H, m), 3.46–3.86 (4H, m), 3.83 (3H, s), 3.93–4.10 (1H, m), 4.24–4.50 (1H, m), 4.60–4.74 (1H, m), 6.87–6.93 (5H, m), 6.95–7.10 (3H, m), 7.40–7.57 (3H, m) MASS (m/z): 613 (M$^+$–H), 123 (bp)

EXAMPLE 252

N-(2-Tetrahydropyranyloxy)-2-[7-[4-(4-methoxyphenoxy)phenyl]-4-(3-thiophenecarbonyl)-1,1-dioxoperhydro-1,4-thiazepin-7-yl]acetamide (83 mg)

NMR (CDCl$_3$, δ): 1.45–1.59 (4H, m), 1.65–1.78 (2H, m), 2.60–2.94 (2H, m), 3.07–3.30 (2H, m), 3.35–3.85 (6H, m), 3.82 (3H, s), 4.04–4.18 (1H, m), 4.24–4.60 (2H, m), 6.89 (4H, d, J=8 Hz), 7.00 (2H, d, J=8 Hz), 7.32–7.70 (5H, m) MASS (m/z): 613 (M$^+$–H, bp)

EXAMPLE 253

N-(2-Tetrahydropyranyloxy)-2-[7-[4-(4-methoxyphenoxy)phenyl]-1,1-dioxoperhydro-4-(2-pyridinecarbonyl)-1,4-thiazepin-7-yl]acetamide (80 mg)

NMR (CDCl$_3$, δ): 1.50–1.57 (4H, m), 1.67–1.78 (2H, m), 2.70–2.05 (2H, m), 3.20–3.65 (6H, m), 3.70–3.86 (2H, m), 3.81 (3H, s), 4.10–4.40 (2H, m), 4.55–4.88 (1H, m), 6.84–7.02 (7H, m), 7.34–7.64 (4H, m), 7.77–7.83 (1H, m), 8.42–8.64 (1H, m) MASS (m/z): 610 (M$^+$+H), 115 (bp)

EXAMPLE 254

N-(2-Tetrahydropyranyloxy)-2-[4-[(2S)-2-hydroxy-2-phenylacetyl]-7-[4-(4-methoxyphenoxy)phenyl]-1,1-dioxoperhydro-1,4-thiazepin-7-yl]acetamide (78 mg)

NMR (CDCl$_3$, δ): 1.49–1.63 (4H, m), 1.67–1.80 (2H, m), 2.58–2.85 (2H, m), 2.98–3.38 (4H, m), 3.47–3.77 (3H, m), 3.82 (3H, s), 4.30–4.92 (4H, m), 5.18–5.45 (1H, m), 6.85–6.93 (4H, m), 6.95–7.00 (2H, m) 7.28–7.45 (7H, m) MASS (m/z): 639 (M$^+$–H), 115 (bp)

EXAMPLE 255

N-(2-Tetrahydropyranyloxy)-2-[7-[4-(4-methoxyphenoxy)phenyl-4-(2-pirazinecarbonyl)-1,1-dioxoperhydro-1,4-thiazepin-7-yl]acetamide (68 mg)

NMR (CDCl$_3$, δ): 1.47–1.60 (4H, m), 1.66–1.77 (2H, m), 2.70–3.03 (2H, m), 3.13–3.62 (6H, m), 3.72–3.88 (4H, m), 3.81 (3H, s), 4.13–4.23 (1H, m), 6.83–6.92 (5H, m), 7.2 (1H, d, J=8 Hz), 7.44–7.60 (2H, m), 8.38–8.58 (1H, m), 8.67 (1H, s), 8.86–9.05 (1H, m) MASS (m/z): 611 (M$^+$–H), 74 (bp)

EXAMPLE 256

To a solution of N-(2-tetrahydropyranyloxy)-2-[7-(5-(4-chlorophenyl)-2-thienyl)-1,1-dioxoperhydro-1,4-thiazepin-7-yl]acetamide (100 mg) and triethylamine (22.3 mg) in acetonitrile (2 ml) was added N-(2-methoxyethylaminosulfonyloxy)succinimide (55.6 mg) and the mixture was stirred at ambient temperature for 1 hour. The mixture was partitioned with ethyl acetate and water. The organic layer was separated, washed with 5% citric acid solution, water, saturated sodium bicarbonate solution and brine, dried over magnesium sulfate, and evaporated in vacuo. The residue was purified by silica gel column chromatography eluting with a mixture of chloroform and methanol (200:1, 100:1, 200:3) to give N-(2-tetrahydropyranyloxy)-2-[(S)-7-(5-(4-chlorophenyl)-2-thienyl)-4-(2-methoxyethylaminosulfonyl)-1,1-dioxoperhydro-1,4-thiazepin-7-yl]acetamide (80.0 mg) as a colorless amorphous powder.

NMR (CDCl$_3$, δ): 1.46–1.93 (6H, br), 2.85–3.02 (1H, br), 3.12–3.33 (5H, br), 3.38 (3H, s), 3.35–3.68 (6H, br), 3.77–4.16 (4H, br), 4.68, 4.94 (1H, br), 4.83 (1H, t, J=7 Hz), 7.22 (2H, s), 7.33 (2H, d, J=8 Hz), 7.49 (2H, m), 8.58, 8.72 (1H, br) MASS (m/z): 634 (M–H)

EXAMPLE 257

To a solution of N-(2-tetrahydropyranyloxy)-2-[7-(5-(4-(5-oxazolyl)phenyl)-2-thienyl)-1,1-dioxoperhydro-1,4-thiazepin-7-yl]acetamide (100 mg) in N,N-dimethylformamide (3 ml) was added triethylamine (57 mg) and cyclopropylaminocarbonyloxybenzene (40 mg) and the reaction mixture was heated at 50° C. for 4 hours. The mixture was added ethyl acetate and the solution was washed with successively water, a 5% aqueous citric acid-solution, a satuated aqueous sodium hydrogencarbonate and brine, dried over anhydrous magnesium sulfate and concentrated in vacuo. The residue was purified by column chromatography on silica gel 60 (2% methanol-chloroform) to give N-(2-tetrahydropyranyloxy)-2-[4-cyclopropylaminocarbonyl-7-(5-(4-(5-oxazolyl)phenyl)-2-thienyl)-1,1-dioxoperhydro-1,4-thiazepin-7-yl]acetamide (65 mg) as a pale yellow powder.

NMR (CDCl$_3$, δ): 0.45–0.58 (2H, br), 0.67–0.80 (2H, m), 1.22–1.33 (1H, m), 1.44–1.86 (6H, m), 2.61–2.94 (3H, m), 3.18–4.27 (9H, m), 4.62 (½H, br s), 4.86 (½H, br s), 5.20 (1H, br), 7.20–7.31 (1H, br), 7.38 (1H, s), 7.57–7.66 (5H, m), 7.94 (1H, s), 9.50 (1H, br s), 9.56 (1H, br s) MASS (ESI-): 613.3 (M–H)

EXAMPLE 258

N-(2-Tetrahydropyranyloxy)-2-[(S)-7-(5-(4-methylthiophenyl)-2-thienyl)-4-((5-methyl-3-isoxazolyl)aminocarbonyl)-1,1-dioxoperhydro-1,4-thiazepin-7-yl]acetamide (111 mg) was obtained in a similar manner to that of Example 257.

NMR (CDCl$_3$, δ): 1.40–1.88 (6H, m), 2.27–2.42 (3H, m), 2.51 (3H, s), 2.69–3.25 (5H, m), 3.31–4.35 (6H, m), 4.57–4.90 (2H, m), 6.53–6.65 (2H, m), 7.13–7.56 (6H, m), 8.40–8.52 (1H, m), 9.40–9.53 (1H, m) MASS (ESI-): 633 (M–H)

EXAMPLE 259

To a solution of 2-nitrobenzoic acid (33 mg) in N,N-dimethylformamide (2 ml) was added 1-hydroxybenzotriazole (27 mg) and 1,3-diisopropylcarbodiimide (25 mg) at ambient temperature. After 1 minute, the solution was added to N-[2-[7-(5-bromo-2-thienyl)-1,1-dioxoperhydro-1,4-thiazepin-7-yl]acetyl] hydroxylamine trityl crowns (32 µmol, 16.0 µmol/crown) and the reaction mixture was left overnight at ambient temperature. The crowns were washed with N,N-dimethylformamide, methanol and dichloromethane, successively and air dried. To a solution of 4-(5-oxazolyl) phenylboronic acid pinacol cyclic ester (431 mg) in degassed N,N-dimethylformamide (4 ml) were added tetrakis(triphenylphosphine)palladium (206 mg), a solution of sodium carbonate (843 mg) in degassed water (2 ml) and the crowns in an atmosphere of nitrogen. After resulting mixture was heated at 60° C. for 20 hours, the crowns were washed with degassed N,N-dimethylformamide, a solution of sodium diethyldithiocarbamate (500 mg) and diisopropylethylamine (0.5 ml) in N,N-dimethylformamide (100 ml), N,N-dimethylformamide, methyl sulfoxide, water, methanol and dichloromethane, successively. The crowns were treated with 5% trifluoroacetic acid in dichloromethane for 1 hour at ambient temperature and removed from the solution. After the solvent was removed under a stream of nitrogen, to give N-hydroxy-2-[4-(2-nitrobenzoyl)-7-(5-(4-(5-oxazolyl) phenyl)-2-thienyl)-1,1-dioxoperhydro-1,4-thiazepin-7-yl] acetamide (9 mg) as a powder.

MASS (ESI–): 595 (M–H)

The following compounds were obtained in a similar manner to that of Example 259.

EXAMPLE 260

N-Hydroxy-2-[4-(2-furoyl)-7-(5-(4-(5-oxazolyl)phenyl)-2-thienyl)-1,1-dioxoperhydro-1,4-thiazepin-7-yl]acetamide (11.0 mg)

MASS (ESI+): 542 (M+H)

EXAMPLE 261

N-Hydroxy-2-[4-benzoyl-7-(5-(3-(methylaminocarbonylamino)phenyl)-2-thienyl)-1,1-dioxoperhydro-1,4-thiazepin-7-yl]acetamide (3.7 mg)

MASS (ESI–): 555–0.3 (M–H)

EXAMPLE 262

N-Hydroxy-2-[4-(4-methoxybenzoyl)-7-(5-(3-(methylaminocarbonylamino)phenyl)-2-thienyl)-1,1-dioxoperhydro-1,4-thiazepin-7-yl]acetamide (3.7 mg)

MASS (ESI–): 585.4 (M–H)

EXAMPLE 263

N-Hydroxy-2-[7-(5-(3-(methylaminocarbonylamino) phenyl)-2-thienyl)-4-(2-thienylcarbonyl)-1,1-dioxoperhydro-1,4-thiazepin-7-yl]acetamide (3.3 mg)

MASS (ESI–): 563.4 (M+H)

EXAMPLE 264

N-Hydroxy-2-[7-(5-(3-(methylaminocarbonylamino) phenyl)-2-thienyl)-4-(quinolin-3-ylcarbonyl)-1,1-dioxoperhydro-1,4-thiazepin-7-yl]acetamide (4.0 mg)

MASS (ESI+): 608.5 (M+H)

EXAMPLE 265

N-Hydroxy-2-[4-hexanoyl-7-(5-(3-(methylaminocarbonylamino)phenyl)-2-thienyl)-1,1-dioxoperhydro-1,4-thiazepin-7-yl]acetamide (3.9 mg)

MASS (ESI+): 551.5 (M+H)

EXAMPLE 266

N-Hydroxy-2-[4-(2-fluorobenzoyl)-7-(5-(4-(5-oxazolyl) phenyl)-2-thienyl)-1,1-dioxoperhydro-1,4-thiazepin-7-yl] acetamide (10.5 mg)

MASS (ESI+): 570 (M+H)

EXAMPLE 267

N-Hydroxy-2-[4-(4-chlorobenzoyl)-7-(5-(4-(5-oxazolyl) phenyl)-2-thienyl)-1,1-dioxoperhydro-1,4-thiazepin-7-yl] acetamide (10.9 mg)

MASS (ESI+): 587 (M+H)

EXAMPLE 268

To a solution of 2-phenoxybenzoic acid (43 mg) in N,N-dimethylformamide (2 ml) was added 1-hydroxybenzotriazole (27 mg) and 1,3-diisopropylcarbodiimide (25 mg) at ambient temperature. After 1 minute, the solution was added to N-[2-[7-(5-bromo-2-thienyl)-1,1-dioxoperhydro-1,4-thiazepin-7-yl]acetyl] hydroxylamine trityl crowns (32 µmol, 16.0 µmol/crown) and the reaction mixture was left overnight at ambient temperature. The crowns were washed with N,N-dimethylformamide, methanol and dichloromethane, successively and air dried. To a solution of 4-(5-oxazolyl) phenylboronic acid pinacol cyclic ester (431 mg) in degassed N,N-dimethylformamide (4 ml) were added tetrakis(triphenylphosphine)palladium (206 mg), a solution of sodium carbonate (843 mg) in degassed water (2 ml) and the crowns in an atmosphere of nitrogen. After resulting mixture was heated at 60° C. for 20 hours, the crowns were washed with degassed N,N-dimethylformamide, a solution of sodium diethyldithiocarbamate (500 mg) and diisopropylethylamine (0.5 ml) in N,N-dimethylformamide (100 ml), N,N-dimethylformamide, methyl sulfoxide, water, methanol and dichloromethane, successively. The crowns were treated with 5% trifluoroacetic acid in dichloromethane for 1 hour at ambient temperature and removed from the solution. After the solvent was removed under a stream of nitrogen, the residue was purified by reverse phase HPLC (0.1% trifluoroacetic acid in acetonitrile, 1–60% gradient) to give N-hydroxy-2-[7-(5-(4-(5-oxazolyl)phenyl)-2-thienyl)-4-(2-phenoxybenzoyl)-1,1-dioxoperhydro-1,4-thiazepin-7-yl]acetamide (1.4 mg) as a powder.

MASS (ESI−): 642 (M−H)

The following compounds were obtained in a similar manner to that of Example 268.

EXAMPLE 269

N-Hydroxy-2-[4-(2-hydroxy-3-methoxybenzoyl)-7-(5-(4-(5-oxazoyl)phenyl)-2-thienyl)-1,1-dioxoperhydro-1,4-thiazepin-7-yl]acetamide (1.0 mg)

MASS (ESI+): 598 (M+H)

EXAMPLE 270

N-Hydroxy-2-[7-(5-(4-(5-oxazolyl)phenyl)-2-thienyl)-4-(2-phenoxyacetyl)-1,1-dioxoperhydro-1,4-thiazepin-7-yl]acetamide (9.7 mg)

MASS (ESI+): 582 (M+H)

EXAMPLE 271

N-Hydroxy-2-[4-(2-(2-methoxyethoxy)acetyl)-7-(5-(4-(5-oxazolyl)phenyl)-2-thienyl)-1,1-dioxoperhydro-1,4-thiazepin-7-yl]acetamide (9.1 mg)

MASS (ESI+): 564 (M+H)

EXAMPLE 272

N-Hydroxy-2-[4-(2-hydroxybenzoyl)-7-(5-(4-(5-oxazolyl)phenyl)-2-thienyl)-1,1-dioxoperhydro-1,4-thiazepin-7-yl]acetamide (1.4 mg)

MASS (ESI−): 566 (M−H)

EXAMPLE 273

N-Hydroxy-2-[7-(5-(4-(5-oxazolyl)phenyl)-2-thienyl)-4-(quinolin-8-ylcarbonyl)-1,1-dioxoperhydro-1,4-thiazepin-7-yl]acetamide (2.2 mg)

MASS (ESI+): 603 (M+H)

EXAMPLE 274

N-Hydroxy-2-[4-(2,3-dichlorobenzoyl)-7-(5-(4-(5-oxazolyl)phenyl)-2-thienyl)-1,1-dioxoperhydro-1,4-thiazepin-7-yl]acetamide (14.7 mg)

MASS (ESI+): 620 (M+H)

EXAMPLE 275

N-Hydroxy-2-[4-(2,5-dichlorobenzoyl)-7-(5-(4-(5-oxazolyl)phenyl)-2-thienyl)-1,1-dioxoperhydro-1,4-thiazepin-7-yl]acetamide (14.6 mg)

MASS (ESI+): 620 (M+H)

EXAMPLE 276

N-Hydroxy-2-[7-(5-(4-(5-oxazolyl)phenyl)-2-thienyl)-4-(2,4-ditrifluoromethylbenzoyl)-1,1-dioxoperhydro-1,4-thiazepin-7-yl]acetamide (11.8 mg)

MASS (ESI+): 688 (M+H)

EXAMPLE 277

To a solution of ethyl chloroformate (22 mg) in dichloromethane (2 ml) was added pyridine (15.8 mg) and N-[2-[7-(5-bromo-2-thienyl)-1,1-dioxoperhydro-1,4-thiazepin-7-yl]acetyl]hydroxylamine trityl crowns (32 μmol, 16.0 μmol/crown). The reaction mixture was left for 1 hour at ambient temperature. The crowns were washed with N,N-dimethylformamide, methanol and dichloromethane, successively and air dried. To a solution of 4-(5-oxazolyl)phenylboronic acid pinacol cyclic ester (431 mg) in degassed N,N-dimethylformamide (4 ml) were added tetrakis(triphenylphosphine)palladium (206 mg), a solution of sodium carbonate (843 mg) in degassed water (2 ml) and the crowns in an atmosphere of nitrogen. After resulting mixture was heated at 60° C. for 20 hours, the crowns were washed with degassed N,N-dimethylformamide, a solution of sodium diethyldithiocarbamate (500 mg) and diisopropylethylamine (0.5 ml) in N,N-dimethylformamide (100 ml), N,N-dimethylformamide, methyl sulfoxide, water, methanol and dichloromethane, successively. The crowns were treated with 5% trifluoroacetic acid in dichloromethane for 1 hour at ambient temperature and removed from the solution. After the solvent was removed under a stream of nitrogen, to give N-hydroxy-2-[4-ethoxycarbonyl-7-(5-(4-(5-oxazolyl)phenyl)-2-thienyl)-1,1-dioxoperhydro-1,4-thiazepin-7-yl]acetamide (9 mg) as a powder.

MASS (ESI+): 520 (M+H)

The following compounds were obtained in a similar manner to that of Example 277.

EXAMPLE 278

N-Hydroxy-2-[7-(5-(3-(methylaminocarbonylamino)phenyl)-2-thienyl)-4-phenoxycarbonyl-1,1-dioxoperhydro-1,4-thiazepin-7-yl]acetamide (3.7 mg)

MASS (ESI+): 573.4 (M+H)

EXAMPLE 279

N-Hydroxy-2-[4-isobutoxycarbonyl-7-(5-(3-(methylaminocarbonylamino)phenyl)-2-thienyl)-1,1-dioxoperhydro-1,4-thiazepin-7-yl]acetamide (3.6 mg)

MASS (ESI+): 553 (M+H)

EXAMPLE 280

N-Hydroxy-2-[4-ethoxycarbonyl-7-(5-(3-(methylaminocarbonylamino)phenyl)-2-thienyl)-1,1-dixoperhydro-1,4-thiazepin-7-yl]acetamide (3.2 mg)

MASS (ESI+): 525.4 (M+H)

EXAMPLE 281

N-Hydroxy-2-[4-(2-methoxyethoxycarbonyl)-7-(5-(4-(5-oxazolyl)phenyl)-2-thienyl)-1,1-dioxoperhydro-1,4-thiazepin-7-yl]acetamide (10.3 mg)

MASS (ESI+): 550 (M+H)

EXAMPLE 282

To a solution of 2-chlorophenylisocyanate (23 mg) in dichloromethane (2 ml) was added N-[2-[7-(5-bromo-2-thienyl)-1,1-dioxoperhydro-1,4-thiazepin-7-yl]acetyl)hydroxylamine trityl crowns (28 μmol, 14.0 μmol/crown) and the reaction mixture was left overnight at ambient temperature. The crowns were washed with N,N- dimethylformamide, methanol and dichloromethane, successively and air dried. To a solution of 4-(5-oxazolyl) phenylboronic acid pinacol cyclic ester (431 mg) in degassed N,N-dimethylformamide (4 ml) were added tetrakis(triphenylphosphine)palladium (206 mg), a solution of sodium carbonate (843 mg) in degassed water (2 ml) and the crowns in an atmosphere of nitrogen. After resulting mixture was heated at 60° C. for 10 hours, the crowns were washed with degassed N,N-dimethylformamide, a solution of sodium diethyldithiocarbamate (500 mg) and diisopropylethylamine (0.5 ml) in N,N-dimethylformamide (100 ml), N,N-dimethylformamide, methyl sulfoxide, water, methanol and dichloromethane, successively. The crowns were treated with 5% trifluoroacetic acid in dichloromethane for 1 hour at ambient temperature and removed from the solution. After the solvent was removed under a stream of nitrogen, the residue was purified by reverse phase HPLC (0.1% trifluoroacetic acid in acetonitrile, 1–60% gradient) to give N-hydroxy-2-[4-(2-chlorophenylaminocarbonyl)-7-(5-(4-(5-oxazolyl)phenyl)-2-thienyl)-1,1-dioxoperhydro-1,4-thiazepin-7-yl]acetamide (1.4 mg) as a powder.

MASS (ESI+): 601 (M+H)

The following compounds were obtained in a similar manner to that of Example 282.

EXAMPLE 283

N-Hydroxy-2-[4-(3-chlorophenylaminocarbonyl)-7-(5-(4-(5-oxazolyl)phenyl)-2-thienyl)-1,1-dioxoperhydro-1,4-thiazepin-7-yl]acetamide (0.5 mg)

MASS (ESI+): 601 (M+H)

EXAMPLE 284

N-Hydroxy-2-[4-(4-chlorophenylaminocarbonyl)-7-(5-(4-(5-oxazolyl)phenyl)-2-thienyl)-1,1-dioxoperhydro-1,4-thiazepin-7-yl]acetamide (1.0 mg)

MASS (ESI+): 603 (M+H)

EXAMPLE 285

N-Hydroxy-2-[4-(2-methylphenylaminocarbonyl)-7-(5-(4-(5-oxazolyl)phenyl)-2-thienyl)-1,1-dioxoperhydro-1,4-thiazepin-7-yl]acetamide (1.1 mg)

MASS (ESI+): 581 (M+H)

EXAMPLE 286

N-Hydroxy-2-[4-(2-methoxyphenylaminocarbonyl)-7-(5-(4-(5-oxazolyl)phenyl)-2-thienyl)-1,1-dioxoperhydro-1,4-thiazepin-7-yl]acetamide (1.2 mg)

MASS (ESI+): 597 (M+H)

EXAMPLE 287

N-Hydroxy-2-[4-(2,3-dichlorophenylaminocarbonyl)-7-(5-(4-(5-oxazolyl)phenyl)-2-thienyl)-1,1-dioxoperhydro-1,4-thiazepin-7-yl]acetamide (1.0 mg)

MASS (ESI+): 635 (M+H)

EXAMPLE 288

N-Hydroxy-2-[4-(2,5-dichlorophenylaminocarbonyl)-7-(5-(4-(5-oxazolyl)phenyl)-2-thienyl)-1,1-dioxoperhydro-1,4-thiazepin-7-yl]acetamide (0.6 mg)

MASS (ESI+): 635 (M+H)

EXAMPLE 289

To a solution of 1-tert-butoxycarbonylpiperidine-4-carboxylic acid (40 mg) in N,N-dimethylformamide (2 ml) were added 1-hydroxybenzotriazole (27 mg) and 1,3-diisopropylcarbodiimide (25 mg) at ambient temperature. After 1 minute, the solution was added to N-[2-[7-(5-bromo-2-thienyl)-1,1-dioxoperhydro-1,4-thiazepin-7-ylacetyl] hydroxylamine trityl crowns (32 μmol, 16.0 μmol/crown) and the reaction mixture was left overnight at ambient temperature. The crowns were washed with N,N-dimethylformamide, methanol and dichloromethane, successively and air dried. To a solution of 4-(5-oxazolyl) phenylboronic acid pinacol cyclic ester (431 mg) in degassed N,N-dimethylformamide (4 ml) were added tetrakis(triphenylphosphine)palladium (206 mg), a solution of sodium carbonate (843 mg) in degassed water (2 ml) and the crowns in an atmosphere of nitrogen. After resulting mixture was heated at 60° C. for 20 hours, the crowns were washed with degassed N,N-dimethylformamide, a solution of sodium diethyldithiocarbamate (500 mg) and diisopropylethylamine (0.5 ml) in N,N-dimethylformamide (100 ml), N,N-dimethylformamide, methyl sulfoxide, water, methanol and dichloromethane, successively. The crowns were treated with 25% trifluoroacetic acid in dichloromethane for 1 hour at ambient temperature and removed from the solution. After the solvent was removed under a stream of nitrogen, to the residue were added water (2 ml) and 1N hydrochloric acid (1 ml) and the solution was lyophilized to give N-hydroxy-2-[7-(5-(4-(5-oxazolyl) phenyl)-2-thienyl)-4-(4-piperidinylcarbonyl)-1,1-dioxoperhydro-1,4-thiazepin-7-yl]acetamide hydrochloride (11.4 mg) as a powder.

NMR (DMSO-$d_6$, δ): 1.61–1.86 (4H, m), 2.62–3.05 (8H, m), 3.24–3.36 (4H, m), 3.48–3.98 (2H, m), 7.20–7.28 (1H, m), 7.55–7.59 (1H, m), 7.73–7.80 (4H, m), 8.21–8.32 (1H, m), 8.48–8.61 (1H, m)

MASS (ESI+): 559 (M+H)

EXAMPLE 290

A mixture of N-(2-tetrahydropyranyloxy)-2-[7-(5-(4-chlorophenyl)-2-thienyl)-1,1-dioxoperhydro-1,4-thiazepin-7-ylacetamide (90 mg), 1-phenyl-1-cyclopropanecarboxylic acid (35.1 mg), 1-(3-dimethylaminopropyl)-3-ethylcarbodiimide hydrochloride (41.5 mg) and 1-hydroxybenzotirazole (31.7 mg) in anhydrous N,N-dimethylformamide (3 ml) was stirred at ambient temperature for 3 hours. The mixture was partitioned between water and ethyl acetate. The organic layer was separated, washed with 5% citric acid water solution, water, saturated sodium bicarbonate solution and brine. To the reaction mixture were added 4N hydrochloric acid-ethyl acetate solution (0.5 ml), chloroform (1 ml) and methanol (1.5 ml) and the reaction mixture was stirred at ambient temperature for 30 minutes. After evaporation of solvent, the residue was purified by HPLC (0.1% trifluoroacetic acid in 20% acetonitrile-water ~0.1% trifluoroacetic acid in 80% acetonitrile-water) to give N-hydroxy-2-[7-(5-(4-chlorophenyl)-2-thienyl)-4-((1-phenylcyclopropyl)carbonyl)-1,1-dioxoperhydro-1,4-thiazepin-7-yl]acetamide (46 mg) as a pale yellow powder.

NMR (DMSO-$d_6$, δ): 0.91–1.11 (1H, m), 1.11–1.39 (1H, m), 1.39–1.60 (2H, m), 2.56–3.20 (4H, m), 3.20–4.04 (6H, m), 7.08–7.44 (6H, m), 7.44–7.54 (3H, m), 7.60–7.73 (2H, m), 8.83–8.91 (1H, m) MASS (ES−)(m/z): 557.17, 559.19

The following compounds were obtained in a similar manner to that of Example 290

EXAMPLE 291

N-Hydroxy-2-[7-(5-(4-ethylphenyl)-2-thienyl)-4-(2-pyrazinylcarbonyl)-1,1-dioxoperhydro-1,4-thiazepin-7-yl] acetamide (37 mg)

NMR (DMSO-d₆, δ): 1.20 (3H, t, J=7.5 Hz), 2.62 (2H, q, J=7.5 Hz), 2.81–3.16 (4H, m), 3.51–4.00 (5H, m), 4.00–4.17 (1H, m), 7.17–7.24 (1H, m), 7.36 (2H, d, J=8 Hz), 7.52–7.61 (2H, m), 8.67–8.75 (1H, m), 8.75–8.83 (1H, m), 8.90 (1H, d, J=9 Hz) MASS (ES+)(m/z): 515.27

EXAMPLE 292

N-Hydroxy-2-[7-(5-(4-ethylphenyl)-2-thienyl)-4-(2-thienylcarbonyl)-1,1-dioxoperhydro-1,4-thiazepin-7-yl]acetamide (40 mg)

NMR (DMSO-d₆, δ): 1.20 (3H, t, J=7.5 Hz), 2.62 (2H, q, J=7.5 Hz), 2.75–3.17 (4H, m), 3.56–3.71 (2H, m), 3.76–4.15 (4H, m), 7.15 (1H, br s), 7.25 (2H, d, J=8 Hz), 7.42 (1H, d, J=3 Hz), 7.52 (1H, br s), 7.56 (2H, d, J=8 Hz), 7.80 (1H, d, J=3 Hz) MASS (ES–)(m/z): 517.20

EXAMPLE 293

N-Hydroxy-2-[7-(5-(4-ethylphenyl)-2-thienyl)-4-(3-thienylcarbonyl)-1,1-dioxoperhydro-1,4-thiazepin-7-yl]acetamide (40.2 mg)

NMR (DMSO-d₆, δ): 1.20 (3H, t, J=7.5 Hz), 2.62 (2H, q, J=7.5 Hz), 2.76–3.19 (4H, m), 3.50–4.14 (6H, m), 7.21 (1H, d, J=3 Hz), 7.23–7.31 (3H, m), 7.36–7.46 (1H, m), 7.50–7.66 (3H, m), 7.80–7.90 (1H, m), 8.86 (1H, br peak) MASS (ES–)(m/z): 517.22

EXAMPLE 294

N-Hydroxy-2-[7-(5-(4-ethylphenyl)-2-thienyl)-4-[(2S)-2-hydroxy-2-phenylacetyl]-1,1-dioxoperhydro-1,4-thiazepin-7-yl]acetamide (37.2 mg)

NMR (DMSO-d₆, δ): 1.19 (3H, t, J=7.5 Hz), 2.62 (2H, q, J=7.5 Hz), 2.66–3.10 (4H, m), 3.45–4.16 (6H, m), 5.35–5.50 (1H, m), 7.06–7.50 (9H, m), 7.50–7.65 (2H, m), 8.80–8.99 (1H, br peak) MASS (ES+)(m/z): 541.31

EXAMPLE 295

N-Hydroxy-2-[7-(5-(4-chlorophenyl)-2-thienyl)-4-(4-pyridylcarbonyl)-1,1-dioxoperhydro-1,4-thiazepin-7-yl]acetamide (55 mg)

NMR (DMSO-d₆, δ): 2.74–3.23 (6H, m), 3.42–4.20 (4H, m), 7.21–7.29 (1H, m), 7.45–7.51 (5H, m), 7.51–7.74 (2H, m), 8.75 (2H, br s) MASS (ES+)(m/z): 520.16, 522.14

EXAMPLE 296

N-Hydroxy-2-[7-(5-(4-chlorophenyl)-2-thienyl)-4-(1H-pyrazol-4-ylcarbonyl)-1,1-dioxoperhydro-1,4-thiazepin-7-yl]acetamide (26 mg)

NMR (DMSO-d₆, δ): 2.60–7.42 (10H, m), 7.24 (1H, d, J=3 Hz), 7.45–7.56 (3H, m), 7.64–7.75 (2H, m), 7.93–8.05 (2H, m). MASS (ES+)(m/z): 509.13, 511.13

EXAMPLE 297

N-Hydroxy-2-[7-(5-(4-methoxyphenyl)-2-thienyl)-4-(2-pyridylcarbonyl)-1,1-dioxoperhydro-1,4-thiazepin-7-yl]acetamide (34.1 mg)

NMR (DMSO-d₆, δ): 2.76–3.16 (4H, m), 3.44–4.18 (9H, m), 6.99 (2H, d, J=8 Hz), 7.11–7.21 (1H, m), 7.27–7.38 (1H, m), 7.45–7.66 (4H, m), 7.90–8.00 (1H, m), 8.55–8.65 (1H, m) MASS (ES+)(M/z): 516.27

EXAMPLE 298

N-Hydroxy-2-[7-(5-(4-methoxyphenyl)-2-thienyl)-4-(2-pyrazinylcarbonyl)-1,1-dioxoperhydro-1,4-thiazepin-7-yl]acetamide (36.6 mg)

NMR (DMSO-d₆, δ): 2.80–3.15 (4H, m), 3.46–3.75 (3H, m), 3.80 (3H, s), 3.81–3.99 (2H, m), 3.99–4.17 (1H, m), 6.99 (2H, d, J=8 Hz), 7.16 (0.5H, d, J=3 Hz), 7.20 (0.5H, d, J=3 Hz), 7.33 (0.5H, d, J=3 Hz), 7.35 (0.5H, d, J=3 Hz), 7.53–7.63 (2H, m), 8.70 (1H, d, J=8 Hz), 8.75–8.80 (1H, m), 8.90 (1H, d, J=8 Hz) MASS (ES+)(m/z): 517.26

EXAMPLE 299

N-Hydroxy-2-[7-(5-(4-methoxyphenyl)-2-thienyl)-4-(2-thienylcarbonyl)-1,1-dioxoperhydro-1,4-thiazepin-7-yl]acetamide (33.1 mg)

NMR (DMSO-d₆, δ): 2.63–3.14 (4H, m), 3.44–3.75 (2H, m), 3.79 (3H, s), 3.81–4.45 (4H, m), 6.99 (2H, d, J=8 Hz), 7.16 (1H, br peak), 7.20 (1H, d, J=3 Hz), 7.35 (1H, d, J=3 Hz), 7.51 (1H, br peak), 7.59 (2H, d, J=8 Hz), 7.81 (1H, d, J=4 Hz), 8.90 (1H, s) MASS (ES+)(m/z): 519.19

EXAMPLE 300

N-Hydroxy-2-[7-(5-(4-methoxyphenyl)-2-thienyl)-4-[(2S)-2-hydroxy-2-phenylacetyl]-1,1-dioxoperhydro-1,4-thiazepin-7-yl]acetamide (33.3 mg)

NMR (DMSO-d₆, δ): 2.64–3.08 (4H, m), 3.56–4.18 (9H, m), 5.38 (0.5H, d, J=7 Hz), 5.46 (0.5H, s), 6.95–7.19 (3H, m), 7.26–7.52 (6H, m), 7.52–7.66 (2H, m) MASS (ES+)(m/z): 545.19

EXAMPLE 301

N-Hydroxy-2-[7-(5-(4-methylthiophenyl)-2-thienyl)-4-(2-pyrazinylcarbonyl)-1,1-dioxoperhydro-1,4-thiazepin-7-yl]acetamide (60 mg)

NMR (DMSO-d₆, δ): 2.51 (3H, s), 2.83–3.26 (6H, m), 3.63–4.13 (4H, m), 7.20–7.24 (1H, m), 7.30 (2H, d, J=8.5 Hz), 7.43–7.46 (1H, m), 7.56–7.60 (2H, m), 8.69–8.72 (1H, m), 8.77–8.80 (1H, m), 8.87 (1H, d, J=8.5 Hz), 8.96 (1H, s) MASS (ES–): 531 (M–H)

EXAMPLE 302

N-Hydroxy-2-[7-(5-(4-methylthiophenyl)-2-thienyl)-4-(2-thienylcarbonyl)-1,1-dioxoperhydro-1,4-thiazepin-7-yl]acetamide (70 mg)

NMR (DMSO-d₆, δ): 2.50 (3H, s), 2.73–3.25 (6H, m), 3.49–4.10 (4H, m), 7.15 (1H, br), 7.22 (1H, d, J=4.5 Hz), 7.29 (2H, d, J=8.5 Hz), 7.45 (1H, d, J=4.5 Hz), 7.50 (1H, br), 7.58 (2H, d, J=8.5 Hz), 7.80 (1H, br), 8.91 (1H, s), 10.69 (1H, s) MASS (ES–): 535 (M–H)

EXAMPLE 303

N-Hydroxy-2-[7-(5-(4-methylthiophenyl)-2-thienyl)-4-(3-thienylcarbonyl)-1,1-dioxoperhydro-1,4-thiazepin-7-yl]acetamide (70 mg)

NMR (DMSO-d₆, δ): 2.50 (3H, s), 2.72–3.11 (6H, m), 3.49–4.06 (4H, m), 7.21–7.31 (4H, m), 7.45 (1H, br), 7.59–7.64 (3H, m), 7.82–7.86 (1H, m), 8.86, 8.92 (1H, br), 10.68 (1H, br) MASS (ES–): 535 (M–H)

EXAMPLE 304

N-Hydroxy-2-[7-(5-(4-methylthiophenyl)-2-thienyl)-4-(3-phenylpropanoyl)-1,1-dioxoperhydro-1,4-thiazepin-7-yl]acetamide (70 mg)

NMR (DMSO-d₆, δ): 2.51 (3H, s), 2.60–2.73 (2H, m), 2.80–3.20 (8H, m), 3.53–4.10 (4H, m), 7.19–7.21 (2H, m), 7.25–7.31 (6H, m), 7.43 (1H, d, J=4.5 Hz), 7.56–7.60 (2H, m), 8.93 (1H, s), 10.70 (1H, s) MASS (ES–): 557 (M–H)

EXAMPLE 305

N-Hydroxy-2-[7-(5-(4-methylthiophenyl)-2-thienyl)-4-(2-pyridylcarbonyl)-1,1-dioxoperhydro-1,4-thiazepin-7-yl]acetamide (50 mg)

NMR (DMSO-d$_6$, δ): 2.51 (3H, s), 2.75–3.18 (4H, m), 3.51–4.12 (6H, m), 7.19, 7.22 (H, d, J=4.5 Hz), 7.30 (2H, d, J=8.5 Hz), 7.44, 7.45 (1H, d, J=4.5 Hz), 7.49–7.63 (3H, m), 7.93–7.98 (1H, m), 8.59–8.62 (1H, m), 8.85, 8.95 (1H, s) MASS (ES–): 530 (M–H)

EXAMPLE 306

N-Hydroxy-2-[7-(5-(4-biphenylyl)-2-thienyl)-4-(2-pyridylcarbonyl)-1,1-dioxoperhydro-1,4-thiazepin-7-yl]acetamide (70 mg)

NMR (DMSO-d$_6$, δ): 2.83–3.05 (4H, m), 3.50–4.13 (6H, m), 7.23, 7.25 (1H, d, J=4.5 Hz), 7.38–7.41 (1H, m), 7.46–7.51 (4H, m), 7.61–7.65 (1H, m), 7.65–7.76 (1H, m), 7.93–7.99 (1H, m), 8.59–8.63 (1H, m)

EXAMPLE 307

N-Hydroxy-2-[7-(5-(4-biphenylyl)-2-thienyl)-4-(2-pyridylcarbonyl)-1,1-dioxoperhydro-1,4-thiazepin-7-yl]acetamide (50 mg)

NMR (DMSO-d$_6$, δ): 2.90–3.14 (4H, m), 3.52–4.14 (6H, m), 7.24–7.27 (1H m), 7.36–7.40 (1H, m), 7.45–7.51 (2H, m), 7.52–7.56 (1H, m), 7.72–7.76 (6H, m), 8.70–8.73 (1H, m), 8.76–8.80 (1H, m), 8.90 (1H, d, J=8.5 Hz), 10.68 (1H, d, J=8.5 Hz)

EXAMPLE 308

N-Hydroxy-2-[7-(5-(4-biphenylyl)-2-thienyl)-4-(3-thienylcarbonyl)-1,1-dioxoperhydro-1,4-thiazepin-7-yl]acetamide (50 mg)

NMR (DMSO-d$_6$, δ): 2.72–3.15 (4H, m), 3.70–4.06 (6H, m), 7.27 (2H, d, J=4.5 Hz), 7.36–7.41 (1H, m), 7.46–7.51 (3H, m), 7.55 (1H, br), 7.63 (1H, br), 7.71–7.75 (6H, m), 7.85–7.87 (1H, m), 10.65–10.67 (1H, m)

EXAMPLE 309

N-Hydroxy-2-[7-(5-(4-biphenylyl)-2-thienyl)-4-(cyclopropylcarbonyl)-1,1-dioxoperhydro-1,4-thiazepin-7-yl]acetamide (50 mg)

NMR (DMSO-d$_6$, δ): 0.74–0.85 (4H, m), 1.86–1.90, 1.99–2.03 (1H, m), 2.73–3.15 (4H, m), 3.17–4.26 (6H, m), 7.22–7.26 (1H, m), 7.35–7.39 (1H, m), 7.46–7.50 (3H, m), 7.54–7.56 (1H, m), 7.71–7.75 (6H, m), 10.67–10.70 (1H, m)

EXAMPLE 310

N-Hydroxy-2-[7-(5-(4-biphenylyl)-2-thienyl)-4-(cyclobutylcarbonyl)-1,1-dioxoperhydro-1,4-thiazepin-7-yl]acetamide (50 mg)

NMR (DMSO-d$_6$, δ): 1.70–1.98 (3H, m), 2.05–2.80 (4H, m), 2.74–3.15 (4H, m), 3.50–4.01 (6H, m), 7.23–7.26 (1H, m), 7.35–7.40 (1H, m), 7.46–7.51 (2H, m), 7.54–7.55 (1H, m), 7.71–7.75 (6H, m), 10.67–10.73 (1H, m)

EXAMPLE 311

N-Hydroxy-2-[7-(5-(4-biphenylyl)-2-thienyl)-4-((2S)-2-hydroxy-2-phenylacetyl)-1,1-dioxoperhydro-1,4-thiazepin-7-yl]acetamide (50 mg)

NMR (DMSO-d$_6$, δ): 2.72–3.08 (4H, m), 3.56–4.15 (6H, m), 5.39 (1H, d, J=7.0 Hz), 7.12–7.22 (2H, m), 7.35–7.44 (5H, m), 7.45–7.54 (3H, m) 7.70–7.75 (6H, m)

EXAMPLE 312

N-Hydroxy-2-[7-(5-(4-methylphenyl)-2-thienyl)-4-(2-pyrazinylcarbonyl)-1,1-dioxoperhydro-1,4-thiazepin-7-yl]acetamide (60 mg)

NMR (DMSO-d$_6$, δ): 2.32 (3H, s), 2.74–4.15 (10H, m), 7.19–7.25 (3H, m), 7.40–7.45 (1H, m), 7.52–7.55 (2H, m), 8.69–8.72 (1H, m), 8.75–8.80 (1H, m), 8.90 (1H, d, J=8.5 Hz) MASS (ESI–): 499 (M–H)

EXAMPLE 313

N-Hydroxy-2-17-(5-(4-methylphenyl)-2-thienyl)-4-(2-thienylcarbonyl)-1,1-dioxoperhydro-1,4-thiazepin-7-yl]acetamide (50 mg)

NMR (DMSO-d$_6$, δ): 2.32 (3H, s), 2.74–3.15 (6H, m), 3.56–4.05 (4H, m), 7.15 (1H, br), 7.22 (2H, d, J=8.5 Hz), 7.41 (1H, d, J=4.5 Hz), 7.53 (2H, d, J=8.5 Hz), 7.80 (1H, br), 8.90 (1H, s) MASS (ESI–): 503 (M–H)

EXAMPLE 314

N-Hydroxy-2-[7-(5-(4-methylphenyl)-2-thienyl)-4-(3-thienylcarbonyl)-1,1-dioxoperhydro-1,4-thiazepin-7-yl]acetamide (55 mg)

NMR (DMSO-d$_6$, δ): 2.32 (3H, s), 2.73–3.08 (6H, m), 3.53–3.94 (4H, m), 7.20–7.25 (4H, m), 7.41 (1H, br), 7.52–7.63 (3H, m), 7.83–7.86 (1H, br), 8.85–8.90 (1H, br) MASS (ESI–): 503 (M–H)

EXAMPLE 315

N-Hydroxy-2-[7-(5-(4-ethoxyphenyl)-2-thienyl)-4-(2-thienylcarbonyl)-1,1-dioxoperhydro-1,4-thiazepin-7-yl]acetamide (33.1 mg)

NMR (DMSO-d$_6$, δ): 1.33 (3H, t, J=7.5 Hz), 2.60–3.20 (4H, m), 3.20–4.15 (8H, m), 6.96 (2H, d, J=8 Hz), 7.15 (1H, br s), 7.19 (1H, d, J=3 Hz), 7.33 (1H, d, J=3 Hz), 7.51 (1H, br s), 7.56 (2H, d, J=8 Hz), 7.80 (1H, d, J=3 Hz) MASS (ES–)(m/z): 533.22

EXAMPLE 316

N-Hydroxy-2-[7-(5-(4-ethoxyphenyl)-2-thienyl)-4-(3-thienylcarbonyl)-1,1-dioxoperhydro-1,4-thiazepin-7-yl]acetamide (37 mg)

NMR (DMSO-d$_6$, δ): 1.34 (3H, t, J=7.5 Hz), 2.70–3.16 (4H, m), 3.46–3.99 (6H, m), 4.05 (2H, q, J=7.5 Hz), 6.96 (2H, d, J=8 Hz), 7.17 (1H, d, J=3 Hz), 7.24 (1H, d, J=3 Hz), 7.34 (1H, d, J=3 Hz), 7.50–7.68 (3H, m), 7.81–7.90 (1H, m) MASS (ES–)(m/z): 533.23

EXAMPLE 317

N-Hydroxy-2-[7-(5-(4-ethoxyphenyl)-2-thienyl)-4-(2-pyridylcarbonyl)-1,1-dioxoperhydro-1,4-thiazepin-7-yl]acetamide (38 mg)

NMR (DMSO-d$_6$, δ): 1.34 (3H, t, J=7.5 Hz), 2.75–3.16 (4H, m), 3.45–4.16 (8H, m), 6.96 (2H, d, J=8 Hz), 7.15 (½H, d, J=3 Hz), 7.19 (½H, d, J=3 Hz), 7.31 (½H, d, J=3 Hz), 7.34 (½H, d, J=3 Hz), 7.46–7.66 (4H, m), 7.92–8.00 (1H, m), 8.56–8.64 (1H, m) MASS (ES+)(m/z): 530.28

EXAMPLE 318

N-Hydroxy-2-[7-(5-(4-ethoxyphenyl)-2-thienyl)-4-(2-pyrazinylcarbonyl)-1,1-dioxoperhydro-1,4-thiazepin-7-yl]acetamide (44 mg)

NMR (DMSO-d$_6$, δ): 1.34 (3H, t, J=7.5 Hz), 2.75–3.15 (4H, m), 3.45–4.00 (6H, m), 4.05 (2H, q, J=7.5 Hz), 6.96

(2H, d, J=8 Hz), 7.16 (½H, d, J=3 Hz), 7.20 (½H, d, J=3 Hz), 7.32 (½H, d, J=3 Hz), 7.35 (½H, d, J=3 Hz), 7.54 (1H, d, J=8 Hz), 7.58 (1H, d, J=8 Hz), 8.70 (1H, dd, J=8, 2 Hz), 8.75–8.80 (1H, m), 8.90 (1H, dd, J=8, 2 Hz) MASS (ES−)(m/z): 529.30

EXAMPLE 319

N-Hydroxy-2-[7-(5-(4-ethoxyphenyl)-2-thienyl)-4-[(2S)-2-hydroxy-2-phenylacetyl]-1,1-dioxoperhydro-1,4-thiazepin-7-yl]acetamide (45 mg)

NMR (DMSO-d$_6$, δ): 1.33 (3H, t, J=7.5 Hz), 2.60–3.10 (4H, m), 3.40–4.00 (6H, m), 4.05 (2H, q, J=7.5 Hz), 5.37 (½H, d, J=7 Hz), 5.46 (½H, s), 6.92–7.01 (2H, m), 7.03–7.16 (1H, m), 7.24–7.48 (6H, m), 7.48–7.61 (2H, m) MASS (ES−)(m/z): 557.32

EXAMPLE 320

N-Hydroxy-2-[(S)-4-(cyclobutylcarbonyl)-7-(5-(4-(5-oxazolyl)phenyl)-2-thienyl)-1,1-dioxoperhydro-1,4-thiazepin-7-yl]acetamide (31.6 mg)

NMR (DMSO-d$_6$, δ): 1.66–1.82 (1H, m), 1.82–2.02 (1H, m), 2.02–2.33 (5H, m), 2.60–3.15 (4H, m), 3.22–4.06 (6H, m), 7.20–7.27 (1H, m), 7.52–7.59 (1H, m), 7.70–7.81 (5H, m), 8.48 (1H, s), 8.85–8.96 (1H, m) MASS (ES−)(m/z): 528.29

EXAMPLE 321

N-Hydroxy-2-[(S)-4-(cyclopentylcarbonyl)-7-(5-(4-(5-oxazolyl)phenyl)-2-thienyl)-1,1-dioxoperhydro-1,4-thiazepin-7-yl]acetamide (14 mg)

NMR (DMSO-d$_6$, δ): 1.43–1.91 (8H, m), 2.59–3.17 (5H, m), 3.17–4.00 (5H, m), 4.00–4.20 (1H, m), 7.22 (½H, d, J=3 Hz), 7.26 (½H, d, J=3 Hz), 7.50–7.59 (1H, m), 7.59–7.84 (5H, m), 8.48 (1H, s), 8.91 (1H, br peak) MASS (ES−)(m/z): 542.35

EXAMPLE 322

N-Hydroxy-2-[(S)-4-(3,3-dimethylbutanoyl)-7-(5-[(4-(5-oxazolyl)phenyl)-2-thienyl)-1,1-dioxoperhydro-1,4-thiazepin-7-yl]acetamide (28 mg)

NMR (DMSO-d$_6$, δ): 1.01 (⅔H, s), 1.03 (⅔H, s), 2.24 (1H, s), 2.31 (1H, s), 2.56–3.16 (4H, m), 3.16–4.12 (6H, m), 7.23 (½H, d, J=3 Hz), 7.26 (½H, d, J=3 Hz), 7.53–7.60 (1H, m), 7.70–7.82 (5H, m), 8.48 (1H, s) MASS (ES−)(m/z): 544.31

EXAMPLE 323

N-Hydroxy-2-[(S)-4-(2-ethylbutanoyl)-7-(5-(4-(5-oxazolyl)phenyl)-2-thienyl)-1,1-dioxoperhydro-1,4-thiazepin-7-yl]acetamide (20 mg)

NMR (DMSO-d$_6$, δ): 0.75–0.95 (6H, m), 1.30–1.65 (4H, m), 2.56–3.18 (5H, m), 3.18–3.95 (5H, m), 3.95–4.20 (1H, m), 7.19–7.26 (1H, m), 7.50–7.59 (1H, m), 7.70–7.83 (5H, m), 8.46 (1H, s) MASS (ES+)(m/z): 546.36

EXAMPLE 324

N-Hydroxy-2-[(S)-4-(3-methyl-2-butenoyl)-7-(5-(4-(5-oxazolyl)phenyl)-2-thienyl)-1,1-dioxoperhydro-1,4-thiazepin-7-yl]acetamide (23.5 mg)

NMR (DMSO-d$_6$, δ): 1.79–1.91 (6H, m), 2.61–3.15 (4H, m), 3.50–3.93 (5H, m), 3.93–4.08 (1H, m), 5.90 (½H, s), 6.03 (½H, s), 7.20–7.35 (1H, m), 7.56 (1H, d, J=3 Hz), 7.70–7.82 (5H, m), 8.48 (1H, s), 8.90 (1H, br peak) MASS (ES+)(m/z): 530.29

EXAMPLE 325

N-Hydroxy-2-[7-(5-(4-ethylphenyl)-2-thienyl)-4-(2-pyridylcarbonyl)-1,1-dioxoperhydro-1,4-thiazepin-7-yl]acetamide (47.7 mg)

NMR (DMSO-d$_6$, δ): 1.20 (3H, t, J=7.5 Hz), 2.62 (2H, q, J=7.5 Hz), 2.75–3.16 (4H, m), 3.40–4.00 (5H, m), 4.00–4.16 (1H, m), 7.16–7.24 (1H, m), 7.24–7.32 (3H, m), 7.38–7.45 (1H, m), 7.48–7.70 (4H, m), 7.91–8.01 (1H, m), 8.56–8.66 (1H, m) MASS (ES+)(m/z): 514.32

EXAMPLE 326

To a mixture of N-(2-tetrahydropyranyloxy-2-[7-(5-(4-chlorophenyl)-2-thienyl)-1,1-dioxoperhydro-1,4-thiazepin-7-yl]acetamide (90 mg) and pyridine (0.5 ml) in chloroform (3 ml) was added 2-methoxybenzoyl chloride (37 mg) and the mixture was stirred at ambient temperature for 3 hours. The mixture was pertitioned between water and chloroform. The organic layer was separated, washed with 5% citric acid water solution, water, saturated sodium bicarbonate solution and brine. To the reaction mixture were added 4N hydrogen chloride-ethyl acetate solution (0.5 ml), chloroform (1 ml) and methanol (1.5 ml) and the reaction mixture was stirred at ambient temperature for 30 minutes. After evaporation of solvent, the residue was purified by HPLC (0.1% trifluoroacetic acid in 20% acetonitrile-water ~0.1% trifluoroacetic acid in 80% acetonitrile-water) to give N-hydroxy-2-[7-(5-(4-chlorophenyl)-2-thienyl)-4-(2-methoxybenzoyl)-1,1-dioxoperhydro-1,4-thiazepin-7-yl]acetamide (54 mg) as a pale yellow powder.

NMR (DMSO-d$_6$, δ): 2.56–4.39 (13H, m), 6.95–7.32 (4H, m), 7.36–7.56 (4H, m), 7.62–7.74 (2H, m) MASS (ES+)(m/z): 549.17, 551.21

The following compounds were obtained in a similar manner to that of Example 326.

EXAMPLE 327

N-Hydroxy-2-(7-(5-(4-ethylphenyl)-2-thienyl)-4-(4-morpholinylcarbonyl)-1,1-dioxoperhydro-1,4-thiazepin-7-yl]acetamide (44.2 mg)

NMR (DMSO-d$_6$, δ): 1.20 (3H, t, J=7.5 Hz), 2.61 (2H, q, J=7.5 Hz), 2.67–3.19 (10H, m), 3.52–3.95 (8H, m), 7.16 (1H, d, J=3 Hz), 7.26 (2H, d, J=8 Hz), 7.41 (1H, d, J=3 Hz), 7.55 (2H, d, J=8 Hz), 10.62 (1H, s) MASS (ES+)(m/z): 522.35

EXAMPLE 328

N-Hydroxy-2-[7-(5-(4-ethylphenyl)-2-thienyl)-4-(methylsulfonyl)-1,1-dioxoperhydro-1,4-thiazepin-7-yl]acetamide (37.6 mg)

NMR (DMSO-d$_6$, δ): 1.20 (3H, t, J=7.5 Hz), 2.64 (2H, q, J=7.5 Hz), 2.86–2.96 (2H, m), 3.00 (3H, s), 3.06–3.21 (2H, m), 3.41–3.89 (5H, m), 3.79–4.03 (1H, m), 7.20 (1H, d, J=3 Hz), 7.26 (2H, d, J=8 Hz), 7.41 (1H, d, J=3 Hz), 7.55 (2H, d, J=8 Hz), 10.70 (1H, s) MASS (ES−)(m/z): 485.24

EXAMPLE 329

N-Hydroxy-2-[7-(5-(4-ethylphenyl)-2-thienyl)-4-(3-pyridylsulfonyl)-1,1-dioxoperhydro-1,4-thiazepin-7-yl]acetamide (36.7 mg)

NMR (DMSO-d$_6$, δ): 1.20 (3H, t, J=7.5 Hz), 2.62 (2H, q, J=7.5 Hz), 2.75–3.01 (2H, m), 3.12 (2H, s), 3.61–3.80 (5H, m), 3.94–4.06 (1H, m), 7.16 (1H, d, J=3 Hz), 7.26 (2H, d, J=8 Hz), 7.40 (1H, d, J=3 Hz), 7.55 (2H, d, J=8 Hz), 7.70 (1H, dd, J=8, 5 Hz), 8.26 (1H, dd, J=8, 2 Hz), 8.90 (1H, dd,

J=5, 2 Hz), 9.01 (1H, d, J=2 Hz), 10.70 (1H, s) MASS (ES+)(m/z): 550.25

EXAMPLE 330

N-Hydroxy-2-[7-(5-(4-ethylphenyl)-2-thienyl)-4-ethylsulfonyl-1,1-dioxoperhydro-1,4-thiazepin-7-yl]acetamide (25.7 mg)

NMR (DMSO-d$_6$, δ): 1.14–1.27 (6H, m), 2.61 (2H, q, J=7.5 Hz), 2.85–2.96 (2H, m), 3.06–3.25 (4H, m), 3.25–3.84 (5H, m), 3.91–4.09 (1H, m), 7.20 (1H, d, J=3 Hz), 7.26 (2H, d, J=8 Hz), 7.41 (1H, d, J=3 Hz), 7.56 (2H, d, J=8 Hz), 8.91 (1H, s) MASS (ES–)(m/z): 499.22

EXAMPLE 331

N-Hydroxy-2-[7-(5-(4-ethylphenyl)-2-thienyl)-4-(n-propylsulfonyl)-1,1-dioxoperhydro-1,4-thiazepin-7-yl]acetamide (25.2 mg)

NMR (DMSO-d$_6$, δ): 1.00 (3H, t, J=7.5 Hz), 1.20 (3H, t, J=7.5 Hz), 1.60–1.78 (2H, m), 2.60 (2H, q, J=7.5 Hz), 2.85–2.95 (2H, m), 3.04–3.34 (9H, m), 3.34–4.16 (1H, m), 7.19 (1H, d, J=3 Hz), 7.26 (2H, d, J=8 Hz), 7.41 (1H, d, J=3 Hz), 7.56 (2H, d, J=8 Hz), 8.94 (1H, s) MASS (ES–)(m/z): 513.31

EXAMPLE 332

N-Hydroxy-2-[7-(5-(4-chlorophenyl)-2-thienyl)-4-(3-pyridylsulfonyl)-1,1-dioxoperhydro-1,4-thiazepin-7-yl]acetamide (25 mg)

NMR (DMSO-d$_6$, δ): 2.75–3.21 (6H, m), 3.50–3.82 (3H, m), 3.93–4.08 (1H, m), 7.20 (1H, d, J=3 Hz), 7.45–7.54 (3H, m), 7.61–7.76 (3H, m), 8.26 (1H, d, J=8 Hz), 8.90 (1H, d, J=5 Hz), 9.01 (1H, br s) MASS (ES+)(m/z): 556.14, 558.15

EXAMPLE 333

N-Hydroxy-2-[(S)-7-(5-(4-(5-oxazolyl)phenyl)-2-thienyl)-1,1-dioxoperhydro-4-pivaloyl-1,4-thiazepin-7-yl]acetamide (72 mg)

NMR (DMSO-d$_6$, δ): 1.23 (9H, s), 2.71–3.12 (4H, m), 2.98–3.96 (6H, m), 7.24 (1H, d, J=4 Hz), 7.57 (1H, d, J=4 Hz), 7.76 (1H, s), 7.78 (4H, s), 8.48 (1H, s), 8.91 (1H, s), 10.67 (1H, s) MASS (ES–): 530 (M–H)

EXAMPLE 334

N-Hydroxy-2-[4-[(N,N-dimethylamino)sulfonyl]-7-(5-(4-methoxyphenyl)-2-thienyl)-1,1-dioxoperhydro-1,4-thiazepin-7-yl)acetamide (28 mg)

NMR (DMSO-d$_6$, δ): 2.75 (6H, s), 2.85–2.94 (2H, m), 3.11 (2H, s), 3.50–3.65 (4H, m), 3.65–3.76 (1H, m), 3.79 (3H, s), 3.90–4.05 (1H, m), 6.99 (2H, d, J=8 Hz), 7.16 (1H, d, J==3 Hz), 7.34 (1H, d, J=3 Hz), 7.57 (2H, d, J=8 Hz) MASS (ES–) (m/z): 516.15

EXAMPLE 335

N-Hydroxy-2-[7-(5-(4-methoxyphenyl)-2-thienyl)-4-(1-pyrrolidinylsulfonyl)-1,1-dioxoperhydro-1,4-thiazepin-7-yl]acetamide (25 mg)

NMR (DMSO-d$_6$, δ):1.78–1.94 (4H, m), 2.80–2.96 (2H, m), 3.05–3.25 (6H, m), 3.45–3.86 (8H, m), 3.86–4.05 (1H, m), 6.99 (2H, d, J=8 Hz), 7.15 (1H, d, J=3 Hz), 7.34 (1H, d, J=3 Hz), 7.56 (2H, d, J=8 Hz), 8.93 (1H, br s) MASS (ES–)(m/z): 542.19

EXAMPLE 336

N-Hydroxy-2-[4-(benzylsulfonyl)-7-(5-(4-methoxyphenyl)-2-thienyl)-1,1-dioxoperhydro-1,4-thiazepin-7-yl]acetamide (36 mg)

NMR (DMSO-d$_6$, δ): 2.77–2.91 (2H, m), 3.01–3.12 (2H, m), 3.12–3.59 (5H, m), 3.79 (3H, s), 3.81–3.99 (1H, m), 4.48–4.61 (2H, m), 6.99 (2H, d, J=8 Hz), 7.14 (1H, d, J=3 Hz), 7.32 (1H, d, J=3 Hz), 7.35–7.47 (5H, m), 7.56 (2H, d, J=8 Hz), 8.91 (1H, br s), 10.65 (1H, br s) MASS (ES–)(m/z): 563.28

EXAMPLE 337

N-Hydroxy-2-[7-(5-(4-biphenylyl)-2-thienyl)-4-(4-morpholinylcarbonyl)-1,1-dioxoperhydro-1,4-thiazepin-7-yl]acetamide (50 mg)

NMR (DMSO-d$_6$, δ): 2.73–3.12 (8H, m), 3.44–3.66 (8H, m), 3.81–3.89 (2H, m), 7.21 (1H, d, J=4.5 Hz), 7.35–7.40 (2H, m), 7.46–7.50 (2H, m), 7.53 (1H, d, J=4.5 Hz), 7.71–7.74 (5H, m), 8.92 (1H, s), 10.65 (1H, s) MASS (ESI–): 568 (M–H)

EXAMPLE 338

N-Hydroxy-2-[7-(5-(4-biphenylyl)-2-thienyl)-4-(methylsulfonyl)-1,1-dioxoperhydro-1,4-thiazepin-7-yl]acetamide (50 mg)

NMR (DMSO-d$_6$, δ): 2.92–2.98 (2H, m), 3.01 (3H, s), 3.16–3.20 (2H, m), 3.45–3.75 (5H, m), 3.92–4.00 (1H, m), 7.25 (1H, d, J=4.5 Hz), 7.38–7.40 (1H, m), 7.46–7.50 (2H, m), 7.55 (1H, d, J=4.5 Hz), 7.71–7.75 (6H, m), 8.95 (1H, s), 10.72 (1H, br)

EXAMPLE 339

N-Hydroxy-2-[7-(5-(4-biphenylyl)-2-thienyl)-4-(3-pyridylsulfonyl)-1,1-dioxoperhydro-1,4-thiazepin-7-yl]acetamide (50 mg)

NMR (DMSO-d$_6$, δ): 2.73–3.14 (4H, m), 3.48–3.78 (5H, m), 3.96–4.05 (1H, m), 7.21 (1H, d, J=4.5 Hz), 7.37–7.40 (2H, m), 7.45–7.50 (2H, m), 7.54 (1H, d, J=4.5 Hz), 7.71–7.74 (6H, m), 8.27, 8.57 (2H, d, J=8.5 Hz), 8.90, 9.03 (2H, br), 10.72 (1H, s)

EXAMPLE 340

N-Hydroxy-2-[7-(5-(4-biphenylyl)-2-thienyl)-4-(2-dimethylaminosulfonyl)-1,1-dioxoperhydro-1,4-thiazepin-7-yl]acetamide (50 mg)

NMR (DMSO-d$_6$, δ): 2.76 (6H, s), 2.93 (2H, br), 3.15 (2H, br), 3.56–3.76 (5H, m), 3.94–4.02 (1H, m), 7.24 (1H, d, J=4.5 Hz), 7.38–7.41 (1H, m), 7.46–7.51 (3H, m), 7.55 (1H, d, J=4.5 Hz), 7.71–7.75 (5H, m), 8.96 (1H, s), 10.72 (1H, br) MASS (ESI–): 562 (M–H)

EXAMPLE 341

N-Hydroxy-2-[7-(5-(4-methylphenyl)-2-thienyl)-4-methanesulfonyl-1,1-dioxoperhydro-1,4-thiazepin-7-yl]acetamide (70 mg)

NMR (DMSO-d$_6$, δ): 2.32 (3H, s), 2.88–2.94 (3H, m), 3.00 (3H, s), 3.15 (2H, br), 3.51–3.75 (4H, m), 3.90–4.00 (1H, m), 7.19–7.25 (3H, m), 7.42 (1H, d, J=4.5 Hz), 7.54 (2H, d, J=8.5 Hz), 10.7 (1H, s) MASS (ESI–): 471 (M–H)

EXAMPLE 342

N-Hydroxy-2-((S)-4-(4-morpholinylsulfonyl)-7-(5-(4-(5-oxazolyl)phenyl)-2-thienyl)-1,1-dioxoperhydro-1,4-thiazepin-7-yl)acetamide (35 mg)

NMR (DMSO-d$_6$, δ): 2.85–2.99 (2H, m), 2.99–3.20 (6H, m), 3.53–3.81 (9H, m), 3.93–4.07 (1H, m), 7.24 (1H, d, J=3 Hz), 7.57 (1H, d, J=3 Hz), 7.71–7.84 (5H, m), 8.48 (1H, s), 8.94 (1H, s), 10.70 (1H, s) MASS (ES–)(m/z): 595.19

EXAMPLE 343

N-Hydroxy-2-[(S)-7-(5-(4-(5-oxazolyl)phenyl)-2-thienyl)-1,1-dioxoperhydro-4-(1-pyrrolidinylsulfonyl)-1,4-thiazepin-7-yl]acetamide (53.8 mg)

NMR (DMSO-d$_6$, δ): 1.80–1.96 (4H, m), 2.85–3.01 (2H, m), 3.01–3.25 (6H, m), 3.25–3.89 (5H, m), 3.89–4.04 (1H, m), 7.24 (1H, d, J=3 Hz), 7.56 (1H, d, J=3 Hz), 7.73–7.85 (5H, m), 8.48 (1H, s), 10.73 (1H, s) MASS (ES−) (m/z): 579.16

EXAMPLE 344

N-Hydroxy-2-[(S)-7-(5-(4-(5-oxazolyl)phenyl)-2-thienyl)-1,1-dioxoperhydro-4-(n-propylsulfonyl)-1,4-thiazepin-7-yl]acetamide (31.8 mg)

NMR (DMSO-d$_6$, δ): 0.94–1.06 (3H, m), 1.61–1.78 (2H, m), 2.85–2.99 (2H, m), 2.99–3.24 (4H, m), 3.45–3.66 (4H, m), 3.66–3.83 (1H, m), 3.91–4.09 (1H, m), 7.25 (1H, d, J=3 Hz), 7.55 (1H, d, J=3 Hz), 7.68–7.85 (5H, m), 8.48 (1H, s), 8.93 (1H, s), 10.70 (1H, s) MASS (ES−)(m/z): 552.15

EXAMPLE 345

N-Hydroxy-2-[(S)-4-(2,2-dimethylpropanoyl)-7-(5-(4-(5-oxazolyl)phenyl)-2-thienyl)-1,1-dioxoperhydro-1,4-thiazepin-7-yl]acetamide (16.5 mg)

NMR (DMSO-d$_6$, δ): 1.22 (9H, s), 2.74–3.14 (4H, m), 3.41–3.95 (6H, m), 7.23 (1H, d, J=3 Hz), 7.56 (1H, d, J=3 Hz), 7.71–7.82 (5H, m), 8.48 (1H, s), 8.90 (1H, s) MASS (ES−)(m/z): 530.19

EXAMPLE 346

N-Hydroxy-2-[(S)-7-(5-(4-(5-oxazolyl)phenyl)-2-thienyl)-1,1-dioxoperhydro-4-(1-pyrrolidinylcarbonyl)-1,4-thiazepin-7-yl]acetamide (17.1 mg)

NMR (DMSO-d$_6$, δ): 1.61–1.89 (4H, m), 2.75–3.94 (14H, m), 7.21 (1H, d, J=3 Hz), 7.55 (1H, d, J=3 Hz), 7.71–7.86 (5H, m), 8.48 (1H, s), 8.91 (1H, s) MASS (ES+)(m/z): 545.27

EXAMPLE 347

N-Hydroxy-2-[(S)-7-(5-(4-(5-oxazolyl)phenyl)-2-thienyl)-1,1-dioxoperhydro-4-(1-piperidinylcarbonyl)-1,4-thiazepin-7-yl]acetamide (25.9 mg)

NMR (DMSO-d$_6$, δ): 1.35–1.60 (6H, m), 2.63–3.15 (8H, m), 3.15–3.75 (4H, m), 7.75–3.94 (2H, m), 7.20 (1H, d, J=3 Hz), 7.55 (1R, d, J=3 Hz), 7.70–7.84 (5H, m), 8.48 (1H, s), 8.89 (1H, s), 10.62 (1H, s) MASS (ES+)(m/z): 559.30

EXAMPLE 348

N-Hydroxy-2-[7-(5-(4-ethylphenyl)-2-thienyl)-4-(2-methoxybenzoyl)-1,1-dioxoperhydro-1,4-tiazepin-7-yl]acetamide (43.8 mg)

NMR (DMSO-d$_6$, δ): 1.115–1.26 (3H, m), 2.55–2.66 (2H, m), 2.66–3.25 (4H, m), 3.25–4.36 (9H, m), 6.96–7.32 (6H, m), 7.33–7.46 (2H, m), 7.46–7.61 (2H, m), 8.25–8.99 (1H, m) MASS (ES+) (m/z): 543.26

EXAMPLE 349

To a mixture of N-(2-tetrahydropyranyloxy)-2-[7-(5-(4-ethylphenyl)-2-thienyl)-1,1-dioxoperhydro-1,4-thiazepin-7-yl]acetamide (80 mg) in chloroform (3 ml) was added isopropyl isocyanate (16.6 mg) and the mixture was stirred at ambient temperature for 3 hours. The mixture was partitioned between water and chloroform. The organic layer was separated, washed with 5% citric acid water solution, water, saturated sodium bicarbonate solution and brine. To the reaction mixture were added 4N hydrogen chloride ethyl acetate solution (0.5 ml), chloroform (1 ml) and methanol (1.5 ml) and the reaction mixture was stirred at ambient temperature for 30 minutes. After evaporation of solvent, the residue was purified by HPLC (0.1% trifluoroacetic acid in 20% acetonitrile-water ~0.1% trifluoroacetic acid in 80% acetonitrile-water) to give N-hydroxy-2-[7-(5-(4-ethylphenyl)-2-thienyl)-4-isopropylcarbamoyl-1,1-dioxoperhydro-1,4-thiazepin-7-yl]acetamide (36 mg) as a pale yellow powder.

NMR (DMSO-d$_6$, δ): 1.04–1.13 (6H, m), 1.20 (3H, t, J=7.5 Hz), 2.52 (2H, q, J=7.5 Hz), 2.68–2.94 (3H, m), 3.10 (1H, d, J=15 Hz), 3.45–3.86 (7H, m), 6.20 (1H, d, J=8 Hz), 7.16 (1H, d, J=3 Hz), 7.25 (2H, d, J=8 Hz), 7.40 (1H, d, J=3 Hz), 7.54 (2H, d, J=8 Hz), 10.65 (1H, s) MASS (ES+)(m/z): 494.32

The following compounds were obtained in a similar manner to that of Example 349.

EXAMPLE 350

N-Hydroxy-2-[7-(5-(4-methylthiophenyl)-2-thienyl)-4-cyclohexylaminocarbonyl-1,1-dioxoperhydro-1,4-thiazepin-7-yl]acetamide (25 mg)

NMR (DMSO-d$_6$, δ): 1.05–1.28, 1.55–1.80 (11H, m), 2.50 (3H, s), 2.70–3.25 (6H, m), 3.50–3.75 (4H, m), 6.20 (1H, d, J=7.5 Hz)., 7.16 (1H, d, J=4.5 Hz), 7.30 (2H, d, J=8.5 Hz), 7.42 (1H, d, J=4.5 Hz), 7.58 (2H, d, J=8.5 Hz), 8.90 (1H, s) MASS (ESI−): 550 (M−H)

EXAMPLE 351

N-Hydroxy-2-[7-(5-(4-methylthiophenyl)-2-thienyl)-4-tert-butylaminocarbonyl-1,1-dioxoperhydro-1,4-thiazepin-7-yl]acetamide (35 mg)

NMR (DMSO-d$_6$, δ): 1.27 (9H, s), 2.51 (3H, s), 2.75–3.12 (6H, m), 3.48–3.83 (4H, m), 5.71 (1H, s), 7.16 (1H, d, J=4.5 Hz), 7.29 (2H, d, J=8.5 Hz), 7.42 (1H, d, J=4.5 Hz), 7.59 (2H, d, J=8.5 Hz), 8.91 (1H, s) MASS (ESI−): 524 (M−H)

EXAMPLE 352

N-Hydroxy-2-[7-(S-(4-biphenylyl)-2-thienyl)-4-(isopropylaminocarbonyl)-1,1-dioxoperhydro-1,4-thiazepin-7-yl]acetamide (50 mg)

NMR (DMSO-d$_6$, δ): 1.07–1.10 (6H, m), 2.73–3.13 (5H, m), 3.48–3.84 (6H, m), 6.21 (1H, d, J=7.5 Hz), 7.21 (1H, d, J=4.5 Hz), 7.37–7.40 (1H, m), 7.46–7.51 (2H, m), 7.53 (1H, d, J=4.5 Hz), 7.71–7.74 (6H, m), 8.91 (1H, br), 10.66 (1H, br) MASS (ESI−): 540 (M−H)

The following compounds were obtained in a similar manner to that of Example 290.

EXAMPLE 353

N-Hydroxy-2-[7-(5-(4-ethylphenyl)-2-thienyl)-4-[(1-methyl-1H-imidazol-2-yl)carbonyl]-1,1-dioxoperhydro-1,4-thiazepin-7-yl]acetamide (36.4 mg)

NMR (DMSO-d$_6$, δ): 1.20 (3H, t, J=7.5 Hz), 2.63 (2H, q, J=7.5 Hz), 2.75–3.14 (4H, m), 3.14–4.42 (9H, m), 7.09–7.15 (1H, m), 7.20 (1H, d, J=3 Hz), 7.26 (2H, d, J=8 Hz), 7.38–7.45 (2H, m), 7.345 (2H, d, J=8 Hz) MASS (ES+)(m/z): 517.26

EXAMPLE 354

N-Hydroxy-2-[7-(5-(4-chlorophenyl)-2-thienyl)-4-((3-thienylacetyl)carbonyl)-1,1-dioxoperhydro-1,4-thiazepin-7-yl]acetamide (27 mg)

NMR (DMSO-d₆, δ): 2.63–3.46 (6H, m), 3.46–4.11 (6H, m), 6.97–7.06 (1H, m), 7.19–7.24 (1H, m), 7.25–7.33 (1H, m), 7.44–7.55 (3H, m), 763–7.72 (2H, m), 8.90 (1H, s) MASS (ES+)(m/z): 539.19, 541.22

EXAMPLE 355

N-Hydroxy-2-[7-(5-(4-chlorophenyl)-2-thienyl)-4-(3-pyridylcarbonyl)-1,1-dioxoperhydro-1,4-thiazepin-7-yl]acetamide (33 mg)

NMR (DMSO-d₆, δ): 2.71–3.26 (6H, m), 3.45–4.21 (4H, m), 7.16–7.29 (1H, m), 7.43–7.61 (4H, m), 7.61–7.74 (2H, m), 7.90–7.01 (1H, m), 8.70 (2H, br s) MASS (ES+)(m/z): 520.14, 522.13

EXAMPLE 356

N-Hydroxy-[(S)-4-((S)-2-amino-3,3-dimethylbutyryl)-7-(5-(4-ethylphenyl)-2-thienyl)-1,1-dioxoperhydro-1,4-thiazepin-7-yl]acetamide hydrochloride (46 mg) was obtained from N-(2-tetrahydropyranyloxy)-2-[(S)-7-(5-(4-ethylphenyl)-2-thienyl)-1,1-dioxoperhydro-1,4-thiazepin-7-yl]acetamide (270 g) and (S)-2-(N-tert-butoxycarbonylamino)-3,3-dimethylbutyric acid in a similar manner to that of Example 290.

NMR (DMSO-d₆, δ): 1.03 (9H, s), 1.19 (3H, t, J=8 Hz), 2.62 (2H, q, J=8 Hz), 2.78–4.48 (11H, m), 7.16–7.23 (1H, m), 7.27 (2H, d, J=7 Hz), 7.36–7.46 (1H, m), 7.50–7.62 (2H, m), 8.10–8.26 (1H, m), 8.39 (1H, br), 10.68–10.81 (1H, m) MASS (ESI–): 550 (M–H)

The following compounds were obtained in a similar manner to that of Example 39.

EXAMPLE 357

N-(2-Tetrahydropyranyloxy)-2-[4-methanesulfonyl-7-(5-(2-(methylcarbamoyl)benzofuran-5-yl)-2-thienyl)-1,1-dioxoperhydro-1,4-thiazepin-7-yl]acetamide (140 mg)

NMR (CDCl₃, δ): 1.46–1.90 (6H, br), 2.93 (3H, s), 2.88–3.03 (1H, br), 3.07 (3H, m), 3.14–3.35 (3H, br), 3.42–3.68 (5H, br), 3.76–3.93 (2H, br), 4.10–4.28 (1H, br), 4.68, 4.93 (1H, br), 6.93, 6.96, 7.04 (1H, d, J=3 Hz), 7.18–7.30 (2H, m), 7.42–7.48 (2H, m), 7.56–7.64 (1H, br), 7.83 (1H, m), 8.75 (1H, br) MASS (m/z): 638 (M–H)

EXAMPLE 358

N-(2-Tetrahydropyranyloxy)-2-[4-ethylaminocarbonyl-7-(5-(2-(methylcarbamoyl)benzofuran-5-yl)-2-thienyl)-1,1-dioxoperhydro-1,4-thiazepin-7-yl]acetamide (84.0 mg)

NMR (DMSO-d₆, δ): 1.03 (3H, t, J=7 Hz), 1.38–1.77 (6H, br), 2.80, 2.81 (3H, s), 2.88–3.28 (4H, m), 3.35–3.97 (10H, br), 4.52, 4.78 (1H, br), 6.53 (1H, br), 7.22, 7.24 (1H, d, J=3 Hz), 7.46, 7.48 (1H, d, J=3 Hz), 7.53 (1H, s), 7.67–7.78 (2H, m), 8.03 (1H, s), 8.73 (1H, br) MASS (m/z): 631 (M–H)

EXAMPLE 359

N-(2-Tetrahydropyranyloxy)-2-[7-(5-(2-(hydroxymethyl)benzofuran-5-yl)-2-thienyl)-4-methoxycarbonyl]-1,1-dioxoperhydro-1,4-thiazepin-7-yl]acetamide (195 mg)

NMR (CDCl₃, δ): 1.40–1.85 (6H, br), 2.70–4.15 (12H, br), 3.73, 3.80 (3H, s), 4.72–4.91 (3H, m), 6.55, 6.67 (1H, br), 6.77, 6.81, 6.95 (1H, d, J=3 Hz), 7.17–7.33 (1H, br), 7.42–7.56 (2H, br), 7.70–7.77 (1H, br), 8.21, 8.38 (1H, br) MASS (m/z): 591 (M–H)

EXAMPLE 360

N-(2-Tetrahydropyranyloxy)-2-[4-methoxycarbonyl-7-(5-(4-(5-oxazolyl)phenyl)-2-thienyl)-1,1-dioxoperhydro-1,4-thiazepin-7-yl]acetamide (280 mg)

NMR (CDCl₃, δ): 1.42–1.88 (6H, br), 2.68–4.22 (12H, br), 3.73, 3.77 (3H, s), 4.55–4.66, 4.88 (1H, br), 7.20–7.30 (2H, br), 7.39 (1H, s), 7.58–7.72 (4H, br), 7.94 (1H, s), 8.52–8.73 (1H, br) MASS (m/z): 588 (M–H)

EXAMPLE 361

N-(2-Tetrahydropyranyloxy)-2-[4-methanesulfonyl-7-(5-(4-(5-oxazolyl)phenyl)-2-thienyl)-1,1-dioxoperhydro-1,4-thiazepin-7-yl]acetamide (215 mg)

NMR (CDCl₃, δ): 1.46–1.93 (6H, br), 2.93 (3H, s), 2.88–3.03 (1H, br), 3.14–3.36 (3H, br), 3.37–3.66 (5H, br), 3.75–3.96 (2H, br), 4.08–4.25 (1H, br), 4.68, 4.93 (1H, br), 7.22–7.32 (2H, m), 7.39 (1H, s), 7.65 (4H, br), 7.94 (1H, s), 8.66–8.75 (1H, br) MASS (m/z): 608 (M–H)

EXAMPLE 362

N-(2-Tetrahydropyranyloxy)-2-[4-ethylaminocarbonyl-7-(5-(4-(5-oxazolyl)phenyl)-2-thienyl)-1,1-dioxoperhydro-1,4-thiazepin-7-yl]acetamide (142 mg)

NMR (CDCl₃, δ): 1.25 (3H, t, J=7 Hz), 1.45–1.93 (6H, br), 2.82–4.32 (12H, br), 3.49 (2H, br), 4.61, 4.75–4.92 (1H, br), 7.23–7.32 (2H, m), 7.38 (1H, s), 7.64 (4H, m), 7.94 (1H, s), 8.96, 9.03 (1H, br) MASS (m/z): 601(M–H)

EXAMPLE 363

N-(2-Tetrahydropyranyloxy)-2-[4-(2-methoxybenzoyl)-7-(5-(4-(5-oxazolyl)phenyl)-2-thienyl)-1,1-dioxoperhydro-1,4-thiazepin-7-yl]acetamide (200 mg)

NMR (CDCl₃, δ): 1.40–1.90 (6H, br), 2.75–4.20 (12H, br), 3.86 (3H, s), 4.45–4.70 (1H, br), 6.83–7.35 (6H, br), 7.38, 7.39 (1H, s), 7.48–7.70 (4H, br), 7.94 (1H, s), 8.43, 8.60 (1H, br) MASS (m/z): 664 (M–H)

EXAMPLE 364

N-(2-Tetrahydropyranyloxy)-2-[4-(3-methoxybenzoyl)-7-(5-(4-(5-oxazolyl)phenyl)-2-thienyl)-1,1-dioxoperhydro-1,4-thiazepin-7-yl]acetamide (237 mg)

NMR (CDCl₃, δ): 1.40–1.95 (6H, br), 2.73–4.36 (12H, br), 3.77, 3.82 (3H, s), 4.46, 4.62, 4.75, 4.88 (1H, br), 6.75–7.00 (4H, br), 7.08–7.34 (2H, br), 7.38 (1H, s), 7.56–7.70 (4H, br), 7.94 (1H, s), 8.36, 8.42, 8.47, 8.55 (1H, br) MASS (m/z): 664 (M–H)

EXAMPLE 365

N-(2-Tetrahydropyranyloxy)-2-[4-(4-methoxybenzoyl)-7-(5-(4-(5-oxazolyl)phenyl)-2-thienyl)-1,1-dioxoperhydro-1,4-thiazepin-7-yl]acetamide (214 mg)

NMR (CDCl₃, δ): 1.40–1.90 (6H, br), 2.72–4.35 (12H, br), 3.86 (3H, s), 4.45, 4.55–4.75, 4.85 (1H, br), 6.84–6.96 (2H, d, J=8 Hz), 7.20–7.45 (4H, br), 7.38 (1H, s), 7.58–7.72 (4H, br), 7.95 (1H, s), 8.42–8.52, 8.54–8.62 (1H, br) MASS (m/z): 664 (M–H)

EXAMPLE 366

N-(2-Tetrahydropyranyloxy)-2-[7-(5-(4-(5-oxazolyl)phenyl)-2-thienyl)-4-phenylsulfonyl-1,1-dioxoperhydro-1,4-thiazepin-7-yl]acetamide (190 mg)

NMR (CDCl₃, δ): 1.40–1.90 (6H, br), 2.75–4.20 (12H, br), 4.75, 4.98 (1H, br), 7.20–7.30 (2H, br), 7.38 (1H, s), 7.45–7.83 (9H, m), 7.94 (1H, s), 8.70 (1H, br) MASS (m/z): 670 (M–H)

EXAMPLE 367

N-(2-Tetrahydropyranyloxy)-2-[7-(5-(4-(5-oxazolyl)phenyl)-2-thienyl)-4-phenylaminocarbonyl-1,1-dioxoperhydro-1,4-thiazepin-7-yl]acetamide (55.0 mg)

NMR (CDCl$_3$, δ): 1.44–1.90 (6H, br), 2.84–4.40 (12H, br), 4.59, 4.81 (1H, br), 6.97–7.42 (7H, m), 7.37 (1H, s), 7.43–7.66 (4H, m), 7.92 (1H, s), 8.77, 8.82 (1H, br) MASS (m/z): 649 (M−H)

EXAMPLE 368

N-(2-Tetrahydropyranyloxy)-2-[4-(2-methylbenzoyl)-7-(5-(4-(5-oxazolyl)phenyl)-2-thienyl)-1,1-dioxoperhydro-1,4-thiazepin-7-yl]acetamide (137 mg)

NMR (CDCl$_3$, δ): 1.40–1.90 (6H, br), 1.95 (3H, br), 2.67–4.31 (12H, br), 4.43–4.89 (1H, br), 7.15–7.35 (6H, br), 7.40 (1H, s), 7.58–7.74 (4H, br), 7.95 (1H, s), 8.39, 8.49 (1H, s) MASS (m/z): 648 (M−H)

EXAMPLE 369

N-(2-Tetrahydropyranyloxy)-2-[7-(5-(4-(5-oxazolyl)phenyl)-2-thienyl)-4-(4-pyridylcarbonyl)-1,1-dioxoperhydro-1,4-thiazepin-7-yl]acetamide (190 mg)

NMR (CDCl$_3$, δ): 1.40–1.88 (6H, br), 2.73–4.00 (11H, br), 4.23–4.52, 4.58, 4.76, 4.87 (2H, br), 7.13–7.34 (4H, br), 7.39 (1H, s), 7.55–7.72 (4H, br), 7.93 (1H, s), 8.33, 8.40, 8.48, 8.54 (1H, br), 8.60–9.73 (2H, br) MASS (m/z): 635 (M−H)

EXAMPLE 370

N-(2-Tetrahydropyranyloxy)-2-[7-(5-(4-(5-oxazolyl)phenyl)-2-thienyl)-4-(3-(4-pyridyl)acryloyl)-1,1-dioxoperhydro-1,4-thiazepin-7-yl]acetamide (113 mg)

NMR (CDCl$_3$, δ): 1.40–1.85 (6H, br), 2.76–4.10 (11H, br), 4.23–4.57, 4.54, 4.73 (2H, br), 6.98–7.30 (4H, br), 7.32–7.44 (2H, br), 7.40 (1H, s), 7.53–7.70 (4H, m), 7.95 (1H, s), 8.60–8.68 (3H, br) MASS (m/z): 661 (M−H)

EXAMPLE 371

N-(2-Tetrahydropyranyloxy)-2-[7-(5-(4-(5-oxazolyl)phenyl)-2-thienyl)-4-(2-pyridylacetyl)-1,1-dioxoperhydro-1,4-thiazepin-7-yl]acetamide (125 mg)

NMR (CDCl$_3$, δ): 1.35–1.90 (6H, br), 2.80–4.20 (12H, br), 4.10–4.58, 4.73, 5.02 (3H, br), 7.00–7.43 (5H, br), 7.38 (1H, s), 7.55–7.80 (4H, br), 7.94 (1H, s), 8.39–8.60 (2H, br) MASS (m/z):. 649 (M−H)

EXAMPLE 372

N-(2-Tetrahydropyranyloxy)-2-14-dimethylaminocarbonyl-7-(5-(4-(5-oxazolyl)phenyl)-2-thienyl)-1,1-dioxoperhydro-1,4-thiazepin-7-yl]acetamide (115 mg)

NMR (CDCl$_3$, δ): 1.44–2.02 (6H, br), 2.81 (6H, s), 2.89–3.10 (1H, br), 3.16–3.35 (2H, br), 3.37–3.60 (3H, br), 3.60–3.95 (5H, br), 3.96–4.16 (1H, br), 4.60, 4.86 (1H, br), 7.20–7.34 (2H, m), 7.38 (1H, s), 7.64 (4H, m), 7.94 (1H, s), 8.72, 8.91 (1H, br) MASS (m/z): 601 (M−H)

EXAMPLE 373

N-(2-Tetrahydropyranyloxy)-2-[7-(5-(4-(5-oxazolyl)phenyl)-2-thienyl)-4-(2-propyloxybenzoyl)-1,1-dioxoperhydro-1,4-thiazepin-7-yl]acetamide (115 mg)

NMR (CDCl$_3$, δ): 0.90–1.12 (3H, br), 1.43–1.90 (6H, br), 1.90–2.05 (2H, br), 2.75–4.20 (14H, br), 4.50–5.00 (1H, br), 6.83–7.40 (7H, br), 7.58–7.70 (4H, br), 7.93 ($_1$H, br), 8.50–8.85 (1H, br) MASS (m/z): 692 (M−H)

EXAMPLE 374

N-(2-Tetrahydropyranyloxy)-2-[4-dimethylaminosulfonyl-[7-(5-(4-(5-oxazolyl)phenyl)-2-thienyl)-1,1-dioxoperhydro-1,4-thiazepin-7-yl]acetamide (214 mg)

NMR (CDCl$_3$, δ): 1.42–2.05 (6H, br), 2.83 (6H, s), 2.85–4.13 (12H, br), 4.70, 4.92 (1H, br), 7.20–7.30 (2H, br), 7.38 (1H, s), 7.60–7.72 (4H, br), 7.93 (1H, s), 8.66–8.76 (1H, br) MASS (m/z): 637 (M−H)

EXAMPLE 375

N-(2-Tetrahydropyranyloxy)-2-[4-benzylsulfonyl-7-(5-(4-(5-oxazolyl)phenyl)-2-thienyl)-1,1-dioxoperhydro-1,4-thiazepin-7-yl]acetamide (140 mg)

NMR (CDCl$_3$, δ): 1.44–1.93 (6H, br), 2.80–4.15 (12H, br), 4.26–4.42 (2H, br), 4.72, 4.92 (1H, br), 7.34–7.57 (8H, br), 7.57–7.75 (4H, br), 7.93 (1H, s), 8.78 (1H, br) MASS (m/z): 684 (M−H)

EXAMPLE 376

N-(2-Tetrahydropyranyloxy)-2-[4-(3-chlorobenzoyl)-7-(5-(4-(5-oxazolyl)phenyl)-2-thienyl)-1,1-dioxoperhydro-1,4-thiazepin-7-yl]acetamide (270 mg)

NMR (CDCl$_3$, δ): 1.45–1.74 (6H, m), 2.78–4.86 (13H, m), 7.08–7.43 (6H, m), 7.59–7.65 (5H, m), 7.94 (1H, s) MASS (ESI−): 668.0 (M−H)

EXAMPLE 377

N-(2-Tetrahydropyranyloxy)-2-[4-benzyloxycarbonyl)-7-(5-(4-(5-oxazolyl)phenyl)-2-thienyl)-1,1-dioxoperhydro-1,4-thiazepin-7-yl]acetamide (190 mg)

NMR (CDCl$_3$, δ): 1.45–2.00 (6H, m), 2.70–4.16 (12H, m), 4.56–4.88 (1H, m), 5.16 (2H, d, J=11.0 Hz), 6.92 (2H, d, J=7.5 Hz), 7.16–7.85 (10H, m), 7.95 (1H, s), 8.54–8.63 (1H, s) MASS (ESI−): 664.0 (M−H)

EXAMPLE 378

N-(2-Tetrahydropyranyloxy)-2-[4-benzoyl-7-(5-(4-(5-methyl-1,2,4-oxazolyl-3-yl)phenyl)-2-thienyl)-1,1-dioxoperhydro-1,4-thiazepin-7-yl]acetamide (105 mg)

NMR (CDCl$_3$, δ): 1.40–1.73 (6H, m), 2.67 (3H, s), 2.72–4.28 (12H, m), 4.42–4.86 (1H, m), 6.84–7.22 (2H, m), 7.28–7.38 (5H, m), 7.64–7.71 (2H, m), 8.03–8.08 (2H, m), 8.33 (½H, br), 8.45 (½H, br) MASS (ESI−): 649.1 (M−H)

EXAMPLE 379

N-(2-Tetrahydropyranyloxy)-2-[4-((2S)-2-tert-butoxycarbonylamino-2-phenylacetyl)-7-(5-(4-(5-oxazolyl)phenyl)-2-thienyl)-1,1-dioxoperhydro-1,4-thiazepin-7-yl]acetamide (300 mg)

NMR (CDCl$_3$, δ): 1.40–1.95 (15H, m), 3.03–4.78 (13H, m), 4.88–5.85 (1H, m), 6.89 (1H, br), 7.26–7.40 (6H, m), 7.60–7.67 (4H, m), 7.93 (1H, br), 10.05–10.53 (1H, m) MASS (ESI−): 7.63.1 (M−H)

EXAMPLE 380

N-(2-Tetrahydropyranyloxy)-2-[7-(5-(4-(5-oxazolyl)phenyl)-2-thienyl)-4-(2-thiophenesulfonyl)-1,1-dioxoperhydro-1,4-thiazepin-7-yl]acetamide (275 mg)

NMR (CDCl$_3$, δ): 1.52–1.74 (6H, m), 2.84–4.14 (12H, m), 4.71–4.83 (1H, m), 7.14–7.20 (2H, m), 7.29 (1H, br s), 7.38 (1H, br s), 7.51–7.54 (1H, m), 7.59–7.67 (5H, m), 7.94 (1H, s), 8.66–8.70 (1H, m) MASS (ESI−): 676.2 (M−H)

EXAMPLE 381

N-(2-Tetrahydropyranyloxy)-2-[4-(4-morpholinocarbonyl)-7-(5-(4-(5-oxazolyl)phenyl)-2-thienyl)-1,1-dioxoperhydro-1,4-thiazepin-7-yl]acetamide (145 mg)

NMR (CDCl₃, δ): 1.51–1.74 (6H, m), 2.72–4.12 (20H, m), 4.58 (½H, br), 4.85 (½H, br), 7.21–7.30 (2H, m), 7.38 (1H, s), 7.60–7.67 (4H, m), 7.93 (1H, s), 8.54 (½H, s), 8.72 (½H, s) MASS (ESI): 643.2 (M–H)

EXAMPLE 382

N-(2-Tetrahydropyranyloxy)-2-[4-benzoyl-7-(5-(4-biphenylyl)-2-thienyl)-1,1-dioxoperhydro-1,4-thiazepin-7-yl]acetamide (255 mg)

NMR (CDCl₃, δ): 1.43–1.85 (6H, br), 2.72–4.30 (12H, m), 4.45–4.85 (1H, m), 6.85–7.48 (10H, m), 7.60–7.68 (6H, m), 8.30–8.49 (1H, m) MASS (ESI–): 643.3 (M–H)

EXAMPLE 383

N-(2-Tetrahydropyranyloxy)-2-[4-(2-acetylbenzoyl)-7-(5-(4-(5-oxazolyl)phenyl)-2-thienyl)-1,1-dioxoperhydro-1,4-thiazepin-7-yl]acetamide (125 mg)

NMR (CDCl₃, δ): 1.43–1.75 (6H, m), 2.62 (3H, br), 2.75–3.90 (12H, m), 4.48–4.93 (1H, m), 6.91–7.08 (1H, m), 7.17–7.68 (9H, m), 7.82–7.95 (2H, m), 8.43–8.65 (1H, m) MASS (ESI–): 676.3 (M–H)

EXAMPLE 384

N-(2-Tetrahydropyranyloxy)-2-[4-(2-trifluoromethylbenzoyl)-7-(5-(4-(5-oxazolyl)phenyl)-2-thienyl)-1,1-dioxoperhydro-1,4-thiazepin-7-yl)acetamide (180 mg)

NMR (CDCl₃, δ): 1.44–1.55 (2H, m), 1.70 (4H, br), 2.75–3.30 (6H, m), 3.38–3.86 (5H, m), 4.42–4.65 (1H, m), 4.70–4.89 (1H, m), 6.88 (1H, d, J=7.5 Hz), 7.01 (1H, br s), 7.14–7.22 (1H, m), 7.27–7.33 (1H, m), 7.40 (1H, s), 7.52 (1H, d, J=7.5 Hz), 7.60–7.75 (5H, m), 7.86 (½H, s), 7.94 (½H, s), 8.24–8.44 (1H, m) MASS (ESI–): 702.0 (M–H)

EXAMPLE 385

N-(2-Tetrahydropyranyloxy)-2-[4-(2,3-dimethoxybenzoyl)-7-(5-(4-(5-oxazolyl)phenyl)-2-thienyl)-1,1-dioxoperhydro-1,4-thiazepin-7-yl]acetamide (140 mg)

NMR (CDCl₃, δ): 1.40–1.52 (2H, m), 1.61–1.70 (4H, m), 2.78–3.27 (4H, m), 3.34–3.63 (7H, m), 3.78–3.88 (6H, m), 4.33–4.56 (1H, m), 4.62–4.74 (1/H, m), 4.84–4.94 (½H, m), 6.47–6.70 (1H, m), 6.90–7.02 (2H, m), 7.08–7.14 (1H, m), 7.27–7.38 (1H, m), 7.57–7.65 (5H, m), 7.92 (1H, br s), 8.24–8.40 (½H, m), 8.76–9.02 (½H, m) MASS (ESI–): 694.4 (M–H)

EXAMPLE 386

N-(2-Tetrahydropyranyloxy)-2-[4-(2,4-dimethoxybenzoyl)-7-(5-(4-(5-oxazolyl)phenyl)-2-thienyl)-1,1-dioxoperhydro-1,4-thiazepin-7-yl]acetamide (140 mg)

NMR (CDCl₃, δ): 1.46–1.54 (2H, br), 1.70–1.75 (4H, m), 2.77–3.22 (4H, m), 3.37–3.72 (6H, m), 3.81 (6H, s), 3.87–4.02 (1H, m), 4.47 (1H, br), 4.70 (½H, br), 4.87 (½H, br), 6.40–6.57 (2H, m), 6.86–7.17 (1H, m), 7.27–7.32 (2H, m), 7.39 (1H, d, J=6.0 Hz), 7.65 (4H, d, J=8.0 Hz), 7.95 (1H, s), 8.67–8.71 (1H, m) MASS (ESI–): 694.1 (M–H)

EXAMPLE 387

N-(2-Tetrahydropyranyloxy)-2-[7-(5=(4-(5-oxazolyl)phenyl)-2-thienyl)-4-(3-phenylpropionyl)-1,1-dioxoperhydro-1,4-thiazepin-7-yl]acetamide (140 mg)

NMR (CDCl₃, δ): 1.49–1.71 (6H, m), 2.45–3.88 (14H, m), 4.14–4.33 (2H, m), 4.51–4.83 (1H, m), 6.94–7.02 (1H, m), 7.17–7.31 (6H, m), 7.38 (1H, s), 7.58–7.65 (4H, m), 7.95 (1H, s), 8.65–8.73 (1H, m) MASS (ESI–): 662.2 (M–H)

EXAMPLE 388

N-(2-Tetrahydropyranyloxy)-2-[7-(5-(4-(5-oxazolyl)phenyl)-2-thienyl)-4-((R)-1-phenylethylamino) carbonyl-1,1-dioxoperhydro-1,4-thiazepin-7-yl]acetamide (175 mg)

NMR (CDCl₃, δ): 1.48–1.70 (9H, m), 2.72–4.25 (12H, m), 4.58–4.85 (1H, m), 4.96–5.17 (1H, m), 7.21–7.38 (7H, m), 7.57–7.67 (5H, m), 7.92 (1H, s), 8.80–8.90 (1H, m) MASS (ESI–): 677.4 (M–H)

EXAMPLE 389

N-(2-Tetrahydropyranyloxy)-2-[7-(5-(4-(5-oxazolyl)phenyl)-2-thienyl)-4-(1-phenyl-1-cyclopropanecarbonyl)-1,1-dioxoperhydro-1,4-thiazepin-7-yl]acetamide (95 mg)

NMR (CDCl₃, δ): 1.48–1.71 (10H, m), 2.58–4.33 (12H, m), 4.46–4.87 (1H, m), 7.07–7.33 (6H, m), 7.49 (1H, br), 7.65 (5H, br), 7.93 (1H, s), 8.20–8.47 (1H, m) MASS (ESI–): 674.3 (M–H)

EXAMPLE 390

N-(2-Tetrahydropyranyloxy)-2-[4-(indol-2-ylcarbonyl)-7-(5-(4-(5-oxazolyl)phenyl)-2-thienyl)-1,1-dioxoperhydro-1,4-thiazepin-7-yl]acetamide (65 mg)

NMR (CDCl₃, δ): 1.38–1.70 (6H, m), 2.82–5.00 (13H, m), 6.90–7.78 (13H, m), 9.47 (1H, s) MASS (ESI–): 673.0 (M–H)

EXAMPLE 391

N-(2-Tetrahydropyranyloxy)-2-[4-(2,5-dimethoxybenzoyl)-7-(5-(4-(5-oxazolyl)phenyl)-2-thienyl)-1,1-dioxoperhydro-1,4-thiazepin-7-yl]acetamide (204 mg)

NMR (CDCl₃, δ): 1.40–2.00 (6H, br), 2.70–3.85 (12H, br), 3.78, 3.80 (6H, s), 4.45–4.95 (1H, br), 6.75–7.02 (3H, br), 7.05–7.38 (2H, br), 7.40 (1H, m), 7.58–7.68 (4H, br), 7.94 (1H, m), 8.33–8.75 (1H, br) MASS (m/z): 694 (M–H)

EXAMPLE 392

N-(2-Tetrahydropyranyloxy)-2-[7-(5-(4-(5-oxazolyl)phenyl)-2-thienyl)-4-(2,3,4-trimethoxybenzoyl)-1,1-dioxoperhydro-1,4-thiazepin-7-yl]acetamide (210 mg)

NMR (CDCl₃, δ): 1.35–1.85 (6H, br), 2.75–4.00 (12H, br), 3.87 (9H, s), 4.20–4.95 (1H, br), 6.55–6.80 (1H, br), 7.10–7.35 (3H, br), 7.38 (1H, m), 7.55–7.70 (4H, br), 7.94 (1H, m), 8.55, 8.80 (1H, br) MASS (m/z): 724 (M–H)

EXAMPLE 393

N-(2-Tetrahydropyranyloxy)-2-[4-((S)-2-hydroxy-2-phenylacetyl)-7-(5-(4-(5-oxazolyl)phenyl)-2-thienyl)-1,1-dioxoperhydro-1,4-thiazepin-7-yl]acetamide (112 mg)

NMR (CDCl₃, δ): 1.45–1.90 (6H, br), 2.60–4.00 (12H, br), 4.40–5.50 (2H, br), 6.90–7.05 (1H, br), 7.12–7.70 (11H, br), 7.93 (1H, s), 8.22, 8.37, 8.63 (1H, br) MASS (m/z): 664 (M–H)

EXAMPLE 394

N-(2-Tetrahydropyranyloxy)-2-[4-(2-ethoxybenzoyl)-7-(5-(4-(5-oxazolyl)phenyl)-2-thienyl)-1,1-dioxoperhydro-1,4-thiazepin-7-yl]acetamide (118 mg)

NMR (CDCl₃, δ): 1.35–2.10 (9H, br), 2.75–4.20 (14H, br), 4.46, 4.60–5.03 (1H, br), 6.85–7.13 (3H, br), 7.20–7.45 (4H, br), 7.57–7.72 (4H, br), 7.93 (1H, s), 8.44, 8.50–8.70 (1H, br) MASS (m/z): 678 (M–H)

EXAMPLE 395

N-(2-Tetrahydropyranyloxy)-2-[7-(5-(4-(5-oxazolyl)phenyl)-2-thienyl)-4-(2-trifluoromethoxybenzoyl)-1,1-dioxoperhydro-1,4-thiazepin-7-yl]acetamide (55.0 mg)

NMR (CDCl$_3$, δ): 1.40–1.85 (6H, br), 2.70–4.00 (12H, br), 4.44–4.93 (1H, br), 7.15–7.55 (7H, br), 7.58–7.83 (4H, br), 7.96 (1H s), 8.48, 8.50–8.70 (1H, br) MASS (m/z): 718 (M–H)

EXAMPLE 396

N-(2-Tetrahydropyranyloxy)-2-[4-(2,4-dichlorobenzoyl)-7-(5-(4-(5-oxazolyl)phenyl)-2-thienyl)-1,1-dioxoperhydro-1,4-thiazepin-7-yl]acetamide (61.0 mg)

NMR (CDCl$_3$, δ): 1.40–1.90 (6H, br), 2.74–4.03 (12H, br), 4.44–4.95 (1H, br), 7.14–7.55 (6H, br), 7.57–7.72 (4H, br), 7.95 (1H, s), 8.39, 8.48–8.65 (1H, br) MASS (m/z): 704 (M–H)

EXAMPLE 397

N-(2-Tetrahydropyranyloxy)-2-[4-(4-chloro-2-methoxybenzoyl)-7-(5-(4-(5-oxazolyl)phenyl)-2-thienyl)-1,1-dioxoperhydro-1,4-thiazepin-7-yl]acetamide (135 mg)

NMR (CDCl$_3$, δ): 1.46–1.90 (6H, br), 3.05–3.93 (12H, br), 3.86, 3.87 (3H, s), 4.45–4.62, 4.69, 4.90 (1H, br), 6.86–7.38 (5H, br), 7.40 (1H, s), 7.58–7.70 (4H, br), 7.94, 7.95 (1H, s), 8.54 (1H, br)

EXAMPLE 398

N-(2-Tetrahydropyranyloxy)-2-[4-((R)-2-methoxy-2-phenylacetyl)-7-(5-(4-(5-oxazolyl)phenyl)-2-thienyl)-1,1-dioxoperhydro-1,4-thiazepin-7-yl]acetamide (115 mg)

NMR (CDCl$_3$, δ): 1.44–2.00 (6H, br), 2.60–4.20 (12H, br), 3.49, 3.57 (3H, s), 4.30–4.65, 4.85, 4.98–5.07, 5.13 (2H, br), 7.13–7.48 (8H, br), 7.58–7.73 (4H, br), 7.93 (1H, s), 8.35–8.45, 8.57 (1H, br) MASS (m/z): 678 (M–H)

EXAMPLE 399

N-(2-Tetrahydropyranyloxy)-2-[4-cinnamoyl-7-(5-(4-(5-oxazolyl)phenyl)-2-thienyl)-1,1-dioxoperhydro-1,4-thiazepin-7-yl]acetamide (110 mg)

NMR (CDCl$_3$, δ): 1.40–1.8 (6H, br), 2.84–4.20 (12H, br), 4.53–4.73, 4.90 (1H, br), 6.90–7.00 (1H, br), 7.32–7.44 (1H, br), 7.46–7.83 (9H, br), 7.93 (1H, s), 8.48, 8.60 (1H, br) MASS (m/z): 660 (M–H)

EXAMPLE 400

N-(2-Tetrahydropyranyloxy)-2-[4-benzoyl-7-(5-phenyl-2-thienyl)-1,1-dioxoperhydro-1,4-thiazepin-7-yl]acetamide (113 mg)

NMR (CDCl$_3$, δ): 1.40–1.93 (6H, br), 2.73–4.35 (12H, br), 4.45, 4.60, 4.73, 4.88 (1H, br), 6.86–7.66 (12H, br), 8.23, 8.32–8.45 (1H, br) MASS (m/z): 567 (M–H)

EXAMPLE 401

N-(2-Tetrahydropyranyloxy)-2-[4-benzoyl-7-(5-(4-isopropylphenyl)-2-thienyl)-1,1-dioxoperhydro-1,4-thiazepin-7-yl]acetamide (236 mg)

NMR (CDCl$_3$, δ): 1.29 (6H, d, J=7 Hz), 1.40–1.80 (6H, br), 2.73–4.35 (13H, br), 4.47, 4.61, 4.75, 4.88 (1H, br), 7.07–7.55 (1H, br), 8.23, 8.35–8.45 (1H, br) MASS (m/z): 609 (M–H)

EXAMPLE 402

N-(2-Tetrahydropyranyloxy)-2-[(S)-7-(5-(4-(5-oxazolyl)phenyl)-2-thienyl)-1,1-dioxoperhydro-4-isopropylcarbamoyl-1,4-thiazepin-7-ylacetamide (0.96 mg)

NMR (DMSO-d$_6$, δ): 1.03–1.16 (6H, m), 1.38–1.67 (6H, m), 2.68–2.95 (3H, m), 3.10–3.93 (9H, m), 4.52, 4.75 (1H, s), 6.23 (1H, t, J=8 Hz), 7.20, 7.23 (1H, d, J=5 Hz), 7.53, 7.55 (1H, d, J=5 Hz), 7.70–7.83 (5H, m), 8.47 (1H, s) MASS (ESI–): 615 (M–H)

EXAMPLE 403

N-(2-Tetrahydropyranyloxy)-2-[7-(5-(4-(1,1-dioxo-2-isothiadiazolyl)phenyl)-2-thienyl-4-benzoyl-1,1-dioxoperhydro-1,4-thiazepin-7-yl]acetamide (244 mg)

NMR (CDCl$_3$, δ): 1.35–1.75 (6H, m), 2.75–3.20 (5H, m), 3.44–3.76 (6H, m), 4.19–4.93 (2H, m), 7.11–7.43 (7H, m), 7.45–7.55 (2H, m), 7.65–7.74 (2H, m), 7.76–7.88 (3H, m), 7.98–8.07 (1H, m), 8.17–8.38 (1H, m) MASS (ESI–): 686 (M–H)

EXAMPLE 404

N-(2-Tetrahydropyranyloxy)-2-[7-(5-(4-cyanophenyl)-2-thienyl)-4-benzoyl-1,1-dioxoperhydro-1,4-thiazepin-7-yl]acetamide (258 mg)

NMR (CDCl$_3$, δ): 1.45–2.00 (6H, m), 2.73–3.26 (5H, m), 3.36–3.90 (6H, m), 4.19–4.93 (2H, m), 7.09–7.45 (7H, m), 7.60–7.70 (4H, m), 8.39–8.54 (1H, m) MASS (ESI–): 592 (M–H)

EXAMPLE 405

N-(2-Tetrahydropyranyloxy)-2-[7-(5-(4-trifluoromethylphenyl)-2-thienyl)-4-benzoyl-1,1-dioxoperhydro-1,4-thiazepin-7-yl]acetamide (222 mg)

NMR (CDCl$_3$, δ): 1.39–1.75 (6H, m), 2.71–3.26 (5H, m), 3.31–4.04 (5H, m), 4.19–4.35 (1H, m), 4.39–4.63 (1H, m), 4.66–4.89 (1H, m), 7.00–7.49 (9H, m), 7.58–7.73 (2H, m), 8.31–8.48 (1H, m)

EXAMPLE 406

N-(2-Tetrahydropyranyloxy)-2-[7-(5-(4-cyanomethylphenyl)-2-thienyl)-4-benzoyl-1,1-dioxoperhydro-1,4-thiazepin-7-yl]acetamide (272 mg)

NMR (CDCl$_3$, δ): 1.39–1.75 (6H, m), 2.71–3.26 (5H, m), 3.31–4.04 (7H, m), 4.19–4.35 (1H, m), 4.39–4.63 (1H, m), 4.66–4.39 (1H, m), 7.06–7.45 (9H, m), 7.50–7.63 (2H, m), 8.27–8.45 (1H, m) MASS (ESI–): 606 (M–H)

EXAMPLE 407

N-(2-Tetrahydropyranyloxy)-2-[(S)-4-tert-buthylaminocarbonyl-7-(5-(4-(1,3-oxazol-5-yl)phenyl)-2-thienyl)-1,1-dioxoperhydro-1,4-thiazepin-7-yl]acetamide (1.1 g)

NMR (CDCl$_3$, δ): 1.37 (9H, s), 1.45–1.76 (6H, m), 2.80–2.96 (2H, m), 3.12–3.27 (2H, m), 3.36–3.66 (5H, m), 3.70–3.87 (1H, m), 4.00–4.15 (2H, m), 4.62 (0.5H, br), 4.85 (0.5H, br), 7.28 (1H, s), 7.38 (1H, d, J=4.2 Hz), 7.63–7.65 (5H, m), 7.94 (1H, s) MASS (ESI–): 629 (M–H)

EXAMPLE 408

N-(2-Tetrahydropyranyloxy)-2-[(S)-4-cyclopropylcarbonyl-7-(5-(4-(1,3-oxazol-5-yl)phenyl)-2-thienyl)-1,1-dioxoperhydro-1,4-thiazepin-7-yl]acetamide (1.25 g)

NMR (CDCl$_3$, δ): 0.75–1.11 (4H, m), 1.41–1.90 (7H, m), 2.81–2.99 (2H, m), 3.10–3.61 (6H, m), 3.70–3.96 (3H, m), 4.06–4.23 (1H, m), 4.59 (0.5H, br), 4.85 (0.5H, br), 7.27–7.28 (2H, m), 7.38 (1H, s), 7.63–7.65 (4H, m), 7.94 (1H, s) MASS (ESI–): 598 (M–H)

EXAMPLE 409

N-(2-Tetrahydropyranyloxy)-2-[7-(5-(6-quinolinyl)-2-thienyl)-4-benzoyl-1,1-dioxoperhydro-1,4-thiazepin-7-yl]acetamide (250 mg)

NMR (CDCl$_3$, δ): 1.45–1.65 (6H, m), 2.83–3.26 (4H, m), 3.45–3.95 (7H, m), 4.21–4.35 (1H, m), 4.50–4.86 (1H, m), 7.28–7.45 (8H, m), 7.85–8.00 (2H, m), 8.08–8.15 (2H, m), 8.90 (2H, br) MASS (ESI+): 620 (M+H)

EXAMPLE 410

N-(2-Tetrahydropyranyloxy)-2-[7-(5-(3-methyl-2-oxo-2,3-dihydro-1,3-benzothiazol-6-yl)-2-thienyl)-4-benzoyl-1,1-dioxoperhydro-1,4-thiazepin-7-yl]acetamide (180 mg)

MASS (ESI−): 654 (M−H)

The following compounds were obtained in a similar manner to that of Example 6.

EXAMPLE 411

N-(2-Tetrahydropyranyloxy)-2-[4-benzoyl-7-(5-(4-fluorophenyl)-2-thienyl)-1,1-dioxoperhydro-1,4-thiazepin-7-yl]acetamide (75 mg)

NMR (CDCl$_3$, δ): 1.48–1.81 (6H, m), 2.72–4.37 (12H, m), 4.43–4.85 (1H, m), 6.85–7.17 (3H, m), 7.30–7.58 (8H, m), 8.24–8.35 (1H, m) MASS (ESI−): 585.1 (M−H)

EXAMPLE 412

N-(2-Tetrahydropyranyloxy)-2-[(S)-7-(5-(4-methylthiophenyl)-2-thienyl)-1,1-dioxoperhydro-4-(3-thiophenecarbonyl)-1,4-thiazepin-7-yl]acetamide (2.85 g)

NMR (DMSO-d$_6$, δ): 1.32–1.74 (6H, m), 2.50 (3H, s), 2.68–4.14 (12H, m), 4.38–7.81 (1H, m), 7.15–7.27 (2H, m), 7.29 (2H, d, J=8 Hz), 7.37–7.48 (2H, m), 7.60 (3H, d, J=8 Hz), 7.83 (1H, s) MASS (ESI−): 619 (M−H)

EXAMPLE 413

N-(2-Tetrahydropyranyloxy)-2-[(S)-4-benzoyl-7-(5-(4-chlorophenyl)-2-thienyl)-1,1-dioxoperhydro-1,4-thiazepin-7-yl]acetamide (1.47 g)

NMR (CDCl$_3$, δ): 1.40–1.90 (6H, br), 2.75–4.10 (11H, br), 4.20–4.38, 4.44, 4.57, 4.70, 4.86 (2H, br), 7.08–7.54 (11H, br), 8.33, 8.42 (1H, br) MASS (m/z): 601 (M−H)

EXAMPLE 414

N-(2-Tetrahydropyranyloxy)-2-[(S)-4-benzoyl-7-(5-(4-methylthiophenyl)-2-thienyl)-1,1-dioxoperhydro-1,4-thiazepin-7-yl]acetamide (220 mg)

NMR (CDCl$_3$, δ): 1.50–1.80 (6H, m), 2.51 (3H, s), 2.73–3.00 (2H, m), 3.02–3.26 (2H, m), 3.28–4.00 (7H, m), 4.19–4.23 (1H, m), 4.43, 4.71 (1H, s), 7.10–7.15 (1H, m), 7.16–7.51 (10H, m) MASS (ESI−): 613 (M−H)

EXAMPLE 415

N-(2-Tetrahydropyranyloxy)-2-[7-(5-(2-furyl)-2-thienyl)-4-benzoyl-1,1-dioxoperhydro-1,4-thiazepin-7-yl]acetamide (200 mg)

NMR (CDCl$_3$, δ): 1.38–1.65 (6H, m), 2.61–3.20 (6H, m), 3.38–3.93 (6H, m), 4.45 (0.5H, s), 4.76 (0.5H, s), 6.59 (1H, br), 6.76–6.80 (1H, m), 7.15–7.23 (1H, m), 7.25–7.33 (1H, m), 7.40–7.49 (5H, m), 7.55–7.63 (1H, m), 7.71 (1H, s) MASS (ESI−): 557 (M−H)

EXAMPLE 416

N-(2-Tetrahydropyranyloxy)-2-[7-(5-(2-thienyl)-2-thienyl)-4-benzoyl-1,1-dioxoperhydro-1,4-thiazepin-7-yl]acetamide (150 mg)

MASS (ESI−): 573 (M−H)

The following compounds were obtained in a similar manner to that of Example 17.

EXAMPLE 417

N-Hydroxy-2-[4-methanesulfonyl-7-(5-(2-methylcarbamoylbenzofuran-5-yl)-2-thienyl)-1,1-dioxoperhydro-1,4-thiazepin-7-yl]acetamide (63.0 mg)

NMR (DMSO-d$_6$, δ): 2.80, 2.81 (3H, s), 2.90–3.10 (4H, br), 10–3.17 (3H, s), 3.40–4.22 (6H, br), 7.23 (1H, d, J=3 Hz), 7.43–7.62 (2H, m), 7.65–7.82 (2H, m), 8.04 (1H, s), 8.72 (1H, br), 8.95 (1H, s), 10.72 (1H, br) MASS (m/z): 554 (M−H)

EXAMPLE 418

N-Hydroxy-2-[4-ethylaminocarbonyl-7-(5-(2-methylcarbamoylbenzofuran-5-yl)-2-thienyl)-1,1-dioxoperhydro-1,4-thiazepin-7-yl]acetamide (56.5 mg)

NMR (DMSO-d$_6$, δ): 1.04 (3H, t, J=7 Hz), 2.80, 2.81 (3H, s), 2.73–2.98, 3.03–3.26 (4H, br), 3.40–3.90 (8H, br), 6.53 (1H, br), 7.22 (1H, d, J=3 Hz), 7.47 (1H, d, J=3 Hz), 7.54 (1H, s), 7.67–7.78 (2H, m), 8.03 (1H, s), 8.74 (1H, br), 8.91 (1H, s), 10.69 (1H, s) MASS (m/z): 547 (M−H)

EXAMPLE 419

N-Hydroxy-2-[7-(5-(2-hydroxymethylbenzofuran-5-yl)-2-thienyl)-4-methoxycarbonyl-1,1-dioxoperhydro-1,4-thiazepin-7-yl]acetamide (82.3 mg)

NMR (DMSO-d$_6$, δ): 2.68–3.18 (4H, br), 3.25–3.98 (6H, br), 3.64, 3.67 (3H, s), 4.58 (2H, s), 6.79 (1H, s), 7.22 (1H, d, J=3 Hz), 7.44 (1H, d, J=3 Hz), 7.58 (2H, br), 7.87 (1H, s), 10.68 (1H, s) MASS (m/z)507 (M−H)

EXAMPLE 420

N-Hydroxy-2-[4-methoxycarbonyl-7-(5-(4-(5-oxazolyl)phenyl)-2-thienyl)-1,1-dioxoperhydro-1,4-thiazepin-7-yl]acetamide (65.0 mg)

NMR (DMSO-d$_6$, δ): 2.65–3.20 (4H, br), 3.64, 3.67 (3H, s), 3.25–4.00 (6H, br), 7.25 (1H, d, J=3 Hz), 7.57 (1H, d, J=3 Hz), 7.75–7.90 (5H, m), 8.48 (1H, s), 8.92 (1H, br), 10.68 (1H, s) MASS (m/z): 504 (M−H)

EXAMPLE 421

N-Hydroxy-2-[4-methanesulfonyl-7-(5-(4-(5-oxazolyl)phenyl)-2-thienyl)-1,1-dioxoperhydro-1,4-thiazepin-7-yl]acetamide (83.9 mg)

NMR (DMSO-d$_6$, δ): 2.90–3.25 (4H, br), 3.01 (3H, s), 3.40–4.15 (6H, br), 7.26 (1H, d, J=3 Hz), 7.57 (1H, d, J=3 Hz), 7.73–7.84 (5H, m), 8.48 (1H, s), 10.64 (1H, br) MASS (m/z): 524 (M−H)

EXAMPLE 422

N-Hydroxy-2-[4-ethylaminocarbonyl-7-(5-(4-(5-oxazolyl)phenyl)-2-thienyl)-1,1-dioxoperhydro-1,4-thiazepin-7-yl]acetamide (33.5 mg)

NMR (DMSO-d$_6$, δ): 1.05 (3H, t, J=7 Hz), 2.70–3.18 (6H, br), 3.45–3.93 (6H, br), 6.52 (1H, br), 7.22 (1H, d, J=3 Hz), 7.56 (1H, d, J=3 Hz), 7.77 (5H, m), 8.48 (1H, s), 8.89 (1H, br), 10.66 (1H, br) MASS (m/z): 517 (M−H)

EXAMPLE 423

N-Hydroxy-2-[4-(2-methoxybenzoyl)-7-(5-(4-(5-oxazolyl)phenyl)-2-thienyl)-1,1-dioxoperhydro-1,4-thiazepin-7-yl]acetamide (59.0 mg)

NMR (DMSO-d$_6$, δ): 2.65–3.28 (4H, br), 3.45–4.00 (6H, br), 3.78, 3.86 (3H, s), 6.98–7.33 (4H, m), 7.36–7.48 (1H, m), 7.53–7.65 (1H, m), 7.72–7.85 (5H, br), 8.49 (1H, s), 8.90 (1H, br), 10.74 (1H, br) MASS (m/z): 580 (M–H)

EXAMPLE 424

N-Hydroxy-2-[4-(3-methoxybenzoyl)-7-(5-(4-(5-oxazolyl)phenyl)-2-thienyl)-1,1-dioxoperhydro-1,4-thiazepin-7-yl]acetamide (76.0 mg)

NMR (DMSO-d$_6$, δ): 2.73–3.20 (4H, br), 3.30–4.20 (6H, br), 3.77, 3.80 (3H, s), 6.95–7.10 (3H, br), 7.22–7.32 (1H, m), 7.33–7.45 (1H, m), 7.53–7.64 (1H, m), 7.75–7.90 (5H, br), 8.48 (1H, s), 10.64, 10.68 (1H, br) MASS (m/z): 580 (M–H)

EXAMPLE 425

N-Hydroxy-2-[4-(4-methoxybenzoyl)-7-(5-(4-(5-oxazolyl)phenyl)-2-thienyl)-1,1-dioxoperhydro-1,4-thiazepin-7-yl)acetamide (67.2 mg)

NMR (DMSO-d$_6$, δ): 2.75–3.25 (4H, br), 3.45–4.20 (6H, br), 3.80 (3H, s), 6.96 (2H, d, J=8 Hz), 7.24 (1H, br), 7.42 (2H, d, J=8 Hz), 7.57 (1H, br), 7.79 (5H, br), 8.48 (1H, s), 8.78–8.96 (1H, br), 10.67 (1H, br) MASS (m/z): 580 (M–H)

EXAMPLE 426

N-Hydroxy-2-[7-(5-(4-(5-oxazolyl)phenyl)-2-thienyl)-4-phenylsulfonyl-1,1-dioxoperhydro-1,4-thiazepin-7-yl]acetamide (30.5 mg)

NMR (DMSO-d$_6$, δ): 2.75–3.03 (2H, br), 3.13 (2H, br), 3.36–3.53 (2H, br), 3.60–3.80 (3H, br), 3.93–4.07 (1H, br), 7.22 (1H, d, J=3 Hz), 7.57 (1H, d, J=31 Hz), 7.67 (2H, m), 7.70–7.85 (6H, br), 7.87 (2H, d, J=8 Hz), 8.49 (1H, s), 8.96 (1H, s), 10.72 (1H, s) MASS (m/z): 586 (M–H)

EXAMPLE 427

N-Hydroxy-2-[7-(5-(4-(5-oxazolyl)phenyl)-2-thienyl)-4-phenylaminocarbonyl-1,1-dioxoperhydro-1,4-thiazepin-7-yl]acetamide (22.0 mg)

NMR (DMSO-d$_6$, δ): 2.80–3.22 (4H, br), 3.50–4.10 (6H, br), 6.98 (1H, m), 7.20–7.32 (3H, m), 7.51 (2H, d, J=8 Hz), 7.58 (1H, d, J=3 Hz), 7.76 (5H, br), 8.50 (2H, m), 10.72 (1H, br) MASS (m/z): 565 (M–H)

EXAMPLE 428

N-Hydroxy-2-[4-(2-methylbenzoyl)-7-(5-(4-(5-oxazolyl)phenyl)-2-thienyl)-1,1-dioxoperhydro-1,4-thiazepin-7-yl]acetamide (63.5 mg)

NMR (DMSO-d$_6$, δ): 2.25 (3H, s), 2.70–3.25 (4H, br), 3.30–4.20 (6H, br), 7.16–7.40 (5H, br), 7.56, 7.61 (1H, d, J=3 Hz), 7.77 (5H, br), 8.48 (1H, s), 8.85, 8.93 (1H, br), 10.64, 10.68 (1H, br) MASS (m/z): 564 (M–H)

EXAMPLE 429

N-Hydroxy-2-[7-(5-(4-(5-oxazolyl)phenyl)-2-thienyl)-4-(4-pyridinecarbonyl)-1,1-dioxoperhydro-1,4-thiazepin-7-yl]acetamide hydrochloride (122 mg)

NMR (DMSO-d$_6$, δ): 2.73–3.30 (4H, br), 3.45–4.23 (6H, br), 7.29, 7.31 (1H, d, J=3 Hz), 7.59, 7.61 (1H, d, J=3 Hz), 7.73–7.85 (6H, m), 7.94, 8.01 (2H, d, J=8 Hz), 8.49 (1H, s), 8.87, 8.94 (2H, d, J=8 Hz), 10.76 (1H, br) MASS (m/z): 551 (M–H)

EXAMPLE 430

N-Hydroxy-2-[7-(5-(4-(5-oxazolyl)phenyl)-2-thienyl)-4-(3-(4-pyridyl)acryloyl)-1,1-dioxoperhydro-1,4-thiazepin-7-yl]acetamide hydrochloride (39.0 mg)

NMR (DMSO-d$_6$, δ): 2.65–3.28 (4H, br), 3.40–4.50 (6H, br), 7.29 (1H, m), 7.57 (1H, m), 7.67–7.82 (7H, m), 7.89 (1H, d, J=15 Hz), 8.33 (1H, d, J=8 Hz), 8.40 (1H, d, J=8 Hz), 8.48 (1H, s), 8.93 (2H, m), 10.73 (1H, br) MASS (m/z): 577 (M–H)

EXAMPLE 431

N-Hydroxy-2-[7-(5-(4-(5-oxazolyl)phenyl)-2-thienyl)-4-(2-pyridylmethylcarbonyl)-1,1-dioxoperhydro-1,4-thiazepin-7-yl]acetamide hydrochloride (57.5 mg)

NMR (DMSO-d$_6$, δ): 2.75–3.33 (4H, br), 3.57–4.55 (8H, br), 7.28, 7.36 (1H, d, J=3 Hz), 7.59, 7.71 (1H, d, J=3 Hz), 7.75–7.86 (6H, br), 7.93–8.05 (2H, br), 8.49 (1H, s), 8.53–8.64 (1H, br), 8.93 (1H, br), 10.72–10.90 (1H, br) MASS (m/z): 565 (M–H)

EXAMPLE 432

N-Hydroxy-2-[4-dimethylaminocarbonyl-7-(5-(4-(5-oxazolyl)phenyl)-2-thienyl)-1,1-dioxoperhydro-1,4-thiazepin-7-yl]acetamide (73.5 mg)

NMR (DMSO-d$_6$, δ): 2.70 (6H, s), 2.75–3.15 (4H, br), 3.40–3.95 (6H, m), 7.23 (1H, d, J=3 Hz), 7.57 (1H, d, J=3 Hz), 7.73–7.82 (5H, m), 8.48 (1H, s), 8.93 (1H, br), 10.68 (1H, s) MASS (m/z): 517 (M–H)

EXAMPLE 433

N-Hydroxy-7-(5-(4-(5-oxazolyl)phenyl)-2-thienyl)-4-(2-propyloxybenzoyl)-1,1-dioxoperhydro-1,4-thiazepin-7-yl]acetamide (70.8 mg)

NMR (DMSO-d$_6$, δ): 0.98 (3H, t, J=7 Hz), 1.65–1.88 (2H, br), 2.70–3.20 (4H, br), 3.40–4.25 (8H, br), 6.96–7.32 (4H, m), 7.36–7.45 (1H, br), 7.55–7.64 (1H, m), 7.73–7.86 (5H, m), 8.48 (1H, s), 10.59–10.78 (1H, br) MASS (m/z): 608 (M–H)

EXAMPLE 434

N-Hydroxy-2-[4-dimethylaminosulfonyl-7-(5-(4-(5-oxazolyl)phenyl)-2-thienyl)-1,1-dioxoperhydro-1,4-thiazepin-7-yl]acetamide (65.8 mg)

NMR (DMSO-d$_6$, δ): 2.76 (6H, s), 2.88–2.98 (2H, br), 3.13–3.20 (2H, br), 3.40–3.83 (5H, br), 3.94–4.10 (1H, br), 7.25 (1H, d, J=3 Hz), 7.58 (1H, d, J=3 Hz), 7.77 (5H, m), 8.48 (1H, s), 8.94 (1H, br), 10.72 (1H, br) MASS (m/z): 553 (M–H)

EXAMPLE 435

N-Hydroxy-2-[4-benzylsulfonyl-7-(5-(4-(5-oxazolyl)phenyl)-2-thienyl)-1,1-dioxoperhydro-1,4-thiazepin-7-yl]acetamide (79.5 mg)

NMR (DMSO-d$_6$, δ): 2.85–2.97 (2H, br), 3.13 (2H, br), 3.30–3.67 (5H, br), 3.85–4.03 (1H, br), 4.58 (2H, s), 7.23 (1H, d, J=3 Hz), 7.38–7.47 (5H, br), 7.57 (1H, d, J=3 Hz), 7.76–7.85 (5H, br), 8.48 (1H, s), 8.93 (1H, br), 10.72 (1H, s) MASS (m/z): 600 (M–H)

EXAMPLE 436

N-Hydroxy-2-[7-(5-(4-chlorophenyl)-2-thienyl)-(4-(2-pyridinecarbonyl)-1,1-dioxoperhydro-1,4-thiazepin-7-yl]acetamide hydrochloride (112 mg)

NMR (DMSO-d$_6$, δ): 2.73–3.18 (4H, br), 3.52–4.18 (6H, br), 7.23, 7.26 (1H, d, J=3 Hz), 7.45–7.56 (5H, m), 7.62–7.73 (3H, m), 7.97 (1H, dt, J=2, 8 Hz), 8.62 (1H, m), 10.68 (1H, br) MASS (m/z): 518 (M–H)

EXAMPLE 437

N-Hydroxy-2-[7-(5-(4-chlorophenyl)-2-thienyl)-(4-(2-pyrazinecarbonyl)-1,1-dioxoperhydro-1,4-thiazepin-7-yl]acetamide (50.0 mg)

NMR (DMSO-d$_6$, δ): 2.85–3.20 (4H, br), 3.40–4.20 (6H, br), 7.23, 7.26 (1H, d, J=3 Hz), 7.49 (2H, d, J=8 Hz), 7.52 (1H, m), 7.65–7.75 (2H, m), 8.71 (1H, m), 8.79 (1H, m), 8.90 (1H, d, J=8 Hz), 10.65, 10.69 (1H, s) MASS (m/z): 510 (M–H)

EXAMPLE 438

N-Hydroxy-2-[4-acetyl-7-(5-(4-chlorophenyl)-2-thienyl)-1,1-dioxoperhydro-1,4-thiazepin-7-yl]acetamide (45.0 mg)

NMR (DMSO-d$_6$, δ): 2.03, 2.09 (3H, s), 2.65–3.15 (4H, br), 3.30–4.10 (6H, br), 7.23, 7.26 (1H, d, J=3 Hz), 7.45–7.58 (3H, m), 7.68 (2H, d, J=8 Hz), 8.92 (1H, br), 10.67, 10.72 (1H, s) MASS (m/z): 455 (M–H)

EXAMPLE 439

N-Hydroxy-2-[4-(2-chlorobenzoyl)-7-(5-(4-chlorophenyl)-2-thienyl)-1,1-dioxoperhydro-1,4-thiazepin-7-yl]acetamide (70.3 mg)

NMR (DMSO-d$_6$, δ): 2.65–3.20 (4H, br), 3.40–4.38 (6H, br), 7.21–7.29 (1H, br), 7.30–7.63 (7H, br), 7.64–7.77 (2H, br), 8.81, 8.88, 8.96 (1H, br), 10.58–10.80 (1H, br) MASS (m/z): 553 (M–H)

EXAMPLE 440

N-Hydroxy-2-[7-(5-(4-chlorophenyl)-2-thienyl)-4-((S)-2-hydroxy-2-phenylacetyl)-1,1-dioxoperhydro-1,4-thiazepin-7-yl]acetamide (59.0 mg)

NMR (DMSO-d$_6$, δ): 2.70–3.14 (4H, br), 3.40–4.00 (6H, br), 5.38, 5.47, 5.73, 5.92 (2H, m), 7.11–7.25 (1H, m), 7.25–7.45 (5H, br), 7.45–7.57 (3H, br), 7.62–7.77 (2H, m), 8.84, 8.88–8.97 (1H, m), 10.57, 10.63–10.70 (1H, m) MASS (m/z): 547 (M–H)

EXAMPLE 441

N-Hydroxy-2-[7-(5-(4-chlorophenyl)-2-thienyl)-4-(2-ethoxybenzoyl)-1,1-dioxoperhydro-1,4-thiazepin-7-yl]acetamide (55.6 mg)

NMR (DMSO-d$_6$, δ): 1.25–1.48 (3H, br), 2.65–3.30 (4H, br), 3.40–4.32 (8H, br), 6.96–7.29 (4H, m), 7.35–7.44 (1H, m), 7.45–7.57 (3H, m), 7.62–7.74 (2H, m), 8.78, 8.88, 8.96 (1H, br), 10.56–10.80 (1H, br) MASS (m/z): 561 (M–H)

EXAMPLE 442

N-Hydroxy-2-[7-(5-(4-chlorophenyl)-2-thienyl)-4-methanesulfonyl-1,1-dioxoperhydro-1,4-thiazepin-7-yl]acetamide (36.9 mg)

NMR (DMSO-d$_6$, δ): 2.88–2.98 (2H, br), 3.00 (3H, s), 3.05–3.25 (2H, br), 3.30–3.78 (5H, m), 3.90–4.03 (1H, m), 7.23 (1H, d, J=3 Hz), 7.48 (2H, d, J=8 Hz), 7.51 (1H, d, J=3 Hz), 7.66–7.74 (2H, m), 8.94 (1H, s), 10.71 (1H, br) MASS (m/z): 491 (M–H)

EXAMPLE 443

N-Hydroxy-2-[7-(5-(4-chlorophenyl)-2-thienyl)-4-(2-thiophenesulfonyl)-1,1-dioxoperhydro-1,4-thiazepin-7-yl]acetamide (71.9 mg)

NMR (DMSO-d$_6$, δ): 2.72–3.04 (4H, br), 3.25–3.56 (3H, br), 3.60–3.80 (2H, br), 3.92–4.06 (1H, m), 7.21 (1H, d, J=3 Hz), 7.31 (1H, m), 7.45–7.55 (3H, m), 7.66 (2H, d, J=8 Hz), 7.76 (1H, m), 8.07 (1H, m), 8.94 (1H, br), 10.69 (1H, s) MASS (m/z): 559 (M–H)

EXAMPLE 444

N-Hydroxy-2-[7-(5-(4-chlorophenyl)-2-thienyl)-4-isopropylcarbonyl-1,1-dioxoperhydro-1,4-thiazepin-7-yl]acetamide (65.0 mg)

NMR (DMSO-d$_6$, δ): 0.92–1.15 (6H, m), 2.58–3.30 (5H, br), 3.30–4.18 (6H, br), 7.22, 7.24 (1H, d, J=3 Hz), 7.42–7.56 (3H, m), 7.68 (2H, d, J=8 Hz), 8.84–8.97 (1H, br), 10.68 (1H, br) MASS (m/z): 483 (M–H)

EXAMPLE 445

N-Hydroxy-2-[4-benzylsulfonyl-7-(5-(4-chlorophenyl)-2-thienyl)-1,1-dioxoperhydro-1,4-thiazepin-7-yl]acetamide (44.0 mg)

NMR (DMSO-d$_6$, δ): 2.72–3.30 (4H, m), 3.30–3.65 (5H, br), 3.85–4.05 (1H, br), 4.56 (2H, s), 7.21 (1H, d, J=3 Hz), 7.35–7.60 (8H, m), 7.67 (2H, d, J=8 Hz), 8.92 (1H, s), 10.69 (1H, s) MASS (m/z): 567 (M–H)

EXAMPLE 446

N-Hydroxy-2-[(S)-7-(5-(4-chlorophenyl)-2-thienyl)-4-ethanesulfonyl-1,1-dioxoperhydro-1,4-thiazepin-7-yl]acetamide (54.8 mg)

NMR (DMSO-d$_6$, δ): 1.21 (3H, t, J=7 Hz), 2.93 (2H, br), 3.11–3.30 (4H, br), 3.50–3.68 (4H, br), 3.69–3.85 (1H, br), 3.93–4.07 (1H, br), 7.22 (1H, br), 7.44–7.54 (3H, br), 7.66 (2H, d, J=8 Hz), 8.91 (1H, br), 10.68 (1H, br) MASS (m/z): 505 (M–H)

EXAMPLE 447

N-Hydroxy-2-(S)-4-(1-acetyl-4-piperidinecarbonyl)-7-(5-(4-chlorophenyl)-2-thienyl)-1,1-dioxoperhydro-1,4-thiazepin-7-yl]acetamide (35.0 mg)

NMR (DMSO-d$_6$, δ): 1.30–1.83 (4H, br), 1.99 (3H, s), 2.60–4.12, 4.29–4.46 (15H, br), 7.22, 7.26 (1H, d, J=3 Hz), 7.46–7.58 (3H, m), 7.67 (2H, d, J=8 Hz), 10.62–10.77 (1H, br) MASS (m/z): 566 (M–H)

EXAMPLE 448

N-Hydroxy-2-[(S)-7-(5-(4-chlorophenyl)-2-thienyl)-4-propylsulfonyl-1,1-dioxoperhydro-1,4-thiazepin-7-yl]acetamide (39.0 mg)

NMR (DMSO-d$_6$, δ): 1.03 (3H, t, J=7 Hz), 1.62–1.82 (2H, m), 2.93 (2H, br), 3.08–3.30 (4H, br), 3.40–3.65 (4H, br), 3.65–3.85 (1H, m), 3.96–4.10 (1H, m), 7.22 (1H, d, J=3 Hz), 7.46–7.57 (3H, m), 7.68 (2H, d, J=8 Hz), 8.93 (1H, br) MASS (m/z): 519 (M–H)

EXAMPLE 449

N-Hydroxy-2-[(S)-7-(5-(4-chlorophenyl)-2-thienyl)-4-isobutylcarbonyl-1,1-dioxoperhydro-1,4-thiazepin-7-yl]acetamide (59.0 mg)

NMR (DMSO-d$_6$, δ): 0.85–1.02 (6H, m), 2.01–2.16 (1H, m), 2.22 (1H, d, J=8 Hz), 2.28 (1H, d, J=8 Hz), 2.60–3.20 (4H, br), 3.40–4.14 (6H, br), 7.22, 7.24 (1H, d, J=3 Hz), 7.44–7.54 (3H, m), 7.67 (2H, d, J=8 Hz), 8.90, 8.94 (1H, br), 10.67 (1H, br) MASS (m/z): 497 (M–H)

EXAMPLE 450

N-Hydroxy-2-[(S)-7-(5-(4-chlorophenyl)-2-thienyl)-4-(4-morpholinesulfonyl)-1,1-dioxoperhydro-1,4-thiazepin-7-yl]acetamide (49.4 mg)

NMR (DMSO-d$_6$, δ): 2.86–2.97 (2H, br), 3.04–3.20 (6H, br), 3.54–3.85 (9H, br), 3.94–4.08 (1H, br), 7.22 (1H, d, J=3 Hz), 7.45–7.57 (3H, m), 7.68 (2H, d, J=8 Hz), 8.94 (1H, s), 10.70 (1H, br) MASS (m/z): 562 (M–H)

EXAMPLE 451

N-Hydroxy-2-[(S)-7-(5-(4-chlorophenyl)-2-thienyl)-4-(1-pyrrolidinesulfonyl)-1,1-dioxoperhydro-1,4-thiazepin-7-yl]acetamide (61.6 mg)

NMR (DMSO-d$_6$, δ): 1.80–1.95 (4H, br), 2.85–3.03 (2H, br), 3.10–3.18 (2H br), 3.18–3.27 (4H, br), 3.50–3.84 (5H, br), 3.90–4.04 (1H, br), 7.22 (1H, d, J=3 Hz), 7.47 (2H, d, J=8 Hz), 7.50 (1H, d, J=3 Hz), 7.68 (2H, d, J=8 Hz), 8.93 (1H, s), 10.68 (1H, br) MASS (m/z): 546 (M–H)

EXAMPLE 452

N-Hydroxy-2-[(S)-7-(5-(4-chlorophenyl)-2-thienyl)-4-(N-(2-methoxyethyl)-N-methylaminosulfonyl)-1,1-dioxoperhydro-1,4-thiazepin-7-yl]acetamide (53.1 mg)

NMR (DMSO-d$_6$, δ): 2.79 (3H, s), 2.86–2.98 (2H, br), 3.15 (2H, s), 3.28 (3H, s), 3.20–3.35 (2H, br), 3.40–3.78 (7H, br), 3.86–4.03 (1H, br), 7.22 (1H, d, J=3 Hz), 7.48 (2H, d, J=8 Hz), 7.50 (1H, d, J=3 Hz), 7.68 (2H, d, J=8 Hz), 8.93 (1H, s), 10.70 (1H, s) MASS (m/z): 564 (M–H)

EXAMPLE 453

N-Hydroxy-2-[(S)-7-(5-(4-chlorophenyl)-2-thienyl)-4-methoxymethylcarbonyl-1,1-dioxoperhydro-1,4-thiazepin-7-yl]acetamide (30.0 mg)

NMR (DMSO-d$_6$, δ): 2.60–3.17 (4H, br), 3.30, 3.32 (3H, s), 3.42–4.03 (6H, br), 4.07–4.23 (2H, br), 7.23, 7.25 (1H, d, J=3 Hz), 7.45–7.56 (3H, m), 7.68 (2H, d, J=8 Hz), 8.91 (1H, m), 10.67, 10.68 (1H, s) MASS (m/z): 485 (M–H)

EXAMPLE 454

N-Hydroxy-2-[(S)-7-(5-(4-chlorophenyl)-2-thienyl)-4-cyclopropylmethylcarbonyl-1,1-dioxoperhydro-1,4-thiazepin-7-yl]acetamide (50.0 mg)

NMR (DMSO-d$_6$, δ): 0.10–0.28 (2H, br), 0.44–0.58 (2H, br), 0.95–1.12 (1H, br), 2.26–2.40 (2H, br), 2.64–3.18 (4H, br), 3.41–4.12 (6H, br), 7.23, 7.26 (1H, d, J=3 Hz), 7.43–7.56 (3H, m), 7.67 (2H, d, J=8 Hz), 8.89, 8.93 (1H, br), 10.66 (1H, br) MASS (m/z): 405 (M–H)

EXAMPLE 455

N-Hydroxy-2-[(S)-7-(5-(4-chlorophenyl)-2-thienyl)-4-(2-pyridylmethylcarbonyl)-1,1-dioxoperhydro-1,4-thiazepin-7-yl]acetamide hydrochloride (35.0 mg)

NMR (DMSO-d$_6$, δ): 2.70–3.25 (4H, br), 3.30–4.25 (6H, br), 4.32–4.45 (2H, br), 7.26, 7.32 (1H, d, J=3 Hz), 7.45–7.56 (4H, m), 7.68 (2H, d, J=8 Hz), 7.85–7.94 (2H, br), 8.38–8.52 (1H, br), 8.87, 8.88 (1H, s), 10.63, 10.69 (1H, br) MASS (m/z): 532 (M–H)

EXAMPLE 456

N-Hydroxy-2-[(S)-7-(5-(4-chlorophenyl)-2-thienyl)-4-((R)-2-methoxy-2-phenylacetyl)-1,1-dioxoperhydro-1,4-thiazepin-7-yl]acetamide (35.0 mg)

NMR (DMSO-d$_6$, δ): 2.60–3.12 (4H, br), 3.28, 3.30 (3H, s), 3.30–4.14 (6H, br), 5.18, 5.28 (1H, s), 7.13, 7.24 (1H, d, J=3 Hz), 7.33–7.45 (5H, br), 7.45–7.57 (3H, br), 7.63–7.84 (2H, m), 8.90 (1H, br), 10.67 (1H, MASS (m/z): 561 (M–H)

EXAMPLE 457

N-Hydroxy-2-[(S)-7-(5-(4-chlorophenyl)-2-thienyl)-4-(4-methoxy-1-piperidinesulfonyl)-1,1-dioxoperhydro-1,4-thiazepin-7-yl]acetamide (49.2 mg)

NMR (DMSO-d$_6$, δ): 1.46–1.63 (2H, br), 1.83–1.96 (2H, br), 2.85–3.05 (4H, br), 3.07–3.17 (1H, br), 3.25 (3H, s), 3.22–3.40 (4H, br), 3.50–3.80 (5H, br), 3.90–4.03 (1H, br), 7.22 (1H, d, J=3 Hz), 7.48 (2H, d, J=8 Hz), 7.52 (1H, d, J=3 Hz), 7.68 (2H, d, J=8 Hz), 8.93 (1H, s), 10.68 (1H, br) MASS (m/z): 590 (M–H)

EXAMPLE 458

N-Hydroxy-2-[(S)-7-(5-(4-chlorophenyl)-2-thienyl)-4-(2-methoxyethylaminosulfonyl)-1,1-dioxoperhydro-1,4-thiazepin-7-yl]acetamide (44.1 mg)

NMR (DMSO-d$_6$, δ): 2.86–3.18 (6H, br), 3.27 (3H, s), 3.32–3.76 (7H, br), 3.84–3.98 (1H, br), 4.36 (1H, br), 7.22 (1H, d, J=3 Hz), 7.48 (2H, d, J=8 Hz), 7.52 (1H, d, J=3 Hz), 7.67 (2H, d, J=8 Hz), 8.92 (1H, s), 10.69 (1H, br) MASS (m/z): 550 (M–H)

EXAMPLE 459

N-Hydroxy-2-[4-(3-chlorobenzoyl)-7-(5-(4-(5-oxazolyl)phenyl)-2-thienyl)-1,1-dioxoperhydro-1,4-thiazepin-7-yl]acetamide (120 mg)

NMR (DMSO-d$_6$, δ): 2.72–3.18 (4H, m), 3.32–4.17 (6H, m), 7.24–7.28 (1H, m), 7.39–7.46 (1H, m), 7.48–7.62 (4H, m), 7.75–7.80 (5H, m), 8.48 (1H, s) MASS (ESI–): 585.8 (M–H)

EXAMPLE 460

N-Hydroxy-2-[4-benzoyl-7-(5-(3-(ethylaminocarbonylamino)phenyl)-2-thienyl)-1,1-dioxoperhydro-1,4-thiazepin-7-yl]acetamide (56 mg)

NMR (DMSO-d$_6$, δ): 1.05 (3H, t, J=7.0 Hz), 2.22–3.16 (6H, m), 3.42–4.15 (6H, m), 6.15 (1H, t, J=6.0 Hz), 7.18–7.24 (4H, m), 7.33–7.47 (6H, m), 7.80–7.82 (1H, m), 8.60 (1H, s), 8.81 (½H, s), 8.90 (½H, s) MASS (ESI–): 569.1 (M–H)

EXAMPLE 461

N-Hydroxy-2-[4-benzyloxycarbonyl-7-(5-(4-(5-oxazolyl)phenyl)-2-thienyl)-1,1-dioxoperhydro-1,4-thiazepin-7-yl]acetamide (25 mg)

NMR (DMSO-d$_6$, δ): 2.75–3.26 (4H, m), 3.37–3.80 (6H, m), 5.13 (2H, br), 7.21–7.26 (1H, m), 7.32–7.42 (5H, m), 7.56 (1H, br), 7.73–7.80 (5H, m), 8.48 (1H, s), 8.92 (1H, s) MASS (ESI–): 580.0 (M–H)

EXAMPLE 462

N-Hydroxy-2-[4-benzoyl-7-(5-(4-(5-methyl-1,2,4-oxadiazol-3-yl)phenyl)-2-thienyl)-1,1-dioxoperhydro-1,4-thiazepin-7-yl]acetamide (80 mg)

NMR (DMSO-d$_6$, δ): 2.66 (3H, s), 2.73–3.17 (4H, m), 3.47–4.15 (6H, m), 7.25–7.30 (1H, m), 7.41–7.45 (5H, m), 7.60–7.65 (1H, m), 7.87 (2H, d, J=8.0 Hz), 8.03 (2H, d, J=8.0 Hz) MASS (ESI–): 565.1 (M–H)

EXAMPLE 463

N-Hydroxy-2-[7-(5-(4-(5-oxazolyl)phenyl)-2-thienyl)-4-(2-thiophenesulfonyl)-1,1-dioxoperhydro-1,4-thiazepin-7-yl]acetamide (30 mg)

NMR (DMSO-d$_6$, δ): 2.73–3.13 (4H, m), 3.38–4.04 (6H, m), 7.22 (1H, d, J=4.0 Hz), 7.28–7.30 (1H, m), 7.56 (1H, d, J=3.0 Hz), 7.73–7.80 (5H, m), 8.07 (1H, d, J=6.0 Hz), 8.48 (1H, s), 8.94 (1H, br), 10.72 (1H, s) MASS (ESI–): 592.0 (M–H)

EXAMPLE 464

N-Hydroxy-2-[4-(4-morpholinocarbonyl)-7-(5-(4-(5-oxazolyl)phenyl)-2-thienyl)-1,1-dioxoperhydro-1,4-thiazepin-7-yl]acetamide (85 mg)

NMR (DMSO-$d_6$, δ): 2.73–3.15 (8H, m), 3.48–3.88 (10H, m), 7.22 (1H, d, J=3.0 Hz), 7.56 (1H, d, J=3.0 Hz), 7.75–7.80 (5H, m), 8.47 (1H, s), 8.91 (1H, s), 10.64 (1H, s) MASS (ESI-): 559.3 (M-H)

EXAMPLE 465

N-Hydroxy-2-[4-benzoyl-7-(5-(4-biphenylyl)-2-thienyl)-1,1-dioxoperhydro-1,4-thiazepin-7-yl]acetamide (95 mg)

NMR (DMSO-$d_6$, δ): 2.73–3.18 (4H, m), 3.37–4.13 (6H, m), 7.20–7.55 (10H, m), 7.70–7.74 (6H, m), 8.48–8.92 (1H, m) MASS (ESI-): 559.1 (M-H)

EXAMPLE 466

N-Hydroxy-2-[4-(1-isoquinolinecarbonyl)-7-(5-(4-(5-oxazolyl)phenyl)-2-thienyl)-1,1-dioxoperhydro-1,4-thiazepin-7-yl]acetamide (60 mg)

NMR (DMSO-$d_6$, δ): 2.67–3.15 (4H, m), 3.75–4.28 (6H, m), 7.16 (1H, d, J=3.0 Hz), 7.31 (1H, d, J=3.0 Hz), 7.52 (1H, d, J=3.0 Hz), 7.60 (1H, d, J=3.0 Hz), 7.65–7.80 (9H, m), 7.84–8.12 (2H, m), 8.47–8.55 (2H, m) MASS (ESI-): 601.3 (M-H)

EXAMPLE 467

N-Hydroxy-2-[14-(2-acetylbenzoyl)-7-(5-(4-(5-oxazolyl)phenyl)-2-thienyl)-1,1-dioxoperhydro-1,4-thiazepin-7-yl]acetamide (20 mg)

NMR (DMSO-$d_6$, δ): 2.60 (3H, br), 2.63–3.23 (4H, m), 3.50–4.29 (6H, m), 7.22–7.28 (1H, m), 7.40 (1H, br d, J=7.0 Hz), 7.54–7.62 (2H, m), 7.65–7.72 (1H, m), 7.75–7.80 (5H, m), 8.02–8.10 (1H, m), 8.47 (1H, s) MASS (ESI-): 592.2 (M-H)

EXAMPLE 468

N-Hydroxy-2-[7-(5-(4-(5-oxazolyl)phenyl)-2-thienyl)-4-(((S)-1-phenylethylamino)carbonyl)-1,1-dioxoperhydro-1,4-thiazepin-7-yl]acetamide (65 mg)

NMR (DMSO-$d_6$, δ): 1.40 (3H, d, J=7.0 Hz), 2.72–3.12 (4H, m), 3.45–3.98 (6H, m), 4.86–4.94 (1H, m), 6.86 (1H, br d, J=7 Hz), 7.14–7.20 (2H, m), 7.26–7.38 (4H, m), 7.54–7.57 (1H, m), 7.73–7.80 (5H, m), 8.48 (1H, s) MASS (ESI-): 593.2 (M-H)

EXAMPLE 469

N-Hydroxy-2-[4-diethylaminosulfonyl-7-(5-(4-(5-oxazolyl)phenyl)-2-thienyl)-1,1-dioxoperhydro-1,4-thiazepin-7-yl]acetamide (70 mg)

NMR (DMSO-$d_6$, δ): 1.30 (6H, t, J=6.0 Hz), 2.68–3.22 (8H, m), 3.45–3.70 (6H, m), 7.24 (1H, d, J=3.0 Hz), 7.56 (1H, d, J=3.0 Hz), 7.73–7.80 (5H, m), 8.48 (1H, s) MASS (ESI-): 581.2 (M-H)

EXAMPLE 470

N-Hydroxy-2-[7-(5-(4-(5-oxazolyl)phenyl)-2-thienyl)-4-propylaminocarbonyl-1,1-dioxoperhydro-1,4-thiazepin-7-yl]acetamide (40 mg)

NMR (DMSO-$d_6$, δ): 0.85 (3H, t, J=7.5 Hz), 1.36–1.49 (2H, m), 2.72–3.13 (4H, m), 3.40–3.87 (6H, m), 6.53 (1H, t, J=7.0 Hz), 7.22 (1H, d, J=3.0 Hz), 7.55 (1H, d, J=3.0 Hz), 7.73–7.80 (5H, m), 8.48 (1H, s) MASS (ESI-): 531.4 (M-H)

EXAMPLE 471

N-Hydroxy-2-[4-(3-methylpyridin-2-ylcarbonyl)-7-(5-(4-(5-oxazolyl)phenyl)-2-thienyl)-1,1-dioxoperhydro-1,4-thiazepin-7-yl]acetamide hydrochloride (48 mg)

NMR (DMSO-$d_6$, δ): 2.29 (3H, br), 2.72–3.15 (4H, m), 3.33–4.12 (6H, m), 7.21–7.28 (1H, m), 7.37–7.42 (1H, m), 7.55–7.60 (1H, m), 7.73–7.82 (6H, m), 8.42 (1H, br), 8.48 (1H, s) MASS (ESI-): 565.3 (M-H)

EXAMPLE 472

N-Hydroxy-2-[4-tert-butylaminocarbonyl-7-(5-(4-(5-oxazolyl)phenyl)-2-thienyl)-1,1-dioxoperhydro-1,4-thiazepin-7-yl]acetamide (68 mg)

NMR (DMSO-$d_6$, δ): 1.28 (9H, m), 2.72–3.13 (4H, m), 3.40–3.82 (6H, m), 5.72 (1H, br), 7.21 (1H, d, J=3.0 Hz), 7.55 (1H, d, J=3.0 Hz), 7.73–7.80 (5H, m), 8.48 (1H, s) MASS (ESI-): 545.2 (M-H)

EXAMPLE 473

N-Hydroxy-2-[4-cyclopropylaminocarbonyl-7-(5-(4-(5-oxazolyl)phenyl)-2-thienyl)-1,1-dioxoperhydro-1,4-thiazepin-7-yl]acetamide (50 mg)

NMR (DMSO-$d_6$, δ): 0.40–0.44 (2H, m), 0.53–0.57 (2H, m), 1.04–1.08 (1H, m), 2.72–3.17 (4H, m), 3.40–3.94 (6H, m), 7.21 (1H, d, J=3.0 Hz), 7.55 (1H, d, J=3.0 Hz), 7.72–7.77 (5H, m), 8.48 (1H, s) MASS (ESI-): 529.3 (M-H)

EXAMPLE 474

N-Hydroxy-2-[4-(2-trifluoromethylbenzoyl)-7-(5-(4-(5-oxazolyl)phenyl)-2-thienyl)-1,1-dioxoperhydro-1,4-thiazepin-7-yl]acetamide (100 mg)

NMR (DMSO-$d_6$, δ): 2.66–3.12 (4H, m), 3.18–3.28 (1H, m), 3.42–3.56 (2H, m), 3.63–4.08 (2H, m), 4.20–4.39 (1H, m), 7.20–7.30 (1H, m), 7.48–7.68 (4H, m), 7.74–7.88 (6H, m), 8.46 (1H, s) MASS (ESI-): 617.9 (M-H)

EXAMPLE 475

N-Hydroxy-2-[4-(2,3-dimethoxybenzoyl)-7-(5-(4-(5-oxazolyl)phenyl)-2-thienyl)-1,1-dioxoperhydro-1,4-thiazepin-7-yl]acetamide (90 mg)

NMR (DMSO-$d_6$, δ): 2.62–3.15 (4H, m), 3.40–3.68 (3H, m), 3.74 (3H, s), 3.85 (3H, s), 3.87–4.35 (3H, m), 6.76–6.93 (1H, m), 7.08–7.25 (3H, m), 7.54–7.59 (1H, m), 7.73–7.80 (5H, m), 8.47 (1H, s), 8.80–8.96 (1H, m) MASS (ESI-): 610.0 (M-H)

EXAMPLE 476

N-Hydroxy-2-[4-(2,4-dimethoxybenzoyl)-7-(5-(4-(5-oxazolyl)phenyl)-2-thienyl)-1,1-dioxoperhydro-1,4-thiazepin-7-yl]acetamide (60 mg)

NMR (DMSO-$d_6$, δ): 2.65–2.94 (2H, m), 3.06–3.16 (2H, m), 3.40–3.65 (4H, m), 3.78 (3H, s), 3.80 (3H, s), 3.82–3.87 (1H, m), 3.98–4.17 (1H, m), 6.57–6.63 (2H, m), 7.08–7.21 (1H, m), 7.25 (1H, d, J=4.0 Hz), 7.54–7.59 (1H, m), 7.73–7.78 (5H, m), 8.48 (1H, s), 8.87–8.95 (1H, m) MASS (ESI-): 610.0 (M-H)

EXAMPLE 477

N-Hydroxy-2-[7-(5-(4-(5-oxazolyl)phenyl)-2-thienyl)-4-(3-phenylpropionyl)-1,1-dioxoperhydro-1,4-thiazepin-7-yl]acetamide (25 mg)

NMR (DMSO-$d_6$, δ): 2.71–3.24 (4H, m), 3.41–3.95 (10H, m), 7.23–7.30 (5H, m), 7.56 (1H, d, J=5.0 Hz), 7.74–7.76 (5H, m), 8.48 (1H, s), 8.92 (1H, br) MASS (ESI-): 578.2 (M-H)

EXAMPLE 478

N-Hydroxy-2-[7-(5-(4-(5-oxazolyl)phenyl)-2-thienyl)-4-propionyl-1,1-dioxoperhydro-1,4-thiazepin-7-yl]acetamide (45 mg)

NMR (DMSO-$d_6$, δ): 0.97–1.05 (3H, m), 2.26–2.41 (2H, m), 2.56–3.16 (4H, m), 3.44–4.17 (6H, m), 7.22–7.27 (1H, m), 7.55–7.58 (1H, m), 7.73–7.80 (5H, m), 8.47 (1H, s) MASS (ESI-): 502.2 (M-H)

EXAMPLE 479

N-Hydroxy-2-[4-cyclopropylcarbonyl-7-(5-(4-(5-oxazolyl)phenyl)-2-thienyl)-1,1-dioxoperhydro-1,4-thiazepin-7-yl]acetamide (65 mg)

NMR (DMSO-$d_6$, δ): 0.72–0.90 (4H, m), 2.72–3.14 (4H, m), 3.55–4.27 (6H, m), 7.22–7.26 (1H, m), 7.55–7.58 (1H, m), 7.74–7.78 (5H, m), 8.47 (1H, s) MASS (ESI-): 514.3 (M-H)

EXAMPLE 480

N-Hydroxy-2-[7-(5-(4-(5-oxazolyl)phenyl)-2-thienyl)-4-(2-(2-thienyl) ethylaminocarbonyl)-1,1-dioxoperhydro-1,4-thiazepin-7-yl]acetamide (55 mg)

NMR (DMSO-$d_6$, δ): 2.72–3.38 (8H, m), 3.45–3.92 (6H, m), 6.75 (1H, dd, J=6.0, 6.0 Hz), 6.93–6.97 (1H, m), 7.22 (1H, d, J=6.0 Hz), 7.33 (1H, d, J=7.0 Hz), 7.57 (1H, d, J=4.0 Hz), 7.73–7.80 (4H, m), 8.48 (1H, s), 8.90 (1H, br) MASS (ESI-): 599.2 (M-H)

EXAMPLE 481

N-Hydroxy-2-[7-(5-(4-(5-oxazolyl)phenyl)-2-thienyl)-4-((R)-1-phenylethylamino)carbonyl-1,1-dioxoperhydro-1,4-thiazepin-7-yl]acetamide (100 mg)

NMR (DMSO-$d_6$, δ): 1.39 (3H, d, J=7.0 Hz), 2.73–3.13 (4H, m), 3.45–4.01 (6H, m), 6.85 (1H, br), 7.15–7.22 (2H, m), 7.25–7.37 (4H, m), 7.54 (1H, br), 7.73–7.80 (5H, m), 8.48 (1H, s), 10.67 (½H, s), 10.70 (½H, s) MASS (ESI-): 593.2 (M-H)

EXAMPLE 482

N-Hydroxy-2-[7-(5-(4-(5-oxazolyl)phenyl)-2-thienyl)-4-(1-phenyl-1-cyclopropanecarbonyl)-1,1-dioxoperhydro-1,4-thiazepin-7-yl]acetamide (50 mg)

NMR (DMSO-$d_6$, δ): 1.13–1.59 (4H, m), 2.58–3.05 (4H, m), 3.45–3.92 (6H, m), 7.13–7.40 (6H, m), 7.52–7.57 (1H, m), 7.72–7.80 (5H, m), 8.47 (1H, s) MASS (ESI-): 590.2 (M-H)

EXAMPLE 483

N-Hydroxy-2-[4-((2S)-2-hydroxy-3-phenylpropionyl)-7-(5-(4-(5-oxazolyl)phenyl)-2-thienyl)-1,1-dioxoperhydro-1,4-thiazepin-7-yl]acetamide (36 mg)

NMR (DMSO-$d_6$, δ): 2.71–3.18 (6H, m), 3.55–4.02 (6H, m), 4.40–4.57 (1H, m), 7.17–7.32 (6H, m), 7.57 (1H, d, J=4.0 Hz), 7.74–7.81 (5H, m), 8.48 (1H, s) MASS (ESI-): 594.2 (M-H)

EXAMPLE 484

N-Hydroxy-2-[4-cyclohexylaminocarbonyl-7-(5-(4-(5-oxazolyl)phenyl)-2-thienyl)-1,1-dioxoperhydro-1,4-thiazepin-7-yl]acetamide (75 mg)

NMR (DMSO-$d_6$, δ): 1.17–1.77(6H, m), 1.55–1.81 (5H, m), 2.72–3.12 (4H, m), 3.43–3.86 (6H, m), 6.49 (1H, d, J=7.5 Hz), 7.20 (1H, d, J=3.0 Hz), 7.55 ($_1$H, d, J=3.0 Hz), 7.72–7.80 (5H, m), 8.46 (1H, s), 10.65 (1H, s) MASS (ESI-): 571.2 (M-H)

EXAMPLE 485

N-Hydroxy-2-[4-benzylaminocarbonyl-7-(5-(4-(5-oxazolyl)phenyl)-2-thienyl)-1,1-dioxoperhydro-1,4-thiazepin-7-yl]acetamide (75 mg)

NMR (DMSO-$d_6$, δ): 2.73–3.14 (4H, m), 3.43–3.94 (6H, m), 4.28 (2H, d, J=6.0 Hz), 7.15–7.34 (7H, m), 7.55 (1H, d, J=5.0 Hz), 7.73–7.80 (4H, m), 8.48 (1H, s) MASS (ESI-): 579.2 (M-H)

EXAMPLE 486

N-Hydroxy-2-[4-(2-naphthylcarbonyl)-7-(5-(4-(5-oxazolyl)phenyl)-2-thienyl)-1,1-dioxoperhydro-1,4-thiazepin-7-yl]acetamide (65 mg)

NMR (DMSO-$d_6$, δ): 2.73–3.20 (4H, m), 3.62–4.04 (6H, m), 7.23–7.30 (1H, m), 7.53–7.60 (4H, m), 7.72–7.80 (5H, m), 7.96–8.03 (4H, m), 8.47 (1H, s) MASS (ESI-): 600.3 (M-H)

EXAMPLE 487

N-Hydroxy-2-[7-(5-(4-(5-oxazolyl)phenyl)-2-thienyl)-4-(2-phenylbenzoyl)-1,1-dioxoperhydro-1,4-thiazepin-7-yl] acetamide (70 mg)

NMR (DMSO-$d_6$, δ): 2.66–3.07 (4H, m), 3.53–4.22 (6H, m), 7.14–7.22 (1H, m), 7.32–7.57 (10H, m), 7.70–7.81 (5H, m), 8.46 (1H, s) MASS (ESI-): 626.3 (M-H)

EXAMPLE 488

N-Hydroxy-2-[4-cyclohexylcarbonyl-7-(5-(4-(5-oxazolyl)phenyl)-2-thienyl)-1,1-dioxoperhydro-1,4-thiazepin-7-yl]acetamide (55 mg)

NMR (DMSO-$d_6$, δ): 1.21–1.42 (4H, br), 1.57–1.76 (6H, br), 2.56–3.02 (4H, m), 3.37–4.08 (6H, m), 7.22–7.27 (1H, m), 7.54–7.57 (1H, m), 7.72–7.77 (5H, m), 8.47 (1H, s) MASS (ESI-): 556.3 (M-H)

EXAMPLE 489

N-Hydroxy-2-[4-(indol-2-ylcarbonyl)-7-(5-(4-(5-oxazolyl)phenyl)-2-thienyl)-1,1-dioxoperhydro-1,4-thiazepin-7-yl]acetamide (25 mg)

NMR (DMSO-$d_6$, δ): 2.84–3.12 (4H, m), 3.64–4.13 (2H, m), 6.88–6.97 (1H, m), 7.05 (1H, dd, J=6.0, 6.0 Hz), 7.20 (1H, dd, J=6.0, 6.0 Hz), 7.27–7.29 (1H, m), 7.44 (1H, d, J=8.0 Hz), 7.58–7.70 (3H, m), 7.76 (4H, br s), 8.48 (1H, s), 8.85–8.93 (1H, m), 10.67 (1H, s), 11.65 (1H, s) MASS (ESI-): 589.0 (M-H)

EXAMPLE 490

N-Hydroxy-2-[4-(4-methylpyrimidin-5-ylcarbonyl)-7-(5-(4-(5-oxazolyl)phenyl)-2-thienyl)-1,1-dioxoperhydro-1,4-thiazepin-7-yl]acetamide (55 mg)

NMR (DMSO-$d_6$, δ): 2.47 (3H, s), 2.70–3.20 (4H, m), 3.41–4.19 (6H, m), 7.24–7.29 (1H, m), 7.55–7.60 (1H, m), 7.73–7.80 (5H, m), 8.48 (1H, s), 8.70–8.76 (1H, m), 9.10–9.14 (1H, m) MASS (ESI-): 566.2 (M-H)

EXAMPLE 491

N-Hydroxy-2-[4-(benzo[b]thiophen-2-ylcarbonyl)-7-(5-(4-(5-oxazolyl)phenyl)-2-thienyl)-1,1-dioxoperhydro-1,4-thiazepin-7-yl]acetamide (75 mg)

NMR (DMSO-d$_6$, δ): 2.61–3.12 (4H, m), 3.67–4.06 (6H, m), 7.27 (1H, d, J=3.0 Hz), 7.39–7.59 (3H, m), 7.70–7.81 (5H, m), 7.90–8.06 (3H, m), 8.47 (1H, s) MASS (ESI-): 606.2 (M-H)

EXAMPLE 492

N-Hydroxy-2-[4-(2,5-dimethoxybenzoyl)-7-(5-(4-(5-oxazolyl)phenyl)-2-thienyl)-1,1-dioxoperhydro-1,4-thiazepin-7-yl]acetamide (112 mg)

NMR (DMSO-d$_6$, δ): 2.70–3.30 (4H, br), 3.40–4.50 (12H, br), 6.72–7.12 (3H, br), 7.15–7.32 (1H, br), 7.52–7.67 (1H, br), 7.70–7.87 (5H, br), 8.49 (1H, br), 10.65, 10.75 (1H, br) MASS (m/z): 610 (M-H)

EXAMPLE 493

N-Hydroxy-2-[7-(5-(4-(5-oxazolyl)phenyl)-2-thienyl)-4-(2,3,4-trimethoxybenzoyl)-1,1-dioxoperhydro-1,4-thiazepin-7-yl]acetamide (97.0 mg)

NMR (DMSO-d$_6$, δ): 2.70–3.30 (4H, br), 3.48–4.33 (6H, br), 3.82 (9H, s), 6.85–7.15 (2H, br), 7.20–7.43 (1H, br), 7.54–7.73 (1H, br), 7.74–7.95 (5H, br), 8.45–8.65 (1H, br), 10.65–10.85 (1H, br) MASS (m/z): 640 (M-H)

EXAMPLE 494

N-Hydroxy-2-[4-((S)-2-hydroxy-2-phenylacetyl)-7-(5-(4-(5-oxazolyl)phenyl)-2-thienyl)-1,1-dioxoperhydro-1,4-thiazepin-7-yl]acetamide (25.2 mg)

NMR (DMSO-d$_6$ 6): 2.70–3.15 (4H, br), 3.40–4.18 (7H, br), 5.37, 5.48 (1H, s), 7.12–7.24 (1H, br), 7.25–7.45 (5H, br), 7.54 (1H, br), 7.70–7.84 (5H, br), 8.48 (1H, s), 10.56, 10.64 (1H, br) MASS (m/z): 580 (M-H)

EXAMPLE 495

N-Hydroxy-2-[4-(2-ethoxybenzoyl)-7-(5-(4-(5-oxazolyl)phenyl)-2-thienyl)-1,1-dioxoperhydro-1,4-thiazepin-7-yl]acetamide (54.4 mg)

NMR (DMSO-d$_6$, δ): 1.25–1.48 (3H, br), 2.70–3.20 (4H, br), 3.30–4.28 (8H, br), 6.96–7.32 (4H, m), 7.34–7.46 (1H, m), 7.55–7.63 (1H, m), 7.73–7.85 (5H, m), 8.48 (1H, s), 10.58–10.76 (1H, br) MASS (m/z): 594 (M-H)

EXAMPLE 496

N-Hydroxy-2-[7-(5-(4-(5-oxazolyl)phenyl)-2-thienyl)-4-(2-trifluoromethoxybenzoyl)-1,1-dioxoperhydro-1,4-thiazepin-7-yl]acetamide (24.2 mg)

NMR (DMSO-d$_6$, δ): 2.60–3.20 (4H, br), 3.30–4.25 (6H, br), 7.23, 7.28 (1H, d, J=3 Hz), 7.45–7.65 (5H, br), 7.73–7.87 (5H, br), 8.48 (1H, s), 8.85, 8.95 (1H, br), 10.60–10.80 (1H, br) MASS (m/z): 634 (M-H)

EXAMPLE 497

N-Hydroxy-2-[4-(2,4-dichlorobenzoyl)-7-(5-(4-(5-oxazolyl)phenyl)-2-thienyl)-1,1-dioxoperhydro-1,4-thiazepin-7-yl]acetamide (95.4 mg)

NMR (DMSO-d$_6$, δ): 2.75–3.35 (4H, br), 3.35–4.10 (6H, br), 7.25–7.30 (1H, br), 7.52–7.67 (4H, br), 7.75–7.90 (6H, m), 8.48 (1H, s), 10.65–10.78 (1H, br) MASS (m/z): 618 (M-H)

EXAMPLE 498

N-Hydroxy-2-[4-(4-chloro-2-methoxybenzoyl)-7-(5-(4-(5-oxazolyl)phenyl)-2-thienyl)-1,1-dioxoperhydro-1,4-thiazepin-7-yl]acetamide (112 mg)

NMR (DMSO-d$_6$, δ): 2.65–3.25 (4H, br), 3.30–4.30 (6H, br), 3.75–3.95 (3H, br), 7.05–7.16, 7.16–7.38 (5H, br), 7.56–7.66 (1H, m), 7.75–7.84 (5H, m), 8.48 (1H, s), 10.63, 10.73 (1H, br) MASS (m/z): 614 (M-H)

EXAMPLE 499

N-Hydroxy-2-[4-((R)-2-methoxy-2-phenylacetyl)-7-(5-(4-(5-oxazolyl)phenyl)-2-thienyl)-1,1-dioxoperhydro-1,4-thiazepin-7-yl]acetamide (53.5 mg)

NMR (DMSO-d$_6$, δ): 2.70–3.15 (4H, m), 3.30–3.32 (3H, m), 3.25–4.10 (6H, br), 5.18, 5.28 (1H, m), 7.16–7.25 (1H, m), 7.33–7.47 (6H, m), 7.58 (1H, m), 7.72–7.84 (5H, br), 8.48 (1H, s), 10.61–10.70 (1H, br) MASS (m/z): 594 (M-H)

EXAMPLE 500

N-Hydroxy-2-[4-cinnamoyl-7-(5-(4-(5-oxazolyl)phenyl)-2-thienyl)-1,1-dioxoperhydro-1,4-thiazepin-7-yl]acetamide (40.0 mg)

NMR (DMSO-d$_6$, δ): 2.73–3.18 (4H, br), 3.30–4.23 (6H, br), 7.15–7.35 (2H, m), 7.37–7.50 (4H, m), 7.50–7.65 (2H, m), 7.70–7.85 (7H, br), 8.48 (1H, s), 10.69 (1H, s) MASS (m/z): 576 (M-H)

EXAMPLE 501

N-Hydroxy-2-[4-methanesulfonyl-7-(5-(4-propylphenyl)-2-thienyl)-1,1-dioxoperhydro-1,4-thiazepin-7-yl]acetamide (54.7 mg)

NMR (DMSO-d$_6$, δ): 0.90 (3H, t, J=7 Hz), 1.55–1.72 (2H, m), 2.58 (2H, t, J=7 Hz), 2.90–3.05 (2H, br), 2.98 (3H, s), 3.10–3.25 (2H, br), 3.40–3.80 (5H, br), 3.93–4.06 (1H, br), 7.20 (1H, d, J=3 Hz), 7.25 (2H, d, J=8 Hz), 7.42 (1H, d, J=3 Hz), 7.55 (2H, d, J=8 Hz), 8.93 (1H, br), 10.69 (1H, br) MASS (m/z): 499 (M-H)

EXAMPLE 502

N-Hydroxy-2-[4-dimethylaminosulfonyl-7-(5-(4-propylphenyl)-2-thienyl)-1,1-dioxoperhydro-1,4-thiazepin-7-yl]acetamide (68.6 mg)

NMR (DMSO-d$_6$, δ): 0.90 (3H, t, J=7 Hz), 1.56–1.73 (2H, m), 2.57 (2H, t, J=7 Hz), 2.75 (6H, s), 2.88–2.98 (2H, br), 3.14 (2H, br), 3.40–3.83 (5H, br), 3.93–4.10 (1H, br), 7.20 (1H, d, J=3 Hz), 7.25 (2H, d, J=8 Hz), 7.41 (1H, d, J=3 Hz), 7.55 (2H, d, J=8 Hz), 8.94 (1H, s), 10.70 (1H, br) MASS (m/z): 528 (M-H)

EXAMPLE 503

N-Hydroxy-2-[7-(5-(4-propylphenyl)-2-thienyl)-4-(3-pyridinesulfonyl)-1,1-dioxoperhydro-1,4-thiazepin-7-yl]acetamide hydrochloride (51.8 mg)

NMR (DMSO-d$_6$, δ): 0.90 (3H, t, J=7 Hz), 1.53–1.72 (2H, m), 2.60 (2H, t, J=7 Hz), 2.72–3.05, 3.15 (4H, br), 3.70–4.20 (6H, br), 7.17 (1H, d, J=3 Hz), 7.25 (2H, d, J=8 Hz), 7.41 (1H, d, J=3 Hz), 7.54 (2H, d, J=8 Hz), 7.72 (1H, m), 8.29 (1H, m), 8.91 (1H, d, J=3 Hz), 9.03 (1H, s), 10.72 (1H, br) MASS (m/z): 562 (M-H)

EXAMPLE 504

N-Hydroxy-2-[4-benzoyl-7-(5-phenyl-2-thienyl)-1,1-dioxoperhydro-1,4-thiazepin-7-yl]acetamide (23.0 mg)

NMR (DMSO-d$_6$, δ): 2.75–3.25 (4H, br), 3.45–4.22 (6H, br), 7.18–7.28 (1H, br), 7.28–7.37 (1H, br), 7.37–7.57 (8H, br), 7.58–7.77 (2H, br), 10.62, 10.73 (1H, br) MASS (m/z): 483 (M-H)

EXAMPLE 505

N-Hydroxy-2-[4-benzoyl-7-(5-(4-isopropylphenyl)-2-thienyl)-1,1-dioxoperhydro-1,4-thiazepin-7-yl]acetamide (156 mg)

NMR (DMSO-$d_6$, δ): 1.21 (6H, d, J=7 Hz), 2.70–3.18 (5H, br), 3.30–4.22 (6H, br), 7.21, 7.23 (1H, d, J=3 Hz), 7.31 (2H, d, J=8 Hz), 7.36–7.53 (6H, br), 7.52–7.62 (2H, m), 8.83, 8.92 (1H, s), 10.60–10.72 (1H, br) MASS (m/z): 525 (M–H)

EXAMPLE 506

N-Hydroxy-2-[4-benzoyl-7-(5-(4-fluorophenyl)-2-thienyl)-1,1-dioxoperhydro-1,4-thiazepin-7-yl]acetamide (17 mg)

NMR (DMSO-$d_6$, δ): 2.72–3.24 (4H, m), 3.43–4.15 (6H, m), 7.20–7.30 (3H, m), 7.38–7.46 (6H, m), 7.65–7.74 (2H, m), 8.83–8.91 (1H, m) MASS (ESI-): 501.0 (M–H)

EXAMPLE 507

N-Hydroxy-2-[7-(5-(4-fluorophenyl)-2-thienyl)-4-((S)-2-hydroxy-2-phenylacetyl)-1,1-dioxoperhydro-1,4-thiazepin-7-yl]acetamide (68.5 mg)

NMR (DMSO-$d_6$, δ): 2.70–3.10 (4H, br), 3.40–3.98 (6H, br), 5.35–5.50 (1H, m), 5.73, 5.90 (1H, m), 7.05–7.48 (9H, br), 7.60–7.75 (2H, br), 8.83, 8.88–8.93 (1H, m), 10.58–10.75 (1H, br) MASS (m/z): 531 (M–H)

EXAMPLE 508

N-Hydroxy-2-[7-(5-(4-fluorophenyl)-2-thienyl)-4-(2-methoxybenzoyl)-1,1-dioxoperhydro-1,4-thiazepin-7-yl]acetamide (75.8 mg)

NMR (DMSO-$d_6$, δ): 2.65–3.25 (4H, br), 3.40–4.33 (6H, br), 3.77, 3.83 (3H, s), 6.97–7.33 (6H, m), 7.37–7.48 (2H, m), 7.63–7.78 (2H, m), 8.75–9.03 (1H, br), 10.58–10.77 (1H, br) MASS (m/z): 531 (M–H)

EXAMPLE 509

N-Hydroxy-2-[7-(5-(4-fluorophenyl)-2-thienyl)-4-methanesulfonyl-1,1-dioxoperhydro-1,4-thiazepin-7-yl]acetamide (61.3 mg)

NMR (DMSO-$d_6$, δ): 2.88–2.98 (2H, br), 3.00 (3H, s), 3.10–3.25 (2H, m), 3.40–3.78 (5H, m), 3.90–4.03 (1H, br), 7.22 (1H, d, J=3 Hz), 7.23–7.34 (2H, m), 7.45 (1H, d, J=3 Hz), 7.66–7.76 (2H, m), 8.93 (1H, br), 10.69 (1H, br) MASS (m/z): 475 (M–H)

EXAMPLE 510

N-Hydroxy-2-[7-(5-(4-fluorophenyl)-2-thienyl)-4-(3-thiophenecarbonyl)-1,1-dioxoperhydro-1,4-thiazepin-7-yl]acetamide (54.2 mg)

NMR (DMSO-$d_6$, δ): 2.75–3.30 (4H, br), 3.30–4.20 (6H, br), 7.15–7.30 (4H, br), 7.35–7.48 (1H, br), 7.55–7.75 (3H, br), 7.78–7.92 (1H, br), 8.80–8.97(1H, br), 10.57–10.72 (1H, br) MASS (m/z): 507 (M–H)

EXAMPLE 511

N-Hydroxy-2-[7-(5-(4-fluorophenyl)-2-thienyl)-4-(3-pyridinesulfonyl)-1,1-dioxoperhydro-1,4-thiazepin-7-yl]acetamide hydrochloride (58.2 mg)

NMR (DMSO-$d_6$, δ): 2.76–3.04 (4H, br), 3.45–4.00 (6H, br);
7.19 (1H, d, J=3 Hz), 7.25 (2H, m), 7.44 (1H, d, J=3 Hz), 7.65–7.80 (3H, m), 8.29 (1H, m), 8.92 (1H, dd, J=2, 4 Hz), 9.03 (1H, d, J=2 Hz), 10.74 (1H, br) MASS (m/z): 538 (M–H)

EXAMPLE 512

N-Hydroxy-2-[7-(5-(4-cyanophenyl)-2-thienyl)-4-(2-methoxybenzoyl)-1,1-dioxoperhydro-1,4-thiazepin-7-yl]acetamide (91.0 mg)

NMR (DMSO-$d_6$, δ): 2.65–3.25 (4H, m), 3.30–4.25 (6H, br), 3.77, 3.86 (3H, s), 6.97–7.25 (3H, br), 7.22–7.34 (1H, br), 7.36–7.48 (1H, br), 7.71 (1H, m), 7.80–7.94 (4H, m), 8.76–9.02 (1H, br), 10.68 (1H, br) MASS (m/z): 538 (M–H)

EXAMPLE 513

N-Hydroxy-2-[7-(5-(5-chloro-2-thienyl)-2-thienyl)-4-(2-pyridinecarbonyl)-1,1-dioxoperhydro-1,4-thiazepin-7-yl]acetamide hydrochloride (62.6 mg)

NMR (DMSO-$d_6$, δ): 2.73–3.18 (4H, br), 3.50–3.90 (6H, br), 7.10–7.35 (4H, m), 7.50–7.58 (1H, m), 7.62–7.69 (1H, m), 7.95–8.05 (1H, m), 8.60–8.67 (1H, m), 10.68 (1H, br) MASS (m/z): 524 (M–H)

EXAMPLE 514

N-Hydroxy-2-[7-(5-(5-chloro-2-thienyl)-2-thienyl)-4-(3-thiophenecarbonyl)-1,1-dioxoperhydro-1,4-thiazepin-7-yl]acetamide (37.0 mg)

NMR (DMSO-$d_6$, δ): 2.65–3.25 (4H, br), 3.30–4.18 (6H, br), 7.23 (1H, d, J=3 Hz), 7.14–7.33 (4H, br), 7.56–7.68 (1H, br), 7.80–7.92 (1H, br), 8.82–8.96 (1H, br), 10.63 (1H, br) MASS (m/z): 529 (M–H)

EXAMPLE 515

N-Hydroxy-2-[7-(5-(5-chloro-2-thienyl)-2-thienyl)-4-(2-pyrazinecarbonyl)-1,1-dioxoperhydro-1,4-thiazepin-7-yl]acetamide (20.3 mg)

NMR (DMSO-$d_6$, δ): 2.60–3.25 (4H, br), 3.30–4.18 (6H, br), 7.12–7.24 (3H, m), 7.25–7.33 (1H, m), 8.70 (1H, m), 8.78 (1H, m), 8.85–8.96 (2H, m), 10.59–10.70 (1H, br) MASS (m/z): 525 (M–H)

EXAMPLE 516

N-Hydroxy-2-[4-methanesulfonyl-7-(5-(4-methoxymethylphenyl)-2-thienyl)-1,1-dioxoperhydro-1,4-thiazepin-7-yl]acetamide (75.1 mg)

NMR (DMSO-$d_6$, δ): 2.88–2.97 (2H, br), 3.00 (3H, s), 3.14–3.22 (2H, br), 3.30 (3H, s), 3.41–3.80 (5H, m), 3.90–4.04 (1H, br), 4.43 (2H, s), 7.22 (1H, d, J=3 Hz), 7.37 (2H, d, J=8 Hz), 7.48 (1H, d, J=3 Hz), 7.63 (2H, d, J=8 Hz), 8.92 (1H, br), 10.69 (1H, br) MASS (m/z): 501 (M–H)

EXAMPLE 517

N-Hydroxy-2-[(S)-7-(5-(4-(5-oxazolyl)phenyl)-2-thienyl)-1,1-dioxoperhydro-4-isopropylcarbamoyl-1,4-thiazepin-7-yl]acetamide (710 mg)

NMR (DMSO-$d_6$, δ): 1.07 (3H, d, J=6 Hz), 1.10 (3H, d, J=6 Hz), 2.69–3.02 (3H, m), 3.06–3.89 (8H, m), 6.20 (1H, d, J=8 Hz), 7.20 (1H, d, J=3 Hz), 7.50 (1H, d, J=3 Hz), 7.72–7.88 (5H, m), 8.47 (11, s), 8.91 (1H, s), 10.67 (1H, s) MASS (ESI-): 531 (M–H)

EXAMPLE 518

N-Hydroxy-2-[(S)-7-(5-(4-chlorophenyl)-2-thienyl)-1,1-dioxoperhydro-4-(2-pyridinecarbonyl)-1,4-thiazepin-7-yl]acetamide (1.12 g)

NMR (DMSO-$d_6$, δ): 2.70–3.14 (4H, m), 3.45–4.16 (6H, m), 7.67–7.78 (1H, m), 7.45–7.55 (4H, m), 7.58–7.74 (3H, m), 7.96 (1H, t, J=7 Hz), 8.56–8.65 (1H, m), 10.64, 10.68 (1H, s) MASS (ESI–): 518 (M–H)

EXAMPLE 519

N-Hydroxy-2-[(S)-7-(5-(4-ethylphenyl)-2-thienyl)-1,1-dioxoperhydro-4-(2-pyrazinecarbonyl)-1,4-thiazepin-7-yl]acetamide (1.19 g)

NMR (DMSO-$d_6$, δ): 1.19 (3H, t, J=8 Hz), 2.62 (2H, q, J=8 Hz), 2.82–3.15 (4H, m), 3.46–4.17 (6H, m), 7.17–7.33 (3H, m), 7.38–7.46 (1H, m), 7.54, 7.58 (2H, d, J=5 Hz), 8.66–8.75 (1H, m), 8.78–8.84 (1H, m), 8.85–8.99 (2H, m), 10.64, 10.68 (1H, s) MASS (ESI–): 513 (M–H)

EXAMPLE 520

N-Hydroxy-2-[(S)-7-(5-(4-ethylphenyl)-2-thienyl)-4-(3-thiophenecarbonyl)-1,1-dioxoperhydro-1,4-thiazepin-7-yl]acetamide (1.03 g)

NMR (DMSO-$d_6$, δ): 1.19 (3H, d, J=8 Hz), 2.62 (2H, q, J=8 Hz), 2.70–3.22 (4H, m), 3.42–4.12 (6H, m), 7.22 (1H, d, J=3 Hz), 7.26 (3H, d, J=8 Hz), 7.36–7.45 (1H, m), 7.51–7.67 (3H, m), 7.80–7.89 (1H, m), 8.90 (1H, br) MASS (ESI–): 517 (MH)

EXAMPLE 521

N-Hydroxy-2-[7-(5-(4-(2-oxazolyl)phenyl)-2-thienyl)-4-(3-thiophenecarbonyl)-1,1-dioxoperhydro-1,4-thiazepin-7-yl]acetamide (80 mg)

NMR,(DMSO-$d_6$, δ): 2.76–3.18 (4H, m), 3.28–4.04 (6H, m), 7.20–7.33 (2H, m), 7.41 (1H, s), 7.55–7.70 (2H, m), 7.76–7.95 (3H, m), 8.02 (2H, d, J=8 Hz), 8.25 (1H, s), 10.64, 10.68 (1H, s) MASS (ESI–): 556 (M–H)

EXAMPLE 522

N-Hydroxy-2-[(S)-7-(5-(4-(5-oxazolyl)phenyl)-2-thienyl)-1,1-dioxoperhydro-4-(3,3-dimethylbutyryl)-1,4-thiazepin-7-yl]acetamide (2.45 g)

NMR (DMSO-$d_6$, δ): 1.02, 1.03 (9H, s), 2.24, 2.31 (2H, s), 2.60–3.15 (4H, m), 3.42–4.12 (6H, m), 7.24, 7.27 (1H, d, J=4 Hz), 7.56, 7.58 (1H, d, J=4 Hz), 7.76 (1H, s), 7.77 (4H, s), 8.90, 8.94 (1H, s), 10.68 (1H, s) MASS (ESI–): 544 (M–H)

EXAMPLE 523

N-Hydroxy-2-[(S)-7-(5-(4-methylthiophenyl)-2-thienyl)-1,1-dioxoperhydro-4-(3-thiophenecarbonyl)-1,4-thiazepin-7-yl]acetamide (1.78 g)

NMR (DMSO-$d_6$, δ): 2.49 (3H, s), 2.70–3.19 (4H, m), 3.50–4.14 (6H, m), 7.18–7.28 (2H, m), 7.29 (2H, d, J=8 Hz), 7.45 (1H, d, J=4 Hz), 7.59 (3H, d, J=8 Hz), 7.85 (1H, s), 8.89 (1H, s), MASS (ESI–): 535 (M–H)

EXAMPLE 524

N-Hydroxy-2-[1,1-dioxoperhydro-7-(4-phenoxyphenyl)-4-(2-pyrazinecarbonyl)-1,4-thiazepin-7-yl]acetamide (22 mg)

NMR (DMSO-$d_6$, δ): 2.75–2.98 (2H, m), 3.15–3.99 (6H, m), 4.23–4.45 (2H, m), 6.87–7.04 (5H, m), 7.10–7.17 (1H, m), 7.28–7.37 (4H, m), 7.44–7.59 (2H, m), 8.43 and 8.64 (1H, s) MASS (m/z): 495 (M$^+$–H), (bp)

EXAMPLE 525

N-Hydroxy-2-[4-dimethylamino)sulfonyl)-1,1-dioxoperhydro-7-(4-phenoxyphenyl)-1,4-thiazepin-7-yl]acetamide (30 mg)

NMR (DMSO-$d_6$, δ): 2.74 (6H, s), 3.06–3.13 (2H, m), 3.25–3.40 (3H, m), 3.47–3.58 (3H, m), 3.77–3.86 (1H, m), 3.94–4.05 (1H, m), 6.95 (2H, d, J=7.5 Hz), 7.08 (2H, d, J=7.5 Hz), 7.20 (1H, t, J=7.5 Hz), 7.45 (4H, q, J=7.5 Hz), 8.88 (1H, s), 10.67 (1H, s) MASS (m/z): 496 (M$^+$–H), 175 (bp)

EXAMPLE 526

N-Hydroxy-2-[4-cyclopropanecarbonyl)-1,1-dioxoperhydro-7-(4-phenoxyphenyl)-1,4-thiazepin-7-yl]acetamide (43 mg)

NMR (DMSO-$d_6$, δ): 0.68–0.90 (4H, m), 1.84–2.00 (1H, m), 2.68–2.83 (2H, m), 3.06–3.28 (2H, m), 3.39–3.48 (2H, m), 3.53–4.08 (3H, m), 4.27–4.37 (1H, m), 6.94 (2H, d, J=7.5 Hz), 7.07 (2H, d, J=7.5 Hz), 7.20 (1H, t, J=7.5 Hz), 7.42–7.53 (4H, m), 8.85 (1H, d, J=7.5 Hz), 10.63 (1H, d, J=7.5 Hz) MASS (ESI–): 457 (M$^+$–H), 175 (bp)

EXAMPLE 527

N-Hydroxy-2-[1,1-dioxoperhydro-7-(4-phenoxyphenyl)-4-(2-thiophenecarbonyl)-1,4-thiazepin-7-yl]acetamide (54 mg)

NMR (DMSO-$d_6$, δ): 2.72–2.83 (2H, m), 2.98–3.10 (1H, m), 3.18–3.29 (3H, m), 3.50–3.61 (2H, m), 3.85–4.11 (2H, m), 6.95 (2H, d, J=7.5 Hz), 7.07 (2H, d, J=7.5 Hz), 7.14–7.24 (2H, m), 7.45 (3H, t, J=7.5 Hz), 7.52 (1H, d, J=7.5 Hz), 7.80 (1H, d, J=6.5 Hz), 8.83 (1H, d, J=7.5 Hz), 10.63 (1H, d, J=7.5 Hz) MASS (m/z): 499 (M$^+$–H), 175 (bp)

EXAMPLE 528

N-Hydroxy-2-[4-cyclohexylcarbonyl-1,1-dioxoperhydro-7-(4-phenoxyphenyl)-1,4-thiazepin-7-yl]acetamide (54 mg)

NMR (DMSO-$d_6$, δ): 1.12–1.29 (4H, m), 1.65–1.78 (4H, m), 2.60–2.76 (2H, m), 2.93–3.04 (2H, m), 3.20–3.30 (4H, m), 3.43–3.60 (3H, m), 3.74–3.94 (2H, m), 6.22 (1H, d, J=7 Hz), 6.94 (2H, d, J=7.5 Hz), 7.07 (2H, d, J=7.5 Hz), 7.21 (1H, t, J=7 Hz), 7.40–7.48 (4H, m), 8.82 (1H, s), 10.60 (1H, s) MASS (m/z): 514 (M$^+$–H), 175 (bp)

EXAMPLE 529

N-Hydroxy-2-[4-tert-butylcarbamoyl-1,1-dioxoperhydro-7-(4-phenoxyphenyl)-1,4-thiazepin-7-yl]acetamide (25.6 mg)

NMR (DMSO-$d_6$, δ): 1.27 (9H, s), 2.57–2.75 (2H, m), 2.90–3.17 (2H, m), 3.20–3.29 (2H, m), 3.39–3.63 (2H, m), 3.74–3.93 (2H, m), 5.75 (1H, s), 6.93 (2H, d, J=8 Hz), 7.07 (2H, d, J=8 Hz), 7.20 (1H, t, J=8 Hz), 7.44 (4H, q, J=8 Hz), 8.84 (1H, s) MASS (m/z): 488 (M$^+$–H), 145 (bp)

EXAMPLE 530

N-Hydroxy-2-[1,1-dioxoperhydro-7-(4-phenoxyphenyl)-4-propylcarbamoyl-1,4-thiazepin-7-yl]acetamide (43 mg)

NMR (DMSO-$d_6$, δ): 0.82 (3H, t, J=7 Hz), 1.43 (2H, quintet, J=7 Hz), 2.61–2.78 (2H, m), 2.92–3.05 (3H, m), 3.17–3.30 (3H, m), 3.40–3.59 (2H, m), 3.76–3.95 (2H, m), 6.54 (1H, t, J=7 Hz), 6.94 (2H, d, J=8 Hz), 7.07 (2H, d, J=7.5 Hz), 7.20 (1H, t, J=7.5 Hz), 7.40–7.50 (4H, m), 8.83 (1H, d, J=7.5 Hz) MASS (m/z): 474 (M$^+$–H), 69 (bp)

EXAMPLE 531

N-Hydroxy-2-[4-[(2S)-2-hydroxy-2-phenylacetyl]-1,1-dioxoperhydro-7-(4-phenoxyphenyl)-1,4-thiazepin-7-yl]acetamide (45 mg)

NMR (DMSO-d$_6$, δ): 2.62–2.75 (2H, m), 2.88–3.29 (2H, m), 3.40–3.80 (2H, m), 3.86–4.09 (1H, m), 4.20–4.31 (1H, m), 5.37–5.45 (1H, m), 5.70–5.87 (1H, m), 6.89–6.95 (2H, m), 7.07 (2H, d, J=8 Hz), 7.20 (1H, t, J=8 Hz), 7.29–7.48 (9H, m), 8.74–8.88 (1H, m) MASS (m/z): 523 (M$^+$–H), 81 (bp)

EXAMPLE 532

N-Hydroxy-2-[7-(4-phenoxyphenyl-4-(3-thiophenecarbonyl)-1,1-dioxoperhydro-1,4-thiazepin-7-yl]acetamide (42 mg), NMR (DMSO-d$_6$, δ) 2.56–2.86 (2H, m), 2.95–4.23 (8H, m), 6.95 (2H, t, J=8 Hz), 7.07 (2H, d, J=8 Hz), 7.15–7.33 2H, m), 7.43 (2H, t, J=8 Hz), 7.47–7.66 (3H, m), 7.78–7.94 (1H, m), 8.78, 8.85 (1H, s), 10.56, 10.13 (1H, s) MASS (ESI–): 499 (M–H)

EXAMPLE 533

N-Hydroxy-2-[7-[4-(4-methylphenoxy)phenyl]-1,1-dioxoperhydro-4-(2-pyrazinecarbonyl)-1,4-thiazepin-7-yl]acetamide (35 mg)

NMR (DMSO-d$_6$, δ): 2.31 (3H, s), 2.63–3.23 (4H, m), 3.52–4.00 (5H, m), 4.17–4.29 (1H, m), 6.90 (2H, t, J=7.5 Hz), 6.97 (2H, d, J=8 Hz), 7.23 (2H, d, J=8 Hz), 7.48 (2H, d, J=8 Hz), 8.69 (1H, s), 8.78 (1H, s), 8.90 (1H, s) MASS (m/z): 509 (M$^+$–H), 175 (bp)

EXAMPLE 534

N-Hydroxy-2-[4-cyclopropanecarbonyl-7-[4-(4-methylphenoxy)phenyl]-1,1-dioxoperhydro-1,4-thiazepin-7-yl]acetamide (40 mg)

NMR (DMSO-d$_6$, δ): 0.67–0.90 (4H, s), 1.85–2.00 (1H, m), 2.31 (3H, s), 2.63–2.83 (2H, m), 3.00–3.27 (2H, m), 3.42–4.12 (5H, m), 4.25–4.37 (1H, m), 6.90 (2H, dd, J=8, 2 Hz), 6.98 (2H, dd, J=7.5, 2 Hz), 7.24 (2H, d, J=8 Hz), 7.48 (2H, d, J=8 Hz), 8.84 (1H, s) MASS (m/z): 471 (M$^+$–H), 91 (bp)

EXAMPLE 535

N-Hydroxy-2-[7-[4-(4-methylphenoxy)phenyl)-4-(2-thiophenecarbonyl)-1,1-dioxoperhydro-1,4-thiazepin-7-yl]acetamide (32.6 mg)

NMR (DMSO-d$_6$, δ): 2.31 (3H, s), 2.70–2.83 (1H, m), 2.97–3.10 (1H, m), 3.17–3.27 (2H, m), 3.45–3.60 (2H, m), 3.80–4.17 (4H, m), 6.90 (2H, d, J=7 Hz), 6.98 (2H, d, J=8 Hz), 7.11 (1H, t, J=7 Hz), 7.24 (2H, d, J=8 Hz), 7.49 (2H, d, J=8 Hz), 7.80 (1H, bd, J=7 Hz), 8.82 (1H, s), 10.60 (1H, s) MASS (m/z): 513 (M$^+$–H), 145 (bp)

EXAMPLE 536

N-Hydroxy-2-[7-[4-(4-methylphenoxy)phenyl]-1,1-dioxoperhydro-1,4-thiazepin-4-(3-thiophenecarbonyl)-7-yl]acetamide (40 mg)

NMR (DMSO-d$_6$, δ): 2.31 (3H, s), 2.65–2.80 (1H, m), 2.95–3.10 (1H, m), 3.16–3.27 (2H, m), 3.45–3.60 (2H, m), 3.65–4.17 (4H, m), 6.87 (2H, t, J=7 Hz), 6.97 (2H, d, J=8 Hz), 7.21 (3H, d, J=8 Hz), 7.49 (2H, br s), 7.63 (1H, br s), 7.82–7.90 (1H, m), 8.77–8.83 (1H, m) MASS (m/z): 513 (M$^+$–H), 175 (bp)

EXAMPLE 537

N-Hydroxy-2-[4-tert-butylcarbamoyl-[7-[4-(4-methylphenoxy)phenyl]-1,1-dioxoperhydro-1,4-thiazepin-7-yl]acetamide (69 mg)

NMR (DMSO-d$_6$, δ): 1.27 (9H, s), 2.31 (3H, s), 2.59–2.74 (3H, m), 2.90–3.07 (1H, m), 3.17–3.27-(2H, m), 3.45–3.60 (2H, m), 3.74–3.93 (2H, m), 5.74 (1H, s), 6.89 (2H, d, J=8 Hz), 6.98 (2H, d, J=8 Hz), 7.22 (2H, d, J=8 Hz), 7.43 (2H, d, J=8 Hz), 8.83 (1H, s), 10.61 (1H, s) MASS (m/z): 502 (M$^+$–H), 174 (bp)

EXAMPLE 538

N-Hydroxy-2-[4-[(2S)-2-hydroxy-2-phenylacetyl]-7-[4-(4-methylphenoxy)phenyl]-1,1-dioxoperhydro-7-(4-phenoxyphenyl)-1,4-thiazepin-7-yl]acetamide (20 mg)

NMR (DMSO-d$_6$, δ): 2.31 (3H, s), 2.57–2.79 (2H, m), 2.94–3.213 (2H, m), 3.43–4.05 (3H, m), 4.11–4.28 (1H, m), 5.36–5.45 (1H, m), 5.80–5.88 (1H, m), 6.84–6.90 (2H, m), 6.97 (2H, d, J=8 Hz), 7.24 (2H, d, J=8 Hz), 7.29–7.45 (7H, m), 8.73–8.88 (1H, m)

EXAMPLE 539

N-Hydroxy-2-[7-[4-(4-methylphenoxy)phenyl]-1,1-dioxoperhydro-4-(2-pyridinecarbonyl)-1,4-thiazepin-7-yl]acetamide hydrochloride (53 mg)

NMR (DMSO-d$_6$, δ): 2.31 (3H, s), 2.60–3.30 (6H, m), 3.83–3.98 (2H, m), 4.15–4.30 (2H, m), 6.90 (2H, t, J=8 Hz), 6.97 (2H, d, J=8 Hz), 7.23 (2H, d, J=8 Hz), 7.40–7.53 (4H, m), 7.59–7.67 (1H, m), 7.92–8.00 (1H, m), 8.60 (1H, d, J=7 Hz), 10.19 (1H, s), 10.58–10.67 (1H, s) MASS (m/z): 508 (M$^+$–H), 174 (bp)

EXAMPLE 540

N-Hydroxy-2-[4-(dimethylamino)sulfonyl-7-[4-(4-methylphenoxy)phenyl]-1,1-dioxoperhydro-7-(4-phenoxyphenyl)-1,4-thiazepin-7-yl]acetamide (53 mg)

NMR (DMSO-d$_6$, δ): 2.31 (3H, s), 2.74 (3H, s), 3.03–3.13 (2H, m), 3.21–3.32 (4H, m), 3.45–3.56 (2H, m), 3.77–3.87 (1H, m), 3.94–4.05 (1H, m), 6.90 (2H, d, J=8 Hz), 6.98 (2H, d, J=8 Hz), 7.24 (2H, d, J=8 Hz), 7.45 (2H, d, J=8 Hz), 8.89 (1H, s), 10.67 (1H, s) MASS (m/z): 510 (M$^+$–H), 137 (bp)

EXAMPLE 541

N-Hydroxy-2-[4-benzoyl-7-[4-(4-methylphenoxy)phenyl]-1,1-dioxoperhydro-1,4-thiazepin-7-yl]acetamide (40 mg)

NMR (DMSO-d$_6$, δ): 2.31 (3H, s), 2.62–2.83 (1H, m), 2.95–3.07 (1H, m), 3.15–3.27 (2H, m), 3.48–3.60 (2H, m), 3.69–4.25 (4H, m), 6.85–6.97 (4H, m), 7.23 (2H, d, J=8 Hz), 7.41–7.54 (7H, m), 8.75 (1H, s), 8.84 (1H, s) MASS (m/z): 507 (M$^+$–H), 174 (bp)

EXAMPLE 542

N-Hydroxy-2-[7-[4-(4-chlorophenoxy)phenyl]-1,1-dioxoperhydro-4-(2-pyrazinecarbonyl)-1,4-thiazepin-7-yl]acetamide (45 mg)

NMR (DMSO-d$_6$, δ): 2.65–3.03 (2H, m), 3.10–3.26 (4H, m), 3.55–3.97 (5H, m), 4.17–4.28 (1H, m), 6.98 (2H, t, J=7.5 Hz), 7.09 (2H, d, J=7.5 Hz), 7.47 (2H, d, J=7.5 Hz), 7.52–7.55 (2H, m), 8.78 (1H, dd, J=7.5, 2 Hz), 8.88 (1H, d, J=7.5 Hz), 10.60–10.65 (1H, m) MASS (m/z): 529 (M$^+$–H), 145 (bp)

EXAMPLE 543

N-Hydroxy-2-[7-[4-(4-chlorophenoxy)phenyl]-4-methanesulfonyl-1,1-dioxoperhydro-1,4-thiazepin-7-yl]acetamide (70 mg)

NMR (DMSO-d$_6$, δ): 2.72–2.80 (1H, m), 3.00 (3H, s), 3.11–3.27 (2H, m), 3.40–3.57 (4H, m), 3.74–4.00 (3H, m), 6.99 (2H, d, J=8 Hz), 7.10 (2H, d, J=8 Hz), 7.41–7.52 (4H, m), 8.87 (1H, s), 10.66 (1H, s) MASS (m/z): 501 (M$^+$–H), 175 (bp)

EXAMPLE 544

N-Hydroxy-2-[7-[4-(4-chlorophenoxy)phenyl]-4-cyclopropanecarbonyl-1,1-dioxoperhydro-1,4-thiazepin-7-yl]acetamide (80 mg)

NMR (DMSO-d$_6$, δ): 0.67–0.93 (4H, m), 1.84–2.00 (1H, m), 2.62–2.84 (2H, m), 3.06–3.24 (2H, m), 3.40–3.50 (3H, m), 3.58–4.11 (2H, m), 4.27–4.40 (1H, m), 7.00 (2H, dd, J=7.5, 2 Hz), 7.10 (2H, dd, J=7.5, 2 Hz), 7.44–7.55 (4H, m), 8.85 (1H, d, J=7.5 Hz) MASS (m/z): 491 (M$^+$–H), 175 (bp)

EXAMPLE 545

N-Hydroxy-2-[7-[4-(4-chlorophenoxy)phenyl]-1,1-dioxoperhydro-1,4-thiazepin-4-(3-thiophenecarbonyl)-7-yl]acetamide (34.2 mg)

NMR (DMSO-d$_6$, δ): 2.65–2.83 (2H, m), 2.97–3.10 (1H, m), 3.17–3.27 (3H, m), 3.48–3.60 (2H, m), 3.67–3.90 (1H, m), 3.96–4.08 (1H, m), 6.99 (2H, t, J=7.5 Hz), 7.09 (2H, d, J=7.5 Hz), 7.23–7.30 (1H, m), 7.47 (2H, d, J=7.5 Hz), 7.52 (2H, t, J=7.5 Hz), 7.63 (1H, t, J=4 Hz), 7.82–7.90 (1H, m), 8.78–8.84 (1H, m) MASS (m/z): 535 (M$^+$–H), 85 (bp)

EXAMPLE 546

N-Hydroxy-2-[7-[4-(4-chlorophenoxy)phenyl]-1,1-dioxoperhydro-1,4-thiazepin-4-(2-thiophenecarbonyl)-7-yl]acetamide (85 mg)

NMR (DMSO-d$_6$, δ): 2.69–2.83 (2H, m), 2.93–2.10 (2H, m), 3.16–3.24 (2H, m), 3.45–3.60 (2H, m), 3.77–4.13 (4H, m), 6.97 (2H, d, J=8 Hz), 7.07 (2H, d, J=8 Hz), 7.24 (1H, s), 7.45 (2H, d, J=8 Hz), 7.51 (2H, d, J=8 Hz), 7.78 (1H, d, J=2 Hz), 8.80 (1H, s) MASS (m/z): 533 (M$^+$–H), 145 (bp)

EXAMPLE 547

N-Hydroxy-2-[4-tert-butylcarbamoyl-7-[4-(4-chlorophenoxy)phenyl]-1,1-dioxoperhydro-1,4-thiazepin-7-yl]acetamide (39 mg)

NMR (DMSO-d$_6$, δ): 1.27 (9H, s), 2.54–2.75 (2H, m), 2.92–3.05 (2H, m), 3.21–3.30 (2H, m), 3.44–3.63 (2H, m), 3.73–3.94 (2H, m), 5.75 (1H, s), 6.98 (2H, d, J=8 Hz), 7.19 (2H, d, J=8 Hz), 7.46 (2H, d, J=8 Hz), 7.49 (2H, d, J=8 Hz), 8.83 (1H, s) MASS (m/z): 522 (M$^+$–H), 82 (bp)

EXAMPLE 548

N-Hydroxy-2-[7-[4-(4-chlorophenoxy)phenyl]-4-[(2S)-2-hydroxy-2-phenylacetyl]-1,1-dioxoperhydro-1,4-thiazepin-7-yl]acetamide (31 mg)

NMR (DMSO-d$_6$, δ): 2.65–2.80 (2H, m), 2.88–3.23 (2H, m), 3.50–3.80 (2H, m), 3.85–4.10 (1H, m), 4.19–4.30 (1H, m), 5.37–5.47 (1H, m), 5.69–5.90 (1H, m), 6.93–7.02 (2H, m), 7.07–7.15 (2H, m), 7.31–7.52 (9H, m), 8.72–8.94 (1H, m) MASS (m/z): 557 (M$^+$–H), 175 (bp)

EXAMPLE 549

N-Hydroxy-2-[7-[4-(4-chlorophenoxy)phenyl]-1,1-dioxoperhydro-4-(2-pyridinecarbonyl)-1,4-thiazepin-7-yl]acetamide (17 mg)

NMR (DMSO-d$_6$, δ): 2.73–3.21 (5H, m), 3.58–3.80 (3H, m), 3.97–4.00 (1H, m), 4.19–4.30 (1H, m), 6.99 (2H, d, J=8 Hz), 7.09 (2H, d, J=8 Hz), 7.45–7.57 (5H, m), 7.60–7.67 (1H, m), 7.93–8.00 (1H, m), 8.58–8.64 (1H, m) MASS (m/z): 528 (M$^+$–H), 159 (bp)

EXAMPLE 550

N-Hydroxy-2-[7-[4-(4-chlorophenoxy)phenyl]-4-(dimethylamino)sulfonyl-1,1-dioxoperhydro-1,4-thiazepin-7-yl]acetamide (50 mg)

NMR (DMSO-d$_6$, δ): 2.74 (6H, s), 3.01–3.14 (3H, s), 3.20–3.28 (2H, m), 3.43–4.05 (5H, m), 6.99 (2H, d, J=8 Hz), 7.09 (2H, d, J=8 Hz), 7.47 (2H, d, J=8 Hz), 7.49 (2H, d, J=8 Hz) MASS (m/z): 530 (M$^+$–H), 82 (bp)

EXAMPLE 551

N-Hydroxy-2-[7-[4-(4-chlorophenoxy)phenyl]-4-(2-thiophene)sulfonyl-1,1-dioxoperhydro-1,4-thiazepin-7-yl]acetamide (25 mg)

NMR (DMSO-d$_6$, δ): 2.71–2.79 (1H, m), 2.94–3.14 (2H, m), 3.27–3.37 (3H, m), 3.50–3.68 (2H, m), 3.77–3.85 (1H, m), 4.00–4.10 (1H, m), 6.97 (2H, d, J=8 Hz), 7.09 (2H, d, J=8 Hz), 7.27 (1H, t, J=3 Hz), 7.43–7.48 (4H, m), 7.75 (1H, d, J=3 Hz), 8.05 (1H, d, J=3 Hz), 8.88 (1H, s), 10.68 (1H, s) MASS (m/z): 569 (M$^+$–H), 175 (bp)

EXAMPLE 552

N-Hydroxy-2-[4-benzoyl-7-[4-(4-chlorophenoxy)phenyl]-1,1-dioxoperhydro-1,4-thiazepin-7-yl]acetamide (26 mg)

NMR (DMSO-d$_6$, δ): 2.60–2.84 (2H, m), 3.00–3.11 (2H, m), 3.18–3.27 (2H, m), 3.52–3.60 (2H, m), 3.70–3.93 (2H, m), 6.96 (1H, d, J=8 Hz), 7.02 (2H, d, J=8 Hz), 7.19 (2H, d, J=8 Hz), 7.47 (6H, s), 7.55 (2H, t, J=8 Hz), 8.75 and 8.84 (1H, s) MASS (m/z): 527 (M$^+$–H), 145 (bp)

EXAMPLE 553

N-Hydroxy-2-[7-[4-(4-chlorophenoxy)phenyl]-4-cyclohexylcarbamoyl-1,1-dioxoperhydro-1,4-thiazepin-7-yl]acetamide (42 mg)

NMR (DMSO-d$_6$, δ): 1.16–1.28 (5H, m), 1.54–1.60 (1H, m), 1.64–1.78 (5H, m), 2.60–2.78 (2H, m), 3.20–3.29 (4H, m), 3.40–3.60 (2H, m), 3.75–3.90 (2H, m), 6.22 (1H, d, J=7.5 Hz), 6.97 (2H, d, J=8 Hz), 7.09 (2H, d, J=8 Hz), 7.46 (2H, d, J=8 Hz), 7.47 (2H, d, J=8 Hz), 8.81 (1H, s) MASS (m/z): 548 (M$^+$–H), 145 (bp)

EXAMPLE 554

N-Hydroxy-2-[7-[4-(4-chlorophenoxy)phenyl]-4-(2-methoxybenzoyl)-1,1-dioxoperhydro-1,4-thiazepin-7-yl]acetamide (36 mg)

NMR (DMSO-d$_6$, δ): 2.70–3.26 (4H, m), 3.45–3.66 (4H, m), 3.75–3.86 (4H, m), 3.25–3.33 (1H, m), 6.94–7.19 (7H, m), 7.38–7.54 (5H, m), 8.82–8.90 (1H, s) MASS (m/z): 557 (M$^+$–H), 127 (bp)

EXAMPLE 555

N-Hydroxy-2-[7-[4-(4-fluorophenoxy)phenyl]-1,1-dioxoperhydro-4-(2-pyrazinecarbonyl)-1,4-thiazepin-7-yl]acetamide (43 mg)

NMR (DMSO-d$_6$, δ): 2.62–3.30 (6H, m), 3.74–4.00 (3H, m), 4.17–4.29 (1H, m), 6.93 (2H, t, J=8 Hz), 7.11–7.17 (2H, m), 7.78 (2H, t, J=8 Hz), 7.51 (2H, t, J=8 Hz), 8.70 (1H, s), 8.79 (1H, d, J=2 Hz), 8.90 (1H, s), 10.60–10.66 (1H, m) MASS (m/z): 513 (M$^+$–H), 81 (bp)

EXAMPLE 556

N-Hydroxy-2-[7-[4-(4-fluorophenoxy)phenyl]-4-methanesulfonyl-1,1-dioxoperhydro-1,4-thiazepin-7-yl]acetamide (39 mg)

NMR (DMSO-$d_6$, δ): 2.70–2.80 (1H, m), 2.99 (3H, s), 3.05–3.32 (4H, m), 3.50–3.55 (3H, m), 3.74–3.83 (1H, m), 3.93–4.04 (1H, m), 6.93 (2H, d, J=8 Hz), 7.12–7.17 (2H, m), 7.28 (2H, d, J=8 Hz), 7.48 (2H, d, J=8 Hz) MASS (m/z): 485 ($M^+$–H), 81 (bp)

EXAMPLE 557

N-Hydroxy-2-[4-cyclopropanecarbonyl-7-[4-(4-fluorophenoxy)phenyl]-1,1-dioxoperhydro-1,4-thiazepin-7-yl]acetamide (5 mg)

NMR (DMSO-$d_6$, δ): 0.67–0.90 (4H, m), 1.83–2.00 (1H, m), 2.61–2.84 (2H, m), 2.87–3.27 (2H, m), 3.37–3.51 (3H, m), 3.57–4.13 (2H, m), 4.25–4.37 (1H, m), 6.90–6.95 (2H, m), 7.10–7.15 (2H, m), 7.28 (2H, t, J=8 Hz), 7.50 (2H, t, J=8 Hz), 8.85 (1H, s), 10.63 (1H, s)

EXAMPLE 558

N-Hydroxy-2-[7-[4-(4-fluorophenoxy)phenyl]-1,1-dioxoperhydro-1,4-thiazepin-4-(2-(thiophenecarbonyl)-7-yl]acetamide (25 mg)

NMR (DMSO-$d_6$, δ): 2.70–2.83 (2H, m), 2.94–3.24 (3H, m), 3.47–3.60 (2H, m), 3.80–4.17 (3H, m), 6.92 (2H, d, J=8 Hz), 7.11–7.17 (3H, m), 7.24–7.30 (2H, m), 7.51 (3H, d, J=8 Hz), 7.70 (1H, d, J=8 Hz), 8.83 (1H, s) MASS (m/z): 517 ($M^+$–H), 174 (bp)

EXAMPLE 559

N-Hydroxy-2-[7-[4-(4-fluorophenoxy)phenyl]-4-(3-thiophenecarbonyl)-1,1-dioxoperhydro-1,4-thiazepin-7-yl]acetamide (25 mg)

NMR (DMSO-$d_6$, δ): 2.64–2.80 (2H, m), 2.99–3.09 (2H, m), 3.14–3.25 (1H, m), 3.47–3.59 (1H, m), 3.65–3.90 (3H, m), 3.97–4.18 (1H, m), 6.90 (2H, t, J=8 Hz), 7.10–7.15 (2H, m), 7.21–7.30 (3H, m), 7.48 (2H, br s), 7.63 (1H, s), 7.80–7.90 (1H, m), 8.78–8.85 (1H, m) MASS (m/z): 517 ($M^+$–H), 82 (bp)

EXAMPLE 560

N-Hydroxy-2-[7-[4-(4-fluorophenoxy)phenyl]-4-[(2S)-2-hydroxy-2-phenylacetyl]-1,1-dioxoperhydro-1,4-thiazepin-7-yl]acetamide (47 mg)

NMR (DMSO-$d_6$, δ): 2.65–2.76 (2H, m), 2.87–3.21 (4H, m), 3.35–3.70 (3H, m), 3.85–4.06 (1H, m), 5.38–5.45 (1H, m), 6.87–6.94 (2H, m), 7.10–7.15 (2H, m), 7.23–7.48 (9H, m), 10.48–10.65 (1H, m) MASS (m/z): 541 ($M^+$–H, bp)

EXAMPLE 561

N-Hydroxy-2-[7-[4-(4-fluorophenoxy)phenyl]-1,1-dioxoperhydro-4-(2-pyridinecarbonyl)-1,4-thiazepin-7-yl]acetamide hydrochloride (47 mg)

NMR (DMSO-$d_6$, δ): 2.58–3.50 (5H, m), 3.88–4.00 (4H, m), 4.17–4.26 (1H, m), 6.91 (2H, t, J=8 Hz), 7.10–7.15 (2H, m), 7.27 (2H, t, J=8 Hz), 7.43–7.54 (3H, m), 7.60–7.68 (1H, m), 7.96 (1H, d, J=8 Hz), 8.58–8.61 (1H, m) MASS (m/z): 512 ($M^+$–H), 81 (bp)

EXAMPLE 562

N-Hydroxy-2-[4-(dimethylamino)sulfonyl-7-[4-(4-fluorophenoxy)phenyl]-1,1-dioxoperhydro-1,4-thiazepin-7-yl]acetamide (43 mg)

NMR (DMSO-$d_6$, δ): 2.74 (6H, s), 3.02–3.12 (3H, m), 3.20–3.25 (2H, m), 3.44–4.05 (5H, m), 6.93 (2H, d, J=8 Hz), 7.10–7.16 (2H, m), 7.09 (2H, d, J=8 Hz), 7.25 (2H, t, J=8 Hz), 7.47 (2H, d, J=8 Hz), 8.88 (1H, s), 10.67 (1H, s) MASS (m/z): 514 ($M^+$–H), 165 (bp)

EXAMPLE 563

N-Hydroxy-2-[4-benzoyl-7-(4-(4-fluorophenoxy)phenyl]-1,1-dioxoperhydro-1,4-thiazepin-7-yl]acetamide (23 mg)

NMR (DMSO-$d_6$, δ): 2.72–2.84 (1H, m), 2.98–3.25 (4H, m), 3.50–3.60 (1H, m), 3.69–4.05 (3H, m), 4.15–4.25 (1H, m), 6.89 (1H, d, J=8 Hz), 6.95 (1H, d, J=8 Hz), 7.09–7.16 (2H, m), 7.25 (2H, t, J=7 Hz), 7.37–7.45 (6H, m), 7.52 (1H, t, J=8 Hz), 8.73–8.85 (1H, m) MASS (m/z): 511 ($M^+$–H), 45 (bp)

EXAMPLE 564

N-Hydroxy-2-[(S)-7-[4-(4-chlorophenoxy)phenyl]-4-(dimethylamino)sulfonyl-1,1-dioxoperhydro-1,4-thiazepin-7-yl]acetamide (697 mg)

NMR (DMSO-$d_6$, δ): 2.74 (6H, s), 3.03–3.15 (3H, s), 3.20–3.28 (2H, m), 3.42–4.05 (5H, m), 6.99 (2H, d, J=8 Hz), 7.10 (2H, d, J=8 Hz), 7.48 (2H, d, J=8 Hz), 7.49 (2H, d, J=8 Hz), 8.89 (1H, s) MASS (m/z): 530 ($M^+$–H), 82 (bp)

EXAMPLE 565

N-Hydroxy-2-[(S)-7-(4-(4-chlorophenoxy)phenyl)-4-(3-thiophenecarbonyl)-1,1-dioxoperhydro-1,4-thiazepin-7-yl]acetamide (174 mg)

NMR (DMSO-$d_6$, δ): 2.59–2.85 (2H, m), 2.96–4.20 (8H, m), 6.82–7.04 (2H, m), 7.06–7.14 (2H, m), 7.21–7.32 (1H, m), 7.40–7.65 (5H, m), 7.78–7.92 (1H, m), 8.78–8.84 (1H, s) MASS (m/z): 535 (M–H)

EXAMPLE 566

N-Hydroxy-2-[(S)-7-[4-(4-chlorophenoxy)phenyl]-4-cyclopropanecarbonyl-1,1-dioxoperhydro-1,4-thiazepin-7-yl]acetamide (569 mg)

NMR (DMSO-$d_6$, δ): 0.67–0.90 (4H, m), 1.84–2.00 (1H, m), 2.60–2.84 (2H, m), 2.87–3.24 (2H, m), 3.40–3.50 (3H, m), 3.58–4.13 (2H, m), 4.25–4.37 (1H, m), 6.99 (2H, dd, J=7.5, 2 Hz), 7.10 (2H, dd, J=7.5, 2 Hz), 7.44–7.55 (4H, m), 8.80–8.90 (1H, m) MASS (m/z): 491 ($M^+$–H), 159 (bp)

EXAMPLE 567

N-Hydroxy-2-[(S)-7-(5-(4-ethylphenyl)-2-thienyl)-4-(2-pyridylcarbonyl)-1,1-dioxoperhydro-1,4-thiazepin-7-yl]acetamide (703 mg)

NMR (DMSO-$d_6$, δ): 1.19 (3H, t, J=7.5 Hz), 2.61 (2H, q, J=7.5 Hz), 2.75–4.00 (9H, m), 4.00–4.16 (1H, m), 7.18 (0.5H, d, J=3 Hz), 7.21 (0.5H, d, J=3 Hz), 7.26 (2H, d, J=8 Hz), 7.38–7.44 (1H, m), 7.46–7.59 (3H, m), 7.59–7.65 (1H, m), 7.91–8.00 (1H, m), 8.56–8.64 (1H, m), 8.83 (0.5H, s), 8.92 (0.5H, s) MASS (ES–)(m/z): 512.31

EXAMPLE 568

N-Hydroxy-2-[(S)-7-(5-(4-methoxyphenyl)-2-thienyl)-4-(3-thienylcarbonyl)-1,1-dioxoperhydro-1,4-thiazepin-7-yl]acetamide (1.18 g)

NMR (DMSO-$d_6$, δ): 2.75–3.14 (4H, m), 3.46–4.14 (9H, m), 6.98 (2H, d, J=8 Hz), 7.18 (1H, d, J=3 Hz), 7.25 (1H, d, J=3 Hz), 7.30–7.36 (1H, m), 7.52–7.68 (3H, m), 7.81–7.89 (1H, m), 8.80–8.93 (1H, m) MASS (ES–)(m/z): 519.18

EXAMPLE 569

N-Hydroxy-2-[(S)-4-benzoyl-7-(5-(4-chlorophenyl)-2-thienyl)-1,1-dioxoperhydro-1,4-thiazepin-7-yl]acetamide (770 mg)

NMR (DMSO-$d_6$, δ): 2.70–3.18 (4H, br), 3.30–4.18 (6H, br), 7.23, 7.27 (1H, d, J=3 Hz), 7.40–7.57 (8H, m), 7.70 (2H, t, J=8 Hz), 10.62, 10.68 (1H, br) MASS (m/z): 517 (M−H)

EXAMPLE 570

N-Hydroxy-2-[7-(5-(2-phenylethynyl)-2-thienyl)-4-benzoyl-1,1-dioxoperhydro-1,4-thiazepin-7-yl]acetamide (55 mg)

NMR (DMSO-$d_6$, δ): 2.68–3.15 (5H, m), 3.46–4.16 (5H, m), 7.17–7.24 (1H, m), 7.35–7.59 (11H, m), 8.82–8.95 (1H, m) MASS (ESI−): 507 (M−H)

EXAMPLE 571

N-Hydroxy-2-[7-(5-(1-hexynyl)-2-thienyl)-4-benzoyl-1,1-dioxoperhydro-1,4-thiazepin-7-yl]acetamide (54 mg)

NMR (DMSO-$d_6$, δ): 0.91 (3H, t, J=6.8 Hz), 1.35–1.58 (4H, m), 2.41–3.11 (5H, m), 3.43–4.14 (7H, m), 7.05–7.18 (2H, m), 7.35–7.50 (5H, m), 8.80–8.92 (1H, m), 10.55–10.65 (1H, m) MASS (ESI−): 487 (M−H)

EXAMPLE 572

N-Hydroxy-2-[7-(5-(4-(1,1-dioxo-2-isothiadiazolyl)phenyl)-2-thienyl)-4-benzoyl-1,1-dioxoperhydro-1,4-thiazepin-7-yl]acetamide (116 mg)

NMR (DMSO-$d_6$, δ): 2.36–3.17 (7H, m), 3.46–4.17 (9H, m), 7.19–7.27 (1H, m), 7.38–7.51 (7H, m), 7.60–7.71 (2H, m), 8.80–8.95 (1H, m) MASS (ESI−): 602 (M−H)

EXAMPLE 573

N-Hydroxy-2-[7-(5-(4-cyanophenyl)-2-thienyl)-4-benzoyl-1,1-dioxoperhydro-1,4-thiazepin-7-yl]acetamide (144 mg)

NMR (DMSO-$d_6$, δ): 2.71–3.20 (5H, m), 3.46–4.15 (5H, m), 7.25–7.34 (1H, m), 7.38–7.51 (5H, m), 7.67–7.75 (1H, m), 7.80–7.92 (4H, m), 8.82–8.94 (1H, m) MASS (ESI−): 508 (M−H)

EXAMPLE 574

N-Hydroxy-2-[7-(5-(4-trifluoromethylphenyl)-2-thienyl)-4-benzoyl-1,1-dioxoperhydro-1,4-thiazepin-7-yl]acetamide (27 mg)

NMR (DMSO-$d_6$, δ): 2.71–3.24 (4H, m), 3.48–4.19 (6H, m), 7.25–7.33 (1H, m), 7.37–7.51 (5H, m), 7.61–7.70 (1H, m), 7.74–7.80 (2H, m), 7.82–7.94 (2H, m), 8.80–8.95 (1H, m), 10.66 (1H, s) MASS (ESI−): 551 (M−H)

EXAMPLE 575

N-Hydroxy-2-[7-(5-(4-cyanomethylphenyl)-2-thienyl)-4-benzoyl-1,1-dioxoperhydro-1,4-thiazepin-7-yl]acetamide (139 mg)

NMR (DMSO-$d_6$, δ): 2.71–3.24 (6H, m), 3.48–4.16 (6H, m), 7.18–7.28 (1H, m), 7.35–7.55 (7H, m), 7.61–7.70 (1H, m), 7.63–7.74 (2H, m), 8.76–8.95 (1H, m) MASS (ESI−): 522 (M−H)

EXAMPLE 576

N-Hydroxy-2-[(S)-7-(5-(4-methylthiophenyl)-2-thienyl)-4-((5-Methyl-3-isoxazolyl)aminocarbonyl)-1,1-dioxoperhydro-1,4-thiazepin-7-yl]acetamide (56 mg)

NMR (DMSO-$d_6$, δ): 2.35 (3H, s), 2.43–2.55 (3H, m), 2.70–3.14 (4H, m), 3.49–3.93 (6H, m), 6.52 (1H, s), 7.20 (1H, d, J=3.7 Hz), 7.29 (2H, d, J=9 Hz), 7.44 (1H, d, J=3.7 Hz), 7.58 (2H, d, J=9 Hz), 8.90 (1H, s), 9.68 (1H, s), 10.65 (1H, m) MASS (ESI−): 549 (M−H)

EXAMPLE 577

N-Hydroxy-2-[(S)-7-(5-(4-chlorophenyl)-2-thienyl)-4-dimethylaminosulfonyl-1,1-dioxoperhydro-1,4-thiazepin-7-yl]acetamide (640 mg)

NMR (DMSO-$d_6$, δ): 2.75 (6H, s), 2.85–2.96 (2H, m), 3.10–3.15 (2H, m), 3.51–3.65 (4H, m), 3.68–3.77 (1H, m), 3.91–4.05 (1H, m), 7.22 (1H, d, J=3.9 Hz), 7.51 (1H, d, J=8.7 Hz), 7.52 (1H, d, J=3.9 Hz), 7.68 (1H, d, J=8.7 Hz), 8.94 (1H, s), 10.70 (1H, s) MASS (ESI−): 520 (M−H)

EXAMPLE 578

N-Hydroxy-2-[(S)-4-tert-butylaminocarbonyl-7-(5-(4-(1,3-oxazol-5-yl)phenyl)-2-thienyl)-1,1-dioxoperhydro-1,4-thiazepin-7-yl]acetamide (700 mg)

NMR (DMSO-$d_6$, δ): 1.28 (9H, s), 2.84–2.89 (2H, m), 3.08–3.13 (1H, m), 3.40–3.52 (2H, m), 3.60–3.85 (5H, m), 5.72 (1H, s), 7.22 (1H, d, J=4.2 Hz), 7.56 (1H, d, J=4.2 HZ), 7.76–7.77 (5H, m), 8.48 (1H, s), 8.90 (1H, s), 10.6 (1H, s) MASS (ESI−): 545 (M−H)

EXAMPLE 579

N-Hydroxy-2-[(S)-4-cyclopropylcarbonyl-7-(5-(4-(1,3-oxazol-5-yl)phenyl)-2-thienyl)-1,1-dioxoperhydro-1,4-thiazepin-7-yl]acetamide (500 mg)

NMR (DMSO-$d_6$, δ): 0.74–0.86 (4H, m), 1.84–1.92 (0.5H, m), 1.95–2.03 (0.5H, m), 2.65–3.15 (4H, m), 3.50–4.26 (6H, m), 7.24–7.27 (1H, m), 7.56–7.59 (1H, m), 7.76–7.78 (5H, m), 8.48 (1H, s), 8.92 (1H, br) MASS (ESI−): 514 (M−H)

EXAMPLE 580

N-Hydroxy-2-[7-(5-(6-quinolinyl)-2-thienyl)-4-benzoyl-1,1-dioxoperhydro-1,4-thiazepin-7-yl]acetamide (130 mg)

NMR (DMSO-$d_6$, δ): 2.85–3.23 (6H, m), 3.55–4.10 (4H, m), 7.31–7.37 (1H, m), 7.45 (5H, br), 7.74–7.76 (1H, m), 7.85–7.89 (1H, m), 8.23–8.50 (3H, m), 8.81–8.90 (1H, m), 9.10 (1H, m) MASS (ESI+): 536 (M+H)

EXAMPLE 581

N-Hydroxy-2-[(S)-4-benzoyl-7-(5-(4-methylthiophenyl)-2-thienyl)-1,1-dioxoperhydro-1,4-thiazepin-7-yl]acetamide (30 mg)

NMR (DMSO-$d_6$, δ): 2.50 (3H, s), 2.73–3.15 (6H, m), 3.50–3.68 (2H, m), 3.82–3.97 (2H, m), 7.23 (1H, d, J=4.5 Hz), 7.30 (2H, d, J=7.5 Hz), 7.40–7.46 (6H, m), 7.60 (2H, d, J=7.5 Hz), 8.90 (1H, s), 10.66 (1H, s) MASS (ESI−): 529 (M−H)

EXAMPLE 582

N-Hydroxy-2-[7-(5-(4-methylthiophenyl)-2-thienyl)-4-dimethylaminosulfonyl-1,1-dioxoperhydro-1,4-thiazepin-7-yl]acetamide (70 mg)

NMR (DMSO-$d_6$, δ): 2.50 (3H, s), 2.75 (6H, s), 2.90 (2H, br), 3.12 (2H, br), 3.50–3.72 (5H, m), 3.92–4.01 (1H, m), 7.19 (1H, d, J=4.5 Hz), 7.30 (2H, d, J=8.5 Hz), 7.45 (1H, d, J=4.5 Hz), 7.59 (2H, d, J=8.5 Hz), 8.94 (1H, s) MASS (ESI−): 532 (M−H)

EXAMPLE 583

N-Hydroxy-2-[7-(5-(4-methylthiophenyl)-2-thienyl)-4-(3-pyridylsulfonyl)-1,1-dioxoperhydro-1,4-thiazepin-7-yl]acetamide (50 mg)

NMR (DMSO-d$_6$, δ): 2.73–2.96 (4H, m), 3.12 (2H, s), 3.59–3.76 (3H, m), 3.95–4.03 (1H, m), 7.17 (1H, d, J=4.5 Hz), 7.30 (2H, d, J=8.5 Hz), 7.44 (1H, d, J=4.5 Hz), 7.58 (2H, d, J=8.5 Hz), 7.69–7.72 (1H, m), 8.26–8.29 (1H, m), 8.90–8.91 (1H, m), 9.03 (1H, s), 10.71 (1H, s) MASS (ESI−): 566 (M−H)

EXAMPLE 584

N-Hydroxy-2-[7-(5-(4-methylthiophenyl)-2-thienyl)-4-methanesulfonyl-1,1-dioxoperhydro-1,4-thiazepin-7-yl]acetamide (45 mg)

NMR (DMSO-d$_6$, δ): 2.50 (3H, s), 2.92 (2H, br), 3.00 (3H, s), 3.15 (2H, br), 3.43–3.74 (5H, m), 3.91–4.00 (1H, m), 7.20 (1H, d, J=4.5 Hz), 7.30 (2H, d, J=7.5 Hz), 7.45 (1H, d, J=4.5 Hz), 7.59 (2H, d, J=7.5 Hz), 8.93 (1H, br) MASS (ESI−) 503 (M−H)

EXAMPLE 585

N-Hydroxy-2-[7-(5-(2-naphthyl)-2-thienyl)-4-cyclopropylcarbonyl-1,1-dioxoperhydro-1,4-thiazepin-7-yl]acetamide (100 mg)

NMR (DMSO-d$_6$, δ): 0.7–0.85 (4H, m), 1.85–1.90, 1.98–2.04 (1H, m), 2.73–3.16 (4H, m), 3.56–4.27 (6H, m), 7.25–7.30 (1H, m), 7.48–7.56 (2H, m), 7.61–7.65 (1H, m), 7.84 (1H, d, J=8.5 Hz), 7.90–7.99 (2H, m), 8.19 (1H, s), 8.93 (1H, br) MASS (ESI−): 497 (M−H)

EXAMPLE 586

N-Hydroxy-2-[7-(5-(2-naphthyl)-2-thienyl)-4-dimethylaminosulfonyl-1,1-dioxoperhydro-1,4-thiazepin-7-yl]acetamide (80 mg)

NMR (DMSO-d$_6$, δ): 2.76 (6H, s), 2.95 (2H, br), 3.16 (2H, br), 3.57–3.76 (5H, m), 3.97–4.03 (1H, m), 7.27 (1H, d, J=4.5 Hz), 7.5–7.54 (2H, m), 7.63 (1H, d, J=4.5 Hz), 7.84 (1H, d, J=8.5 Hz), 7.92 (1H, d, J==8.5 Hz), 7.98 (2H, d, J=7.5 Hz), 8.19 (1H, s), 8.95 (1H, s) MASS (ESI−): 537 (M−H)

EXAMPLE 587

N-Hydroxy-2-[7-(5-(4-methylphenyl)-2-thienyl)-4-(2-pyridylcarbonyl)-1,1-dioxoperhydro-1,4-thiazepin-7-yl]acetamide hydrochloride (83 mg)

NMR (DMSO-d$_6$, δ): 2.32 (3H, s), 2.80–3.14 (4H, m), 3.48–4.15 (6H, m), 7.16–7.24 (3H, m), 7.40–7.44 (1H, m), 7.50–7.55 (3H, m), 7.61–7.65 (1H, m), 7.94–8.00 (1H, m), 8.60–8.64 (1H, m)

EXAMPLE 588

N-Hydroxy-2-[7-(5-(4-methylphenyl)-2-thienyl)-4-dimethylaminosulfonyl-1,1-dioxoperhydro-1,4-thiazepin-7-yl]acetamide (93 mg)

NMR (D$_2$O, δ): 2.32 (3H, s), 2.75 (6H, s), 2.86–2.93 (2H, m), 3.12 (2H, br), 3.54–3.75 (5H, m), 3.93–4.01 (1H, m), 7.19 (1H, d, J=4.5 Hz), 7.23 (2H, d, J=8.5 Hz), 7.41 (1H, d, J=4.5 Hz), 7.54 (2H, d, J=8.5 Hz), 8.94 (1H, br) MASS (ESI−): 500 (M−H)

EXAMPLE 589

N-Hydroxy-2-[7-(5-(4-methylphenyl)-2-thienyl)-4-((S)-2-hydroxy-2-phenylacetyl)-1,1-dioxoperhydro-1,4-thiazepin-7-yl]acetamide (60 mg)

NMR (DMSO-d$_6$, δ): 2.32 (3H, s), 2.66–3.08 (4H, m), 3.40–4.15 (6H, m), 5.38, 5.73 (1H, m), 5.46, 5.90 (1H, d, J=7.5 Hz), 7.08–7.16 (1H, m), 7.21–7.25 (2H, m), 7.35–7.43 (5H, m), 7.50–7.55 (2H, m), 8.84–8.94 (1H, m) MASS (ESI−): 527 (M−H)

EXAMPLE 590

N-Hydroxy-2-[7-(5-(3-methyl)-2-oxo-2,3-dihydro-1,3-benzothiazol-6-yl)-2-thienyl)-4-benzoyl-1,1-dioxoperhydro-1,4-thiazepin-7-yl]acetamide (100 mg)

NMR (DMSO-d$_6$, δ): 2.73–3.17 (5H, m), 3.43 (3H, s), 3.55–4.13 (5H, m), 7.20–7.25 (1H, m), 7.35 (1H, d, J=7.5 Hz), 7.44–7.49 (6H, m), 7.64–7.70 (1H, m), 8.00–8.05 (1H, m) MASS (ESI−): 570 (M−H)

EXAMPLE 591

N-Hydroxy-2-[7-(5-(2-(4-aminosulfonylphenyl)ethyl)-2-thienyl)-4-benzoyl-1,1-dioxoperhydro-1,4-thiazepin-7-yl]acetamide (100 mg)

NMR (DMSO-d$_6$, δ): 2.75–3.15 (4H, m), 3.50–3.95 (6H, m), 7.21–7.25 (1H, m), 7.43–7.49 (8H, m), 7.75 (2H, d, J=7.5 Hz), 7.85 (2H, d, J=7.5 Hz), 8.85–8.92 (1H, m) MASS (ESI−): 586 (M−H)

EXAMPLE 592

N-Hydroxy-2-[7-(5-(2-furyl)-2-thienyl)-4-benzoyl-1,1-dioxoperhydro-1,4-thiazepin-7-yl]acetamide (120 mg)

NMR (DMSO-d$_6$, δ): 2.70–3.15 (4H, m), 3.47–3.99 (6H, m), 6.59–6.61 (1H, m), 6.77–6.81 (1H, m), 7.17–7.21 (1H, m), 7.28–7.31 (1H, m), 7.43–7.49 (5H, m), 7.73 (1H, s), 8.80, 8.90 (1H, s), 10.60, 10.65 (1H, s) MASS (ESI−): 473 (M−H)

EXAMPLE 593

N-Hydroxy-2-[7-(5-(2-(thienyl)-2-thienyl)-4-benzoyl-1,1-dioxoperhydro-1,4-thiazepin-7-yl]acetamide (70 mg)

NMR (DMSO-d$_6$, δ): 2.71–3.15 (4H, m), 3.48–3.96 (6H, m), 7.09–7.11 (1H, m), 7.15–7.20 (1H, m), 7.24–7.29 (1H, m), 7.30–7.35 (1H, m), 7.40–7.48 (5H, m), 7.54 (1H, d, J=7.5 Hz), 8.82–8.90 (1H, m) MASS (ESI−): 489 (M−H)

EXAMPLE 594

N-Hydroxy-2-[7-(5-(4-methylphenyl)-2-thienyl)-4-(3-pyridylsulfonyl)-1,1-dioxoperhydro-1,4-thiazepin-7-yl]acetamide (85 mg)

NMR (DMSO-d$_6$, δ): 2.32 (3H, s), 2.72–2.96 (3H, m), 3.12 (2H, s), 3.55–3.77 (4H, m), 3.96–4.03 (1H, m), 7.16 (1H, d, J=4.5 Hz), 7.23 (2H, d, J=8.5 Hz), 7.40 (1H, d, J=4.5 Hz), 7.53 (2H, d, J=8.5 Hz), 7.69–7.73 (1H, m), 8.25–8.28 (1H, m), 8.90–8.91 (1H, m), 9.02 (1H, br), 10.70 (1H, s) MASS (ESI−): 534 (M−H)

EXAMPLE 595

N-Hydroxy-2-[4-(4-methoxyphenylsulfonyl)-7-(5-(4-(5-oxazolyl)phenyl)-2-thienyl)-1,1-dioxoperhydro-1,4-thiazepin-7-yl]acetamide (48 mg)

NMR (DMSO-d$_6$, δ): 2.56–3.04 (2H, m), 3.04–3.20 (2H, m), 3.20–3.54 (2H, m), 3.54–3.76 (3H, m), 3.76–4.07 (4H; m), 7.12–7.24 (3H, m), 7.56 (1H, d, J=3 Hz), 7.71–7.84 (7H, m), 8.49 (1H, s), 8.95 (1H, s) MASS (ES−)(m/z): 616.15

EXAMPLE 596

N-Hydroxy-2-[7-(5-(4-(5-oxazolyl)phenyl)-2-thienyl)-1,1-dioxoperhydro-4-(1H-pyrazol-4-ylcarbonyl)-1,4-thiazepin-7-yl]acetamide (67 mg)

NMR (DMSO-d$_6$, δ): 2.25–3.20 (4H, m), 3.20–4.10 (6H, m), 7.26 (1H, d, J=3 Hz), 7.56 (1H, d, J=3 Hz), 7.73–7.82 (5H, m), 7.94–8.04 (2H, m), 8.49 (1H, s) MASS (ES−)(m/z): 540.18

EXAMPLE 597

N-Hydroxy-2-[7-(5-(4-(5-oxazolyl)phenyl)-2-thienyl)-1,1-dioxoperhydro-4-(1-piperidinylsulfonyl)-1,4-thiazepin-7-yl)acetamide (28 mg)

NMR (DMSO-d$_6$, δ): 1.44–1.61 (6H, m), 2.85–2.95 (2H, m), 3.06–3.22 (6H, m), 3.41–3.85 (5H, m), 3.85–4.06 (1H, m), 7.24 (1H, d, J=3 Hz), 7.56 (1H, d, J=3 Hz), 7.73–7.83 (5H, m), 8.49 (1H, s), 8.95 (1H, s) MASS (ES−)(m/z): 593.34

EXAMPLE 598

N-Hydroxy-2-[(S)-4-benzoyl-7-(5-(4-ethoxyphenyl)-2-thienyl)-1,1-dioxoperhydro-1,4-thiazepin-7-yl]acetamide (1.62 g)

NMR (DMSO-d$_6$, δ): 1.34 (3H, t, J=7.5 Hz), 2.75–3.40 (4H, m), 3.40–4.00 (6H, m), 4.05 (2H, q, J=7.5 Hz), 6.96 (2H, d, J=8 Hz), 7.14–7.21 (1H, m), 7.28–7.36 (1H, m), 7.36–7.50 (5H, m), 7.50–7.60 (2H, m), 8.86 (1H, br peak) MASS (ES−)(m/z): 527.27

EXAMPLE 599

N-Hydroxy-2-[4-[(N,N-dimethylamino)sulfonyl]-7-(5-(4-ethoxyphenyl)-2-thienyl)-1,11-dioxoperhydro-1,4-thiazepin-7-yl]acetamide (14 mg)

NMR (DMSO-d$_6$, δ): 1.34 (3H, t, J=7.5 Hz), 2.75 (6H, s), 2.76–3.99 (10H, m), 4.05 (2H, q, J=7.5 Hz), 6.98 (2H, d, J=8 Hz) 7.16 (1H, d, J=3 Hz), 7.33 (1H, d, J=3 Hz), 7.55 (2H, d, J=8 Hz) MASS (ES−)(m/z): 530.17

EXAMPLE 600

N-Hydroxy-2-[7-(5-(4-ethoxyphenyl)-2-thienyl)-4-(3-pyridinylsulfonyl)-1,1-dioxoperhydro-1,4-thiazepin-7-yl] acetamide hydrochloride (42 mg)

NMR (DMSO-d$_6$, δ): 1.33 (3H, t, J=7.5 Hz), 2.69–2.99 (2H, m), 2.99–3.21 (2H, m), 3.38–4.00 (6H, m), 4.05 (2H, q, J=7.5 Hz), 6.96 (2H, d, J=8 Hz), 7.14 (1H, d, J=3 Hz), 7.32 (1H, d, J=3 Hz), 7.55 (2H, d, J=8 Hz), 7.70 (1H, dd, J=8, 5 Hz), 8.28 (1H, dd, J=8, 2 Hz), 8.90 (1H, dd, J=5, 2 Hz), 9.04 (1H, d, J=2 Hz) MASS (ES−)(m/z): 564.27 (M(Free)−H)

EXAMPLE 601

N-Hydroxy-2-[4-benzoyl-7-(4-(4-methoxyphenoxy)phenyl]-1,1-dioxoperhydro-1,4-thiazepin-7-yl]acetamide (25 mg)

NMR (DMSO-d$_6$, δ): 2.70–2.83 (1H, m), 2.97–3.10 (2H, m), 3.14–3.28 (2H, m), 3.47–3.63 (3H, m), 3.76 (3H, s), 3.82–4.24 (2H, m), 6.82–6.90 (2H, m), 6.98–7.09 (4H, m), 7.40–7.52 (7H, m); 8.74–8.85 (1H, m), 10.59 (1H, s)

EXAMPLE 602

N-Hydroxy-2-[4-cyclopropanecarbonyl-7-[4-(4-methoxyphenoxy)phenyl]-1,1-dioxoperhydro-1,4-thiazepin-7-yl]acetamide (50 mg)

NMR (DMSO-d$_6$, δ): 0.65–0.90 (4H, m), 1.83–2.00 (1H, m), 2.62–2.83 (2H, m), 3.03–3.28 (2H, m), 3.36–4.13 (5H, m), 3.76 (3H, s), 4.25–4.38 (1H, m), 6.84–6.90 (2H, m), 6.97–7.09 (4H, m), 7.42–7.49 (2H, m), 10.59–10.67 (1H, m) MASS (m/z): 530 (M$^+$−H), 82 (bp)

EXAMPLE 603

N-Hydroxy-2-[7-[4-(4-methoxyphenoxy)phenyl]-4-(2-thiophenecarbonyl)-1,1-dioxoperhydro-1,4-thiazepin-7-yl] acetamide (52.2 mg)

NMR (DMSO-d$_6$, δ): 2.63–2.82 (1H, m), 2.93–3.28 (2H, m), 3.45–3.67 (5H, m), 3.83–4.16 (2H, m), 6.85 (2H, d, J=7 Hz), 7.02 (4H, q, J=8 Hz), 7.16 (1H, t, J=4 Hz), 7.40–7.50 (3H, m), 7.80 (1H, d, J=7 Hz), 10.60 (1H, MASS (m/z): 530 (M$^+$−H), 82 (bp)

EXAMPLE 604

N-Hydroxy-2-[7-[4-(4-methoxyphenoxy)phenyl]-4-(3-thiophenecarbonyl)-1,1-dioxoperhydro-1,4-thiazepin-7-yl] acetamide (21 mg)

NMR (DMSO-d$_6$, δ): 2.65–2.82 (1H, m), 2.95–3.10 (1H, m), 3.15–3.45 (2H, m), 3.48–3.60 (1H, m), 3.64–3.90 (4H, m), 3.76 (3H, s), 3.94–4.19 (1H, m), 6.55 (1H, s), 6.81–6.90 (2H, m), 6.97 (2H, d, J=8 Hz), 7.03 (4H, q, J=8 Hz), 7.22–7.31 (1H, m), 7.47 (2H, br s), 7.64 (1H, br s), 7.81–7.91 (1H, m), 8.60–8.86 (1H, m) MASS (m/z): 529 (M$^+$−H), 113 (bp)

EXAMPLE 605

N-Hydroxy-2-[7-[4-(4-methoxyphenoxy)phenyl]-1,1-dioxoperhydro-4-(2-pyridinecarbonyl)-1,4-thiazepin-7-yl] acetamide hydrochloride (58.2 mg)

NMR (DMSO-d$_6$, δ): 2.58–3.40 (7H, m), 3.76 (3H, s), 3.83–3.94 (2H, m), 4.05–4.30 (1H, m), 6.87 (2H, t, J=8 Hz), 7.03 (4H, q, J=8 Hz), 7.40–7.54 (4H, m), 7.58–7.67 (1H, m), 7.91–7.99 (1H, m), 8.57–8.62 (1H, m) MASS (m/z): 526 (M$^+$−H), 191 (bp)

EXAMPLE 606

N-Hydroxy-2-[4-[(2S)-2-hydroxy-2-phenylacetyl]-7-[4-(4-methoxyphenoxy)phenyl]-1,1-dioxoperhydro-1,4-thiazepin-7-yl]acetamide (55.6 mg)

NMR (DMSO-d$_6$, δ): 2.62–2.74 (2H, m), 2.95–3.20 (6H, m), 3.76 (3H, s), 3.85–4.27 (2H, m), 5.37–5.44 (1H, m), 6.80–6.82 (2H, m), 7.02 (4H, q, J=8 Hz), 7.27–7.53 (7H, m), 10.47–10.65 (1H, m) MASS (m/z): 553 (M$^+$−H), 127 (bp)

EXAMPLE 607

N-Hydroxy-2-[4-(dimethylamino)sulfonyl-7-[4-(4-methoxyphenoxy)phenyl]-1,1-dioxoperhydro-1,4-thiazepin-7-yl]acetamide (39.6 mg)

NMR (DMSO-d$_6$, δ): 2.74 (6H, s), 3.03–3.10 (1H, m), 3.24–3.30 (1H, m), 3.42–3.64 (7H, m), 3.94–4.04 (1H, m), 3.76 (3H, s), 6.85 (2H, d, J=8 Hz), 7.02 (4H, q, J=8 Hz), 7.43 (2H, d, J=8 Hz), 10.67 (1H, s) MASS (m/z): 527 (M$^+$), 191 (bp)

EXAMPLE 608

N-Hydroxy-2-[7-[4-(4-methoxyphenoxy)phenyl]-1,1-dioxoperhydro-4-(2-pyrazinecarbonyl)-1,4-thiazepin-7-yl] acetamide (37 mg)

NMR (DMSO-d$_6$, δ): 2.73–3.40 (5H, m), 3.58–3.84 (3H, m), 3.76 (3H, s), 4.15–4.30 (2H, m), 6.87 (2H, t, J=8 Hz), 7.03 (4H, q, J=8 Hz), 7.46 (2H, d, J=8 Hz), 8.70 (1H, s), 8.79 (1H, d, J=2 Hz), 8.90 (1H, s)

The following compounds were obtained in a similar manner to that of Example 17.

EXAMPLE 609

N-Hydroxy-2-[4-((R)-2-amino-2-phenylacetyl)-7-(5-(4-chlorophenyl)-2-thienyl)-1,1-dioxoperhydro-1,4-thiazepin- 7-yl]acetamide hydrochloride (40.9 mg) from N-(2-tetrahydropyranyloxy)-2-[4-((R)-2-t-butoxycarbonylamino-2-phenylacetyl-7-(5-(4-chlorophenyl)-2-thienyl)-1,1-dioxoperhydro-1,4-thiazepin-7-yl]acetamide (60.0 mg)

NMR (DMSO-$d_6$, δ): 2.55–3.20 (4H, m), 3.50–4.10, 4.30–4.45 (6H, br), 5.41, 5.68 (1H, br), 7.23 (1H, d, J=3 Hz), 7.40–7.63 (9H, br), 7.64–7.73 (2H, m), 8.55–8.82 (3H, br), 10.57, 10.68 (1H, s) MASS (m/z): 546 (M–H)

EXAMPLE 610

N-Hydroxy-2-[(S)-7-(5-(4-chlorophenyl)-2-thienyl)-4-(4-piperidinecarbonyl)-1,1-dioxoperhydro-1,4-thiazepin-7-yl]acetamide hydrochloride (91.5 mg) from N-(2-tetrahydropyranyloxy)-2-[(S)-4-(1-t-butoxycarbonyl-4-piperidinecarbonyl)-7-(5-(4-chlorophenyl)-2-thienyl)-1,1-dioxoperhydro-1,4-thiazepin-7-yl]acetamide (120 mg)

NMR (DMSO-$d_6$, δ): 1.68–1.93 (4H, br), 2.60–4.03 (15H, br), 7.23, 7.26 (1H, d, J=3 Hz), 7.44–7.55 (3H, m), 7.67 (2H, d, J=8 Hz), 8.40–8.60 (1H, br), 8.72–8.92 (2H, br), 10.68, 10.71 (1H, br) MASS (m/z): 524 (M–H)

EXAMPLE 611

N-Hydroxy-2-[4-((2S)-2-amino-2-phenylacetyl)-7-(5-(4-(5-oxazolyl)phenyl)-2-thienyl)-1,1-dioxoperhydro-1,4-thiazepin-7-yl]acetamide (85 mg) from N-(2-tetrahydropyranyloxy)-2-[4-((2S)-2-tert-butoxycarbonylamino-2-phenylacetyl)-7-(5-(4-(5-oxazolyl)phenyl)-2-thienyl)-1,1-dioxoperhydro-1,4-thiazepin-7-yl]acetamide (300 mg)

NMR (DMSO-$d_6$, δ): 2.62–3.12 (4H, m), 3.35–3.90 (7H, m), 6.85 (1H, d, J=7.5 Hz), 7.22 (1H, br), 7.44–7.62 (6H, m), 7.67–7.82 (4H, m), 8.47 (1H, s), 8.59 (2H, br), 10.55–10.68 (1H, m) MASS (ESI–): 579.2 (M–H)

EXAMPLE 612

N-Hydroxy-2-[4-(2-aminoacetyl)-7-(5-(4-(5-oxazolyl)phenyl)-2-thienyl)-1,1-dioxoperhydro-1,4-thiazepin-7-yl]acetamide hydrochloride (80 mg) from N-(2-tetrahydropyranyloxy)-2-[4-(2-tert-butoxycarbonylaminoacetyl)-7-(5-(4-(5-oxazolyl)phenyl)-2-thienyl)-1,1-dioxoperhydro-1,4-thiazepin-7-yl]acetamide (110 mg)

NMR (DMSO-$d_6$, δ): 2.70–3.12 (4H, m), 3.42–4.06 (8H, m), 7.25–7.32 (1H, m), 7.56–7.60 (1H, m), 7.75–7.82 (5H, m), 8.12–8.24 (3H, m), 8.50 (1H, s) MASS (ESI–): 503.2 (M–H)

EXAMPLE 613

N-Hydroxy-2-[4-((2R)-2-amino-2-phenylacetyl)-7-(5-(4-(5-oxazolyl)phenyl)-2-thienyl)-1,1-dioxoperhydro-1,4-thiazepin-7-yl]acetamide hydrochloride (85 mg) from N-(2-tetrahydropyranyloxy)-2-[4-((2R)-2-tert-butoxycarbonylamino-2-phenylacetyl)-7-(5-(4-(5-oxazolyl)phenyl)-2-thienyl)-1,1-dioxoperhydro-1,4-thiazepin-7-yl]acetamide (110 mg)

NMR (DMSO-$d_6$, δ): 2.59–3.18 (4H, m), 3.64–4.00 (7H, m), 7.21–7.25 (1H, m), 7.45–7.60 (6H, m), 7.69–7.82 (5H, m), 8.47 (1H, s), 8.00–8.73 (3H, br) MASS (ESI–): 579.2 (M–H) Free 580.68

EXAMPLE 614

N-Hydroxy-2-[4-((R)-2-amino-2-phenylacetyl)-7-(5-(4-fluorophenyl)-2-thienyl)-1,1-dioxoperhydro-1,4-thiazepin-7-yl]acetamide hydrochloride (66.5 mg) from N-(2-tetrahydropyranyloxy)-2-[4-((R)-2-t-butoxycarbonylamino-2-phenylacetyl)-7-(5-(4-fluorophenyl)-2-thienyl)-1,1-dioxoperhydro-1,4-thiazepin-7-yl]acetamide (105 mg)

NMR (DMSO-$d_6$, δ): 2.55–3.30 (4H, br), 3.30–4.10 (6H, br), 5.38–5.45, 5.55–5.73 (1H, br), 7.02, 7.17–7.77 (11H, m), 8.53–8.78 (4H, br), 10.57, 10.67–10.78 (1H, m) MASS (m/z): 530 (M–H)

EXAMPLE 615

N-Hydroxy-2-[(S)-4-((S)-2-amino-3-methylbutyryl)-7-(5-(4-ethylphenyl)-2-thienyl)-1,1-dioxoperhydro-1,4-thiazepin-7-yl]acetamide hydrochloride (44 mg) from N-(2-tetrahydropyranyloxy)-2-[(S)-4-((S)-2-(N-tert-butoxycarbonylamino)-3-methylbutyryl)-7-(5-(4-ethylphenyl)-2-thienyl)-1,1-dioxoperhydro-1,4-thiazepin-7-yl]acetamide (68 mg)

NMR (DMSO-$d_6$, δ): 0.84–1.10 (16H, m), 1.19 (3H, t, J=8 Hz), 2.03–2.18 (1H, m), 2.62 (2H, q, J=8 Hz), 2.77–4.45 (11H, m), 7.16–7.22 (3H, m), 7.36–7.47 (1H, m), 7.50–7.65 (2H, m), 8.12–8.35 (2H, m) MASS (ESI–): 542 (M–H)

EXAMPLE 616

N-Hydroxy-2-[(S)-4-(3-aminopropionyl)-7-(5-(4-ethylphenyl)-2-thienyl)-1,1-dioxoperhydro-1,4-thiazepin-7-yl]acetamide (75 mg) from N-(2-tetrahydropyranyloxy)-2-[(S)-4-(3-N-tert-butoxycarbonylaminopropionyl)-7-(5-(4-ethylphenyl)-2-thienyl)-1,1-dioxoperhydro-1,4-thiazepin-7-yl]acetamide (115 mg)

NMR (DMSO-$d_6$, δ): 1.19 (3H, t, J=8 Hz), 2.62 (2H, q, J=8 Hz), 2.68–4.10 (14H, m), 7.18–7.32 (3H, m), 7.43 (1H, t, J=3 Hz), 7.55 (2H, d, J=7 Hz), 7.86 (2H, br), 8.89, 8.94 (1H, s), 10.73, 10.78 (1H, s) MASS (ESI–): 478 (M–H)

EXAMPLE 617

N-Hydroxy-2-[7-(5-(4-biphenylyl)-2-thienyl)-4-aminomethylcarbonyl-1,1-dioxoperhydro-1,4-thiazepin-7-yl]acetamide (50 mg) from N-(2-tetrahydropyranyloxy)-2-[7-(5-(4-biphenylyl)-2-thienyl)-4-tert-butoxycarbonylaminomethylcarbonyl)-1,1-dioxoperhydro-1,4-thiazepin-7-yl]acetamide (100 mg)

NMR (DMSO-$d_6$, δ): 2.73–2.80 (1H, m), 2.93–3.10 (3H, m), 3.75–4.00 (8H, m), 7.25, 7.29 (1H, d, J=4.5 Hz), 7.35–7.40 (1H, m), 7.46–7.51 (2H, m), 7.52, 7.53 (1H, d, J=4.5 Hz), 7.57–7.75 (7H, m), 8.10 (3H, br) MASS (ESI+): 514 (M+H)

The following compounds were obtained in a similar manner to that of Example 28.

EXAMPLE 618

N-(2-Tetrahydropyranyloxy)-2-[(S)-7-(5-(4-chlorophenyl)-2-thienyl)-1,1-dioxoperhydro-1,4-thiazepin-7-yl]acetamide (4.70 g)

NMR (CDCl$_3$, δ): 1.40–1.93 (6H, br), 2.53–2.76 (1H, br), 2.95–3.65 (10H, br), 3.73–3.90 (1H, br), 4.61, 4.87 (1H, br), 7.17–7.26 (2H, m), 7.33 (2H, d, J=8 Hz), 7.51 (2H, d, J=8 Hz), 8.26–8.52 (1H, br) MASS (m/z): 499 (M+H)

EXAMPLE 619

N-(2-Tetrahydropyranyloxy)-2-[7-[4-(4-methoxyphenoxy)phenyl]-1,1-dioxoperhydro-1,4-thiazepin-7-yl]acetamide (1.474 g)

NMR (CDCl$_3$, δ): 1.50–1.60 (4H, m), 1.74 (2H, s), 2.53–2.64 (1H, m), 3.11–3.63 (12H, m), 3.78–3.90 (1H, m), 6.98 (4H, d, J=8 Hz), 7.33 (2H, d, J=8 Hz), 7.57 (2H, d, J=8 Hz) MASS (m/z): 503 (M$^+$+H), 123 (bp)

EXAMPLE 620

N-(2-Tetrahydropyranyloxy)-2-[7-(5-(4-propylphenyl)-2-thienyl)-1,1-dioxoperhydro-1,4-thiazepin-7-yl]acetamide (1.65 g)

NMR (CDCl$_3$, δ): 0.95 (3H, t, J=7 Hz), 1.40–1.93 (8H, br), 2.60 (2H, t, J=7 Hz), 2.49–2.70 (1H, br), 2.96–3.34 (7H, br), 3.35–3.57 (3H, br), 3.68–3.83 (1H, br), 4.58, 4.86 (1H, br), 7.14–7.26 (4H, m), 7.50 (2H, d, J=8 Hz), 8.22, 8.41 (1H, br) MASS (m/z): 507 (M+H)

EXAMPLE 621

N-(2-Tetrahydropyranyloxy)-2-[7-(5-(4-fluorophenyl)-2-thienyl)-1,1-dioxoperhydro-1,4-thiazepin-7-yl]acetamide (4.09 g)

NMR (CDCl$_3$, δ): 1.42–1.93 (6H, br), 2.53–2.76 (1H, br), 2.97–3.68 (10H, br), 3.70–3.98 (1H, br), 4.62, 4.88 (1H, br), 7.03–7.12 (2H, m), 7.18 (1H, d, J=3 Hz), 7.24 (1H, d, J=3 Hz), 7.48–7.60 (2H, m), 8.40, 8.53 (1H, br) MASS (m/z): 481 (M−H). 483 (M+H)

EXAMPLE 622

N-(2-Tetrahydropyranyloxy)-2-[7-(5-(4-cyanophenyl)-2-thienyl)-1,1-dioxoperhydro-1,4-thiazepin-7-yl]acetamide (1.16 g)

NMR (CDCl$_3$, δ): 1.44–1.95 (6H, br), 2.58–2.80 (1H, br), 3.02–3.63 (10H, br), 3.75–3.98 (1H, br), 4.63, 4.89 (1H, br), 7.28 (1H, d, J=3 Hz), 7.36 (1H, d, J=3 Hz), 7.62–7.75 (4H, br), 8.32, 8.43 (1H, br) MASS (m/z): 488 (M−H)

EXAMPLE 623

N-(2-Tetrahydropyranyloxy)-2-[7-(5-(5-chloro-2-thienyl)-2-thienyl)-1,1-dioxoperhydro-1,4-thiazepin-7-yl]acetamide (580 g)

NMR (CDCl$_3$, δ): 1.40–1.90 (6H, br), 2.50–2.75 (1H, br), 2.95–3.72 (10H, br), 3.72–4.00 (1H, br), 4.60, 4.88 (1H, br), 6.84 (1H, d, J=3 Hz), 6.94 (1H, d, J=3 Hz), 7.01 (1H, d, J=3 Hz), 7.15 (1H, d, J=3 Hz), 8.30, 8.44 (1H, br) MASS (m/z): 503 (M−H)

EXAMPLE 624

N-(2-Tetrahydropyranyloxy)-2-[7-(5-(4-methoxymethylphenyl)-2-thienyl)-1,1-dioxoperhydro-1,4-thiazepin-7-yl]acetamide (855 g)

NMR (CDCl$_3$, δ): 1.40–1.90 (6H, br), 2.50–2.66 (1H, br), 2.96–3.35 (7H, br), 3.41 (3H, s), 3.41–3.58 (3H, br), 3.68–3.83 (1H, br), 4.47 (2H, s), 4.59, 4.86 (1H, br), 7.23 (2H, m), 7.34 (2H, d, J=8 Hz), 7.57 (2H, d, J=8 Hz), 8.22, 8.39 (1H, br) MASS (m/z): 509 (M+H)

EXAMPLE 625

N-(2-Tetrahydropyranyloxy)-2-[7-[4-(4-chlorophenoxy)phenyl]-1,1-dioxoperhydro-1,4-thiazepin-7-yl]acetamide (932 mg)

NMR (CDCl$_3$, δ): 1.50–1.65 (4H, m), 1.75 (2H, s), 2.52–2.65 (1H, m), 3.10–3.64 (11H, m), 3.78–3.89 (1H, m), 6.99 (4H, d, J=8 Hz), 7.32 (2H, d, J=8 Hz), 7.57 (2H, d, J=8 Hz) MASS (m/z): 509 (M$^+$+H), 74 (bp)

EXAMPLE 626

N-(2-Tetrahydropyranyloxy)-2-[7-[4-(4-methylphenoxy)phenyl]-1,1-dioxoperhydro-1,4-thiazepin-7-yl]acetamide (1.8 g)

NMR (CDCl$_3$, δ): 1.50–1.62 (4H, m), 1.73 (2H, s), 2.35 (3H, s), 2.47–2.59 (1H, m), 3.05–3.30 (9H, m), 3.35–3.46 (1H, m), 3.52–3.63 (1H, m), 3.75–3.85 (1H, m), 6.94 (2H, d, J=8 Hz), 6.97 (2H, d, J=8 Hz), 7.17 (2H, d, J=8 Hz), 7.54 (2H, d, J=8 Hz) MASS (m/z): 489 (M$^+$+H), 74 (bp)

EXAMPLE 627

N-(2-Tetrahydropyranyloxy)-2-[7-[4-(4-fluorophenoxy)phenyl]-1,1-dioxoperhydro-1,4-thiazepin-7-yl]acetamide (1.3 g)

NMR (CDCl$_3$, δ): 1.48–1.62 (4H, m), 1.74 (2H, s), 2.51–2.61 (1H, m), 3.09–3.60 (11H, m), 3.77–3.88 (1H, m), 6.94 (2H, d, J=8 Hz), 7.00–7.07 (4H, m), 7.54 (2H, d, J=8 Hz) MASS (m/z): 492 (M$^+$+H), 85 (bp)

EXAMPLE 628

N-(2-Tetrahydropyranyloxy)-2-[(S)-7-[4-(4-chlorophenoxy)phenyl]-1,1-dioxoperhydro-1,4-thiazepin-7-yl]acetamide (881 g)

NMR (CDCl$_3$, δ): 1.50–1.60 (4H, m), 1.74 (2H, s), 2.53–2.64 (1H, m), 3.11–3.63 (12H, m), 3.78–3.90 (1H, m), 6.98 (4H, d, J==8 Hz), 7.33 (2H, d, J=8 Hz), 7.57 (2H, d, J=8 Hz) MASS (m/z): 509 (M$^+$+H), 85 (bp)

EXAMPLE 629

N-(2-Tetrahydropyranyloxy)-2-[7-(5-(4-methoxyphenyl)-2-thienyl)-1,1-dioxoperhydro-1,4-thiazepin-7-yl]acetamide (955 mg)

NMR (DMSO-d$_6$, δ): 1.36–1.70 (6H, m), 2.56–3.35 (8H, m), 3.35–3.54 (3H, m), 3.69–3.95 (4H, m), 4.53 (0.5H, br s), 4.76 (0.5H, br s), 7.00 (2H, d, J=8 Hz), 7.10–7.26 (1H, m), 7.26–7.34 (1H, m), 7.56 (2H, d, J=8 Hz) MASS (ES+) (m/z): 495.37

EXAMPLE 630

N-(2-Tetrahydropyranyloxy)-2-[7-(5-(2-naphthyl)-2-thienyl)-1,1-dioxoperhydro-1,4-thiazepin-7-yl]acetamide (1.8 g)

NMR (CDCl$_3$, δ): 1.45–1.60 (6H, m), 2.65–2.71 (1H, m), 2.80–3.52 (11H, m), 3.76–3.91 (1H, m), 4.55, 4.78 (1H, s), 7.22–7.26 (1H, m), 7.50–7.62 (3H, m), 7.84 (1H, d, J=8.5 Hz), 7.90–7.99 (3H, m), 8.17 (1H, s)

EXAMPLE 631

N-(2-Tetrahydropyranyloxy)-2-[7-(5-(4-methylthiophenyl)-2-thienyl)-1,1-dioxoperhydro-1,4-thiazepin-7-yl]acetamide (2.3 g)

NMR (CDCl$_3$, δ): 1.48–1.71 (6H, m), 2.51 (3H, s), 2.95–3.25 (6H, m), 3.36–3.49 (2H, m), 3.69–3.77 (1H, m), 4.60, 4.85 (1H, br), 7.20–7.26 (4H, m), 7.50 (2H, d, J=8.5 Hz), 8.35, 8.48 (1H, br) MASS (ESI−): 509 (M−H)

EXAMPLE 632

N-(2-Tetrahydropyranyloxy)-2-[7-(5-(4-biphenylyl)-2-thienyl)-1,1-dioxoperhydro-1,4-thiazepin-7-yl]acetamide (2.1 g)

NMR (CDCl$_3$, δ): 1.49–1.86 (6H, m), 2.56–2.65 (2H, m), 3.01–3.35 (7H, m), 3.49–3.53 (2H, m), 3.73–3.80 (1H, m), 4.60, 4.86 (1H, br), 7.35–7.38 (1H, m), 7.43–7.48 (2H, m), 7.60–7.67 (7H, m), 8.02 (1H, s) MASS (ESI−): 539 (M−H)

EXAMPLE 633

N-(2-Tetrahydropyranyloxy)-2-[7-(5-(4-methylphenyl)-2-thienyl)-1,1-dioxoperhydro-1,4-thiazepin-7-yl]acetamide (2.5 g)

NMR (DMSO-d$_6$, δ): 1.48–1.75 (6H, m), 2.36 (3H, s), 2.50–2.60 (1H, m), 2.97–3.30 (7H, m), 3.37–3.54 (3H, m), 3.66–3.77 (1H, m), 4.58, 4.85 (1H, s), 7.16–7.24 (4H, m), 7.47 (2H, d, J=7.55 Hz) MASS (ES–): 477 (M–H)

EXAMPLE 634

N-(2-Tetrahydropyranyloxy)-2-[7-(5-(4-ethoxy]phenyl)-2-thienyl)-1,1-dioxoperhydro-1,4-thiazepin-7-yl]acetamide (1 g)

NMR (DMSO-d$_6$, δ): 1.34 (0.3H, t, J=7.5 Hz), 1.39–1.65 (6H, m), 2.56–3.99 (12H, m), 4.05 (2H, q, J=7.5 Hz), 4.51 (½H, br s), 4.77 (½H, br s), 6.96 (2H, d, J=8 Hz), 7.10 (½H, d, J=3 Hz), 7.15 (½H, d, J=3 Hz), 7.28 (½H, d, J=3 Hz) 7.30 (½H, d, J=3 Hz), 7.55 (2H, d, J=8 Hz) MASS (ES–) (m/z): 509.12

EXAMPLE 635

To a solution of 20% piperidine in N,N-dimethylformamide (100 ml) were added N-[2-[7-(5-bromo-2-thienyl)-4-(9-fluorenylmethoxycarbonyl)-1,1-dioxoperhydro-1,4-thiazepin-7-yl]acetyl]hydroxylamine trityl crowns (14.3 μmol/crown×50), and the reaction mixture was left for 1 hour at ambient temperature. The crowns were washed with N,N-dimethylformamide, methanol and dichloromethane, successively and air dried to give N-[2-[7-(5-bromo-2-thienyl)-1,1-dioxoperhydro-1,4-thiazepin-7-yl]acetyl]hydroxylamine trityl crowns (14.3 μmol/crown× 50).

The following compounds were obtained in a similar manner to that of Example 30.

EXAMPLE 636

N-(2-Tetrahydropyranyloxy)-2-[(S)-7-(5-(4-chlorophenyl)-2-thienyl)-4-(9-fluorenylmethoxycarbonyl)-1,1-dioxoperhydro-1,4-thiazepin-7-yl]acetamide (9.61 g)

NMR (CDCl$_3$, δ): 1.44–1.90 (6H, br), 2.53–4.10 (13H, br), 4.10–4.73, 4.81–5.00 (3H, br), 7.05–7.18 (2H, br), 7.22–7.47 (8H, br), 7.52–7.61 (2H, br), 7.72–7.85 (2H, br), 8.13, 8.28, 8.38, 8.44 (1H, br)

EXAMPLE 637

N-(2-Tetrahydropyranyloxy)-2-[4-(9-fluorenylmethoxycarbonyl)-7-(5-(4-propylphenyl)-2-thienyl)-1,1-dioxoperhydro-1,4-thiazepin-7-yl]acetamide (3.02 g)

NMR (CDCl$_3$, δ): 0.94 (3H, t, J=7 Hz), 1.40–1.90 (8H, br), 2.38–4.07 (12H, br), 2.60 (2H, t, J=7 Hz), 4.18, 4.31, 4.40–4.69, 4.75–4.92 (4H, m), 7.05–7.62 (12H, m), 7.68–7.83 (2H, m), 8.05, 8.23, 8.25, 8.36 (1H, br)

EXAMPLE 638

N-(2-Tetrahydropyranyloxy)-2-[4-(9-fluorenylmethoxycarbonyl)-7-(5-(4-fluorophenyl)-2-thienyl)-1,1-dioxoperhydro-1,4-thiazepin-7-yl]acetamide (7.03 g)

NMR (CDCl$_3$, δ): 1.42–1.93 (6H, br), 2.50–4.13 (12H, br), 4.17–4.63, 4.69, 4.82–5.00 (4H, br), 6.97–7.20 (4H, m), 7.23–7.63 (8H, m), 7.73–7.84 (2H, m), 8.22, 8.35–8.44, 8.48 (1H, br) MASS (m/z): 705 (M+H)

EXAMPLE 639

N-(2-Tetrahydropyranyloxy)-2-[7-(5-(4-cyanophenyl)-2-thienyl)-4-(9-fluorenylmethoxycarbonyl)-1,1-dioxoperhydro-1,4-thiazepin-7-yl]acetamide (2.35 g)

NMR (CDCl$_3$, δ): 1.47–1.90 (6H, br), 2.52–4.15 (1H, br), 4.15–5.13 (4H, m), 7.12–7.47 (7H, m), 7.50–7.66 (5H, br), 7.72–7.84 (2H, br), 8.22, 8.33, 8.54 (1H, br)

EXAMPLE 640

N-(2-Tetrahydropyranyloxy)-2-[7-(5-(5-chloro-2-thienyl)-2-thienyl)-4-(9-fluorenylmethoxycarbonyl)-1,1-dioxoperhydro-1,4-thiazepin-7-yl]acetamide (1.05 g)

NMR (CDCl$_3$, δ): 1.45–1.90 (6H, br), 2.45–4.10 (12H, br), 4.18–4.34, 4.38–4.65, 4.72, 4.80–5.04 (4H, br), 6.81, 6.87–7.05, 7.08 (4H, m), 7.29–7.47, 7.48–7.62 (6H, m), 7.72–7.85 (2H, m), 8.25, 8.38, 8.43 (1H, br)

EXAMPLE 641

N-(2-Tetrahydropyranyloxy)-2-[4-(9-fluorenylmethoxycarbonyl)-7-(5-(4-methoxymethylphenyl)-2-thienyl)-1,1-dioxoperhydro-1,4-thiazepin-7-yl]acetamide (1.91 g)

NMR (CDCl$_3$, δ): 1.45–1.88 (6H, br), 2.50–4.12 (12H, br), 3.41 (3H, s), 4.18–4.36, 4.40–4.72, 4.78–4.95 (4H, br), 4.47 (2H, s), 7.08, 7.15–7.20 (2H, br), 7.30–7.46 (7H, br), 7.48–7.63 (3H, br), 7.73–7.82 (2H, br), 8.08, 8.27, 8.39 (1H, br)

EXAMPLE 642

N-(2-Tetrahydropyranyloxy)-2-[(S)-7-(5-(4-chlorophenyl)-2-thienyl)-1,1-dioxoperhydro-4-(2-pyridinecarbonyl)-1,4-thiazepin-7-yl]acetamide (2.10 g)

NMR (DMSO-d$_6$, δ): 1.32–1.68 (6H, m), 2.70–4.15 (12H, m), 4.40–4.78 (1H, m), 7.19–7.28 (1H, m), 7.44–7.54 (4H, m), 7.57–7.72 (3H, m), 7.95 (1H, t, J=8 Hz), 8.56–8.64 (1H, m) MASS (ESI–): 602 (M–H)

EXAMPLE 643

N-(2-Tetrahydropyranyloxy)-2-[(S)-7-(5-(4-ethylphenyl)-2-thienyl)-1,1-dioxoperhydro-4-(2-pyrazinecarbonyl)-1,4-thiazepin-7-yl]acetamide (2.32 g)

NMR (DMSO-d$_6$, δ): 1.19 (3H, t, J=8 Hz), 1.35–1.73 (6H, m), 2.56 (2H, q, J=8 Hz), 2.71–3.22 (4H, m), 3.32–4.13 (8H, m), 4.40–4.80 (1H, m), 7.17–7.31 (3H, m), 7.36–7.45 (1H, m), 7.54, 7.57 (2H, d, J=8 Hz), 8.26–8.32 (1H, m), 8.66–8.72 (1H, m), 8.85–8.92 (1H, m) MASS (ESI–): 597 (MH)

EXAMPLE 644

N-(2-Tetrahydropyranyloxy)-2-[(S)-7-(5-(4-ethylphenyl)-2-thienyl)-1,1-dioxoperhydro-4-(3-thiophenecarbonyl)-1,4-thiazepin-7-yl]acetamide (1.70 g)

NMR (DMSO-d$_6$, δ): 1.20 (3H, t, J=8 Hz), 1.36–1.64 (6H, m), 2.63 (2H, q, J=8 Hz), 2.76–4.12 (12H, m), 4.39–7.82 (1H, m), 7.18–7.30 (4H, m), 7.36–7.44 (1H, m), 7.52–7.66 (3H, m), 7.82–7.87 (1H, m), 8.32 (1H, s) MASS (ESI–): 601 (MH)

EXAMPLE 645

N-(2-Tetrahydropyranyloxy)-2-[7-(5-(4-(2-oxazolyl)phenyl)-2-thienyl)-1,1-dioxoperhydro-4-(3-thiophenecarbonyl)-1,4-thiazepin-7-yl]acetamide (310 mg)

NMR (DMSO-d$_6$, δ): 1.33–1.72 (6H, m), 2.70–4.13 (12H, m), 4.38–4.91 (1H, m), 7.22–7.34 (2H, m), 7.41 (1H, s), 7.54–7.67 (2H, m), 7.78–7.93 (3H, m), 8.02 (2H, d, J=8 Hz), 8.25 (1H, s) MASS (ESI–): 640 (M–H)

EXAMPLE 646

N-(2-Tetrahydropyranyloxy)-2-[(S)-7-(5-(4-(5-oxazolyl)phenyl)-2-thienyl)-1,1-dioxoperhydro-4-(3,3-dimethylbutyryl)-1,4-thiazepin-7-yl]acetamide (4.00 mg)

NMR (DMSO-d$_6$, δ): 1.02, 1.03 (9H, s), 1.38–1.67 (6H, m), 2.24, 2.30 (2H, s), 2.56–4.02 (12H, m), 4.44–4.79 (1H, m), 7.21–7.39 (1H, m), 7.52–7.60 (1H, m), 7.76 (1H, s), 7.78 (4H, s), 8.48 (1H, s) MASS (ESI–): 628 (M–H)

EXAMPLE 647

N-(2-Tetrahydropyranyloxy)-2-[(S)-7-(5-bromo-2-thienyl)-1,1-dioxoperhydro-4-(3-thiophenecarbonyl)-1,4-thiazepin-7-yl]acetamide (8.12 mg)

NMR (DMSO-d$_6$, δ): 1.37–1.74 (6H, m), 2.63–3.18 (4H, m), 3.25–4.09 (8H, m), 4.32–4.81 (1H, m), 7.05 (1H, d, J=4 Hz), 7.15–7.27 (2H, m), 7.56–7.67 (1H, m), 7.82 (1H, s) MASS (ESI–): 574, 576 (M–H)

EXAMPLE 648

N-(2-Tetrahydropyranyloxy)-2-[7-[4-(4-chlorophenoxy)phenyl]-4-(9-fluorenylmethoxycarbonyl)-1,1-dioxoperhydro-1,4-thiazepin-7-yl]acetamide (1.523 g)

NMR (CDCl$_3$, δ): 1.51–1.62 (4H, m), 1.68–1.80 (2H, m), 2.47–2.61 (2H, m), 2.85–3.18 (3H, m), 3.25–3.70 (5H, m), 3.86–4.15 (2H, m), 4.18–4.30 (1H, m), 4.34–4.60 (2H, m), 4.70–4.80 (1H, m), 6.92–6.99 (4H, m), 7.30–7.66 (10H, m), 7.77–7.87 (2H, m), 8.51–8.55 (1H, m)

EXAMPLE 649

N-(2-Tetrahydropyranyloxy)-2-[4-(9-fluorenylmethoxycarbonyl)-7-[4-(4-methylphenoxy)phenyl]-1,1-dioxoperhydro-1,4-thiazepin-7-yl]acetamide (3.4 g)

NMR (CDCl$_3$, δ): 1.50–1.62 (4H, m), 1.68–1.80 (2H, m), 2.33 and 2.36 (3H, s), 2.47–2.69 (2H, m), 2.90–3.18 (3H, m), 3.33–3.68 (5H, m), 3.84–4.09 (2H, m), 4.17–4.30 (1H, m), 4.37–4.56 (2H, m), 4.90–5.07 (1H, m), 6.85–6.99 (4H, m), 7.08–7.17 (2H, m), 7.31–7.50 (7H, m), 7.55–7.60 (1H, m), 7.78 (2H, d, J=8 Hz), 8.39–8.47 (1H, m) MASS (ESI–): 709 (M$^+$+–H), 123 (bp)

EXAMPLE 650

N-(2-Tetrahydropyranyloxy)-2-[4-(9-fluorenylmethoxycarbonyl)-7-[4-(4-fluorophenoxy)phenyl]-1,1-dioxoperhydro-1,4-thiazepin-7-yl]acetamide (2.4 g)

NMR (CDCl$_3$, δ): 1.49–1.62 (4H, m), 1.68–1.80 (2H, m), 2.43–2.65 (2H, m), 2.83–3.17 (3H, m), 3.26–3.69 (5H, m), 3.83–4.11 (2H, m), 4.17–4.29 (1H, m), 4.32–4.57 (2H, m), 4.98–5.14 (H, m), 6.89 (2H, d, J=8 Hz), 6.94–7.05 (4H, m), 7.30–7.61 (8H, m), 7.78 (2H, d, J=8 Hz), 8.48–8.53 (1H, m) MASS (m/z): 715 (M$^+$+H), 115 (bp)

EXAMPLE 651

N-(2-Tetrahydropyranyloxy)-2-[(S)-7-[4-(4-chlorophenoxy)phenyl]-4-(9-fluorenylmethoxycarbonyl)-1,1-dioxoperhydro-1,4-thiazepin-7-yl]acetamide (1.523 g)

NMR (CDCl$_3$, δ): 1.51–1.64 (4H, m), 1.68–1.83 (2H, m), 2.47–2.63 (2H, m), 2.83–3.18 (3H, m), 3.23–3.70 (5H, m), 3.83–4.15 (2H, m), 4.18–4.30 (1H, m), 4.34–4.60 (2H, m), 4.70–4.95 (1H, m), 6.90–6.99 (4H, m), 7.310–7.66 (10H, m), 7.76–7.88 (2H, m), 8.56–8.64 (1H, m)

EXAMPLE 652

N-(2-Tetrahydropyranyloxy)-2-[(S)-7-(5-(4-ethylphenyl)-2-thienyl)-1,1-dioxoperhydro-4-(2-pyridinecarbonyl)-1,4-thiazepin-7-yl]acetamide (1.5 g)

NMR (DMSO-d$_6$, δ): 1.20 (3H, t, J=7.5 Hz), 1.32–1.69 (6H, m), 2.61 (2H, q, J=7.5 Hz), 2.75–3.95 (11H, m), 3.95–4.20 (1H, m), 4.40–4.80 (1H, m), 7.16–7.31 (3H, m), 7.35–7.46 (1H, m), 7.46–7.66 (4H, m), 7.90–8.01 (1H, m), 8.56–8.65 (1H, m) MASS (ES–)(m/z): 611.37

EXAMPLE 653

N-(2-Tetrahydropyranyloxy)-2-[(S)-7-(5-(4-methoxyphenyl)-2-thienyl)-1,1-dioxoperhydro-4-(3-thienylcarbonyl)-1,4-thiazepin-7-yl]acetamide (2.1 g)

NMR (DMSO-d$_6$, δ): 1.35–1.65 (6H, m), 2.76–3.25 (6H, m), 3.44–4.16 (9H, m), 4.39–4.80 (1H, m), 6.98 (2H, d, J=8 Hz), 7.15–7.28 (2H, m), 7.28–7.39 (1H, m), 7.53–7.68 (3H, m), 7.81–7.88 (1H, m) MASS (ES–)(m/z): 603.28

EXAMPLE 654

N-(2-Tetrahydropyranyloxy)-2-[4-(9-fluorenylmethoxycarbonyl)-7-(5-(4-methoxyphenyl)-2-thienyl)-1,1-dioxoperhydro-1,4-thiazepin-7-yl]acetamide (2.32 g)

NMR (DMSO-d$_6$, δ): 1.36–1.69 (6H, m), 2.61–3.26 (6H, m), 3.26–3.94 (9H, m), 4.22–4.54 (3H, m), 4.70–4.80 (1H, m), 6.92–7.08 (2H, m), 7.08–7.25 (1H, m), 7.25–7.50 (5H, m), 7.50–7.77 (4H, m), 7.85–8.00 (2H, m) MASS (ES+) (m/z): 717.55

EXAMPLE 655

N-(2-Tetrahydropyranyloxy)-2-[(S)-7-(5-(4-chlorophenyl)-2-thienyl)-4-dimethylaminosulfonyl-1,1-dioxoperhydro-1,4-thiazepin-7-yl]acetamide (1.44 g)

NMR (CDCl$_3$, δ): 1.43–1.93 (6H, m), 2.75–2.99 (7H, m), 3.10–3.70 (7H, m), 3.75–4.18 (4H, m), 4.64–4.94 (1H, m), 7.22 (2H, s), 7.32 (2H, d, J=9 Hz), 7.45–7.54 (2H, m), 8.66–8.76 (1H, m) MASS (ESI–): 604 (M–H)

EXAMPLE 656

N-(2-Tetrahydropyranyloxy)-2-[4-(9-fluorenylmethoxycarbonyl)-7-(5-(4-methylthiophenyl)-2-thienyl)-1,1-dioxoperhydro-1,4-thiazepin-7-yl]acetamide (4.8 g)

NMR (CDCl$_3$, δ): 1.40–1.75 (6H, m), 2.50 (3H, s), 2.53–4.00 (13H, m), 4.11–4.90 (3H, m), 7.15–7.82 (14H, m)

EXAMPLE 657

N-(2-Tetrahydropyranyloxy)-2-[4-(9-fluorenylmethoxycarbonyl)-7-(5-(2-naphthyl)-2-thienyl)-1,1-dioxoperhydro-1,4-thiazepin-7-yl]acetamide (4.0 g)

NMR (CDCl$_3$, δ): 1.38–1.69 (6H, m), 2.60–3.15 (3H, m), 3.20–4.09 (8H, m), 4.11–4.90 (5H, m), 7.15–7.82 (17H, m), 8.00 (2H, d, J=7.2 Hz)

EXAMPLE 658

N-(2-Tetrahydropyranyloxy)-2-[4-(9-fluorenylmethoxycarbonyl)-7-(5-(4-biphenylyl)-2-thienyl)-1,1-dioxoperhydro-1,4-thiazepin-7-yl]acetamide (4.2 g)

NMR (CDCl$_3$, δ): 1.43–1.68 (6H, m), 2.52–2.65 (2H, m), 2.80–4.80 (14H, m), 7.20–7.80 (19H, m)

EXAMPLE 659

N-(2-Tetrahydropyranyloxy)-2-[4-(9-fluorenylmethoxycarbonyl)-7-(5-(4-methylphenyl)-2-thienyl)-1,1-dioxoperhydro-1,4-thiazepin-7-yl]acetamide (7.0 g)

NMR (CDCl$_3$, δ): 1.45–1.75 (6H, m), 2.35 (3H, s), 2.50–4.00 (13H, m), 4.11–4.90 (3H, m), 7.15–7.82 (14H, m)

EXAMPLE 660

N-(2-Tetrahydropyranyloxy)-2-[(S)-4-benzoyl-7-(5-(4-ethoxyphenyl)-2-thienyl)-1,1-dioxoperhydro-1,4-thiazepin-7-yl]acetamide (3.93 g)

NMR (DMSO-d$_6$, δ): 1.34 (3H, t, J=7.5 Hz), 1.36–1.65 (6H, m), 2.56–3.22 (5H, m), 3.35–3.99 (7H, m), 4.05 (2H, q, J=7.5 Hz), 4.36–4.80 (1H, m), 6.95 (2H, d, J=8 Hz), 7.11–7.22 (1H, m), 7.26–7.36 (1H, m), 7.36–7.50 (5H, m), 7.50–7.61 (2H, m) MASS (ES−)(m/z): 611.37

EXAMPLE 661

N-(2-Tetrahydropyranyloxy)-2-[7-(5-(4-ethoxyphenyl)-2-thienyl)-4-(9-fluorenylmethoxycarbonyl)-1,1-dioxoperhydro-1,4-thiazepin-7-yl]acetamide (2.35 g)

NMR (DMSO-d$_6$, δ): 1.26–1.39 (3H, m), 1.39–1.65 (6H, m), 2.56–3.90 (12H, m), 3.96–4.02 (3H, m), 4.25–4.54 (3H, m), 6.91–7.04 (2H, m), 7.06–7.23 (1H, m), 7.29–7.46 (5H, m), 7.55 (2H, d, J=8 Hz), 7.62–7.75 (2H, m), 7.86–7.96 (2H, m)

EXAMPLE 662

N-(2-Tetrahydropyranyloxy)-2-[4-(9-fluorenylmethoxycarbonyl)-7-[4-(4-methoxyphenoxy)phenyl]-1,1-dioxoperhydro-1,4-thiazepin-7-yl]acetamide (2.5 g)

NMR (CDCl$_3$, δ): 1.49–1.62 (4H, m), 1.68–1.80 (2H, m), 2.43–2.65 (2H, m), 2.83–3.17 (3H, m), 3.26–3.69 (5H, m), 3.83–4.11 (2H, m), 4.17–4.29 (1H, m), 4.32–4.57 (2H, m), 4.98–5.14 (1H, m), 6.89 (2H, d, J=8 Hz), 6.94–7.05 (4H, m), 7.30–7.61 (8H, m), 7.78 (2H, d, J=8 Hz), 8.48–8.53 (1H, m) MASS (m/z): 727 (M$^+$+H), 85 (bp)

EXAMPLE 663

To a solution of 2-[7-(5-bromo-2-thienyl)-4-(9-fluorenylmethoxycarbonyl)-1,1-dioxoperhydro-1,4-thiazepin-7-yl]acetic acid (5.92 g) in N,N-dimethylformamide (50 ml) were added 1-hydroxybenzotriazole (1.35 g) and diisopropylcarbodiimide (1.27 g) at ambient temperature. After 1 minute, the solution was added to hydroxylamine trityl crowns (17.9 μmol/crown×50), the reaction mixture was left overnight at 40° C. The crowns were washed with N,N-dimethylformamide, methanol and dichloromethane, successively and air dried to give N-[2-[7-(5-bromo-2-thienyl)-4-(9-fluorenylmethoxycarbonyl)-1,1-dioxoperhydro-1,4-thiazepin-7-yl]acetyl]hydroxylamine trityl crowns (14.3 μmol/crown×50).

EXAMPLE 664

To a solution of N-(2-tetrahydropyranyloxy)-2-[7-(5-(3-aminophenyl)-2-thienyl)-4-benzoyl-1,1-dioxoperhydro-1,4-thiazepin-7-yl]acetamide (150 mg) in dichloromethane (3 ml) was added ethyl isocyanate (22 mg) at 0° C. and the reaction mixture was stirred at ambient temperature for 5 hours. The mixture was poured into water and was extracted with ethyl acetate. The organic layer was washed with water, saturated aqueous sodium hydrogencarbonate and brine, dried over anhydrous magnesium sulfate and concentrated in vacuo. The residue was purified by column chromatography on silica gel 60 (3% methanol-chloroform) to give N-(2-tetrahydropyranyloxy)-2-[4-benzoyl-7-(5-(3-(ethylaminocarbonylamino)phenyl)-2-thienyl)-1,1-dioxoperhydro-1,4-thiazepin-7-yl]acetamide (75 mg) as a white powder.

NMR (CDCl$_3$, δ): 1.37–1.62 (9H, m), 2.72–4.83 (15H, m), 6.97–7.65 (14H, m) MASS (ESI-)): 653.1 (M+H)

EXAMPLE 665

To a mixture of N-(2-tetrahydropyranyloxy)-2-[7-(5-bromo-2-thienyl)-4-benzoyl-1,1-dioxoperhydro-1,4-thiazepin-7-yl]acetamide (200 mg), palladium(II) acetate (1.57 mg), triphenylphosphine (7.34 mg), copper(II) iodide (6.7 mg) and triethylamine (106 mg) in dimethylformamide was added ethynylbenzene (46.5 mg) at room temperature under nitrogen. After stirring for 2 hours at 60° C., the mixture was diluted with ethyl acetate, washed with 3% aqueous sodium bicarbonate and brine, dried over sodium sulfate and filtered. The obtained filtrate was concentrated and purified by column chromatography on silica gel (eluent: 0–2% methanol in chloroform) to give N-(2-tetrahydropyranyloxy)-2-[7-(5-(2-phenylethynyl)-2-thienyl)-4-benzoyl-1,1-dioxoperhydro-1,4-thiazepin-7-yl]acetamide (230 mg) as yellow amorphous solid.

NMR (CDCl$_3$, δ): 1.40–1.85-(6H, m), 2.71–3.20 (5H, m), 3.38–3.96 (6H, m), 4.16–4.90 (2H, m), 6.85–7.55 (12H, m), 8.00–8.35 (1H, m) MASS (ESI-): 591 (M-H)

The following compounds were obtained in a similar manner to that of Example 665.

EXAMPLE 666

N-(2-Tetrahydropyranyloxy)-2-[7-(5-(1-hexynyl)-2-thienyl)-4-benzoyl-1,1-dioxoperhydro-1,4-thiazepin-7-yl]acetamide (130 mg)

NMR (CDCl$_3$, δ): 0.95 (3H, t, J=6.8 Hz), 1.40–1.85 (10H, m), 2.42 (2H, t, J=6.8 Hz), 2.69–3.20 (5H, m), 3.34–4.00 (6H, m), 4.16–4.88 (2H, m), 6.94–7.05 (2H, m), 7.23–7.46 (5H, m), 8.20–8.49 (1H, m) MASS (ESI-): 571 (M-H)

EXAMPLE 667

N-(2-Tetrahydropyranyloxy)-2-[7-(5-(2-(4-aminosulfonylphenyl)ethynyl)-2-thienyl)-4-benzoyl-1,1-dioxoperhydro-1,4-thiazepin-7-yl]acetamide (200 mg)

NMR (DMSO-d$_6$, δ): 1.40–1.65 (6H, m), 2.73–3.21 (4H, m), 3.47–3.95 (8H, m), 4.46 (0.5H, br), 4.78 (0.5H, br), 7.20–7.26 (1H, m), 7.44–7.51 (6H, m), 7.72–7.76 (2H, m), 7.85 (2H, d, J=8.5 Hz) MASS (ESI-): 670 (M-H)

EXAMPLE 668

N-Hydroxy-2-[4-((2S)-2-amino-2-phenylacetyl)-7-(5-(4-(5-oxazolyl)phenyl)-2-thienyl)-1,1-dioxoperhydro-1,4-thiazepin-7-yl]acetamide hydrochloride (79 mg) was obtained in a similar manner to that of Example 17.

NMR (DMSO-d$_6$, δ): 2.62–3.15 (4H, m), 3.41–4.06 (7H, m), 6.86 (1H, d, J=7.5 Hz), 7.23 (1H, br), 7.44–7.59 (6H, m), 7.68–7.82 (4H, m), 8.47 (1H, s), 8.58–8.74 (2H, br), 10.60–10.76 (1H, m) MASS (ESI-): 579.2 (M-H)

The following compounds were obtained in a similar manner to that of Example 1.

EXAMPLE 669

N-(2-Tetrahydropyranyloxy)-2-[7-(5-bromo-2-thienyl)-1,1-dioxoperhydro-4-(3-pyridylsulfonyl)-1,4-thiazepin-7-yl]acetamide hydrochloride (205 mg)

NMR (CDCl$_3$, δ): 1.40–1.90 (6H, m), 2.80–2.96 (1H, m), 2.96–3.70 (8H, m), 3.70–4.00 (2H, m), 4.00–4.20 (1H, m), 4.65–5.16 (1H, m), 6.95–7.06 (2H, m), 7.52 (1H, dd, J=8.2 Hz), 8.09 (1H, dd, J=8, 2 Hz), 8.55 (1H, s), 8.86 (1H, dd, J=5, 2 Hz), 9.02 (1H, s) MASS (ES−)(m/z): 605.98, 608.18

EXAMPLE 670

N-(2-Tetrahydropyranyloxy)-2-[(S)-4-(dimethylaminocarbonyl)-7-(5-(4-ethylphenyl)-2-thienyl)-1,1-dioxoperhydro-1,4-thiazepin-7-yl]acetamide (100 mg)

NMR (CDCl$_3$, δ): 1.24 (3H, t, J=7.5 Hz), 1.40–1.86 (6H, m), 2.65 (2H, q, J=7.5 Hz), 2.71–4.10 (18H, m), 4.47, 4.84 (1H, br s), 7.13–7.24 (4H, m), 7.48 (2H, br d, J=7 Hz), 8.44, 8.67 (1H, br s)

EXAMPLE 671

N-(2-Tetrahydropyranyloxy)-2-[(S)-7-(5-(4-ethylphenyl)-2-thienyl)-1,1-dioxoperhydro-4-(morpholinosulfonyl)-1,4-thiazepin-7-yl]acetamide (65.8 mg)

NMR (CDCl$_3$, δ): 1.26 (3H, t, J=8 Hz), 1.54–1.73 (6H, m), 2.67 (2H, q, J=8 Hz), 2.85–4.13 (20H, m), 4.64–4.88 (1H, m), 7.19–7.22 (4H, m), 7.50 (2H, d, J=8 Hz), 8.30–8.42 (1H, m) MASS (ESI-): 640.22 (M−H)

EXAMPLE 672

N-(2-Tetrahydropyranyloxy)-2-[(S)-7-(5-(4-ethylphenyl)-2-thienyl)-1,1-dioxoperhydro-4-[N-methyl-N-(2-methoxyethyl)aminosulfonyl]-1,4-thiazepin-7-yl]acetamide (84.1 mg)

NMR (CDCl$_3$, δ): 1.25 (3H, t, J=8 Hz), 1.45–1.75 (6H, m), 2.66 (2H, q, J=8 Hz), 2.87–2.94 (4H, m), 3.06–4.14 (18H, m), 4.65–4.87 (1H, m), 7.18–7.21 (4H, m), 7.49 (2H, d, J=8 Hz), 8.36–8.48 (1H, m) MASS: (ESI−) 642.23 (M−H), and (ESI+) 644.30 (MH)

EXAMPLE 673

N-(2-Tetrahydropyranyloxy)-2-[(S)-7-[5-(4-ethylphenyl)-2-thienyl]-1,1-dioxoperhydro-4-(3-methyl-2-butenyl)-1,4-thiazepin-7-yl]acetamide (64.6 mg)

NMR (CDCl$_3$, δ): 1.26 (3H, t, J=8 Hz), 1.42–1.99 (12H, m), 2.67 (2H, q, J=8 Hz), 2.795–4.27 (12H, m), 4.54–4.85 (1H, m), 5.69–5.91 (1H, m), 7.19–7.25 (4H, m), 7.48–7.52 (2H, m), 8.13–8.32 (1H, m) MASS: (ESI−) 573.31 (M−H) and (ESI+) 575.32 (MH)

The following compounds were obtained in a similar manner to that of Example 33.

EXAMPLE 674

N-(2-Tetrahydropyranyloxy)-2-[7-(5-bromo-2-thienyl)-1,1-dioxoperhydro-4-(3-pyridylcarbonyl)-1,4-thiazepin-7-yl]acetamide (321 mg)

NMR (CDCl$_3$, δ): 1.43–2.04 (6H, m), 2.70–3.23 (4H, m), 3.51–4.45 (8H, m), 4.45–4.90 (1H, m), 6.86–7.11 (2H, m), 7.34–7.50 (1H, m), 7.68–7.81 (1H, m), 8.52–8.75 (2H, m) MASS (ES−)(m/z): 570, 572

EXAMPLE 675

N-(2-Tetrahydropyranyloxy)-2-[7-(5-bromo-2-thienyl)-1,1-dioxoperhydro-4-[(1-methyl-1H-pyrrol-2-yl)carbonyl]-1,4-thiazepin-7-yl]acetamide (214 mg)

NMR (CDCl$_3$, δ): 1.45–1.83 (6H, m), 2.73–3.00 (4H, m), 3.00–3.85 (6H, m), 3.85–4.29 (2H, m), 4.46–4.82 (1H, m), 6.03–6.09 (1H, m), 6.26 (1H, br peak), 6.70 (1H, s), 6.86–7.00 (2H, m), 8.09 (½H, s), 8.21 (½H, s) MASS (ES−)(m/z): 571.97, 573.99

EXAMPLE 676

N-(2-Tetrahydropyranyloxy)-2-[7-(5-bromo-2-thienyl)-1,1-dioxoperhydro-4-(3-pyridylacetyl)-1,4-thiazepin-7-yl]acetamide (300 mg)

NMR (CDCl$_3$, δ): 1.44–1.86 (6H, m), 2.68–3.12 (2H, m), 3.12–4.00 (1H, m), 4.17–4.40 (1H, m), 4.50–4.96 (1H, m), 6.94–7.09 (2H, m), 7.56–7.67 (1H, m), 8.25–8.75 (3H, m) MASS (ES+)(m/z): 586.08, 588.09

EXAMPLE 677

N-(2-Tetrahydropyranyloxy)-2-[7-(5-bromo-2-thienyl)-1,1-dioxoperhydro-4-(4-pyridylacetyl)-1,4-thiazepin-7-yl]acetamide (305 mg)

NMR (CDCl$_3$, δ): 1.46–1.85 (6H, m), 2.70–3.10 (2H, m), 3.10–3.94 (11H, m), 4.18–4.38 (1H, m), 4.50–4.90 (1H, m), 6.94–7.05 (2H, m), 7.11–7.25 (2H, m), 8.53–8.60 (2H, m) MASS (ES+)(m/z): 586.08, 588.08

EXAMPLE 678

N-(2-Tetrahydropyranyloxy)-2-[(S)-7-[5-(4-ethylphenyl)-2-thienyl]-1,1-dioxoperhydro-4-(5-methyl-3-isoxazolylcarbonyl)-1,4-thiazepin-7-yl]acetamide (79.8 mg)

NMR (CDCl$_3$, δ): 1.25 (3H, t, J=8 Hz), 1.40–1.80 (6H, m), 2.45 (3H, s), 2.66 (2H, q, J=8 Hz), 2.75–4.55 (12H, m), 4.57–4.84 (1H, m), 6.29–6.35 (1H, m), 7.14–7.22 (4H, m), 7.47 (2H, d, J=7 Hz), 8.21–8.46 (1H, m) MASS: (ESI−) 600.31 (M−H) and (ESI+) 602.48 (MH)

EXAMPLE 679

N-(2-Tetrahydropyranyloxy)-2-[(S)-4-cyclobutylcarbonyl-7-[5-(4-ethylphenyl)-2-thienyl]-1,1-dioxoperhydro-1,4-thiazepin-7-yl]acetamide (85.6 mg)

NMR (CDCl$_3$, δ): 1.25 (3H, t, J=8 Hz), 1.39–2.49 (12H, m), 2.62–2.70 (2H, m), 2.75–4.33 (12H, m), 4.53–4.83 (1H, m), 7.20–7.21 (4H, m), 7.47–7.50 (2H, m), 8.11–8.54 (1H, m) MASS: (ESI−) 573.23 (M−H) and (ESI+) 575.30 (MH)

The following compounds were obtained in a similar manner to that of Example 290.

EXAMPLE 680

N-Hydroxy-2-[4-(N,N-dimethylaminosulfonyl)-7-(5-(4-ethylphenyl)-2-thienyl)-1,1-dioxoperhydro-1,4-thiazepin-7-yl]acetamide (32 mg)

NMR (DMSO-d$_6$, δ): 1.20 (3H, t, J=7.5 Hz), 2.62 (2H, q, J=7.5 Hz), 2.75 (6H, s), 2.86–2.94 (2H, m), 3.09–3.16 (2H, m), 3.42–4.09 (6H, m), 7.19 (l, d, J=3 Hz) 7.26 (2H, d, J=8 Hz), 7.41 (1H, d, J=3 Hz), 7.55 (2H, d, J=8 Hz) MASS (ES−)(m/z): 514.28

The following compounds were obtained in a similar manner to that of Example 39.

EXAMPLE 681

N-(2-Tetrahydropyranyloxy)-2-[7-(5-(4-(5-oxazolyl)phenyl)-2-thienyl)-1,1-dioxoperhydro-4-(3-pyridylsulfonyl)-1,4-thiazepin-7-yl]acetamide (65 mg)

NMR (CDCl$_3$, δ): 1.44–1.93 (6H, m), 2.87–3.04 (1H, m), 3.04–4.00 (10H, m), 4.00–4.24 (1H, m), 4.71 (½H, s), 4.94 (½H, s), 7.30 (1H, s), 3.38 (1H, s), 7.54 (1H, dd, J=8, 5 Hz), 7.60–7.70 (4H, m), 7.95 (1H, s), 8.10 (1H, dd, J=8, 2 Hz), 8.59 (1H, s), 8.88 (1H, dd, J=5, 2 Hz), 9.05 (1H, s) MASS (ES−)(m/z): 671.11

EXAMPLE 682

N-(2-Tetrahydropyranyloxy)-2-[7-(5-(4-(5-oxazolyl)phenyl)-2-thienyl)-1,1-dioxoperhydro-4-(3-pyridylcarbonyl)-1,4-thiazepin-7-yl]acetamide (80 mg)

NMR (CDCl₃, δ): 1.38–1.81 (6H, m), 2.72–4.06 (12H, m), 4.30–4.90 (1H, m), 7.20–7.42 (4H, m), 7.58–7.78 (5H, m), 7.94 (1H, s), 8.53–8.73 (2H, m)

EXAMPLE 683

N-(2-Tetrahydropyranyloxy)-2-[7-(5-(4-(5-oxazolyl) phenyl)-2-thienyl)-1,1-dioxoperhydro-4-[(1-methyl-1H-pyrrol-2-yl)carbonyl]-1,4-thiazepin-7-yl]acetamide (114 mg)

NMR (CDCl₃, δ): 1.39–1.80 (6H, m), 2.78–4.30 (12H, m), 4.52 (½H, s), 4.76 (½H, s), 6.05 (1H, s), 6.25 (1H, br peak), 6.68 (1H, s), 7.19–7.32 (2H, m), 7.40 (1H, s), 7.60 (2H, d, J=8 Hz), 7.65 (2H, d, J=8 Hz), 7.95 (1H, s) MASS (ES–) (m/z): 637.2

EXAMPLE 684

N-(2-Tetrahydropyranyloxy)-2-[7-(5-(4-(5-oxazolyl) phenyl)-2-thienyl)-1,1-dioxoperhydro-4-(3-pyridylacetyl)-1,4-thiazepin-7-yl]acetamide (107 mg)

NMR (CDCl₃, δ): 1.40–1.84 (6H, m), 2.55–4.00 (13H, m), 4.20–4.42 (1H, m), 4.54–4.91 (1H, m), 7.26–7.34 (2H, m), 7.40 (1H, s), 7.55–7.70 (5H, m), 7.95 (1H, s), 8.36–8.55 (3H, m)

EXAMPLE 685

N-(2-Tetrahydropyranyloxy)-2-[7-(5-(4-(5-oxazolyl) phenyl)-2-thienyl)-1,1-dioxoperhydro-4-(4-pyridylacetyl)-1,4-thiazepin-7-yl]acetamide (104 mg)

NMR (CDCl₃, δ): 1.40–1.85 (6H, m), 2.60–3.92 (13H, m), 4.20–4.39 (1H, m), 4.50–4.90 (1H, m), 7.10–7.34 (4H, m), 7.40 (1H, s), 7.56–7.70 (4H, m), 7.95 (1H, s), 8.50–8.60 (2H, m) MASS (ES+)(m/z): 651.15

The following compounds were obtained in a similar manner to that of Example 17.

EXAMPLE 686

N-Hydroxy-2-[7-(5-(4-(5-oxazolyl)phenyl)-2-thienyl)-1,1-dioxoperhydro-4-(3-pyridylsulfonyl)-1,4-thiazepin-7-yl]acetamide (32 mg)

NMR (DMSO-d₆, δ): 2.74–3.05 (2H, m), 3.05–3.16 (2H, m), 3.40–3.90 (5H, m), 3.90–4.07 (1H, m), 7.21 (1H, d, J=3 Hz), 7.56 (1H, d, J=3 Hz), 7.67–7.83 (6H, m), 8.27 (1H, dd, J=8, 2 Hz), 8.47 (1H, s), 8.90 (1H, dd, J=8, 5 Hz), 8.95 (1H, s), 9.03 (1H, d, J=2 Hz) MASS (ES–)(m/z): 587.11

EXAMPLE 687

N-Hydroxy-2-[7-(5-(4-(5-oxazolyl)phenyl)-2-thienyl)-1,1-dioxoperhydro-4-(3-pyridylcarbonyl)-1,4-thiazepin-7-yl]acetamide hydrochloride (28 mg)

NMR (DMSO-d₆, δ): 2.75–3.21 (4H, m), 3.45–4.20 (6H, m), 7.25–7.30 (1H, m), 7.55 (⅓H, d, J=3 Hz), 7.60 (⅔H, d, J=3 Hz), 7.64–7.71 (1H, m), 7.71–7.82 (5H, m), 8.05–8.14 (1H, m), 8.48 (1H, s), 8.72–8.81 (1H, m) MASS (ES–) (m/z): 551.04 (M(Free)–H)

EXAMPLE 688

N-Hydroxy-2-[7-(5-(4-(5-oxazolyl)phenyl)-2-thienyl)-1,1-dioxoperhydro-4-[(1-methyl-1H-pyrrol-2-yl)carbonyl]-1,4-thiazepin-7-yl]acetamide (47 mg)

NMR (DMSO-d₆, δ): 2.76–3.12 (4H, m), 3.40–4.05 (9H, m), 6.00–6.05 (1H, m), 6.41 (1H, br peak), 6.90 (1H, br s), 7.25 (1H, d, J=3 Hz), 7.56 (1H, d, J=3 Hz), 7.74–7.82 (5H, m), 8.48 (1H, s), 8.90 (1H, s) MASS (ES–)(m/z): 553.18

EXAMPLE 689

N-Hydroxy-2-[7-(5-(4-(5-oxazolyl)phenyl)-2-thienyl)-1,1-dioxoperhydro-4-(3-pyridylacetyl)-1,4-thiazepin-7-yl]acetamide hydrochloride (84 mg)

NMR (DMSO-d₆, δ): 2.56–3.16 (4H, m), 3.16–4.20 (8H, m), 7.26 (½H, d, J=3 Hz), 7.32 (½H, d, J=3 Hz), 7.56–7.63 (1H, m), 7.73–7.84 (5H, m), 8.00–8.09 (1H, m), 8.40–8.51 (2H, m), 8.79–8.90 (2H, m) MASS (ES+)(m/z): 567.11

EXAMPLE 690

N-Hydroxy-2-[7-(5-(4-(5-oxazolyl)phenyl)-2-thienyl)-1,1-dioxoperhydro-4-(4-pyridylacetyl)-1,4-thiazepin-7-yl]acetamide hydrochloride (72 mg)

NMR (CDCl₃, δ): 2.66–3.16 (4H, m), 3.16–4.13 (6H, m), 4.19 (1H, s), 4.26 (1H, s), 7.26 (½H, d, J=3 Hz), 7.30 (½H, d, J=3 Hz), 7.56–7.60 (1H, m), 7.74–7.83 (5H, m), 7.95 (1H, d, J=8 Hz), 8.00 (1H, d, J=8 Hz), 8.50 (1H, s), 8.85–8.91 (2H, m), 10.70–10.80 (1H) MASS (ES+)(m/z): 567.25

EXAMPLE 691

N-Hydroxy-2-[(S)-4-(dimethylaminocarbonyl)-7-(5-(4-ethylphenyl)-2-thienyl)-1,1-dioxoperhydro-1,4-thiazepin-7-yl]acetamide (64 mg)

NMR (CDCl₃, δ): 1.24 (3H, t, J=7.5 Hz), 2.65 (2H, q, J=7.5 Hz), 2.76 (6H, s), 2.82–4.04 (12H, m), 7.12–7.23 (4H, m), 7.48 (2H, br d, J=7 Hz) MASS (ESI+): 480

EXAMPLE 692

N-Hydroxy-2-[(S)-4-(cyclohexylmethyl)-7-(5-(4-ethylphenyl)-2-thienyl)-1,1-dioxoperhydro-1,4-thiazepin-7-yl]acetamide hydrochloride (64 mg)

NMR (DMSO-d₆, δ): 0.86–1.05 (2H, m), 1.09–1.35 (7H, m), 1.67–1.92 (6H, m), 2.25–2.45 (2H, m), 2.64 (2H, q, J=8 Hz), 2.79–4.00 (10H, m), 4.20–4.40 (1H, m), 7.24 (1H, d, J=3 Hz), 7.29 (2H, d, J=7 Hz), 7.46 (1H, d, J=3 Hz), 7.56 (2H, d, J=7 Hz), 8.95, 10.19 (1H, br), 10.41, 10.75 (1H, br s) MASS (ESI+): 505

EXAMPLE 693

N-Hydroxy-2-[(S)-7-[5-(4-ethylphenyl)-2-thienyl]-1,1-dioxoperhydro-4-(5-methyl-3-isoxazolyl)carbonyl-1,4-thiazepin-7-yl]acetamide (49.1 mg)

NMR (CDCl₃, δ): 1.25 (3H, t, J=8 Hz), 2.54 (3H, s), 2.75–4.56 (10H, m), 6.29–6.38 (1H, m), 7.15–7.22 (4H, m), 7.48 (2H, d, J=8 Hz), 8.44–8.68 (1H, m) MASS: (ESI–) 516.32 (M–H) and (ESI+) 518.31 (MH)

EXAMPLE 694

N-Hydroxy-2-[(S)-7-[5-(4-ethylphenyl)-2-thienyl]-1,1-dioxoperhydro-4-[(6-methylpyridin-2-yl)methyl]-1,4-thiazepin-7-yl]acetamide hydrochloride (46.9 mg)

NMR (DMSO-d₆, δ): 1.20 (3H, t, J=8 Hz), 2.59–2.66 (5H, m), 2.89–4.69 (12H, m), 7.23 (1H, d, J=4 Hz), 7.28 (2H, d, J=8 Hz), 7.45 (1H, d, J=4 Hz), 7.49 (1H, d, J=8 Hz), 7.56 (2H, d, J=8 Hz), 7.62 (1H, d, J=8 Hz), 7.99 (1H, t, J=8 Hz) MASS: (ESI–) 512.36 (M–H) and (ESI+) 514.39 (MH)

EXAMPLE 695

N-Hydroxy-2-[(S)-7-[5-(4-ethylphenyl)-2-thienyl]-1,1-dioxoperhydro-4-(3-methyl-2-butenyl)-1,4-thiazepin-7-yl]acetamide hydrochloride (21.1 mg)

NMR (DMSO-d₆, δ): 1.21 (3H, t, J=8 Hz), 1.76 (3H, s), 1.83 (3H, s), 2.64 (2H, q, J=8 Hz), 2.76–4.38 (12H, m), 5.32

(1H, m), 7.23 (1H, m), 7.28 (2H, d, J=8 Hz), 7.45 (1H, m), 7.57 (2H, d, J=8 Hz), 8.99 (1H, br), 10.75–10.78 (1H, m) MASS: (ESI–) 475.24 (M–H) and (ESI+) 477.27 (MH)

EXAMPLE 696

N-Hydroxy-2-[(S)-4-cyclobutylcarbonyl-7-[5-(4-ethylphenyl)-2-thienyl]-1,1-dioxoperhydro-1,4-thiazepin-7-yl]acetamide (59.8 mg)

NMR (CDCl$_3$, δ): 1.25 (3H, t, J=8 Hz), 1.80–2.46 (6H, m), 2.66 (2H, q, J=8 Hz), 2.78–4.26 (10H, m), 7.19–7.23 (4H, m), 7.47–7.52 (2H, m), 8.43–8.83 (1H, m) MASS: (ESI–) 489.19 (M–H) and (ESI+) 491.25 (MH)

EXAMPLE 697

N-Hydroxy-2-[(S)-7-[5-(4-ethylphenyl)-2-thienyl]-1,1-dioxoperhydro-4-(morpholinosulfonyl)-1,4-thiazepin-7-yl]acetamide (34.7 mg)

NMR (CDCl$_3$, δ): 1.25 (3H, t, J=7 Hz), 2.66 (2H, q, J=8 Hz), 2.82–4.15 (18H, m), 7.209–7.22 (4H, m), 7.50 (2H, d, J=8 Hz), 8.49 (1H, br) MASS (ESI–): 556.21 (M–H)

EXAMPLE 698

N-Hydroxy-2-[(S)-7-[5-(4-ethylphenyl)-2-thienyl]-1,1-dioxoperhydro-4-[N-methyl-N-(2-methoxyethyl)aminosulfonyl]-1,4-thiazepin-7-yl]acetamide (55.6 mg)

NMR (CDCl$_3$, δ): 1.25 (3H, t, J=8 Hz), 2.66 (2H, q, J=8 Hz), 2.87–2.96 (4H, m), 3.09–4.10 (18H, m), 7.18–7.22 (4H, m), 7.49 (2H, d, J=8 Hz), 8.59–8.68 (1H, m) MASS (ESI–): 558.24 (M–H)

EXAMPLE 699

N-Hydroxy-2-[(S)-7-[5-(4-ethylphenyl)-2-thienyl]-1,1-dioxoperhydro-4-(2-thienylmethyl)-1,4-thiazepin-7-yl]acetamide hydrochloride (41.8 mg)

NMR (DMSO-d$_6$, δ): 1.20 (3H, t, J=8 Hz), 2.63 (2H, q, J=8 Hz), 2.73–4.75 (12H, m), 7.15–7.22 (2H, m), 7.28 (2H, d, J=8 Hz), 7.39–7.46 (2H, m), 7.56 (2H, d, J=8 Hz), 7.73 (1H, br), 10.75 (1H, br) MASS: (ESI–) 573.31 and (ESI+) 575.31 (MH)

EXAMPLE 700

N-Hydroxy-2-[(S)-7-[5-(4-ethylphenyl)-2-thienyl]-1,1-dioxoperhydro-4-(3-methylbutenyl)-1,4-thiazepin-7-yl]acetamide (33.5 mg)

NMR (CDCl$_3$, δ): 1.25 (3H, t, J=8 Hz), 1.85–1.95 (6H, m), 2.66 (2H, q, J=8 Hz), 2.81–4.33 (10H, m), 5.72–5.88 (1H, m), 7.18–7.22 (4H, m), 7.47–7.52 (2H, m), 8.83–8.94 (1H, m) MASS: (ESI–) 489.17 (M–H) and (ESI+) 491.21 (MH)

EXAMPLE 701

To a solution of N-(2-tetrahydropyranyloxy)-2-[(S)-7-(5-(4-ethylphenyl)-2-thienyl]-1,1-dioxoperhydro-4-propanesulfonyl-1,4-thiazepin-7-yl]acetamide (3.51 g) in methanol (8 ml) and chloroform (8 ml) was added toluenesulfonic acid monohydrate (112 mg). The resulting mixture was stirred for 4 hours at room temperature. The solvent was evaporated off to give a pale yellow solid. Silica gel column chromatography (eluent: methanol in chloroform from 0 to 4%) afforded N-hydroxy-2-[(S)-7-[5-(4-ethylphenyl)-2-thienyl]-1,1-dioxoperhydro-4-propanesulfonyl-1,4-thiazepin-7-yl]acetamide (2.41 mg) as a white solid.

NMR (DMSO-d$_6$, δ): 0.99 (3H, t, J=7 Hz), 1.19 (3H, t, J=8 Hz), 1.69 (2H, quintet, J=8 Hz), 2.62 (2H, q, J=8 Hz), 2.85–2.96 (2H, m), 3.08–3.22 (4H, m), 3.29–3.35 (4H, m), 3.47–3.63 (2H, m), 3.71–4.05 (2H, m), 7.19 (1H, d, J=4 Hz), 7.27 (2H, d, J=8 Hz), 7.42 (1H, d, J=4 Hz), 7.56 (2H, d, J=8 Hz), 8.93 (1H, s), 10.69 (1H, s) MASS (ESI–): 513.32 (M–H)

EXAMPLE 702

To a solution of 2-[(S)-7-[5-(4-ethylphenyl)-2-thienyl]-1,1-dioxoperhydro-4-propanesulfonyl-1,4-thiazepin-7-yl] acetic acid (3.95 g) in dimethylformamide (DMF) (40 ml) were added N-(2-tetrahydropyranyloxy)amine (1.30 g), 1-(3-dimethylaminopropyl)-3-ethylcarbodiimide hydrochloride (EDC; 1.82 g), and 1-hydroxybenzotriazole (HOBt; 1.28 g) at 0° C. The resulting mixture was stirred for 3 hours at room temperature. Ethyl acetate (500 ml) was added and the solution was washed with water (300 ml×3), saturated sodium bicarbonate, and brine, dried over magnesium sulfate, and evaporated to give a pale yellow solid. Silica gel column chromatography (eluent: 0 to 0.3% methanol in chloroform) afforded N-(2-tetrahydropyranyloxy)-2-[(S)-7-[5-(4-ethylphenyl)-2-thienyl]-1,1-dioxoperhydro-4-propanesulfonyl-1,4-thiazepin-7-yl]acetamide (4.34 g) as a pale yellow solid.

NMR (CDCl$_3$, δ): 1.07 (3H, t, J=7 Hz), 1.24 (3H, t, J=8 Hz), 1.44–1.93 (8H, m), 2.65 (2H, q, J=8 Hz), 2.84–4.23 (14H, m), 4.67–4.89 (1H, m), 7.17–7.21 (4H, m), 7.49 (2H, dd, J=2 and 8 Hz), 8.60–8.64 (1H, m) MASS (ESI+): 599.29 (MH)

EXAMPLE 703

To a solution of N-(2-tetrahydropyranyloxy)-2-[(S)-7-(5-(4-ethylphenyl)-2-thienyl]-1,1-dioxoperhydro-1,4-thiazepin-7-yl]acetamide (100 mg) and cyclohexanecarbaldehyde (46 mg) in ethanol were added sodium cyanoborohydride (26 mg) and acetic acid (1 drop) in an ice-water bath. After 1 hour stirring, to the reaction mixture was added water. The mixture was extracted with ethyl acetate. The organic layer was washed with water twice and brine, dried over magnesium sulfate and evaporated. The residue was purified by flash silica gel chromatography eluting with hexane-ethyl acetate=5-1, 2-1, 1-2 to give N-(2-tetrahydropyranyloxy)-2-[(S)-4-(cyclohexylmethyl)-7-(5-(4-ethylphenyl)-2-thienyl]-1,1-dioxoperhydro-1,4-thiazepin-7-yl]acetamide (91 mg) as colorless amorphous.

NMR (CDCl$_3$, δ): 0.78–0.95 (2H, m), 1.16–1.30 (7H, m), 1.35–1.97 (11H, m), 2.25–2.45 (2H, m), 2.65 (2H, q, J=8 Hz), 2.74–2.93 (2H, m), 2.97–3.56 (6H, m), 3.64–3.85 (2H, m), 4.63, 4.87 (1H, br s), 7.11–7.24 (4H, m), 7.44–7.53 (2H, m), 8.66, 8.43 (1H, br s) MASS (ESI+): 589

EXAMPLE 704

To the solution of N-(2-tetrahydropyranyloxy)-2-[(S)-7-[5-(4-ethylphenyl)-2-thienyl]-1,1-dioxoperhydro-1,4-thiazepin-7-yl]acetamide (100 mg) and 6-methylpyridine-2-carbaldehyde (49.2 mg) in ethanol (5 ml) was added sodium triacetoxyborohydride (81.6 mg) and a drop of acetic acid. The resulting mixture was stirred for 1 hour at room temperature. The solvent was evaporated and the residue was partitioned into ethyl acetate (20 ml)/water (20 ml). The organic layer was washed with brine (20 ml), dried over magnesium sulfate, and evaporated to give a yellow gum. Silica gel column chromatography (eluent: acetone hexane (2:3)] was performed to give N-(2-tetrahydropyranyloxy)-2-[(S)-7-[5-(4-ethylphenyl)-2-thienyl]-1,1-dioxoperhydro-4-[(6-methylpyridin-2-yl)methyl]-1,4-thiazepin-7-yl] acetamide (85.9 mg) as a yellowish solid.

NMR (CDCl$_3$, δ): 1.24 (3H, t, J=8 Hz), 1.40–1.92 (6H, m), 2.60–2.68 (5H, m), 2.73–4.13 (13H, m), 4.89–5.14 (1H, m), 7.04 (1H, d, J=7 Hz), 7.12–7.24 (5H, m), 7.49 (2H, d, J=7 Hz), 7.60 (2H, t, J=8 Hz), 11.53–11.75 (1H, m) MASS (ESI+): 598.46 (MH)

EXAMPLE 705

To a solution of N-2-(tetrahydropyranyloxy)-2-[(S)-7-[5-(4-ethylphenyl)-2-thienyl]-1,1-dioxoperhydro-1,4-thiazepin-7-yl]acetamide (100 mg) and 3-methyl]-2-butenyl (19.5 mg) in 1,2-dichloroethane (5 ml) was added sodium triacetoxyborohydride (86.1 mg) at 0° C. The resulting mixture was stirred for 0.5 hour at room temperature under a nitrogen atmosphere. The reaction mixture was partitioned into ethyl acetate (20 ml)/water (20 ml). The organic layer was washed with brine (20 ml), dried over magnesium sulfate, and evaporated to give a yellow foam. Silica gel column chromatography [eluent: ethyl acetate/chloroform (1:7) then chloroform/methanol (10:1)] gave N-(2-tetrahydropyranyloxy)-2-[(S)-7-[5-(4-ethylphenyl)-2-thienyl]-1,1-dioxoperhydro-4-(3-methyl-2-butenyl)-1,4-thiazepin-7-yl]acetamide (36.9 mg) as a yellow sticky solid.

NMR (CDCl$_3$, δ): 1.24 (3H, t, J=8 Hz), 1.38–1.85 (12H, m), 2.64 (2H, q, J=8 Hz), 2.84–4.00 (14H, m), 4.63–4.89 (1H, m), 5.20–5.22 (1H, m), 7.15–7.22 (4H, m), 7.46–7.50 (2H, m), 8.76–8.91 (1H, m) MASS (ESI+): 561.36 (MH)

EXAMPLE 706

To a solution of N-(2-tetrahydropyranyloxy)-2-[(S)-7-[5-(4-ethylphenyl)-2-thienyl]-1,1-dioxoperhydro-1,4-thiazepin-7-yl]acetamide (70.0 mg) and 2-thiophenecarbaldehyde (19.1 mg) in ethanol (1 ml) was added sodium cyanoborohydride (10.7 mg) and a drop of acetic acid at 0° C. The resulting mixture was stirred for 3 hours at room temperature. The reaction was quenched by the addition of saturated sodium bicarbonate (1 ml), and the solvent was evaporated off. The residue was dissolved in ethyl acetate (20 ml), and washed with water, brine, dried over magnesium sulfate, and evaporated. Silica gel column chromatography [eluent: acetone/chloroform (10:1)] afforded N-(2-tetrahydropyranyloxy)-2-[(S)-7-[5-(4-ethylphenyl)-2-thienyl]-1,1-dioxoperhydro-4-(2-thienylmethyl)-1,4-thiazepin-7-yl]acetamide (74.4 mg) as a colorless oil.

NMR (CDCl$_3$, b): 1.24 (3H, t, J=8 Hz), 1.26–1.96 (6H, m), 2.64 (2H, q, J=8 Hz), 2.85–4.01 (14H, m), 4.63–4.88 (1H, m), 6.91–6.95 (2H, m), 7.15–7.23 (5H, m), 7.46–7.50 (2H, m), 8.92–9.15 (1H, m) MASS (ESI+): 589.19 (MH)

The following compounds were obtained in a similar manner to that of Example 290.

EXAMPLE 707

N-Hydroxy-2-[(S)-4-(cyclopropylacetyl)-7-(5-(4-(5-oxazolyl)phenyl)-2-thienyl)-1,1-dioxoperhydro-1,4-thiazepin-7-yl]acetamide (42 mg)

NMR (DMSO-d$_6$, δ): 0.07–0.20 (2H, m), 0.41–0.52 (2H, m), 0.91–1.10 (1H, m), 2.23–2.40 (2H, m), 2.60–3.26 (4H, m), 3.36–4.10 (6H, m), 7.23 (½H, d, J=3 Hz), 7.26 (½H, d, J=3 Hz), 7.55–7.60 (1H, m), 7.71–7.82 (5H, m), 8.45 (1H, s), 8.90 (½H, s), 8.95 (½H, s) MASS (ES−)(m/z): 528.16

EXAMPLE 708

N-Hydroxy-2-[(S)-4-(cyclopentylacetyl)-7-(5-(4-(5-oxazolyl)phenyl)-2-thienyl)-1,1-dioxoperhydro-1,4-thiazepin-7-yl]acetamide (43 mg)

NMR (DMSO-d$_6$, δ): 1.04–1.21 (2H, m), 1.41–1.67 (4H, m), 1.67–1.85 (2H, m), 2.10–2.25 (1H, m), 2.30–2.44 (2H, m), 2.56–3.16 (4H, m), 3.40–3.95 (5H, m), 3.95–4.11 (1H, m), 7.23 (½H, d, J=3 Hz), 7.25 (½H, d, J=3 Hz), 7.54–7.59 (1H, m), 7.70–7.82 (5H, m), 8.48 (1H, s), 8.91 (1H, br peak) MASS (ES−)(m/z): 556.18

EXAMPLE 709

N-Hydroxy-2-[(S)-4-(cyclohexylacetyl)-7-(5-(4-(5-oxazolyl)phenyl)-2-thienyl)-1,1-dioxoperhydro-1,4-thiazepin-7-yl]acetamide (43 mg)

NMR (DMSO-d$_6$, δ): 0.84–1.06 (2H, m), 1.06–1.32 (3H, m), 1.55–1.84 (6H, m), 2.15–2.32 (2H, m), 2.57–3.24 (4H, m), 3.40–3.95 (5H, m), 3.94–4.11 (1H, m), 7.23 (½H, d, J=3 Hz), 7.26 (½H, d, J=3 Hz), 7.54–7.60 (1H, m), 7.71–7.83 (5H, m), 8.48 (1H, s), 8.92 (1H, br peak) MASS (ES−)(m/z): 570.17

The following compound is obtained in a similar manner to those of Example 256 and Example 17.

EXAMPLE 710

N-Hydroxy-2-[(S)-(2-methoxyethylaminosulfonyl)-7-(5-(4-(5-oxazolyl)phenyl)-2-thienyl)-1,1-dioxoperhydro-1,4-thiazepin-7-yl]acetamide (49 mg)

NMR (DMSO-d$_6$, δ): 2.86–2.96 (2H, m), 3.01–3.09 (2H, m), 3.09–3.22 (2H, m), 3.27 (3H, s), 3.39 (2H, t, J=5 Hz), 3.44–3.81 (5H, m), 3.81–4.00 (1H, m), 7.23 (1H, d, J=3 Hz), 7.46 (1H, br peak), 7.56 (1H, d, J=3 Hz), 7.71–7.84 (5H, m), 8.48 (1H, s), 8.92 (1H, br peak) MASS (ES−)(m/z): 583.10

The following compound is obtained in a similar manner to those of Example 1 and Example 17.

EXAMPLE 711

N-Hydroxy-2-[(S)-7-(5-(4-(5-oxazolyl)phenyl)-2-thienyl)-1,1-dioxoperhydro-4-(N-(2-methoxyethyl)-N-methylaminosulfonyl)-1,4-thiazepin-7-yl]acetamide (42 mg)

NMR (DMSO-d$_6$, δ): 2.80 (3H, s), 2.87–3.00 (2H, m), 3.09–3.20 (2H, m), 3.20–3.32 (5H, m), 3.44–3.78 (7H, m), 3.86–4.01 (1H, m), 7.24 (1H, d, J=3 Hz), 7.57 (1H, d, J=3 Hz), 7.72–7.83 (5H, m), 8.48 (1H, s), 8.94 (1H; br peak) MASS (ES−)(m/z): 597.10

The following compound is obtained in a similar manner to that of Example 1.

EXAMPLE 712

N-(2-Tetrahydropyranyloxy)-2-[4-(dimethylamino)sulfonyl-7-[4-(4-ethylphenoxy)phenyl]-1,1-dioxoperhydro-1,4-thiazepin-7-yl]acetamide (79 mg)

NMR (CDCl$_3$, δ): 1.25 (3H, t, J=7 Hz), 1.50–1.60 (4H, m), 1.69–1.83 (2H, m), 2.65 (2H, q, J=7 Hz), 2.81 (6H, s), 3.17–3.66 (8H, m), 3.80–4.15 (4H, m), 4.64–4.93 (1H, m), 6.97 (4H, d, J=8 Hz), 7.18 (2H, d, J=8 Hz), 7.47 (2H, d, J=8 Hz), 8.56 (1H, s) MASS (m/z): 610 (M$^+$+H), 115 (bp)

The following compounds were obtained in a similar manner to that of Example 33.

EXAMPLE 713

N-(2-Tetrahydropyranyloxy)-2-[7-[4-(4-ethylphenoxy)phenyl]-1,1-dioxoperhydro-4-(2-pyrazinecarbonyl)-1,4-thiazepin-7-yl]acetamide (756 mg)

NMR (CDCl$_3$, δ): 1.25 (3H, t, J=7 Hz), 1.50–1.57 (4H, m), 1.68–1.75 (2H, m), 2.60–2.69 (2H, m), 2.75–3.05 (2H, m), 3.15–3.65 (6H, m), 3.75–3.90 (4H, m), 4.14–4.252 (1H, m), 6.85–7.00 (4H, m), 7.17 (2H, t, J=8 Hz), 7.50 (1H, d, J=8 Hz), 7.60 (1H, d, J=8 Hz), 8.40–8.59 (1H, m), 8.69 (1H, s), 8.89–9.05 (1H, m) MASS (m/z): 609 (M$^+$+H), 115 (bp)

EXAMPLE 714

N-(2-Tetrahydropyranyloxy)-2-[7-[4-(4-ethylphenoxy)phenyl]-1,1-dioxoperhydro-4-benzoyl-1,4-thiazepin-7-yl]acetamide (80 mg)

NMR (CDCl$_3$, δ): 1.25 (3H, t, J=7 Hz), 1.47–1.70 (6H, m), 2.65 (2H, q, J=7 Hz), 2.72–2.90 (1H, m), 2.93–3.18 (2H, m), 3.35–4.00 (7H, m), 4.07–4.19 (1H, m), 4.28–4.43 (1H, m), 4.54–4.69 (1H, m), 6.70–7.01 (4H, m), 7.17 (3H, d, J=8 Hz), 7.33–7.48 (5H, m), 7.63–7.71 (1H, m) MASS (m/z): 607 (M$^+$+H), 115 (bp)

EXAMPLE 715

N-(2-Tetrahydropyranyloxy)-2-[7-[4-(4-ethylphenoxy)phenyl]-4-cyclopropylcarbonyl-1,1-dioxoperhydro-1,4-thiazepin-7-yl]acetamide (71 mg)

NMR (CDCl$_3$, δ): 1.25 (3H, t, J=7 Hz), 0.78–1.11 (4H, m), 1.47–1.65 (4H, m), 1.69–1.74 (2H, m), 1.78–1.89 (1H, m), 2.64 (2H, q, J=7 Hz), 2.75–2.97 (3H, m), 3.22–3.45 (4H, m), 3.50–3.60 (1H, m), 3.72–3.88 (2H, m), 4.10–4.20 (2H, m), 4.43–4.87 (2H, m), 6.94 (4H, d, J=8 Hz), 7.15 (2H, d, J=8 Hz), 7.40–7.60 (2H, m) MASS (m/z): 571 (M$^+$+H), 115 (bp)

EXAMPLE 716

N-(2-Tetrahydropyranyloxy)-2-[7-[4-(4-ethylphenoxy)phenyl]-4-(2-thiophenecarbonyl)-1,1-dioxoperhydro-1,4-thiazepin-7-yl]acetamide (80 mg)

NMR (CDCl$_3$, δ): 1.25 (3H, t, J=7 Hz), 1.46–1.62 (4H, m), 1.65–1.77 (2H, m), 2.65 (2H, q, J=7 Hz), 2.75–2.94 (2H, m), 3.10–3.42 (4H, m), 3.46–3.84 (4H, m), 3.92–4.10 (1H, m), 4.20–4.70 (2H, m), 6.95 (4H, d, J=8 Hz), 7.03–7.08 (1H, m), 7.17 (2H, d, J=8 Hz), 7.42–7.57 (4H, m) MASS (m/z): 613 (M$^+$+H), 115 (bp)

EXAMPLE 717

N-(2-Tetrahydropyranyloxy)-2-[7-[4-(4-ethylphenoxy)phenyl]-4-(3-thiophenecarbonyl)-1,1-dioxoperhydro-1,4-thiazepin-7-yl]acetamide (74 mg)

NMR (CDCl$_3$, δ): 1.24 (3H, t, J=7 Hz), 1.47–1.57 (4H, m), 1.65–1.79 (2H, m), 2.25 (2H, q, J=7 Hz), 2.72–2.97 (2H, m), 3.05–3.30 (2H, m), 3.36–3.67 (4H, m), 3.72–3.90 (4H, m), 4.02–4.18 (1H, m), 6.95 (4H, d, J=8 Hz), 7.17 (2H d, J=8 Hz), 7.33–7.70 (5H, m) MASS (m/z): 613 (M$^+$+H), 115 (bp)

EXAMPLE 718

N-(2-Tetrahydropyranyloxy)-2-[7-[4-(4-ethylphenoxy)phenyl]-1,1-dioxoperhydro-4-(2-pyridinecarbonyl)-1,4-thiazepin-7-yl]acetamide (84 mg)

NMR (CDCl$_3$, δ): 1.24 (3H, t, J=7 Hz), 1.47–1.57 (4H, m), 1.67–1.75 (2H, m), 2.58–2.69 (2H, m), 2.72–3.03 (2H, m), 3.20–3.64 (6H, m), 3.74–3.87 (2H, m), 4.10–4.23 (2H, m), 4.52–4.88 (1H, m), 6.85–6.99 (4H, m), 7.10–7.20 (2H, m), 7.37 (1H, t, J=8 Hz), 7.50 (1H, d, J=8 Hz), 7.60 (2H, d, J=8 Hz), 7.72–7.85 (2H, m) MASS (m/z): 608 (M$^-$–H), 85 (bp)

EXAMPLE 719

N-(2-Tetrahydropyranyloxy)-2-[7-[4-(4-ethylphenoxy)phenyl]-4-[(2S)-2-hydroxy-2-phenylacetyl]-1,1-dioxoperhydro-1,4-thiazepin-7-yl]acetamide (69 mg)

NMR (CDCl$_3$, δ): 1.25 (3H, t, J=7 Hz), 1.50–1.62 (4H, m), 1.67–1.81 (2H, m), 2.65 (2H, q, J=7 Hz), 2.70–2.85 (2H, m), 3.009–3.39 (4H, m), 3.47–3.95 (3H, m), 4.32–4.95 (4H, m), 5.05–5.46 (1H, m), 6.97 (4H, d, J=8 Hz), 7.19 (2H, d, J=8 Hz), 7.30–7.56 (7H, m) MASS (m/z): 637 (M$^+$+H), 115 (bp)

The following compounds were obtained in a similar manner to that of Example 290.

EXAMPLE 720

N-Hydroxy-2-[(S)-7-(5-(4-chlorophenyl)-2-thienyl)-4-(cyclobutylcarbonyl)-1,1-dioxoperhydro-1,4-thiazepin-7-yl]acetamide (39.5 mg)

NMR (DMSO-d$_6$, δ): 1.65–1.82 (1H, m), 1.82–2.01 (1H, m), 2.01–2.33 (5H, m), 2.33–3.17 (4H, m), 3.17–4.06 (6H, m), 7.20 (½H, d, J=3 Hz), 7.23 (½H, d, J=3 Hz), 7.44–7.56 (3H, m), 7.63–7.73 (2H, m), 8.94 (1H, br peak) MASS (ES+)(m/z): 497.21

EXAMPLE 721

N-Hydroxy-2-[(S)-7-(5-(4-chlorophenyl)-2-thienyl)-4-(cyclopentylcarbonyl)-1,1-dioxoperhydro-1,4-thiazepin-7-yl]acetamide (29.8 mg)

NMR (DMSO-d$_6$, δ): 1.45–1.95 (9H, m), 2.62–3.19 (4H, m), 3.41–4.23 (6H, m), 7.20 (½H, d, J=3 Hz), 7.25 (½H, d, J=3 Hz), 7.41–7.57 (3H, m), 7.57–7.76 (2H, m), 8.90 (½H, s), 8.95 (½H, s) MASS (ES+)(m/z): 511.20, 513.29

EXAMPLE 722

N-Hydroxy-2-[(S)-7-(5-(4-chlorophenyl)-2-thienyl)-4-(3-methyl-2-butenoyl)-1,1-dioxoperhydro-1,4-thiazepin-7-yl]acetamide (32.6 mg)

NMR (DMSO-d$_6$, δ): 1.80–1.94 (6H, m), 2.62–3.15 (4H, m), 3.50–4.07 (6H, m), 5.91 (1H, s), 6.02 (1H, s), 7.21 (1H, s), 7.44–7.55 (3H, m), 7.67 (2H, d, J=8 Hz), 8.91 (1H, s) MASS (ES+)(m/z): 497.22, 499.23

EXAMPLE 723

N-Hydroxy-2-[(S)-7-(5-(4-chlorophenyl)-2-thienyl)-4-(cyclopentylacetyl)-1,1-dioxoperhydro-1,4-thiazepin-7-yl]acetamide (25.4 mg)

NMR (DMSO-d$_6$, δ): 1.03–1.23 (2H, m), 1.41–1.69 (4H, m), 1.69–1.88 (2H, m), 2.11–2.30 (1H, m), 2.30–2.45 (2H, m), 2.58–3.16 (4H, m), 3.43–4.11 (6H, m), 7.20 (½H, d, J=3 Hz), 7.25 (½H, d, J=3 Hz), 7.44–7.55 (3H, m), 7.61–7.72 (2H, m), 8.90 (1H, br peak) MASS (ES+)(m/z): 525.22, 527.25

EXAMPLE 724

N-Hydroxy-2-[(S)-7-(5-(4-chlorophenyl)-2-thienyl)-4-(3-cyclohexen-1-ylcarbonyl)-1,1-dioxoperhydro-1,4-thiazepin-7-yl]acetamide (37 mg)

NMR (DMSO-d$_6$, δ): 1.39–1.62 (1H, m), 1.70–1.86 (1H, m), 1.94–2.33 (5H, m), 2.56–3.16 (4H, m), 3.40–4.20 (6H, m), 5.61–5.76 (2R, m), 7.18–7.28 (1H, m), 7.43–7.56 (3H, m), 7.63–7.73 (2H, m), 8.90 (½H, s), 8.94 (½H, s) MASS (ES–)(m/z): 521.34

EXAMPLE 725

N-Hydroxy-2-[(S)-7-(5-(4-methoxyphenyl)-2-thienyl)-1,1-dioxoperhydro-4-(3-methylbutanoyl)-1,4-thiazepin-7-yl]acetamide (40 mg)

NMR (DMSO-d$_6$, δ): 0.87–0.99 (6H, m), 1.98–2.14 (1H, m), 2.14–2.38 (2H, m), 2.57–3.21 (4H, m), 3.40–3.95 (8H, m), 3.95–4.12 (1H, m), 6.94–7.04 (2H, m), 7.16 (½H, d, J=3 Hz), 7.19 (½H, d, J=3 Hz), 7.31–7.36 (1H, m), 7.57 (2H, d, J=8 Hz), 8.88 (½H, s), 8.93 (½H, s) MASS (ES-)(m/z): 493.22

The following compound is obtained in a similar manner to that of Example 349.

EXAMPLE 726

N-Hydroxy-2-[(S)-7-(5-(4-chlorophenyl)-2-thienyl)-4-phenylcarbamoyl-1,1-dioxoperhydro-1,4-thiazepin-7-yl] acetamide (38.7 mg)

NMR (DMSO-$d_6$, δ): 2.70–3.21 (4H, m), 3.50–4.02 (6H, m), 6.92–7.04 (1H, m), 7.19–7.31 (3H, m), 7.32–7.56 (5H, m), 7.66 (2H, d, J=8 Hz), 8.49 (1H, s), 8.91 (1H, s), 10.65 (1H, s) MASS (ES-)(m/z): 532.22, 534.28

The following compounds were obtained in a similar manner to that of Example 326.

EXAMPLE 727

N-Hydroxy-2-[(S)-7-(5-(4-chlorophenyl)-2-thienyl)-4-ethoxycarbonyl-1,1-dioxoperhydro-1,4-thiazepin-7-yl] acetamide (16.1 mg)

NMR (DMSO-$d_6$, δ): 1.14–1.35 (3H, m), 2.68–3.14 (4H, m), 3.47–3.96 (6H, m), 4.01–7.18 (2H, m), 7.18–7.28 (1H, m), 7.43–7.56 (3H, m), 7.67 (2H, d, J=8 Hz), 8.90 (1H, s), 10.65 (1H, s) MASS (ES+)(m/z): 487.19, 489.19

EXAMPLE 728

N-Hydroxy-2-[(S)-7-(5-(4-chlorophenyl)-2-thienyl)-4-benzyloxycarbonyl-1,1-dioxoperhydro-1,4-thiazepin-7-yl] acetamide (11.4 mg)

NMR (DMSO-$d_6$, δ): 2.69–3.15 (4H, m), 3.50–4.02 (6H, m), 5.06–5.76 (2H, m), 7.18–7.28 (1H, m), 7.28–7.45 (5H, m), 7.45–7.59 (3H, m), 7.59–7.76 (2H, m), 8.91 (1H, br peak), 10.68 (1H, s) MASS (ES+) (m/z): 549.12

EXAMPLE 729

N-Hydroxy-2-[(S)-7-(5-(4-chlorophenyl)-2-thienyl)-4-(1-pyrrolidinylcarbonyl)-1,1-dioxoperhydro-1,4-thiazepin-7-yl]acetamide (16.5 mg)

NMR (DMSO-$d_6$, δ): 1.61–1.88 (4H, m), 2.78–3.15 (4H, m), 3.15–3.91 (8H, m), 7.20 (1H, d, J=3 Hz), 7.45–7.55 (3H, m), 7.68 (2H, d, J=8 Hz), 8.91 (1H, s), 10.66 (1H, s) MASS (ES+)(m/z): 512.18, 514.18

EXAMPLE 730

N-Hydroxy-2-[(S)-7-(5-(4-chlorophenyl)-2-thienyl)-4-(1-piperidinylcarbonyl)-1,1-dioxoperhydro-1,4-thiazepin-7-yl]acetamide (26.5 mg)

NMR (DMSO-$d_6$, δ): 1.36–1.62 (6H, m), 2.60–3.15 (8H, m), 3.26–3.75 (4H, m), 3.75 (2H, m), 7.18 (1H, d, J=3 Hz), 7.43–7.54 (3H, m), 7.66 (2H, d, J=8 Hz), 8.90 (1H, br peak), 10.62 (1H, s) MASS (ES+)(m/z): 526.21, 528.06

EXAMPLE 731

N-Hydroxy-2-[(S)-7-(5-(4-methoxyphenyl)-2-thienyl)-4-(1-piperidinylcarbonyl)-1,1-dioxoperhydro-1,4-thiazepin-7-yl]acetamide (32.2 mg)

NMR (DMSO-$d_6$, δ): 1.37–1.58 (6H, m), 2.58–3.20 (8H, m), 3.40–3.55 (2H, m), 3.55–3.69 (2H, m), 3.75–3.93 (4H, m), 4.04–4.17 (1H, m), 6.98 (2H, d, J=8 Hz), 7.13 (1H, d, J=3 Hz), 7.33 (1H, d, J=3 Hz), 7.56 (2H, d, J=8 Hz), 8.88 (1H, br peak), 10.62 (1H, br peak) MASS (ES+)(m/z): 522.33

EXAMPLE 732

N-Hydroxy-2-[(S)-7-(5-(4-methoxyphenyl)-2-thienyl)-4-(n-propylsulfonyl)-1,1-dioxoperhydro-1,4-thiazepin-7-yl] acetamide (27 mg)

NMR (DMSO-$d_6$, δ): 0.99 (3H, t, J=7.5 Hz), 1.61–1.76 (2H, m), 2.84–2.96 (2H, m), 3.06–3.22 (4H, m), 3.45–3.66 (4H, m), 3.66–3.86 (4H, m), 3.94–4.07 (1H, m), 6.98 (2H, d, J=8 Hz), 7.16 (1H, d, J=3 Hz), 7.34 (1H, d, J=3 Hz), 7.56 (2H, d, J=8 Hz), 8.92 (1H, br peak) MASS (ES-)(m/z): 515.14

EXAMPLE 733

N-Hydroxy-2-[(S)-7-(5-(4-methoxyphenyl)-2-thienyl)-4-(4-morpholinylsulfonyl)-1,1-dioxoperhydro-1,4-thiazepin-7-yl]acetamide (32 mg)

NMR (DMSO-$d_6$, δ): 2.85–2.94 (2H, m), 3.04–3.16 (6H, m), 3.52–3.76 (9H, m), 3.79 (3H, s), 3.92–4.07 (1H, m), 6.99 (2H, d, J=8 Hz), 7.16 (1H, d, J=3 Hz), 7.34 (1H, d, J=3 Hz), 7.56 (2H, d, J=8 Hz), 10.69 (1H, s) MASS (ES-)(m/z): 558.19

EXAMPLE 734

N-Hydroxy-2-[(S)-4-ethylsulfonyl-7-(5-(4-methoxyphenyl)-2-thienyl)-1,1-dioxoperhydro-1,4-thiazepin-7-yl]-acetamide (19 mg)

NMR (DMSO-$d_6$, δ): 1.22 (3H, t, J=7.5 Hz), 2.84–2.96 (2H, m), 3.09–3.25 (4H, m), 3.46–3.68 (4H, m), 3.68–3.82 (4H, M), 3.94–4.08 (1H, m), 6.98 (2H, d, J=8 HZ), 7.16 (1H, d, J=3 Hz), 7.34 (1H, d, J=3 Hz), 7.56 (2H, d, J=8 Hz), 8.91 (1H, br peak) MASS (ES-)(m/z): 501.16

The following compounds were obtained in a similar manner to that of Example 39.

EXAMPLE 735

N-(2-Tetrahydropyranyloxy)-2-[(S)-7-(5-(4-methylphenyl)-2-thienyl)-1,1-dioxoperhydro-4-(3-thiophenecarbonyl)-1,4-thiazepin-7-yl]acetamide (2.43 g)

NMR (DMSO-$d_6$, δ): 1.33–1.66 (6H, m), 2.32 (3H, s), 2.70–3.23 (4H, m), 3.36–4.02 (8H, m), 4.38–4.81 (1H, m), 7.18–7.31 (4H, m), 7.36–7.45 (1H, m), 7.50–7.68 (3H, m), 7.84 (1H, s) MASS (ESI+): 589 (M+H)

EXAMPLE 736

N-(2-Tetrahydropyranyloxy)-2-[(S)-7-(5-(4-methylphenyl)-2-thienyl)-4-(2-pyridylcarbonyl)-1,1-dioxoperhydro-1,4-thiazepin-7-yl]acetamide (2.3 g)

NMR (CDCl$_3$, δ): 1.48–1.66 (6H, m), 2.36 (3H, s), 2.81–3.06 (2H, m), 3.08–3.94 (9H, m), 4.16–4.41 (1H, m), 4.55–4.59 (0.5H, m), 4.80–4.85 (0.5H, m), 7.07–7.24 (4H, m), 7.30–7.45 (3H, m), 7.75–7.81 (2H, m), 8.43–8.69 (1H, m) MASS (ESI+): 584 (M+H)

The following compounds were obtained in a similar manner to that of Example 17.

EXAMPLE 737

N-Hydroxy-2-[(S)-7-(5-(4-methylphenyl)-2-thienyl)-1,1-dioxoperhydro-4-(3-thiophenecarbonyl)-1,4-thiazepin-7-yl] acetamide (1.58 g)

NMR (DMSO-$d_6$, δ): 2.32 (3H, s), 2.70–3.18 (4H, m), 3.47–4.12 (6H, m), 7.19–7.31 (4H, m), 7.38–7.46 (1H, m), 7.50–7.69 (3H, m), 7.81–7.90 (1H, m) MASS (ESI-): 503 (M-H)

EXAMPLE 738

N-Hydroxy-2-[(S)-4-methanesulfonyl-7-(5-(4-propylphenyl)-2-thienyl)-1,1-dioxoperhydro-1,4-thiazepin-7-yl]acetamide (1.62 g)

NMR (DMSO-d$_6$, δ): 0.90 (3H, t, J=7 Hz), 1.56–1.70 (2H, m), 2.58 (2H, t, J=7 Hz), 2.90–2.98 (2H, br), 3.00 (3H, s), 3.08–3.24 (2H, m), 3.42–3.80 (5H, m), 3.92–4.06 (1H, m), 7.20 (1H, d, J=3 Hz), 7.25 (2H, d, J=8 Hz), 7.42 (1H, d, J=3 Hz), 7.55 (2H, d, J=8 Hz), 8.93 (1H, s), 10.69 (1H, s)

EXAMPLE 739

N-Hydroxy-2-[(S)-4-(2-pyridinecarbonyl)-7-(5-(4-trifluoromethoxyphenyl)-2-thienyl)-1,1-dioxoperhydro-1,4-thiazepin-7-yl]acetamide (2.48 g)

NMR (DMSO-d$_6$, δ): 2.74–3.22 (4H, m), 3.40–4.20 (6H, m), 7.24, 7.27 (1H, d, J=3 Hz), 7.43 (2H, d, J=8 Hz), 7.51 (2H, m), 7.63 (1H, m), 7.77 (2H, t, J=8 Hz), 7.96 (1H, t, J=8 Hz), 8.61 (1H, m), 10.63, 10.69 (1H, s) MASS (m/z): 568 (M–H), 570 (M+H)

EXAMPLE 740

N-Hydroxy-2-[(S)-4-(3-thiophenecarbonyl)-7-(5-(4-trifluoromethoxyphenyl)-2-thienyl)-1,1-dioxoperhydro-1,4-thiazepin-7-yl]acetamide (2.58 g)

NMR (DMSO-d$_6$, δ): 2.80–3.26 (4H, br), 3.40–4.18 (6H, br), 7.26 (2H, m), 7.42 (2H, d, J=8 Hz), 7.53 (1H, br), 7.63 (1H, br), 7.72–7.90 (3H, m), 8.88 (1H, br), 10.62, 10.68 (1H, br) MASS (m/z): 573 (M–H)

EXAMPLE 741

N-Hydroxy-2-[(S)-7-(5-(4-methylphenyl)-2-thienyl)-4-(2-pyridylcarbonyl)-1,1-dioxoperhydro-1,4-thiazepin-7-yl]acetamide (1.8 g)

NMR (DMSO-d$_6$, δ): 2.31 (3H, s), 2.77–3.08 (4H, m), 3.49–4.08 (6H, m), 7.16–7.24 (3H, m), 7.39–7.43 (1H, m), 7.50–7.55 (3H, m), 7.59–7.64 (1H, m), 7.92–7.97 (1H, m), 8.58–8.61 (1H, m), 8.84–8.94 (1H, br), 10.67 (1H, br)

EXAMPLE 742

N-Hydroxy-2-[7-[4-(4-ethylphenoxy)phenyl]-1,1-dioxoperhydro-4-(2-pyrazinecarbonyl)-1,4-thiazepin-7-yl]acetamide (46 mg)

NMR (DMSO-d$_6$, δ): 1.20 (3H, t, J=7 Hz), 2.62 (2H, q, J=7 Hz), 2.69–3.37 (4H, m), 3.67–3.83 (4H, m), 4.15–4.25 (2H, m), 6.92 (2H, d, J=8 Hz), 6.99 (2H, d, J=8 Hz), 7.26 (2H, t, J=7 Hz), 7.49 (2H, t, J=8 Hz), 8.20 (1H, d, J=2 Hz), 8.79 (1H, d, J=2 Hz), 8.90 (1H, s)

EXAMPLE 743

N-Hydroxy-2-[4-benzoyl-7-[4-(4-ethylphenoxy)phenyl]-1,1-dioxoperhydro-1,4-thiazepin-7-yl]acetamide (60 mg)

NMR (DMSO-d$_6$, δ): 1.19 (3H, t, J=7 Hz), 2.62 (2H, q, J=7 Hz), 2.70–2.83 (2H, m), 2.97–3.24 (2H, m), 3.50–3.62 (2H, m), 3.68–3.93 (2H, m), 3.99–4.25 (2H, m), 6.87–7.02 (4H, m), 7.26 (2H, d, J=8 Hz), 7.43–7.54 (7H, m)

EXAMPLE 744

N-Hydroxy-2-[4-cyclopropanecarbonyl-7-[4-(4-ethylphenoxy)phenyl]-1,1-dioxoperhydro-1,4-thiazepin-7-yl]acetamide (40 mg)

NMR (DMSO-d$_6$, δ): 0.67–0.90 (4H, m), 1.19 (3H, t, J=7 Hz), 1.84–1.99 (1H, m), 2.62 (2H, t, J=7 Hz), 2.72–2.83 (2H, m), 3.05–3.27 (2H, m), 3.60–4.14 (5H, m), 4.24–4.37 (1H, m), 6.92 (2H, dd, J=8, 2 Hz), 7.00 (2H, dd, J=7.5, 2 Hz), 7.26 (2H, d, J=7.5 Hz), 7.49 (2H, t, J=8 Hz)

EXAMPLE 745

N-Hydroxy-2-[7-[4-(4-ethylphenoxy)phenyl]-1,1-dioxoperhydro-1,4-thiazepin-4-(2-thiophenecarbonyl)-7-yl]acetamide (32.6 mg)

NMR (DMSO-d$_6$, δ): 1.19 (3H, t, J=7 Hz), 2.62 (2H, q, J=7 Hz), 2.70–2.83 (1H, m), 2.90–3.29 (3H, m), 3.50–3.63 (2H, m), 3.75–4.17 (4H, m), 6.92 (2H, d, J=8 Hz), 7.00 (2H, d, J=7.5 Hz), 7.16 (1H, t, J=7 Hz), 7.26 (2H, d, J=8 Hz), 7.50 (3H, d, J=8 Hz), 7.82 (1H, d, J=7 Hz)

EXAMPLE 746

N-Hydroxy-2-[7-[4-(4-ethylphenoxy)phenyl]-1,1-dioxoperhydro-1,4-thiazepin-4-(3-thiophenecarbonyl)-7-yl]acetamide (40 mg)

NMR (DMSO-d$_6$, δ): 1.19 (3H, t, J=7 Hz), 2.62 (2H, q, J=7 Hz), 2.68–2770 (1H, m), 2.95–3.09 (1H, m), 3.15–3.28 (2H, m), 3.50–3.60 (2H, m), 3.65–4.20 (4H, m), 6.87–6.95 (2H, m), 6.99 (2H, d, J=8 Hz), 7.27 (3H, d, J=8 Hz), 7.45–7.54 (2H, m), 7.60–7.65 (1H, m), 7.82–7.92 (1H, m)

EXAMPLE 747

N-Hydroxy-2-[7-[4-(4-ethylphenoxy)phenyl]-1,1-dioxoperhydro-4-(2-pyridinecarbonyl)-1,4-thiazepin-7-yl]acetamide hydrochloride (53 mg)

NMR (DMSO-d$_6$, δ): 1.19 (3H, t, J=7 Hz), 2.62 (2H, q, J=7 Hz), 2.73–3.43 (3H, m), 3.52–3.77 (5H, m), 4.16–4.25 (2H, m), 6.91 (2H, t, J=8 Hz), 6.99 (2H, d, J=8 Hz), 7.27 (2H, d, J=8 Hz), 7.44–7.54 (4H, m), 7.60–7.67 (1H, m), 7.92–8.00 (1H, m), 8.60 (1H, d, J=2 Hz) MASS (m/z): 524(M$^-$+H), 191 (bp)

EXAMPLE 748

N-Hydroxy-2-[4-[(2S)-2-hydroxy-2-phenylacetyl]-7-[4-(4-ethylphenoxy)phenyl]-1,1-dioxoperhydro-1,4-thiazepin-7-yl]acetamide (44 mg)

NMR (DMSO-d$_6$, δ): 1.19 (3H, t, J=7 Hz), 2.62 (2H, q, J=7 Hz), 2.73–3.43 (3H, m), 3.52–3.77 (5H, m), 4.16–4.25 (2H, m), 6.91 (2H, t, J=8 Hz), 6.99 (2H, d, J=8 Hz), 7.27 (2H, d, J=8 Hz), 7.44–7.54 (4H, m), 7.60–7.67 (1H, m), 7.92–8.00 (1H, m), 8.60 (1H, d, J=2 Hz)

EXAMPLE 749

N-Hydroxy-2-[4-(dimethylamino)sulfonyl-7-[4-(4-ethylphenoxy)phenyl]-1,1-dioxoperhydro-1,4-thiazepin-7-yl]acetamide (53 mg)

NMR (DMSO-d$_6$, δ): 1.19 (3H, t, J=7 Hz), 2.62 (2H, q, J=7 Hz), 2.73 (6H, s), 3.04–3.30 (3H, m), 3.46–3.66 (5H, m), 3.76–4.08 (2H, m), 6.91 (2H, d, J=8 Hz), 6.99 (2H, d, J=8 Hz), 7.27 (2H, d, J=8 Hz), 7.45 (2H, d, J=8 Hz), 7.60–7.67 (1H, m), 8.88 (1H, s)

EXAMPLE 750

N-(2-Tetrahydropyranyloxy)-2-[7-[4-(4-ethylphenoxy)phenyl]-1,1-dioxoperhydro-1,4-thiazepin-7-yl]acetamide (1.613 g) was obtained in a similar manner to that of Example 28.

NMR (CDCl$_3$, δ): 1.25 (3H, t, J=7 Hz), 1.49–1.63 (4H, m), 1.72 (2H, s), 2.35 (3H, s), 2.48–2.59 (1H, m), 2.65 (2H, q, J=7 Hz), 3.05–3.28 (9H, m), 3.34–3.47 (1H, m), 3.49–3.61 (1H, m), 3.73–3.85 (1H, m), 6.96 (4H, d, J=8 Hz), 7.17 (2H, d, J=8 Hz), 7.54 (2H, d, J=8 Hz)

The following compounds were obtained in a similar manner to that of Example 30.

EXAMPLE 751

N-(2-Tetrahydropyranyloxy)-2-[(S)-4-methanesulfonyl-7-(5-(4-propylphenyl)-2-thienyl)-1,1-dioxoperhydro-1,4-thiazepin-7-yl]acetamide (2.26 g)

NMR (CDCl₃, δ): 0.95 (3H, t, J=7 Hz), 1.45–1.93 (8H, br), 2.60 (2H, t, J=7 Hz), 2.83–2.97 (1H, br), 2.93 (3H, s), 3.10–3.28 (3H, br), 3.28–3.70 (5H, br), 3.70–3.94 (2H, br), 4.07–4.26 (1H, br), 4.67, 4.88 (1H, br), 7.13–7.30 (4H, m), 7.49 (2H, d, J=8 Hz), 8.43, 8.50 (1H, br) MASS (m/z): 583 (M–H)

EXAMPLE 752

N-(2-Tetrahydropyranyloxy)-2-[(S)-4-(2-pyridinecarbonyl)-7-(5-(4-trifluoromethoxyphenyl)-2-thienyl)-1,1-dioxoperhydro-1,4-thiazepin-7-yl] acetamide (4.20 g)

NMR (CDCl₃, δ): 1.42–1.90 (6H, br), 2.82–4.18 (11H, br), 4.18–4.47, 4.56–4.67, 4.75–4.93 (2H, m), 7.07–7.26 (3H, m), 7.26–7.43 (1H, m), 7.47–7.66 (3H, m), 7.74–7.86 (2H, m), 8.38–8.54, 8.56–8.69 (2H, m) MASS (m/z): 652 (M–H), 654 (M+H)

EXAMPLE 753

N-(2-Tetrahydropyranyloxy)-2-[(S)-4-(3-thiophenecarbonyl)-7-(5-(4-trifluoromethoxyphenyl)-2-thienyl)-1,1-dioxoperhydro-1,4-thiazepin-7-yl]acetamide (4.84 g)

NMR (CDCl₃, δ): 1.44–1.90 (6H, br), 2.74–4.40 (12H, br), 4.47–4.58, 4.73, 4.85 (1H, br), 7.05–7.44 (7H, br), 7.50–7.65 (2H, br), 8.37, 8.48 (1H, br) MASS (m/z): 657 (M–H), 659 (M+H)

EXAMPLE 754

N-(2-Tetrahydropyranyloxy)-2-[(S)-7-(5-bromo-2-thienyl)-4-(2-pyridinecarbonyl)-1,1-dioxoperhydro-1,4-thiazepin-7-yl]acetamide (8.88 g)

NMR (CDCl₃, δ): 1.46–1.93 (6H, br), 2.80–4.46 (12H, br), 4.56–4.68, 4.75–4.93 (1H, br), 6.87–7.07 (2H, m), 7.33–7.43 (1H, br), 7.57–7.66, 7.73–7.88 (2H, m), 8.38–8.67 (2H, m) MASS (m/z): 572, 574 (M+H)

EXAMPLE 755

N-(2-Tetrahydropyranyloxy)-2-[4-(9-fluorenylmethoxycarbonyl)-7-[4-(4-ethylphenoxy)phenyl]-1,1-dioxoperhydro-1,4-thiazepin-7-yl]acetamide (2.9 g)

NMR (CDCl₃, δ): 1.23 (3H, t, J=7 Hz), 1.50–1.60 (4H, m), 1.67–1.80 (2H, m), 2.47–2.69 (4H, m), 2.90–3.30 (3H, m), 3.32–3.66 (5H, m), 3.80–4.09 (2H, m), 4.17–4.30 (1H, m), 4.35–4.57 (2H, m), 4.65–5.07 (1H, m), 6.87–6.97 (4H, m), 7.09–7.20 (2H, m), 7.30–7.50 (7H, m), 7.54–7.62 (1H, m), 7.79 (2H, d, J=8 Hz), 8.33–8.42 (1H, m) MASS (m/z): 725 (M⁺+H), 85 (bp)

What is claimed is:

1. A compound of the formula:

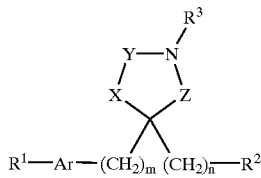

in which R¹ is halo, lower alkoxy, optionally substituted aryl, optionally substituted aryloxy, optionally substituted heterocyclic group or optionally substituted lower alkynyl,
R² is amidated carboxy selected from N-hydroxycarbamoyl and N-(protected hydroxy) carbamoyl,
Ar is aryl or heterocyclic group,
X is thia, sulfinyl or sulfonyl,
Y and Z are each an ethylene group,
m and n are each an integer of 0 to 2,
or a salt thereof,
wherein the above-mentioned optional substituents for aryl, aryloxy, heterocyclic group and lower alkynyl in R¹ are each selected from the group consisting of:
(S1) lower alkoxy,
(S2) lower alkoxycarbonylamino,
(S3) lower alkylaminocarbonylamino,
(S4) lower alkoxy(lower)alkanoylamino,
(S5) aryloxy(lower)alkanoylamino,
(S6) halo,
(S7) lower alkyl,
(S8) lower alkylthio,
(S9) heterocyclic group selected from:
unsaturated 3- to 8-membered heteromonocyclic group containing 1 or 2 oxygen atoms and 1 to 3 nitrogen atoms, which is optionally substituted by lower alkyl, and
saturated 3- to 8-membered heteromonocyclic group containing 1 or 2 sulfur atoms and 1 to 3 nitrogen atoms, which is optionally substituted by oxo,
(S10) lower alkenyl,
(S11) amino,
(S12) lower alkanoylamino,
(S13) hydroxy,
(S14) lower alkylsulfonyl,
(S15) aryloxy,
(S16) aryl optionally substituted by halogen,
(S17) lower alkylcarbamoyl(lower)alkenyl,
(S18) lower alkylcarbamoyl,
(S19) trihalo(lower)alkyl,
(S20) cyano,
(S21) cyano(lower)alkyl,
(S22) lower alkoxy(lower)alkyl,
(S23) hydroxy(lower)alkyl,
(S24) oxo,
(S25) aminosulfonyl,
(S26) nitro,
(S27) lower alkanoyl,
(S28) trihalo(lower)alkyloxy,
(S29) lower alkoxycarbonyl,
(S30) lower cycloalkyl,
(S31) lower alkoxy(lower)alkoxy, and
(S32) fluorenyl;
and above-mentioned heterocyclic groups for R¹ and Ar are each selected from:
(H1) unsaturated 3- to 8-membered, heteromonocyclic group containing 1 to 4 nitrogen atoms,
(H2) saturated 3- to 8-membered, heteromonocyclic group containing 1 to 4 nitrogen atoms,
(H3) unsaturated 3- to 8-membered, heteromonocyclic group containing 1 or 2 sulfur atoms,
(H4) unsaturated condensed 7- to 13-membered, heterocyclic group containing 1 to 5 nitrogen atoms,
(H5) unsaturated 3- to 8-membered, heteromonocyclic group containing 1 or 2 oxygen atoms,
(H6) saturated 3- to 8-membered, heteromonocyclic group containing 1 or 2 oxygen atoms,
(H7) unsaturated 3- to 8-membered, heteromonocyclic group containing 1 or 2 oxygen atoms and 1 to 3 nitrogen atoms,
(H8) unsaturated condensed 7- to 13-membered, heterocyclic group containing 1 or 2 oxygen atoms,
(H9) unsaturated condensed 7- to 13-membered, heterocyclic group containing 1 or 2 sulfur atoms, (H10) saturated 3- to 8-membered, heteromonocyclic group containing 1 or 2 oxygen atoms and 1 to 3 nitrogen atoms,
(H11) unsaturated condensed 7- to 13-membered, heterocyclic group containing 1 or 2 oxygen atoms and 1 to 3 nitrogen atoms,
(H12) unsaturated 3- to 8-membered, heteromonocyclic group containing 1 or 2 sulfur atoms and 1 to 3 nitrogen atoms,
(H13) saturated 3- to 8-membered, heteromonocyclic group containing 1 or 2 sulfur atoms and 1 to 3 nitrogen atoms, and
(H14) unsaturated condensed 7- to 13-membered, heterocyclic group containing 1 or 2 sulfur atoms and 1 to 3 nitrogen atoms,
and $R^3$ is hydrogen or a moiety selected from the group consisting of
(A1) lower alkylsufonyl optionally substituted by aryl
(A2) lower alkoxycarbonyl optionally substituted by lower alkoxy,
(A3) ar(lower)alkoxycarbonyl,
(A4) fluorenylmethoxycarbonyl,
(A5) mono- or di(lower)alkylaminosulfonyl optionally substituted by lower alkoxy,
(A6) mono- or di(lower)alkylcarbamoyl optionally substituted by aryl or unsaturated 3- to 8-membered, heteromonocyclic group containing 1 or 2 sulfur atoms,
(A7) aroyl optionally substituted by the group consisting of:
  lower alkoxy,
  halo,
  lower alkyl,
  hydroxy,
  aryloxy,
  aryl,
  trihalo(lower)alkyl,
  nitro,
  lower alkanoyl, and
  trihalo(lower)alkyloxy;
(A8) heterocyclic-carbonyl or heterocyclic-sulfonyl, wherein the heterocyclic group being selected from:
  (H1) unsaturated 3- to 8-membered, heteromonocyclic group containing 1 to 4 nitrogen atoms,
  (H2) saturated 3- to 8-membered, heteromonocyclic group containing 1 to 4 nitrogen atoms,
  (H3) unsaturated 3- to 8-membered, heteromonocyclic group containing 1 or 2 sulfur atoms,
  (H4) unsaturated condensed 7- to 13-membered, heterocyclic group containing 1 to 5 nitrogen atoms,
  (H5) unsaturated 3- to 8-membered, heteromonocyclic group containing 1 or 2 oxygen atoms,
  (H9) unsaturated condensed 7- to 13-membered, heterocyclic group containing 1 or 2 sulfur atoms, and
  (H10) saturated 3- to 8-membered, heteromonocyclic group containing 1 or 2 oxygen atoms and 1 to 3 nitrogen atoms,
  these heterocyclic group being optionally substituted by the group consisting of:
    (S1) lower alkoxy,
    (S7) lower alkyl, and
    (S27) lower alkanoyl,
(A9) lower cycloalkylcarbamoyl,
(A10) arylcarbamoyl, wherein the aryl group is optionally substituted by the group consisting of halogen, lower alkyl and lower alkoxy,
(A11) $C_6$–$C_{10}$ arylsulfonyl optionally substituted by lower alkoxy,
(A12) heterocycliccarbamoyl, wherein the heterocyclic group is (H7) unsaturated 3- to 8-membered, heteromonocyclic group containing 1 or 2 oxygen atoms and 1 to 3 nitrogen atoms, optionally substituted by lower alkyl,
(A13) lower cycloalkylcarbonyl optionally substituted by aryl,
(A14) lower alkenoyl optionally substituted by aryl,
(A15) heterocyclic(lower)alkenoyl, wherein the heterocyclic group is unsaturated 3- to 8-membered, heteromonocyclic group containing 1 to 4 nitrogen atoms,
(A16) lower alkanoyl optionally substituted by the group consisting of aryl, hydroxy, lower cycloalkyl, amino, lower alkoxycarbonylamino, lower alkoxy, lower alkoxy(lower)alkoxy, aryloxy, and heterocyclic group consisting of unsaturated 3- to 8-membered, heteromonocyclic group containing 1 or 2 sulfur atoms and unsaturated 3- to 8-membered, heteromonocyclic group containing 1 to 4 nitrogen atoms,
(A17) aryloxycarbonyl, and
(A18) lower cycloalkenecarbonyl.

2. The compound of claim 1, wherein the formula:

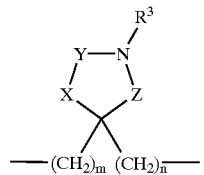

is the following formula:

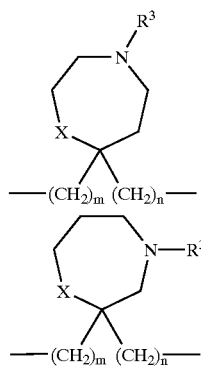

in which $R^3$ and X are each as defined in claim 1, m is an integer of 0 to 1, and n is an integer of 1 or 2.

3. The compound of claim 2, wherein the compound has the following formula:

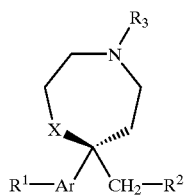

wherein $R^1$, $R^2$, $R^3$, and Ar are each as defined in claim 2, and
X is sulfonyl.

4. The compound of claim 3, wherein
R¹ is -halo;
   lower alkoxy;
   (C₆–C₁₀)aryl optionally substituted by
   (S1) lower alkoxy,
   (S2) lower alkoxycarbonylamino,
   (S3) lower alkylaminocarbonylamino,
   (S4) lower alkoxy(lower)alkanoylamino,
   (S5) C₆–C₁₀ aryloxy(lower)alkanoylamino,
   (S6) halo,
   (S7) lower alkyl,
   (S8) lower alkylthio,
   (S9) heterocyclic group selected from:
      unsaturated 5- or 6-membered, heteromonocyclic group containing 1 or 2 oxygen atoms and 1 to 3 nitrogen atoms, which is optionally substituted by lower alkyl, and
      saturated 5- or 6-membered, heteromonocyclic group containing 1 or 2 sulfur atoms and 1 to 3 nitrogen atoms, which is optionally substituted by oxo,
   (S10) lower alkenyl,
   (S11) amino,
   (S12) lower alkanoylamino,
   (S15) C₆–C₁₀ aryloxy,
   (S16) C₆–C₁₀ aryl,
   (S18) lower alkylcarbamoyl,
   (S19) trihalo(lower)alkyl
   (S20) cyano,
   (S21) cyano(lower)alkyl;
   (S22) lower alkoxy(lower)alkyl, and
   (S28) trihalo(lower)alkyloxy;
   (C₆–C₁₀)aryloxy optionally substituted by the group consisting of lower alkoxy, lower alkyl and halo;
   heterocyclic group selected from
   (H3) unsaturated 5- or 6-membered, heteromonocyclic group containing 1 or 2 sulfur atoms,
   (H4) unsaturated bicyclic 9- or 10-membered, heterocyclic group containing 1 to 5 nitrogen atoms,
   (H5) unsaturated 5- or 6-membered, heteromonocyclic group containing 1- or 2 oxygen atoms,
   (H8) unsaturated bicyclic 9- or 10-membered, heterocyclic group containing 1 or 2 oxygen atoms, and
   (H14) unsaturated bicyclic 9- or 10-membered, heterocyclic group containing 1 or 2 sulfur atoms and 1 to 3 nitrogen atoms,
      these heterocyclic group being optionally substituted by the group consisting of halogen, hydroxy(lower)alkyl, lower alkylcarbamoyl, lower alkyl and oxo; or
   lower alkynyl optionally substituted by (C₆–C₁₀)aryl or aminosulfonyl(C₆–C₁₀)aryl;
R² is N-hydroxycarbamoyl or N-(tetrahydropyranyloxy)carbamoyl;
R³ is -hydrogen; or
   a moiety selected from the group consisting of:
   (A1) lower alkylsufonyl optionally substituted by C₆–C₁₀ aryl,
   (A2) lower alkoxycarbonyl optionally substituted by lower alkoxy,
   (A3) C₆–C₁₀ ar(lower)alkoxycarbonyl,
   (A4) fluorenylmethoxycarbonyl,
   (A5) mono- or di(lower)alkylaminosulfonyl optionally substituted by lower alkoxy,
   (A6) mono- or di(lower)alkylcarbamoyl optionally substituted by C₆–C₁₀ aryl or (H3) unsaturated 5- or 6-membered, heteromonocyclic group containing 1 or 2 sulfur atoms,
   (A7) C₆–C₁₀ aroyl,
      C₆–C₁₀ aroyl substituted by lower alkoxy,
      C₆–C₁₀ aroyl substituted by halogen,
      C₆–C₁₀ aroyl substituted by lower alkyl,
      C₆–C₁₀ aroyl substituted by hydroxy,
      C₆–C₁₀ aroyl substituted by C₆–C₁₀ aryloxy,
      C₆–C₁₀ aroyl substituted by C₆–C₁₀ aryl,
      C₆–C₁₀ aroyl substituted by trihalo(lower)alkyl,
      C₆–C₁₀ aroyl substituted by nitro,
      C₆–C₁₀ aroyl substituted by lower alkanoyl,
      C₆–C₁₀ aroyl substituted by trihalo(lower)alkyloxy,
      C₆–C₁₀ aroyl substituted by the group consisting of lower alkoxy and halogen,
      C₆–C₁₀ aroyl substituted by the group consisting of lower alkoxy and hydroxy,
   (A8) heterocyclic-carbonyl or heterocyclic-sulfonyl, wherein the heterocyclic group being selected from;
      (H1) unsaturated 5- or 6-membered, heteromonocyclic group containing 1 to 4 nitrogen atoms, optionally substituted by lower alkyl or lower alkoxy;
      (H2) saturated 5- or 6-membered, heteromonocyclic group containing 1 to 4 nitrogen atoms optionally substituted by lower alkanoyl or lower alkoxy;
      (H3) unsaturated 5- or 6-membered, heteromonocyclic group containing 1 or 2 sulfur atoms;
      (H4) unsaturated bicyclic 9- or 10-membered, heterocyclic group containing 1 to 5 nitrogen atoms;
      (H5) unsaturated 5- or 6-membered, heteromonocyclic group containing 1 or 2 oxygen atoms;
      (H9) unsaturated bicyclic 9- or 10-membered, heterocyclic group containing 1 or 2 sulfur atoms; and
      (H10) saturated 5- or 6-membered, heteromonocyclic group containing 1 or 2 oxygen atoms and 1 to 3 nitrogen atoms;
   (A9) lower cycloalkylcarbamoyl,
   (A10) C₆–C₁₀ arylcarbamoyl, halo(C₆–C₁₀)-arylcarbamoyl,
      lower alkyl(C₆–C₁₀)-arylcarbamoyl,
      lower alkoxy(C₆–C₁₀)-arylcarbamoyl,
   (A11) C₆–C₁₀ arylsulfonyl optionally substituted by lower alkoxy,
   (A12) heterocycliccarbamoyl, wherein the heterocyclic group is (H7) unsaturated 5- or 6-membered, heteromonocyclic group containing 1 or 2 oxygen atoms and 1 to 3 nitrogen atoms optionally substituted by lower alkyl,
   (A13) lower cycloalkylcarbonyl optionally substituted by C₆–C₁₀ aryl,
   (A14) lower alkenoyl optionally substituted by C₆–C₁₀ aryl,
   (A15) heterocyclic(lower)alkenoyl, wherein the heterocyclic group is unsaturated 5- or 6-membered, heteromonocyclic group containing 1 to 4 nitrogen atoms,
   (A16) lower alkanoyl optionally substituted by the group consisting of C₆–C₁₀ aryl, hydroxy, lower cycloalkyl, amino, lower alkoxycarbonylamino, lower alkoxy, lower alkoxy(lower)alkoxy,
      C₆–C₁₀ aryloxy, and heterocyclic group consisting of unsaturated 5- or 6-membered, heteromonocyclic group containing 1 or 2 sulfur atoms and unsaturated 5- or 6-membered, heteromonocyclic group containing 1 to 4 nitrogen atoms,
   (A17) C₆–C₁₀ aryloxycarbonyl, and
   (A18) lower cycloalkenecarbonyl, and Ar is C$_6$–C$_{10}$ aryl or (H3) unsaturated 5- or 6-membered, heteromonocyclic group containing 1 or 2 sulfur atoms.

5. The compound of claim 4, wherein
R$^1$ is -lower alkoxy;
optionally substituted phenyl or naphthyl selected from
(Sa0) phenyl or naphthyl,
(Sa1) lower alkoxyphneyl,
(Sa2) lower alkoxycarbonylaminophenyl,
(Sa3) lower alkylaminocarbonylaminophenyl,
(Sa4) lower alkoxy(lower)alkanoylaminophenyl,
(Sa5) phenoxy(lower)alkanoylaminophenyl,
(Sa6) halophenyl,
(Sa7) lower alkylphenyl,
(Sa8) lower alkylthiophenyl,
(Sa9) oxazolylphenyl, oxadiazolylphenyl optionally substituted by lower alkyl, isothiazolidinylphenyl optionally substituted by oxo,
(Sa10) lower alkenylphenyl,
(Sa11) aminophenyl,
(Sa12) lower alkanoylaminophenyl,
(Sa15) phenoxyphenyl,
(Sa16) phenyl,
(Sa18) lower alkylcarbamoylphenyl,
(Sa19) trihalo(lower)alkylphenyl,
(Sa20) cyanophenyl,
(Sa21) cyano(lower)alkylphenyl,
(Sa22) lower alkoxy(lower)alkylphenyl; and
(Sa28) trihalo(lower)alkyloxyphenyl;
phenoxy, lower alkoxyphenoxy, lower alkylphenoxy, halophenoxy;
optionally substituted heterecyclic group selected from
(H3) thienyl optionally substituted by halogen,
(H4) quinolyl,
(H5) furyl,
(H8) benzofuranyl, hydroxy(lower)alkylbenzofuranyl, lower alkylcarbamoylbenzofuranyl;
(H14) dihydrobenzothiazolyl substituted by lower alkyl and oxo; or
lower alkynyl, phenyl(lower)alkynyl or aminosulfonyphenyl(lower)alkynyl;
R$^2$ is N-hydroxycarbamoyl,
R$^3$ is a moiety selected from the group consisting of;
(A1) lower alkylsufonyl optionally substituted by phenyl,
(A2) lower alkoxycarbonyl optionally substituted by lower alkoxy,
(A3) phenyl(lower)alkoxycarbonyl,
(A4) fluorenylmethoxycarbonyl,
(A5) mono- or di(lower)alkylaminosulfonyl optionally substituted by lower alkoxy,
(A6) mono- or di(lower)alkylcarbamoyl optionally substituted by phenyl or thienyl,
(A7) benzoyl,
naphthoyl,
benzoyl substituted by lower alkoxy,
benzoyl substituted by halogen,
benzoyl substituted by lower alkyl,
benzoyl substituted by hydroxy,
benzoyl substituted by phenoxy,
benzoyl substituted by phenyl,
benzoyl substituted by trihalo(lower)alkyl,
benzoyl substituted by nitro,
benzoyl substituted by lower alkanoyl,
benzoyl substituted by trihalo(lower)alkyloxy,
benzoyl substituted by lower alkoxy and halogen,
benzoyl substituted by lower alkoxy and hydroxy,
(A8) heterocyxlic-carbonyl or heterocyclic-sulfonyl selected from:
(Ha1) imidazolylcarbonyl optionally substituted by lower alkyl, pyrazolylcarbonyl, pyridylcarbonyl optionally substituted by lower alkyl, pyridylsulfonyl, pyrimidinylcarbonyl optionally substituted by lower alkyl, pyrazinylcarbonyl,
(Ha2) pyrrolidinylcarbonyl, pyrrolidinylsulfonyl, piperidinylcarbonyl optionally substituted by lower alkanoyl, piperidinylsulfonyl optionally substituted by lower alkoxy,
(Ha3) thienylcarbonyl, thienylsulfonyl,
(Ha4) indolylcarbonyl, quinolylcarbonyl, isoquinolylcarbonyl,
(Ha5) furylcarbonyl,
(Ha9) benzothienylcarbonyl, and
(Ha10) morpholinylcarbonyl, morpholinylsulfonyl,
(A9) lower cycloalkylcarbamoyl,
(A10) phenylcarbamoyl, halophenylcarbamoyl, lower alkylphenylcarbamoyl, lower alkoxyphenylcarbamoyl,
(A11) phenylsulfonyl optionally substituted by lower alkoxy,
(A12) isoxazolylcarbamoyl, lower alkylisoxazolylcarbamoyl,
(A13) lower cycloalkylcarbonyl optionally substituted by phenyl,
(A14) lower alkenoyl optionally substituted by phenyl,
(A15) pyridyl(lower)alkenoyl,
(A16) lower alkanoyl, phenyl(lower)alkanoyl, hydroxy (lower)alkanoyl, lower cycloalkyl(lower)alkanoyl, amino(lower)alkanoyl, lower alkoxycarbonylamino (lower)alkanoyl, lower alkoxy(lower)alkanoyl, lower alkoxy(lower)alkoxy(lower)alkanoyl, phenoxy(lower)alkanoyl, lower akanoyl substituted by amino and phenyl, lower alkanoyl substituted by lower alkoxycarbonylamino and phenyl, lower akanoyl substituted by hydroxy and phenyl, lower alkanoyl lower alkoxy and phenyl, pyridyl(lower) alkanoyl, thienyl(lower)alkanoyl,
(A17) phenoxycarbonyl,
(A18) lower cycloalkenecarbonyl, and
Ar is thienyl.

6. The compound of claim 5, wherein the compound has the following formula:

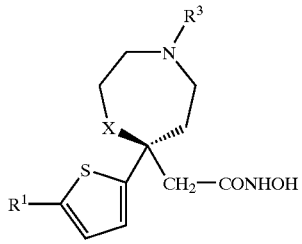

wherein R$^1$, R$^3$ and X are each as defined in claim 5.

7. The compound of claim 6, wherein
R$^1$ is -optionally substituted phenyl or naphthyl selected from
(Sa0) phenyl, naphthyl,
(Sa1) lower alkoxyphenyl,
(Sa2) lower alkoxycarbonylaminophenyl,
(Sa3) lower alkylaminocarbonylaminophenyl, (Sa4) lower alkoxy(lower)alkanoylaminophenyl,
(Sa5) phenoxy(lower)alkanoylaminophenyl,
(Sa6) halophenyl,
(Sa7) lower alkylphenyl,
(Sa8) lower alkylthiophenyl,
(Sa9) oxazolylphenyl, lower alkyloxadiazolylphenyl, 1,1-dioxoisothiazolidinylphenyl,
(Sa10) lower alkenylphenyl,
(Sa11) aminophenyl,
(Sa12) lower alkanoylaminophenyl,
(Sa16) biphenylyl,
(Sa19) trihalo(lower)alkylphenyl,
(Sa20) cyanophenyl,
(Sa21) cyano(lower)alkylphenyl,
(Sa22) lower alkoxy(lower)alkylphenyl, and
(Sa28) trihalo(lower)alkyloxyphenyl; and
optionally substituted heterecyclic group selected from
(H3) thienyl, halothienyl,
(H4) quinolyl,
(H5) furyl,
(H8) benzofuranyl, hydroxy(lower)alkylbenzofuranyl, lower alkylcarbamoylbenzofuranyl, and
(H14) dihydrobenzothiazolyl, dihydrobenzothiazolyl substituted by lower alkyl and oxo;
$R^3$ is a moiety selected from the group consisting of;
(A1) lower alkylsufonyl, phenyl(lower)alkylsufonyl,
(A2) lower alkoxycarbonyl, lower alkoxy(lower)alkoxycarbonyl,
(A3) phenyl(lower)alkoxycarbonyl,
(A4) fluorenylmethoxycarbonyl,
(A5) mono- or di(lower)alkylaminosulfonyl, N-(lower)alkoxy(lower)alkylaminosulfonyl, N-(lower)alkyl-N-(lower)alkoxy(lower)-alkylaminosulfonyl,
(A6) mono- or di(lower)alkylcarbamoyl, phenyl(lower)alkylcarbamoyl, thienyl(lower)alkylcarbamoyl,
(A7) benzoyl, 2-naphthoyl, lower alkoxybenzoyl, mono- or di- or trihalobenzoyl, lower alkylbenzoyl, hydroxybenzoyl, phenoxybenzoyl, phenylbenzoyl, mono- or bis(trihalo(lower)alkyl)benzoyl, nitrobenzoyl, lower alkanoylbenzoyl, trihalo(lower)alkyloxybenzoyl, benzoyl substituted by lower alkoxy and halogen, and benzoyl substituted by lower alkoxy and hydroxy,
(A8) heterocyclic-carbonyl or heterocyclic-sulfonyl selected from:
  (Ha1) imidazolylcarbonyl, lower alkylimidazolylcarbonyl, pyrazolylcarbonyl, pyridylcarbonyl, lower alkylpyridylcarbonyl, pyridylsulfonyl, pyrimidinylcarbonyl, lower alkylpyrimidinylcarbonyl, pyrazinylcarbonyl,
  (Ha2) pyrrolidinylcarbonyl, pyrrolidinylsulfonyl, piperidinylcarbonyl, lower alkanoylpiperidinylcarbonyl, piperidinylsulfonyl, lower alkoxypiperidinylsulfonyl,
  (Ha3) thienylcarbonoyl, thienylsulfonyl,
  (Ha4) indolylcarbonyl, quinolylcarbonyl, isoquinolylcarbonyl,
  (Ha5) furylcarbonyl,
  (Ha9) benzothienylcarbonyl,
  (Ha10) morpholinylcarbonyl, morpholinylsulfonyl,
(A9) lower cycloalkylcarbamoyl,
(A10) phenylcarbamoyl, halophenylcarbamoyl, lower alkylphenylcarbamoyl, lower alkoxyphenylcarbamoyl,
(A11) phenylsulfonyl, lower alkoxyphenylsulfonyl,
(A12) isoxazolylcarbamoyl, lower alkylisoxazolylcarbamoyl,
(A13) lower cycloalkylcarbonyl, phenyl(lower)cycloalkylcarbonyl,
(A14) lower alkenoyl, phenyl(lower)alkenoyl,
(A15) pyridyl(lower)alkenoyl,
(A16) lower alkanoyl, phenyl(lower)alkanoyl, hydroxy(lower)alkanoyl, lower cycloalkyl(lower)alkanoyl, amino(lower)alkanoyl, lower alkoxy(lower)alkanoyl, lower alkoxy(lower)alkoxy(lower)alkanoyl, phenoxy(lower)alkanoyl,
  lower akanoyl substituted by amino and phenyl, lower akanoyl substituted by hydroxy and phenyl, lower alkanoyl substituted by lower alkoxy and phenyl, pyridyl(lower)alkanoyl, thienyl(lower)alkanoyl,
(A17) phenoxycarbonyl, and
(A18) lower cycloalkenecarbonyl.
8. The compound of claim 7, wherein
$R^1$ is (Sa0) phenyl, 2-naphthyl,
(Sa1) 4-methoxyphenyl, 4-ethoxyphenyl,
(Sa2) 3-(methoxycarbonylamino)phenyl, 3-(ethoxycarbonylamino)phenyl,
(Sa3) 3-(methylaminocarbonylamino)phenyl, 3-(ethylaminocarbonylamino)phenyl,
(Sa4) 3-(ethoxyacetylamino)phenyl,
(Sa5) 3-(phenoxyacetylamino)phenyl,
(Sa6) 4-chlorophenyl, 4-fluorophenyl,
(Sa7) 4-methylphenyl, 4-ethylphenyl, 4-propylphenyl, 4-isopropylphenyl,
(Sa8) 4-methylthiophenyl,
(Sa9) 2-(or 5-)oxazolylphenyl, 5-methyl-1,2,4-oxadiazol-3-ylphenyl, 1,1-dioxoisothiazolidin-2-ylphenyl,
(Sa10) 4-vinylphenyl,
(Sa11) 3-aminophenyl,
(Sa12) 3-acetylaminophenyl,
(Sa16) 4-biphenylyl,
(Sa19) 4-trifluoromethylphenyl,
(Sa20) 4-cyanophenyl,
(Sa21) 4-cyanomethylphenyl, or
(Sa22) 4-methoxymethylphenyl,
(Sa28) 4-trifluoromethyloxyphenyl,
optionally substituted heterecyclic group selected from
(H3) 2-thienyl, 5-chloro-2-thienyl,
(H4) 6-quinolyl,
(H5) 2-furyl,
(H8) 2-(hydroxymethyl)-5-benzofuranyl, 2-(methylcarbamoyl)-5-benzofuranyl, and
(H14) 3-methyl-2-oxo-2,3-dihydrobenzothiazolyl,
$R^3$ is a moiety selected from the group consisting of;
(A1) methylsulfonyl, ethylsulfonyl, propylsulfonyl, benzylsulfonyl,
(A2) methoxycarbonyl, ethoxycarbonyl, isobutoxycarbonyl, t-butoxycarbonyl, 2-methoxyethoxycarbonyl,
(A3) benzyloxycarbonyl,
(A4) fluorenylmethoxycarbonyl,
(A5) dimethylaminosulfonyl, diethylaminosulfonyl, N-(2-methoxyethyl)aminosulfonyl, N-methyl-N-(2-methoxyethyl)aminosulfonyl,
(A6) ethylcarbamoyl, propylcarbamoyl, isopropylcarbamoyl, t-butylcarbamoyl, dimethylcarbamoyl, benzylcarbamoyl, 1-phenylethylcarbamoyl, 2-(2-thienyl)ethylcarbamoyl,
(A7) benzoyl, 2-naphthoyl, 2- or 3- or 4-methoxybenzoyl, 2-ethoxybenzoyl, 2-propoxybenzoyl, 2,3- or 2,4- or 2,5- dimethoxybenzoyl, 2,3,4-trimethoxybenzoyl, 2- or 3- or 4-chlorobenzoyl, 2,3- or 2,4- or 2,5-dichlorobenzoyl, 2-fluorobenzoyl, 2-methylbenzoyl, 2-hydroxybenzoyl, 2-phenoxybenzoyl, 2-phenylbenzoyl, 2-trifluoromethylbenzoyl, 2,4-bis(trifluoromethyl)benzoyl, 2-nitrobenzoyl, 2-acetylbenzoyl, 2-trifluoromethyloxybenzoyl, 2-methoxy-4-chlorobenzoyl, 3-methoxy-2-hydroxybenzoyl, (A8) heterocyclic-carbonyl or heterocyclic-sulfonyl selected from:
  (Ha1) 1-methyl-2-imidazolylcarbonyl, 4-pyrazolylcarbonyl, 2- or 3- or 4-pyridylcarbonyl, 3-methyl-2-pyridylcarbonyl, 3-pyridylsulfonyl, 4-methyl-5-pyrimidinylcarbonyl, 2-pyrazinylcarbonyl,
  (Ha2) 1-pyrrolidinylcarbonyl, 1-pyrrolidinylsulfonyl, 1- or 4-piperidinylcarbonyl, 1-acetyl-4-piperidinylcarbonyl, 1-piperidinylsulfonyl, 4-methoxy-1-piperidinylsulfonyl,
  (Ha3) 2- or 3-thienylcarbonyl, 2-thienylsulfonyl,
  (Ha4) 2-indolylcarbonyl, 3- or 8-quinolylcarbonyl, 1-isoquinolylcarbonyl,
  (Ha5) 2-furylcarbonyl,
  (Ha9) 2-benzothienylcarbonyl,
  (Ha10) 4-morpholinylcarbonyl, 4-morpholinylsulfonyl,
(A9) cyclopropylcarbamoyl, cyclohexylcarbamoyl,
(A10) phenylcarbamoyl, 2-, 3- or 4-chlorophenylcarbamoyl, 2,3- or 2,5-dicholophenylcarbamoyl, 2-methylphenylcarbamoyl, 2-methoxyphenylcarbamoyl,
(A11) phenylsulfonyl, 4-methoxyphenylsulfonyl,
(A12) 5-methyl-3-isoxazolylcarbamoyl,
(A13) cyclopropylcarbonyl, cyclobutylcarbonyl, cyclopentylcarbonyl, cyclohexylcarbonyl, 1-phenyl-1-cyclopropylcarbonyl,
(A14) 3-methylcrotonoyl, 3-phenylacryloyl,
(A15) 3-pyridylacryloyl,
(A16) acetyl, propionyl, isobutyryl, isovaleryl, pivaloyl, hexanoyl, 3,3-dimethylbutyryl, 2-ethylbutyryl, 3-phenylpropionyl, 2-amino-2-phenylacetyl, 2-hydroxy-2-phenylacetyl, 2-hydroxy-3-phenylpropionyl, 2-methoxy-2-pheylacetyl, cyclopropylacetyl, cyclopentylacetyl, aminoacetyl, 3-aminopropionyl, 2-aminoisovaleryl, 2-aminopivaloyl, methoxyacetyl, (2-methoxyethoxy)acetyl, phenoxyacetyl, 2-pyridylacetyl, 3-thienylacetyl,
(A17) phenoxycarbonyl, and
(A18) 3-cyclohexenecarbonyl.

9. The compound of claim 7, wherein
$R^1$ is -optionally substituted phenyl selected from:
  (Sa1) lower alkoxyphenyl,
  (Sa6) halophenyl,
  (Sa7) lower alkylphenyl,
  (Sa8) lower alkylthiophenyl,
  (Sa9) oxazolylphenyl, lower alkyloxadiazolylphenyl 1,1-dioxoisothiazolidinylphenyl, and
  (Sa28) trihalo(lower)alkyloxyphenyl;
$R^3$ is a moiety selected from the group consisting of;
  (A1) lower alkylsufonyl, phenyl(lower)alkylsufonyl,
  (A5) mono- or di(lower)alkylaminosulfonyl, N-(lower) alkoxy(lower)alkylaminosulfonyl, N-(lower)alkyl-N-(lower)-alkoxy(lower)-alkylaminosulfonyl (A7) benzoyl, 2-naphthoyl, lower alkoxybenzoyl, mono- or di- or trihalobenzoyl, lower alkylbenzoyl, hydroxybenzoyl, phenoxybenzoyl, phenylbenzoyl, mono- or bis(trihalo(lower)alkyl)benzoyl, nitrobenzoyl, lower alkanoylbenzoyl, trihalo(lower)alkyloxybenzoyl, benzoyl substituted by lower alkoxy and halogen, benzoyl substituted by lower alkoxy and hydroxy, (A8) heterocyclic-carbonyl or heterocyclic-sulfonyl selected from:
  (Ha1) imidazolylcarbonyl, lower alkylimidazolylcarbonyl, pyrazolylcarbonyl, pyridylcarbonyl, lower alkylpyridylcarbonyl, pyridylsulfonyl, pyrimidinylcarbonyl, lower alkylpyrimidinylcarbonyl, pyrazinylcarbonyl,
  (Ha2) pyrrolidinylcarbonyl, pyrrolidinylsulfonyl, piperidinylcarbonyl, lower alkanoylpiperidinylcarbonyl, piperidinylsulfonyl, lower alkoxypiperidinylsulfonyl,
  (Ha3) thienylcarbonoyl, thienylsulfonyl,
  (Ha4) indolylcarbonyl, quinolylcarbonyl, isoquinolylcarbonyl,
  (Ha5) furylcarbonyl,
  (Ha9) benzothienylcarbonyl,
  (Ha10) morpholinylcarbonyl, morpholinylsulfonyl,
(A13) lower cycloalkylcarbonyl, phenyl(lower)cycloalkylcarbonyl,
(A14) lower alkenoyl, phenyl(lower)alkenoyl, and
(A16) lower alkanoyl, phenyl(lower)alkanoyl, hydroxy(lower)alkanoyl, lower cycloalkyl(lower)alkanoyl, amino(lower)alkanoyl, lower alkoxy(lower)alkanoyl, lower alkoxy(lower)alkoxy(lower)alkanoyl, phenoxy(lower)alkanoyl, lower akanoyl substituted by amino and phenyl, lower akanoyl substituted by hydroxy and phenyl, lower alkanoyl substituted by lower alkoxy and phenyl, pyridyl(lower)alkanoyl, thienyl(lower)alkanoyl.

10. The compound of claim 9, wherein
$R^1$ is (Sa1) 4-methoxyphenyl, 4-ethoxyphenyl,
  (Sa6) 4-chlorophenyl, 4-fluorophenyl,
  (Sa7) 4-methylphenyl, 4-ethylphenyl, 4-propylphenyl, 4-isopropylphenyl,
  (Sa8) 4-methylthiophenyl,
  (Sa9) 2-(or 5-)oxazolylphenyl, 5-methyl-1,2,4-oxadiazol-3-ylphenyl, 1,1-dioxoisothiazolidin-2-ylphenyl,
  (Sa28) 4-trifluoromethyloxyphenyl,
$R^3$ is a moiety selected from the group consisting of;
  (A1) methylsulfonyl, ethylsulfonyl, propylsulfonyl, benzylsulfonyl,
  (A5) dimethylaminosulfonyl, diethylaminosulfonyl, N-(2-methoxyethyl)aminosulfonyl, N-methyl-N-(2-methoxyethyl)aminosulfonyl,
  (A7) benzoyl, 2-naphthoyl, 2- or 3- or 4-methoxybenzoyl, 2-ethoxybenzoyl, 2-propoxybenzoyl, 2,3- or 2,4- or 2,5-dimethoxybenzoyl, 2,3,4-trimethoxybenzoyl, 2- or 3- or 4-chlorobenzoyl, 2,3- or 2,4- or 2,5-dichlorobenzoyl, 2-fluorobenzoyl, 2-methylbenzoyl, 2-hydroxybenzoyl, 2-phenoxybenzoyl, 2-phenylbenzoyl, 2-trifluoromethylbenzoyl, 2,4-bis(trifluoromethyl)benzoyl, 2-nitrobenzoyl, 2-acetylbenzoyl, 2-trifluoromethyloxybenzoyl, 2-methoxy-4-chlorobenzoyl, 3-methoxy-2-hydroxybenzoyl,
  (A8) 1-methyl-2-imidazolylcarbonyl, 4-pyrazolylcarbonyl, 2- or 3- or 4-pyridylcarbonyl, 3-methyl-2-pyridylcarbonyl, 3-pyridylsulfonyl, 4-methyl-5-pyrimidinylcarbonyl, 2-pyrazinylcarbonyl, 1-pyrrolidinylcarbonyl, 1-pyrrolidinylsulfonyl, 1- or 4-piperidinylcarbonyl, 1-acetyl-4-piperidinylcarbonyl, 1-piperidinylsulfonyl, 4-methoxy-1-piperidinylsulfonyl, 2- or 3-thienylcarbonyl, 2-thienylsulfonyl, 2-indolylcarbonyl, 3- or 8-quinolylcarbonyl, 1-isoquinolylcarbonyl, 2-furylcarbonyl, 2-benzothienylcarbonyl, 4-morpholinylcarbonyl, 4-morpholinylsulfonyl, (A13) cyclopropylcarbonyl, cyclobutylcarbonyl, cyclopentylcarbonyl, cyclohexylcarbonyl, 1-phenyl-1-cyclopropylcarbonyl, (A14) 3-methylcrotonoyl, 3-phenylacryloyl, (A16) acetyl, propionyl, isobutyryl, isovaleryl, pivaloyl, hexanoyl, 3,3-dimethylbutyryl, 2-ethylbutyryl, 3-phenylpropionyl, 2-amino-2-phenylacetyl, 2-t-butoxycarbonylamino-2-phenylacetyl, 2-hydroxy-2-phenylacetyl, 2-hydroxy-3-phenylpropionyl, 2-methoxy-2-pheylacetyl, cyclopropylacetyl, cyclopentylacetyl, aminoacetyl, t-butoxycarbonylaminoacetyl, 3-aminopropionyl, 3-t-butoxycarbonylaminopropionyl, 2-aminoisovaleryl, 2-t-butoxycarbonylaminoisovaleryl, 2-aminopivaloyl, 2-t-butoxycarbonylaminopivaloyl, methoxyacetyl, (2-methoxyethoxy)acetyl, phenoxyacetyl, 2-pyridylacetyl, 3-thienylacetyl.

11. The compound of claim 4, wherein $R^1$ is -($C_6$–$C_{10}$)aryloxy optionally substituted by the group consisting of lower alkoxy, lower alkyl and halo;

$R^2$ is N-hydroxycarbamoyl;

$R^3$ is a moiety selected from the group consisting of:
(A1) lower alkylsufonyl,
(A3) $C_6$–$C_{10}$ ar(lower)alkoxycarbonyl,
(A4) fluorenylmethoxycarbony,
(A5) mono- or di(lower)alkylaminosulfonyl optionally substituted by lower alkoxy,
(A6) mono- or di(lower)alkylcarbamoyl,
(A7) $C_6$–$C_{10}$ aroyl,
$C_6$–$C_{10}$ aroyl substituted by lower alkoxy,
(A8) heterocyclic-carbonyl or heterocyclic-sulfonyl, wherein the heterocyclic group being selected from;
(H1) unsaturated 5- or 6-membered, heteromonocyclic group containing 1 to 4 nitrogen atoms,
(H2) saturated 5- or 6-membered, heteromonocyclic group containing 1 to 4 nitrogen atoms,
(H3) unsaturated 5- or 6-membered, heteromonocyclic group containing 1 or 2 sulfur atoms, and
(H10) saturated 5- or 6-membered, heteromonocyclic group containing 1 or 2 oxygen atoms and 1 to 3 nitrogen atoms;
(A9) lower cycloalkylcarbamoyl,
(A13) lower cycloalkylcarbonyl,
(A16) lower alkanoyl optionally substituted by the group consisting of $C_6$–$C_{10}$ aryl, hydroxy and 2-hydroxy-2-phenylacetyl, and Ar is phenyl.

12. The compound of claim 11, wherein the compound has the following formula:

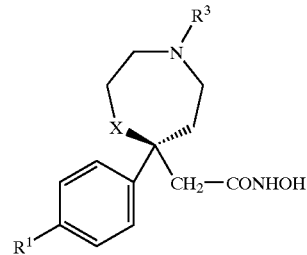

wherein $R^1$, $R^3$ and X are each as defined in claim 11.

13. The compound of claim 12, wherein $R^1$ is -($C_6$–$C_{10}$)aryloxy optionally substituted by the group consisting of lower alkoxy, lower alkyl and halo, $R^3$ is a moiety selected from the group consisting of:
(A1) lower alkylsufonyl,
(A3) $C_6$–$C_{10}$ ar(lower)alkoxycarbonyl,
(A4) fluorenylmethoxycarbonyl,
(A5) mono- or di(lower)alkylaminosulfonyl,
(A6) mono- or di(lower)alkylcarbamoyl,
(A7) $C_6$–$C_{10}$ aroyl, $C_6$–$C_{10}$ aroyl substituted by lower alkoxy,
(A8) heterocyclic-carbonyl or heterocyclic-sulfonyl, wherein the heterocyclic group being selected from;
(H1) unsaturated 5- or 6-membered, heteromonocyclic group containing 1 to 4 nitrogen atoms,
(H2) saturated 5- or 6-membered, heteromonocyclic group containing 1 to 4 nitrogen atoms,
(H3) unsaturated 5- or 6-membered, heteromonocyclic group containing 1 or 2 sulfur atoms, and
(H10) saturated 5- or 6-membered, heteromonocyclic group containing 1 or 2 oxygen atoms and 1 to 3 nitrogen atoms,
(A9) lower cycloalkylcarbamoyl,
(A13) lower cycloalkylcarbonyl, and
(A16) lower alkanoyl, lower alkanoyl substituted by the group consisting of C6–C10 and hydroxy.

14. The compound of claim 13, wherein $R^1$ is -phenoxy, lower alkoxyphenoxy, lower alkylphenoxy or halophenoxy;

$R^3$ is a moiety selected from the group consisting of:
(A1) lower alkylsufonyl,
(A3) phenyl(lower)alkoxycarbonyl,
(A4) fluorenylmethoxycarbonyl,
(A5) di(lower)alkylaminosulfonyl,
(A6) (lower)alkylcarbamoyl,
(A7) benzoyl, benzoyl substituted by lower alkoxy,
(A8) heterocyclic-carbonyl or heterocyclic-sulfonyl, selected from;
(H1) pyridylcarbonyl, pyrazinylcarbonyl,
(H2) piperidinylcarbonyl,
(H3) thienylcarbonyl, thienylsulfonyl, and
(H10) morpholinylsulfonyl,
(A9) lower cycloalkylcarbamoyl,
(A13) lower cycloalkylcarbonyl, and
(A16) lower alkanoyl, lower alkanoyl substituted by phenyl and hydroxy.

15. The compound of claim 14, wherein $R^1$ is -phenoxy, 4-methoxyphenoxy, 4-ethoxyphenoxy, 4-methylphenoxy, 4-chlorophenoxy, 4-fluorphenyl, $R^3$ is a moiety selected from the group consisting of:
(A1) methylsulfonyl, ethylsulfonyl, propylsulfonyl, (A3) benzyloxycarbonyl,
(A4) 9-fluorenylmethoxycarbonyl,
(A5) dimethylaminosulfonyl,
(A6) propylcarbamoyl, isopropylcarbamoyl, t-butylcarbamoyl,
(A7) benzoyl, 2-methoxybenzoyl,
(A8) heterocyclic-carbonyl or heterocyclic-sulfonyl, selected from;
  (H1) 2-pyridylcarbonyl, 2-pyrazinylcarbonyl,
  (H2) 1-piperidinylcarbonyl,
  (H3) 2- or 3-thienylcarbonyl, 2-thienylsulfonyl, and
  (H10) 1-morpholinylsulfonyl,
(A9) cyclohexylcarbamoyl,
(A13) cyclopropylcarbonyl, and
(A16) isovaleryl, 2-hydroxy-2-phenylacetyl.

16. A process for the preparation of the compound of claim 1, which comprises (a) acylating a compound of the formula:

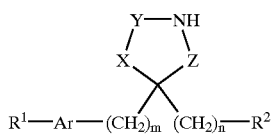 (I-a)

or its reactive derivative at the amino group, or a salt thereof to give a compound of the formula:

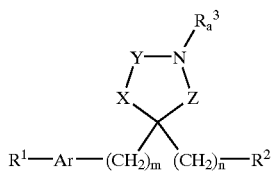 (I-b)

or a salt thereof; or (b) reacting a compound of the formula:

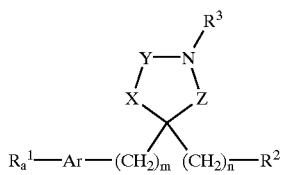 (I-c)

or a salt thereof with a compound of the formula:

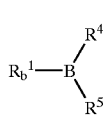 (II)

to give a compound of the formula:

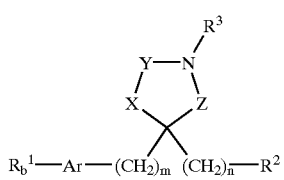 (I-d)

or a salt thereof; or (c) subjecting a compound of the formula:

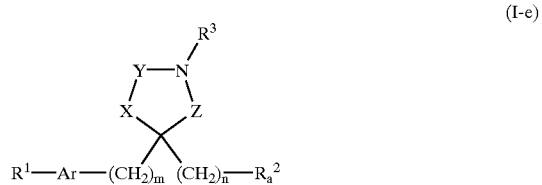 (I-e)

or a salt thereof to a removal reaction of the hydroxycarbamoyl-protective group, to give a compound of the formula:

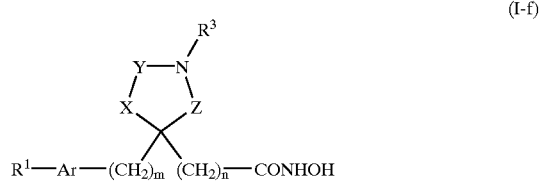 (I-f)

or a salt thereof; or (d) subjecting a compound of the formula:

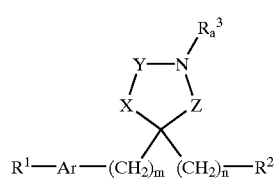 (I-b)

or a salt thereof to a removal reaction of the acyl group, to give a compound of the formula:

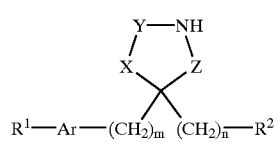 (I-a)

or a salt thereof; or (e) amidating a compound of the formula:

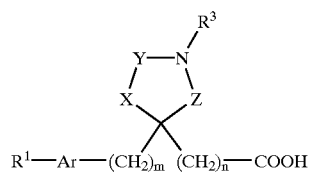 (III)

or its reactive derivative at the carboxy group, or a salt thereof, to give a compound of the formula:

(I)

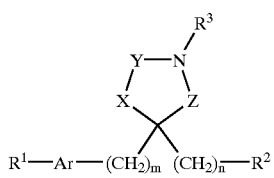

or a salt thereof; or
(f) subjecting a compound of the formula:

(I-g)

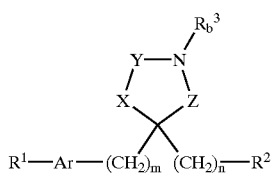

or a salt thereof to a removal reaction of the amino- or imino-protective group, to give a compound of the formula:

(I-h)

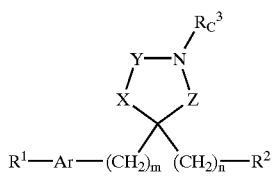

or a salt thereof; or
(g) acylating a compound of the formula:

(I-i)

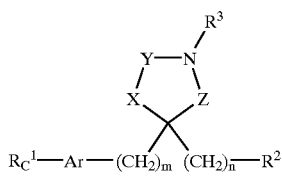

or a salt thereof to give a compound of the formula:

(I-j)

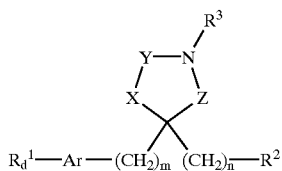

or a salt thereof; or
(h) reacting a compound of the formula:

(I-c)

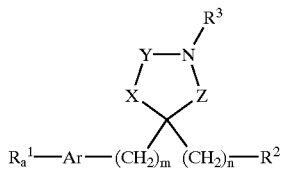

or a salt thereof with a compound of the formula:

 (IV)

to give a compound of the formula:

(I-k)

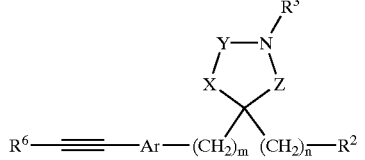

or a salt thereof; or
(i) reacting a compound of the formula:

(I-a)

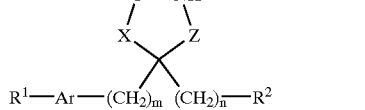

or a salt thereof with a compound of the formula:

$R^7$—CHO (V)

to give a compound of the formula:

(I-l)

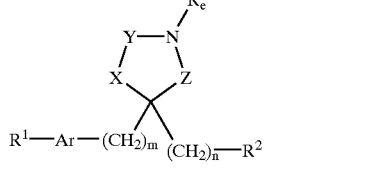

or a salt thereof,
wherein
$R^1$, $R^2$, $R^3$, Ar, X, Y, Z, m and n are each as defined above,
$R_a^1$ is halo,
$R_b^1$ is optionally substituted aryl or optionally substituted heterocyclic group,
$R_c^1$ is aryl, aryloxy or heterocyclic group having at least amino- or imino-moiety,
$R_d^1$ is aryl, aryloxy or heterocyclic group having at least acylamino- or acylimino-moiety, $R_a^2$ is protected hydroxycarbamoyl,
$R_a^3$ is a moiety defined in $R^3$ of claim 1,
$R_b^3$ is acyl having at least protected amino- or protected imino-moiety,
$R_c^3$ is acyl having at least amino- or imino-moiety,
$R_d^3$ is optionally substituted lower alkyl,
$R^4$ and $R^5$ are each hydroxy, lower alkyl, or combined together to form lower alkylene,
a formula: H—≡—$R^6$ is optionally substituted lower alkynyl, and
a formula: $R^7$—CHO is optionally substituted aldehyde.

17. A pharmaceutical composition comprising as an active ingredient the compound of claim 1 and a pharmaceutically acceptable, substantially non-toxic carrier or excipient.

18. The compound of claim 1, which is N-Hydroxy-2-[(S)-7-(5-(4-ethylphenyl)-2-thienyl)-4-(2-pyridylcarbonyl)-1,1-dioxoperhydro-1,4-thiazepin-7-yl]acetamide.

19. The pharmaceutical composition of claim 17, which comprises N-Hydroxy-2-[(S)-7-(5-(4-ethylphenyl)-2-thienyl)-4-(2-pyridylcarbonyl)-1,1-dioxoperhydro-1,4-thiazepin-7-yl]acetamide as an active ingredient.

20. The compound of claim 1, wherein Y and Z are ethylene.

* * * * *